(12) United States Patent
Geuns-Meyer et al.

(10) Patent No.: US 7,880,000 B2
(45) Date of Patent: *Feb. 1, 2011

(54) PROTEIN KINASE MODULATORS AND METHOD OF USE

(75) Inventors: Stephanie D. Geuns-Meyer, Medford, MA (US); Brian L. Hodous, Cambridge, MA (US); Stuart C. Chaffee, Cambridge, MA (US); Paul A. Tempest, Brookline, MA (US); Philip R. Olivieri, Medford, MA (US); Rebecca E. Johnson, Arlington, VA (US); Brian K. Albrecht, Cambridge, MA (US); Vinod F. Patel, Acton, MA (US); Victor J. Cee, Mansfield, MA (US); Joseph L. Kim, Wayland, MA (US); Steven Bellon, Wellesley, MA (US); Xiaotian Zhu, Newton, MA (US); Yuan Cheng, Newbury Park, CA (US); Ning Xi, Thousand Oaks, CA (US); Karina Romero, Cambridge, MA (US); Hanh Nho Nguyen, Arlington, MA (US); Holly L. Deak, Brookline, MA (US)

(73) Assignee: Amgen Inc., Thousand Oaks, CA (US)

( * ) Notice: Subject to any disclaimer, the term of this patent is extended or adjusted under 35 U.S.C. 154(b) by 1143 days.

This patent is subject to a terminal disclaimer.

(21) Appl. No.: 11/126,000

(22) Filed: May 9, 2005

(65) Prior Publication Data

US 2006/0009453 A1    Jan. 12, 2006

Related U.S. Application Data

(60) Provisional application No. 60/569,193, filed on May 7, 2004.

(51) Int. Cl.
*C07D 401/14*    (2006.01)
*C07D 403/14*    (2006.01)
*A61K 31/53*     (2006.01)
*A61K 31/4427*   (2006.01)
*A61K 31/506*    (2006.01)
*A61P 19/02*     (2006.01)
*A61P 35/00*     (2006.01)

(52) U.S. Cl. .............. 544/320; 544/322; 544/182; 514/272; 514/274; 514/242

(58) Field of Classification Search .......... 544/320, 544/322, 182; 514/272, 275, 242
See application file for complete search history.

(56) References Cited

U.S. PATENT DOCUMENTS

| 4,318,854 | A  | 3/1982  | Trybulski      |
| 6,060,491 | A  | 5/2000  | Pruitt et al.  |
| 6,143,764 | A  | 11/2000 | Kubo et al.    |
| 6,352,989 | B1 | 3/2002  | Miyazaki et al.|
| 7,135,550 | B2* | 11/2006 | Come et al. ............ 530/350 |
| 7,560,551 | B2* | 7/2009  | Cee et al. ............... 544/237 |
| 2003/0087908 | A1 | 5/2003 | Geuns-Meyers et al. |
| 2004/0039061 | A1 | 2/2004 | Suzuki et al. |
| 2007/0185324 | A1* | 8/2007 | De Morin et al. ......... 544/60 |
| 2009/0163501 | A1 | 6/2009 | Cee et al. |

FOREIGN PATENT DOCUMENTS

| EP | 0 014 470 A2 | 8/1980 |
| WO | WO93/21158 | 10/1993 |
| WO | WO00/47212 | 8/2000 |
| WO | WO 01/25220 A1 | 4/2001 |
| WO | WO 02/12198 A2 | 2/2002 |
| WO | WO02/32872 | 4/2002 |
| WO | WO02/083628 | 10/2002 |
| WO | WO03/000660 | 1/2003 |
| WO | WO03/037891 | 5/2003 |
| WO | WO 2004/005281 A1 | 1/2004 |
| WO | WO2004/092196 | 10/2004 |
| WO | WO 2005/026129 A1 | 3/2005 |
| WO | WO 2005/033086 A1 | 4/2005 |

OTHER PUBLICATIONS

Mass, R. D., Int. J. Radiation Oncology Bio. Phys. vol. 58(3): 932-940, 2004.*
Fabbro et al. Pharmacology & therapeutics 93, 79-98, 2002.*

(Continued)

*Primary Examiner*—Venkataraman Balasubramanian
(74) *Attorney, Agent, or Firm*—G. Prabhakar Reddy

(57) ABSTRACT

The present invention relates to chemical compounds having a general formula I

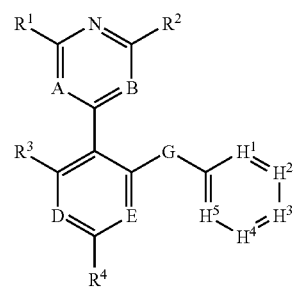

wherein A, B, D, E, G, $H^{1-5}$ and $R^{1-4}$ are defined herein, and synthetic intermediates, which are capable of modulating various protein kinase receptor enzymes and, thereby, influencing various disease states and conditions related to the activities of these kinases. For example, the compounds are capable of modulating kinase enzymes thereby influencing the process of angiogenesis and treating angiogenesis-related diseases and other poliferative disorders, including cancer and inflammation. The invention also includes pharmaceutical compositions, including the compounds, and methods of treating disease states related to the activity of protein kinases.

19 Claims, No Drawings

OTHER PUBLICATIONS

Cecil Textbook of Medicine, edited by Bennet, J.C., and Plum F., 20th edition, vol. 1, 1004-1010, 1996.*
De Morin et al., US 2007/0185324; CA 147: 143458, 2007; Caplus Abstract.*
Coffen, et al., "2-Benzazepines. 8.[1] Zerovalent Nickel Mediated Biaryl Synthesis of an Anxiolytic Pyrimido [5,4-*d*] [2] Benzazepine", *J. Org. Chem*, 49(2), 296-300 (1984).
Earley, et al., "2-Benzazepines. 7. Synthesis of Pyrimido [5,4-d] [2] Benzazepines", *Journal of Heterocyclic Chemistry*, 20(5), 1195-1197 (1983).
Kasum, et al., "A Classical Approach to the Synthesis of Perloline", *Australian Journal of Chemistry*, 36(7), 1455-1467 (1983).
Kuno, et al., "Studies on Cerebral Protective Agents. I. Novel 4-Arylpyrimidine Derivatives with Anti-Anoxic and Anti-Lipid Peroxidation Activities", *Chemical and Pharmaceutical Bulletin*, 40(6), 1452-1461 (1992).
Modi, et al., "Synthesis and Antibacterial Activity of Some 2-Amino-4-[2'-(2", 6"-dinitro-4"-Trifluoromethylphenoxy)-5'-methyl-phen-1'-yl]-6-Substituted Phenyl Pyrimidines", *Asian Journal of Chemistry*, 6(4), 945-949 (1994).
Modi, et al., "Synthesis and Antibacterial Activity of Some 2-Acetamido-4-[2'-(2", 6"-dinitro-4"-Trifluoromethylphenoxy)-5'-methyl-phen-1'-yl]-6-Substituted Phenyl Pyrimidines", *Asian Journal of Chemistry*, Notes 6(4), 1061-1062 (1994).

* cited by examiner

PROTEIN KINASE MODULATORS AND METHOD OF USE

This application claims the benefit of U.S. Provisional Application No. 60/569,193, filed May 7, 2004 which is hereby incorporated by reference herein.

FIELD OF THE INVENTION

The invention relates to the field of pharmaceutical agents and, more specifically, is directed to compounds, compositions, uses and methods for treating angiogenesis and cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. For example, protein tyrosine kinases (PTKs) are enzymes, which catalyze the phosphorylation of specific tyrosine residues in cellular proteins. Examples of kinases in the protein kinase family include, without limitation, ab1, Akt, Aurora-A, Aurora-B, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Due to their activity in numerous cellular processes, protein kinases have emerged as important therapeutic targets.

Protein kinases play a central role in the regulation and maintenance of a wide variety of cellular processes and cellular function. For example, kinase activity acts as molecular switches regulating cell proliferation, activation, and/or differentiation. Uncontrolled or excessive kinase activity has been observed in many disease states including benign and malignant proliferation disorders as well as diseases resulting from inappropriate activation of the immune system (autoimmune disorders), allograff rejection, and graft vs host disease. In addition, endothelial cell specific receptor PTKs, such as VEGF-2, Tie-2 and Lck mediate the angiogenic process and are, therefore, involved in supporting the progression of cancers and other diseases involving uncontrolled vascularization.

Angiogenesis is the process of developing new blood vessels, particularly capillaries, from pre-existing vasculature and is an essential component of embryogenesis, normal physiological growth, repair, and tumor expansion. Angiogenesis remodels small vessels into larger conduit vessels, a physiologically important aspect of vascular growth in adult tissues. Vascular growth is required for beneficial processes such as tissue repair, wound healing, recovery from tissue ischemia and menstrual cycling.

Certain diseases and/or pathological conditions develop as a result of, or are known to be associated with, the regulation and/or deregulation of angiogenesis. For example, ocular neovascularisation such as retinopathies (including diabetic retinopathy), age-related macular degeneration, psoriasis, hemangioblastoma, hemangioma, and arteriosclerosis have been found to be caused, in part, due to the loss of regulation and/or maintenance of vascular growth. Inflammatory diseases such as a rheumatoid or rheumatic inflammatory disease, and especially arthritis (including rheumatoid arthritis) where new capillary blood vessels invade the joint and destroy cartilage, have been associated with angiogenesis. In addition, chronic inflammatory disorders such as chronic asthma, arterial or post-transplantational atherosclerosis, endometriosis, and neoplastic diseases including so-called solid tumors and liquid tumors (for example, leukemias), have been found to be linked to the regulation and control of angiogenesis.

The involvement of angiogenesis in major diseases has lead to the identification and development of various targets for inhibiting angiogenesis. These targets relate to various receptors, enzymes, and other proteins in the angiogenic process or cascade of events leading to angiogenesis, such as, for example, activation of endothelial cells by an angiogenic signal, synthesis and release of degradative enzymes, endothelial cell migration, proliferation of endothelial cells, and formation of capillary tubules.

One target identified in the cascade of events leading to angiogenesis is the Tie receptor family. The Tie-1 and Tie-2 receptors are single-transmembrane, tyrosine kinase receptors (Tie stands for tyrosine kinase receptors with immunoglobulin and EGF homology domains). Tie-2 is an endothelial cell specific receptor tyrosine kinase, which is involved in angiogenic processes, such as vessel branching, sprouting, remodeling, maturation and stability. Tie-2 is the first mammalian receptor for which both agonist ligand(s) (for example, Angiopoietin-1 ("Ang1") which binds to and stimulates phosphorylation and signal transduction of Tie-2), and context dependent agonist/antagonist ligand(s) (for example, Angiopoietin-2 ("Ang2")) have been identified. Knock out and transgenic manipulation of the expression of Tie-2 and its ligands indicates that tight spacial and temporal control of Tie-2 signaling is important for the proper development of new vascularization.

Biological models suggest that the stimulation of Tie-2 by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial death, especially in the absence of growth/survival stimuli.

Recently, upregulation of Tie-2 expression has been found in the vascular synovial pannus of arthritic joints of humans, consistent with the role in inappropriate neovasculariation. This finding suggests that Tie-2 plays a role in the progression of rheumatoid arthritis. Point mutations producing constitutively activated forms of Tie-2 have been identified in association with human venous malformation disorders. Tie-2 inhibitors would, therefore, be useful in treating such disorders, as well as in other instances of improper neovasacularization. However, with the recent recognition of Ang3 and Ang4 as additional Tie-2 binding ligands, targeting a Tie-2 ligand-receptor interaction as an anti-angiogenic therapeutic approach is less favorable. Accordingly, a Tie-2 receptor kinase inhibition approach has become a strategy of choice.

Another angiogenic factor responsible for regulating the growth and differentiation of the vascular system and its components, both during embryonic development and normal growth, as well as in a wide number of pathological anomalies and diseases, is Vascular Endothelial Growth Factor ("VEGF"; originally termed "Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF). It is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are also transmembrane receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the belief that the VEGF released by tumor cells stimulates the growth of blood capillaries and the proliferation of tumor endothelium in a paracrine manner, and through the improved blood supply, accelerate tumor growth. Increased VEGF expression could explain the occurrence of cerebral edema in patients with glioma. Direct evidence of the role of VEGF as a tumor angiogenesis factor in vivo has been shown in studies in which VEGF expression or VEGF activity was inhibited. This was achieved with anti-VEGF antibodies, with dominant-negative VEGFR-2 mutants, which inhibited signal transduction, and with antisense-VEGF RNA techniques. All approaches led to a reduction in the growth of glioma cell lines or other tumor cell lines in vivo as a result of inhibited tumor angiogenesis.

VEGF's are unique in that they are the primary angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, the regulation of angiogenesis via the VEGF receptor activity has become an important therapeutic target.

Angiogenesis is regarded as an absolute prerequisite for tumors that grow beyond a diameter of about 1-2 mm. Up to this size, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into vascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

The inhibition of vascular growth in this context has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Regulating angiogenesis by inhibiting certain recognized pathways in this process would therefore, be useful in treating diseases, such as ocular neovascularization, including retinopathy, age-related macular degeneration, psoriasis, hemangioblastoma, hemangioma, arteriosclerosis, inflammatory disease rheumatoid arthritis, chronic inflammatory disorders such as chronic asthma, arterial or post-transplantational atherosclerosis, endometriosis, and neoplastic diseases such as leukemias, otherwise known to be associated with deregulated angiogenesis. Treatment of malaria and related viral diseases may also be mediated by HGF and cMet.

Other receptor tyrosine kinases such as FGFR-1, PDGFR, FLK-1 (Fetal Liver Kinase-1) and c-Met have also been suggested to play a role in angiogenesis. C-met is a unique receptor tyrosine kinase, which comprises, in its native form, a 190 kDa heterodimeric (a disulfide-linked 50 kDa α-chain and a 145 kDa β-chain) membrane-spanning tyrosine kinase protein (Proc. Natl. Acad. Sci. USA, 84:6379-6383 (1987)). C-Met is mainly expressed in epithelial cells and stimulation of c-Met leads to scattering, angiogenesis, proliferation and metastasis. (See Cytokine and Growth Factor Reviews, 13:41-59 (2002)). The ligand for c-Met is hepatocyte growth factor (also known as scatter factor, HGF and SF). HGF is a heterodimeric protein secreted by cells of mesodermal origin (Nature, 327:239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Basel, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Over-expression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met protooncogene have been postulated to play a role in microglial reactions to CNS injuries (Oncogene, 8:219-222 (1993)).

In view of the role of HGF and/or c-Met in potentiating or promoting such diseases or pathological conditions, it would be useful to have a means of substantially reducing or inhibiting one or more of the biological effects of HGF and its receptor. Thus, a compound that reduces the effect of HGF would be a useful compound.

Non-receptor tyrosine kinases represent a collection of cellular enzymes, which lack extracellular activity and transmembrane sequences. Examples of non-receptor tyrosine kinases identified include over twenty-four individual kinases, comprising eleven (11) subfamilies (Src, Frk, Btk, Csk, Abl, Zap70, Fes/Fps, Fak, jak, Ack, and LIMK). Src is thought to be the largest family including Src, TES, FYN, Lyn, Lck, blk, Fgr, and Yrk. The Src subfamily has been linked to oncogenesis and immune responses. See Bohlen, Oncogene, 8:2025-2031 (1993), which disclosure is incorporated herein by reference in its entirety. These kinases have also been found to be involved in cellular signaling pathways in numerous pathogenic conditions, including cancer, psoriasis, and other hyper-proliferative disorders or hyper-immune responses. Thus, it would be useful to inhibit the activity of non-receptor kinases as well.

Many classes of compounds have been proposed to generally or specifically inhibit kinase activity. For example, the Kirin publication WO 03/000660 describes substituted phenyl compounds, U.S. Pat. No. 6,143,764 describes substituted quinolines, WO 02/32872 describes substituted quinolines, and WO 00/47212 describes substituted quinazoline derivatives. However, there is always a need to improve the pharmacokinetic and pharmacodynamic profile of kinase inhibitor compounds for improved physiological efficacy and enhanced treatment of kinase-related pathological conditions and/or disease states. Further, there is a need to treat disease states associated with angiogenesis such as cancer, rheumatoid arthritis, and other conditions where active angiogenesis is undesirable.

BRIEF DESCRIPTION OF THE INVENTION

The present invention provides a new class of compounds useful in treating pathological conditions and/or disease states related to kinase activity and, in particular, in treating active angiogenesis and related diseases, including cancer and rheumatoid arthritis. In one embodiment of the invention, the compounds, including pharmaceutically acceptable salts thereof, are generally defined by Formula I

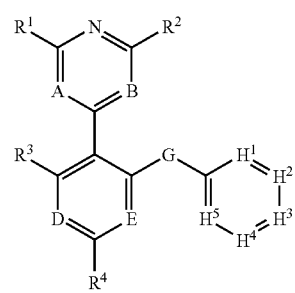

wherein A, B, D, E, G, $H^{1-5}$ and $R^{1-4}$ are defined herein.

In another embodiment, the invention provides compounds of Formulas II and III, which are similar in structure to Formula I above.

The invention also provides processes for making compounds of Formulas I-III, as well as intermediates useful in such processes.

The compounds provided by the invention have kinase modulatory activity and, in particular, inhibitory activity, including, without limitation, Tie-2, Lck, KDR, c-Met and/or Aurora kinase inhibitory activity.

To this end, the invention further provides the use of these compounds, as well as their pharmaceutically acceptable salts, in the preparation and manufacture of a medicament for therapeutic, prophylactic, acute or chronic treatment of an angiogenesis mediated disease state, including those described previously. These compounds are also useful in the manufacture of anti-cancer medicaments. More particularly, these compounds are useful in the manufacture of a medicament to attenuate or prevent disorders through inhibition of Tie-2, Lck, KDR, c-Met and/or Aurora kinase activity. For example, in one embodiment, the invention provides a pharmaceutical composition comprising a therapeutically-effective amount of a compound of Formula I, II or III in association with a least one pharmaceutically-acceptable carrier, adjuvant or diluent.

Further, the invention provides a method of treating angiogenesis related disorders in a subject inflicted with, or susceptible to, such disorder, the method comprising administering to the subject a therapeutically-effective amount of a compound of Formula I, II or III.

DETAILED DESCRIPTION OF THE INVENTION

In one embodiment of the invention, compounds useful for treating angiogenesis related disorders, including cancer and inflammation, are defined by Formula I:

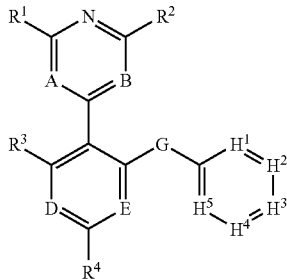

and pharmaceutically acceptable salts thereof, wherein

A is N or $CR^{10}$;
B is N or $CR^{11}$;
D is N or $CR^{12}$;
E is N or CH;
G is $NR^{13}$, O, S, C(O), S(O), $SO_2$, $CR^{13}R^{13}$ or $CR^{13}R^{14}$;
$H^1$ is N or $CR^5$;
$H^2$ is N or $CR^6$;
$H^3$ is N or $CR^7$;
$H^4$ is N or $CR^8$;
$H^5$ is N or $CR^9$;
$R^1$ is H, halo, haloalkyl, $NO_2$, CN, $NR^{13}R^{13}$, $OR^{13}$, $SR^{13}$, $(CHR^{13})_nR^{13}$, or $R^{15}$; alternatively $R^1$ taken together with $R^{10}$ forms a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}$, $NR^{13}R^{14}$ or $NR^{14}R^{14}$;

$R^2$ is H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$; alternatively $R^2$ taken together with $R^{11}$ forms a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}NR^{13}R^{14}$ or $NR^{14}R^{14}$;

each of $R^3$ and $R^4$, independently, is H, halo, haloalkyl, oxo, $NO_2$, CN, $SR^{13}$, $OR^{13}$ $NR^{13}R^{13}$, $NR^{13}R^{14}$, $O(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}(C(O)R^{13}$, $NR^{13}CO(O)R^{14}$, $NR^{13}CO(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}$ $R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively, either of $R^3$ or $R^4$, independently, taken together with $R^{12}$ forms a partially or fully unsaturated 5- or 6-membered ring of carbon atoms optionally including 1-3 heteroatoms selected from O, N, or S, and the ring optionally substituted independently with 1-3 substituents of $R^{13}$;

each of $R^5$ and $R^6$, independently, is H, halo, haloalkyl, oxo, $NO_2$, CN, $SR^{13}$, $OR^{13}$, $NR^{13}R^{13}$, $NR^{13}R^{13}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}(C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively $R^5$ taken together with $R^6$ forms a partially or fully unsaturated 5- or 6-membered ring of carbon atoms optionally including 1-3 heteroatoms selected from O, N, or S, and the ring optionally substituted independently with 1-3 substituents of $R^{13}$;

each of $R^7$ and $R^8$, independently, is $R^{13}$, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{16}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$ or $NR^{13}S(O)_2R^{14}$;

each of $R^9$, $R^{10}$, $R^{11}$ and $R^{12}$, independently, is H, $R^{13}$, halo, haloalkyl, $NO_2$, CN, $SR^{13}$, $OR^{13}$, $NR^{13}R^{13}$, $NR^{13}R^{14}$, $C(O)^{13}$ $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{16}$, $NR^{13}(COOR^{13})$, $OC(O)NR^{13}R^{13}$, $NR^{13}C(O)C(O)R^{13}$, $NR^{13}C(O)$ $NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$ or $NR^{13}S(O)_2R^{14}$;

each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with one or more substituents of $R^{15}$, $R^{16}$ or $R^{17}$;

$R^{14}$ is $C(O)R^{18}$, $COOR^{18}$, $S(O)_2R^{18}$ or $R^{16}$; alternatively $R^{14}$ taken together with $R^{13}$ forms a partially or fully unsaturated 5- or 6-membered ring of carbon atoms optionally including 1-3 heteroatoms selected from O, N and S, and the ring optionally substituted independently with 1-3 substituents of oxo, halo, haloalkyl, $NO_2$, CN, $R^{17}$ or $R^{18}$;

$R^{15}$ is halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}$ $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with one or more substituents of $R^{17}$, $R^{18}$ or $R^{20}$;

$R^{17}$ is halo, haloalkyl, oxo, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{19}$ or $R^{20}$, each of which is optionally substituted with 1-3 substituents of $R^{21}$;

$R^{19}$, independently, is $C(O)R^{20}$, $C(O)R^{21}$, $COOR^{20}$, $COOR^{21}$, $S(O)_2R^{20}$ or $S(O)_2R^{21}$;

$R^{20}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{21}$;

each $R^{21}$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2, 3, 4 or 5, provided that (1) when A is N, then B is not N, and when B is N, then A is not N; (2) no more than one of $H^1$, $H^2$, $H^3$, $H^4$ and $H^5$ is N; (3) when either of $R^1$ or $R^2$ is substituted or unsubstituted NH-phenyl, then no more than four of $R^5$, $R^6$, $R^7$, $R^8$ and $R^9$ is H; and (4) when $R^1$ is Phenyl, then neither of $R^6$ and $R^8$ is, independently, $NO_2$.

Accordingly, the above embodiment of the present invention does not encompass triazine D-ring compounds, wherein both A and B are N, respectively. Triazine D-ring compounds (Formula III) of the present invention are described in another embodiment hereinbelow. In addition, the above embodiment does not include compounds wherein either of $R^1$ or $R^2$ is an amine-linked aniline and all five of $R^5$, $R^6$, $R^7$, $R^8$ and $R^9$ are H, respectively. Finally, the above embodiment does not include compounds wherein $R^1$ is Phenyl, and either of $R^6$ and $R^8$ is, independently, $NO_2$.

In another embodiment, the compounds of Formula I include N as A and $CR^{11}$ as B, in conjunction with any of the above or below embodiments.

In another embodiment, the compounds of Formula I include N as B and $CR^{10}$ as A, in conjunction with any of the above or below embodiments.

In another embodiment, the compounds of Formula I include $CR^{10}$ as A and $CR^{11}$ as B, in conjunction with any of the above or below embodiments.

In another embodiment, the compounds of Formula I include N as D, in conjunction with any of the above or below embodiments.

In another embodiment, the compounds of Formula I include $CR^{12}$ as D, in conjunction with any of the above or below embodiments.

In another embodiment, the compounds of Formula I include CH as E, in conjunction with any of the above or below embodiments.

In another embodiment, the compounds of Formula I include $CR^{12}$ as D and N as E, in conjunction with any of the above or below embodiments.

In another embodiment, the compounds of Formula I include $CR^{12}$ as D, N as E, and H, halo, $NO_2$, CN, $C_{1-10}$alkyl or $C_{1-10}$alkoxyl as $R^2$, in conjunction with any of the above or below embodiments.

In another embodiment, the compounds of Formula I include $NR^{13}$, O, $CHR^{13}$, S, C(O), S(O) or $SO_2$ as G, in conjunction with any of the above or below embodiments.

In another embodiment, the compounds of Formula I include $NR^{13}$, O, $CHR^{13}$, S, C(O), S(O) or $SO_2$ and as G and H, halo, $NO_2$, CN, $C_{1-10}$alkyl or $C_{1-10}$alkoxyl as $R^2$, in conjunction with any of the above or below embodiments.

In another embodiment, the compounds of Formula I include $NR^{13}$ as G, in conjunction with any of the above or below embodiments.

In another embodiment, the compounds of Formula I include O as G, in conjunction with any of the above or below embodiments.

In another embodiment, the compounds of Formula I include $CHR^{13}$ as G, in conjunction with any of the above or below embodiments.

In another embodiment, the compounds of Formula I include S as G, in conjunction with any of the above or below embodiments.

In another embodiment, the compounds of Formula I include C(O) as G, in conjunction with any of the above or below embodiments.

In another embodiment, the compounds of Formula I include S(O) as G, in conjunction with any of the above or below embodiments.

In another embodiment, the compounds of Formula I include $SO_2$ as G, in conjunction with any of the above or below embodiments.

In another embodiment, the compounds of Formula I include H as each of $R^3$, $R^4$ and $R^9$, and CH or $CR^{12}$ as D, in conjunction with any of the above or below embodiments.

In another embodiment, the compounds of Formula I include H as each of $R^3$, $R^4$ and $R^9$, CH or $CR^{12}$ as D, and H, halo, $NO_2$, CN, $C_{1-10}$alkyl or $C_{1-10}$alkoxyl as $R^2$, in conjunction with any of the above or below embodiments.

In another embodiment, the compounds of Formula I include H as each of $R^3$, $R^4$ and $R^9$, in conjunction with any of the above or below embodiments.

In another embodiment, the compounds of Formula I include CH or $CR^{12}$ as D, in conjunction with any of the above or below embodiments.

In another embodiment, the compounds of Formula I include N or $CR^5$ as $H^1$, in conjunction with any of the above or below embodiments.

In another embodiment, the compounds of Formula I include N or $CR^6$ as $H^2$, in conjunction with any of the above or below embodiments.

In another embodiment, the compounds of Formula I include N or $CR^7$ as $H^3$, in conjunction with any of the above or below embodiments.

In another embodiment, the compounds of Formula I include N or $CR^8$ as $H^4$, in conjunction with any of the above or below embodiments.

In another embodiment, the compounds of Formula I include N or $CR^9$ as $H^5$, in conjunction with any of the above or below embodiments.

In another embodiment, the compounds of Formula I include N or $CR^5$ as $H^1$, N or $CR^6$ as $H^2$, $CR^7$ as $H^3$, N or $CR^8$ as $H^4$, and N or $CR^9$ as $H^5$, in conjunction with any of the above or below embodiments.

In another embodiment, the compounds of Formula I include N or $CR^5$ as $H^1$, N or $CR^6$ as $H^2$, N or $CR^7$ as $H^3$, $CR^8$ as $H^4$, and N or $CR^9$ as $H^5$, in conjunction with any of the above or below embodiments.

In another embodiment, the compounds of Formula I include $CR^5$ as $H^1$, $CR^6$ as $H^2$, $CR^7$ as $H^3$, $CR^8$ as $H^4$, and $CR^9$ as $H^5$, in conjunction with any of the above or below embodiments.

In another embodiment, the compounds of Formula include $CR^5$ as $H^1$, $CR^6$ as $H^2$, $CR^7$ as $H^3$, $CR^8$ as $H^4$, and $CR^9$ as $H^5$, and each of $CR^5$, $CR^6$, $CR^7$, $CR^8$ and $CR^9$, independently, is not hydrogen (H), in conjunction with any of the above or below embodiments.

In another embodiment, the compounds of Formula I include $R^{15}$ as $R^1$, in conjunction with any of the above or below embodiments.

In another embodiment, the compounds of Formula I include H, halo, haloalkyl, $NO_2$, CN, $NR^{13}R^{13}$, $OR^{13}$, $SR^{13}$, or $(CHR^{13})_n R^{13}$ as $R^1$, in conjunction with any of the above or below embodiments.

In another embodiment, the compounds of Formula I include H, $NR^{13}R^{13}$, $OR^{13}$, $SR^{13}$ or $CH_2R^{13}$ as $R^1$, in conjunction with any of the above or below embodiments.

In another embodiment, the compounds of Formula I include $C_{1-10}$alkyl, $C_{1-10}$alkoxyl, $C_{1-10}$alkyl-amino-, aryl-amino-aryl, heteroaryl, heterocyclyl, heteroaryl-amino-, aryl-alkyl-amino-, heterocyclyl-alkyl-amino- and heteroaryl-alkyl-amino-as $R^1$, in conjunction with any of the above or below embodiments.

In another embodiment, the compounds of Formula I include $R^1$ taken together with $R^{10}$ to form a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}$ or $NR^{13}R^{14}$, in conjunction with any of the above or below embodiments.

In another embodiment, the compounds of Formula I include H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$, as $R^2$, in conjunction with any of the above or below embodiments.

In another embodiment, the compounds of Formula I include H, halo, haloalkyl, $NO_2$, CN, $SR^{13}$, $OR^{13}$, $NR^{13}R^{13}$, $C_{1-10}$ alkyl, $C_{1-10}$alkenyl or $C_{1-10}$alkynyl, wherein the $C_{1-10}$alkyl, $C_{1-10}$alkenyl and $C_{1-10}$alkynyl, is optionally substituted with one or more substituents of $R^{13}$, as $R^2$, in conjunction with any of the above or below embodiments.

In another embodiment, the compounds of Formula I include $C_{1-10}$alkyl, $C_{1-10}$alkoxyl, $C_{1-10}$alkyl-amino-, aryl-amino-, aryl, heteroaryl, heterocyclyl, heteroaryl-amino-, aryl-alkyl-amino-, heterocyclyl-alkyl-amino- and heteroaryl-alkyl-amino-as $R^2$, in conjunction with any of the above or below embodiments.

In another embodiment, the compounds of Formula I include H as $R^2$, in conjunction with any of the above or below embodiments.

In another embodiment, the compounds of Formula I include $R^2$ taken together with $R^{11}$ to form a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}$, $NR^{13}R^{14}$ or $NR^{14}R^{14}$, in conjunction with any of the above or below embodiments.

In another embodiment, the compounds of Formula I include H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$, as each $R^3$, in conjunction with any of the above or below embodiments.

In another embodiment, the compounds of Formula I include H, halo, haloalkyl, $NO_2$, CN, $SR^{13}$, $OR^{13}$, $NR^{13}R^{13}$, $C_{1-10}$alkyl, $C_{1-10}$alkenyl or $C_{1-10}$alkynyl, wherein the $C_{1-10}$alkyl, $C_{1-10}$alkenyl and $C_{1-10}$alkynyl, is optionally substituted with one or more substituents of $R^{13}$, as $R^3$, in conjunction with any of the above or below embodiments.

In another embodiment, the compounds of Formula I include $C_{1-10}$alkyl, $C_{1-10}$alkoxyl, $C_{1-10}$alkyl-amino-, aryl-amino-, aryl, heteroaryl, heterocyclyl, heteroaryl-amino-, aryl-alkyl-amino-, heterocyclyl-alkyl-amino- and heteroaryl-alkyl-amino-as $R^3$, in conjunction with any of the above or below embodiments.

In another embodiment, the compounds of Formula I include H as $R^3$, in conjunction with any of the above or below embodiments.

In another embodiment, the compounds of Formula I include $R^3$ taken together with $R^{12}$ to form a partially or fully unsaturated 5- or 6-membered ring of carbon atoms optionally including 1-3 heteroatoms selected from O, N, or S, and the ring optionally substituted independently with 1-3 substituents of $R^{13}$, in conjunction with any of the above or below embodiments.

In another embodiment, the compounds of Formula I include H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)(O)NR^{13}R^{13}$, $NR^{13}C(O)C(O)NR^{13}R^{14}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$, as each $R^4$, in conjunction with any of the above or below embodiments.

In another embodiment, the compounds of Formula I include H, halo, haloalkyl, $NO_2$, CN, $SR^{13}$, $OR^{13}$, $NR^{13}R^{13}$, $C_{1-10}$alkyl, $C_{1-10}$alkenyl or $C_{1-10}$alkynyl, wherein the $C_{1-10}$alkyl, $C_{1-10}$alkenyl and $C_{1-10}$alkynyl, is optionally substituted with one or more substituents of $R^{13}$, as $R^4$, in conjunction with any of the above or below embodiments.

In another embodiment, the compounds of Formula I include $C_{1-10}$alkyl, $C_{1-10}$alkoxyl, $C_{1-10}$alkyl-amino-, arylamino-, aryl, heteroaryl, heterocyclyl, heteroaryl-amino-, aryl-alkyl-amino-, heterocyclyl-alkyl-amino- and heteroaryl-alkyl-amino- as $R^4$, in conjunction with any of the above or below embodiments.

In another embodiment, the compounds of Formula I include H as $R^4$, in conjunction with any of the above or below embodiments.

In another embodiment, the compounds of Formula I include $R^4$ taken together with $R^{12}$ to form a partially or fully unsaturated 5- or 6-membered ring of carbon atoms optionally including 1-3 heteroatoms selected from O, N, or S, and the ring optionally substituted independently with 1-3 substituents of $R^{13}$, in conjunction with any of the above or below embodiments.

In another embodiment, the compounds of Formula I include H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$, as $R^5$, in conjunction with any of the above or below embodiments.

In another embodiment, the compounds of Formula I include H, Cl, Br, F, I, $CF_3$, $CF_2CF_3$, $NO_2$, CN, acetyl, oxo, haloalkyl, haloalkoxyl, CN, OH, SH, $NO_2$, $NH_2$, acetyl, $C_{1-10}$-alkylamino-, benzyl or phenyl as $R^5$, in conjunction with any of the above or below embodiments.

In another embodiment, the compounds of Formula I include H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$, as $R^6$, in conjunction with any of the above or below embodiments.

In another embodiment, the compounds of Formula I include H, Cl, Br, F, I, $CF_3$, $CF_2CF_3$, $NO_2$, CN, acetyl, oxo, haloalkyl, haloalkoxyl, CN, OH, SH, $NO_2$, $NH_2$, acetyl, $C_{1-10}$-alkylamino-, benzyl or phenyl as $R^6$, in conjunction with any of the above or below embodiments.

In another embodiment, the compounds of Formula I include $R^5$ taken together with $R^6$ to form a partially or fully unsaturated 5- or 6-membered ring of carbon atoms optionally including 1-3 heteroatoms selected from O, N, or S, and the ring optionally substituted independently with 1-3 substituents of $R^{13}$, in conjunction with any of the above or below embodiments.

In another embodiment, the compounds of Formula I include $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$, $C_{1-10}$alkyl optionally substituted with one or more substituents of $R^{15}$ or $R^{16}$, or $C_{1-10}$alkenyl optionally substituted with one or more substituents of $R^{15}$ or $R^{16}$, as $R^7$, in conjunction with any of the above or below embodiments.

In another embodiment, the compounds of Formula I include $SR^{13}$, $OR^{13}$, $NR^{13}R^{13}$, $C(O)R^{13}$, $COOR^{13}$, $C(O)NR^{13}R^{13}$, $NR^{13}C(O)R^{13}$, $NR^{13}(COOR^{13})$, $NR^{13}C(O)NR^{13}R^{13}$, $C(S)R^{13}$, $C(S)NR^{13}R^{13}$, $NR^{13}C(S)R^{13}$, $NR^{13}C(S)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$ or $C_{1-10}$alkyl substituted with $SR^{13}$, $OR^{13}$, $NR^{13}R^{13}$, $C(O)R^{13}$, $COOR^{13}$, $C(O)NR^{13}R^{13}$, $NR^{13}C(O)R^{13}$, $NR^{13}(COOR^{13})$, $NR^{13}C(O)NR^{13}R^{13}$, $C(S)R^{13}C(S)NR^{13}R^{13}$, $NR^{13}C(S)R^{13}$, $NR^{13}C(S)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$ as $R^7$, in conjunction with any of the above or below embodiments.

In another embodiment, the compounds of Formula I include H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl as $R^7$, in conjunction with any of the above or below embodiments.

In another embodiment, the compounds of Formula I include H, halo, haloalkyl, $C_{1-10}$-alkyl, $C_{1-10}$-alkylamino-, $C_{1-10}$-dialkylamino- or $C_{1-10}$-alkoxyl as $R^7$, in conjunction with any of the above or below embodiments.

In another embodiment, the compounds of Formula I include $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(C)C(O)NR^{13}R^{13}$, $NR^{13}C(O)C(O)NR^{13}R^{13}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)NR^{13}R^{13}$, $NR^{13}S(O)_2R^{13}$, $NR^{13}S(O)_2R^{14}$, $C_{1-10}$alkyl optionally substituted with one or more substituents of $R^{15}$ or $R^{16}$, or $C_{1-10}$alkenyl optionally substituted with one or more substituents of $R^{15}$ or $R^{16}$, as $R^8$, in conjunction with any of the above or below embodiments.

In another embodiment, the compounds of Formula I 13 include $SR^{13}$, $OR^{13}$, $NR^{13}R^{13}$, $C(O)R^{13}$, $COOR^{13}$, $C(O)NR^{13}R^{13}$, $NR^{13}C(O)R^{13}$, $NR^{13}(COOR^{13})$, $NR^{13}C(O)NR^{13}R^{13}$, $C(S)R^{13}$, $C(S)NR^{13}R^{13}$, $NR^{13}C(S)R^{13}$, $NR^{13}C(S)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$ or $C_{1-10}$alkyl substituted with $SR^{13}$, $OR^{13}$, $NR^{13}R^{13}$, $C(O)R^{13}$, $COOR^{13}$, $C(O)NR^{13}R^{13}$, $NR^{13}C(O)R^{13}$, $NR^{13}(COOR^{13})$, $NR^{13}C(O)NR^{13}R^{13}$, $C(S)R^{13}$, $C(S)NR^{13}R^{13}$, $NR^{13}C(S)R^{13}$, $NR^{13}C(S)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$ as $R^8$, in conjunction with any of the above or below embodiments.

In another embodiment, the compounds of Formula I include H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl as $R^8$, in conjunction with any of the above or below embodiments.

In another embodiment, the compounds of Formula I include H, halo, haloalkyl, $C_{1-10}$-alkyl, $C_{1-10}$-alkylamino-, $C_{1-10}$-dialkylamino- or $C_{1-10}$-alkoxyl as $R^8$, in conjunction with any of the above or below embodiments.

In another embodiment, the compounds of Formula I include H, $R^{13}$, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{16}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{13}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$ or $NR^{13}S(O)_2R^{14}$ as $R^9$, in conjunction with any of the above or below embodiments.

In another embodiment, the compounds of Formula I include H, $R^{13}$, halo, haloalkyl, $NO_2$, CN, $SR^{13}$, $OR^{13}$, $NR^{13}R^{13}$ or $C(O)R^{13}$ as $R^9$, in conjunction with any of the above or below embodiments.

In another embodiment, the compounds of Formula I include H as $R^9$, in conjunction with any of the above or below embodiments.

In another embodiment, the compounds of Formula I include H, $R^{13}$, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{16}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}CC(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$ or $NR^{13}S(O)_2R^{14}$ as $R^{10}$, in conjunction with any of the above or below embodiments.

In another embodiment, the compounds of Formula I include H as $R^{10}$, in conjunction with any of the above or below embodiments.

In another embodiment, the compounds of Formula I include H, $R^{13}$, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{16}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$ or $NR^{13}S(O)_2R^{14}$ as $R^{11}$, in conjunction with any of the above or below embodiments.

In another embodiment, the compounds of Formula I include H as $R^{11}$, in conjunction with any of the above or below embodiments.

In another embodiment, the compounds of Formula I include H, $R^{13}$, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{16}$, $NR^{13}(COOR^{13})$, $OC(O)NR^{13}R^{13}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2$ $NR^{13}R^{13}$, $NR^{13}S(O)_2R^{13}$ or $NR^{13}S(O)_2R^{14}$ as $R^{12}$, in conjunction with any of the above or below embodiments.

In another embodiment, the compounds of Formula I include H, halo, haloalkyl, $NO_2$, CN, acetyl, $C_{1-10}$-alkyl, $SR^{13}$, $OR^{13}$, $NR^{13}R^{13}$, $C(O)R^{13}$, $COOR^{13}$, $C(O)NR^{13}R^{13}$, $NR^{13}C(O)R^{13}$, $NR^{13}C(O)NR^{13}R^{13}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$ or $R^{16}$ optionally substituted with 1-3 substituents of $R^{17}$, $R^{18}$ or $R^{20}$ as $R^{12}$, in conjunction with any of the above or below embodiments.

In another embodiment, the compounds of Formula I include H, halo, haloalkyl, oxo, $NO_2$, CN, or $C_{1-10}$alkyl, $C_{1-10}$alkenyl, $C_{1-10}$alkynyl, cyclopropyl, cyclobutyl, cyclopentyl, cyclohexyl, tetrahydrofuranyl, tetrahydropyrrolyl, pyranyl, phenyl, naphthyl, benzyl, furanyl, pyrrolyl, thiophenyl, indolyl, imidazolyl, pyrazolyl, oxazolyl, benzimidazolyl, benzopyrazolyl, benzoxazolyl, benzothiozolyl, piperidinyl, piperazinyl, morpholinyl, each of which is optionally independently substituted with 1-3 substituents of $R^{13}$, as $R^{12}$, in conjunction with any of the above or below embodiments.

In another embodiment, the compounds of Formula I include H, $R^{13}$, halo, haloalkyl, $NO_2$, CN, $SR^{13}$, $OR^{13}$, $NR^{13}R^{13}$ or $C(O)R^{13}$ as $R^{12}$, in conjunction with any of the above or below embodiments.

In another embodiment, the compounds of Formula I include H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with one or more substituents of $R^{15}$, $R^{16}$ or $R^{18}$, as $R^{13}$, in conjunction with any of the above or below embodiments.

In another embodiment, the compounds of Formula I include H, $C_{1-10}$alkyl, $C_{1-10}$alkenyl, $C_{1-10}$alkynyl, phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl, naphthyl or benzyl, each of which is optionally independently substituted with 1-3 substituents of $R^{15}$, $R^{16}$ or $R^{18}$, as $R^{13}$, in conjunction with any of the above or below embodiments.

In another embodiment, the compounds of Formula I include H, $C(O)R^{18}$, $COOR^{18}$, $S(O)_2R^{18}$ or $R^{16}$, as $R^{14}$, in conjunction with any of the above or below embodiments.

In another embodiment, the compounds of Formula I include $R^{14}$ taken together with $R^{13}$ to form a partially or fully unsaturated 5- or 6-membered ring of carbon atoms optionally including 1-3 heteroatoms selected from O, N and S, and the ring optionally substituted independently with 1-3 substituents of oxo, halo, haloalkyl, $NO_2$, CN, $R^{17}$ or $R^{18}$, in conjunction with any of the above or below embodiments.

In another embodiment, the compounds of Formula I include H, halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)R^{18}$, $NR^{18}C(O)R^{16}$, $NR^{18}C(O)R^{18}$, $NR^{18}(COOR^{16})$ $NR^{18}(COOR^{18})$, $NR^{18}S(O)_2NR^{16}R^{18}$, $NR^{18}S(O)_2NR^{18}R^{18}$, $NR^{18}S(O_2R^{18}$, $NR^{18}S(O)_2R^{16}$, $NR^{18}C(O)C(O)NR^{16}R^{18}$ or $NR^{18}C(O)C(O)NR^{18}R^{18}$ as $R^{15}$, in conjunction with any of the above or below embodiments.

In another embodiment, the compounds of Formula I include a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with one or more substituents of $R^{17}$, $R^{18}$ or $R^{20}$, as $R^{16}$, in conjunction with any of the above or below embodiments.

In another embodiment, the compounds of Formula I include phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally substituted independently with 1-3 substituents of $R^{17}$, $R^{18}$ or $R^{20}$, as $R^{16}$, in conjunction with any of the above or below embodiments.

In another embodiment, the compounds of Formula I include halo, haloalkyl, oxo, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)^{20}$, $C(O)C(O)R^{18}$, $NR^{18}C(O)NR^{18}R^{18}$, $NR^{18}C(O)NR^{18}R^{20}$, $NR^{18}C(O)C(O R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$ as $R^{17}$, in conjunction with any of the above or below embodiments.

In another embodiment, the compounds of Formula I include H, $C_{1-10}$alkyl, $C_{1-10}$alkenyl, $C_{1-10}$alkynyl, $C_{3-8}$cycloalkyl, $C_{4-8}$cycloalkenyl, $R^{19}$ or $R^{20}$, each of which is optionally substituted with 1-3 substituents of $R^{21}$, as $R^{18}$, in conjunction with any of the above or below embodiments.

In another embodiment, the compounds of Formula I include H, methyl, ethyl, propyl, isopropyl, n-butyl, sec-butyl, t-butyl, pentyl, hexyl, acetyl or $C_{1-10}$-alkoxyl, each of which is optionally independently substituted with 1-3 substituents of $R^{21}$, as $R^{18}$, in conjunction with any of the above or below embodiments.

In another embodiment, the compounds of Formula I include $C(O)R^{20}$, $C(O)R^{21}$, $COOR^{20}$, $COOR^{21}$, $S(O)_2R^{20}$ or $S(O)_2R^{21}$ as $R^{19}$, in conjunction with any of the above or below embodiments.

In another embodiment, the compounds of Formula I include a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{21}$ as $R^{20}$, in conjunction with any of the above or below embodiments.

In another embodiment, the compounds of Formula I include phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally substituted independently with 1-3 substituents of $R^{21}$, as $R^{20}$, in conjunction with any of the above or below embodiments.

In another embodiment, the compounds of Formula I include H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl as each $R^{21}$, in conjunction with any of the above or below embodiments.

In yet another embodiment of the invention, compounds useful for treating angiogenesis and cancer are generally defined of Formula II:

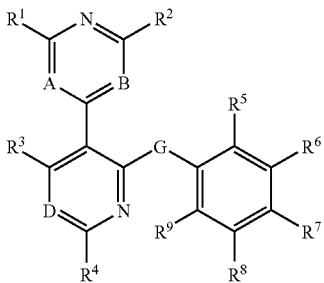

and pharmaceutically acceptable salts thereof, wherein

A is N or $CR^{10}$;

B is N or $CR^{11}$;

D is N or $CR^{12}$;

G is $NR^{13}$, O, S, C(O), S(O), $SO_2$, $CR^{13}R^{13}$ or $CR^{13}R^{14}$;

$R^1$ is H, halo, haloalkyl, $NO_2$, CN, $NR^{13}R^{13}$, $OR^{13}$, $SR^{13}$, $(CHR^{13})_n R^{13}$ or $R^{15}$; alternatively $R^1$ taken together with $R^{10}$ forms a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}$ or $NR^{13}R^{14}$;

$R^2$ is H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$; alternatively $R^2$ taken together with $R^{11}$ forms a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}$, $NR^{13}R^{14}$ or $NR^{14}R^{14}$;

each of $R^3$ and $R^4$, independently, is H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, or $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$; alternatively, either of $R^3$ or $R^4$, independently, taken together with $R^{12}$ forms a partially or fully unsaturated 5- or 6-membered ring of carbon atoms optionally including 1-3 heteroatoms selected from O, N, or S, and the ring optionally substituted independently with 1-3 substituents of $R^{13}$;

each of $R^5$ and $R^6$, independently, is H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively $R^5$ taken together with $R^6$ forms a partially or fully unsaturated 5- or 6-membered ring of carbon atoms optionally including 1-3 heteroatoms selected from O, N, or S, and the ring optionally substituted independently with 1-3 substituents of $R^{13}$;

one of $R^7$ and $R^8$ is $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$, $C_{1-10}$alkyl optionally substituted with one or more substituents of $R^{15}$ or $R^{16}$, or $C_{1-10}$alkenyl optionally substituted with one or more substituents of $R^{15}$ or $R^{16}$; and the other of $R^7$ and $R^8$ is H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl;

each of $R^9$, $R^{10}$, $R^{11}$ and $R^{12}$, independently, is H, $R^{13}$, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{16}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$ or $NR^{13}S(O)_2R^{14}$;

each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with one or more substituents of $R^{15}$, $R^{16}$ or $R^{18}$;

$R^{14}$ is $C(O)R^{18}$, $COOR^{18}$, $S(O)_2R^{18}$ or $R^{16}$;

$R^{15}$ is halo, haloalkyl, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with one or more substituents of $R^{17}$, $R^{18}$ or $R^{20}$;

$R^{17}$ is halo, haloalkyl, oxo, $NO_2$, CN, $SR^{18}$, $OR^{18}$, $OC(O)R^{18}$, $NR^{18}R^{18}$, $NR^{18}R^{18}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{19}$ or $R^{20}$, each of which is optionally substituted with 1-3 substituents of $R^{21}$;

$R^{19}$, independently, is $C(O)R^{20}$, $C(O)R^{21}$, $COOR^{20}$, $COOR^{21}$, $S(O)_2R^{20}$ or $S(O)_2R^{21}$;

$R^{20}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with one or more substituents of $R^{21}$;

each $R^{21}$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2, 3, 4 or 5, provided that (1) when A is N, then B is not N, and when B is N, then A is not N; (2) when either of $R^1$ or $R^2$ is substituted or unsubstituted NH-phenyl, then no more than four of $R^5$, $R^6$, $R^7$, $R^8$ and $R^9$ is H; and (3) when $R^1$ is phenyl, then neither of $R^6$ and $R^8$ is, independently, $NO_2$.

In another embodiment, the invention includes compounds of Formula II, wherein:

A is N;

B is $CR^{11}$;

D is $CR^{12}$;

G is $NR^{13}$, O or S;

$R^1$ is H, $NR^{13}R^{13}$, $OR^{13}$, $SR^{13}$ or $CH_2R^{13}$;

$R^2$ is H, halo, $NO_2$, CN, $C_{1-10}$alkyl or $C_{1-10}$alkoxyl;

each of $R^3$ and $R^4$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$ $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$ $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively, either of $R^3$ or $R^4$, independently, taken together with $R^{12}$ forms a partially or fully unsaturated 5- or 6-membered ring of carbon atoms optionally including 1-3 heteroatoms selected from O, N, or S, and the ring optionally substituted independently with 1-3 substituents of $R^{13}$;

each of $R^5$ and $R^6$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^3S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively $R^5$ taken together with $R^6$ forms a partially or fully unsaturated 5- or 6-membered ring of carbon atoms optionally including 1-3 heteroatoms selected from O, N, or S, and the ring optionally substituted independently with 1-3 substituents of $R^{13}$;

one of $R^7$ and $R^8$ is $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$ or $C_{1-10}$alkyl optionally substituted with one or more substituents of $R^{15}$ or $R^{16}$;

the other of $R^7$ and $R^8$ is H, halo, haloalkyl, haloalkoxyl, CN, OH, $NO_2$, $NH_2$, acetyl, $C_{1-10}$-alkyl, $C_{1-10}$-alkylamino-, $C_{1-10}$-dialkylamino-, $C_{1-10}$-alkoxyl or $C_{1-10}$-thioalkoxyl;

$R^9$ is H;

$R^{11}$ is H;

$R^{12}$ is H, halo, haloalkyl, $NO_2$, CN, acetyl, $C_{1-10}$-alkyl, $SR^{13}$, $OR^{13}$, $NR^{13}R^{13}$, $C(O)R^{13}$, $COOR^{13}$, $C(O)NR^{13}R^{13}$, $NR^{13}C(O)R^{13}$, $NR^{13}C(O)NR^{13}R^{13}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$ or $R^{16}$ optionally substituted with 1-3 substituents of $R^{17}$, $R^{18}$ or $R^{20}$;

each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with one or more substituents of $R^{15}$, $R^{16}$ or $R^{18}$;

$R^{14}$ is $C(O)R^{18}$, $COOR^{18}$, $S(O)_2R^{18}$ or $R^{16}$ $R^{15}$ is halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{18}R^{18}$, $S(O)_2NR^{18}R^{18}$, $S(O)_2R^{18}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with one or more substituents of $R^{17}$, $R^{18}$ or $R^{20}$;

$R^{17}$ is halo, haloalkyl, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{19}$ or $R^{20}$, each of which is optionally substituted with 1-3 substituents of $R^{21}$;

$R^{19}$, independently, is $C(O)R^{20}$, $C(O)R^{21}$, $COOR^{20}$, $COOR^{21}$, $S(O)_2R^{20}$ or $S(O)_2R^{21}$;

$R^{20}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with one or more substituents of $R^{21}$;

each $R^{21}$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$ alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2 or 3.

In another embodiment, the invention includes compounds of Formula II, wherein:

A is $CR^{10}$;

B is N;

D is $CR^{12}$;

G is $NR^{13}$, O or S;

$R^1$ is H, $NR^{13}R^{13}$, $OR^{13}$, $SR^{13}$ or $CH_2R^{13}$; alternatively $R^1$ taken together with $R^{10}$ forms a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}$ or $NR^{13}R^{14}$;

$R^2$ is H, halo, $NO_2$, CN, $C_{1-10}$alkyl or $C_{1-10}$alkoxyl;

each of $R^3$ and $R^4$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively, either of $R^3$ or $R^4$, independently, taken together with $R^{12}$ forms a partially or fully unsaturated 5- or 6-membered ring of carbon atoms optionally including 1-3 heteroatoms selected from O, N, or S, and the ring optionally substituted independently with 1-3 substituents of $R^{13}$;

each of $R^5$ and $R^6$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively $R^5$ taken together with $R^6$ forms a partially or fully unsaturated 5- or 6-membered ring of carbon atoms optionally including 1-3 heteroatoms selected from O, N, or S, and the ring optionally substituted independently with 1-3 substituents of $R^{13}$;

one of $R^7$ and $R^{13}$ is $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$ or $C_{1-10}$alkyl optionally substituted with one or more substituents of $R^{15}$ or $R^{16}$;

the other of $R^7$ and $R^8$ is H, halo, haloalkyl, haloalkoxyl, CN, OH, $NO_2$, $NH_2$, acetyl, $C_{1-10}$-alkyl, $C_{1-10}$-alkylamino-, $C_{1-10}$-dialkylamino-, $C_{1-10}$-alkoxyl or $C_{1-10}$-thioalkoxyl;

$R^9$ is H;

$R^{10}$ is H;

$R^{12}$ is H, halo, haloalkyl, $NO_2$, CN, acetyl, $C_{1-10}$-alkyl, $SR^{13}$, $OR^{13}$, $NR^{13}R^{13}$, $C(O)R^{13}$, $COOR^{13}$, $C(O)NR^{13}R^{13}$, $NR^{13}C(O)R^{13}$, $NR^{13}C(O)NR^{13}R^{13}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$ or $R^{16}$ optionally substituted with 1-3 substituents of $R^{17}$, $R^{18}$ or $R^{20}$;

each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with one or more substituents of $R^{15}$, $R^{16}$ or $R^{18}$;

$R^{14}$ is $C(O)R^{18}$, $COOR^{18}$, $S(O)_2R^{18}$ or $R^{16}$;

$R^{15}$ is halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)N^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with one or more substituents of $R^{17}$, $R^{18}$ or $R^{20}$;

$R^{17}$ is halo, haloalkyl, oxo, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{19}$ or $R^{20}$, each of which is optionally substituted with 1-3 substituents of $R^{21}$;

$R^{19}$, independently, is $C(O)R^{20}$, $C(O)R^{21}$, $COOR^{20}$, $COOR^{21}$, $S(O)_2R^{20}$ or $S(O)_2R^{21}$;

$R^{20}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with one or more substituents of $R^{21}$;

each $R^{21}$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2 or 3.

In another embodiment, the invention includes compounds of Formula II, wherein:

$R^7$ is $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$, $C_{1-10}$alkyl optionally substituted with one or more substituents of $R^{15}$ or $R^{16}$, or $C_{1-10}$alkenyl optionally substituted with one or more substituents of $R^{15}$ or $R^{16}$; and $R^8$ is H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl.

In another embodiment, the invention includes compounds of Formula II, wherein:

$R^7$ is H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl; and $R^8$ is $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{16}$, $NR^{13}(COOR^{13})$, $OC(O)NR^{13}R^{13}$, $NR^{13}C(O)C(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C^{13}(S)R^{13}$, $C(S)NR^{13}R^{13}$ $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$, $C_{1-10}$alkyl optionally substituted with one or more substituents of $R^{15}$ or $R^{16}$, or $C_{1-10}$alkenyl optionally substituted with one or more substituents of $R^{15}$ or $R^{16}$.

In another embodiment, the invention includes compounds of Formula II, wherein:

A is N;

B is $CR^{11}$;

D is N or $CR^{12}$;

G is $NR^{13}$, O or S;

$R^1$ is H, $NR^{13}R^{13}$, $OR^{13}$, $SR^{13}$ or $CH_2R^{13}$;

$R^2$ is H;

each of $R^3$ and $R^4$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$;

each of $R^5$ and $R^6$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively $R^5$ taken together with $R^6$ forms a partially or fully unsaturated 5- or 6-membered ring of carbon atoms optionally including 1-3 heteroatoms selected from O, N, or S, and the ring optionally substituted independently with 1-3 substituents of $R^{13}$;

one of $R^7$ and $R^8$ is $NR^{13}R^{13}$, $C(O)R^{13}$, $COOR^{13}$, $C(O)NR^{13}R^{13}$, $NR^{13}C(O)R^{13}$, $NR^{13}(COOR^{13})$, $NR^{13}C(O)NR^{13}R^{13}$, $C(S)NR^{13}R^{13}$, $NR^{13}C(S)R^{13}$, $NR^{13}C(S)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$ or $C_{1-10}$alkyl optionally substituted with one or more substituents of $NR^{18}R^{18}$, $C(O)R^{18}$, $COOR^{18}$, $C(O)NR^{18}R^{18}$, $NR^{13}C(O)R^{18}$, $NR^{18}(COOR^{18})$, $NR^{18}C(O)NR^{18}R^{18}$, $C(S)NR^{18}R^{18}$, $NR^{18}C(S)R^{18}$, $NR^{18}C(S)NR^{18}R^{18}$, $S(O)_2R^{18}$, $S(O)_2NR^{18}R^{18}$, $NR^{18}S(O)_2NR^{18}R^{18}$, $NR^{18}S(O)_2R^{18}$;

the other of $R^7$ and $R^8$ is H, halo, haloalkyl, haloalkoxyl, CN, OH, $NO_2$, $NH_2$, acetyl, $C_{1-10}$-alkyl, $C_{1-10}$-alkylamino-, $C_{1-10}$-dialkylamino-, $C_{1-10}$-alkoxyl or $C_{1-10}$-thioalkoxyl;

$R^9$ is H;

$R^{11}$ is H;

$R^{12}$ is H, halo, haloalkyl, oxo, $NO_2$, CN, or $C_{1-10}$alkyl, $C_{1-10}$alkenyl, $C_{1-10}$alkynyl, cyclopropyl, cyclobutyl, cyclopentyl, cyclohexyl, tetrahydrofuranyl, tetrahydropyrrolyl, pyranyl, phenyl, naphthyl, benzyl, furanyl, pyrrolyl, thiophenyl, indolyl, imidazolyl, pyrazolyl, oxazolyl, benzimidazolyl, benzopyrazolyl, benzoxazolyl, benzothiozolyl, piperidinyl, piperazinyl, morpholinyl, each of which is optionally independently substituted with 1-3 substituents of $R^{13}$;

each $R^{13}$, independently, is H, $C_{1-10}$alkyl, $C_{1-10}$alkenyl, $C_{1-10}$alkynyl, phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl, naphthyl or benzyl, each of which is optionally independently substituted with 1-5 substituents of $R^{15}$, $R^{16}$ or $R^{18}$;

$R^{15}$ is halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl; purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally substituted independently with 1-3 substituents of $R^{17}$, $R^{18}$ or $R^{20}$;

$R^{17}$ is halo, haloalkyl, oxo, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, methyl, ethyl, propyl, isopropyl, n-butyl, sec-butyl, t-butyl, pentyl, hexyl, acetyl or $C_{1-10}$-alkoxyl, each of which is optionally independently substituted with 1-3 substituents of $R^{21}$;

$R^{20}$ is phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally substituted independently with 1-3 substituents of $R^{21}$;

each $R^{21}$, independently, is H, Cl, Br, F, I, $CF_3$, $CF_2CF_3$, $NO_2$, CN; acetyl, oxo, haloalkyl, haloalkoxyl, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2 or 3.

The embodiments for various of the elements described herein above with respect to compounds of Formula I also apply to compounds of Formula II, where appropriate, as will be appreciated by those skilled in the art.

In another embodiment, the invention includes compounds of Formula III, wherein:

and pharmaceutically acceptable salts thereof, wherein

D is N or $CR^{12}$;

G is O, S, C(O), S(O), $SO_2$ or $(CHR^{13})_m$;

$R^1$ is H, halo, haloalkyl, $NO_2$, CN, $NR^{13}R^{13}$, $OR^{13}$, $SR^{13}$, or $(CHR^{13})_n R^{13}$;

$R^2$ is H, halo, haloalkyl, oxo, $NO_2$, CN, $SR^{13}$, $OR^{13}$, $NR^{13}R^{13}$, $NR^{13}R^{14}$, $C(O)R^{13}R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with one or more substituents of $R^{13}$;

each of $R^3$ and $R^4$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively, either of $R^3$ or $R^4$, independently, taken together with $R^{12}$ forms a partially or fully unsaturated 5- or 6-membered ring of carbon atoms optionally including 1-3 heteroatoms selected from O, N, or S, and the ring optionally substituted independently with 1-3 substituents of $R^{13}$;

each of $R^5$ and $R^6$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C(O)NR^{13}R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with one or more substituents of $R^{13}$; alternatively $R^5$ taken together with $R^6$ forms a partially or fully unsaturated 5- or 6-membered ring of carbon atoms optionally including 1-3 heteroatoms selected from O, N, or S, and the ring optionally substituted independently with 1-3 substituents of $R^{13}$;

one of $R^7$ and $R^8$ is $SR^{13}$, $OR^{13}$, $NR^{13}R^{13}$, $C(O)R^{13}$, $COOR^{13}$, $C(O)NR^{13}R^{13}$, $NR^{13}C(O)R^{13}$, $NR^{13}(COOR^{13})$, $NR^{13}C(O)NR^{13}R^{13}$, $C(S)NR^{13}R^{13}$, $NR^{13}C(S)R^{13}$, $NR^{13}C(S)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$ or $C_{1-10}$alkyl optionally substituted with one or more substituents of $SR^{13}$, $OR^{13}$, $NR^{18}R^{18}$, $C(O)R^{18}$, $COOR^{18}$, $C(O)NR^{18}R^{18}$, $NR^{13}C(O)R^{18}$, $NR^{18}(COOR^{18})$, $NR^{18}C(O)NR^{18}R^{18}$, $C(S)NR^{18}R^{18}$, $NR^{18}C(S)R^{18}$, $NR^{18}C(S)NR^{18}R^{18}$, $S(O)_2R^{18}$, $S(O)_2NR^{18}R^{18}$, $NR^{18}S(O)_2NR^{18}R^{18}$, $NR^{18}S(O)_2R^{18}$;

the other of $R^7$ and $R^8$ is H, halo, haloalkyl, haloalkoxyl, CN, OH, $NO_2$, $NH_2$, acetyl, $C_{1-10}$-alkyl, $C_{1-10}$-alkylamino-, $C_{1-10}$-dialkylamino-, $C_{1-10}$-alkoxyl or $C_{1-10}$-thioalkoxyl;

each of $R^9$ and $R^{12}$, independently, is H, $R^{13}$, halo, haloalkyl, $NO_2$, CN, $SR^{13}$, $OR^{13}$, $NR^{13}R^{13}$ or $C(O)R^{13}$;

each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with 1-5 substituents of $R^{15}$, $R^{16}$ or $R^{17}$;

$R^{14}$ is $C(O)R^{18}$, $COOR^{18}$, $S(O)_2R^{18}$ or $R^{16}$; alternatively $R^{14}$ taken together with $R^{13}$ forms a partially or fully unsaturated 5- or 6-membered ring of carbon atoms optionally including 1-3 heteroatoms selected from O, N and S, and the ring optionally substituted independently with 1-3 substituents of oxo, halo, haloalkyl, $NO_2$, CN, $R^{17}$ or $R^{18}$;

$R^{15}$ is halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally substituted independently with 1-3 substituents of $R^{17}$, $R^{18}$ or $R^{20}$;

$R^{17}$ is halo, haloalkyl, oxo, $NO_2$, CN, $SR^{18}$, $OR^{18}$, $OC(O)R^{18}$, $NR^{18}R^{18}$, $NR^{18}R^{18}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, methyl, ethyl, propyl, isopropyl, n-butyl, sec-butyl, t-butyl, pentyl, hexyl, acetyl or $C_{1-10}$-alkoxyl, each of which is optionally independently substituted with 1-3 substituents of $R^{21}$;

$R^{20}$ is phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally substituted independently with 1-3 substituents of $R^{21}$;

each $R^{21}$, independently, is H, Cl, Br, F, I, $CF_3$, $CF_2CF_3$, $NO_2$, CN; acetyl, oxo, haloalkyl, haloalkoxyl, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and n is 0, 1, 2 or 3, provided that (1) when either of $R^1$ or $R^2$ is substituted or unsubstituted NH-phenyl, then no more than four of $R^5$, $R^6$, $R^7$, $R^8$ and $R^9$ is H; and (4) when $R^1$ is Phenyl, then neither of $R^6$ and $R^8$ is, independently, $NO_2$.

The embodiments for various of the elements described herein above with respect to compounds of Formula I also apply to compounds of Formula III, where appropriate, as will be appreciated by those skilled in the art.

In yet another embodiment, Formulas I, II and III include the exemplary compounds and derivatives, progrugs, solvates, tautomers and pharmaceutically acceptable salt forms thereof, intermediates related thereto, which are described in the Examples herein.

Definitions

The following definitions should further assist in understanding the invention and its scope as described herein.

The terms "agonist" and "agonistic" when used herein refer to or describe a molecule which is capable of, directly or indirectly, substantially inducing, promoting or enhancing biological activity of a biological molecule, such as an enzyme or receptor, including Tie-2 and Lck.

"Angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity, direction and/or flow properties to improve blood perfusion of tissue.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels of Tie-2, and similar kinases, in the mammal.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "mammal" as used herein refers to any mammal classified as a mammal, including humans, cows, horses, dogs and cats. In one embodiment of the invention, the mammal is a human.

A "pharmaceutically-acceptable derivative" denotes any salt (also referred to as "pharmaceutically-acceptable salt"), ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to quantify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The terms "ring" and "ring system" refer to a one or more rings, typically fused together where more than one ring, comprising the delineated number of atoms, said atoms being carbon or, where indicated, a heteroatom such as nitrogen, oxygen or sulfur. The ring itself, as well as any substituents thereon, may be attached at any atom that allows a stable compound to be formed. The term "nonaromatic" ring or ring system refers to the fact that at least one, but not necessarily all, rings in a bicyclic or tricyclic ring system is nonaromatic.

"Leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals preferably having alpha to beta number of carbon atoms. For example a $C_1$-$C_{10}$ alkyl is an alkyl comprising 1 to 10 carbon atoms. Examples of such radicals include methyl, ethyl, n-propyl, isopropyl, n-butyl, isobutyl, sec-butyl, tert-butyl, pentyl, isoamyl, hexyl and the like. It is contemplated herein that alkyl radicals may be optionally substituted with various substituents, where indicated. The term "alkylenyl" embraces bridging divalent alkyl radicals such as methylenyl and ethylenyl.

The term "alkenyl", alone or in combination, embraces linear or branched radicals having at least one carbon-carbon double bond of two or more carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art. It is contemplated herein that alkenyl radicals may be optionally substituted with various substituents, where indicated.

The term "alkynyl", alone or in combination, denotes linear or branched radicals having at least one carbon-carbon triple bond and having two or more carbon atoms. Examples of alkynyl radicals include "lower alkynyl" radicals having two to about six carbon atoms and, for example, lower alkynyl radicals having two to about four carbon atoms. Examples of such radicals include, without limitation, ehtynyl, propynyl (propargyl), butynyl, and the like. It is contemplated herein that alkynyl radicals may be optionally substituted with various substituents, where indicated.

The term "halo", alone or in combination, means halogens such as fluorine, chlorine, bromine or iodine atoms.

The term "haloalkyl", alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms and, for example, lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "hydroxyalkyl", alone or in combination, embraces linear or branched alkyl radicals having one or more carbon atoms any one of which may be substituted with one or more hydroxyl radicals. The term hydroxyalkyl radicals include "lower hydroxyalkyl" radicals having one to six carbon atoms and one to three hydroxyl radicals. Examples of such radicals include hydroxymethyl, hydroxyethyl, hydroxypropyl, hydroxybutyl and hydroxyhexyl.

The term "alkoxy", alone or in combination, embraces linear or branched oxy-containing radicals each having alkyl portions of alpha to beta number of carbon atoms. For example, a $C_{1-10}$alkoxy radical indicates an alkoxide having one to ten carbon atoms, arranged in a linear or branched fashion, attached to an oxygen atom. The term alkoxy radicals include "lower alkoxy" radicals having one to six carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "partially or fully saturated" as used herein, refers to a moiety, linear, branched or cyclic in nature, having no atom-atom double or triple bonds, and one or more atom-atom double or triple bonds, arranged such that wherein the structure is cyclic, the ring structure is not aromatic, as appreciated by those skilled in the art.

The term "fully unsaturated" as used herein, refers to a moiety having double or triple bonds, arranged in a manner such that the structure is aromatic, as appreciated by those skilled in the art.

The term "aryl", alone or in combination, means a carbocyclic aromatic moiety containing one, two or even three rings wherein such rings may be attached together in a fused manner. Thus the term "aryl" embraces aromatic radicals such as phenyl, naphthyl, indenyl, tetrahydronaphthyl, anthracenyl, and indanyl. Said "aryl" group may have 1 to 3 substituents such as lower alkyl, hydroxyl, halo, haloalkyl, nitro, cyano, alkoxy and lower alkylamino, and the like. Phenyl substituted with —O—CH$_2$—O— forms an aryl benzodioxolyl substituent. Aryl as used herein, implies a fully unsaturated ring.

The term "heterocycles" or "heterocyclic radicals", alone or in combination, embraces saturated, partially saturated and unsaturated heteroatom-containing ring radicals, where the heteroatoms may be selected from nitrogen, sulfur and oxygen. This term does not include rings containing —O—O—, —O—S— or —S—S— portions. Said "heterocycle" may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also referred to herein as "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals. Further examples of heteroaryl radicals include quinolyl, isoquinolyl, imidazolyl, pyridyl, thienyl, thiazolyl, oxazolyl, furyl, and pyrazinyl. Other examples of heteroaryl radicals are 5- or 6-membered heteroaryl, containing one or two heteroatoms selected from sulfur, nitrogen and oxygen, such as thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl radicals.

Examples of non-nitrogen containing heteroaryl include, without limitation, pyranyl, 2-furyl, 3-furyl, 2-thienyl, 3-thienyl, benzofuryl, benzothienyl, and the like.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The term "aralkyl" embraces aryl-substituted alkyl radicals. Examples of aralkyl radicals include "lower aralkyl" radicals having aryl radicals attached to alkyl radicals having one to six carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. An example of "alkylthio" is methylthio, (CH$_3$S—).

The term "aminoalkyl" and "diaminoalkyl" embraces "N-alkylamino" and "N,N-dialkylamino", respectively, where amino groups are independently substituted with one alkyl radical and with two alkyl radicals, respectively. Examples of alkylamino radicals include "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like.

The term "C$_{1-10}$alkyl-amino-" denotes amino groups, which have been substituted with one or two alkyl radicals, such as N-methylamino. The alkylamino radicals may be further substituted on the alkyl portion of the radical.

The term "aryl-alkyl-amino-" or "aralkylamino" denotes amino groups, which have been substituted with one or two aryl-substituted-alkyl radicals, such as benzyl-amino. The aralkyl-amino radicals may be further substituted on the aryl or alkyl portion of the radical.

The term "heterocyclyl-alkyl-amino-" denotes amino groups, which have been substituted with one or two heterocyclyl-substituted-alkyl radicals, such as piperidyl-methyl-amino. The heterocyclyl-alkyl-amino radicals may be further substituted on the heterocycle or alkyl portion of the radical.

The term "heteroaryl-alkyl-amino-" or "heteroaralkylamino" denotes amino groups, which have been substituted with one or two heteroaryl-substituted-alkyl radicals, such as pyrimidyl-amino. The heteroaralkyl-amino radicals may be further substituted on the heteroaryl or alkyl portion of the radical.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "cycloalkyl" includes saturated carbocyclic groups. Examples of cycloalkyl groups include $C_3$-$C_6$ rings, such as compounds including, cyclopentyl, cyclopropyl, and cyclohexyl.

The term "cycloalkenyl" includes carbocyclic groups having one or more carbon-carbon double bonds including "cycloalkyldienyl" compounds. Examples of cycloalkenyl groups include $C_3$-$C_6$ rings, such as compounds including, without limitation, cyclopentenyl, cyclopentadienyl, cyclohexenyl and cycloheptadienyl.

The term "comprising" is meant to be open ended, including the indicated component(s) but not excluding other elements.

The terms "Formula I", "Formula II" and "Formula III" include any sub formulas.

The present invention comprises processes for the preparation of a compound of Formulae I and II.

Also included in the family of compounds of Formulas I-III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-III may be prepared from an inorganic acid or from an organic acid. Examples of such inorganic acids are hydrochloric, hydrobromic, hydroiodic, nitric, carbonic, sulfuric and phosphoric acid. Suitable exemplary organic acids include, without limitation, aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formulas I-III include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formulas I-III. When a basic group and an acid group are present in the same molecule, a compound of Formulas I-III may also form internal salts.

General Synthetic Procedures

The compounds of the invention can be synthesized according to the following procedures of Schemes 1-13, wherein the substituents are as defined for Formulas I-III, above, except where further noted. The synthetic methods described below are merely exemplary, and the compounds of the invention may be synthesized by alternate routes as appreciated by persons of ordinary skill in the art.

The following list of abbreviations used throughout the specification represent the following:

| | |
|---|---|
| BSA | bovine serum albumin |
| $Cs_2CO_3$ | cesium carbonate |
| $CHCl_3$ | chloroform |
| $CH_2Cl_2$, DCM | dichloromethane, methylene chloride |
| DIBAL | diisobutylaluminum hydride |
| DIEA, $(iPr_2NEt)$ | diisopropylethylamine |
| DME | dimethoxyethane |
| DMF | dimethylformamide |
| DMAP | 4-dimethylaminopyridine |
| DMSO | dimethylsulfoxide |
| dppa | diphenylphosphoryl azide |
| EDC | 1-(3-dimethylaminopropyl)-3-ethylcarbodiimide hydrochloride |
| $Et_2O$ | diethyl ether |
| EtOAc | ethyl acetate |
| FBS | fetal bovine serum |
| G, gm | gram |
| h, hr | hour |
| HBr | hydrobromic acid |
| HCl | hydrochloric acid |
| HOBt | 1-hydroxybenzotriazole hydrate |
| $H_2$ | hydrogen |
| $H_2O_2$ | hydrogen peroxide |
| HATU | O-(7-azabenzotriazol-1-yl)-N,N,N',N'-tetramethyluroniumhexafluorophosphate |
| HPLC | high pressure liquid chromatography |
| IPA, IpOH | isopropyl alcohol |
| $K_2CO_3$ | potassium carbonate |
| MCPBA | meta-chloroperbenzoic acid |
| $MgSO_4$ | magnesium sulfate |
| MeOH | methanol |
| $N_2$ | nitrogen |
| $NaHCO_3$ | sodium bicarbonate |
| NaOH | sodium hydroxide |
| NaH | sodium hydride |
| $Na_2SO_4$ | sodium sulfate |
| $NH_4Cl$ | ammonium chloride |
| $NH_4OH$ | ammonium chloride |
| NMP | N-methylpyrrolidinone |
| $ID(t-bu)_3$ | tri(tert-butyl)phosphine |
| PBS | phospate buffered saline |
| Pd/C | palladium on carbon |
| $Pd(PPh_3)_4$ | palladium(0)triphenylphosphine tetrakis |
| $Pd(PhCN)_2Cl_2$ | palladium di-cyanophenyl dichloride |
| $Pd(OAc)_2$ | palladium acetate |
| 5 $Pd_2(dba)_3$ | bis(dibenzylideneacetone) palladium |
| PyBop | benzotriazol-1-yl-oxy-tripyrrolidino-phosphonium hexafluorophosphate |
| RT | room temperature |
| rac-BINAP | 2,2'-Bis(diphenylphosphine)-1,1'-binaphthyl |
| TBTU | 0-benzotriazol-1-yl-N,N,N',N'-tetramethyluronium tetrafluoroborate |
| TEA, $Et_3N$ | triethylamine |
| TFA | trifluoroacetic acid |
| THF | tetrahydrofuran |

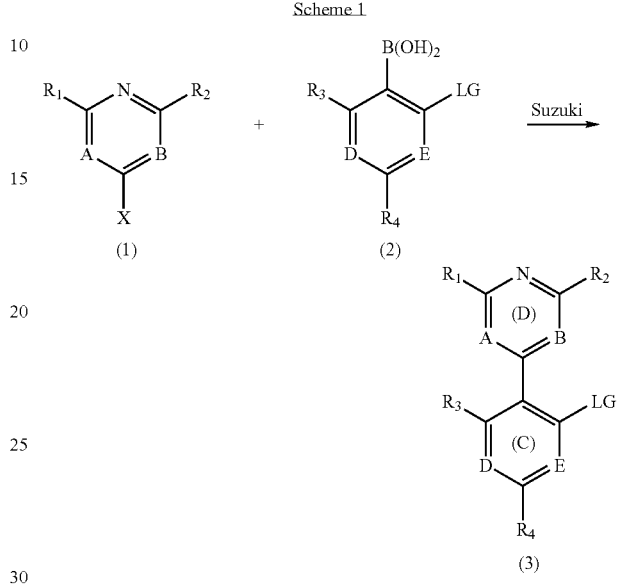

Scheme 1

The biaryl ring system (3), including substituted or unsubstituted pyridyl-pyridines, pyridyl-pyrimidines and pyridyl triazines (all where $D=C^{12}$ and $E=N$) and generally referred to herein as the C-D ring portion of the compounds of Formulas I-III, can be prepared according to the method generally described in Scheme 1. As shown, Suzuki coupling methodology utilizing an aryl halide (1) where X is a halide such as iodide, bromide or chloride, and an aryl borinate (2) in the presence of palladium, such as $Pd(PPh_3)_4$, and a weak base, such as a $Na_2CO_3$, $K_2CO_3$ or $NaHCO_3$ in a polar solvent such as DME can be used to synthesize compound (3). LG is a leaving group, such as F or Cl. Similarly, other known aryl coupling methods, such as use of stannanes, zincates and copper coupling techniques are also suitable to prepare compound (3).

In a similar manner, phenyl-pyridines, phenyl-pyrimidines and phenyl-triazine C-D rings (all where both D and $E=N$) of the compounds of Formulas I-III, can also be prepared according to the Suzuki or other metallation chemistry methods, wherein the aryl borinate (2) is a desirably substituted phenyl borinate, as described in Scheme 1.

Alternatively, amino-substituted pyridyl pyrimidines C-D ring systems (8) can be prepared according to the method shown in scheme 2.

Scheme 2

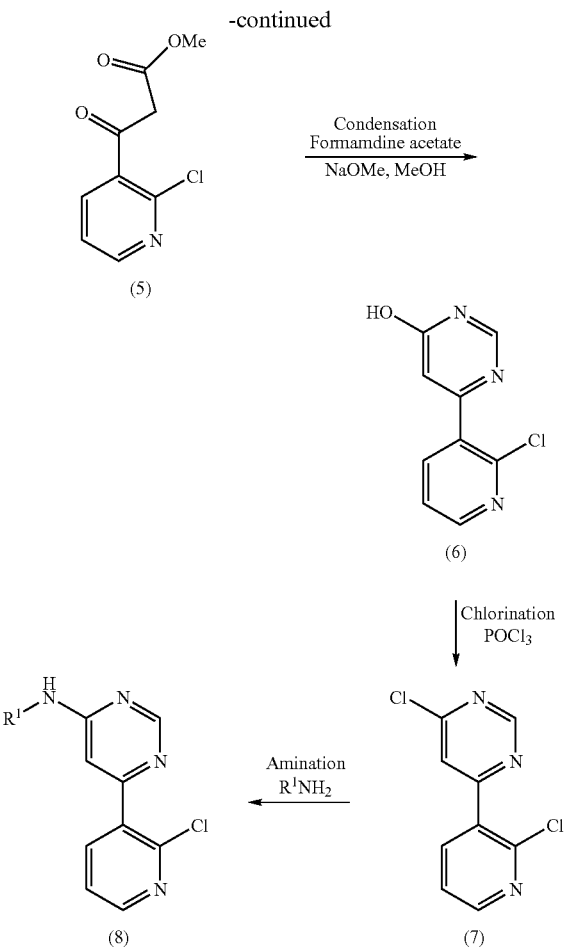

Chloro-nicotinic acid chlorides (4) can be treated with dimethylmalonate in the presence of a suitable base and MgCl to form intermediate (5). Compound (5) can be cyclized to form the hydroxyl-substituted pyrimidyl-pyridine compound (6), in the presence of suitable base and formamidine acetate. Desirable amino-$R^1$ groups can be installed at the 3 position of the 4,6-pyrimidine D-ring by simply treating compound (7) with a primary or secondary amine, having the desired substitution, with heat under conditions milder than those required to displace the pyridyl chloride of compound (6). Further, compound (6) can be treated with p-toluene sulfonyl chloride, or other similar activating reagents to render the pyrimidine hydroxyl group into a suitable leaving group (LG) for displacement with a desired, sufficiently reactive nucleophile, including amines, sulfur, and oxygen nucleophiles. Also, compound (6) may be treated with a base sufficiently strong to deprotonate the hydroxyl proton in order to alkylate the hydroxyl group, thereby forming an ether, alkoxy moiety, and the like. Further, compound (6) can be converted to the corresponding thiol utilizing reactions and techniques known in the art. This thiol (not shown0 may then be converted to corresponding thio-linked $R^1$ groups. In addition, compound (7) can be treated with ammonia to give the amino adduct, which then can be alkylated, acylated, or otherwise substituted with a desired group. Such methods are known to those skilled in the art, and are described in Jerry March's Advanced Organic Chemistry, $4^{th}$ edition (1992), which disclosure is hereby incorporated by reference in its entirety.

The 2,4-regioisomer of the above pyridyl-pyrimidines can also be made using the following Scheme 3.

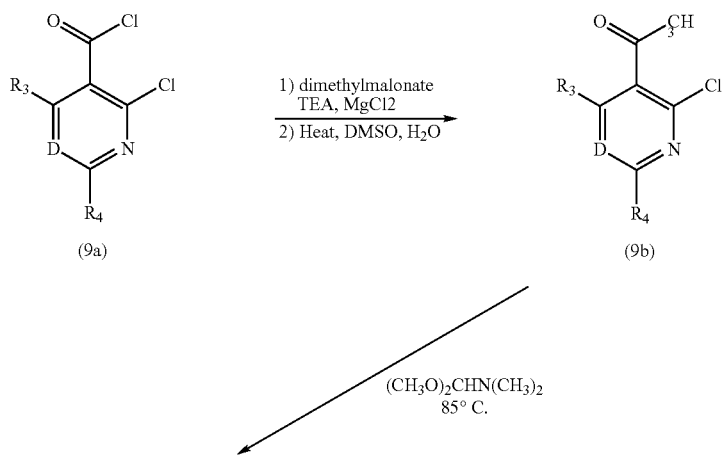

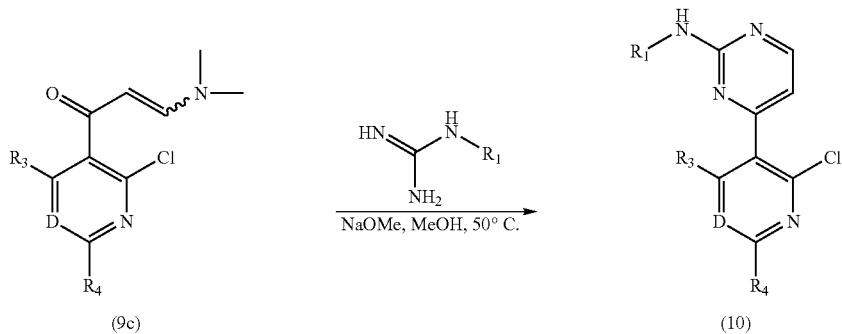

(9c)      HN=C(NH₂)NHR₁, NaOMe, MeOH, 50° C.      (10)

Compound (10) can be made by treating the acid chloride of compound (9a) (ring C) and converting it to the corresponding methyl ketone (9b) followed by treatment with dimethyl formamide dimethylacetal to obtain the corresponding enaminone (9c). Then substituted guanidine.HCl can be treated with a suitable base, such as sodium methoxide, for a time period prior to exposing the guanidine mixture to the enaminone (9c) to form the pyridyl pyrimidine (10). This method allows desired $R^1$ groups to be installed prior to ring closure. Care must be taken to restrict the $R^1$ groups in this method to those, which would not interfere with or react during formation of intermediates 9a-9c and also ring closure to form compound (10), as appreciated by persons of ordinary skill in the art.

Alternatively, compound (9c) can be treated with guanidine.HCl in the presence of NaOH in isopropanol to afford the corresponding 3-amino-pyrimidine D ring (not shown, where $R^1$ is $NH^2$). The $R^1$ position of this intermediated can be modified using reductive alkylation methods with corresponding aldehydes, acylation methods, and other groups, by methods appreciated by persons of ordinary skill in the art, to install the desired groups at this position on the D ring of compounds of Formulas I and II. Alternatively, the 3-aminopyrimidine may be converted to 3-fluoropyrimidine with use of t-butyl nitrate and HF-pyridine, and the fluoride then displaced with a desired $R^1$ group such as $NH_2R$, OR and SR. This latter technique may also be used to convert aminotriazines to the corresponding fluoro-triazines.

Similarly, pyridyl-triazines C-D biaryl ring systems can be made using the method of scheme 4.

Scheme 4

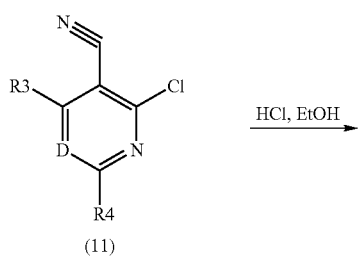

(11)

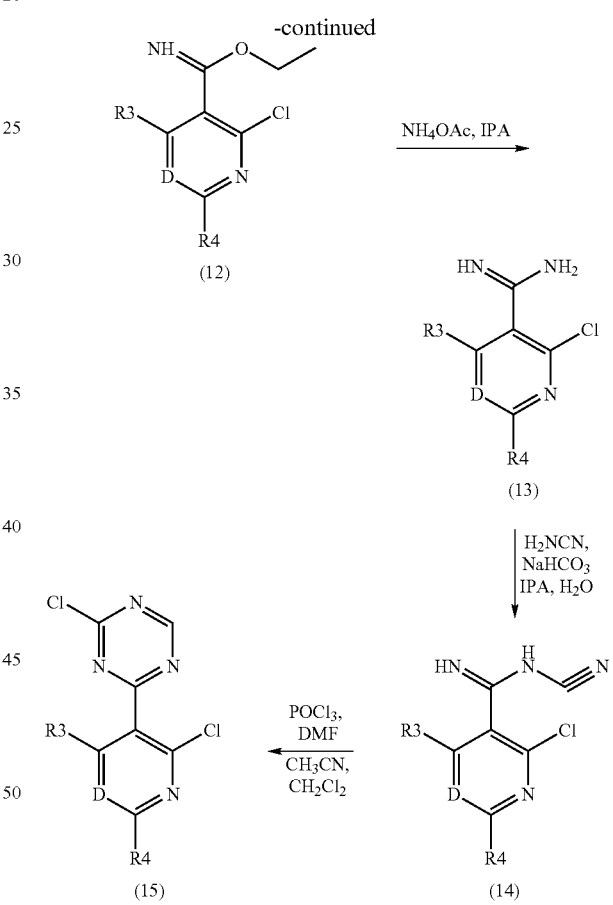

In a manner similar to the method illustrated and described in Scheme 2, desirable amino-$R^1$ groups can be installed at the 3 position of a triazine D ring by treating compound (15) with a primary or secondary amine, having the desired substitution, with heat under conditions less strenuous than required to displace the pyridyl chloride of compound (15).

The C-D ring portion of the compounds of Formulas I-III can be attached to the B ring of compound (17—see scheme 5 below) by a number of conventional methods known in the art, as disclosed in March. Suitable methods are illustrated in schemes 5 and 6 below.

Scheme 5

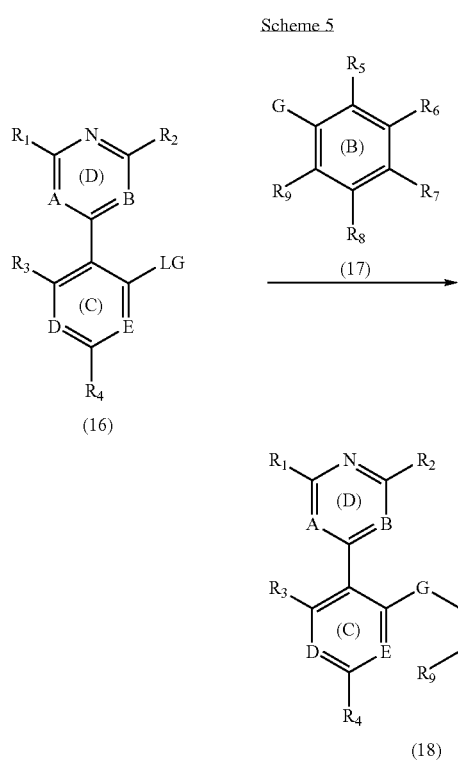

As shown in Scheme 5, compound (18) comprising biaryl ethers and thiols (where G=O and S, respectively) can be prepared by reacting compound (16) (where LG is a leaving group, such as a halide) with a nucleophilic phenyl compound (17) wherein G is a suitable nucleophile, such as NHR or NH$_2$ (Scheme 6), OH, SH or carbon nucleophile, sufficient to displace the chloride from ring C of compound (16). For example, phenols (G=O) and thiols (G=S) can be coupled with activated aryl chlorides to form the biaryl ethers and thiols (compound 18) using weak bases such as TEA, or inorganic bases such as Cs$_2$CO$_3$, in DMSO at elevated temperatures, such as ranging form about 70° C. to about 130° C. Similarly, this transformation can also be carried out in NMP at about 200° C. in a microwave.

Scheme 6

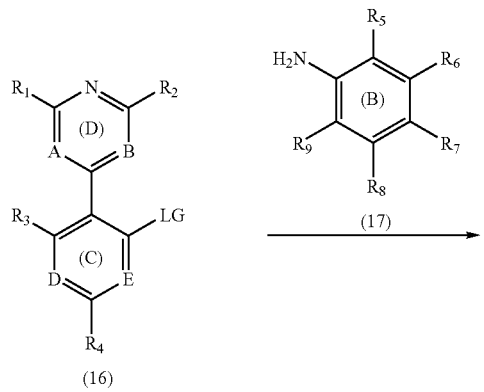

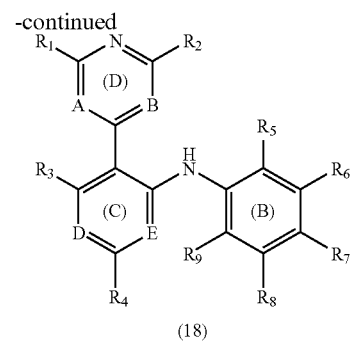

Anilines (compound 17) can be coupled with activated aryl chlorides (compound 16) to form biaryl anilines (compound 18) using Pd catalysis or NEt$_3$.TFA under suitable conditions, which may or may not require the input of heat.

Alternatively, and with reference to Scheme 2, where certain R$^1$ and/or R$^2$ groups hinder or limit the ability to couple ring C to ring B via the nucleophilic displacement method described above, the B-C ring coupling can be effected from intermediate compound (6) in Scheme 2 as follows in Scheme 7.

Scheme 7

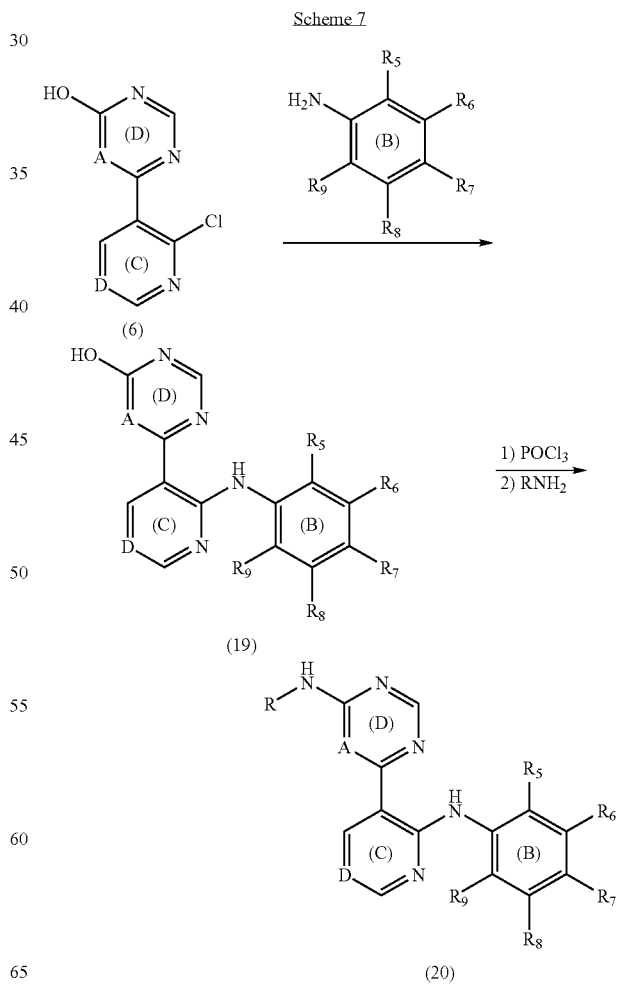

As shown, compound (6) can first be reacted with the desired B ring nucleophilic species prior to converting the pyrimidyl hydroxyl group to the corresponding chloride for subsequent displacement with an amine, or other desired $R^1$ group.

Compounds of the invention (Formulas I-III) wherein D is $CR^{12}$ can be prepared by the general method shown in scheme 8.

(24), Pd(0) mediated-coupling with an aryl boronate in the presence of mild base, such as sodium or potassium carbonate or bicarbonate, in toluene affords compound (25), an aryl pyridyl pyrimidine. Compound (25) can also be prepared using corresponding stannanes or zincates, as known in the art. Alternatively, desired $R^{12}$ groups may be installed onto the C-ring via the iodide, using conventional methods (not shown), as appreciated by those skilled in the art.

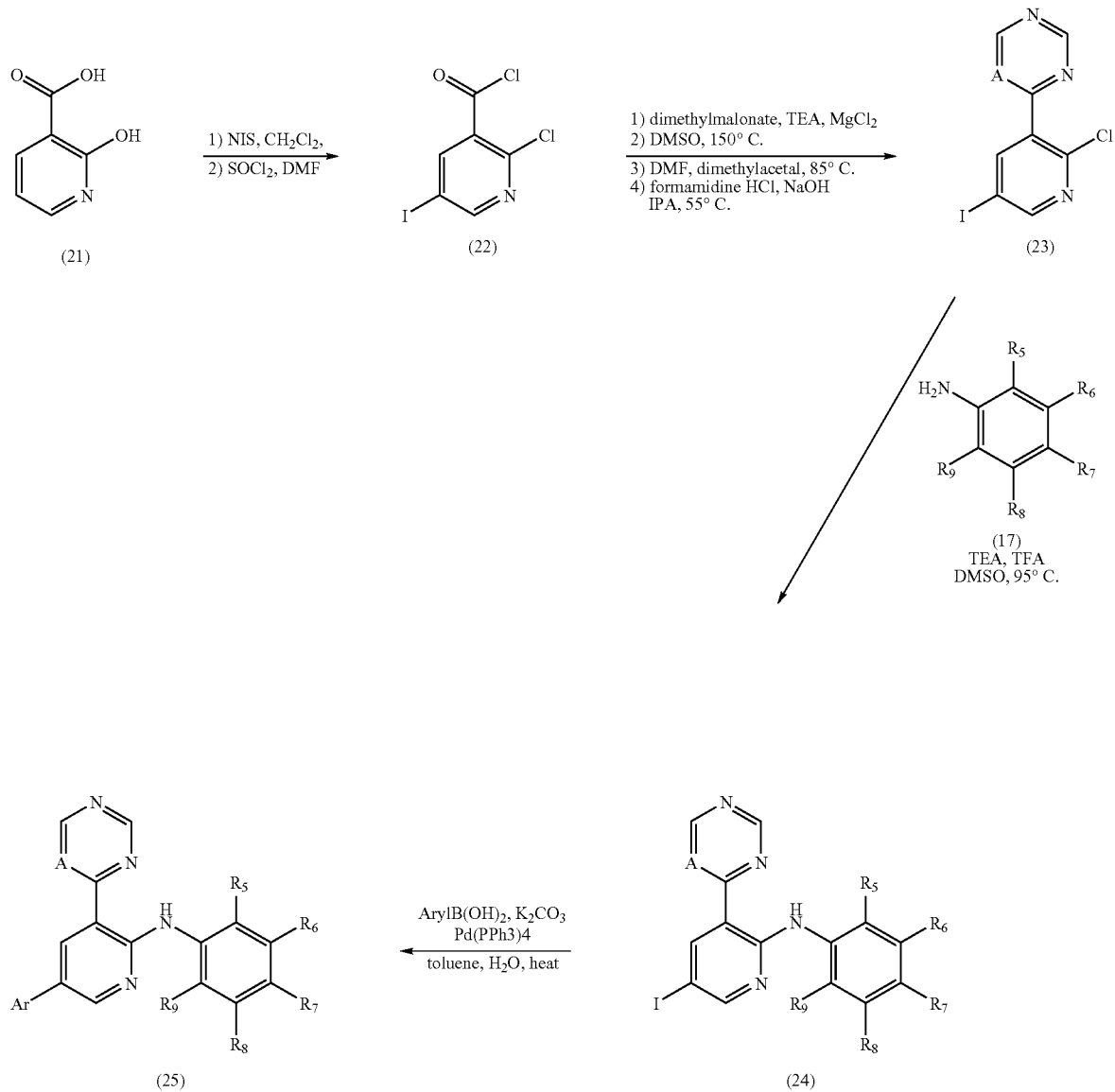

As shown, commercially available 2-hydroxynicotinic acid can be iodinated and subjected to thionyl chloride according to the procedure disclosed in Elworthy et al., J. Med. Chem, 40(17):2674-2687 (1997), which disclosure is incorporated herein by reference in its entirety. Conversion of the iodinated intermediate (compound 22) to the corresponding pyrimidine (compound 23) proceeds as described above in Scheme 2. After displacement of the pyridyl chloride (compound 23) with an aniline (compound 17) to form compound Alternatively, the desired aryl group can be installed on ring C (compound 20) even before building the D-C ring piece of compounds of Formulas I-III. For example, Church et al. describes the synthesis of 5-aryl-2-chloropyridines from phenylacetic acids in J. Org. Chem., 60:3750-3758 (1995), which disclosure is incorporated herein by reference in its entirety. The general method described in Church is shown in Scheme 9 below.

Scheme 9

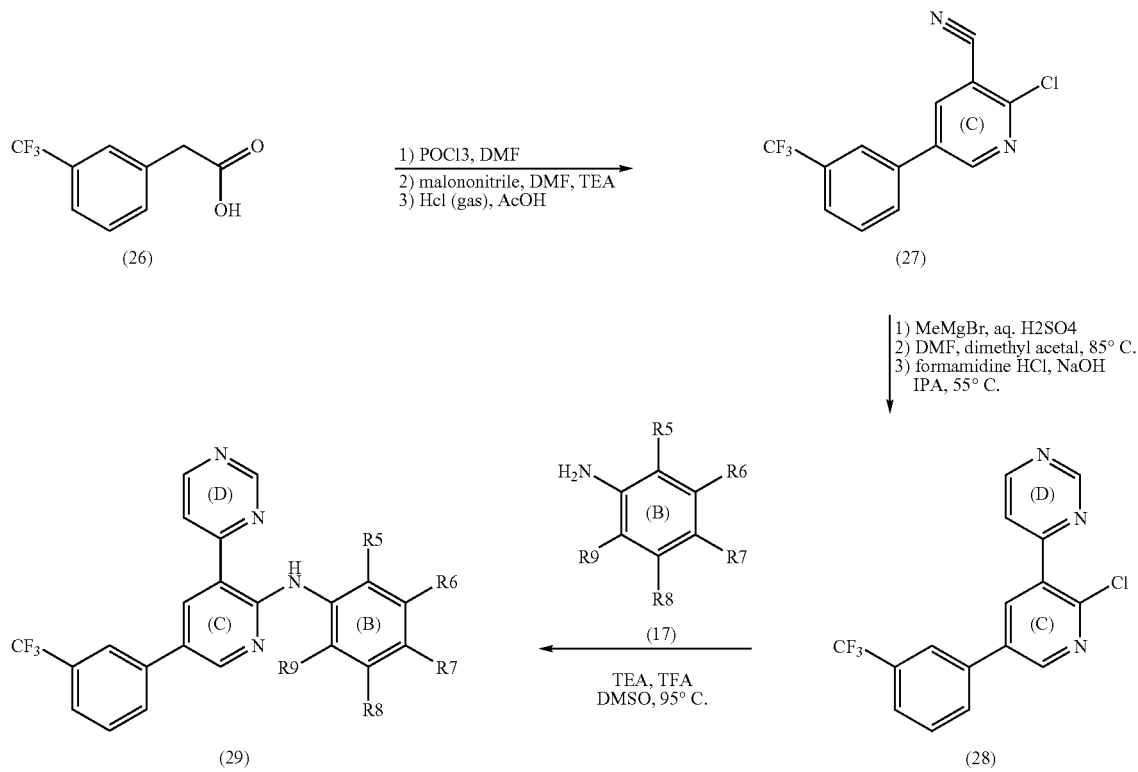

After formation of the methyl ketone intermediate (not shown) by grignard addition to compound (27), elaboration to the pyrimidine and addition of aniline to the chloropyridine may proceed as described before. The method of Scheme 9 can also be used to provide desirable $R^1$ and $R^2$ groups at the 3 or 5-positions, respectively, of a pyrimidine D ring.

The final moieties of the compounds of the invention, generally defined in Formulas I-III, can be attached to the ring B of intermediate compounds (18), (20), (25) and (29) described above, and intermediates (30) and (32) illustrated below, by the general methods described in schemes 10-13 below.

-continued

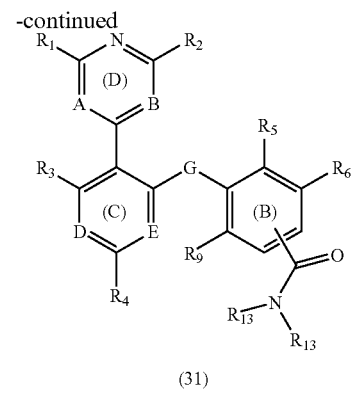

(31)

Scheme 10

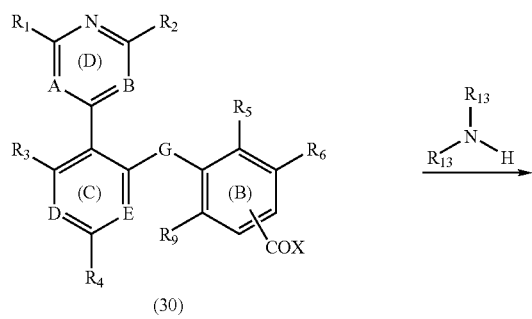

As shown, amides can be prepared according to the method illustrated in Scheme 10. Substituted primary and secondary amines can be coupled with a free acid of ring B using a suitable coupling reagent, such as EDC, TBTU, HBTU, HOBT, DCC, HATU and others known in the art, via the corresponding acid-chloride or other acid halide. The acid-halide in compound (30) is designated as C(O)—X, where X is a suitable halide such as a chloride or fluoride. An acid chloride can be formed by reacting the free acid with oxalyl chloride, $POCl_3$ or similar reagent in a suitable solvent. Te amide bond may also be effected using other known, conventional acid activated leaving groups. Such reactions generally proceed well in an inert, non-nucleophilic solvent(s), such as DMF, DMSO, $CH_2CL_2$ and the like, at ambient temperatures. Poor solubility of the coupling reagent and/or the intermediates may generally require use of polar solvents. In some cases, depending upon the particular substrate or intermediates (30) and/or the amine starting material, heat may be necessary to effect the transformation and/or a higher yield. While Scheme 10 illustrates compound (31) having the amide corresponding to $R^7$ or $R^8$, the invention is not so limited and such method is applicable to ring B having a free acid at any of positions $R^5$, $R^6$, $R^7$, $R^8$ or $R^9$, respectively. Further, while Scheme 10 illustrates an $NHR^{13}R^{13}$ substituted amine, other amine substitutions are contemplated herein, such as $NHR^{13}R^{14}$ substituted amines are also suitable.

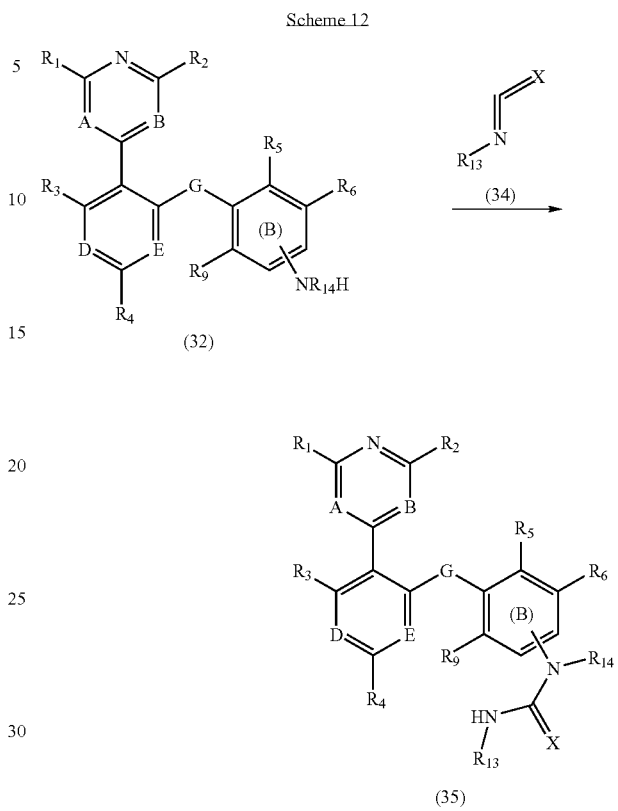

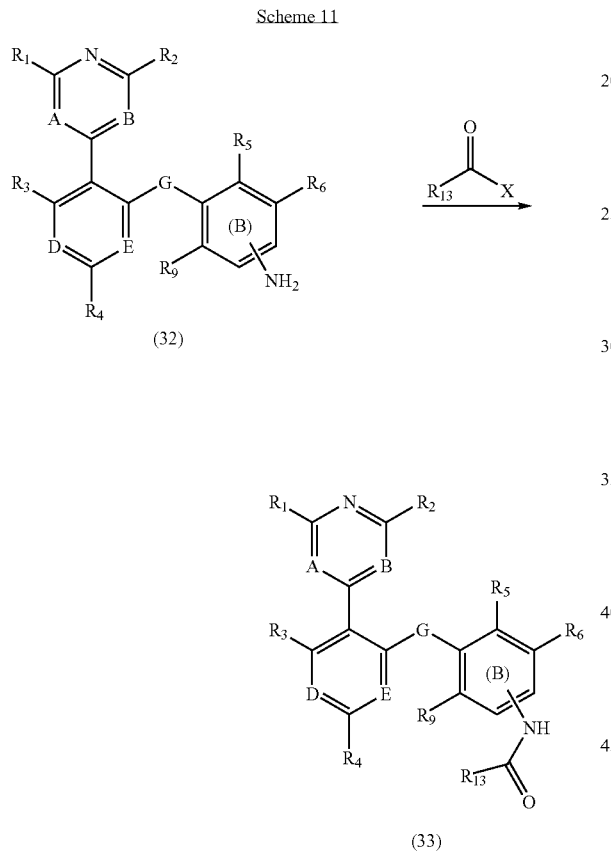

As shown, ureas and thioureas (compound 34 wherein X=O and S, respectively) can be prepared according to the method illustrated in Scheme 12. The desired isocyanates and isothiocyanates are coupled with the amine (32) to form the desired ureas or thioureas (35).

The coupling reaction generally proceeds in an inert, non-nucleophilic, anhydrous solvent, such as DMF, $CHCL_3$ $CH_2Cl_2$, toluene and the like, at mild conditions, such as at room temperature. Further, the amine of compound (32) may be present in any of the R group positions corresponding to those in Formulas I-III for ring B, and not just corresponding to $R^7$ and $R^8$ as shown. Also, the method is not limited to $R^{13}$, but also encompasses groups covered under $R^{14}$, $R^{15}$, and $R^{16}$, as described above.

As shown, reverse amides can be prepared according to the method illustrated in Scheme 11. Substituted free carboxylic acids may be coupled with the amine of compound (32) utilizing common coupling reagents and methods, such as those described in Scheme 10, to form the corresponding amide. Heat may be used where necessary. As in Scheme 10, Scheme 11 is not limited to compounds wherein the amide corresponds to positions $R^7$ or $R^8$ in Formulas I-III. Such method is also applicable to ring B having a free amine at any of positions $R^5$, $R^6$, $R^7$, $R^8$ or $R^9$, respectively, and to the carboxylic acid having groups other than $R^{13}$, such as $R^{14}$, $R^{15}$ and $R^{16}$ substituted acids, are also suitable.

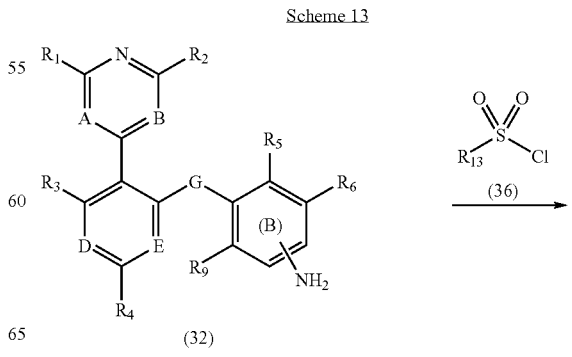

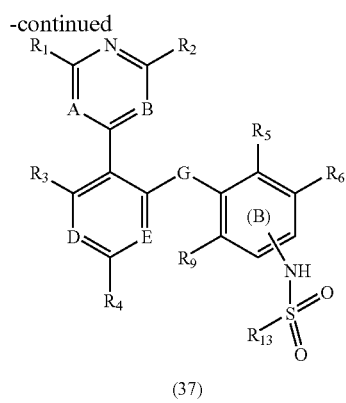

(37)

As shown, sulfonamides (37) can be prepared according to the method illustrated in Scheme 13. Anilines (32) are coupled with substituted sulfonyl chlorides (36) in the presence of a weak base, such as a tertiary amine or pyridine, in inert, non-nucleophilic, anhydrous solvents, such as DMF, $CHCl_3$ $CH_2Cl_2$, toluene and the like, at mild conditions, such as at room temperature, to form the desired sulfonamide (37). In some cases, depending upon the particular intermediates (32) and/or (36), their concentration in the solvent medium and independent reactivity, heat may be necessary to effect the transformation and/or a higher yield.

In addition, the methods described in schemes 10-13 are also applicable to pyridyl B rings (not shown). The specific examples described herein further illustrate amide, urea, carbamate, carbonate, and the like couplings between desired A rings and desired B rings, or desired B-C or B-C-D ring moieties.

Further, as described in schemes 10-12, the substitutions of compounds (36) and (37) are not limited to $R^{13}$ as shown, and encompass other groups as well, such as $R^{14}$, $R^{15}$, $R^{16}$, and $R^{18}$ groups. The various $R^{13}$ substitutions in Schemes 10-13 and $R^{14}$, $R^{15}$, $R^{16}$ and $R^{18}$ group substitutions in compounds of Formulas I-III can be prepared by the general synthetic organic methods described in March Advanced Organic Chemistry and by methods published in the chemical literature, as appreciated by those of ordinary skill in the art. Further, the synthesis of various $R^{13}$, $R^{14}$, $R^{15}$, $R^{16}$ and $R^{18}$ group substitutions are described in the synthesis of the following exemplary compounds of Formulas I-III.

To enhance the understanding of the invention described herein, the following examples are set forth. It should be appreciated that these examples are merely for illustrative purposes only and are not to be construed as limiting the scope of this invention in any manner.

Analytical Methods:

Unless otherwise indicated, all HPLC analyses were run on a Agilent Model 1100 system with an Agilent Technologies Zorbax SB-$C_8$(5µ) reverse phase column (4.6×150 mm; Part no. 883975-906) run at 30° C. with a flow rate of about 1.50 mL/min. The mobile phase used solvent A ($H_2O$/0.1% TFA) and solvent B (AcCN/0.1% TFA) with a 11 min gradient from 5% to 100% AcCN. The gradient was followed by a 2 min return to 5% AcCN and about a 2.5 minute re-equilibration (flush).

LC-MS Method:

Samples were run on a Agilent model-1100 LC-MSD system with an Agilent Technologies XDB-$C_8$ (3.5µ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (AcCN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation with a 20×50 mm column at 20 mL/min. The mobile phase used a mixture of solvent A ($H_2O$/0.1% TFA) and solvent B (AcCN/0.1% TFA) with a 10 min gradient from 5% to 100% solvent B. The gradient is followed by a 2 min return to 5% AcCN.

Proton NMR Spectra:

Unless otherwise indicated, all $^1H$ NMR spectra were run on a Varian series Mercury 300 MHz or on a Bruker 400 MHz instrument. Where so characterized, all observed protons are reported as parts-per-million (ppm) downfield from tetramethylsilane (TMS) or other internal reference in the appropriate solvent indicated.

The following examples represent exemplary methods of synthesizing or preparing desired structural moieties or pieces of the compounds of Formulas I-III, including exemplary A rings, B rings, A-B rings, C-D rings, B-C-D rings and fragments thereof. It should be appreciated that these methods are merely representative examples and other conventional, known or developed alternative methods may also be utilized. These structural moieties will assist in understanding how the many complete compound examples of Formulas I-III described herein below were made.

EXAMPLE 1

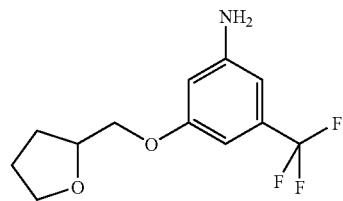

Synthesis of 3-(Tetrahydro-furan-2-ylmethoxy)-5-trifluoromethyl-phenylamine

The title compound was synthesized according to a procedure described in U.S. Pat. Appl. Pub. 2003203922 A1.

EXAMPLE 2

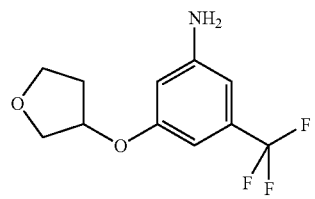

Synthesis of 3-(Tetrahydro-furan-3-yloxy)-5-trifluoromethyl-phenylamine

The title compound was synthesized according to a procedure described in U.S. Pat. Appl. Pub. 2003203922 A1.

EXAMPLE 3

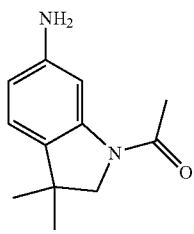

Synthesis of 1-(6-Amino-3,3-dimethyl-2,3-dihydro-indol-1-yl)-ethanone

The title compound was synthesized according to a procedure described in PCT Pat. Appl. WO 2002066470 A1.

EXAMPLE 4

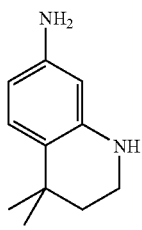

Synthesis of 4,4-Dimethyl-1,2,3,4-tetrahydro-quinolin-7-ylamine

The title compound was synthesized according to a procedure described in U.S. Pat. Appl. 2003134836 A1.

EXAMPLE 5

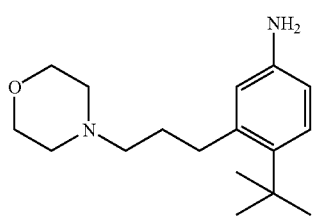

Synthesis of 4-tert-Butyl-3-(3-morpholin-4-yl-propyl)-phenylamine

The title compound was synthesized according to a procedure described in PCT Pat. Appl. WO 2002066470 A1.

EXAMPLE 6

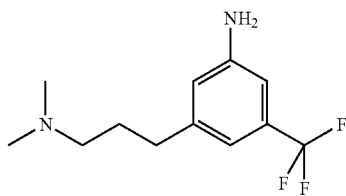

Synthesis of 3-(3-Dimethylamino-propyl)-5-trifluoromethyl-phenylamine

The title compound was synthesized according to a procedure described in PCT Pat. Appl. WO 2002055501 A2.

EXAMPLE 7

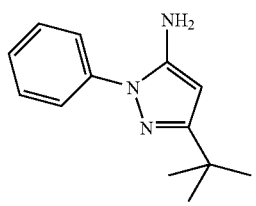

Synthesis of 5-tert-Butyl-2-phenyl-2H-pyrazol-3-ylamine

The title compound was prepared by a procedure described in J. Regan et. al., *J. Med. Chem.* 2002, 45, 2994-3008.

EXAMPLE 8

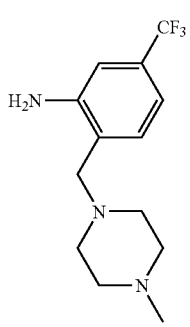

Synthesis of 2-(4-methyl-piperazin-1-ylmethyl)-5-trifluoromethyl-phenylamine

Step 1. Preparation of 1-methyl-4-(2-nitro-4-trifluoromethyl-benzyl)-piperazine

To 1-chloromethyl-2-nitro-4-trifluoromethyl-benzene (1.5 g, 6.2 mmol), N-methylpiperazine (0.83 mL, 7.5 mmol), and THF (31 mL) was added NaHCO$_3$ (1.43 g, 17.1 mmol). The mixture was heated overnight at 75° C. in a sealed tube. The cooled reaction was filtered, concentrated, diluted with CH$_2$Cl$_2$, and extracted with water and brine. The organic layer was dried over Na$_2$SO$_4$, filtered and concentrated to yield 1-methyl-4-(2-nitro-4-trifluoromethyl-benzyl)-piperazine.

Step 2. Preparation of 2-(4-methyl-piperazin-1-ylmethyl)-5-trifluoromethyl-phenylamine To 1-methyl-4-(2-nitro-4-trifluoromethyl-benzyl)-piperazine (543 mg, 1.8 mmol) in MeOH (18 mL) was added 10% Pd/C (95 mg, 0.09 mmol). The mixture was stirred under an atmosphere of hydrogen at RT for 2 h. The resulting mixture was filtered through a pad of Celite and concentrated to yield 2-(4-methyl-piperazin-1-ylmethyl)-5-trifluoromethyl-phenylamine. MS m/z=274 [M+1]$^+$. Calc'd for C$_{13}$H$_{18}$F$_3$N$_3$: 273.30.

The following Examples 9-13 were synthesized in a manner an analogous to that described in Example 8:

EXAMPLE 9

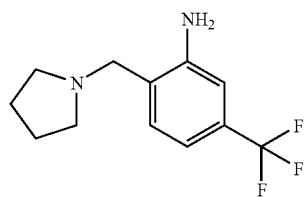

2-(pyrrolidin-1-ylmethyl)-5-(trifluoromethyl)benzenamine

MS m/z=245 [M+1]$^+$. Calc'd for C$_{12}$H$_{15}$F$_3$N$_2$: 244.26.

EXAMPLE 10

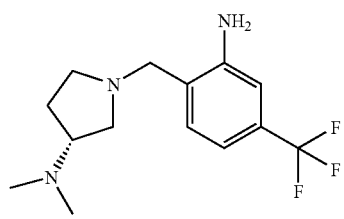

(R)-1-(2-amino-4-(trifluoromethyl)benzyl)-N,N-dimethylpyrrolidin-3-amine

MS m/z=288 [M+1]$^+$. Calc'd for C$_{14}$H$_{20}$F$_3$N$_3$: 287.33.

EXAMPLE 11

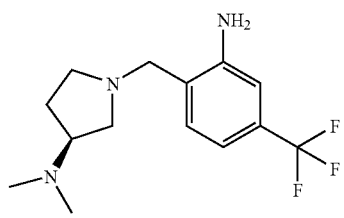

(S)-1-(2-amino-4-(trifluoromethyl)benzyl)-N,N-dimethylpyrrolidin-3-amine

MS m/z=288 [M+1]$^+$. Calc'd for C$_{14}$H$_{20}$F$_3$N$_3$: 287.33.

EXAMPLE 12

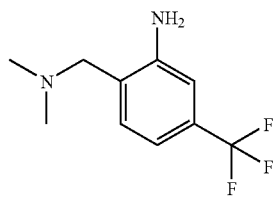

2-((dimethylamino)methyl)-5-(trifluoromethyl)benzenamine

MS m/z=219 [M+1]$^+$. Calc'd for C$_{10}$H$_{13}$F$_3$N$_2$: 218.22.

EXAMPLE 13

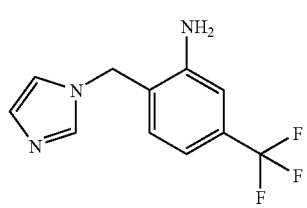

2-((1H-imidazol-1-yl)methyl)-5-(trifluoromethyl) benzenamine

MS m/z=242 [M+1]$^+$. Calc'd for $C_{10}H_{13}F_3N_3$: 241.22.

EXAMPLE 14

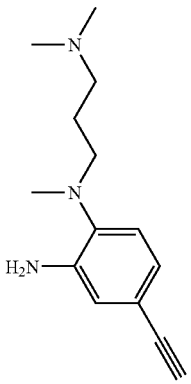

Synthesis of $N^1$-(3-dimethylamino-propyl)-4-ethynyl-$N^1$-methyl-benzene-1,2-diamine Step 1. Preparation of N-(4-ethynyl-2-nitro-phenyl)-N,N', N'-trimethyl-propane-1,3-diamine To N-(4-bromo-2-nitro-phenyl)-N,N',N'-trimethyl-propane-1,3-diamine (940 mg, 2.97 mmol), Pd(PhCN)$_2$Cl$_2$ (34 mg, 0.09 mmol), CuI (11 mg, 0.06 mmol) and dioxane (4 mL) was added P(tBu)$_3$.HBF$_4$ (53 mg, 0.18 mmol), iPr$_2$NH (0.50 mL, 3.6 mmol) and (trimethylsilyl)acetylene (0.49 mL, 3.6 mmol). The mixture was stirred for 3.5 h at RT, diluted with MeOH and stirred at RT with excess saturated aqueous K$_2$CO$_3$ for 2 h. The mixture was filtered through a pad of activated charcoal and concentrated to yield N-(4-ethynyl-2-nitro-phenyl)-N,N',N'-trimethyl-propane-1,3-diamine. MS m/z=262 [M+1]$^+$. Calc'd for $C_{14}H_{19}N_3O_2$: 261.33.

Step 2. Preparation of $N^1$-(3-dimethylamino-propyl)-4-ethynyl-$N^1$-methyl-benzene-1,2-diamine To N-(4-ethynyl-2-nitro-phenyl)-N,N',N'-trimethyl-propane-1,3-diamine (730 mg, 2.79 mmol), EtOH (40 mL) and THF (13 mL) was added concentrated HCl (1.0 mL) and iron metal (10.6 g, 191 mmol). A reflux condenser was attached and the mixture was heated overnight at 90° C. The cooled mixture was filtered through a pad of Celite, concentrated and purified by flash chromatography (90:10:1 CH$_2$Cl$_2$/MeOH/NH$_4$OH) to yield $N^1$-(3-dimethylamino-propyl)-4-ethynyl-$N^1$-methyl-benzene-1,2-diamine. MS m/z=232 [M+1]$^+$. Calc'd for $C_{14}H_{21}N_3$: 231.34.

EXAMPLE 15

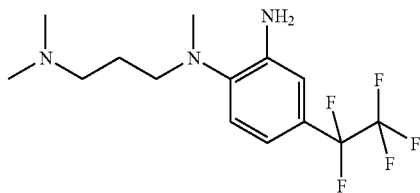

Synthesis of $N^1$-(3-Dimethylamino-propyl)-$N^1$-methyl-4-pentafluoroethylbenzene-1,2-diamine Step 1. Preparation of N-(4-Bromo-2-nitro-phenyl)-N,N',N'-trimethyl-propane-1,3-diamine To a round bottom flask at 0° C. was added 4-Bromo-1-fluoro-2-nitrobenzene (10 g, 45.46 mmol) and N,N, N'-Trimethyl-propane-1,3-diamine (6.99 mL, 47.7 mmol). The reaction was allowed to warm to RT and stirred for 16 h. The reaction was extracted into EtOAc, washed once with saturated aqueous NaHCO$_3$, twice with water, and then dried over Mg$_2$SO$_4$. The organic layer was filtered and concentrated to yield the title compound as a bright orange solid. MS (M+H)$^+$= 316, 318; Calc'd 316.19 for $C_{12}H_{18}BrN_3O_2$.

Step 2. Preparation of N,N, N'-Trimethyl-N'-(2-nitro-4-pentafluoroethyl-phenyl)-propane-1,3-diamine To a pressure vessel was added N-(4-Bromo-2-nitro-phenyl)-N, N',N'-trimethyl-propane-1,3-diamine (Step 1, 5.0 g, 15.8 mmol), copper powder (10.0 g, 158 mmol), and 20 mL DMSO. Pentafluoroethyl iodide (7.8 g, 31.6 mmol) was bubbled in and the vessel sealed. The mixture was then heated to 120° C. and vigorously stirred for 22 h. The reaction was cooled to 0° C. and filtered through a Buchner funnel, rinsing with EtOAc. The filtrate was then washed once with saturated aqueous NaHCO$_3$, twice with water, once with brine, and then dried over Mg$_2$SO$_4$. The crude mixture was then purified by silica gel chromatography using a 10% MeOH/CH$_2$Cl$_2$ gradient to yield the title compound as a brown oil. MS (M+H)$^+$=356; Calc'd 355.30 for $C_{14}H_{18}F_5N_3O_2$.

Step 3. Preparation of $N^1$-(3-Dimethylamino-propyl)-$N^1$-methyl-4-pentafluoroethylbenzene-1,2-diamine N,N, N'-Trimethyl-N'-(2-nitro-4-pentafluoroethyl-phenyl)-propane-1,3-diamine (Step 2, 800 mg, 2.25 mmol) was dissolved in 15 mL MeOH. Palladium (120 mg, 0.307 mmol, 10% w/w on carbon) was added, a balloon containing hydrogen was inserted, and the reaction was stirred at RT for 18 h. The solution was then filtered through a pad of Celite and concentrated, yielding viscous brown oil. The crude mixture was purified using reverse phase chromatography to give the title compound as reddish-brown oil. MS (M+H)$^+$=326; Calc'd 325.32 for $C_{14}H_{20}F_5N_3$.

EXAMPLE 16

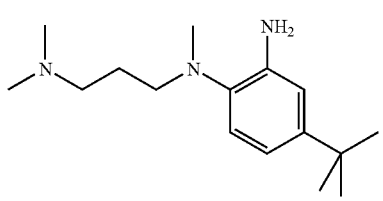

Synthesis of 4-tert-Butyl-N$^1$-(3-dimethylamino-propyl)-N$^1$-methyl-benzene-1,2-diamine Step 1. Preparation of N-(4-tert-Butyl-phenyl)-N,N', N'-trimethyl-propane-1,3-diamine To a sealed tube was added Pd(OAc)$_2$ (105 mg 0.469 mmol), NaO$^t$Bu (1.35 g, 14.07 mmol), 1-Bromo-4-tert-butylbenzene (2.0 g, 9.38 mmol), N,N,N'-Trimethyl-propane-1,3-diamine (1.65 mL, 11.26 mmol), P($^t$BuNCH$_2$CH$_2$)$_3$N (133 µL, 0.375 mmol), and 5 mL toluene. The solution was heated to 80° C. for 1 h, cooled to RT, filtered through a pad of silica gel (rinsing with 10% MeOH/CH$_2$Cl$_2$), and concentrated in vacuo to yield the title compound (2.0 g, 86%) as a dark brown oil. MS (M+H)$^+$=249; Calc'd 248.41 for C$_{16}$H$_{28}$N$_2$.

Step 2. Preparation of N-(4-tert-Butyl-2-nitro-phenyl)-N,N',N'-trimethyl-propane-1,3-diamine Nitronium-tetrafluoroborate (2.14 g, 16.10 mmol) was dissolved in 40 mL aceonitrile, cooled to 0° C. and stirred for 15 min. A solution of N-(4-tert-Butyl-phenyl)-N,N',N'-trimethyl-propane-1,3-diamine (Step 1, 2.0 g, 8.05 mmol) in 40 mL acetonitrile was added drop-wise over 10 min. The solution was stirred for 30 min at 0° C., warmed to RT, and stirred an additional 16 h. The reaction was extracted into EtOAc, washed twice with water, once with brine, dried over Mg$_2$SO$_4$, filtered, and concentrated in vacuo to yield a crude mixture that was purified by silica gel chromatography using a 10% MeOH/CH$_2$Cl$_2$ gradient to give the title compound as a brown oil. The correct regioisomer was determined to be the only product by H-NMR analysis. MS (M+H)$^+$=294; Calc'd 293.40 for C$_{16}$H$_{27}$N$_3$O$_2$.

Step 3. Preparation of 4-tert-Butyl-N$^1$-(3-dimethylamino-propyl)-N$^1$-methyl-benzene-1,2-diamine N-(4-tert-Butyl-2-nitro-phenyl)-N,N',N'-trimethyl-propane-1,3-diamine (Step 2, 200 mg, 0.682 mmol) was dissolved in 7 mL MeOH. Palladium (66 mg, 0.062 mmol, 10% w/w on carbon) was added, a balloon containing hydrogen was inserted, and the reaction was stirred at RT for 18 h. The solution was then filtered through a pad of Celite and concentrated, yielding the title compound as a dark brown solid. MS (M+H)$^+$=264; Calc'd 263.42 for C$_{16}$H$_{29}$N$_3$.

EXAMPLE 17

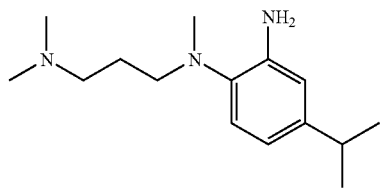

N1-(3-(dimethylamino)propyl)-4-isopropyl-N1-methylbenzene-1,2-diamine

Example 17 was synthesized in a manner analogous to the method described in Example 16. MS (M+H)$^+$=250; Calc'd 249.40 for C$_{15}$H$_{27}$N$_3$.

EXAMPLE 18

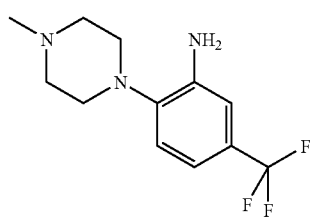

Synthesis of 2-(4-Methyl-piperazin-1-yl)-5-trifluoromethyl-phenylamine

Step 1. Preparation of 1-Methyl-4-(2-nitro-4-trifluoromethyl-phenyl)-piperazine

Example 18 was prepared in accordance to a procedure described in Collins, et. al., *Tetrahedron*, 48, No. 37, pp 7887-7898, 1992. To a solution of 1-Fluoro-2-nitro-4-trifluoromethyl-benzene (1.0 g, 4.78 mmol) in dry THF (24 mL) was added 1-Methyl-piperazine (0.64 mL, 5.74 mmol). The solution turned bright yellow. NaHCO$_3$ (1.1 g, 13 mmol) was added and the reaction was stirred at room temperature and monitored by LCMS: The reaction was filtered and concentrated before being taken up in CH$_2$Cl$_2$ and H$_2$O. The organic layer was separated, dried with MgSO$_4$, filtered, and concentrated to afford the title compound as an orange-brown oil.

Step 2. Preparation of 2-(4-Methyl-piperazin-1-yl)-5-trifluoromethyl-phenylamine To 1-Methyl-4-(2-nitro-4-trifluoromethyl-phenyl)-piperazine (1.46 g, 5.05 mmol) in dry MeOH (50 mL) was added Pd/C (10%, 535 mg). H$_2$ gas was bubbled through the solution at room temperature overnight with vigorous stirring. The reaction mixture was filtered through celite to provide, after concentration, the desired product as a white solid. MS (M+H)$^+$=260; Calc'd 259.28 for C$_{12}$H$_{16}$F$_3$N$_3$.

The following Examples 19-24 were synthesized in a manner analogous to that described in Example 18.

EXAMPLE 19

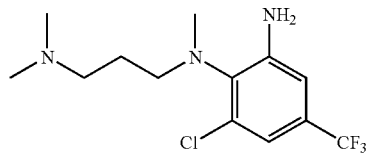

6-chloro-N$^1$-(3-(dimethylamino)propyl)-N$^1$-methyl-4-(trifluoromethyl)benzene-1,2-diamine MS m/z=310 [M+H]$^+$. Calc'd for $C_{13}H_{19}ClF_3N_3$: 309.8.

EXAMPLE 20

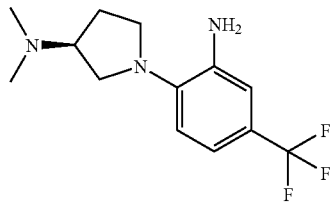

(S)-1-(2-amino-4-(trifluoromethyl)phenyl)-N,N-dimethylpyrrolidin-3-amine

MS m/z=274 [M+H]$^+$. Calc'd for $C_{13}H_{18}F_3N_3$: 273.30.

EXAMPLE 21

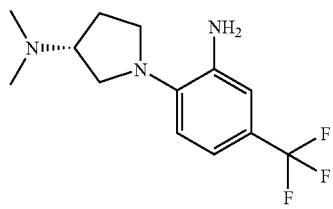

(R)-1-(2-amino-4-(trifluoromethyl)phenyl)-N,N-dimethylpyrrolidin-3-amine

MS m/z=274 [M+H]$^+$. Calc'd for $C_{13}H_{18}F_3N_3$: 273.30.

EXAMPLE 22

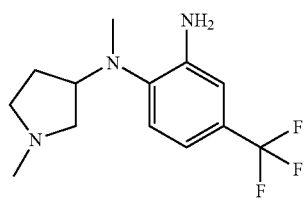

N1-methyl-N1-(1-methylpyrrolidin-3-yl)-4-(trifluoromethyl)benzene-1,2-diamine

MS m/z=274 [M+H]$^+$. Calc'd for $C_{13}H_{18}F_3N_3$: 273.30.

EXAMPLE 23

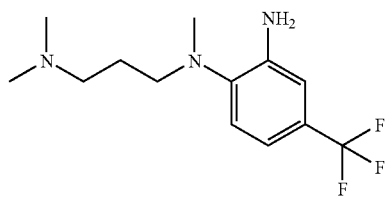

N1-(3-(dimethylamino)propyl)-N1-methyl-4-(trifluoromethyl)benzene-1,2-diamine

MS m/z=276 [M+H]$^+$. Calc'd for $C_{13}H_{20}F_3N_3$: 275.32.

EXAMPLE 24

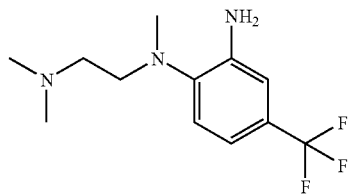

N1-(2-(dimethylamino)ethyl)-N1-methyl-4-(trifluoromethyl)benzene-1,2-diamine

MS m/z=262 [M+H]$^+$. Calc'd for $C_{12}H_{18}F_3N_3$: 261.29.

EXAMPLE 25

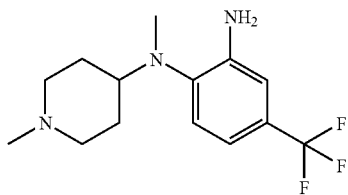

N1-methyl-N1-(1-methylpiperidin-4-yl)-4-(trifluoromethyl)benzene-1,2-diamine

MS m/z=288 [M+H]$^+$. Calc'd for $C_{14}H_{20}F_3N_3$: 287.33.

EXAMPLE 26

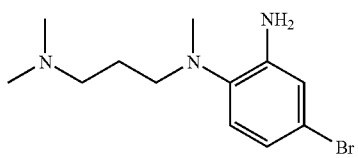

Synthesis of 4-bromo-N1-(3-(dimethylamino)propyl)-N1-methylbenzene-1,2-diamine

To N-(4-Bromo-2-nitro-phenyl)-N,N',N'-trimethyl-propane-1,3-diamine (Example 619, Step 1) (0.54 g, 1.7 mmol) in 20 ml EtOH was added SnCl$_2$ (0.51 g, 2.67 mmol). The mixture was sealed and was heated to 80° C. for 12 h. An additional amount of SnCl$_2$ (0.51 g, 2.67 mmol) was added and heating continued for 12 h. The reaction was cooled to ambient temperature, and was poured into a mixture of EtOAc and saturated aqueous sodium bicarbonate. The mixture was filtered through celite, and the organic layer was removed. The aqueous layer was extracted twice with EtOAc, and the combined organic layers were dried with Na$_2$SO$_4$, filtered, and concentrated to give a cloudy oil. This material was filtered through silica gel with 90/10/1 dichloromethane/MeOH/conc. NH$_4$OH and concentrated in vacuo to give the title compound as a red oil. MS (ES+): 285.9 (M+H)$^+$. Calc'd for $C_{12}H_{20}BrN_3$: 286.21.

EXAMPLE 27

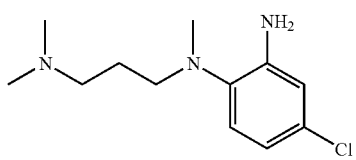

4-chloro-N1-(3-(dimethylamino)propyl)-N1-methylbenzene-1,2-diamine

Example 27 was synthesized in a manner analogous to that described in Example 26. MS m/z=242 [M+H]$^+$. Calc'd for $C_{12}H_{20}ClN_3$: 241.77.

EXAMPLE 28

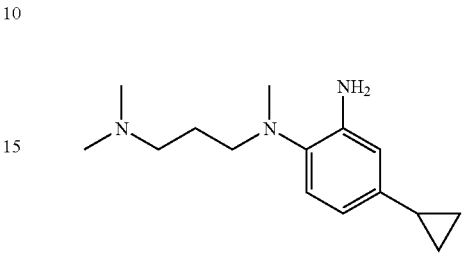

Synthesis of 4-cyclopropyl-N1-(3-(dimethylamino)propyl)-N1-methylbenzene-1,2-diamine Step 1. Preparation of N-(4-Bromo-2-nitro-phenyl)-N,N',N'-trimethyl-propane-1,3-diamine To a round bottom flask at 0° C. was added 4-Bromo-1-fluoro-2-nitrobenzene (10 g, 45 mmol) and N,N,N'-Trimethyl-propane-1,3-diamine (6.99 ml, 47.7 mmol). The reaction was allowed to warm to RT and stirred for 16 h. The reaction was extracted into EtOAc, washed once with saturated aqueous NaHCO$_3$, twice with water, and then dried over Mg$_2$SO$_4$. The organic layer was filtered and concentrated to yield the title compound as a bright orange solid. MS (M+H$^+$)= 316, 318; Calc'd for $C_{12}H_{18}BrN_3O_2$=316.19.

Step 2. Preparation of 4-cyclopropyl-N-(3-(dimethylamino)propyl)-N-methyl-2-nitrobenzenamine To a pressure vessel was added 2-cyclopropyl-4,4,5,5-tetramethyl-1,3,2-dioxaborolane (900 mg, 5.36 mmol), potassium phosphate (3.0 g, 14 mmol), and 0.82 mL water. After stirring at RT for 15 minutes, N-(4-Bromo-2-nitro-phenyl)-N,N',N'-trimethyl-propane-1,3-diamine (Step 1, 1.30 g, 4.12 mmol), palladium acetate (92 mg, 0.412 mmol), tricyclohexylphosphine (231 mg 0.824 mmol), and 21 ml toluene were added. The reaction was sealed and stirred at 80° C. for 19 h. The reaction was then cooled to RT, quenched with EtOAc and extracted into water, washed once with brine, and then dried over Mg$_2$SO$_4$. The crude mixture was then purified by reverse phase chromatography to yield the title compound as a dark red-brown oil. MS (M+H$^+$)=278; Calc'd for $C_{15}H_{23}N_3O_2$=277.36.

Step 3. Preparation of 4-cyclopropyl-N1-(3-(dimethylamino)propyl)-N1-methylbenzene-1,2-diamine 4-cyclopropyl-N-(3-(dimethylamino)propyl)-N-methyl-2-nitrobenzenamine (Step 2, 600 mg, 2.16 mmol) was dissolved in 22 mL MeOH. Palladium (115 mg, 0.108 mmol, 10% w/w on carbon) was added, a balloon containing hydrogen was inserted, and the reaction was stirred at RT for 18 h. The solution was then filtered through a pad of Celite and concentrated, yielding the title compound as viscous red-brown oil. MS (M+H$^+$)=248; Calc'd for $C_{15}H_{25}N_3$=247.38.

EXAMPLE 29

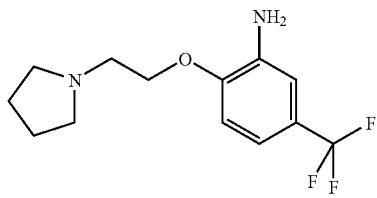

Synthesis of 2-(2-Pyrrolidin-1-yl-ethoxy)-5-trifluoromethyl-phenylamine

Step 1. Preparation of 1-[2-(2-Nitro-4-trifluoromethyl-phenoxy)-ethyl]-pyrrolidine To a suspension of NaH (60%, 248 mg, 6.21 mmol) in dry THF was added 2-Pyrrolidin-1-yl-ethanol (0.68 mL, 5.74 mmol). Bubbling was observed. The reaction was stirred for 5 minutes, at which time 1-Fluoro-2-nitro-4-trifluoromethyl-benzene (0.67 mL, 4.79 mmol) was added. The solution turned red, and LCMS indicated completion of the reaction. The reaction was quenched by addition of H$_2$O, and the mixture was extracted with EtOAc, dried with MgSO$_4$, filtered, and concentrated to afford the title compound as an orange oil.

Step 2. Preparation of 2-(2-Pyrrolidin-1-yl-ethoxy)-5-trifluoromethyl-phenylamine To a solution of 1-[2-(2-Nitro-4-trifluoromethyl-phenoxy)-ethyl]-pyrrolidine (1.70 g, 5.59 mmol) in dry MeOH (56 mL) was added Pd/C (10%, 350 mg). H$_2$ gas was bubbled through the solution, which was then stirred vigorously under an atmosphere of H$_2$. After completion of the reaction by LCMS, the mixture was filtered through celite and concentrated to affod the desired product as a yellow/orange oil. MS (M+H)$^+$=275; Calc'd 274.29 for $C_{13}H_{17}F_3N_2O$.

EXAMPLE 30

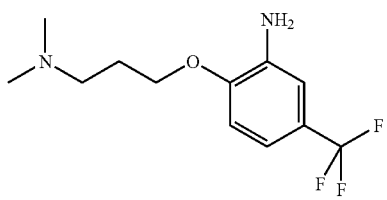

N,N-dimethyl-3-(2-nitro-4-(trifluoromethyl)phenoxy)propan-1-amine

Example 30 was synthesized in a manner analogous to that described in Example 29. MS (m/z): 263 (M+H)$^+$. Calc'd for $C_{12}H_{17}F_3N_2O_3$: 262.27.

EXAMPLE 31

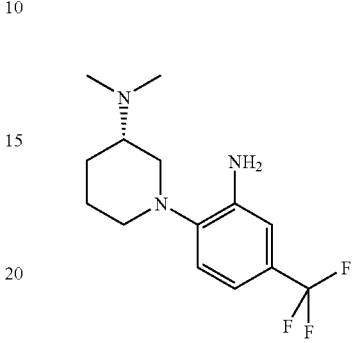

Synthesis of (S)-1-(2-amino-4-(trifluoromethyl)phenyl)-N,N-dimethylpiperidin-3-amine Step 1. (S)-N,N-dimethyl-1-(2-nitro-4-(trifluoromethyl)phenyl)piperidin-3-amine To a light yellow solution of (S)-tert-butyl 3-aminopiperidine-1-carboxylate (0.52 g, 2.6 mmol) in 25 ml MeOH was added sodium cyanoborohydride (0.33 g, 5.2 mmol), AcOH (0.74 ml, 13 mmol), and formaldehyde (37 wt. % solution in water, 1.0 ml). After stirring approximately 12 h, the reaction was quenched by the addition of 5 mL saturated aqueous sodium bicarbonate. The volatile organic solvents were removed in vacuo, and water and EtOAc was added. The organic layer was removed, and the aqueous layer was extracted twice with EtOAc. The combined organic layers were dried with Na$_2$SO$_4$, filtered, and concentrated to give a yellow oil. The resulting material was treated with 4 ml 4N HCl in dioxane at 0° C. After 2 h, the solution was concentrated in vacuo to give a light yellow solid. This solid was treated with 1-fluoro-2-nitro-4-trifluoromethyl-benzene (0.37 mL, 2.6 mmol), sodium bicarbonate (1.0 g, 13 mmol), and 5 ml dry THF. The mixture was heated to 75° C. with a water-cooled reflux condenser for 12 h. The mixture was allowed to cool to ambient temperature, was filtered through a fritted funnel, and concentrated to give the desired product as an orange oil. MS (m/z): 318.0 (M+H)$^+$. Calc'd for $C_{14}H_{18}F_3N_3O_2$: 317.31.

Step 2. (S)-1-(2-amino-4-(trifluoromethyl)phenyl)-N,N-dimethylpiperidin-3-amine (S)-N,N-Dimethyl-1-(2-nitro-4-(trifluoromethyl)phenyl)piperidin-3-amine (0.82 g, 2.6 mmol) was reduced with Pd/C (10%, 0.27 g) in 10 ml methanol. After approximately 12 h, the reaction was flushed with nitrogen and filtered through a pad of celite, rinsing with methanol. Removal of the solvent in vacuo gave the title compound as an orange-red oil. MS (m/z): 288.2 (M+H)$^+$. Calc'd for $C_{14}H_{20}F_3N_3$: 287.32.

EXAMPLE 32

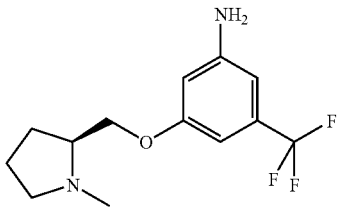

Synthesis of (S)-3-((1-methylpyrrolidin-2-yl)methoxy)-5-(trifluoromethyl) benzenamine The title compound was synthesized by a method similar to that described in WO 2002066470 A1.

EXAMPLE 33

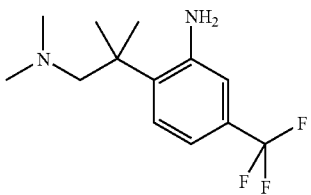

Synthesis of 2-(2-Dimethylamino-1,1-dimethyl-ethyl)-5-trifluoromethyl-phenylamine Step 1. Preparation of 2-Methyl-2-(2-nitro-4-trifluoromethyl-phenyl)-propionitrile The title compound was synthesized according to a method described in Prasad, G., J. Org. Chem. 1991, 56, 7188-7190. To a yellow-brown solution of (2-Nitro-4-trifluoromethyl-phenyl)-acetonitrile (2.5 g, 11 mmol), 18-crown-6 (0.72 g, 2.7 mmol), and methyl iodide (1.5 mL, 24 mmol) in dry THF under nitrogen at −78 degrees C. was added potassium tert-butoxide (2.7 g, 24 mmol) in one portion. The reaction immediately became a deep purple color. The reaction was allowed to stir for 2 h at −78 degrees C., and was then warmed to ambient temperature. A water-cooled reflux condenser was added and the solution heated to 70 degrees C. under nitrogen. Over 40 minutes, the color changed from dark purple to cloudy gray. The mixture was allowed to cool to room temperature, and was concentrated in vacuo. The resulting material was partitioned between 1 N HCl and EtOAc. The organic layer was washed once with brine, dried over sodium sulfate, filtered, and concentrated in vacuo to give a brown oil which was judged to be primarily monoalkylated nitrile. The crude material was resubjected to the reaction conditions using 18-crown-6 (0.72 mg, 2.7 mmol), methyl iodide (0.75 mL, 12 mmol), and potassium tert-butoxide (1.4 g, 12 mmol) as before, with the following modifications: the reaction was allowed to stir only 10 min. at −78 degrees C. before being warmed to room temperature, and the reaction vessel was sealed and heated to 70 degrees C. for 2 h. Upon cooling to room temperature, the reaction was quenched and worked up as before. Purification by flash chromatography afforded the desired product as a light brown solid. MS (M+H)$^+$=259; Calc'd 258.20 for $C_{11}H_9F_3N_2O_2$.

Step 2. Preparation of 2-Methyl-2-(2-nitro-4-trifluoromethyl-phenyl)-propylamine To the solid 2-methyl-2-(2-nitro-4-trifluoromethyl-phenyl)-propionitrile (1.0 g, 3.9 mmol) in a 250 mL round-bottom flask at 0 degrees C. was added a solution of borane in THF (47 mL of a 1 M solution in THF, 47 mmol). The orange-yellow solution was allowed to warm to room temperature and stir for 6 h. The solution was then cooled to 0 degrees C., and was quenched by the careful dropwise addition of 6 N HCl. After gas evolution ceased, a total of 47 mL 6N HCl was added, resulting in a white precipitate. The mixture was concentrated in vacuo to ½ the original volume, and was basified at 0 degrees C. with 6N NaOH. The mixture was extracted with a 100 mL portion of ethyl acetate. The organic layer was dried over sodium sulfate, filtered, and concentrated in vacuo to give a yellow oil. Purification by flash chromatography provided the desired product which contained minor impurities by NMR. MS m/z 263=[M+H]$^+$. Calc'd for $C_{11}H_{13}F_3N_2O_2$: 262.23.

Step 3. Preparation of Dimethyl-[2-methyl-2-(2-nitro-4-trifluoromethyl-phenyl)-propyl]-amine To a solution of 2-Methyl-2-(2-nitro-4-trifluoromethyl-phenyl)-propylamine (0.76 g, 2.9 mmol) in methanol (29 mL) at 0 degrees C. was added formaldehyde (0.60 mL of a 37 wt % solution in water, excess), acetic acid (0.83 mL, 14.5 mmol), and sodium cyanoborohydride (0.36 g, 5.8 mmol). The homogeneous yellow solution was allowed to warm to room temperature and was stirred overnight. After approximately 12 h, the reaction was quenched by the addition of saturated aqueous sodium bicarbonate until basic. The mixture was concentrated in vacuo, and the resulting material was partitioned between ethyl acetate and saturated aqueous sodium bicarbonate. The organic layer was washed once with brine, dried over sodium sulfate, filtered, and concentrated in vacuo to give a yellow oil which contained solid material. The oil was dissolved in dichloromethane and filtered through a plug of cotton. Purification by flash chromatography provided the title compound as a yellow oil.

MS m/z 291=[M+H]$^+$. Calc'd for $C_{13}H_{17}F_3N_2O_2$: 290.29.

Step 4. Preparation of 2-(2-Dimethylamino-1,1-dimethyl-ethyl)-5-trifluoromethyl-phenylamine A 50 mL round-bottom flask containing dimethyl-[2-methyl-2-(2-nitro-4-trifluoromethyl-phenyl)-propyl]-amine (0.61 g, 2.1 mmol) was charged with 10% palladium on carbon (0.23 g, 0.21 mmol) under nitrogen. Ethyl acetate (5 mL) and methanol (5 mL) were added sequentially via syringe. The atmosphere was replaced with hydrogen, and the reaction was stirred rapidly under 1 atm hydrogen overnight. After approximately 12 h, the reaction was flushed with nitrogen and filtered through a pad of celite, rinsing with methanol. Removal of the solvent in vacuo gave the title compound as a clear and colorless oil. MS m/z 261=[M+H]$^+$. Calc'd for $C_{13}H_{19}F_3N_2$: 260.30.

EXAMPLE 34

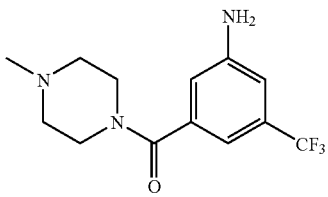

Synthesis of (3-amino-5-(trifluoromethyl)phenyl)(4-methylpiperazin-1-yl)methanone

Step 1. Preparation of (4-methylpiperazin-1-yl)(3-nitro-5-trifluoromethyl)phenyl)-methanone A solution of thionyl chloride (30 ml) and 3-nitro-5-(trifluoromethyl)benzoic acid (10 g) was heated to reflux for 2 h. The reaction mixture was concentrated under reduced pressure and treated with toluene (10 ml) which was then removed under reduced pressure to afford 3-nitro-5-(trifluoromethyl) benzoyl chloride.

To a solution of 3-nitro-5-(trifluoromethyl)benzoyl chloride (2.35 g, 9.3 mmol) in $CH_2Cl_2$ (40 ml) at room temperature was added N-methylpiperazine (1.26 ml, 9.3 mmol) and the mixture was allowed to stir for 30 min. The reaction was concentrated under reduced pressure, taken up in 1 M HCl (50 ml) and the aqueous layer was washed with $Et_2O$ (2×20 ml). The aqueous layer was basified to a pH of about 9 with 6 N NaOH, and the aqueous layer was extracted with $Et_2O$ (3×50 ml). The organic extracts were combined and washed with water (1×20 ml) followed by brine (1×20 ml), and dried over anhydrous sodium sulfate, filtered and concentrated under reduced pressure to afford (4-methylpiperazin-1-yl)(3-nitro-5-trifluoromethyl)phenyl)-methanone as a tan oil, which was used without further purification.

Step 2. Preparation of (3-amino-5-(trifluoromethyl) phenyl)(4-methylpiperazin-1-yl)methanone To an argon purged solution of (4-methylpiperazin-1-yl(3-nitro-5-trifluoromethyl)phenyl)-methanone (1.03 g, 3.25 mmol) was added Pd/C (344 mg, 0.32 mmol, 10%). The mixture was placed under an atmosphere of $H_2$ at RT for 5 h. The reaction was purged with argon and filtered through Celite. The filtrate was concentrated under reduced pressure to afford (3-amino-5-(trifluoromethyl)phenyl)(4-methylpiperazin-1-yl)methanone as an off-white solid. MS m/z=288 [M+H]$^+$. Calc'd for $C_{13}H_{16}F_3N_3O$: 287.3.

EXAMPLE 35

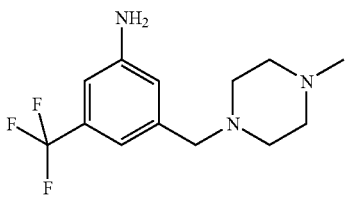

Synthesis of 3-((4-methylpiperazin-1-yl)methyl)-5-(trifluoromethyl)-benzenamine To LAH (1.84 g, 48.5 mmol) in THF (50 ml) at room temperature was added (4-methylpiperazin-1-yl)(3-nitro-5-trifluoromethyl)phenyl)-methanone (1.54 g, 4.85 mmol) in THF (10 ml). The resulting mixture was refluxed for 5 h. The reaction mixture was cooled to 0° C. at which point water (1.84 ml), 15% aq. NaOH (1.84 ml and water (3.68 ml) were successively added. The resulting mixture was allowed to stir at room temperature for 1 h. The mixture was filtered through Celite, concentrated under reduced pressure and purified via flash chromatography (silica gel, 0 to 25% MeOH in $CH_2Cl_2$, gradient elution) to afford 3-((4-methylpiperazin-1-yl)methyl)-5-(trifluoromethyl)benzenamine as a colorless oil. MS m/z=274 [M+H]$^+$. Calc'd for $C_{13}H_{18}F_3N_3$: 273.30.

EXAMPLE 36

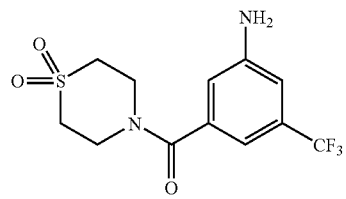

Synthesis of (3-amino-5-(trifluoromethyl)phenyl) (sulfonylmorpholino)methanone

Step 1: Preparation of (3-nitro-5-(trifluoromethyl) phenyl)(thiomorpholino)methanone 3-Nitro-5-(trifluoromethyl)benzoic acid (2.96 g, 12.6 mmol) was allowed to reflux in thionyl chloride (6 mL) for 6 h. The resulting solution was allowed to cool to room temperature and then concentrated under reduced pressure. The resulting solid was taken up in $CH_2Cl_2$ (20 mL) and $^iPr_2NEt$ (2.6 mL, 15.1 mmol) and thiomorpholine (1.4 mL, 13.8 mmol) was added. The reaction was stirred at RT for 1 h and then diluted with $CH_2Cl_2$ (50 mL). The organic layer was washed with aq. HCl (1 M, 25 mL), 9% aq. $Na_2CO_3$ (25 mL)), brine, dried over anhydrous sodium sulfate, filtered and concentrated under reduced pressure to afford (3-nitro-5-(trifluoromethyl)phenyl)(thiomorpholino)-methanone.

Step 2: Preparation of (3-nitro-5-(trifluoromethyl) phenyl)(sulfonylmorpholino)-methanone To a solution of (3-nitro-5-(trifluoromethyl)phenyl)-(thiomorpholino)methanone (1.56 g, 4.88 mmol) in EtOH (50 mL) was added a solution containing ammonium molybdate tetrahydrate (602 mg, 0.49 mmol) and hydrogen peroxide (30%, 4.2 mL, 43.92 mmol). The resulting mixture was allowed to stir overnight. Once the reaction was complete, as observed by TLC (1:1 hexanes:EtOAc), it was poured onto water (100 mL). The aqueous layer was extracted with $CH_2Cl_2$ (3×50 mL). The combined organic layers were washed with water (25 mL), brine (25 mL), dried over anhydrous sodium sulfate, filtered and concentrated under reduced pressure to afford (3-nitro-5Field of the Invention -(trifluoromethyl)phenyl) (sulfonylmorpholino)methanone.

Step 3: Preparation of (3-amino-5-(trifluoromethyl)phenyl) (sulfonylmorpholino)-methanone To an argon purged solution of (3-nitro-5-(trifluoromethyl) phenyl)-(sulfonylmorpholino) methanone (658 mg, 1.87 mmol) in EtOH (20 mL) was added Pd/C (198 mg, 0.187 mmol, 10%). The resulting mixture was allowed to stir under an atmosphere of hydrogen gas for 3 days. The reaction was purged with argon, filtered through Celite and concentrated under reduced pressure to afford (3-amino-5-(trifluoromethyl)phenyl)-(sulfonylmorpholino)methanone which was used without further purification. MS m/z=323 [M+H]$^+$. Calc'd for $C_{12}H_{13}F_3N_2O_3S$: 322.

EXAMPLE 37

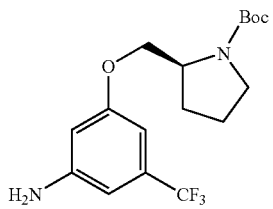

Synthesis of (S)-tert-butyl 2-((3-amino-5-(trifluoromethyl)phenoxy)methyl)pyrrolidine-1-carboxylate Step 1. Preparation of 3-nitro-5-(trifluoromethyl)phenol To a solution of 1-methoxy-3-nitro-5-(trifluoromethyl) benzene (1.0 g, 4.5 mmol) in dichloromethane (10 ml) was added pyridine hydrochloride salt (4.0 g, 35 mmol). After addition dichloromethane was removed under vacuum and the resulting solid mixture was heated at 200° C. overnight in an open reaction flask. After cooling to RT, 10% HCl (50 ml) was added and the mixture was extracted with EtOAc (3×50 ml). The combined organic layer was washed with brine (50 ml) and dried over $Na_2SO_4$. Solvent was removed under vacuum and the residue was purified by flash column chromatography on the silica gel (hexane/EtOAc=3:1) to afford the title compound as a white solid.

Step 2. Preparation of (S)-tert-butyl 2-((3-nitro-5-(trifluoromethyl)phenoxy)methyl)pyrrolidine-1-carboxylate To a solution of 3-nitro-5-(trifluoromethyl)phenol (1.4 g, 6.7 mmol) in benzene (50 ml) was added (S)-tert-butyl 2-(hydroxymethyl)pyrrolidine-1-carboxylate (1.4 g, 6.7 mmol) and triphenylphosphine (1.78 g, 6.7 mmol). Then diisopropyl azodicarboxylate (1.4 g, 6.7 mmol) was added dropwise to the mixture at RT. The resulting mixture was stirred at RT overnight and then solvent was removed under vacuum. The product was purified by flash column chromatography on the silica gel (EtOAc/hexane=5→25%) resulting in an off-white solid.

Step 3. Preparation of (S)-tert-butyl 2-((3-amino-5-(trifluoromethyl)phenoxy)methyl)pyrrolidine-1-carboxylate A mixture of (S)-tert-butyl 2-((3-nitro-5-(trifluoromethyl) phenoxy)methyl)pyrrolidine-1-carboxylate (2.0 g, 5.1 mmol) and Pd/C (10%, 150 mg) in EtOH (30 ml) was stirred under $H_2$ (1 atm) for 5 hr. The mixture was filtered through Celite and washed with MeOH. Evaporation of solvent gave the title product as a light amber oil. MS m/z=361 [M+H]$^+$. Calc'd for $C_{17}H_{23}F_3N_2O_3$: 360.38.

The following Examples 37-24 were synthesized in a manner analogous to that described in Example 36.

EXAMPLE 38

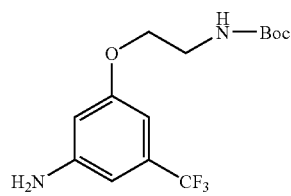

tert-butyl 2-(3-amino-5-(trifluoromethyl)phenoxy) ethylcarbamate

EXAMPLE 39

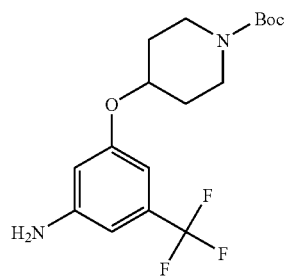

Tert-butyl 4-(3-amino-5-(trifluoromethyl)phenoxy) piperidine-1-carboxylate

EXAMPLE 40

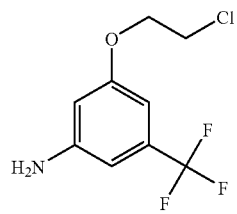

Synthesis of 3-(2-chloroethoxy)-5-(trifluoromethyl)benzenamine

Step 1. Preparation of 1-(2-chloroethoxy)-3-nitro-5-(trifluoromethyl)benzene To a mixture of 3-nitro-5-(trifluoromethyl)phenol (2.10 g, 10.1 mmol) and cesium carbonate (4.00 g, 12.2 mmol) in acetonenitrile (50 ml) was added 2-chloroethyl p-toluenesulfonate (2.9 g, 12 mmol) slowly. The resulting mixture was stirred at RT for 5 hr, poured into water (100 ml) and then extracted with EtOAc (3×80 ml). The combined organic layer was washed with brine (100 ml) and dried over $Na_2SO_4$. Solvent was removed under vacuum and the residue was purified by flash column chromatography on the silica gel (hexane/EtOAc=5 to 25%) to afford the desired compound.

Step 2. Preparation of 1-(2-chloroethoxy)-3-amino-5-(trifluoromethyl)benzene Prepared in an analogous manner to Step 3 for (S)-tert-butyl 2-((3-amino-5-(trifluoromethyl)phenoxy)methyl)pyrrolidine-1-carboxylate of Example 37.

EXAMPLE 41

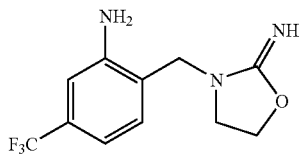

Synthesis of 2-((2-iminooxazolidin-3-yl)methyl)-5-(trifluoromethyl)benzenamine

Step 1. Preparation of 2-(2-nitro-4-(trifluoromethyl)benzylamino)ethanol

In a sealed tube, added 1-(chloromethyl)-2-nitro-4-(trifluoromethyl)benzene (2.0 g, 8.4 mmol), tetrahydrofuran (8.4 mL), and 2-aminoethanol (5.0 mL, 83.5 mmol). Stirred the mixture at room temperature for 45 minutes. Extracted the mixture into ethyl acetate, washed 2 times with water, 1 time with brine solution, dried over magnesium sulfate, filtered, concentrated to yield 2-(2-nitro-4-(trifluoromethyl)benzylamino)ethanol. MS $(M+H)^+$=265; Calc'd 264.21 for $C_{10}H_{11}F_3N_2O_3$.

Step 2. Preparation of 3-(2-nitro-4-(trifluoromethyl)benzyl)oxazolidin-2-imine In a sealed tube, added 2-(2-nitro-4-(trifluoromethyl)benzylamino)ethanol (Step 1, 1.10 g, 4.16 mmol), cyanogen bromide (1.32 g, 12.4 mmol), and tetrahydrofuran (4.2 mL). Stirred at room temperature for 56 hours. Concentrated down to yield 3-(2-nitro-4-(trifluoromethyl)benzyl)oxazolidin-2-imine. MS $(M+H)^+$=290; Calc'd 289.22 for $C_{11}H_{10}F_3N_3O_3$.

Step 3. Preparation of 2-((2-iminooxazolidin-3-yl)methyl)-5-(trifluoromethyl)benzenamine In a 100 mL round bottom flask, added palladium (110 mg, 0.10 mmol, 10% w/w on carbon), methanol (20 mL), and 3-(2-nitro-4-(trifluoromethyl)benzyl)oxazolidin-2-imine (Step 2, 600 mg, 2.07 mmol). Attached a balloon containing hydrogen, stirred at room temperature for 22 hours. Filtered through a pad of Celite, concentrated down to yield 2-((2-iminooxazolidin-3-yl)methyl)-5-(trifluoromethyl)benzenamine as a waxy orange-yellow solid. MS $(M+H)^+$=260; Calc'd 259.22 for $C_{11}H_{12}F_3N_3O$.

EXAMPLE 42

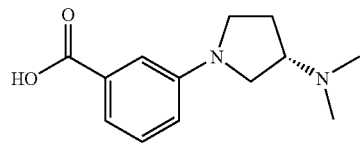

Synthesis of (S)-3-(3-(dimethylamino)pyrrolidin-1-yl)benzoic acid

Step 1. Preparation of (S)-methyl 3-(3-(dimethylamino)pyrrolidin-1-yl)benzoate A mixture of methyl 3-bromobenzoate (1.0 g, 4.7 mmol), 2-(dicyclohexylphosphino)-2'-(N,N-dimethylamino)biphenyl (0.037 g, 0.093 mmol), tris(dibenzylidineacetone)dipalladium (0) (0.021 g, 0.023 mmol), anhydrous $K_3PO_4$ (1.4 g, 6.5 mmol) in 9.3 mL toluene under argon was added (S)-N,N-dimethylpyrrolidin-3-amine (0.71 mL, 5.6 mmol). The reaction was sealed and heated to 80 deg. C. for 3 days. The reaction was cooled to ambient temperature, was diluted with ethyl acetate, and filtered through celite. The filtrate was concentrated in vacuo to give a brown oil, which was further purified by silica gel chromatography, using 90/10/1 dichloromethane/methanol/sat'd ammonium hydroxide as eluent to give (S)-methyl 3-(3-(dimethylamino)pyrrolidin-1-yl)benzoate as a light brown oil.

Step 2. Preparation of (S)-3-(3-(dimethylamino)pyrrolidin-1-yl)benzoic acid

To a solution of (S)-methyl 3-(3-(dimethylamino)pyrrolidin-1-yl)benzoate (0.555 g, 2.24 mmol) in MeOH (2.5 mL) was added 1N NaOH (2.5 mL). The reaction was sealed and heated to 70 deg. C. for 1 h. The reaction was cooled to ambient temperature and was concentrated to ½ the volume in vacuo. Water was added, followed by 1N HCl until pH 5-6 is obtained. The resulting thick oily mixture was extracted seven times with dichloromethane. The aqueous layer was concentrated in vacuo to a solid, which was rinsed with 1:1 MeOH/MC and filtered. The filtrate was concentrated in vacuo to give (S)-3-(3-(dimethylamino)pyrrolidin-1-yl)benzoic acid as a yellow solid. MS m/z=235 $[M+1]^+$. Calc'd for $C_{13}H_{18}N_2O_2$: 234.29.

EXAMPLE 43

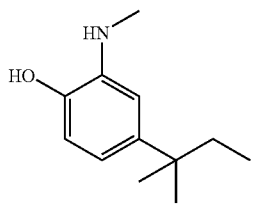

Synthesis of 2-(methylamino)-4-tert-pentylphenol

2-Amino-4-tert-pentylphenol (5.00 g, 27.8 mmol) and potassium carbonate (3.88 g, 28.1 mmol) were mixed at RT for 2.5 hours in DMF (15 mL). Methyl iodide (1.20 mL, 19.3 mmol) was added and the mixture was stirred overnight at RT. Diluted the mixture with EtOAc and extracted with aqueous sodium bicarbonate and water. Dried the organic layers over sodium sulfate, filtered, concentrated and purified by silica gel chromatography (10-15% MTBE/hexanes). Concentrated the product fractions to yield the title compound.

The following Examples 44-47 describe representative syntheses of exemplary A-B rings.

EXAMPLE 44

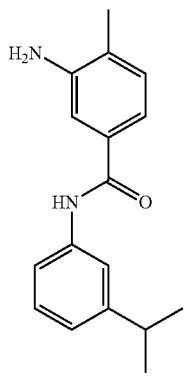

Synthesis of 3-Amino-N-(3-isopropyl-phenyl)-4-methyl-benzamide

Step 1. Preparation of N-(3-Isopropyl-phenyl)-4-methyl-3-nitro-benzamide

To a solution of 4-methyl-3-nitro-benzoyl chloride (2.00 g, 0.010 mol) in THF (30 mL), in a water bath-cooled 100 mL round bottom flask, was added 3-isopropyl-phenylamine (1.35 g, 0.010 mol) dropwise. The reaction was allowed to stir at room temperature for 1 hour before being concentrated. The mixture was taken up in EtOAc and washed with NaHCO₃ (aq., conc.) and then brine. The solution was dried over MgSO₄, filtered, and concentrated to yield the title compound as an orange oil that solidifies upon standing. MS m/z 299=[M+H]⁺. Calc'd for $C_{17}H_{18}N_2O_3$: 298.34.

Step 2. Preparation of 3-Amino-N-(3-isopropyl-phenyl)-4-methyl-benzamide

To N-(3-Isopropyl-phenyl)-4-methyl-3-nitro-benzamide (3.00 g, 0.010 mol) dissolved in EtOAc (60 mL) in a 100 mL round bottom flask was added Pd/C (10%, 250 mg). The flask was capped with a rubber septum and flushed with H₂ gas through a balloon/needle. Postitive H₂ pressure was applied through the balloon/needle and reaction was stirred vigorously at room temperature for 3 days. TLC indicated clean conversion of starting material. The reaction was filtered through a pad of sand/celite. After concentration, the mixture was purified by silica gel chromatography to afford a slightly orange oil. Trituration with a mixture of hexanes and EtOAc afforded the title compound as an off-white solid. MS m/z 269=[M+H]⁺. Calc'd for $C_{17}H_{20}N_2O$: 268.36.

EXAMPLE 45

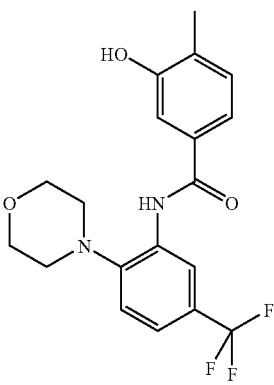

Synthesis of 3-Hydroxy-4-methyl-N-(2-morpholin-4-yl-5-trifluoromethyl-phenyl)-benzamide 3-Hydroxy-4-methylbenzoic acid (530 mg, 3.5 mmol), 3-amino-4-(4-morpholino)benzotrifluoride (890 mg, 3.6 mmol), and DMAP (150 mg, 1.3 mmol) were suspended in 20 mL dry toluene in a 2-neck flask with an attached Dean-Stark trap under N₂. The mixture was stirred in a 130° C. oil bath and brought to a boil before PCl₃ (0.18 mL, 2 mmol) was added dropwise by glass/Teflon syringe over 15 minutes. Heating was continued an additional 45 minutes. After cooling, the mixture was diluted with brine and ethyl acetate, and acidified with 1 N HCl. After extraction, the organic layer was dried with Na₂SO₄, concentrated, and purified by flash chromatography (2% MeOH in CH₂Cl₂). The isolated material was packed into a small filtration apparatus and rinsed with a small amount of CH₂Cl₂ to provide the title compound as a white solid. ¹H NMR (Varian, 400 MHz, DMSO-d₆) d: 9.83 (s, 1H), 9.50 (s, 1H), 8.45 (s, 1H), 7.48 (m, 1H), 7.43 (m, 1H), 7.34 (s, 1H), 7.31 (m, 1H), 7.25 (m, 1H), 3.78 (m, 4H), 2.90 (m, 4H), 2.18 (s, 3H).

EXAMPLE 46

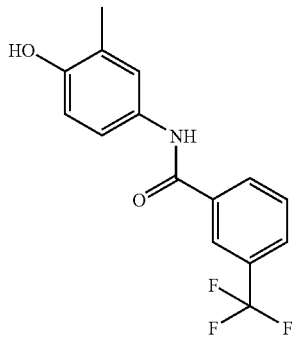

Synthesis of
N-(4-hydroxy-3-methylphenyl)-3-(trifluoromethyl
benzamide

To 3-(trifluoromethyl)benzoic acid (380 mg, 2.00 mmol), 4-amino-2-methylphenol (271 mg, 2.20 mmol) and EDC (767 mg, 4.00 mmol) was added $CH_2Cl_2$ (80 mL). The resulting mixture was stirred for 66 hours at RT, concentrated, dissolved in EtOAc and washed with water. The organics were dried over sodium sulfate, filtered and concentrated. The crude material was purified by silica gel chromatography (0-50% EtOAc/hexanes) to yield N-(4-hydroxy-3-methylphenyl)-3-(trifluoromethyl)benzamide as a white solid. MS m/z=296 [M+1]$^+$. Calc'd for $C_{15}H_{12}F_3NO_2$: 295.26.

EXAMPLE 47

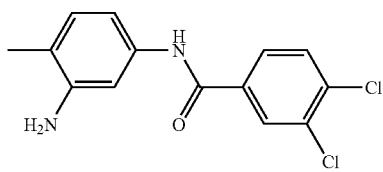

Synthesis of
N-(3-amino-4-methyl-phenyl)-3,4-dichloro-benzamide

To 3,4-dichlorobenzoic acid (200 mg, 1.05 mmol), 2,4-diaminotoluene (513 mg, 4.20 mmol), and EDC (403 mg, 2.10 mmol) was added $CH_2Cl_2$ (40 mL). The mixture was stirred overnight at RT, concentrated, diluted with EtOAc and extracted with water. The organic layer was dried over $Na_2SO_4$, filtered, concentrated, and purified by flash chromatography (n-Hexanes→50% EtOAc/n-Hexanes) yielding N-(3-amino-4-methyl-phenyl)-3,4-dichloro-benzamide. MS m/z=295, 297 [M]$^+$ and [M+2]$^+$. Calc'd for $C_{14}H_{12}Cl_2N_2O$: 295.17.

The following Examples 48-54 describe representative syntheses of exemplary B rings.

EXAMPLE 48

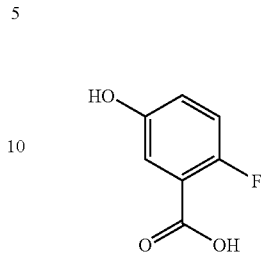

Synthesis of 2-Fluoro-5-hydroxybenzoic acid

To 2-fluoro-5-methoxybenzoic acid (5.00 g, 29.4 mmol) was added 49% aqueous HBr (50 mL) and glacial acetic acid (40 mL). The mixture was heated overnight at 140° C., cooled to RT, diluted with ice water and extracted with EtOAc. The organic layer was dried over $Na_2SO_4$, filtered and concentrated to yield 2-fluoro-5-hydroxybenzoic acid. MS m/z=157 [M+1]$^+$. Calc'd for $C_7H_5FO_3$: 156.11.

EXAMPLE 49

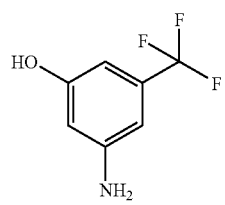

Synthesis of 3-Amino-5-trifluoromethylphenol

To a round bottom flask was added 3-methoxy-5-trifluoromethyl-phenylamine (1.0 g, 5.23 mmol), 10 ml HBr (49% aq.), and 8 mL glacial acetic acid. A reflux condenser was attached and the solution heated to 140° C. for 20 h. The reaction was then diluted with water and neutralized to ~pH 7 by slow addition of saturated $NaHCO_3$. The aqueous solution was then extracted into EtOAc twice. The organic layers were combined, washed once with brine, dried over $Mg_2SO_4$, filtered, and concentrated in vacuo to yield the title compound as a tan solid (750 mg). MS (M+H)$^+$=178; Calc'd 177.12 for $C_7H_6F_3NO$.

EXAMPLE 50

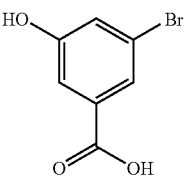

Synthesis of 3-Bromo-5-hydroxy-benzoic acid

The title compound was made according to the method described in *Org. Proc. Res. rev.* 2002, 6, 591-595. To 5-iodo-3-bromo-benzoic acid (500 mg, 1.53 mmol), NaOH (250 mg, 6.1 mmol), Cu$_2$O (240 mg, 1.68 mmol) was added water (4.0 mL)). The mixture was heated for 1.5 h at 140° C. in a sealed tube. The cooled mixture was diluted with water and extracted with CH$_2$Cl$_2$. The aqueous layer was acidified (pH~2) with TFA and extracted with EtOAc. The organic layer was dried over Na$_2$SO$_4$, filtered, concentrated and purified by reverse-phase HPLC to yield 3-bromo-5-hydroxy-benzoic acid. $^1$H NMR (400 MHz, DMSO-d$_6$): 10.30 (s, 1H), 7.46 (m, 1H), 7.31 (m, 1H), 7.17 (m, 1H).

EXAMPLE 51

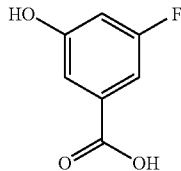

Synthesis of 3-fluoro-5-hydroxy-benzoic acid

3-Fluoro-5-hydroxy-benzoic acid was synthesized in an analogous fashion to 3-bromo-5-hydroxy-benzoic acid, in Example 50. $^1$H NMR (400 MHz, DMSO-d$_6$): 10.26 (s, 1H), 7.16 (br s, 2H), 6.79 (m, 1H).

EXAMPLE 52

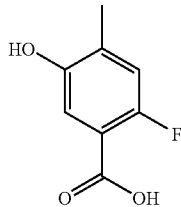

Synthesis of 2-fluoro-5-hydroxy-4-methylbenzoic acid

Step 1. Preparation of 2-fluoro-5-methoxy-4-methylbenzoic acid

Potassium tert-butoxide (7.92 g, 70.5 mmol) was dissolved in THF (150 mL) and cooled to −78° C. 2-Fluoro-5-methoxy-benzoic acid (3.00 g, 17.6 mmol) in THF (100 mL) was added followed by n-butyl lithium (2.5 N in hexanes, 28.2 mL, 70.5 mmol). After 40 minutes, iodomethane (2.2 mL, 35.4 mmol) was added and allowed to stir at −78° C. for 70 minutes before warming to room temperature. The reaction was quenched with saturated ammonium chloride (100 mL) and extracted with ether. The aqueous layer was acidified using 6 N HCl then extracted with ether. The organic layer was dried over sodium sulfate, filtered and concentrated. The crude material was purified by Gilson reverse-phase HPLC (acidic mobile phase) to yield 2-fluoro-5-methoxy-4-methylbenzoic acid as a white solid. MS m/z=185 [M+1]$^+$. Calc'd for C$_9$H$_9$FO$_3$: 184.20.

Step 2. Preparation of 2-fluoro-5-hydroxy-4-methylbenzoic acid

To 2-fluoro-5-methoxy-4-methylbenzoic acid (650 mg, 3.53 mmol) was added 49% aqueous HBr (6.5 mL) and glacial acetic acid (5.5 mL). The mixture was heated overnight at 140° C., cooled to RT, diluted with ice water and extracted with EtOAc. The organic layer was dried over Na$_2$SO$_4$, filtered and concentrated to yield 2-fluoro-5-hydroxy-4-methylbenzoic acid. MS m/z=171 [M+1]$^+$. Calc'd for C$_8$H$_7$FO$_3$: 170.20.

EXAMPLE 53

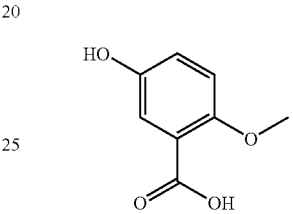

Synthesis of 5-hydroxy-2-methoxybenzoic acid

A solution of 2,5-dimethoxybenzoic acid (10.0 g, 54.9 mmol) in 55 mL concentrated sulfuric acid was heated to 55 deg. C. for 48 h. The reaction was then poured into ice. A precipitate formed, and the mixture was allowed to stand overnight. The resulting crystals were collected by filtration and dried in vacuo. The material was further purified by silica gel chromatography to give 5-hydroxy-2-methoxybenzoic acid as a white solid. MS m/z=169.0 [M+1]$^+$. Calc'd for C$_8$H$_8$O$_4$: 168.15.

EXAMPLE 54

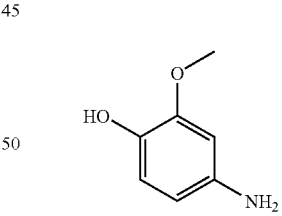

Synthesis of 4-amino-2-methoxyphenol 4-nitroguaiacol (4.0 g, 24 mmol) was placed in Parr shaker bottle under nitrogen and Palladium 5% C (0.5 g, 5 mmol) was added to the bottle. Keeping the bottle under nitrogen, methanol (59 ml, 24 mmol) was added and the bottle was sealed. This was placed in Parr shaker under about 45 psi hydrogen gas pressure and shaken for 48 hrs. After the reaction was complete, the Pd catalyst was filtered off and filtrate concentrated under reduced pressure to give 4-amino-2-methoxyphenol as brown solid. MS m/z=140 [M+1]$^+$. Calc'd for C$_7$H$_9$ClNO$_2$: 139.15.

The following Examples 55-64 describe representative syntheses of exemplary B-C-D rings.

EXAMPLE 55

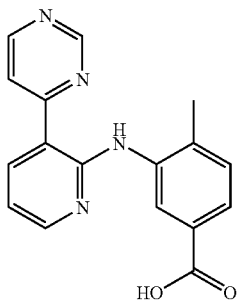

Synthesis of 4-Methyl-3-(3-pyrimidin-4-yl-pyridin-2-ylamino)-benzoic acid 4-(2-Chloro-pyridin-3-yl)-pyrimidine (10.4 g, 54 mmol), 3-amino-4-methylbenzoic acid (19.4 g, 128 mmol), 17 g Et$_3$N-TFA salt (The liquid Et$_3$N-TFA reagent was generated by adding 2.5 mL TFA dropwise to a 0° C. solution of 3 mL Et$_3$N in isopropanol, then concentrating by rotary evaporator followed by 30 minutes under high vacuum.), and 15 mL DMSO were mixed together in a sealed tube under argon. The mixture was stirred at 95° C. for 65 h. After cooling to RT, the residue was sonicated in 100 mL methanol to break up the solids, then filtered to obtain product as a yellow solid.

MS m/z=307 [M+H]$^+$. Calc'd for $C_{17}H_{14}N_4O_2$: 306.33.

EXAMPLE 56

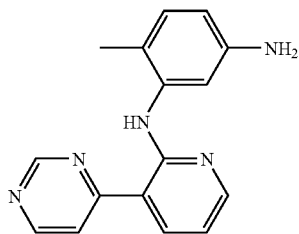

Synthesis of 4-Methyl-N$^3$-(3-pyrimidin-4-yl-pyridin-2-yl)-benzene-1,3-diamine

Step 1. Preparation of (3-amino-4-methyl-phenyl)-carbamic acid tert-butyl ester

The title compound was prepared according to the procedure described in *J. Med. Chem.* 1994, 37, 636-646. To 4-methyl-benzene-1,3-diamine (4.93 g, 40.4 mmol), MeOH (220 mL) and triethylamine (5.1 mL, 36.7 mmol) was added di-tert-butyl dicarbonate (8.00 g, 36.7 mmol). The mixture was stirred overnight at RT and concentrated. The residue was dissolved in EtOAc and extracted with 10% aqueous NaHCO$_3$. The organic layer was dried over Na$_2$SO$_4$, filtered and concentrated about 90% of the way. At this point the product which precipitated out of solution, was filtered and washed with EtOAc to yield (3-amino-4-methyl-phenyl)-carbamic acid tert-butyl ester.

Step 2. Preparation of [4-methyl-3-(3-pyrimidin-4-yl-pyridin-2-ylamino)-phenyl]-carbamic acid tert-butyl ester The title compound was prepared according to the procedure described in *Tetrahedron* 2001, 51, 7027-7034. Pd(OAc)$_2$ (47 mg, 0.21 mmol), and rac-BINAP (131 mg, 0.21 mmol) were stirred in toluene (12 mL) at RT for 12 minutes. This mixture was added to 4-(2-chloro-pyridin-3-yl)-pyrimidine (1.01 g, 5.24 mmol), (3-amino-4-methyl-phenyl)-carbamic acid tert-butyl ester (1.63 g, 7.34 mmol), and K$_2$CO$_3$ (14.5 g, 105 mmol) in toluene (40 mL). The mixture was heated overnight at 130° C. in a sealed tube. The cooled reaction was filtered through a pad of Celite, partially concentrated and the resulting solid was filtered to yield [4-methyl-3-(3-pyrimidin-4-yl-pyridin-2-ylamino)-phenyl]-carbamic acid tert-butyl ester.

Step 3. Preparation of 4-methyl-N$^3$-(3-pyrimidin-4-yl-pyridin-2-yl)-benzene-1,3-diamine The title compound was prepared according to the procedure described in *J. Am. Chem. Soc.* 1993, 115, 905-916. To [4-methyl-3-(3-pyrimidin-4-yl-pyridin-2-ylamino)-phenyl]-carbamic acid tert-butyl ester (550 mg, 1.46 mmol) was added CH$_2$Cl$_2$ (15 mL) and TFA (3.0 mL). The mixture was stirred for 3 h at 0° C., diluted with EtOAc and extracted with 50% aqueous Na$_2$CO$_3$. The organic layer was dried over Na$_2$SO$_4$, filtered and concentrated to yield 4-methyl-N$^3$-(3-pyrimidin-4-yl-pyridin-2-yl)-benzene-1,3-diamine. MS m/z=278 [M+1]$^+$. Calc'd for $C_{16}H_{15}FN_5$: 277.33.

EXAMPLE 57

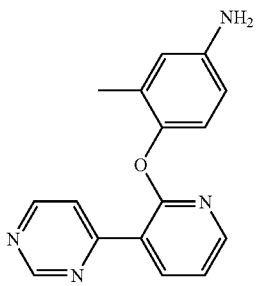

Synthesis of 3-Methyl-4-(3-pyrimidin-4-yl-pyridin-2-yloxy)-phenylamine

To 4-amino-2-methyl-phenol (193 mg, 1.57 mmol) was added Cs$_2$CO$_3$ (1.02 g, 3.14 mmol) and NMP (2.0 mL). The mixture was heated for 5 minutes at 100° C., cooled to RT and 4-(2-chloro-pyridin-3-yl)-pyrimidine (300 mg, 1.57 mmol) was added. The mixture was heated in the microwave to 210° C. for 20 minutes, cooled, filtered through a plug of cotton and purified by reverse-phase HPLC (Gilson, acidic mobile

EXAMPLE 58

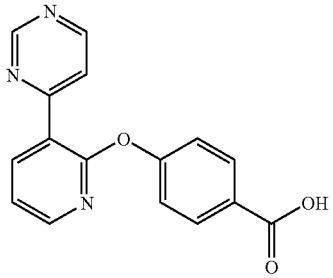

Synthesis of
4-(3-(pyrimidin-4-yl)pyridin-2-yloxy)benzoic acid

A mixture of 4-(2-chloro-pyridin-3-yl)-pyrimidine, 4-hydroxy-benzoic acid and $Cs_2CO_3$ in DMSO was heated in a microwave (Personal Chemistry, Emrys Optimizer) at 200° C. for 10 minutes. The reaction mixture was cooled to RT and diluted with 60 mL of EtOAc. The product was precipitated from the solution. The mixture was then washed with 20 mL of water twice. The solid was collected by filtration and dried in an oven at 50° C. to afford off white solid as desired product. MS m/z=294 [M+1]$^+$. Calc'd for $C_{16}H_{11}N_3O_3$: 293.28.

EXAMPLE 59

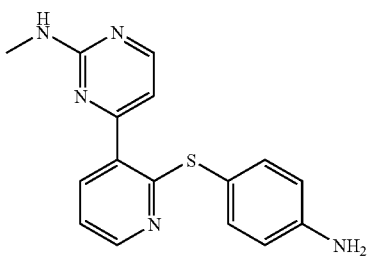

Synthesis of 4-(2-((4-aminophenyl)sulfanyl)-3-pyridinyl)-N-methyl-2-pyrimidinamine To 4-aminothiophenol (1.70 g, 13.6 mmol) and $Cs_2CO_3$ (8.90 g, 27.2 mmol) was added DMSO (18 mL). The mixture was stirred for 5 minutes at 100° C. before the 4-(2-chloro-pyridin-3-yl)-N-methylpyrimidin-2-amine (3.00 g, 13.6 mmol) was added. The resulting mixture was stirred for 16 hours at 130° C., then diluted with water and the resulting solid was filtered. After washing the solid with water and $Et_2O$ it was dried under vacuum to yield the title compound as a tan solid. MS m/z=310 [M+1]$^+$. Calc'd for $C_{16}H_{15}N_3S$: 309.40.

phase) to yield 3-methyl-4-(3-pyrimidin-4-yl-pyridin-2-yloxy)-phenylamine. MS m/z=279 [M+1]$^+$. Calc'd for $C_{16}H_{14}N_4O$: 278.32.

EXAMPLE 60

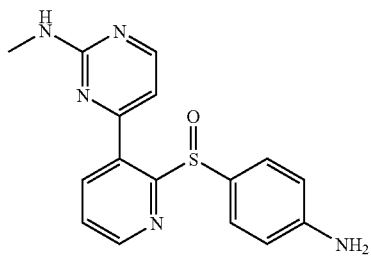

Synthesis of 4-(2-(4-aminophenylsulfinyl)pyridin-3-yl)-N-methylpyrimidin-2-amine To a cold (0° C.) suspension of 4-(2-(4-aminophenylthio)pyridin-3-yl)-N-methylpyrimidin-2-amine (400 mg, 1.28 mmol) in 20 mL of dichloromethane was added dropwise a solution of 3-chloroperoxybenzoic acid (330 mg, 1.28 mmol, 77% maximum purity) in dichloromethane. The reaction was stirred for 7 hours at 0° C. Then the reaction flask was stored in the freezer overnight without stirring. After 17 hours, the reaction was removed from the freezer and was stirred for another 6 hours in an ice-water bath. The solid was filtered off and collected. The product, 4-(2-(4-aminophenylsulfinyl)pyridin-3-yl)-N-methylpyrimidin-2-amine was obtained as an off-white solid. $^1$H NMR (Varian, 300 MHz, CDCl$_3$): 8.76 (s, 1H), 8.35 (s, 1H), 8.00 (d, J=7.7 Hz, 1H), 7.60 (m, 1H), 7.46 (m, 3H), 6.78 (d, J=4.9 Hz, 1H), 6.46 (d, J=8.0 Hz, 2H), 5.63 (br s, 2H), 2.81 (s, 3H).

EXAMPLE 61

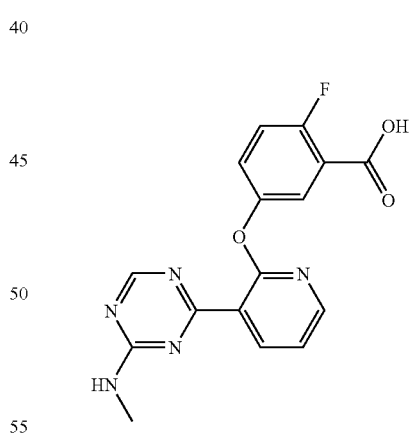

Synthesis of 2-Fluoro-5-[3-(4-methylamino-[1,3,5]triazin-2-yl)-pyridin-2-yloxy]-benzoic acid To [4-(2-chloro-pyridin-3-yl)-[1,3,5]triazin-2-yl]-methylamine (6.90 g, 31.1 mmol), 2-fluoro-5-hydroxybenzoic acid (4.9 g, 31.1 mmol) and $Cs_2CO_3$ (20.3 g, 62.2 mmol) was added DMSO (25 mL). The mixture was heated overnight at 130° C. in a sealed tube. The cooled mixture was diluted with water and extracted with EtOAc. The aqueous layer was acidified (pH~4) with TFA and the resulting solid was filtered, washed with water and dried to yield 2-fluoro-5-[3-(4-methylamino-[1,3,5]triazin-2-yl)-pyridin-2-yloxy]-benzoic acid. MS m/z=342 [M+1]$^+$. Calc'd for $C_{16}H_{12}FN_5O_3$: 341.30.

EXAMPLE 62

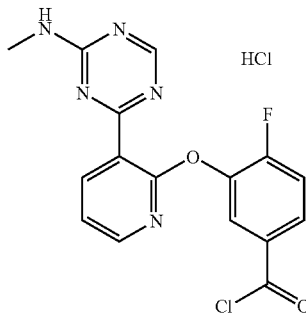

Synthesis of 4-Fluoro-3-[3-(4-methylamino-[1,3,5] triazin-2-yl)-pyridin-2-yloxy]-benzoyl chloride; hydrochloride To a suspension of 4-Fluoro-3-[3-(4-methylamino-[1,3,5]triazin-2-yl)-pyridin-2-yloxy]-benzoic acid (2.0 g, 5.86 mmol) in $CH_2Cl_2$ (60 mL) at 0° C. was added DMF (5 drops) by pipette, followed by oxalyl chloride (0.511 mL, 5.86 mmol) dropwise. Bubbling was evident. The reaction was stirred at 0° C. for 30 minutes, and then at room temperature for 1 hour, over which time the suspended material dissolved. The reaction could be monitored by either LCMS analysis of small aliquots quenched with MeOH, or by the dissolution of all suspended material. Upon completion, the reaction mixture was concentrated to afford the title compound as a light brown solid. Methyl ester: MS m/z 356=[M+H]$^+$. Calc'd for $C_{17}H_{14}FN_5O_3$: 355.33.

EXAMPLE 63

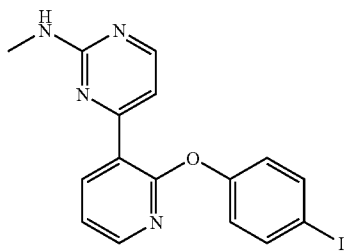

Synthesis of 4-(2-(4-iodophenoxy)pyridin-3-yl)-N-methylpyrimidin-2-amine 4-(2-Chloropyridin-3-yl)-N-methylpyrimidin-2-amine (3.30 g, 15.0 mmol), 4-iodophenol (3.96 g, 18.0 mmol), cesium carbonate (10.6 g, 30.0 mmol), and 15 mL of DMSO were added into a 50-mL round bottom flask. The flask was sealed with a septum and placed in a preheated oil bath at 130° C. After 3 h, the reaction was completed according to TLC and LC-MS analysis. The reaction was cooled to room temperature. Water was added into the reaction mixture until all product precipitated out of the solution. The solid was filtered, ground, and washed with water. The product was collected and dried in a vacuum oven overnight. The product, 4-(2-(4-iodophenoxy)pyridin-3-yl)-N-methylpyrimidin-2-amine was obtained as a light brown solid. $^1$H NMR (Varian, 300 MHz, CDCl$_3$): 8.40 (br s, 1H), 8.34 (d, J=4.1 Hz, 1H), 8.19 (dd, J=4.8, 2.2 Hz, 1H), 7.73 (m, 2H), 7.30 (dd, J=7.4, 4.8 Hz, 1H), 7.19 (m, 2H), 7.00 (m, 2H), 2.84 (d, J=4.8 Hz, 3H).

EXAMPLE 64

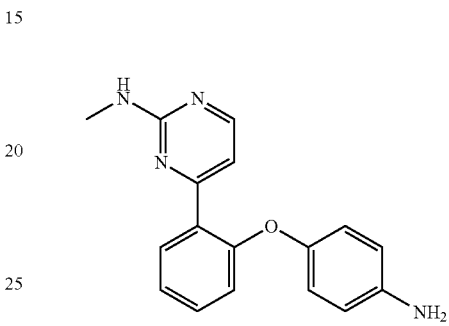

Synthesis of 4-(2-(4-aminophenoxy)phenyl)-N-methylpyrimidin-2-amine

Step 1. Preparation of 4,4,5,5-tetramethyl-2-(2-(4-nitrophenoxy)phenyl)-1,3,2-dioxaborolane To a solution of 2-(4,4,5,5-tetramethyl-1,3,2-dioxaborolan-2-yl)phenol (2.00 g, 9.09 mmol) in DMF was added Potassium carbonate (2.51 g, 18.2 mmol) and 1-fluoro-4-nitrobenzene (0.964 ml, 9.09 mmol). The reaction was flushed with nitrogen, sealed, and heated to 120 deg.C. After 18 h, water was added and the mixture extracted twice with EtOAc. The organic layer was dried over Na$_2$SO$_4$, filtered, and concentrated in vacuo. Purify by silica gel chromatography, eluting with 0-15% EtOAc/hexanes to give 4,4,5,5-tetramethyl-2-(2-(4-nitrophenoxy)phenyl)-1,3,2-dioxaborolane as a white solid. MS m/z=342 [M+1]$^+$. Calc'd for $C_{18}H_{20}BNO_5$: 341.17.

Step 2. Preparation of 2-(methylthio)-4-(2-(4-nitrophenoxy)phenyl)pyrimidine

To a mixture of 4,4,5,5-tetramethyl-2-(2-(4-nitrophenoxy)phenyl)-1,3,2-dioxaborolane (0.936 g, 2.7 mmol), Pd(dppf) Cl$_2$ (0.10 g, 0.14 mmol) in dioxane and Sodium carbonate (2.0 M in water, 2.7 ml, 5.5 mmol) was added 4-chloro-2-methylthiopyrimidine (0.38 ml, 3.3 mmol). The brown mixture was sealed and heated to 80 deg. C. overnight. In the morning the reaction was partitioned between EtOAc/1N NaOH. The aqueous layer was extracted once with EtOAc. The combined organics were dried over anhyd. Na$_2$SO$_4$, filtered, and concentrated to a brown oil. This material was treated with CH$_2$Cl$_2$ and purified by silica gel chromatography eluting with 0-25% EtOAc/hexane. The product-containing fractions were concentrated to afford 2-(methylthio)-4-(2-(4-nitrophenoxy)phenyl)pyrimidine as a clear oil. MS m/z=340 [M+1]$^+$. Calc'd for $C_{17}H_{13}N_3O_3$: 339.37.

Step 3. Preparation of 2-(methylsulfonyl)-4-(2-(4-nitrophenoxy)phenyl)pyrimidine To a stirring solution of 2-(methylthio)-4-(2-(4-nitrophenoxy)phenyl)pyrimidine (0.819 g, 2.4 mmol) at 0 deg. C. was added a yellow solution of ammonium molybdate tetrahydrate (0.30 g, 0.24 mmol) in hydrogen peroxide 30% (1.8 ml, 22 mmol) via pipette. The solution was allowed to warm to ambient temperature at which point a yellow precipitate formed. Let stir 2 h. The desired product predominated, with a small amount of sulfoxide present. Placed in 0 deg. C. freezer overnight. In the morning, continue stirring at room temperature. After approximately 4 h, the reaction was concentrated in vacuo and partitioned between EtOAc and water. The organic layer was dried over anhydrous sodium sulfate and concentrated in vacuo to give 2-(methylsulfonyl)-4-(2-(4-nitrophenoxy)phenyl)pyrimidine. The material was used without further purification. MS m/z=372 [M+1]$^+$. Calc'd for $C_{17}H_{13}N_3SO_5$: 371.37.

Step 4. Preparation of N-methyl-4-(2-(4-nitrophenoxy)phenyl)pyrimidin-2-amine To a mixture of methylamine hydrochloride (0.863 g, 12.8 mmol), 2-(methylsulfonyl)-4-(2-(4-nitrophenoxy)phenyl)pyrimidine (0.791 g, 2.13 mmol) in iPrOH was added n,n-diisopropylethylamine (2.60 ml, 14.9 mmol). The reaction was sealed and heated to 70 deg. C. overnight. The resulting clear yellow solution was judged complete by LCMS in the morning. The reaction was cooled to ambient temperature, resulting in the formation of whit crystals. Filter, rinsing with isopropanol. Concentrate filtrate, partition between EtOAc and 1N NaOH. Dry over anhyd. Na$_2$SO$_4$, filter, concentrate to give N-methyl-4-(2-(4-nitrophenoxy)phenyl)pyrimidin-2-amine as a light yellow solid. MS m/z=323 [M+1]$^+$. Calc'd for $C_{17}H_{14}N_4O_3$: 322.32.

Step 5. 4-(2-(4-aminophenoxy)phenyl)-N-methylpyrimidin-2-amine

To N-methyl-4-(2-(4-nitrophenoxy)phenyl)pyrimidin-2-amine (0.667 g, 2.1 mmol) and palladium, 10 wt. % on activated carbon, wet (0.44 g, 0.41 mmol) in a 100 mL round bottom flask was added MeOH under nitrogen via syringe. The atmosphere was replaced with hydrogen from a balloon and the mixture stirred rapidly for 24 h. The reaction was flushed with nitrogen, and filtered through celite rinsing with 100 mL MeOH. The filtrate was concentrated in vacuo to give 4-(2-(4-aminophenoxy)phenyl)-N-methylpyrimidin-2-amine as a light yellow solid. MS m/z=293 [M+1]$^+$. Calc'd for $C_{17}H_{16}N_4O$: 292.34.

The following Examples 65-80 describe representative syntheses of exemplary C-D rings.

EXAMPLE 65

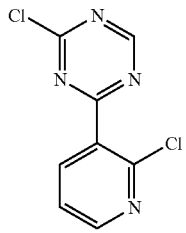

Synthesis of 2-chloro-4-(2-chloro-pyridin-3-yl)-[1,3,5]triazine

Step 1. Preparation of 2-chloro-nicotinamidine

2-Chloro-3-cyanopyridine (5.0 g, 36 mmol) was dissolved in dry EtOH (100 mL) at 0° C. HCl was bubbled through the mixture for three hours and the mixture was sealed and refrigerated (about 8° C.) overnight. After concentration, the residue was stirred with ammonium acetate (5.5 g) in 100 mL IpOH. After 12 h, the pH was adjusted to 9 (from 4) using concentrated NH$_4$OH solution, and stirring continued two more days. The mixture was concentrated and purified by flash chromatography (10:1:0.1 CH$_2$Cl$_2$/MeOH/NH$_4$OH). Trituration in hot tBuOMe/IpOH removed some residual amide side-product to provide the title compound as a white solid.

Step 2. Preparation of amino-(2-chloro-pyridin-3-yl)-methylcyanamide

2-Chloro-nicotinamidine (Step 1) was suspended in 10 mL IpOH with 500 mg solid cyanamide and the stirring solids were dissolved by addition of 5% aqueous NaHCO$_3$ (30 mL). After two days stirring, the amino-(2-chloro-pyridin-3-yl)-methylcyanamide was isolated by EtOAc extraction of the aqueous reaction mixture followed by flash chromatography using 95:5:0.5 CH$_2$Cl$_2$/MeOH/NH$_4$OH. MS m/z=181 [M+H]$^+$. Calc'd for C$_7$H$_6$N$_4$Cl: 181.03.

Step 3. Preparation of 2-chloro-4-(2-chloro-pyridin-3-yl)-[1,3,5]triazine

Amino-(2-chloro-pyridin-3-yl)-methylcyanamide (3.5 g) was added as a solid to a stirring, 0° C. solution of POCl$_3$ (2.3 ml, 25 mmol) and DMF (1.9 mL, 25 mmol) in 100 mL AcCN. The clear solution was stirred at RT for 1 h. Toluene (40 mL) was added and the mixture was concentrated. The residue was immediately filtered through a 200 g plug of silica (loading in 10:1 CH$_2$Cl$_2$/IpOH, eluting with 10:1->4:1 hexane/t-BuOMe). Concentration provided 2-chloro-4-(2-chloro-pyridin-3-yl)-[1,3,5]triazine as a white solid. MS m/z=227 [M+H]$^+$. Calc'd for C$_8$H$_4$Cl$_2$N$_4$: 225.98.

EXAMPLE 66

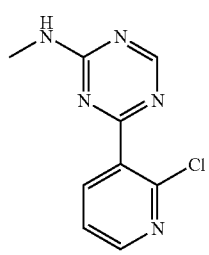

Synthesis of [4-(2-Chloro-pyridin-3-yl)-[1,3,5]triazin-2-yl]-methyl-amine

To 2-chloro-4-(2-chloro-pyridin-3-yl)-[1,3,5]triazine (10.0 g, 44.0 mmol) in 55 ml of methylene chloride was added methylamine (45 ml, 88.0 mmol) as a 2.0 M solution in THF at 0° C. After stirring at room temperature for 18 h, the mixture was diluted with acetone and filtered through a plug of silica gel and concentrated to yield the title compound. MS m/z=222 [M+H]+. Calc'd for $C_9H_8ClN_5$: 221.65.

EXAMPLE 67

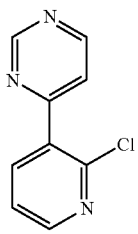

Synthesis of 4-(2-Chloro-pyridin-3-yl)-pyrimidine

Step 1. Preparation of 1-(2-Chloro-pyridin-3-yl)-3-dimethylamino-propenone 1-(2-Chloro-pyridin-3-yl)-ethanone ([Kuo, D. L. Tetrahedron, 48, 42, 9233-9236](21.7 g, 139 mmol) in 46 mL N,N-dimethylformamide, dimethyl acetal (42 g, 350 mmol) was heated under a drying tube at 85° C. for 1.5 h and concentrated. The residue was purified by suction filtration chromatography (using 150 g silica in a Buchner funnel, with rapid collection of fractions eluting with 10:1 and then 5:1 $CH_2Cl_2$/IpOH) to provide the title compound as a yellow solid. MS m/z=211 [M+H]+. Calc'd for $C_{10}H_{11}ClN_2O$: 210.66.

Step 2. Preparation of 4-(2-Chloro-pyridin-3-yl)-pyrimidine

Sodium methoxide was generated over a period of 1.5 h by the intermittent addition of small chunks of sodium metal (8.3 g total, 360 mmol) to 400 mL dry methanol under $N_2$ at room temperature, using a bath of 500 mL IpOH at room temperature as a heat sink. Formamidine acetate (42.7 g, 410 mmol) was added, followed ten minutes later by the enaminone (30.6 g, 146 mmol). The reaction was stirred overnight under a $N_2$-filled balloon at an internal temperature of 40° C. After 20 h, the mixture was stirred at 48° C. for 4 h. Additional formamidine acetate (7.0 g) was added and the mixture was stirred overnight at 44° C. The mixture was concentrated by rotary evaporator, taken up in ethyl acetate and extracted with saturated aqueous $NaHCO_3$. The aqueous layer was back-extracted with EtOAc. The combined organic layers (1.2 L) were dried over $Na_2SO_4$ and concentrated. The residue was purified by flash vacuum filtration chromatography (300 g silica) in 3:1 to 2:1 hexane/EtOAc to provide a solid white title compound. MS m/z=192 [M+H]+. Calc'd for $C_9H_6ClN_3$: 191.62.

EXAMPLE 68

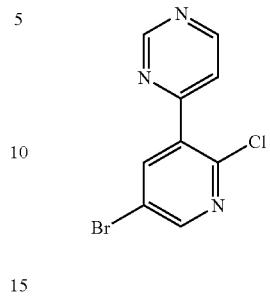

Synthesis of 4-(5-bromo-2-chloropyridin-3-yl)pyrimidine

5-Bromo-2-chloronicotinic acid (10.0 g, 42.3 mmol) was treated with thionyl chloride (10.0 mL, 137 mmol) and heated to 50° C. for 18 hours. The volatiles were removed and the resulting crude acyl chloride was treated with 80 mL anhydrous THF, trimethylsilylacetylene (5.98 mL, 42.3 mmol), and copper iodide (322 mg, 1.79 mmol). The suspension was sparged with argon for 30 seconds then dichloropalladium bistriphenylphospine (594 mg, 0.846 mmol) was added followed by triethylamine (6.18 mL, 44.4 mmol). After a brief exotherm, the reaction mixture was stirred at ambient temperature for 1 hour before addition of formamidine hydrochloride (4.09 g, 50.8 mmol), sodium carbonate monohydrate (15.7 g, 127 mmol), and methanol (100 mL). After stirring at ambient temperature (mild exotherm) for 15 minutes, the reaction was heated to reflux for 3 hours. The mixture was then allowed to cool before it was filtered through Celite and concentrated in vacuo. The resulting oil was purified by column chromatography using 10-70% EtOAc/hexanes and triturated with diethyl ether to afford the title compound as a tan, crystalline solid. MS m/z=270 (M+H)+. Calc'd for $C_9H_5BrClN_3$: 270.52.

EXAMPLE 69

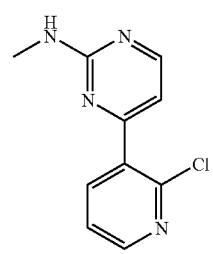

Synthesis of 4-(2-chloropyridin-3-yl)-N-methylpyrimidin-2-amine

Step 1. Preparation of 1-(2-Chloro-pyridin-3-yl)-3-dimethylamino-propenone 1-(2-Chloro-pyridin-3-yl)-ethanone [Kuo, D. L. Tetrahedron, 48, 42, 9233-9236](21.7 g, 139 mmol) in 46 mL N,N-dimethylformamide, dimethyl acetal (42 g, 350 mmol) was heated under a drying tube at 85° C. for 1.5 h and concentrated. The residue was purified by suction filtration chromatography (using 150 g silica in a Buchner funnel, with rapid collection of fractions eluting with 10:1 and then 5:1 CH$_2$Cl$_2$/IpOH) to provide the title compound as a yellow solid. MS m/z=211 [M+H]$^+$. Calc'd for C$_{10}$H$_{11}$ClN$_2$O: 210.66.

Step 2. Preparation of 4-(2-chloropyridin-3-yl)-N-methylpyrimidin-2-amine

Sodium metal (3.40 g, 148 mmol) was added over ~10 minutes to 180 mL of MeOH at RT and allowed to stir for an additional 30 minutes to generate sodium methoxide. Methyl guanidine HCl (20.0 g, 182 mmol) was added and the resulting mixture was stirred for 30 minutes before 1-(2-Chloropyridin-3-yl)-3-dimethylamino-propenone (12.0 g, 57 mmol) was added. An air condenser was attached and the mixture was heated to 50° C. for 23 hours. Part of the MeOH was removed by rotary evaporation and the resulting solid was filtered and washed with saturated sodium bicarbonate and water. The title compound was obtained as a fluffy white solid after drying. MS m/z=221 [M+H]$^+$. Calc'd for C$_{10}$H$_9$ClN$_4$: 220.66.

EXAMPLE 70

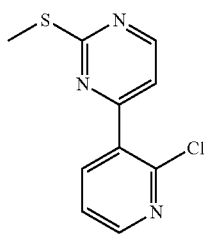

Synthesis of 4-(2-Chloropyridin-3-yl)-2-(methylthio)pyrimidine

The 5 L reactor was purged with Argon then charged with 4-chloro-2-methyl-thiopyrimidine (111 mL, 953 mmol) and 2-choropyridine-3-boronic acid (100 g, 635 mmol). The reactor was put under vacuum and filled with Argon. This was repeated two more times. Ethylene glycol dimethyl ether (500 mL) was added to the mixture followed by Pd(PPh$_3$)$_4$ (58.7 g, 50.8 mmol). The reactor was put under vacuum and filled with Argon. This was repeated two more times then more ethylene glycol dimethyl ether (1500 mL) was added. A solution of sodium bicarbonate (1M soln, 1300 mL) was added to the stirred reaction mixture. A small exotherm was observed. The reaction mixture was stirred and refluxed for 2.75 h then gradually cooled to 25° C. The mixture was diluted with F ethyl acetate (1500 mL) and vigorously stirred. The layers were allowed to separate and the aqueous phase was removed. The organic phase was washed with water (1000 mL), then brine (1000 mL), dried over magnesium sulfate and filtered. The solvents were removed under vacuum to afford the crude product as a light yellow solid. The crude product was separated by column chromatography using a mixture of ethanol and dichloromethane. The title compound was obtained as a fluffy white solid and slurried in ethyl acetate to remove traces of an impurity. MS m/z=238 [M+H]$^+$. Calc'd for C$_{10}$H$_8$ClN$_3$S: 237.71.

EXAMPLE 71

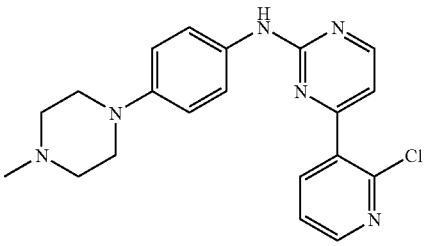

Synthesis of 4-(2-Chloropyridin-3-yl)-N-(4-(4-methylpiperazin-1-yl)phenyl)pyrimidin-2-amine Step 1. Preparation of 4-(2-chloropyridin-3-yl)-2-(methylsulfonyl)pyrimidine In a 25 mL Erlynmeyer flask, combined hydrogen peroxide (0.50 mL, 21 mmol) and ammonium molybdate tetrahydrate (52 mg, 0.042 mmol) to give deep yellow solution. In a second 25 mL round bottom flask, combined 4-(2-chloropyridin-3-yl)-2-(methylthio)pyrimidine (100 mg, 0.421 mmol) and methanol (5.0 mL). The hydrogen peroxide solution was slowly added to the MeOH solution. The mixture was stirred at room temperature for 1 hour. Concentrated MeOH until a light yellow solid crashed out, filtered, washed with water, and dried to yield 4-(2-chloropyridin-3-yl)-2-(methylsulfonyl)pyrimidine as light yellow solid. MS (M+H)$^+$=270.0, 271.9; Calc'd 269.71 for C$_{10}$H$_8$ClN$_3$O$_2$S.

Step 2. Preparation of 4-(2-chloropyridin-3-yl)-N-(4-(4-methylpiperazin-1-yl)phenyl)pyrimidin-2-amine In a 48 mL sealed pressure vessel, was added 4-(4-methylpiperazin-1-yl)benzenamine (0.851 g, 4.45 mmol), potassium carbonate (1.03 g, 7.42 mmol), N,N-dimethylformamide (10 mL) and 4-(2-chloropyridin-3-yl)-2-(methylsulfonyl)pyrimidine (Step 1, 1.0 g). the vessel was heated to 70° C. for 22 hours, cooled to room temperature, diluted with water, extracted into ethyl acetate, washed 1x with water and 1x with NaCl solution. The organics were dried over magnesium sulfate, filtered through fritted Buchner funnel, and concentrated. The crude was chromatographed on silica gel using 15-60% 90:10:1 (CH$_2$Cl$_2$:MeOH:NH$_4$OH/CH$_2$Cl$_2$) as a gradient. Concentrated the product fractions to yield 4-(2-chloropyridin-3-yl)-N-(4-(4-methylpiperazin-1-yl)phenyl)pyrimidin-2-amine as a brown solid. MS (M+H)$^+$=381. Calc'd 380.87 for C$_{20}$H$_{21}$ClN$_6$.

EXAMPLE 72

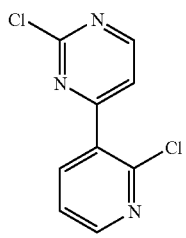

Synthesis of 2-Chloro-4-(2-chloropyridin-3-yl)pyrimidine

To 2,4-dichloropyrimidine (2.00 g, 13.4 mmol), 2-choro-pyridine-3-boronic acid (3.16 g, 20.1 mmol) and Pd(PPh$_3$)$_4$ (1.55 g, 1.30 mmol), was added DME (30.0 mL) and 1 M NaHCO$_3$ (13.0 mL). The resulting mixture was heated to 90° C. for 17 hours, then diluted with EtOAc and extracted with saturated sodium carbonate, water, and brine. The organics were dried over sodium sulfate, filtered and concentrated. The resulting solid was triturated with ether and dried to yield the title compound. MS m/z=226 [M+H]$^+$. Calc'd for C$_9$H$_5$Cl$_2$N$_4$: 225.12.

EXAMPLE 73

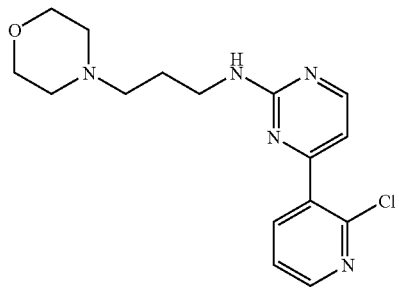

Synthesis of 4-(2-chloropyridin-3-yl)-N-(3-morpholinopropyl)pyrimidin-2-amine To 2-chloro-4-(2-chloropyridin-3-yl)pyrimidine (100 mg, 0.44 mmol) and potassium carbonate (122 mg, 0.88 mmol) was added DMSO (1.0 mL) and 3-morpholinopropan-1-amine (77 mg, 0.53 mmol). The resulting mixture was heated for 15 hours at 80° C. The cooled reaction was diluted with EtOAc and extracted with water. The organic layer was dried over sodium sulfate, filtered and concentrated to yield the title compound as a yellow oil. MS m/z=334 [M+H]$^+$. Calc'd for C$_{16}$H$_{20}$ClN$_5$O: 333.84.

EXAMPLE 74

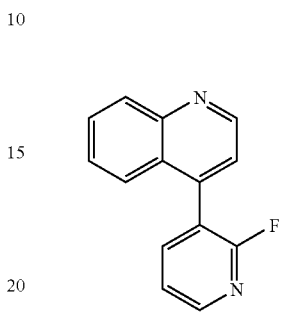

Synthesis of 4-(2-chloropyridin-3-yl)quinoline

4-Chloroquinoline (245 mg, 1.50 mmol), 2-fluoropyridine-3-boronic acid (232 mg, 1.65 mmol), Pd(PPh$_3$)$_4$ (87 mg, 0.08 mmol), DME (4.0 mL) and 1 M NaHCO$_3$ (1.0 mL) were reacted in a manner similar to Example 72. MS m/z=225 [M+1]$^+$. Calc'd for C$_{14}$H$_9$FN$_2$: 224.24.

EXAMPLE 75

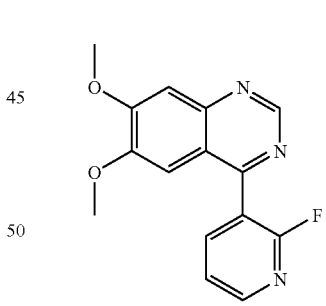

Synthesis of 4-(2-fluoro-pyridin-3-yl)-6,7-dimethoxy-quinazoline

4-Chloro-6,7-dimethoxy-quinazoline (250 mg, 1.11 mmol), 2-fluoropyridine-3-boronic acid (173 mg, 1.22 mmol), Pd(PPh$_3$)$_4$ (128 mg, 0.11 mmol), DME (4.0 mL) and 1 M NaHCO$_3$ (1.0 mL) were reacted in a manner similar to Example 72. MS m/z=286 [M+1]$^+$. Calc'd for C$_{15}$H$_{12}$FN$_3$O$_2$: 285.28.

EXAMPLE 76

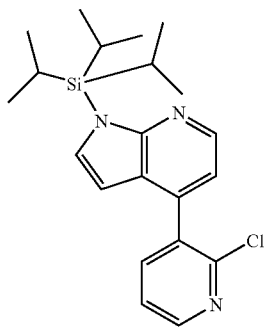

Synthesis of 4-(2-chloropyridine-3-yl)-1-(triisopropylsilyl)-1H-pyrrolo[2, 3,b]pyridine

Step 1. Preparation of 4-chloro-1-(triisopropylsilyl)-1H-pyrrolo[2,3-b]pyridine Sodium hydride (880 mg, 22 mmol, 1.1 equiv, 60% in mineral oil) was washed with 15 mL of dry hexanes under an argon atmosphere. Most of the hexanes were removed and replaced with 40 mL of THF. 4-Chloro-7-azaindole was added portionwise into the sodium hydride suspension. The suspension was stirred until the gas evolution ceased. Triisopropylchlorosilane (3 g, 20 mmol, 1 equiv) was added via syringe. The reaction was placed in a preheated oil bath at 80° C. and monitored by LC-MS and TLC. After 3 hours, the reaction was cooled to room temperature. The reaction was quenched slowly with saturated $NH_4Cl$. The product was extracted with hexanes and $Et_2O$. The organic layers were combined, washed with brine, dried over $MgSO_4$, and concentrated. The residue was passed through a plug of silica gel with an aid of hexanes to remove the baseline spots. The filtrate was concentrated to afford 4-chloro-1-(triisopropylsilyl)-1H-pyrrolo[2,3-b]pyridine as a viscous colorless oil.

Step 2. Preparation of 4-(2-chloropyridine-3-yl)-1-(triisopropylsilyl)-1H-pyrrolo[2,3,b]pyridine 4-Chloro-1-(triisopropylsilyl)-1H-pyrrolo[2,3-b]pyridine (5.03 g, 16.3 mmol, 1 equiv), 2-chlorpyridine-3-boronic acid (4.36 g, 27.7 mmol, 1.7 equiv), palladium acetate (183 mg, 0.815 mmol, 5 mol %), 2-(dicyclohexylphosphino)biphenyl (571 mg, 1.63 mmol, 10 mol %), and finely ground anhydrous $K_3PO_4$ (10.4 g, 48.9 mmol, 3 equiv) were added into a sealed tube. The tube was purged with argon for 5 minutes. Dioxane (30 mL) was added via syringe under a positive argon flow. The tube was sealed and the reaction was stirred at room temperature for 5 minutes. Then the tube was placed in a preheated oil bath at 110° C. for 2 h. The reaction was cooled down to room temperature. The content was filtered through a plug of celite with an aid of diethyl ether. The filtrated was concentrated under reduced pressure. The crude was purified by column chromatography using a mixture of 95:5 Hex: $Et_2O$ as eluent. The product, 4-(2-chloropyridine-3-yl)-1-(triisopropylsilyl)-1H-pyrrolo[2,3,b]pyridine was obtained as a light yellow solid. $^1H$ NMR (Varian, 300 MHz, $CDCl_3$): 8.35 (d, J=4.7 Hz, 1H), 8.30-8.28 (m, 1H), 8.10-8.03 (m, 1H), 7.40-7.30 (m, 2H), 7.15 (dd, J=4.3, 1.7 Hz, 1H), 6.54 (dd, J=3.6, 1.9 Hz, 1H), 1.89 (sept, J=7.4 Hz, 3H), 1.15 (d, J=7.4 Hz, 18H)

EXAMPLE 77

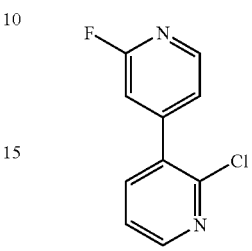

Synthesis of 2-Chloro-2'-fluoro-[3,4']bipyridinyl

To 2-fluoro-4-iodopyridine (9.45 g, 42.4 mmol), 2-chloropyridine-3-boronic acid (10.0 g, 63.5 mmol), $Na_2CO_3$ (13.5 g, 127 mmol), $Pd(OAc)_2$ (480 mg, 2.12 mmol) and P$(tBu)_3 \cdot HBF_4$ (1.23 g, 4.24 mmol) was added dioxane (125 mL) and water (45 mL). The mixture was heated overnight at 100° C. in a sealed tube. The resulting mixture was diluted with EtOAc and extracted with water and brine. The organic layer was dried over $Na_2SO_4$, filtered and concentrated. The resulting solid was triturated with n-Hexanes and dried to yield 2-chloro-2'-fluoro-[3,4']bipyridinyl. MS m/z=209 $[M+1]^+$. Calc'd for $C_{10}H_6ClFN_2$: 208.62.

EXAMPLE 78

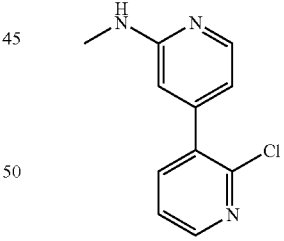

Synthesis of (2-Chloro-[3,4']bipyridinyl-2'-yl)-methyl-amine

To 2-chloro-2'-fluoro-[3,4']bipyridinyl (5.30 g, 25.4 mmol), methylamine hydrochloride (9.00 g, 133 mmol) and $K_2CO_3$ (28.1 g, 203 mmol) was added DMSO (70 mL). The mixture was heated overnight at 80° C. in a sealed tube. The cooled mixture was diluted with water (300 mL) and the resulting solid was filtered, washed with water and dried to yield (2-chloro-[3,4']bipyridinyl-2'-yl)-methyl-amine. MS m/z=220 $[M+1]^+$. Calc'd for $C_{11}H_{10}ClN_3$: 219.68.

EXAMPLE 79

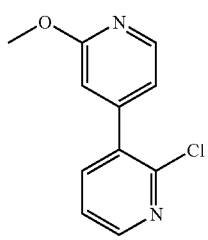

Synthesis of
2-Chloro-3-(2-methoxypyridin-4-yl)pyridine

Step 1. Preparation of 4-iodo-2-methoxypyridine

To 2-fluoro-4-iodopyridine (500 mg, 2.2 mmol) and cesium carbonate (730 mg, 2.2 mmol) was added THF (5 mL) and MeOH (0.091 mL, 2.2 mmol). The resulting mixture was heated to 50° C. for 24 hours in a sealed tube. The cooled mixture was diluted with water and extracted with EtOAc. The organic layer was dried over sodium sulfate, filtered and concentrated to yield the title compound. MS m/z=236 [M+1]$^+$. Calc'd for $C_6H_{61}NO$: 235.03.

Step 2. Preparation of
2-chloro-3-(2-methoxypyridin-4-yl)pyridine

To 4-iodo-2-methoxypyridine (834 mg, 3.55 mmol), 2-chloropyridine-3-boronic acid (838 mg, 5.32 mmol), $Na_2CO_3$ (1.13 g, 10.7 mmol), Pd(OAc)$_2$ (40 mg, 0.18 mmol) and P(tBu)$_3$·HBF$_4$ (104 mg, 0.36 mmol) was added dioxane (12 mL) and water (4 mL). The mixture was heated overnight at 100° C. in a sealed tube. The resulting mixture was diluted with EtOAc and extracted with water and brine. The organic layer was dried over $Na_2SO_4$, filtered and concentrated. The resulting solid was triturated with MeOH and dried to yield the title compound. MS m/z=221 [M+1]$^+$. Calc'd for $C_{11}H_9ClN_2O$: 220.66.

EXAMPLE 80

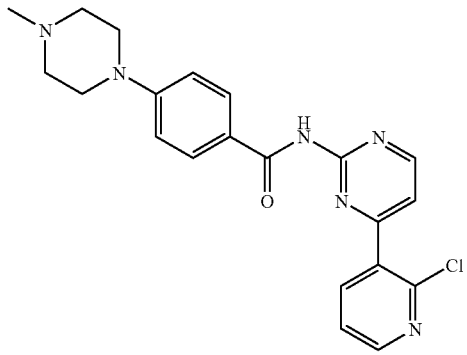

Synthesis of N-(4-(2-chloropyridin-3-yl)pyrimidin-2-yl)-4-(4-methylpiperazin-1-yl)benzamide Step 1. Preparation of
4-(2-chloropyridin-3-yl)pyrimidin-2-amine In an argon purged 500 mL round bottom flask placed in an isopropanol bath (used as a heat sink), added sodium metal (3.40 g, 148 mmol) slowly to methanol (180 mL). Stirred at RT for 30 minutes. Added guanidine hydrochloride (17.0 g, 182 mmol), stirred at RT for 30 minutes, added (E)-1-(2-chloropyridin-3-yl)-3-(dimethylamino)prop-2-en-1-one (12.0 g, 57.0 mmol), attached air condenser, and heated to 50° C. for 24 hours. Removed approximately half of the methanol by rotary evaporation. Filtered solids onto side-armed flask under vacuum, then washed with saturated $NaHCO_3$ and $H_2O$, air dried to yield 4-(2-chloropyridin-3-yl)pyrimidin-2-amine as off-white solid. MS (M+H)$^+$=206. Calc'd 206.63 for $C_9H_7ClN_4$.

Step 2. Preparation of
4-(4-methylpiperazin-1-yl)benzoyl chloride

In a 50 mL round bottom flask, dissolved 4-(4-methylpiperazin-1-yl)benzoic acid (1.00 g, 4.50 mmol) in dichloromethane (5.0 mL). Added oxalyl chloride (1.2 mL, 9.1 mmol) and N,N-dimethylformamide (2 drops). Stirred at RT for 2 hours. Concentrated and isolated 4-(4-methylpiperazin-1-yl)benzoyl chloride as an off-white solid. LC/MS of methyl ester (quenched with methanol) revealed an MS (M+H)$^+$ of 235; Calc'd 234.29 for $C_{13}H_{18}N_2O_2$ (methyl ester).

Step 3. Preparation of N-(4-(2-chloropyridin-3-yl)pyrimidin-2-yl)-4-(4-methylpiperazin-1-yl)benzamide In a 48 mL sealed pressure vessel, added 4-(2-chloropyridin-3-yl)pyrimidin-2-amine (Step 1, 0.72 g, 3.5 mmol), 4-(4-methylpiperazin-1-yl)benzoyl chloride (1.0 g, 4.2 mmol), chloroform (5.0 mL), and N,N-diisopropylethylamine (0.73 mL, 4.2 mmol). The mixture was stirred at 50° C. for 17 hours, and concentrated to yield N-(4-(2-chloropyridin-3-yl)pyrimidin-2-yl)-4-(4-methylpiperazin-1-yl)benzamide as a light brown solid. MS (M+H)$^+$=409; Calc'd 408.88 for $C_{21}H_{21}ClN_6O$.

The following, more specific, representative methods (designated herein as methods A-Q) were used to complete synthesis of exemplary compounds of Formulas I-III. The tabulated list of compounds following each representative A-Q method were synthesized by that method. For example, Examples 81a-197 were made by method A.

Method A

EXAMPLE 81

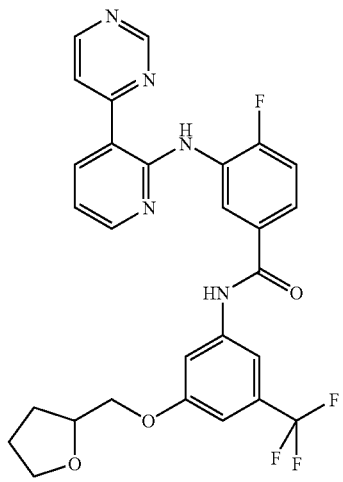

Synthesis of 4-Fluoro-3-(3-pyrimidin-4-yl-pyridin-2-ylamino)-N-[3-(tetrahydro-furan-2-ylmethoxy)-5-trifluoromethyl-phenyl]-benzamide

Step 1. Preparation of 4-Fluoro-3-(3-pyrimidin-4-yl-pyridin-2-ylamino)-benzoic acid 4-(2-Chloro-pyridin-3-yl)-pyrimidine (240 mg, 1.2 mmol), 3-amino-4-fluorobenzoic acid (217 mg, 1.40 mmol), and 340 mg $Et_3N$-TFA salt were mixed together in a sealed tube under argon. (The liquid $Et_3N$-TFA reagent was generated by adding 2.5 mL TFA dropwise to a 0° C. solution of 3 mL $Et_3N$ in isopropanol, then concentrating by rotary evaporator followed by 30 minutes under high vacuum.). The mixture was melted at 95° C., and heating was continued overnight. The residue was triturated with a small amount of methanol and filtered to obtain the title compound as a solid. MS m/z=311 [M+H]$^+$. Calc'd for $C_{16}H_{11}FN_4O_2$: 310.29.

Step 2. Preparation of 4-Fluoro-3-(3-pyrimidin-4-yl-pyridin-2-ylamino)-N-[3-(tetrahydro-furan-2-ylmethoxy)-5-trifluoromethyl-phenyl]-benzamide 4-Fluoro-3-(3-pyrimidin-4-yl-pyridin-2-ylamino)-benzoic acid (142 mg, 0.46 mmol, azeotropically-dried from xylenes) was suspended in 4 mL dry DMF under $N_2$. EDC (105 mg, 0.55 mmol) and DMAP (0.45 mmol) was added, and the mixture was stirred at 68° C. for ten minutes. After cooling, azeotropically-dried 3-(tetrahydro-furan-2-ylmethoxy)-5-trifluoromethyl-phenylamine (synthesized according to general procedures described U.S. Pat. Pub. 2003203922A1) in 3 mL DMF was added to the mixture, which was then stirred under $N_2$ at 68° C. for 18 h. Concentration, trituration with methanol, and filtration provided a yellow solid. Further purification was provided by flash chromatography (1:1:1 $CH_2Cl_2$/hexanes/t-BuOMe to 1% 10:1 MeOH in 1:1:1 $CH_2Cl_2$/hexanes/t-BuOMe). After concentration, trituration again with methanol provided the title compound as a yellow solid. MS m/z=554 [M+H]$^+$. Calc'd for $C_{28}H_{23}F_4N_5O_3$: 553.52.

| Ex. No. | Structure Name | Structure | MW | MS Data |
|---|---|---|---|---|
| 81a | 4-methyl-N-(3-(1-methylethyl)phenyl)-3-((3-(4-pyrimidinyl)-2-pyridinyl)amino)benzamide | 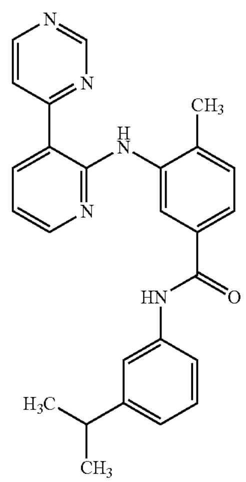 | 423.52 | 424 |
| 82 | N-(4-(1,1-dimethylethyl)phenyl)-4-methyl-3-((3-(4-pyrimidinyl)-2-pyridinyl)amino)benzamide | 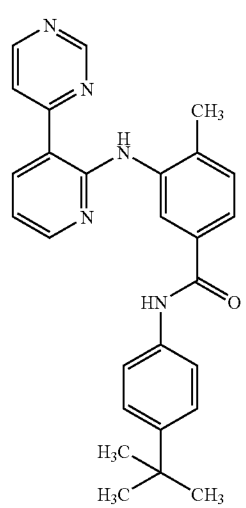 | 437.54 | 446 |

-continued
| Ex. No. | Structure Name | Structure | MW | MS Data |
|---|---|---|---|---|
| 83 | N-(3-(3-(dimethylamino)propyl)-5-(trifluoromethyl)phenyl)-4-methyl-3-((3-(4-pyrimidinyl)-2-pyridinyl)amino)benzamide | 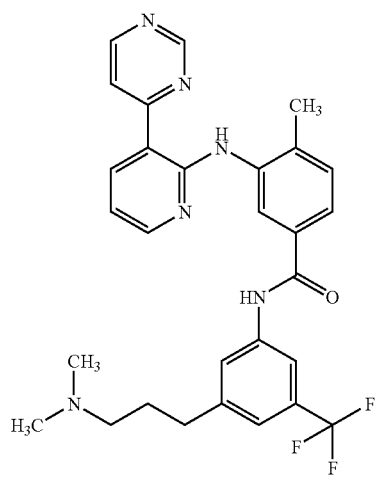 | 534.58 | 535 |
| 84 | N-(5-(1,1-dimethylethyl)-3-isoxazolyl)-4-methyl-3-((3-(4-pyrimidinyl)-2-pyridinyl)amino)benzamide | 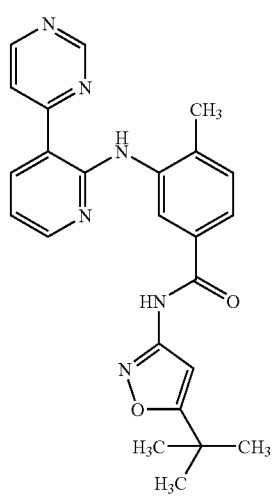 | 428.49 | 429 |
| 85 | 4-methyl-3-((3-(4-pyrimidinyl)-2-pyridinyl)amino)-N-(4-(trifluoromethyl)phenyl)benzamide | 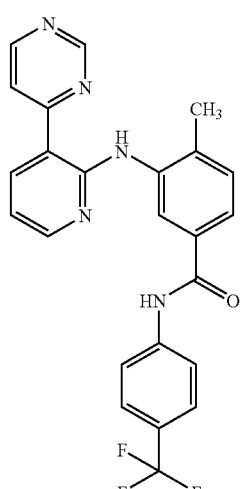 | 449.43 | 450 |

| Ex. No. | Structure Name | Structure | MW | MS Data |
|---|---|---|---|---|
| 86 | 4-chloro-3-((3-(4-pyrimidinyl)-2-pyridinyl)amino)-N-(4-(trifluoromethyl)phenyl)benzamide | 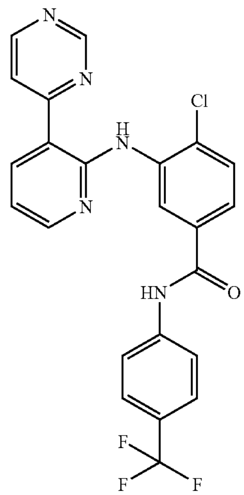 | 469.85 | |
| 87 | N-(4-(1,1-dimethylethyl)-3-(3-(4-morpholinyl)propyl)phenyl)-4-methyl-3-((3-(4-pyrimidinyl)-2-pyridinyl)amino)benzamide | 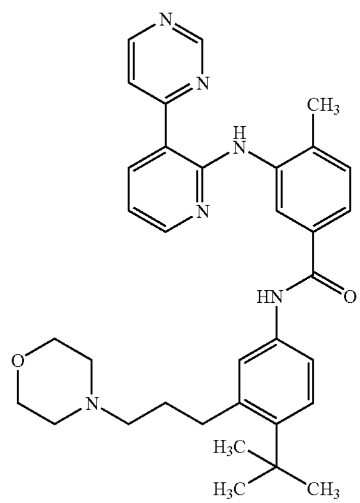 | 564.73 | 565 |
| 88 | 4-methyl-3-((3-(4-pyrimidinyl)-2-pyridinyl)amino)-N-(3-(trifluoromethyl)phenyl)benzamide | 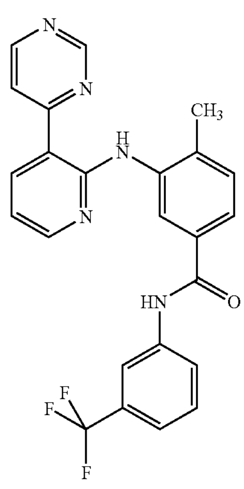 | 449.43 | 450 |

-continued

| Ex. No. | Structure Name | Structure | MW | MS Data |
|---|---|---|---|---|
| 89 | 4-chloro-N-(3-(1-methylethyl)phenyl)-3-((3-(4-pyrimidinyl)-2-pyridinyl)amino)benzamide | 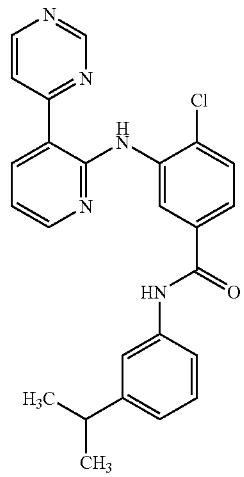 | 443.94 | 444 |
| 90 | 4-fluoro-N-(3-(1-methylethyl)phenyl)-3-((3-(4-pyrimidinyl)-2-pyridinyl)amino)benzamide | 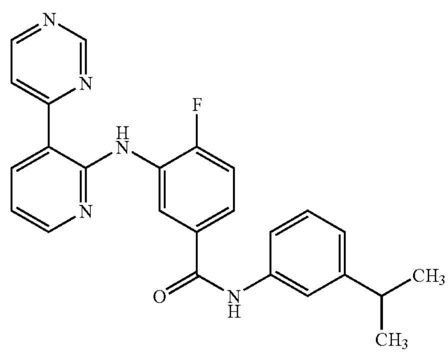 | 427.48 | 428 |
| 91 | 4-fluoro-3-((3-(4-pyrimidinyl)-2-pyridinyl)amino)-N-(3-(trifluoromethyl)phenyl)benzamide | 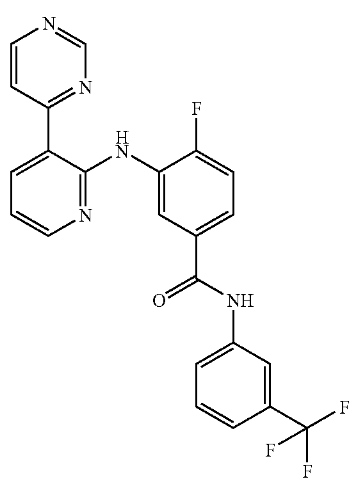 | 453.4 | 454 |

| Ex. No. | Structure Name | Structure | MW | MS Data |
|---|---|---|---|---|
| 92 | 4-fluoro-3-((3-(4-pyrimidinyl)-2-pyridinyl)amino)-N-(3-((3R)-tetrahydro-3-furanyloxy)-5-(trifluoromethyl)phenyl)benzamide | 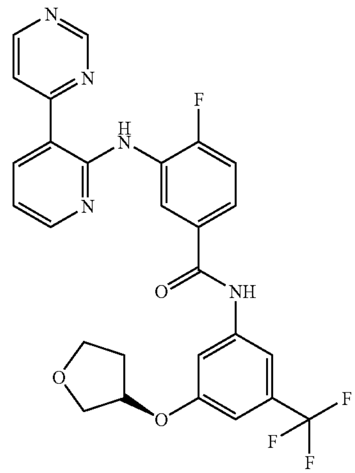 | 539.49 | 540 |
| 93 | N-(1-acetyl-3,3-dimethyl-2,3-dihydro-1H-indol-6-yl)-4-fluoro-3-((3-(4-pyrimidinyl)-2-pyridinyl)amino)benzamide | 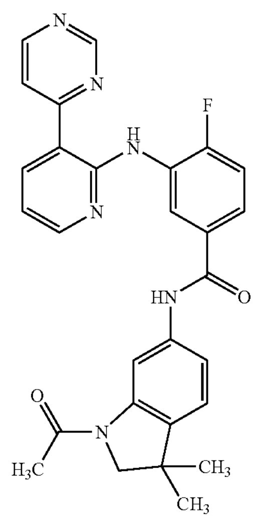 | 496.54 | 497 |
| 94 | N-((1R)-1-cyclohexylethyl)-4-methyl-3-((3-(4-pyrimidinyl)-2-pyridinyl)amino)benzamide | 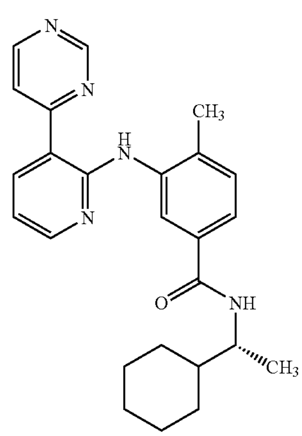 | 415.54 | 416 |

| Ex. No. | Structure Name | Structure | MW | MS Data |
|---|---|---|---|---|
| 95 | N-((1S)-1-cyclohexylethyl)-4-methyl-3-((3-(4-pyrimidinyl)-2-pyridinyl)amino)benzamide | 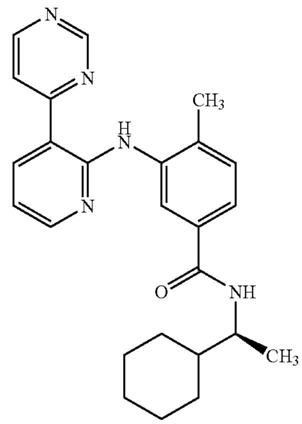 | 415.54 | 416 |
| 96 | N-(4,4-dimethyl-1,2,3,4-tetrahydro-7-quinolinyl)-4-fluoro-3-((3-(4-pyrimidinyl)-2-pyridinyl)amino)benzamide | 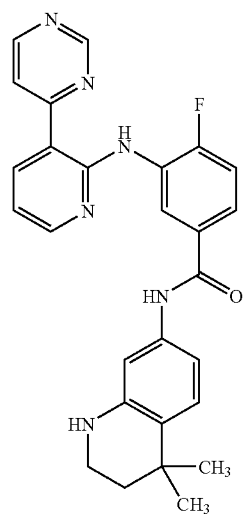 | 468.53 | 469 |
| 97 | N-(3-(1,1-dimethylethyl)-1-methyl-1H-pyrazol-5-yl)-4-methyl-3-((3-(4-pyrimidinyl)-2-pyridinyl)amino)benzamide | 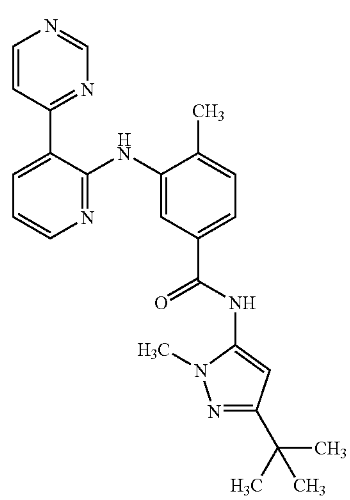 | 441.54 | 442 |

| Ex. No. | Structure Name | Structure | MW | MS Data |
|---|---|---|---|---|
| 98 | 4-(methyloxy)-3-((3-(4-pyrimidinyl)-2-pyridinyl)amino)-N-(3-(trifluoromethyl)phenyl)benzamide | 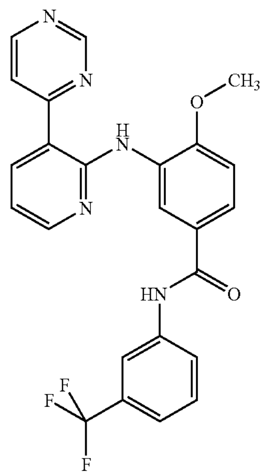 | 465.43 | 466 |
| 99 | N-(3-amino-5-(trifluoromethyl)phenyl)-4-methyl-3-((3-(4-pyrimidinyl)-2-pyridinyl)amino)benzamide | 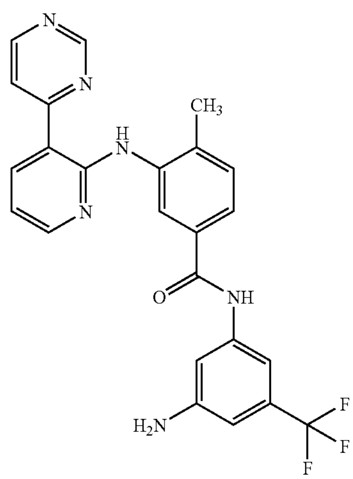 | 464.45 | 465 |
| 100 | N-(2-fluoro-5-(trifluoromethyl)phenyl)-4-methyl-3-((3-(4-pyrimidinyl)-2-pyridinyl)amino)benzamide | 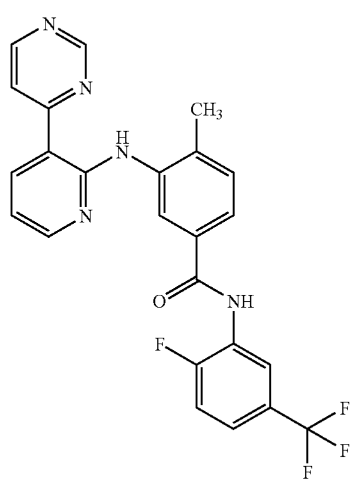 | 467.42 | 468 |

-continued
| Ex. No. | Structure Name | Structure | MW | MS Data |
|---|---|---|---|---|
| 101 | N-(3-chlorophenyl)-4-methyl-3-((3-(4-pyrimidinyl)-2-pyridinyl)amino)benzamide | 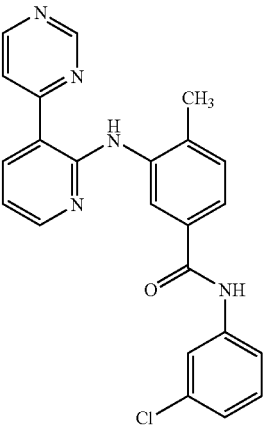 | 415.88 | 416 |
| 102 | 4-methyl-N-(4-(phenyloxy)phenyl)-3-((3-(4-pyrimidinyl)-2-pyridinyl)amino)benzamide | 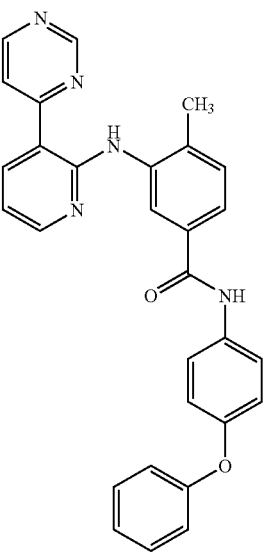 | 473.53 | 474 |
| 103 | N-(2-methyl-5-((6-(trifluoromethyl)-1H-indol-1-yl)carbonyl)phenyl)-3-(4-pyrimidinyl)-2-pyridinamine | 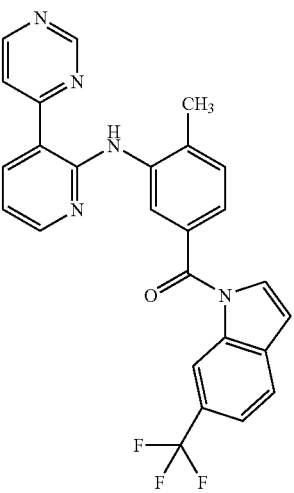 | 473.46 | 474 |

| Ex. No. | Structure Name | Structure | MW | MS Data |
|---|---|---|---|---|
| 104 | N-(4-(dimethylamino)phenyl)-4-methyl-3-((3-(4-pyrimidinyl)-2-pyridinyl)amino)benzamide | 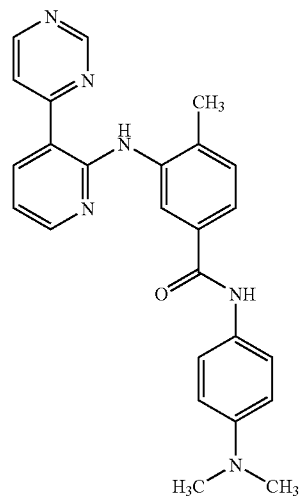 | 424.51 | 425 |
| 105 | 4-methyl-N-(3-(methyloxy)-5-(trifluoromethyl)phenyl)-3-((3-(4-pyrimidinyl)-2-pyridinyl)amino)benzamide | 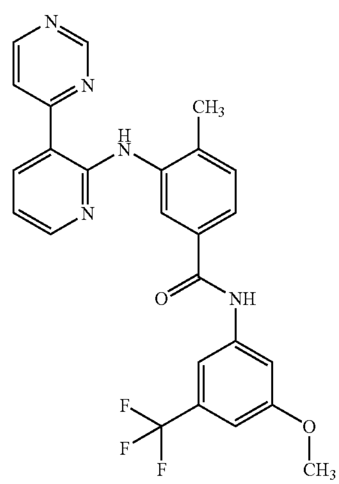 | 479.46 | 480 |
| 106 | N-(2-fluoro-3-(trifluoromethyl)phenyl)-4-methyl-3-((3-(4-pyrimidinyl)-2-pyridinyl)amino)benzamide | 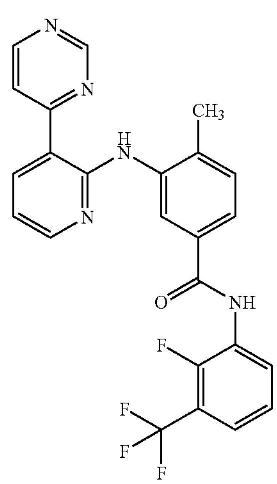 | 497.42 | 468 |

| Ex. No. | Structure Name | Structure | MW | MS Data |
|---|---|---|---|---|
| 107 | N-(2,3-dihydro-1H-inden-5-yl)-4-methyl-3-((3-(4-pyrimidinyl)-2-pyridinyl)amino)benzamide | 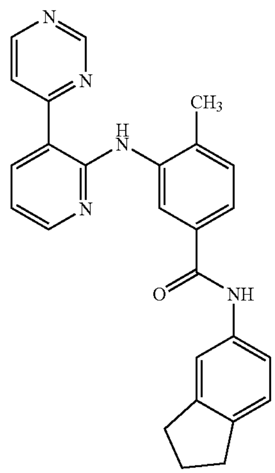 | 421.5 | 422 |
| 108 | 4-methyl-N-(4-((phenylmethyl)oxy)phenyl)-3-((3-(4-pyrimidinyl)-2-pyridinyl)amino)benzamide | 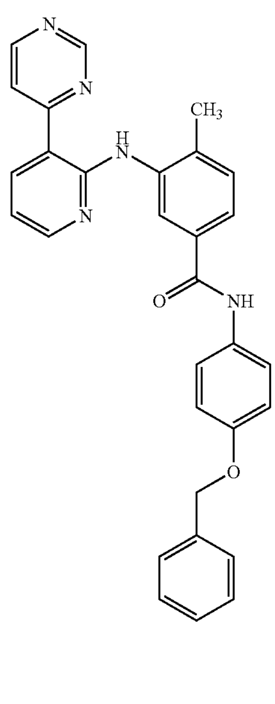 | 487.56 | 488 |

-continued

| Ex. No. | Structure Name | Structure | MW | MS Data |
|---|---|---|---|---|
| 109 | 4-methyl-3-((3-(4-pyrimidinyl)-2-pyridinyl)amino)-N-((3-(trifluoromethyl)phenyl)methyl)benzamide | 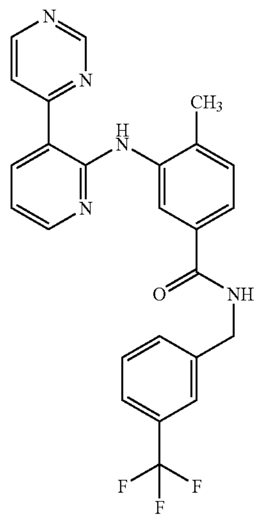 | 463.46 | 464 |
| 110 | N-(3-(dimethylamino)phenyl)-4-methyl-3-((3-(4-pyrimidinyl)-2-pyridinyl)amino)benzamide | 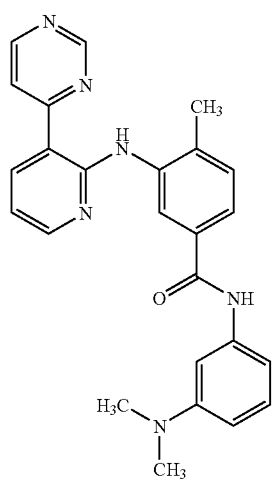 | 424.51 | 425 |
| 111 | N-(4-fluoro-3-(trifluoromethyl)phenyl)-4-methyl-3-((3-(4-pyrimidinyl)-2-pyridinyl)amino)benzamide | 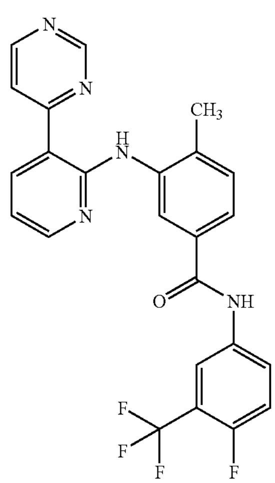 | 467.42 | 468 |

-continued

| Ex. No. | Structure Name | Structure | MW | MS Data |
|---|---|---|---|---|
| 112 | N-(2-chloro-5-(trifluoromethyl)phenyl)-4-methyl-3-((3-(4-pyrimidinyl)-2-pyridinyl)amino)benzamide | 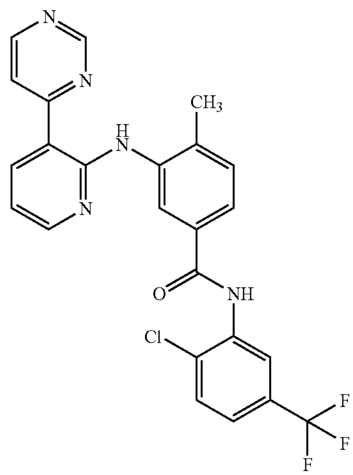 | 483.88 | 484 |
| 113 | 4-methyl-N-(3-methylphenyl)-3-((3-(4-pyrimidinyl)-2-pyridinyl)amino)benzamide | 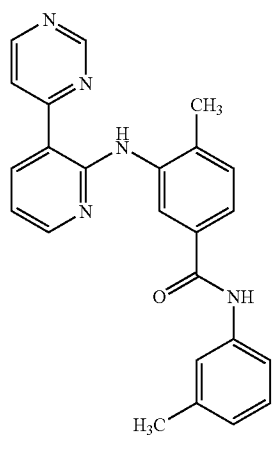 | 395.46 | 396 |
| 114 | 4-methyl-3-((3-(4-pyrimidinyl)-2-pyridinyl)amino)-N-((2-(trifluoromethyl)phenyl)methyl)benzamide | 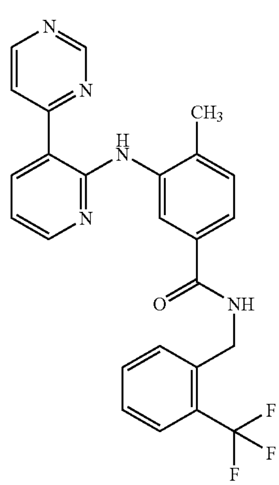 | 463.46 | 464 |

-continued

| Ex. No. | Structure Name | Structure | MW | MS Data |
|---|---|---|---|---|
| 115 | N-(1H-indazol-5-yl)-4-methyl-3-((3-(4-pyrimidinyl)-2-pyridinyl)amino)benzamide | 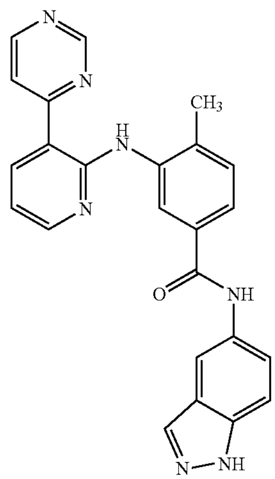 | 421.46 | 422 |
| 116 | N-(4-chloro-3-(trifluoromethyl)phenyl)-4-methyl-3-((3-(4-pyrimidinyl)-2-pyridinyl)amino)benzamide | 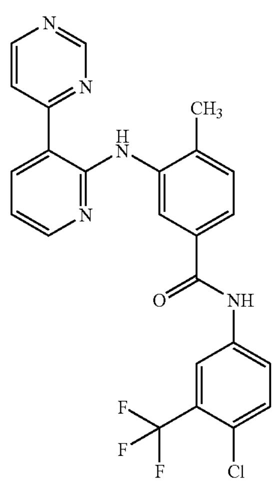 | 483.88 | 484 |
| 117 | 4-methyl-N-(2-methyl-5-(trifluoromethyl)phenyl)-3-((3-(4-pyrimidinyl)-2-pyridinyl)amino)benzamide | 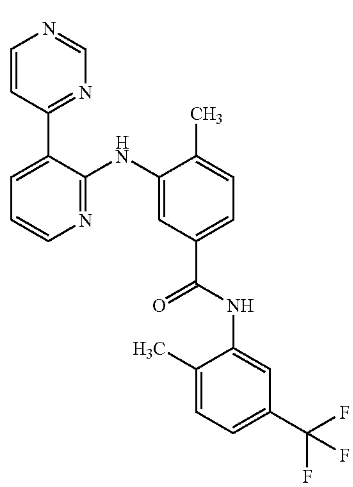 | 463.46 | 464 |

-continued

| Ex. No. | Structure Name | Structure | MW | MS Data |
|---|---|---|---|---|
| 118 | N-(3,4-dimethylphenyl)-4-methyl-3-((3-(4-pyrimidinyl)-2-pyridinyl)amino)benzamide | 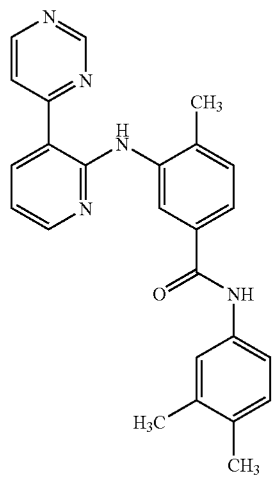 | 409.49 | 410 |
| 119 | 4-methyl-N-(3-((phenylmethyl)oxy)phenyl)-3-((3-(4-pyrimidinyl)-2-pyridinyl)amino)benzamide | 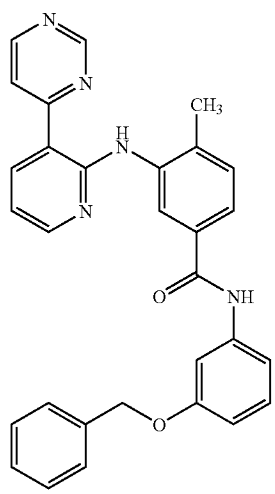 | 487.56 | 488 |
| 120 | 4-methyl-3-((3-(4-pyrimidinyl)-2-pyridinyl)amino)-N-((4-(trifluoromethyl)phenyl)methyl)benzamide | 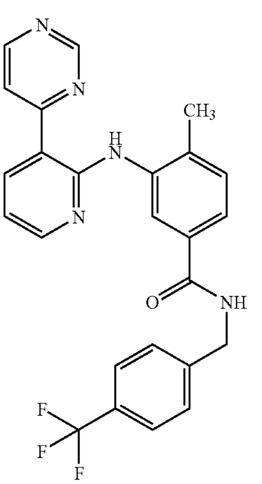 | 463.46 | 464 |

-continued

| Ex. No. | Structure Name | Structure | MW | MS Data |
|---------|----------------|-----------|-----|---------|
| 121 | N-(1H-indazol-6-yl)-4-methyl-3-((3-(4-pyrimidinyl)-2-pyridinyl)amino)benzamide | 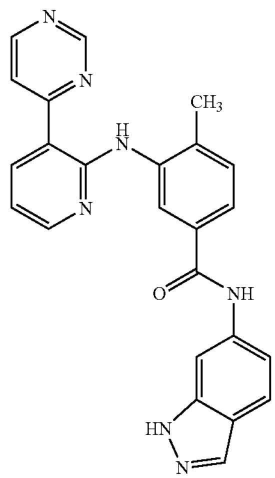 | 421.46 | 422 |
| 122 | 4-methyl-N-(4-(methyloxy)-3-(trifluoromethyl)phenyl)-3-((3-(4-pyrimidinyl)-2-pyridinyl)amino)benzamide | 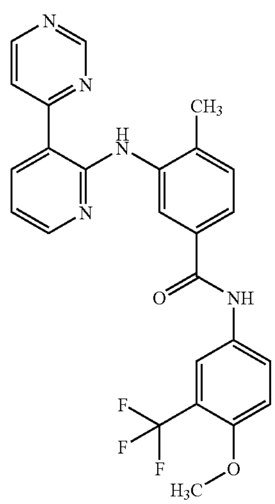 | 479.46 | 480 |
| 123 | 4-methyl-N-(2-(methyloxy)-5-(trifluoromethyl)phenyl)-3-((3-(4-pyrimidinyl)-2-pyridinyl)amino)benzamide | 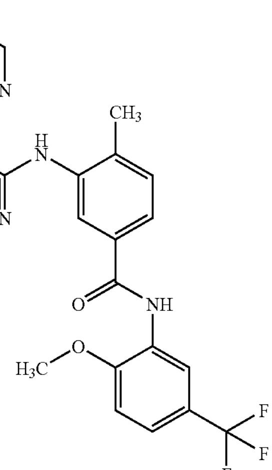 | 479.46 | 480 |

| Ex. No. | Structure Name | Structure | MW | MS Data |
|---|---|---|---|---|
| 124 | N-(4-(aminocarbonyl)phenyl)-4-methyl-3-((3-(4-pyrimidinyl)-2-pyridinyl)amino)benzamide | 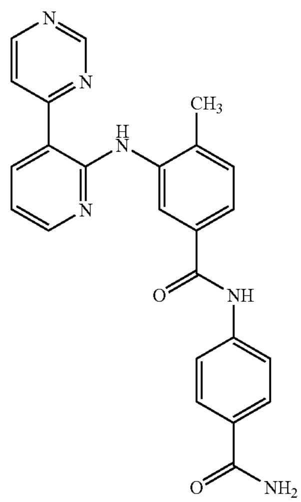 | 424.46 | 425 |
| 125 | N-(3,5-bis(trifluoromethyl)phenyl)-4-methyl-3-((3-(4-pyrimidinyl)-2-pyridinyl)amino)benzamide | 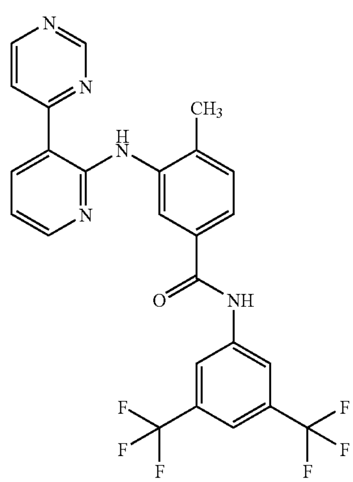 | 517.43 | 518 |
| 126 | N-(3-chloro-4-((trifluoromethyl)oxy)phenyl)-4-methyl-3-((3-(4-pyrimidinyl)-2-pyridinyl)amino)benzamide | 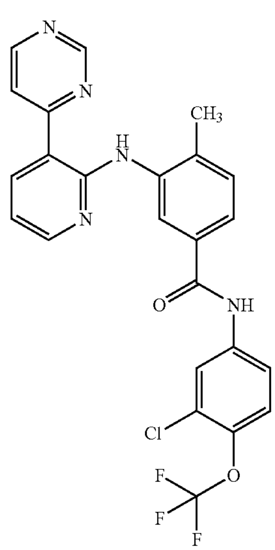 | 499.88 | 500 |

| Ex. No. | Structure Name | Structure | MW | MS Data |
|---|---|---|---|---|
| 127 | N-(4-cyclohexylphenyl)-4-methyl-3-((3-(4-pyrimidinyl)-2-pyridinyl)amino)benzamide | 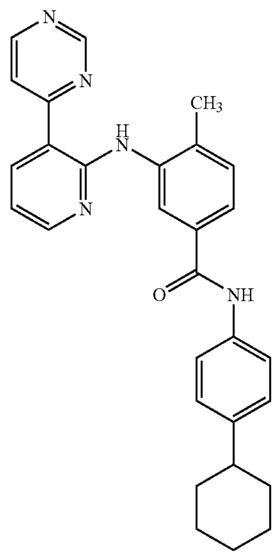 | 463.58 | 464 |
| 128 | N-(3-(dimethylamino)-2,2-dimethylpropyl)-4-methyl-3-((3-(4-pyrimidinyl)-2-pyridinyl)amino)benzamide | 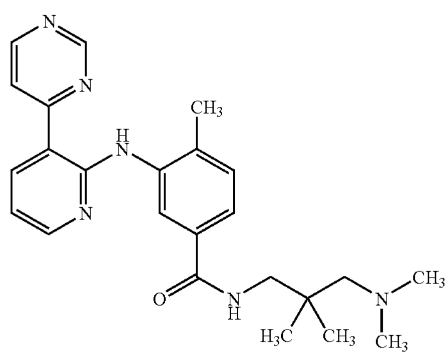 | 418.54 | 419 |
| 129 | N-(3-(hydroxymethyl)phenyl)-4-methyl-3-((3-(4-pyrimidinyl)-2-pyridinyl)amino)benzamide | 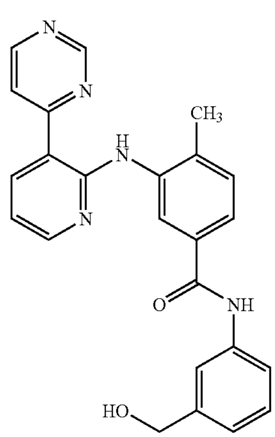 | 411.46 | 412 |

-continued

| Ex. No. | Structure Name | Structure | MW | MS Data |
|---|---|---|---|---|
| 130 | N-(5-chloro-2-fluorophenyl)-4-methyl-3-((3-(4-pyrimidinyl)-2-pyridinyl)amino)benzamide | 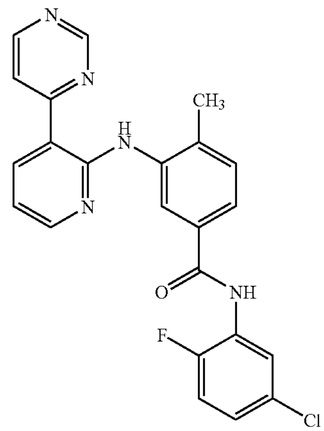 | 433.87 | 434 |
| 131 | N-(3-chloro-4-fluorophenyl)-4-methyl-3-((3-(4-pyrimidinyl)-2-pyridinyl)amino)benzamide | 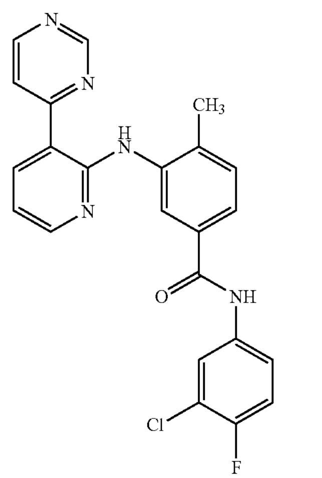 | 433.87 | 434 |
| 132 | N-(3-hydroxy-2,2-dimethylpropyl)-4-methyl-3-((3-(4-pyrimidinyl)-2-pyridinyl)amino)benzamide | 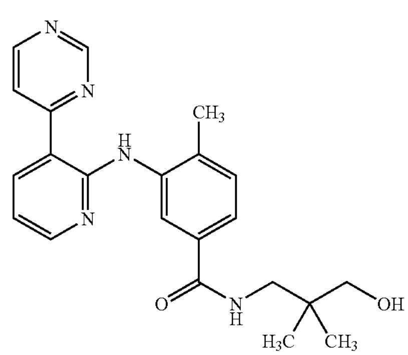 | 391.47 | 392 |

| Ex. No. | Structure Name | Structure | MW | MS Data |
|---|---|---|---|---|
| 133 | N-(3-(aminocarbonyl)phenyl)-4-methyl-3-((3-(4-pyrimidinyl)-2-pyridinyl)amino)benzamide | 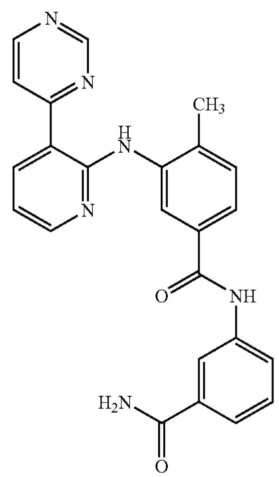 | 424.46 | 425 |
| 134 | N-(3,5-dimethylphenyl)-4-methyl-3-((3-(4-pyrimidinyl)-2-pyridinyl)amino)benzamide | 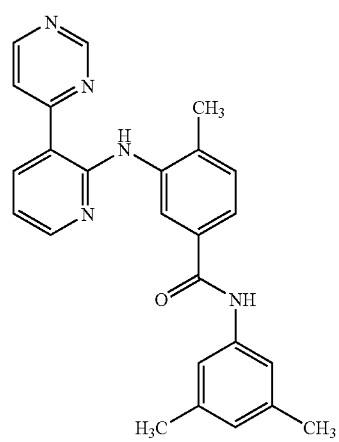 | 409.49 | 391 |
| 135 | N-(3,5-dichlorophenyl)-4-methyl-3-((3-(4-pyrimidinyl)-2-pyridinyl)amino)benzamide | 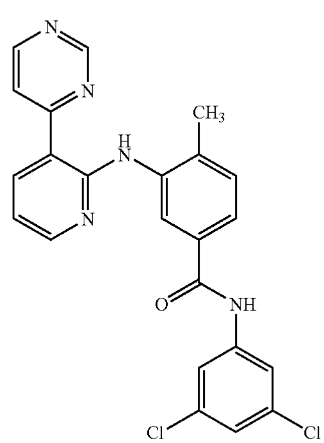 | 450.33 | 450 |

| Ex. No. | Structure Name | Structure | MW | MS Data |
|---|---|---|---|---|
| 136 | 4-methyl-N-(2-(1-methylethyl)phenyl)-3-((3-(4-pyrimidinyl)-2-pyridinyl)amino)benzamide | 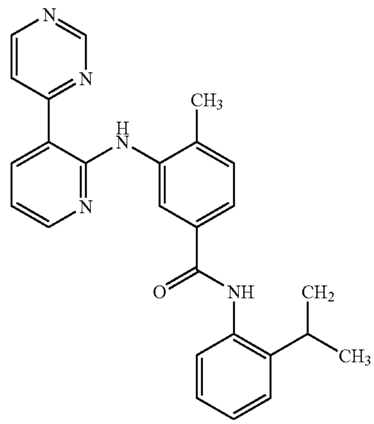 | 423.52 | 424 |
| 137 | N-(3-(1,1-dimethylethyl)phenyl)-4-methyl-3-((3-(4-pyrimidinyl)-2-pyridinyl)amino)benzamide | 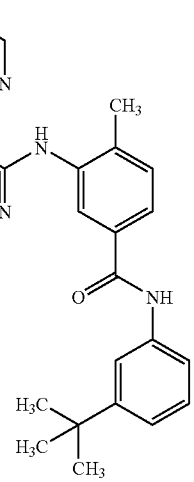 | 437.54 | 438 |
| 138 | 4-methyl-N-(1-naphthalenyl)-3-((3-(4-pyrimidinyl)-2-pyridinyl)amino)benzamide | 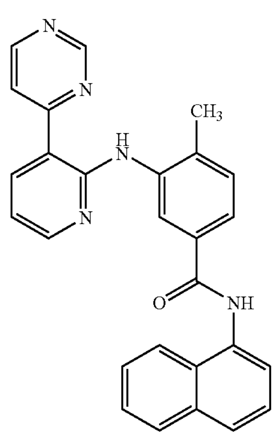 | 431.5 | 432 |

| Ex. No. | Structure Name | Structure | MW | MS Data |
|---|---|---|---|---|
| 139 | N-(3-(ethyloxy)phenyl)-4-methyl-3-((3-(4-pyrimidinyl)-2-pyridinyl)amino)benzamide | 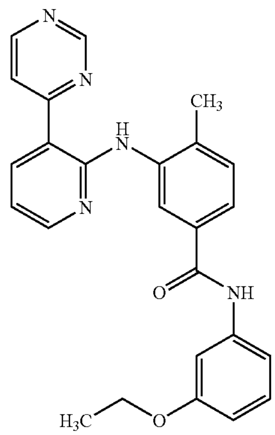 | 425.49 | 426 |
| 140 | N-(4-(1,1-dimethylethyl)cyclohexyl)-4-methyl-3-((3-(4-pyrimidinyl)-2-pyridinyl)amino)benzamide | 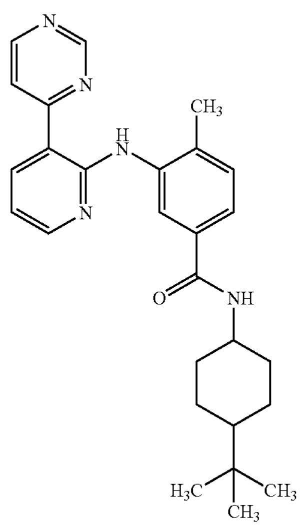 | 443.59 | 444 |
| 141 | N-(2-methyl-5-(1-piperidinylcarbonyl)phenyl)-3-(4-pyrimidinyl)-2-pyridinamine | 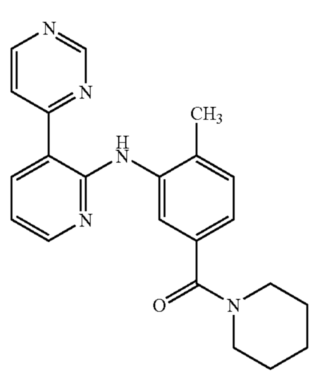 | 373.46 | 374 |

-continued

| Ex. No. | Structure Name | Structure | MW | MS Data |
|---|---|---|---|---|
| 142 | 4-methyl-N-phenyl-3-((3-(4-pyrimidinyl)-2-pyridinyl)amino)benzamide | 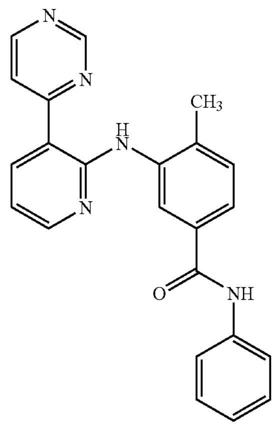 | 381.44 | 302 |
| 143 | N-(5-chloro-2-(methyloxy)phenyl)-4-methyl-3-((3-(4-pyrimidinyl)-2-pyridinyl)amino)benzamide | 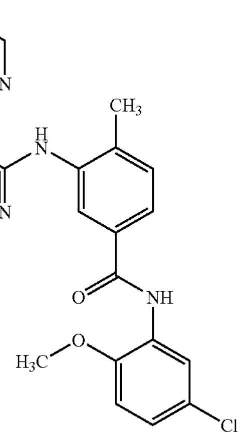 | 445.91 | 446 |
| 144 | 4-methyl-N-(3-(phenylcarbonyl)phenyl)-3-((3-(4-pyrimidinyl)-2-pyridinyl)amino)benzamide | 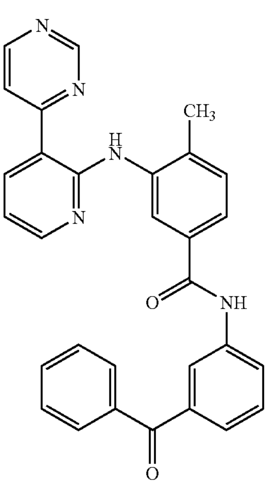 | 485.55 | 486 |

| Ex. No. | Structure Name | Structure | MW | MS Data |
|---|---|---|---|---|
| 145 | N-(cyclopropylmethyl)-4-methyl-3-((3-(4-pyrimidinyl)-2-pyridinyl)amino)benzamide | 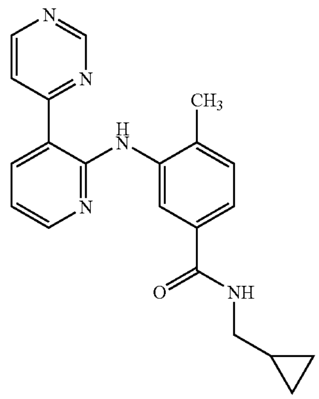 | 359.43 | 360 |
| 146 | N-(3,3-dimethylbutyl)-4-methyl-3-((3-(4-pyrimidinyl)-2-pyridinyl)amino)benzamide | 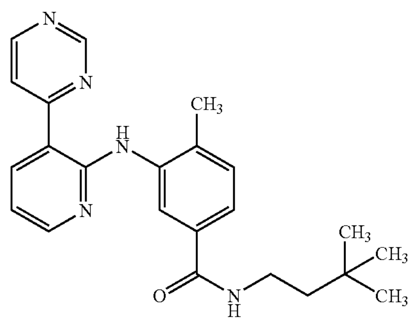 | 389.5 | 390 |
| 147 | 4-methyl-3-((3-(4-pyrimidinyl)-2-pyridinyl)amino)-N-(2-thienylmethyl)benzamide | 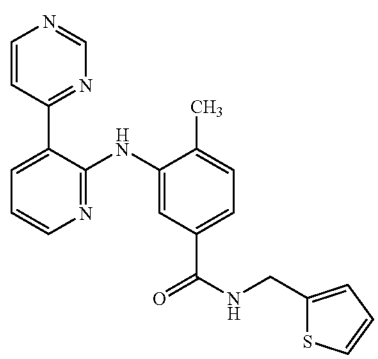 | 401.49 | 402 |
| 148 | N-(cyclohexylmethyl)-4-methyl-3-((3-(4-pyrimidinyl)-2-pyridinyl)amino)benzamide | 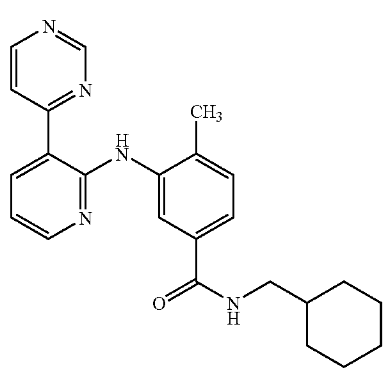 | 401.51 | 402 |

-continued

| Ex. No. | Structure Name | Structure | MW | MS Data |
|---|---|---|---|---|
| 149 | N-(3-(1,1-dimethylethyl)-1-phenyl-1H-pyrazol-5-yl)-4-methyl-3-((3-(4-pyrimidinyl)-2-pyridinyl)amino)benzamide | 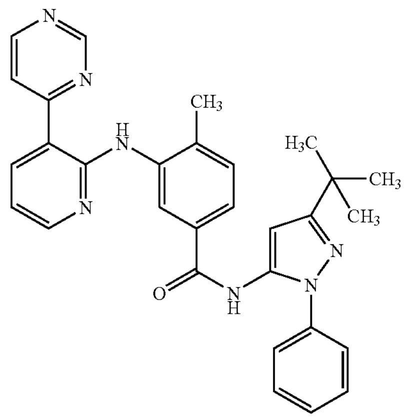 | 503.61 | 504 |
| 150 | N-(2,3-dihydro-1H-inden-4-yl)-4-methyl-3-((3-(4-pyrimidinyl)-2-pyridinyl)amino)benzamide | 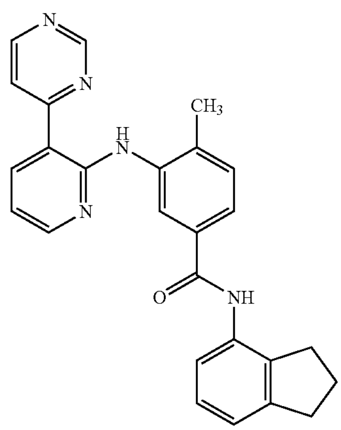 | 421.5 | 422 |
| 151 | 4-methyl-N-(3-((1-methylethyl)oxy)phenyl)-3-((3-(4-pyrimidinyl)-2-pyridinyl)amino)benzamide | 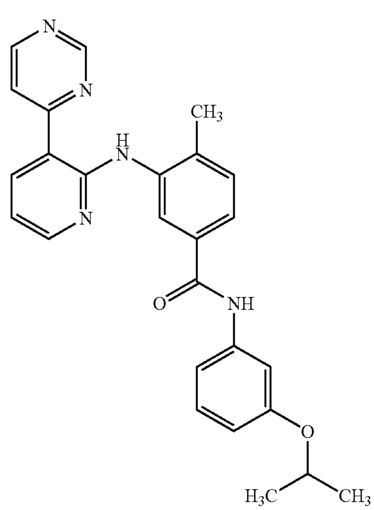 | 439.52 | 440 |

-continued

| Ex. No. | Structure Name | Structure | MW | MS Data |
|---|---|---|---|---|
| 152 | N-(3-chlorophenyl)-N,4-dimethyl-3-((3-(4-pyrimidinyl)-2-pyridinyl)amino)benzamide | 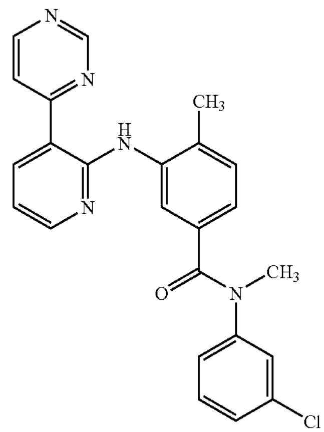 | 429.91 | 430 |
| 153 | N,4-dimethyl-N-phenyl-3-((3-(4-pyrimidinyl)-2-pyridinyl)amino)benzamide | 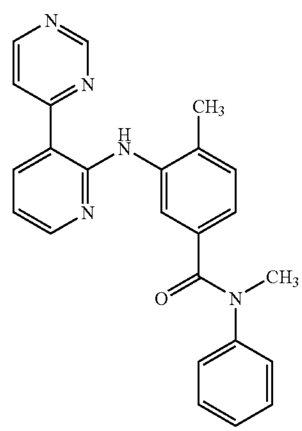 | 395.46 | 396 |
| 154 | N-(2-bromo-5-(trifluoromethyl)phenyl)-4-methyl-3-((3-(4-pyrimidinyl)-2-pyridinyl)amino)benzamide | 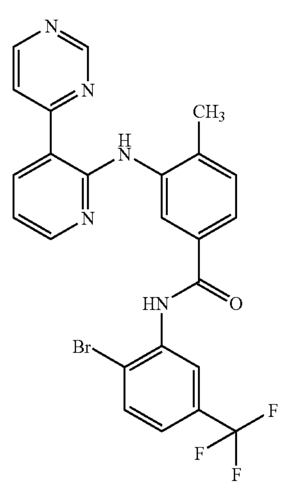 | 528.33 | 528 |

-continued

| Ex. No. | Structure Name | Structure | MW | MS Data |
|---|---|---|---|---|
| 155 | N,4-dimethyl-3-((3-(4-pyrimidinyl)-2-pyridinyl)amino)-N-(3-(trifluoromethyl)phenyl)benzamide | 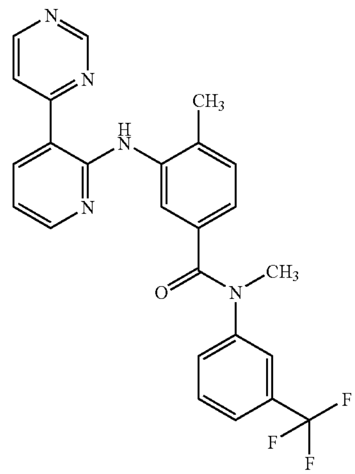 | 463.46 | 464 |
| 156 | 2-chloro-N-(4-methyl-3-((3-(4-pyrimidinyl)-2-pyridinyl)amino)phenyl)-5-(trifluoromethyl)benzamide | 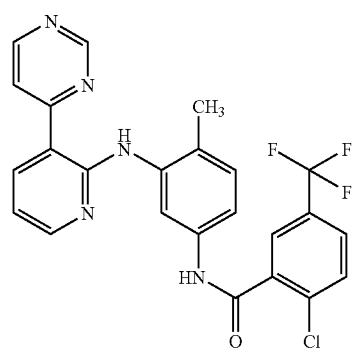 | 483.88 | 484 |
| 157 | 3-chloro-2-fluoro-N-(4-methyl-3-((3-(4-pyrimidinyl)-2-pyridinyl)amino)phenyl)-5-(trifluoromethyl)benzamide | 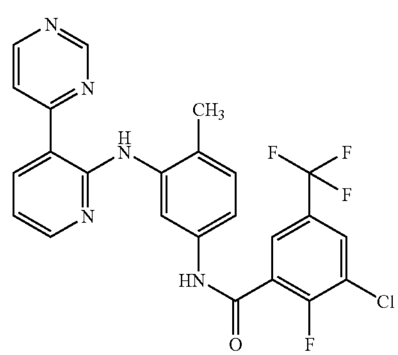 | 501.87 | 502 |

| Ex. No. | Structure Name | Structure | MW | MS Data |
|---|---|---|---|---|
| 158 | 4-methyl-N-(2-(methylsulfanyl)-5-(trifluoromethyl)phenyl)-3-((3-(4-pyrimidinyl)-2-pyridinyl)amino)benzamide | 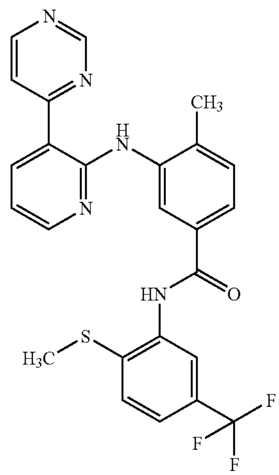 | 495.53 | 496 |
| 159 | 4-methyl-N-(2-(1-piperidinyl)-5-(trifluoromethyl)phenyl)-3-((3-(4-pyrimidinyl)-2-pyridinyl)amino)benzamide | 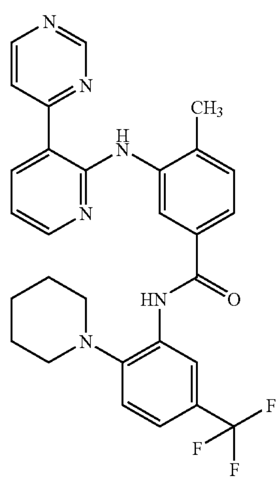 | 532.57 | 533 |
| 160 | 4-methyl-N-(2-((4-(methyloxy)phenyl)oxy)-5-(trifluoromethyl)phenyl)-3-((3-(4-pyrimidinyl)-2-pyridinyl)amino)benzamide | 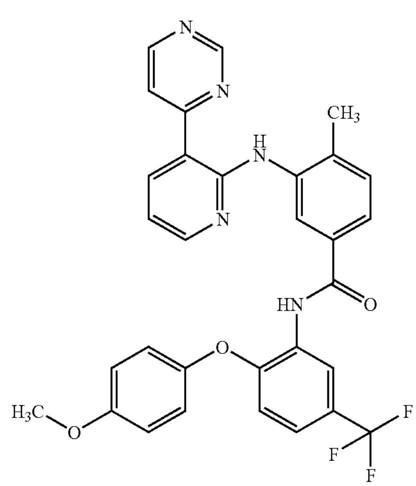 | 571.56 | 572 |

| Ex. No. | Structure Name | Structure | MW | MS Data |
|---|---|---|---|---|
| 161 | 4-methyl-N-(2-nitro-5-(trifluoromethyl)phenyl)-3-((3-(4-pyrimidinyl)-2-pyridinyl)amino)benzamide | 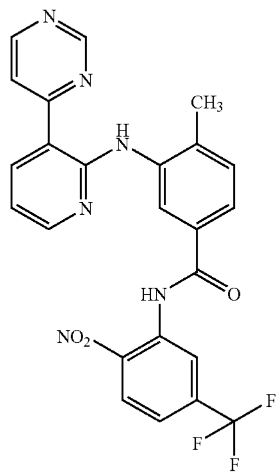 | 494.43 | 495 |
| 162 | N-(5-cyclohexyl-2-(methyloxy)phenyl)-4-methyl-3-((3-(4-pyrimidinyl)-2-pyridinyl)amino)benzamide | 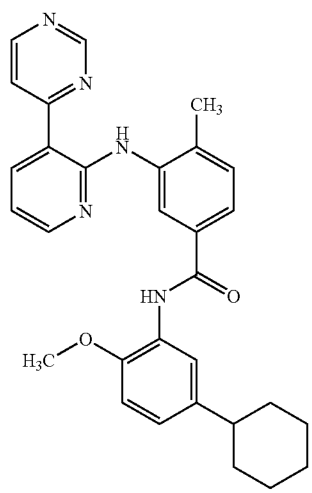 | 493.61 | 494 |
| 163 | N-(5-(1,1-dimethylethyl)-2-(methyloxy)phenyl)-4-methyl-3-((3-(4-pyrimidinyl)-2-pyridinyl)amino)benzamide | 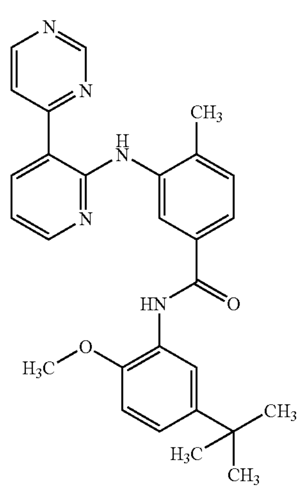 | 467.57 | 468 |

-continued

| Ex. No. | Structure Name | Structure | MW | MS Data |
|---|---|---|---|---|
| 164 | 4-methyl-N-(4-(4-morpholinyl)phenyl)-3-((3-(4-pyrimidinyl)-2-pyridinyl)amino)benzamide | 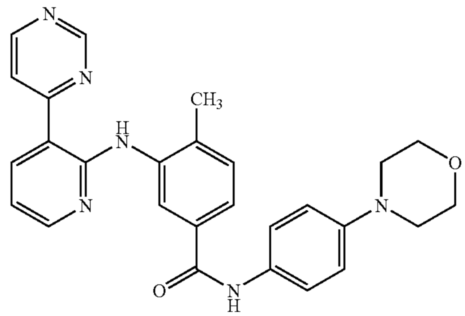 | 466.54 | 467 |
| 165 | N-(4-(acetylamino)phenyl)-4-methyl-3-((3-(4-pyrimidinyl)-2-pyridinyl)amino)benzamide | 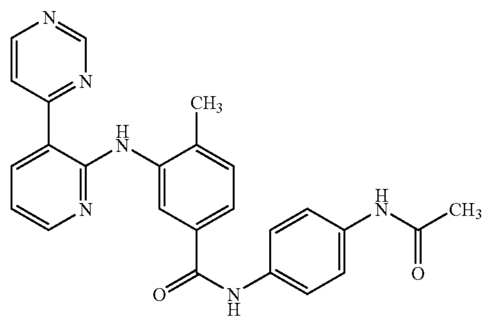 | 438.49 | 439 |
| 166 | N-(4-(diethylamino)phenyl)-4-methyl-3-((3-(4-pyrimidinyl)-2-pyridinyl)amino)benzamide | 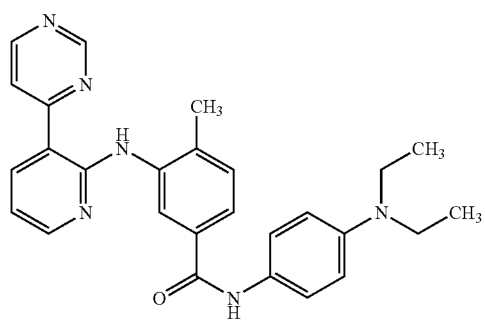 | 452.56 | 453 |
| 167 | N-(4-hydroxyphenyl)-4-methyl-3-((3-(4-pyrimidinyl)-2-pyridinyl)amino)benzamide | 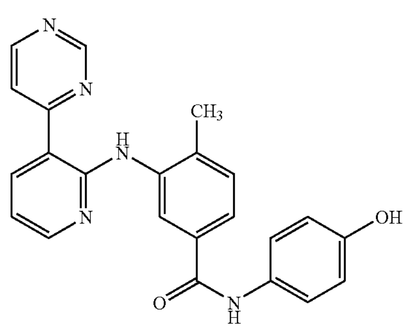 | 397.44 | 398 |

-continued

| Ex. No. | Structure Name | Structure | MW | MS Data |
|---|---|---|---|---|
| 168 | 4-methyl-N-(4-(1-piperidinyl)phenyl)-3-((3-(4-pyrimidinyl)-2-pyridinyl)amino)benzamide | 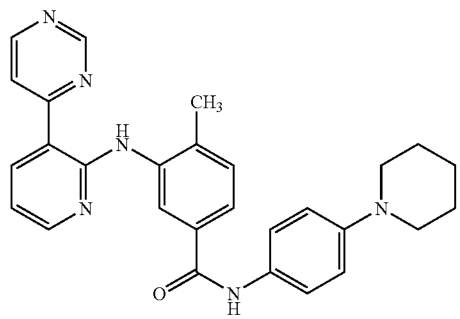 | 464.57 | 465 |
| 169 | N-(4-(1H-imidazol-1-yl)phenyl)-4-methyl-3-((3-(4-pyrimidinyl)-2-pyridinyl)amino)benzamide | 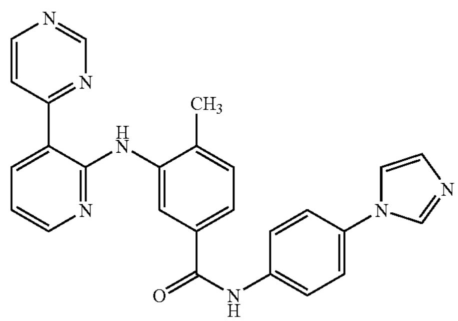 | 447.5 | 448 |
| 170 | 4-methyl-N-(4-(1-methylethyl)phenyl)-3-((3-(4-pyrimidinyl)-2-pyridinyl)amino)benzamide | 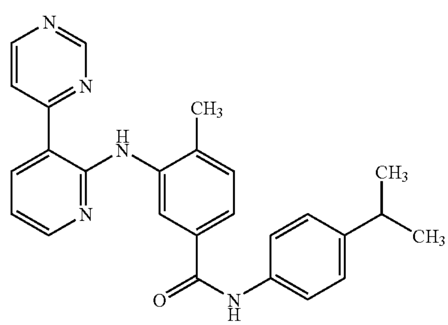 | 423.52 | 424 |
| 171 | 1,1-dimethylethyl (2S)-2-(((3-(((4-methyl-3-((3-(4-pyrimidinyl)-2-pyridinyl)amino)phenyl)carbonyl)amino)-5-(trifluoromethyl)phenyl)oxy)methyl)-1-pyrrolidinecarboxylate | 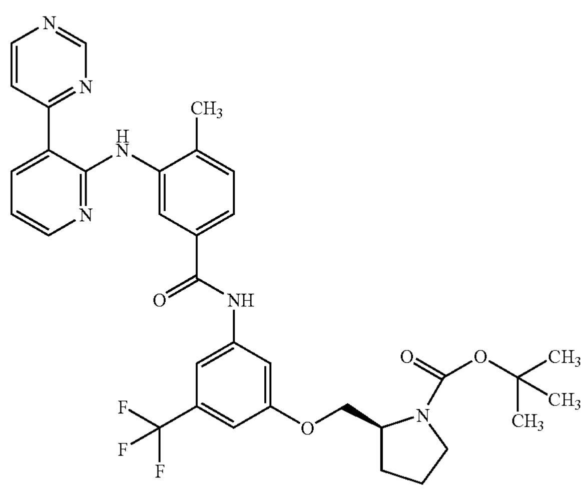 | 648.68 | 649 |

| Ex. No. | Structure Name | Structure | MW | MS Data |
|---|---|---|---|---|
| 172 | 4-methyl-3-((3-(4-pyrimidinyl)-2-pyridinyl)amino)-N-(3-(((2S)-2-pyrrolidinylmethyl)oxy)-5-(trifluoromethyl)phenyl)benzamide | 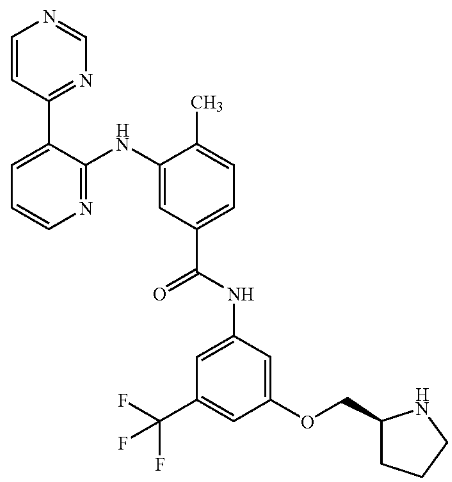 | 548.57 | 549 |
| 173 | 4-methyl-N-(3-((2-(1-piperidinyl)ethyl)oxy)-5-(trifluoromethyl)phenyl)-3-((3-(4-pyrimidinyl)-2-pyridinyl)amino)benzamide | 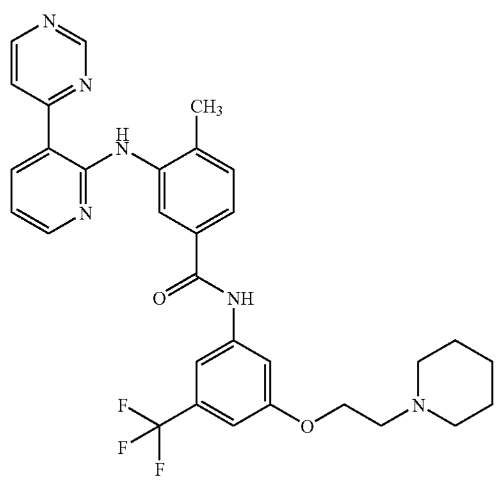 | 576.62 | 577 |
| 174 | 4-methyl-N-(6-((((2S)-1-methyl-2-pyrrolidinyl)methyl)oxy)-2-pyridinyl)-3-((3-(4-pyrimidinyl)-2-pyridinyl)amino)benzamide | 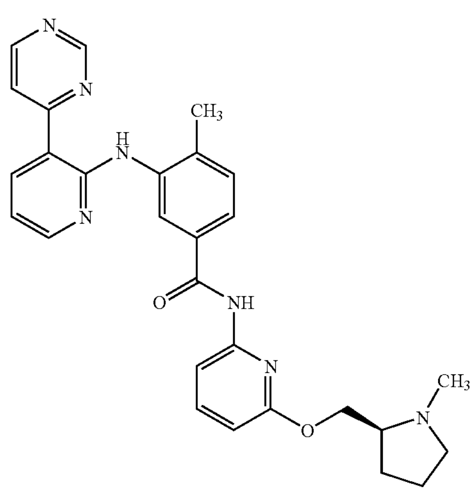 | 495.58 | 496 |

-continued

| Ex. No. | Structure Name | Structure | MW | MS Data |
|---|---|---|---|---|
| 175 | N-(6-(4-ethyl-1-piperazinyl)-2-pyridinyl)-4-methyl-3-((3-(4-pyrimidinyl)-2-pyridinyl)amino)benzamide | 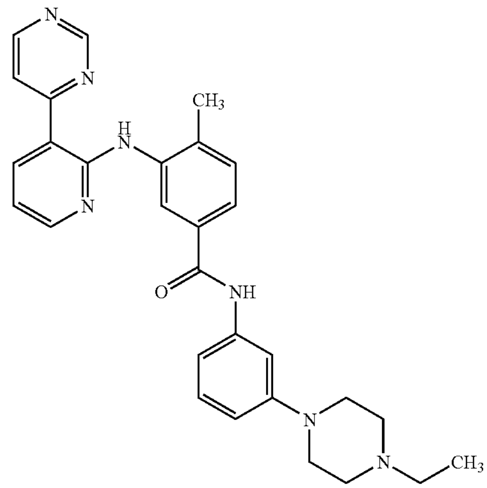 | 494.6 | 495 |
| 176 | 4-methyl-3-((3-(4-pyrimidinyl)-2-pyridinyl)amino)-N-(6-(1-pyrrolidinylmethyl)-2-pyridinyl)benzamide | 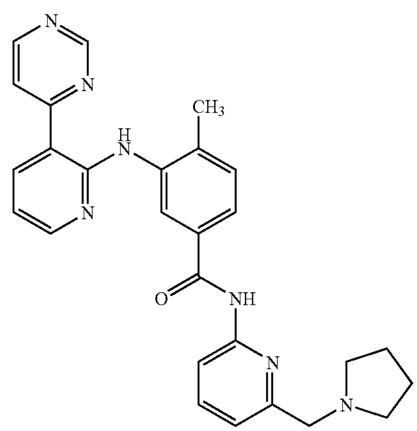 | 465.56 | 466 |
| 177 | 4-methyl-N-(3-(4-morpholinylmethyl)phenyl)-3-((3-(4-pyrimidinyl)-2-pyridinyl)amino)benzamide | 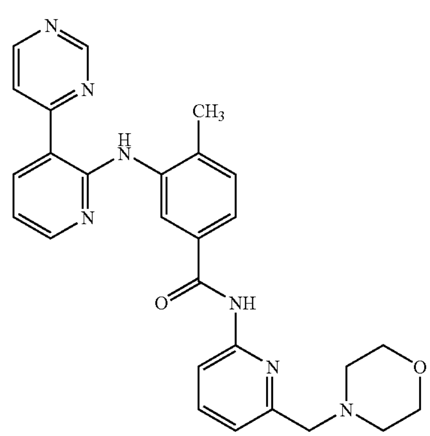 | 480.57 | 481 |

-continued

| Ex. No. | Structure Name | Structure | MW | MS Data |
|---|---|---|---|---|
| 178 | N-(diphenylmethyl)-4-methyl-3-((3-(4-pyrimidinyl)-2-pyridinyl)amino)benzamide | 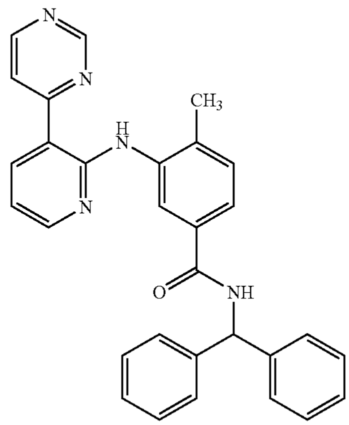 | 471.56 | 472 |
| 179 | 4-methyl-N-(4-(methyloxy)phenyl)-3-((3-(4-pyrimidinyl)-2-pyridinyl)amino)benzamide | 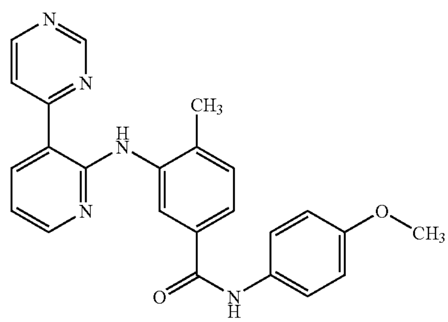 | 411.46 | 412 |
| 180 | 4-methyl-N-(1-methyl-1-phenylethyl)-3-((3-(4-pyrimidinyl)-2-pyridinyl)amino)benzamide | 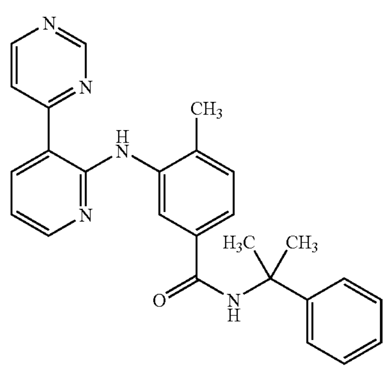 | 423.52 | 424 |
| 181 | 4-methyl-N-(4-(4-methyl-1-piperazinyl)phenyl)-3-((3-(4-pyrimidinyl)-2-pyridinyl)amino)benzamide | 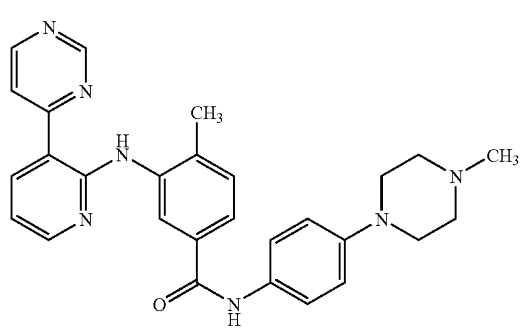 | 479.58 | 480 |

-continued

| Ex. No. | Structure Name | Structure | MW | MS Data |
|---|---|---|---|---|
| 182 | 4-methyl-N-(4-pyridinyl)-3-((3-(4-pyrimidinyl)-2-pyridinyl)amino)benzamide | 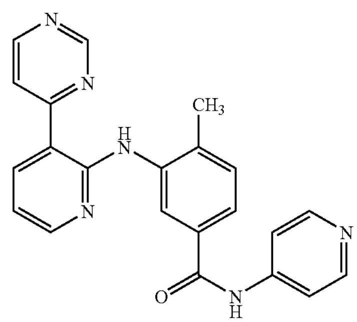 | 382.43 | 383 |
| 183 | N-(4-(acetyl(methyl)amino)phenyl)-4-methyl-3-((3-(4-pyrimidinyl)-2-pyridinyl)amino)benzamide | 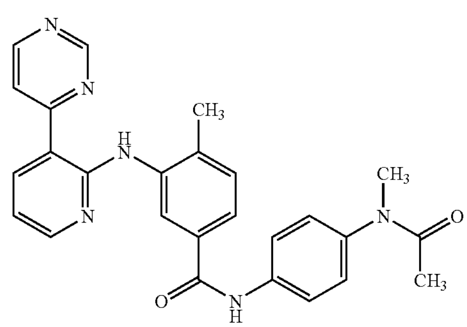 | 452.52 | 453 |
| 184 | N-(4-fluoro-3-(4-morpholinylmethyl)phenyl)-4-methyl-3-((3-(4-pyrimidinyl)-2-pyridinyl)amino)benzamide | 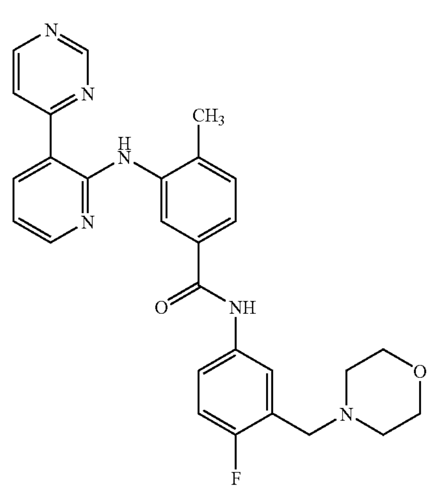 | 498.56 | 499 |

| Ex. No. | Structure Name | Structure | MW | MS Data |
|---|---|---|---|---|
| 185 | N-(4-fluoro-3-(hydroxymethyl)phenyl)-4-methyl-3-((3-(4-pyrimidinyl)-2-pyridinyl)amino)benzamide | 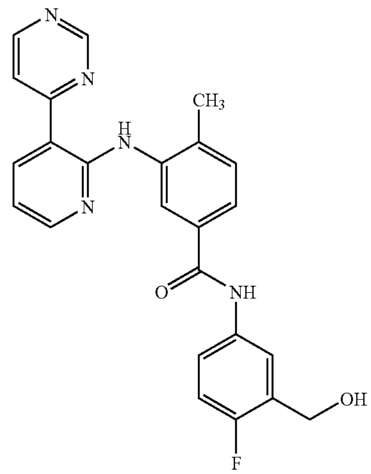 | 429.45 | 430 |
| 186 | 4-methyl-N-(6-(1-piperidinylmethyl)-2-pyridinyl)-3-((3-(4-pyrimidinyl)-2-pyridinyl)amino)benzamide | 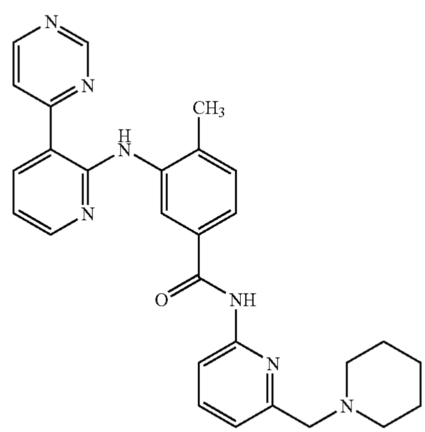 | 479.58 | 480 |
| 187 | 4-methyl-N-(4-(4-pyridinyloxy)phenyl)-3-((3-(4-pyrimidinyl)-2-pyridinyl)amino)benzamide | 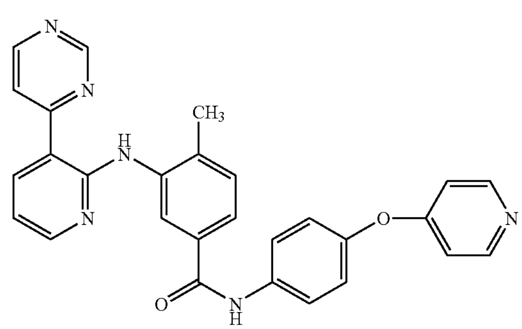 | 474.52 | 475 |

-continued

| Ex. No. | Structure Name | Structure | MW | MS Data |
|---|---|---|---|---|
| 188 | 3-((3-(4-pyrimidinyl)-2-pyridinyl)amino)-N-(3-(trifluoromethyl)phenyl)benzamide | 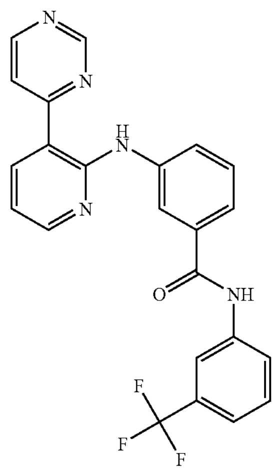 | 435.41 | 436 |
| 189 | N-(3-((1-methylethyl)oxy)phenyl)-3-((3-(4-pyrimidinyl)-2-pyridinyl)amino)benzamide | 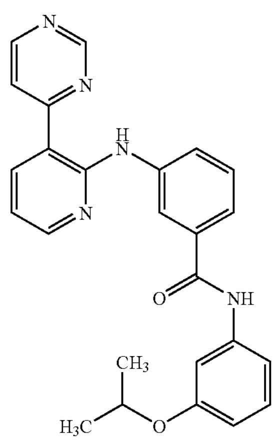 | 425.49 | 426 |
| 190 | N-(4-(2-hydroxyethyl)phenyl)-4-methyl-3-(3-(pyrimidin-4-yl)pyridin-2-ylamino)benzamide | 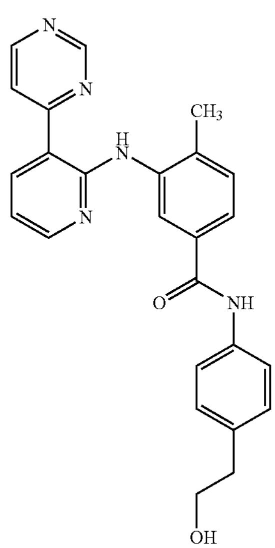 | 425.49 | 426 |

-continued

| Ex. No. | Structure Name | Structure | MW | MS Data |
|---|---|---|---|---|
| 191 | 4-chloro-3-(3-(pyrimidin-4-yl)pyridin-2-ylamino)-N-(3-(trifluoromethyl)phenyl)benzamide | 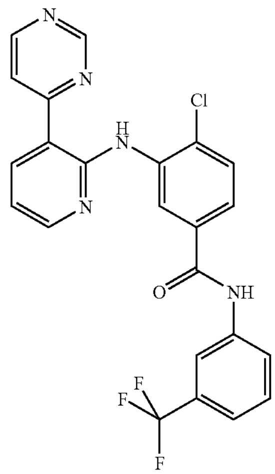 | 469.85 | 470 |
| 192 | 4-chloro-N-(3-chlorophenyl)-3-(3-(pyrimidin-4-yl)pyridin-2-ylamino)benzamide | 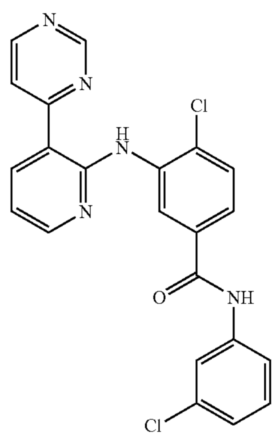 | 436.3 | 437 |
| 193 | N-(4-tert-butylphenyl)-4-chloro-3-(3-(pyrimidin-4-yl)pyridin-2-ylamino)benzamide | 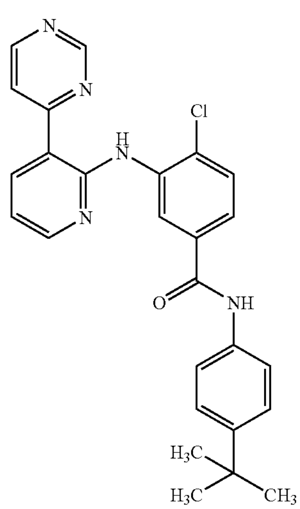 | 457.96 | 458 |

-continued

| Ex. No. | Structure Name | Structure | MW | MS Data |
|---|---|---|---|---|
| 194 | 4-chloro-N-(4-dimethylamino)phenyl)-3-(3-(pyrimidin-4-yl)pyridin-2-ylamino)benzamide | 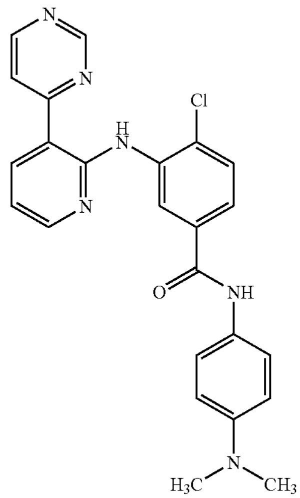 | 444.92 | 445 |
| 195 | 4-chloro-3-(3-(pyrimidin-4-yl)pyridin-2-ylamino)-N-(3-((S)-pyrrolidin-2-ylmethoxy)-5-(trifluoromethyl)phenyl)benzamide | 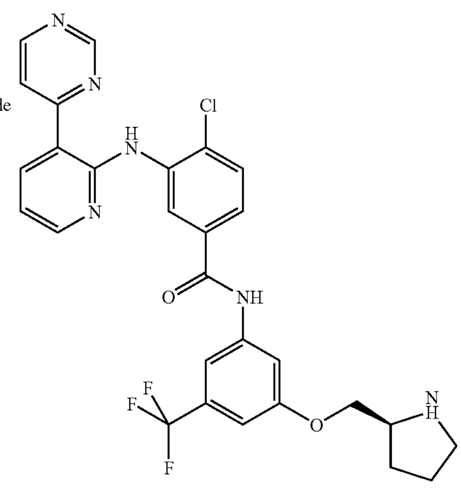 | 568.99 | 469 |
| 196 | 4-methyl-N-(3-((((2S)-1-methyl-2-pyrrolidinyl)methyl)oxy)-5-(trifluoromethyl)phenyl)-3-((3-(4-pyrimidinyl)-2-pyridinyl)amino)benzamide | 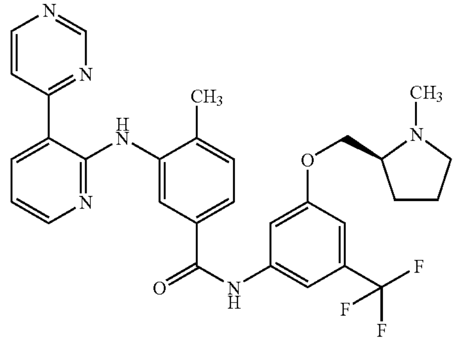 | 562.59 | 563 |

| Ex. No. | Structure Name | Structure | MW | MS Data |
|---|---|---|---|---|
| 197 | N-(3-((2-chloroethyl)oxy)-5-(trifluoromethyl)phenyl)-4-methyl-3-((3-(4-pyrimidinyl)-2-pyridinyl)amino)benzamide | 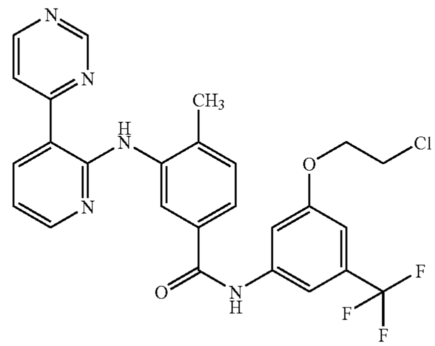 | 527.93 | 528 |

Method B

EXAMPLE 198

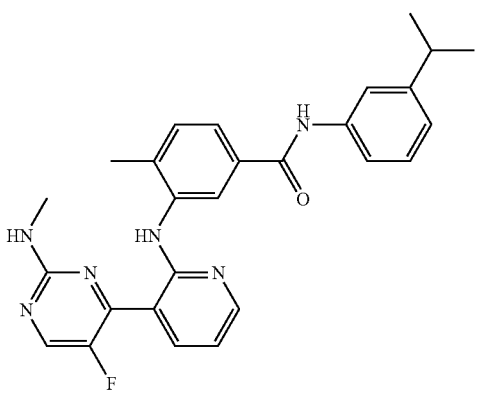

Synthesis of 3-((3-(5-Fluoro-2-(methylamino)-4-pyrimidinyl)-2-pyridinyl)amino)-4-methyl-N-(3-(1-methylethyl)phenyl)benzamide Step 1. Preparation of 2-chloro-4-(2-chloro-pyridin-3-yl)-5-fluoro-pyrimidine To 2,4-dichloro-5-fluoropyrimidine (500 mg, 2.99 mmol), 2-chloropyridine-3-boronic acid (707 mg, 4.49 mmol), Pd(PPh$_3$)$_4$ (346 mg, 0.30 mmol) was added DME (9.0 mL) and 1 M NaHCO$_3$ (3.0 mL). The mixture was heated overnight in a sealed tube at 80° C., cooled to RT, diluted with EtOAc, and washed with water and saturated Na$_2$CO$_3$. The organic layer was dried over Na$_2$SO$_4$, filtered, concentrated and purified by reverse-phase HPLC to provide 2-chloro-4-(2-chloro-pyridin-3-yl)-5-fluoro-pyrimidine. MS m/z=244, 246 [M]$^+$ and [M+2]$^+$. Calc'd for C$_9$H$_4$Cl$_2$FN$_3$: 244.06.

Step 2. Preparation of [4-(2-chloro-pyridin-3-yl)-5-fluoro-pyrimidin-2-yl]-methyl-amine To 2-chloro-4-(2-chloro-pyridin-3-yl)-5-fluoro-pyrimidine (178 mg, 0.73 mmol) and methylamine hydrochloride (74 mg, 1.1 mmol) was added K$_2$CO$_3$ (202 mg, 1.46 mmol) and DMSO (1.5 mL). The mixture was heated overnight in a sealed tube at 55° C. The mixture was cooled to RT, diluted with EtOAc and water, then neutralized with TFA (pH~6-7). The organic layer was washed several times with water, dried over Na$_2$SO$_4$, filtered and concentrated to yield [4-(2-chloro-pyridin-3-yl)-5-fluoro-pyrimidin-2-yl]-methyl-amine. MS m/z=239 [M+1]$^+$. Calc'd for C$_{10}$H$_8$ClFN$_4$: 238.65.

Step 3. Preparation of 3-((3-(5-fluoro-2-(methylamino)-4-pyrimidinyl)-2-pyridinyl)amino)-4-methyl-N-(3-(1-methylethyl)phenyl)benzamide

[4-(2-Chloro-pyridin-3-yl)-5-fluoro-pyrimidin-2-yl]-methyl-amine (62 mg, 0.26 mmol), 3-amino-N-(3-isopropyl-phenyl)-4-methyl-benzamide (84 mg, 0.31 mmol), Pd(OAc)$_2$ (6 mg, 0.03 mmol), rac-BINAP (16 mg, 0.03 mmol) and K$_2$CO$_3$ (719 mg, 5.2 mmol) in toluene (3.0 mL) were reacted overnight at 130° C. The reaction was diluted with water and extracted with EtOAc. The organic layer was dried over anhydrous Na$_2$SO$_4$, filter, concentrated and purified by reverse-phase HPLC (Gilson, acidic mobile phase) yielding the title compound.

MS m/z=471 [M+1]$^+$. Calc'd for C$_{27}$H$_{27}$FN$_6$O: 470.55.

EXAMPLE 199

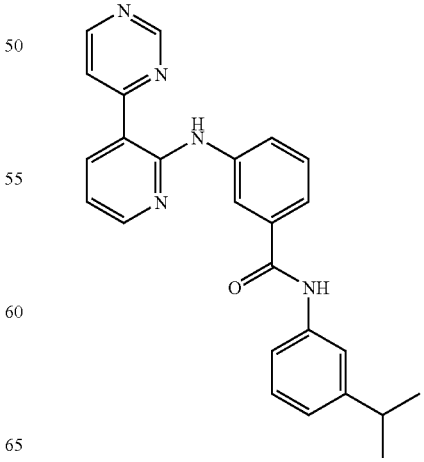

Synthesis of N-(3-(1-methylethyl)phenyl)-3-((3-(4-pyrimidinyl)-2-pyridinyl)amino)benzamide To 3-amino-N-(3-isopropyl-phenyl)-4-methyl-benzamide (300 mg, 1.2 mmol), 4-(2-chloropyridin-3-yl)pyrimidine (100 mg, 0.52 mmol) and DMSO (0.15 mL) was added NEt$_3$-TFA (0.11 mL). The resulting slurry was stirred for 22 hours at 90° C. The crude material was purified by silica gel chromatography (40-60% EtOAc/hexanes) to yield the title compound as a yellow solid. MS m/z=410 [M+1]$^+$. Calc'd for C$_{25}$H$_{23}$N$_5$O: 409.49.

| Ex. No. | Structure Name | Structure | MW | MS Data |
|---|---|---|---|---|
| 200 | 4-methyl-3-((3-(2-(methylamino)-4-pyrimidinyl)-2-pyridinyl)amino)-N-(3-(1-methylethyl)phenyl)benzamide | 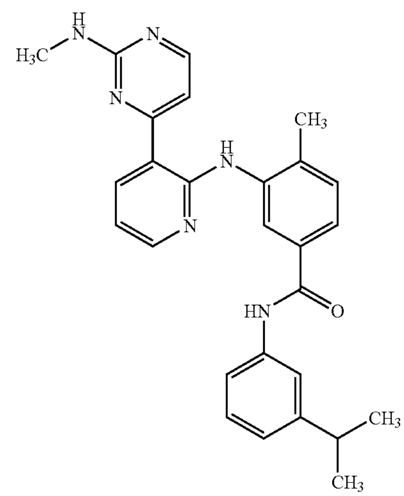 | 452.559 | 453 |
| 201 | N-(5-cyclohexyl-2-(methyloxy)phenyl)-4-methyl-3-((3-(2-(methylamino)-4-pyrimidinyl)-2-pyridinyl)amino)benzamide | 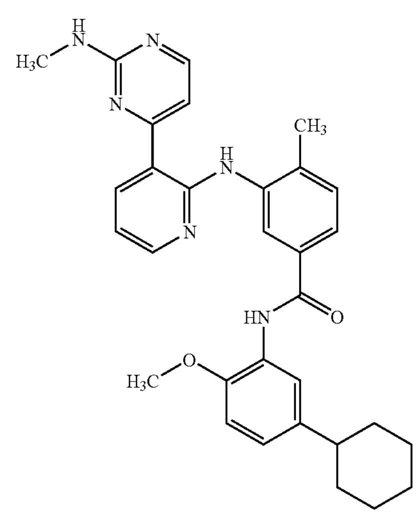 | 522.65 | 523 |

-continued

| Ex. No. | Structure Name | Structure | MW | MS Data |
|---|---|---|---|---|
| 202 | 3-((3-(2-((2-(diethylamino)ethyl)amino)-4-pyrimidinyl)-2-pyridinyl)amino)-4-methyl-N-(3-(1-methylethyl)phenyl)benzamide | 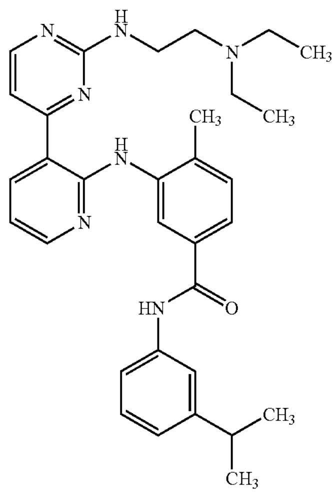 | 537.708 | 538 |
| 203 | N-(5-cyclohexyl-2-(methyloxy)phenyl)-4-methyl-3-((2'-(methylamino)-3,4'-bipyridin-2-yl)amino)benzamide | 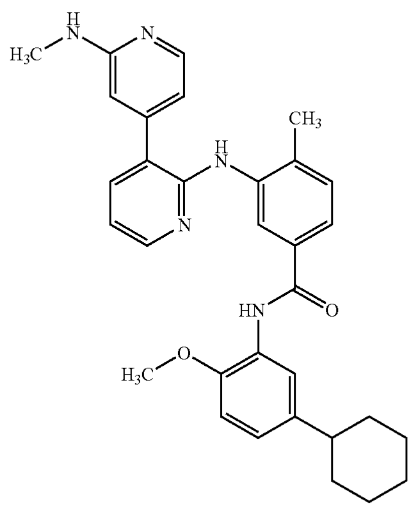 | 521.661 | 522 |
| 204 | N-(5-cyclohexyl-2-(methyloxy)phenyl)-4-methyl-3-((3-(6-(methylamino)-4-pyrimidinyl)-2-pyridinyl)amino)benzamide | 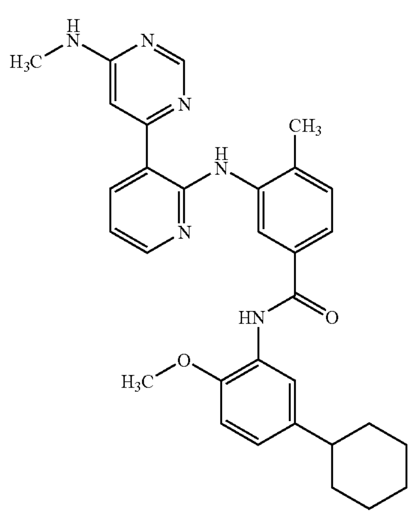 | 522.65 | 523 |

Method C

EXAMPLE 205

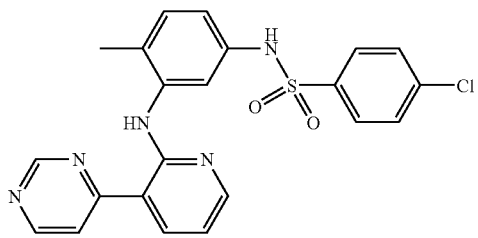

Synthesis of 4-Chloro-N-(4-methyl-3-((3-(4-pyrimidinyl)-2-pyridinyl)amino)phenyl)benzenesulfonamide To a solution of 4-methyl-$N^3$-(3-pyrimidin-4-yl-pyridin-2-yl)-benzene-1,3-diamine (40 mg, 0.14 mmol) in $CH_2Cl_2$ (2.5 mL) was added pyridine (0.012 mL, 0.14 mmol) and 4-chlorobenzenesulfonyl chloride (30 mg, 0.14 mmol). The mixture was stirred overnight at RT, concentrated and purified by flash chromatography (0→50% EtOAc/n-Hexanes) to yield 4-chloro-N-(4-methyl-3-((3-(4-pyrimidinyl)-2-pyridinyl)amino)phenyl)benzenesulfonamide. MS m/z=452 [M+1]$^+$. Calc'd for $C_{22}H_{18}ClN_5O_2S$: 451.94.

EXAMPLE 206

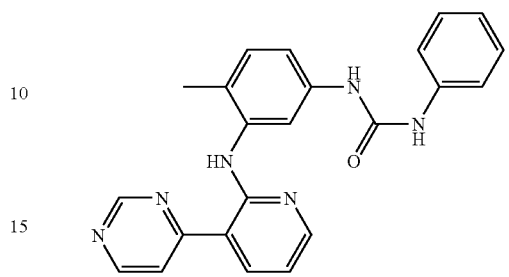

Synthesis of N-(4-Methyl-3-((3-(4-pyrimidinyl)-2-pyridinyl)amino)phenyl)-N'-phenylurea To a solution of 4-methyl-$N^3$-(3-pyrimidin-4-yl-pyridin-2-yl)-benzene-1,3-diamine (30 mg, 0.11 mmol) in toluene (2.0 mL) was added phenyl isocyanate (0.012 mL, 0.11 mmol). The mixture was stirred overnight at RT. The resulting solid was filtered, washed with toluene and dried to yield N-(4-methyl-3-((3-(4-pyrimidinyl)-2-pyridinyl)amino)phenyl)-N'-phenylurea. MS m/z=397 [M+1]$^+$. Calc'd for $C_{23}H_{20}N_6O$: 396.46.

| Ex. No. | Structure Name | Structure | MW | MS Data |
|---|---|---|---|---|
| 207 | N-(4-methyl-3-((3-(4-pyrimidinyl)-2-pyridinyl)amino)phenyl)-3-(trifluoromethyl)benzenesulfonamide | 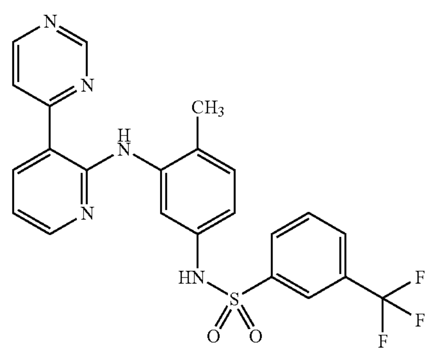 | 485.49 | 486 |
| 208 | 2,3-dichloro-N-(4-methyl-3-((3-(4-pyrimidinyl)-2-pyridinyl)amino)phenyl)benzenesulfonamide | 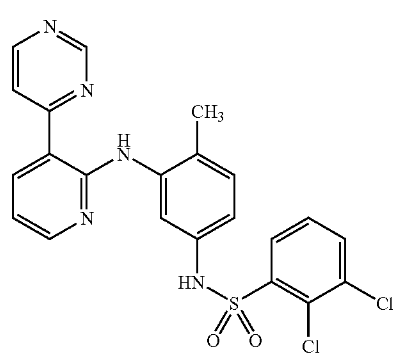 | 486.38 | 486 |

-continued

| Ex. No. | Structure Name | Structure | MW | MS Data |
|---|---|---|---|---|
| 209 | N-(4-methyl-3-((3-(4-pyrimidinyl)-2-pyridinyl)amino)phenyl)-3,5-bis(trifluoromethyl)benzenesulfonamide | 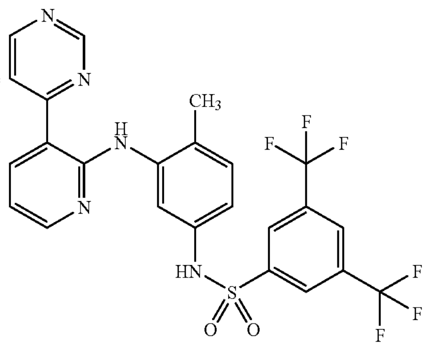 | 553.49 | 554 |
| 210 | N-(4-methyl-3-((3-(4-pyrimidinyl)-2-pyridinyl)amino)phenyl)benzenesulfonamide | 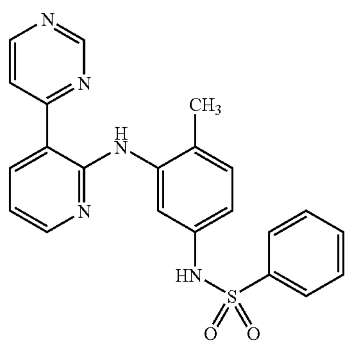 | 417.49 | 418 |
| 211 | N-(4-methyl-3-((3-(4-pyrimidinyl)-2-pyridinyl)amino)phenyl)benzamide | 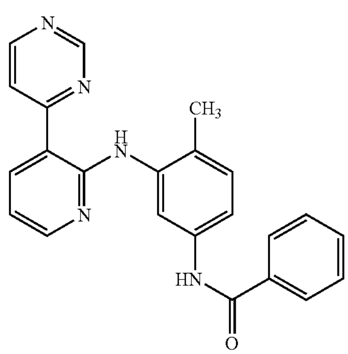 | 381.44 | 382 |
| 212 | N-(4-methyl-3-((3-(4-pyrimidinyl)-2-pyridinyl)amino)pheny)-N'-(3-(trifluoromethyl)phenyl)urea | 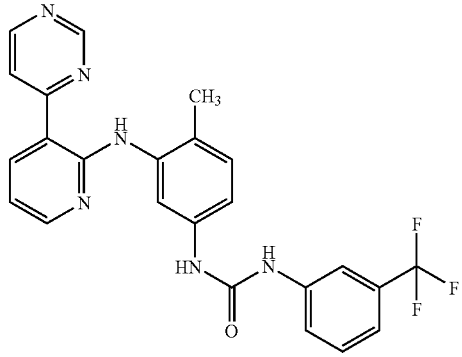 | 464.45 | 465 |

-continued

| Ex. No. | Structure Name | Structure | MW | MS Data |
|---|---|---|---|---|
| 213 | N-(2-fluoro-3-(trifluoromethyl)phenyl)-N'-(4-methyl-3-((3-(4-pyrimidinyl)-2-pyridinyl)amino)phenyl)urea | 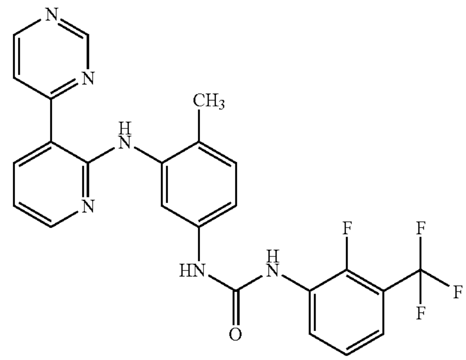 | 482.44 | 483 |
| 214 | N-(2-fluoro-5-(trifluoromethyl)phenyl)-N'-(4-methyl-3-((3-(4-pyrimidinyl)-2-pyridinyl)amino)phenyl)urea | 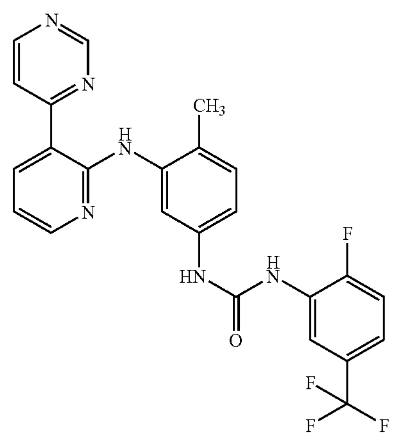 | 482.44 | 483 |

Method D

EXAMPLE 215

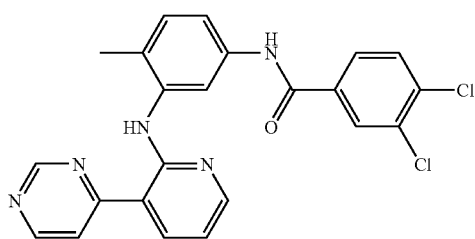

Synthesis of 3,4-Dichloro-N-(4-methyl-3-((3-(4-pyrimidinyl)-2-pyridinyl)amino)phenyl)benzamide Step 1. Preparation of N-(3-amino-4-methyl-phenyl)-3,4-dichloro-benzamide To 3,4-dichlorobenzoic acid (200 mg, 1.05 mmol), 2,4-diaminotoluene (513 mg, 4.20 mmol), and EDC (403 mg, 2.10 mmol) was added $CH_2Cl_2$ (40 mL). The mixture was stirred overnight at RT, concentrated, diluted with EtOAc and extracted with water. The organic layer was dried over $Na_2SO_4$, filtered, concentrated, and purified by flash chromatography (n-Hexanes→50% EtOAc/n-Hexanes) yielding N-(3-amino-4-methyl-phenyl)-3,4-dichloro-benzamide. MS m/z=295, 297 $[M]^+$ and $[M+]^+$. Calc'd for $C_{14}H_{12}Cl_2N_2O$: 295.17.

Step 2. Preparation of 3,4-dichloro-N-(4-methyl-3-((3-(4-pyrimidinyl)-2-pyridinyl)amino)phenyl)benzamide 4-(2-Chloro-pyridin-3-yl)-pyrimidine (60 mg, 0.30 mmol), N-(3-amino-4-methyl-phenyl)-3,4-dichloro-benzamide (107 mg, 0.36 mmol), $Pd(OAc)_2$ (4 mg, 0.012 mmol), rac-BINAP (8 mg, 0.012 mmol) and $K_2CO_3$ (829 mg, 6.0 mmol) in toluene (3.0 mL) were reacted overnight at 130° C. The reaction was diluted with water and extracted with EtOAc. The organic layer was dried over anhydrous $Na_2SO_4$, filter, concentrated and purified by reverse-phase HPLC (Gilson, acidic mobile phase) yielding the title compound. MS m/z=450, 452 $[M]^+$ and $[M+2]^+$. Calc'd for $C_{23}H_{17}Cl_2N_5O$: 450.33.

| Ex. No. | Structure Name | Structure | MW | MS Data |
|---|---|---|---|---|
| 216 | N-(4-methyl-3-((3-(4-pyrimidinyl)-2-pyridinyl)amino)phenyl)-3-(trifluoromethyl)benzamide | 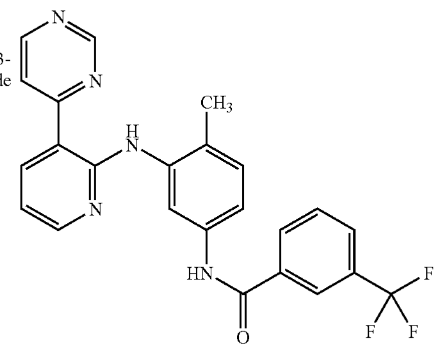 | 449.43 | 450 |
| 217 | 2,3-dichloro-N-(4-methyl-3-((3-(4-pyrimidinyl)-2-pyridinyl)amino)phenyl)benzamide | 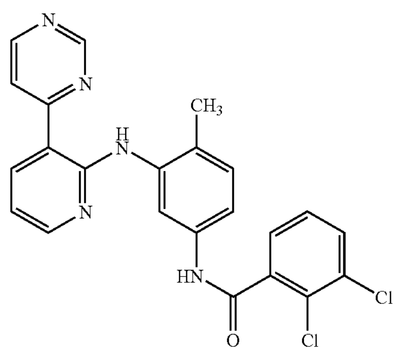 | 450.33 | 450 |
| 218 | 3-methyl-N-(4-methyl-3-((3-(4-pyrimidinyl)-2-pyridinyl)amino)phenyl)cyclohexanecarboxamide | 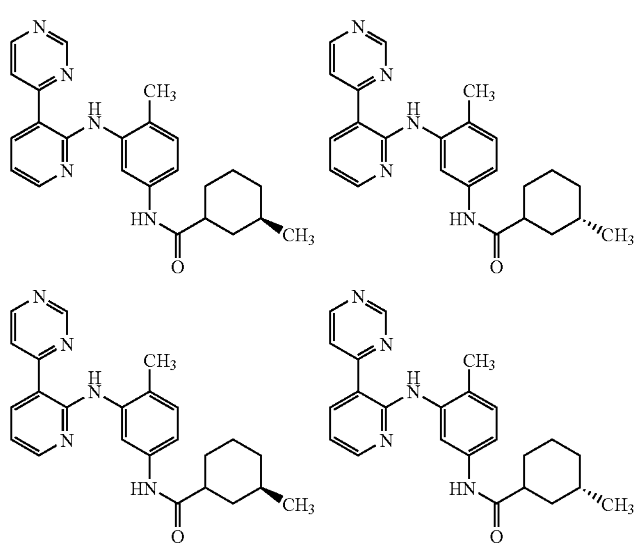 | 401.51 | 402 |

-continued

| Ex. No. | Structure Name | Structure | MW | MS Data |
|---|---|---|---|---|
| 219 | 1-ethyl-3-methyl-N-(4-methyl-3-((3-(4-pyrimidinyl)-2-pyridinyl)amino)phenyl)-1H-pyrazole-5-carboxamide | 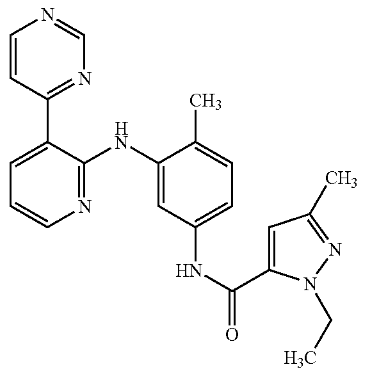 | 413.48 | 414 |
| 220 | 3,5-dichloro-N-(4-methyl-3-((3-(4-pyrimidinyl)-2-pyridinyl)ainino)phenyl)benzamide | 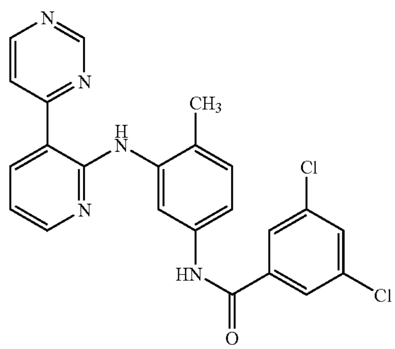 | 450.33 | 450 |

Method E

EXAMPLE 221

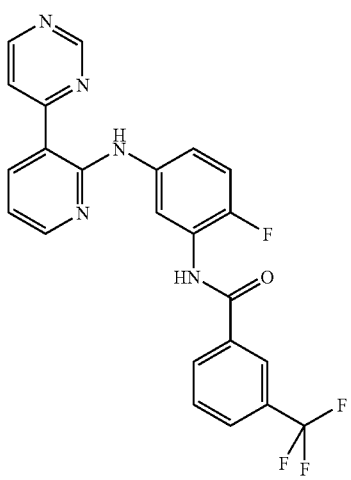

Synthesis of N-(2-fluoro-5-((3-(4-pyrimidinyl)-2-pyridinyl)amino)phenyl)-3-(trifluoromethyl)benzamide Step 1. Preparation of N-(4-fluoro-3-nitrophenyl)-3-(pyrimidin-4-yl)pyridin-2-amine 4-(2-Chloro-pyridin-3-yl)-pyrimidine (60 mg, 0.30 mmol), 4-fluoro-3-nitrobenzenamine (56 mg, 0.36 mmol), Pd(OAc)$_2$ (4 mg, 0.012 mmol), rac-BINAP (8 mg, 0.012 mmol) and K$_2$CO$_3$ (829 mg, 6.0 mmol) in toluene (3.0 mL) were reacted overnight at 130° C. The reaction was diluted with water and extracted with EtOAc. The organic layer was dried over anhydrous Na$_2$SO$_4$, filter, concentrated and purified by silica gel chromatography (0-100% EtOAc/hexanes) yielding the title compound. MS m/z=312 [M+1]$^+$. Calc'd for C$_{15}$H$_{10}$FN$_5$O$_2$: 311.28.

Step 2. Preparation of 4-fluoro-N'-(3-(pyrimidin-4-yl)pyridin-2-yl)benzene-1,3-diamine N-(4-fluoro-3-nitrophenyl)-3-(pyrimidin-4-yl)pyridin-2-amine (62 mg, 0.20 mmol) was dissolved in THF (6 mL) and treated with Pd/C (5% Pd. 102 mg). The atmosphere was purged with hydrogen and the reaction was stirred under a balloon of H$_2$ for 2.5 days at RT. The mixture was filtered through a pad of Celite, concentrated and purified by silica gel chromatograpy (0-100% EtOAc/hexanes) to yield the title compound as a bright yellow solid. MS m/z=282 [M+1]$^+$. Calc'd for C$_{15}$H$_{12}$FN$_5$: 281.30.

Step 3. Preparation of N-(2-fluoro-5-((3-(4-pyrimidinyl)-2-pyridinyl)amino)phenyl)-3-(trifluoromethyl)benzamide To 4-fluoro-N$^1$-(3-(pyrimidin-4-yl)pyridin-2-yl)benzene-1,3-diamine (25 mg, 0.089 mmol) in CH$_2$Cl$_2$ (1.5 mL) was added 3-(trifluoromethyl)benzoyl chloride (21 mg, 0.098 mmol). The mixture was stirred overnight at RT. The crude material was purified by preparative TLC (100% EtOAc), which yielded the title compound as a yellow solid. MS m/z=454 [M+1]$^+$. Calc'd for C$_{23}$H$_{15}$F$_4$N$_5$: 453.40.

| Ex. No. | Structure Name | Structure | MW | MS Data |
|---|---|---|---|---|
| 222 | 3-(trifluoromethyl)-N-(2,4,6-trimethyl-3-(3-(pyrimidin-4-yl)pyridin-2-ylamino)phenyl)benzamide | 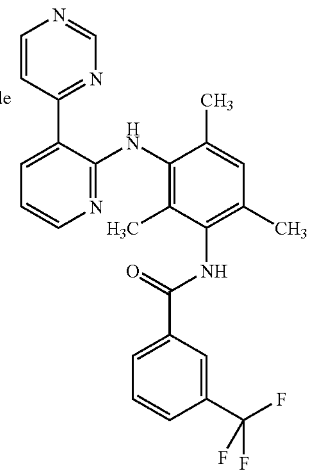 | 477.49 | |
| 223 | N-(2,4-dimethyl-3-(3-(pyrimidin-4-yl)pyridin-2-ylamino)phenyl)-3-(trifluoromethyl)benzamide | 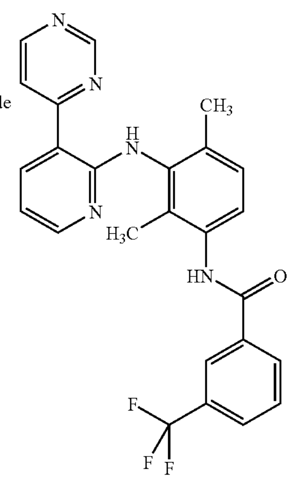 | 463.46 | 464 |
| 224 | 3-chloro-N-(2,4-dimethyl-3-(3-(pyrimidin-4-yl)pyridin-2-ylamino)phenyl)benzamide | 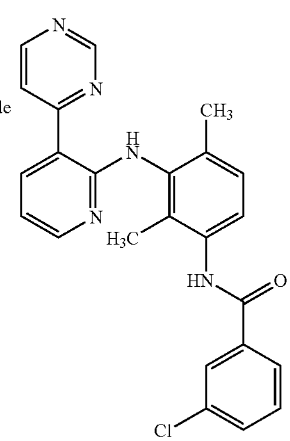 | 429.91 | 430 |

| Ex. No. | Structure Name | Structure | MW | MS Data |
|---|---|---|---|---|
| 225 | 3-chloro-N-(4-methoxy-3-(3-(pyrimidin-4-yl)pyridin-2-ylamino)phenyl)benzamide | 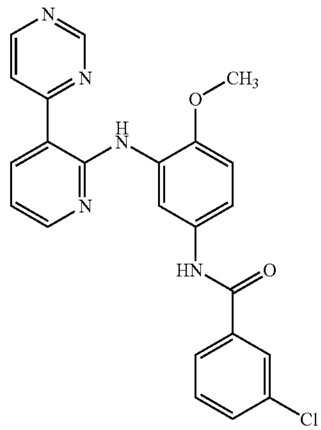 | 431.88 | 432 |

Method F

EXAMPLE 226

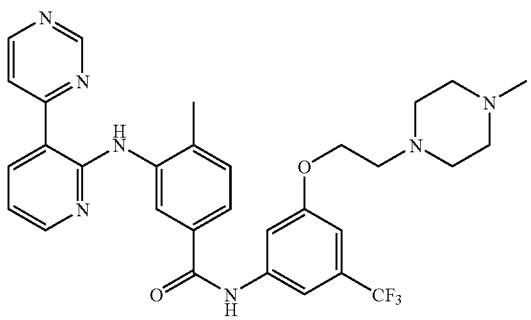

Synthesis of 4-methyl-N-(3-(2-(4-methylpiperazin-1-yl)ethoxy)-5-(trifluoromethyl)phenyl)-3-(3-(pyrimidin-4-yl)pyridin-2-ylamino)benzamide A mixture of N-(3-(2-chloroethoxy)-5-(trifluoromethyl)phenyl)-4-methyl-3-(3-(pyrimidin-4-yl)pyridin-2-ylamino)benzamide (200 mg, 0.38 mmol), 1-methylpiperazine (76 mg, 0.76 mmol) and sodium iodide (catalytic amount) in DMF (5 ml) was heated at 100° C. for 20 hr. After cooling to RT, water (50 ml) was added and the mixture was extracted with EtOAc (3×50 ml). The combined organic layer was washed with brine (3×50 ml) and dried over $Na_2SO_4$. The solvent was removed in vacuo and the product was purified by flash column chromatography eluting with MeOH(NH3)/DCM (1 to 5%) to afford the title compound as a light yellow solid. MS m/z=592 [M+1]$^+$. Calc'd for $C_{31}H_{32}F_3N_7O_2$: 591.6.

| Ex. No. | Structure Name | Structure | MW | MS Data |
|---|---|---|---|---|
| 227 | 4-methyl-N-(3-(2-morpholinoethoxy)-5-(trifluoromethyl)phenyl)-3-(3-(pyrimidin-4-yl)pyridin-2-ylamino)benzamide | 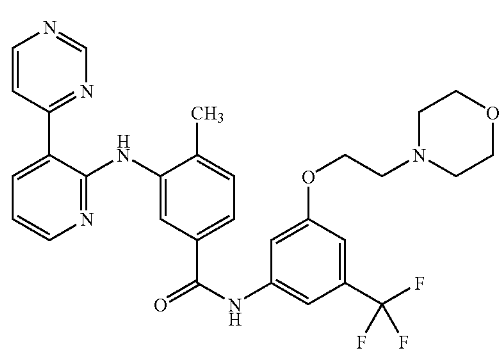 | 578.59 | 579 |

-continued

| Ex. No. | Structure Name | Structure | MW | MS Data |
|---|---|---|---|---|
| 228 | N-(3-(2-(2-((isopropylamino)methyl)pyrrolidin-1-yl)ethoxy)-5-(trifluoromethyl)phenyl)-4-methyl-3-(3-(pyrimidin-4-yl)pyridin-2-ylamino)benzamide | 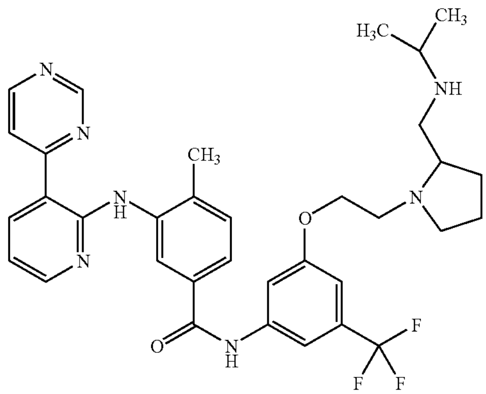 | 633.72 | 634 |
| 229 | N-(3-(2-((S)-2-(hydroxymethyl)pyrrolidin-1-yl)ethoxy)-5-(trifluoromethyl)phenyl)-4-methyl-3-(3-(pyrimidin-4-yl)pyridin-2-ylamino)benzamide | 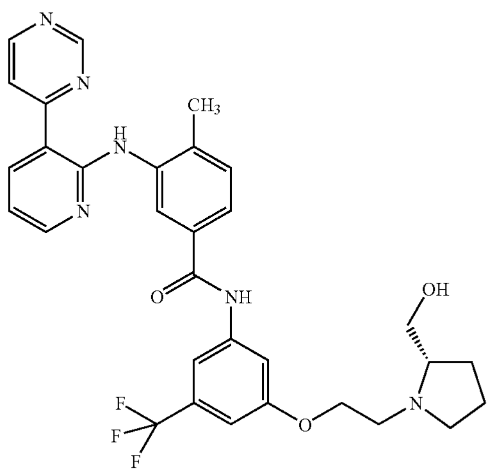 | 592.72 | 593 |
| 230 | tert-butyl 4-(2-(3-(4-methyl-3-(3-(pyrimidin-4-yl)pyridin-2-ylamino)benzamido)-5-(trifluoromethyl)phenoxy)ethyl)piperazine-1-carboxylate | 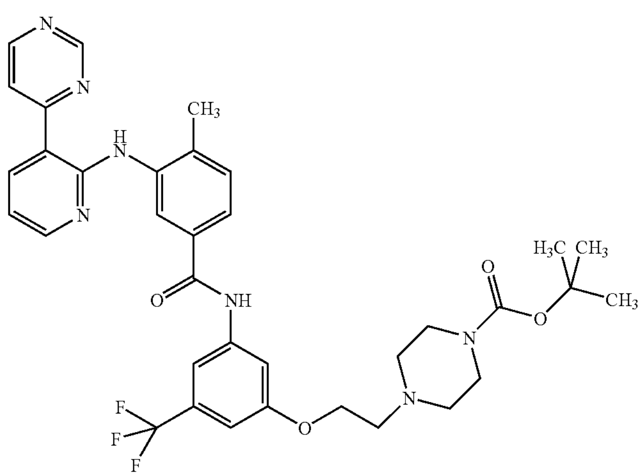 | 677.72 | 678 |

| Ex. No. | Structure Name | Structure | MW | MS Data |
|---|---|---|---|---|
| 231 | 4-methyl-N-(3-(2-(piperazin-1-yl)ethoxy)-5-(trifluoromethyl)phenyl)-3-(3-(pyrimidin-4-yl)pyridin-2-ylamino)benzamide | 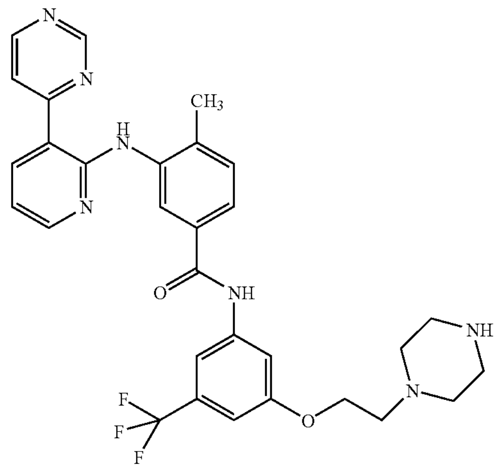 | 577.61 | 578 |

Method G

EXAMPLE 232

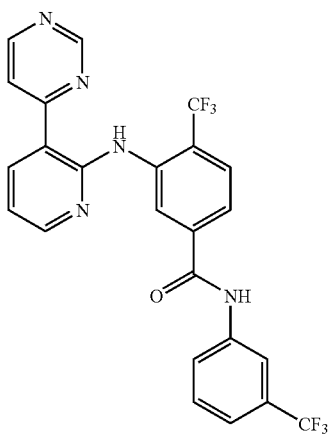

Synthesis of 3-(3-(pyrimidin-4-yl)pyridin-2-ylamino)-4-(trifluoromethyl)-N-(3-(trifluoromethyl)phenyl)benzamide Step 1. Preparation of ethyl 3-nitro-4-(trifluoromethyl)benzoate 3-Nitro-4-(trifluoromethyl)benzoic acid (10 g, 43 mmol) was taken up in 100 ml of ethanol and sulfuric acid (11 ml) was added to the mixture. The reaction was heated to reflux for 12 hours. The volatiles were removed in vacuo. The residue obtained was diluted with ethyl acetate and water. The layers were separated and the organic layer was washed with an aqueous solution of saturated sodium bicarbonate, water and brine. The organic layer was then dried with sodium sulfate and the volatiles removed in vacuo to give ethyl 3-nitro-4-(trifluoromethyl)benzoate a clear yellow oil.

Step 2. Preparation of ethyl 3-amino-4-(trifluoromethyl)benzoate

Ethyl 3-nitro-4-(trifluoromethyl)benzoate (11.58 g, 44 mmol) was taken up in EtOH (150 ml) and vacuum purged. Then, under a nitrogen atmosphere, Pd/C (1.15 g) was added. The mixture was stirred at RT overnight under a hydrogen atmosphere using a balloon. The reaction was filtered through a pad of celite and the filtrate reduced under reduced pressure to give ethyl 3-amino-4-(trifluoromethyl)benzoate a white solid.

Step 3. Preparation of ethyl 3-(3-(pyrimidin-4-yl)pyridin-2-ylamino)-4-(trifluoromethyl)benzoate 4-(2-Chloropyridin-3-yl)pyrimidine (1.5 g, 7.8 mmol), ethyl 3-amino-4-(trifluoromethyl)benzoate (2.0 g, 8.6 mmol), Sodium tert-butoxide (1.1 g, 12 mmol), rac-2,2'-Bis(diphenylphosphino)-1,1'-binaphthyl (0.49 g, 0.78 mmol) were all mixed together in toluene (25 ml) and degassed under vacuum. Nitrogen was bubbled into the reaction for 5 minutes and then Palladium (II) acetate (0.088 g, 0.39 mmol) was added. The mixture was heated to 80° C. and stirred overnight. The reaction was diluted with ethyl acetate and washed with an aqueous saturated solution of sodium bicarbonate, water and brine. The organic layer was then dried with sodium sulfate and purified by column chromatography on silica gel using a gradient 5 to 40% ethyl acetate in hexanes to afford ethyl 3-(3-(pyrimidin-4-yl)pyridin-2-ylamino)-4-(trifluoromethyl)benzoate as a brown solid. MS m/z=389 [M+1]$^+$. Calc'd for $C_{19}H_{15}F_3N_4O_2$: 388.11.

Step 4. Preparation of 3-(3-(pyrimidin-4-yl) pyridin-2-ylamino)-4-(trifluoromethyl) benzoic acid Ethyl 3-(3-(pyrimidin-4-yl)pyridin-2-ylamino)-4-(trifluoromethyl)benzoate (2.50 g, 6 mmol) was suspended in EtOH (30 ml) and treated with 5N Sodium hydroxide (4 ml). The mixture was stirred at reflux overnight. The reaction was cooled down and the volatiles removed in vacuo. The residue was washed with diluted acetic acid (10:1 water: acetic acid) and then washed with water, to give 3-(3-(pyrimidin-4-yl)pyridin-2-ylamino)-4-(trifluoromethyl) benzoic acid as a yellow solid, after drying in a vacuum oven at 60° C. overnight. MS m/z=361 [M+1]$^+$. Calc'd for $C_{17}H_{11}F_3N_4O_2$: 360.08.

Step 5. Preparation of 3-(3-(pyrimidin-4-yl)pyridin-2-ylamino)-4-(trifluoromethyl)-N-(3-(trifluoromethyl)phenyl)benzamide 3-(3-(Pyrimidin-4-yl)pyridin-2-ylamino)-4-(trifluoromethyl)benzoic acid (0.13 g, 0.36 mmol), 3-(trifluoromethyl) benzenamine (0.070 g, 0.43 mmol), TBTU (0.14 g, 0.43 mmol), DIPEA (0.13 ml, 0.72 mmol) were all mixed together in a 25 ml flask containing 3 ml of DMF. The mixture was stirred together at room temperatur for 16 hours. The reaction was then diluted with an aqueous saturated solution of sodium bicarbonate and extracted with DCM. The organic layer was washed (2×) with an aqueous saturated solution of sodium bicarbonate, then with water and then brine. The organic layer was then dried with sodium sulfate and the purified by column chromatography on silica gel using a gradient of 30 to 80% EtOAc in hexanes to give 3-(3-(pyrimidin-4-yl)pyridin-2-ylamino)-4-(trifluoromethyl)-N-(3-(trifluoromethyl)phenyl) benzamide as an off-white solid. MS m/z=504 [M+1]$^+$. Calc'd for $C_{24}H_{15}F_6N_5O$: 503.12.

| Ex. No. | Structure Name | Structure | MW | MS Data |
|---|---|---|---|---|
| 233 | 3-(3-(pyrimidin-4-yl)pyridin-2-ylamino)-N-(3-((S)-pyrrolidin-2-ylmethoxy)-5-(trifluoromethyl)phenyl)-4-(trifluoromethyl)benzamide | 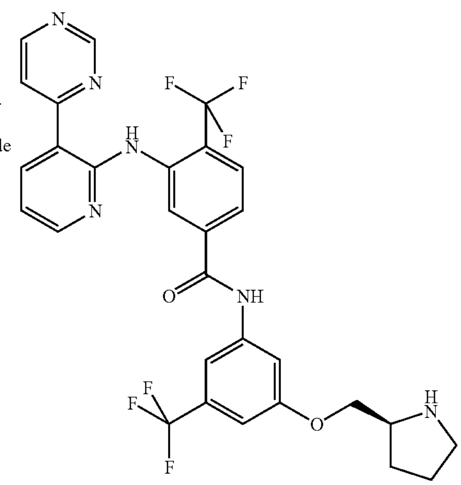 | 602.54 | 603 |
| 234 | N-(3-chlorophenyl)-3-(3-(pyrimidin-4-yl)pyridin-2-ylamino)-4-(trifluoromethyl)benzamide | 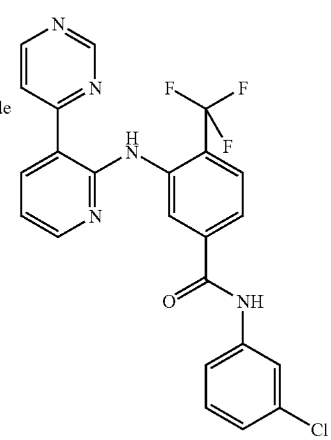 | 469.85 | 471 |

| Ex. No. | Structure Name | Structure | MW | MS Data |
|---|---|---|---|---|
| 235 | N-(3-isopropylphenyl)-3-(3-(pyrimidin-4-yl)pyridin-2-ylamino)-(trifluoromethyl)benzamide | 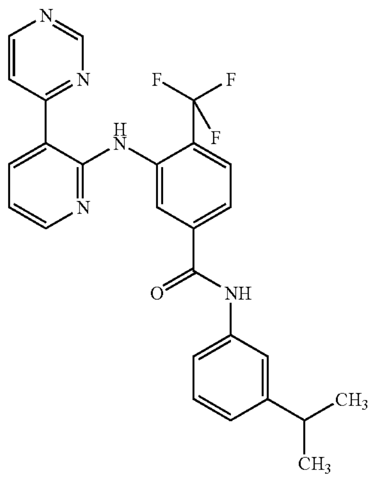 | 477.49 | 478 |
| 236 | N-(4-tert-butylphenyl)-3-(3-(pyrimidin-4-yl)pyridin-2-ylamino)-4-(trifluoromethyl)benzamide | 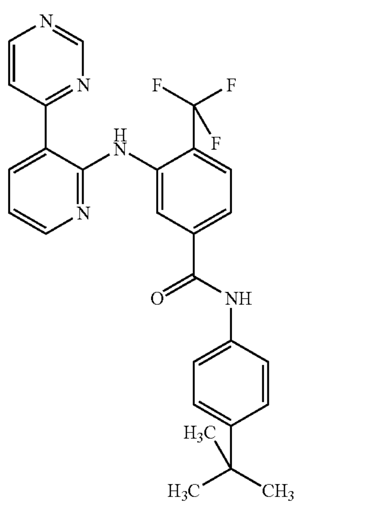 | 491.51 | 492 |
| 237 | N-(3-(dimethylamino)phenyl)-3-(3-(pyrimidin-4-yl)pyridin-2-ylamino)-4-(trifluoromethyl)benzamide | 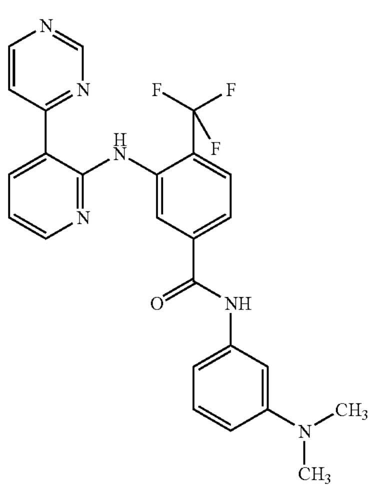 | 478.48 | 479 |

-continued

| Ex. No. | Structure Name | Structure | MW | MS Data |
|---|---|---|---|---|
| 238 | N-(3-tert-butyl-1-methyl-1H-pyrazol-5-yl)-3-(3-(pyrimidin-4-yl)pyridin-2-ylamino)-4-(trifluoromethyl)benzamide | 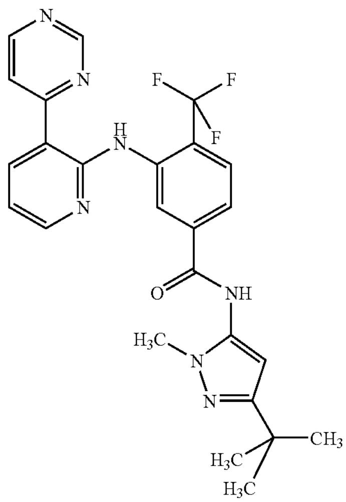 | 495.51 | 496 |
| 239 | N-(2,3-dihydro-1H-inden-5-yl)-3-(3-(pyrimidin-4-yl)pyridin-2-ylamino)-4-(trifluoromethyl)benzamide | 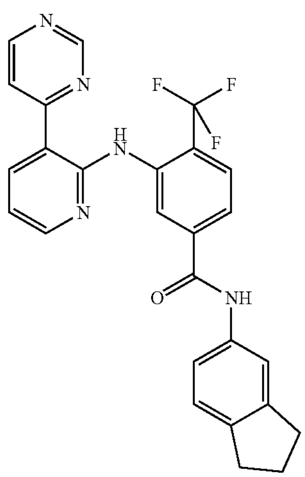 | 475.47 | 476 |
| 240 | N-(3-methoxyphenyl)-3-(3-(pyrimidin-4-yl)pyridin-2-ylamino)-4-(trifluoromethyl)benzamide | 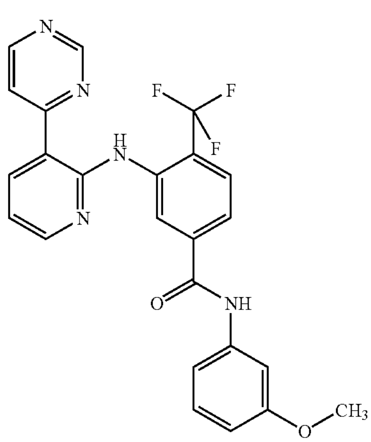 | 465.43 | 466 |

-continued

| Ex. No. | Structure Name | Structure | MW | MS Data |
|---|---|---|---|---|
| 241 | N-(3-isopropoxyphenyl)-3-(3-(pyrimidin-4-yl)pyridin-2-ylamino)-4-(trifluoromethyl)benzamide | 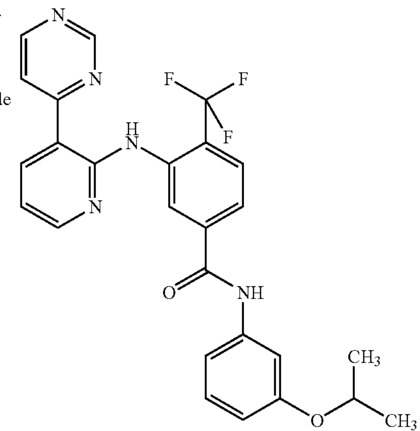 | 493.49 | 494 |

Method H

EXAMPLE 242

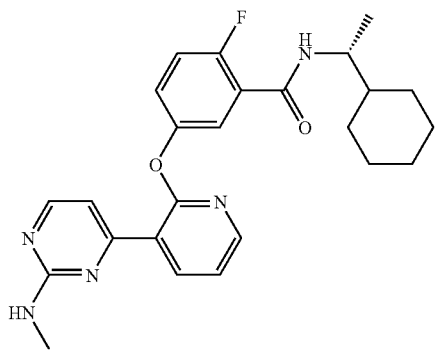

Synthesis of N-((1R)-1-Cyclohexylethyl)-2-fluoro-5-((3-(2-(methylamino)-4-pyrimidinyl)-2-pyridinyl)oxy)benzamide To a solution of 2-fluoro-5-[3-(2-methylamino-pyrimidin-4-yl)-pyridin-2-yloxy]-benzoyl chloride hydrochloride (86 mg, 0.22 mmol) in THF (2.0 mL) was added (R)-1-cyclohexyl-ethylamine (0.029 mL, 0.20 mmol). The mixture was stirred overnight at RT, quenched with excess NEt$_3$, concentrated and purified by preparative TLC (100% EtOAc) to yield N-((1R)-1-cyclohexylethyl)-2-fluoro-5-((3-(2-(methylamino)-4-pyrimidinyl)-2-pyridinyl)oxy)benzamide. MS m/z=450 [M+1]$^+$. Calc'd for C$_{25}$H$_{28}$FN$_5$O$_2$: 449.53.

| Ex. No. | Structure Name | Structure | MW | MS Data |
|---|---|---|---|---|
| 243 | 4-methyl-3-((3-(4-pyrimidinyl)-2-pyridinyl)oxy)-N-(3-(trifluoromethyl)phenyl)benzamide | 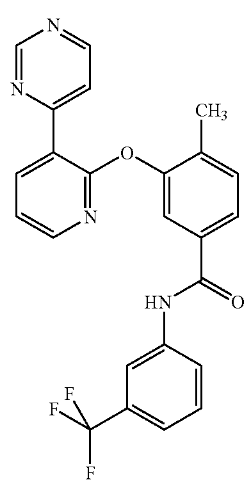 | 450.42 | 473 |

-continued

| Ex. No. | Structure Name | Structure | MW | MS Data |
|---|---|---|---|---|
| 244 | 4-methyl-3-((3-(4-pyrimidinyl)-2-pyridinyl)oxy)-N-((1S)-1,2,2-trimethylpropyl)benzamide | 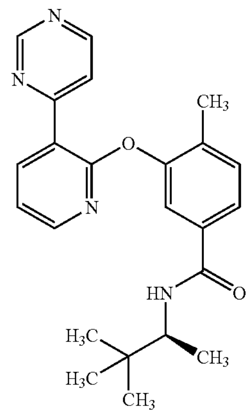 | 390.48 | 391 |
| 245 | 4-methyl-3-((3-(4-pyrimidinyl)-2-pyridinyl)oxy)-N-((1R)-1,2,2-trimethylpropyl)benzamide | 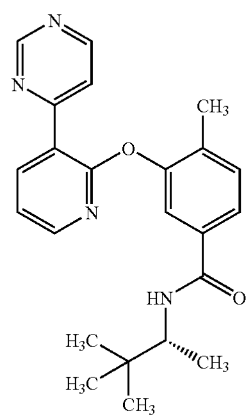 | 390.48 | 391 |
| 246 | N-(3-(dimethylamino)-2,2-dimethylpropyl)-4-methyl-3-((3-(4-pyrimidinyl)-2-pyridinyl)oxy)benzamide | 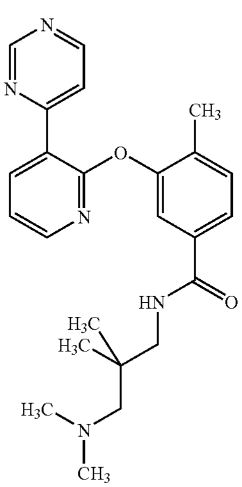 | 419.53 | 420 |

-continued

| Ex. No. | Structure Name | Structure | MW | MS Data |
|---|---|---|---|---|
| 247 | N-(3-(1,1-dimethylethyl)-1-phenyl-1H-pyrazol-5-yl)-4-methyl-3-((3-(4-pyrimidinyl)-2-pyridinyl)oxy)benzamide | 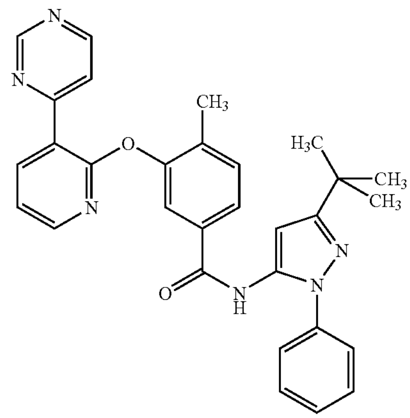 | 504.59 | 505 |
| 248 | N-(5-cyclohexyl-2-(methyloxy)phenyl)-4-methyl-3-((3-(4-pyrimidinyl)-2-pyridinyl)oxy)benzamide | 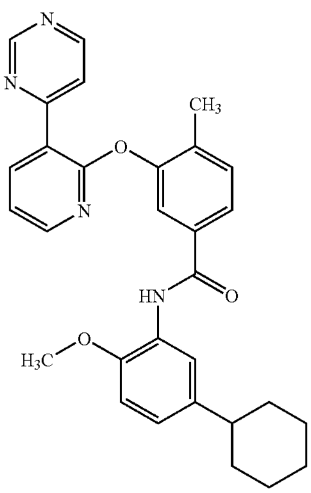 | 494.59 | 495 |
| 249 | N-(5-(1,1-dimethylethyl)-2-(methyloxy)phenyl)-4-methyl-3-((3-(4-pyrimidinyl)-2-pyridinyl)oxy)benzamide | 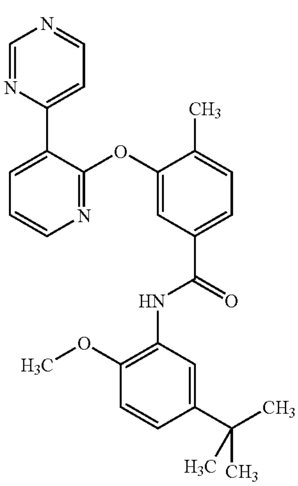 | 468.55 | 469 |

-continued

| Ex. No. | Structure Name | Structure | MW | MS Data |
|---|---|---|---|---|
| 250 | N-(2-chloro-5-(trifluoromethyl)phenyl)-4-methyl-3-((3-(4-pyrimidinyl)-2-pyridinyl)oxy)benzamide | 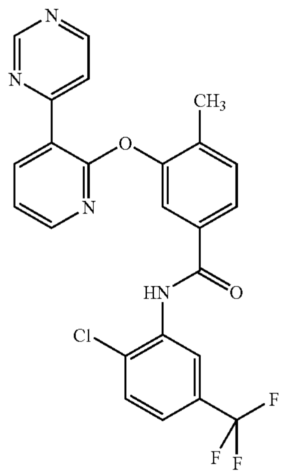 | 484.86 | 485 |
| 251 | 4-methyl-3-((3-(4-pyrimidinyl)-2-pyridinyl)oxy)-N-(2-(1-pyrrolidinyl)-5-(trifluoromethyl)phenyl)benzamide | 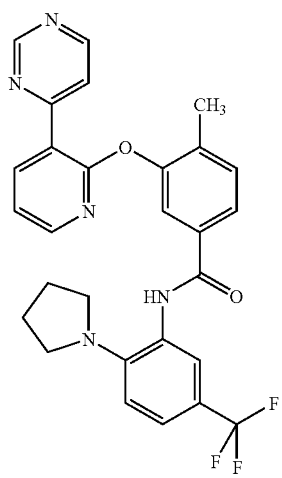 | 519.52 | 542 |
| 252 | 4-methyl-N-(2-(methylsulfanyl)-5-(trifluoromethyl)phenyl)-3-((3-(4-pyrimidinyl)-2-pyridinyl)oxy)benzamide | 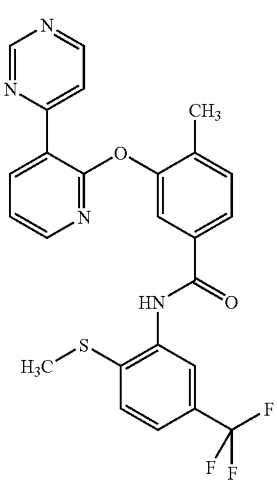 | 496.51 | 497 |

| Ex. No. | Structure Name | Structure | MW | MS Data |
|---|---|---|---|---|
| 253 | 4-methyl-N-(2-(1-piperidinyl)-5-(trifluoromethyl)phenyl)-3-((3-(4-pyrimidinyl)-2-pyridinyl)oxy)benzamide | 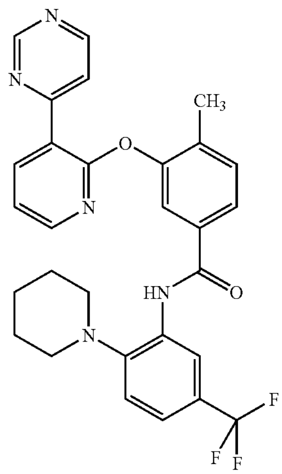 | 533.55 | 534 |
| 254 | N-(2-bromo-5-(trifluoromethyl)phenyl)-4-methyl-3-((3-(4-pyrimidinyl)-2-pyridinyl)oxy)benzamide | 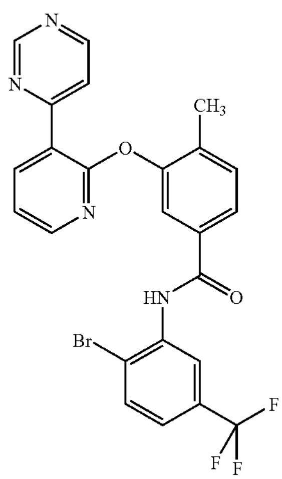 | 529.31 | 529 |
| 255 | N-(2,5-dichlorophenyl)-4-methyl-3-((3-(4-pyrimidinyl)-2-pyridinyl)oxy)benzamide | 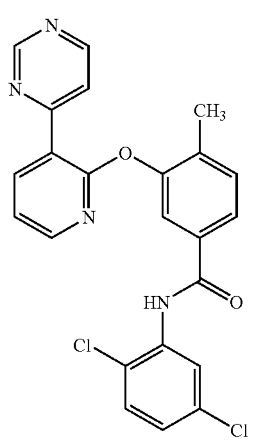 | 451.31 | 451 |

-continued

| Ex. No. | Structure Name | Structure | MW | MS Data |
|---|---|---|---|---|
| 256 | 4-methyl-N-(2-(4-morpholinyl)-5-(trifluoromethyl)phenyl pyrimidinyl)-2-pyridinyl)oxy)benzamide | 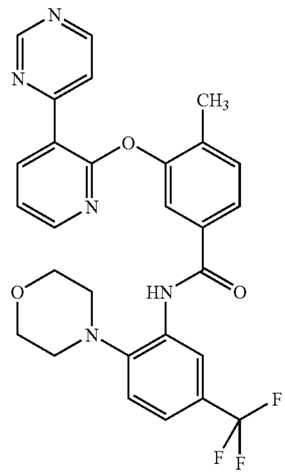 | 535.52 | 536 |
| 257 | 4-methyl-N-(4-(methyloxy)-1,1'-biphenyl-3-yl)-3-((3-(4-pyrimidinyl)-2-pyridinyl)oxy)benzamide | 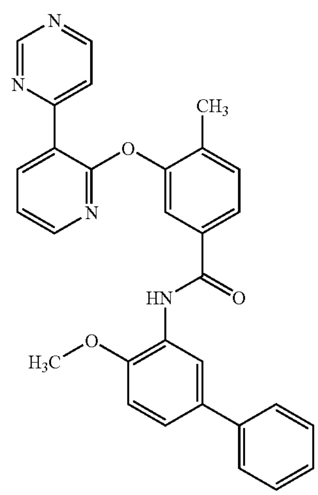 | 488.55 | 489 |
| 258 | methyl 4-(methyloxy)-3-(((4-methyl-3-((3-(4-pyrimidinyl)-2-pyridinyl)oxy)phenyl)carbonyl)amino)benzoate | 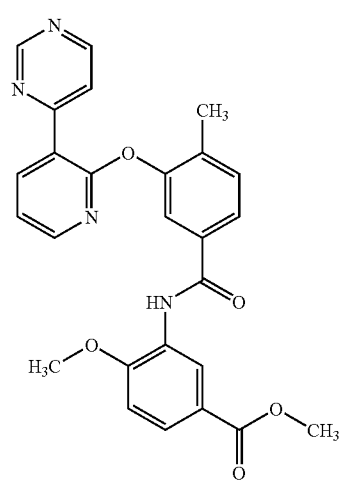 | 470.48 | 471 |

| Ex. No. | Structure Name | Structure | MW | MS Data |
|---|---|---|---|---|
| 259 | N-(2,5-bis(methyloxy)phenyl)-4-methyl-3-((3-(4-pyrimidinyl)-2-pyridinyl)oxy)benzamide | 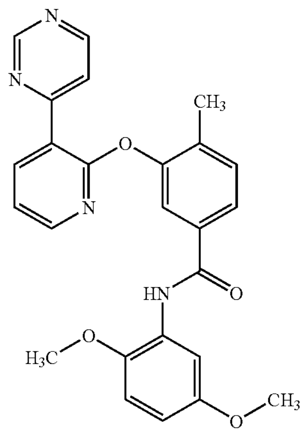 | 442.47 | 443 |
| 260 | 4-methyl-N-(2-methyl-5-(methyloxy)phenyl)-3-((3-(4-pyrimidinyl)-2-pyridinyl)oxy)benzamide | 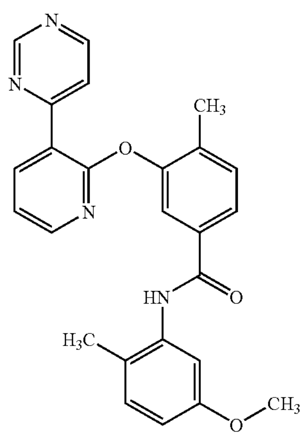 | 426.47 | 427 |
| 261 | N-(1,1'-biphenyl-3-yl)-4-methyl-3-((3-(4-pyrimidinyl)-2-pyridinyl)oxy)benzamide | 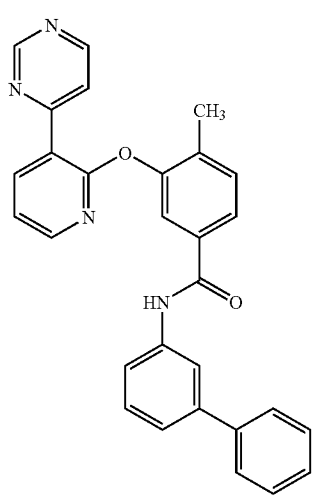 | 458.52 | 459 |

| Ex. No. | Structure Name | Structure | MW | MS Data |
|---|---|---|---|---|
| 262 | 4-methyl-3-((3-(2-(methylamino)-4-pyrimidinyl)-2-pyridinyl)oxy)-N-(3-(trifluoromethyl)phenyl)benzamide | 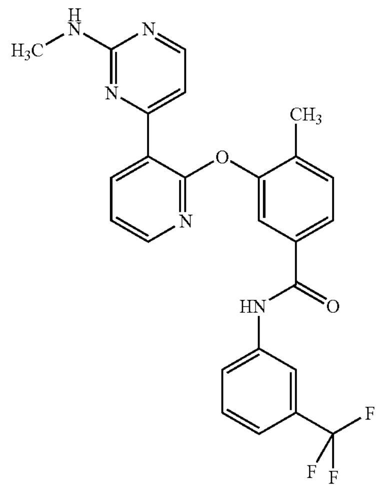 | 479.46 | 480 |
| 263 | 4-methyl-N-(2-(methyloxy)-5-(trifluoromethyl)phenyl)-3-((3-(4-pyrimidinyl)-2-pyridinyl)oxy)benzamide | 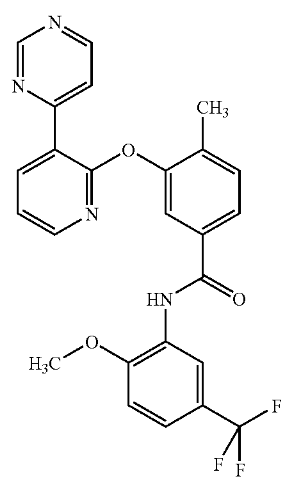 | 480.44 | 481 |
| 264 | N-(5-cyclohexyl-2-(methyloxy)phenyl)-4-methyl-3-((3-(2-(methylamino)-4-pyrimidinyl)-2-pyridinyl)oxy)benzamide | 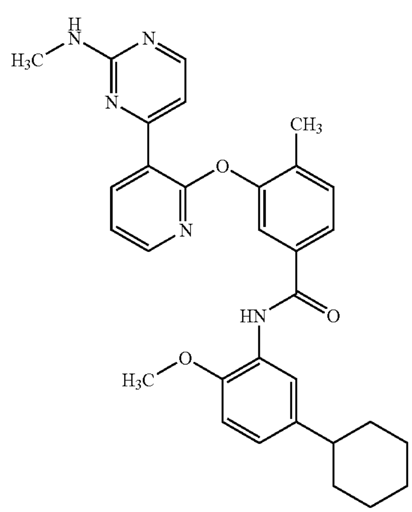 | 523.63 | 524 |

-continued

| Ex. No. | Structure Name | Structure | MW | MS Data |
|---|---|---|---|---|
| 265 | 4-methyl-3-((3-(2-(methylamino)-4-pyrimidinyl)-2-pyridinyl)oxy)-N-(4-(methyloxy)-1,1'-biphenyl-3-yl)benzamide | 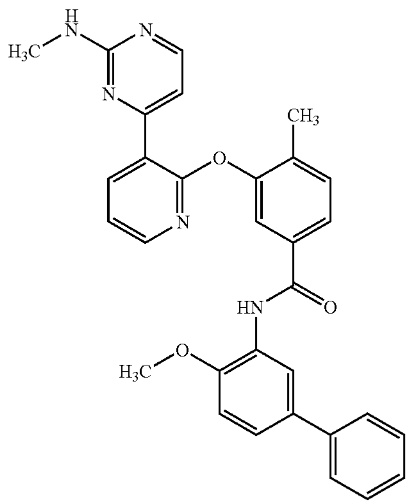 | 517.59 | 518 |
| 266 | 4-methyl-3-((3-(2-(methylamino)-4-pyrimidinyl)-2-pyridinyl)oxy)-N-(2-(1-piperidinyl)-5-(trifluoromethyl)phenyl)benzamide | 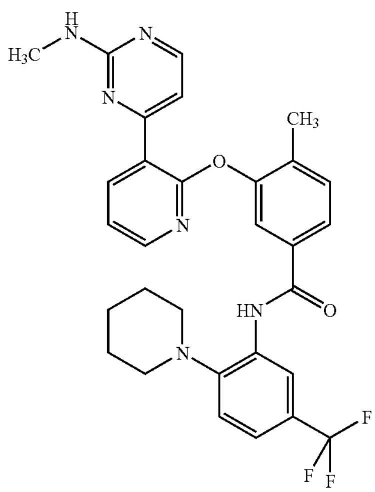 | 562.59 | 563 |
| 267 | 4-methyl-3-((3-(2-(methylamino)-4-pyrimidinyl)-2-pyridinyl)oxy)-N-(3-((((2R)-1-methyl-2-pyrrolidinyl)methyl)oxy)-5-(trifluoromethyl)phenyl)benzamide | 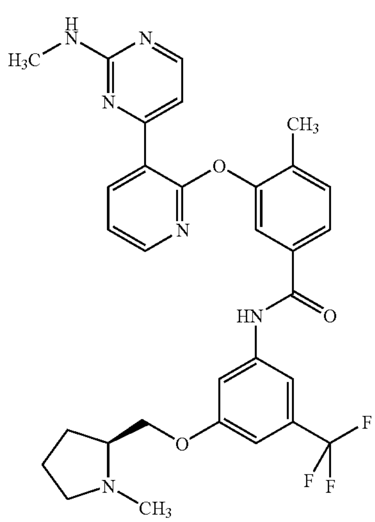 | 592.62 | 593 |

| Ex. No. | Structure Name | Structure | MW | MS Data |
|---|---|---|---|---|
| 268 | 4-methyl-N-(2-methyl-5-(trifluoromethyl)phenyl)-3-((3-(4-pyrimidinyl)-2-pyridinyl)oxy)benzamide | 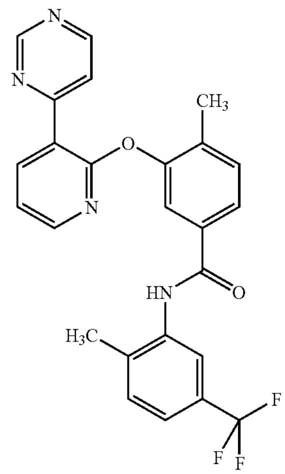 | 464.44 | 465 |
| 269 | 4-methyl-N-(2-methyl-5-(1-methylethyl)phenyl)-3-((3-(4-pyrimidinyl)-2-pyridinyl)oxy)benzamide | 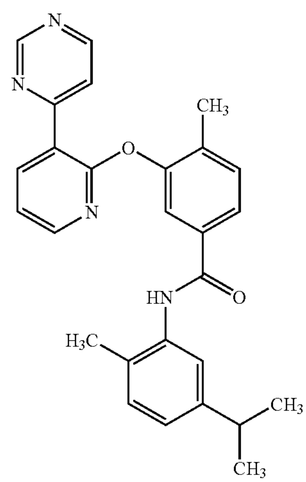 | 438.53 | 439 |
| 270 | N-(3-(1,1-dimethylethyl)-1-phenyl-1H-pyrazol-5-yl)-4-methyl-3-((3-(2-(methylamino)-4-pyrimidinyl)-2-pyridinyl)oxy)benzamide | 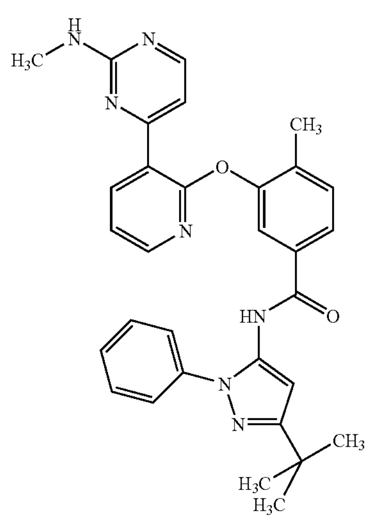 | 533.63 | 534 |

-continued

| Ex. No. | Structure Name | Structure | MW | MS Data |
|---|---|---|---|---|
| 271 | 3-methyl-N-(4-(1-methylethyl)phenyl)-4-((3-(4-pyrimidinyl)-2-pyridinyl)oxy)benzamide | 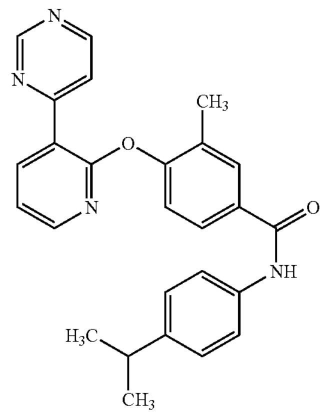 | 424.5 | 425 |
| 272 | 3-methyl-N-(3-(1-methylethyl)phenyl)-4-((3-(4-pyrimidinyl)-2-pyridinyl)oxy)benzamide | 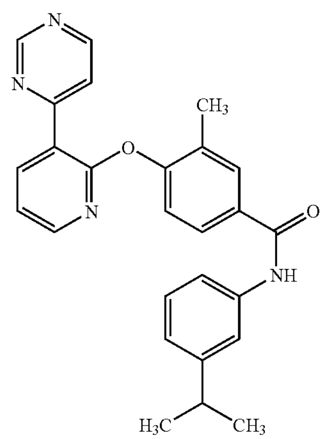 | 424.5 | 425 |
| 273 | 4-methyl-N-(2-methyl-3,5-bis(trifluoromethyl)phenyl)-3-((3-(4-pyrimidinyl)-2-pyridinyl)oxy)benzamide | 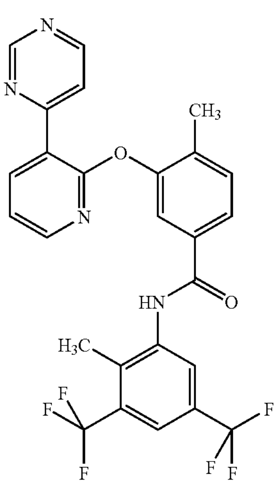 | 532.44 | 533 |

| Ex. No. | Structure Name | Structure | MW | MS Data |
|---|---|---|---|---|
| 274 | 4-methyl-3-((3-(2-(methylamino)-4-pyrimidinyl)-2-pyridinyl)oxy)-N-(2-(methyloxy)phenyl)benzamide | 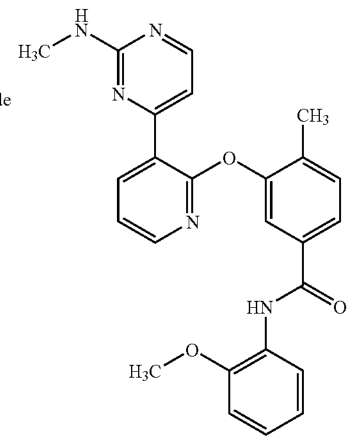 | 441.49 | 442 |
| 275 | N-(1,3-diphenyl-1H-pyrazol-5-yl)-4-methyl-3-((3-(4-pyrimidinyl)-2-pyridinyl)oxy)benzamide | 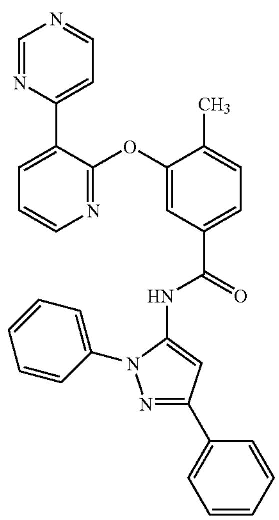 | 524.58 | 525 |
| 276 | 4-methyl-3-((3-(2-(methylamino)-4-pyrimidinyl)-2-pyridinyl)oxy)-N-(2-(4-morpholinyl)-5-(trifluoromethyl)phenyl)benzamide | 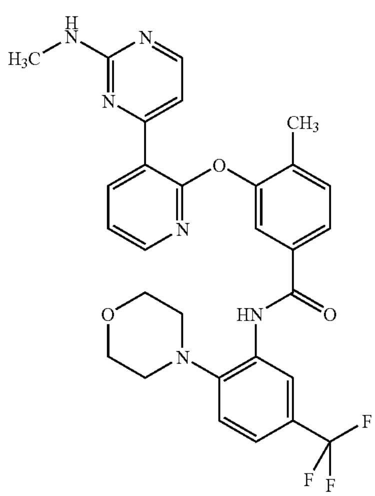 | 564.57 | 565 |

-continued

| Ex. No. | Structure Name | Structure | MW | MS Data |
|---|---|---|---|---|
| 277 | 4-methyl-3-((3-(2-(methylamino)-4-pyrimidinyl)-2-pyridinyl)oxy)-N-((1R)-1-phenylethyl)benzamide | 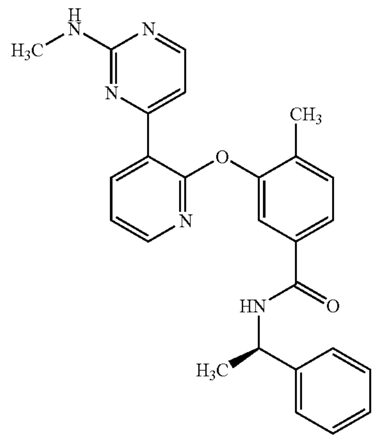 | 439.52 | 440 |
| 278 | 4-methyl-3-((3-(2-(methylamino)-4-pyrimidinyl)-2-pyridinyl)oxy)-N-((1S)-1-phenylethyl)benzamide | 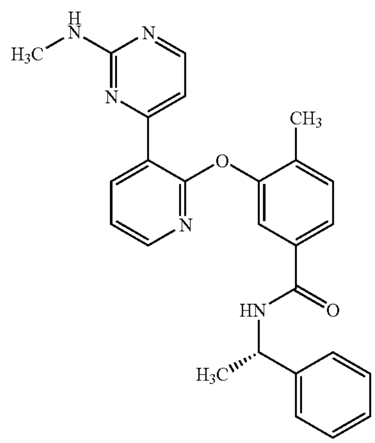 | 439.52 | 440 |
| 279 | 4-methyl-3-((3-(2-(methylamino)-4-pyrimidinyl)-2-pyridinyl)oxy)-N-phenylbenzamide | 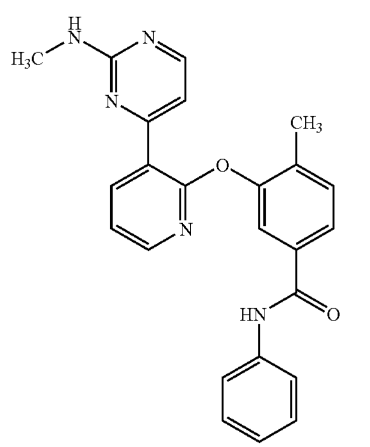 | 411.46 | 412 |

-continued

| Ex. No. | Structure Name | Structure | MW | MS Data |
|---|---|---|---|---|
| 280 | 4-methyl-3-((3-(2-(methylamino)-4-pyrimidinyl)-2-pyridinyl)oxy)-N-(4-(1-methylethyl)phenyl) benzamide | 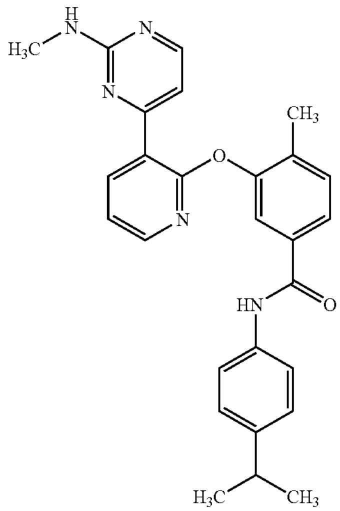 | 453.54 | 454 |
| 281 | 4-methyl-3-((3-(2-(methylamino)-4-pyrimidinyl)-2-pyridinyl)oxy)-N-(2-methyl-3-(trifluoromethyl)phenyl) benzamide | 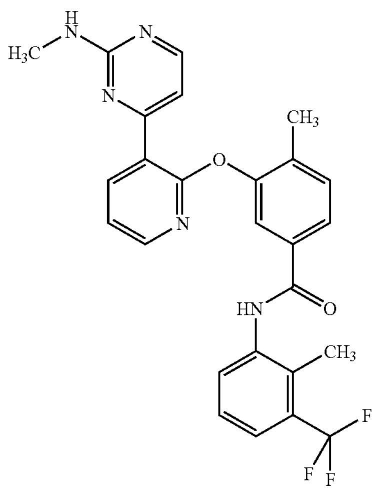 | 493.49 | 494 |
| 282 | 4-methyl-3-((3-(2-(methylamino)-4-pyrimidinyl)-2-pyridinyl)oxy)-N-(3-((phenylmethyl)oxy) phenyl)benzamide | 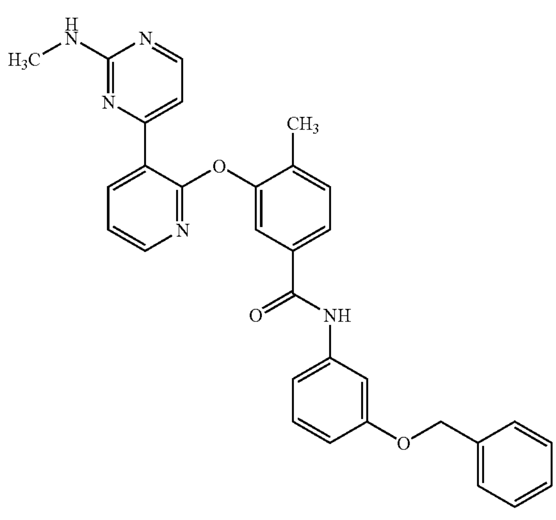 | 517.59 | 518 |

-continued

| Ex. No. | Structure Name | Structure | MW | MS Data |
|---|---|---|---|---|
| 283 | 4-methyl-3-((3-(2-(methylamino)-4-pyrimidinyl)-2-pyridinyl)oxy)-N-propylbenzamide | 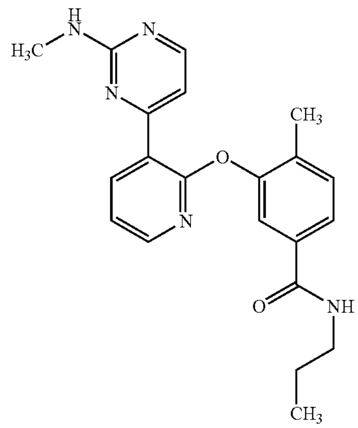 | 377.45 | 378 |
| 284 | N-(2-hydroxyethyl)-4-methyl-3-((3-(2-(methylamino)-4-pyrimidinyl)-2-pyridinyl)oxy)benzamide | 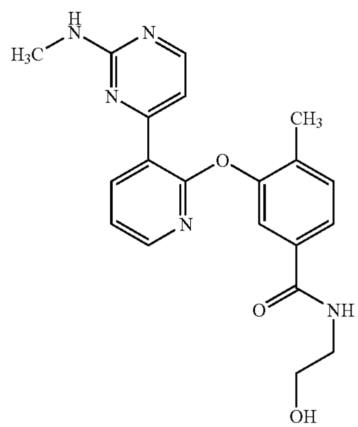 | 379.42 | 380 |
| 285 | 3-((3-(2-((2-(diethylamino)ethyl)amino)-4-pyrimidinyl)-2-pyridinyl)oxy)-4-methyl-N-(3-(1-methylethyl)phenyl)benzamide | 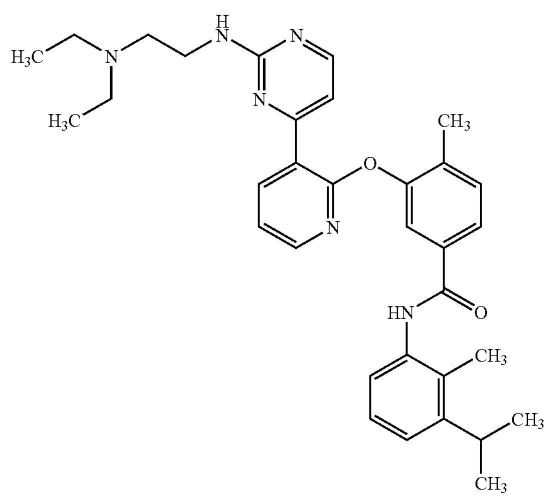 | 538.69 | 539 |

| Ex. No. | Structure Name | Structure | MW | MS Data |
|---|---|---|---|---|
| 286 | 4-methyl-3-((3-(2-(methylamino)-4-pyrimidinyl)-2-pyridinyl)oxy)-N-(3-(phenylmethyl)phenyl)benzamide | 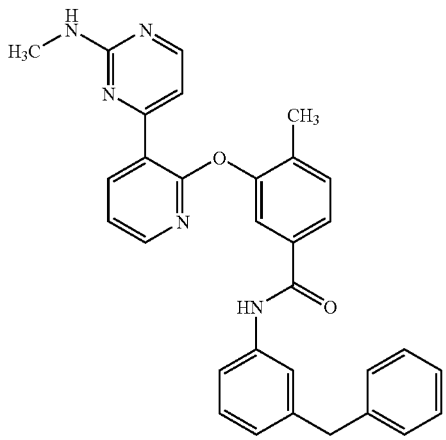 | 501.59 | 502 |
| 287 | N-(5-cyclohexyl-2-(methyloxy)phenyl)-3-((3-(2-((2-(diethylamino)ethyl)amino)-4-pyrimidinyl)-2-pyridinyl)oxy)-4-methylbenzamide | 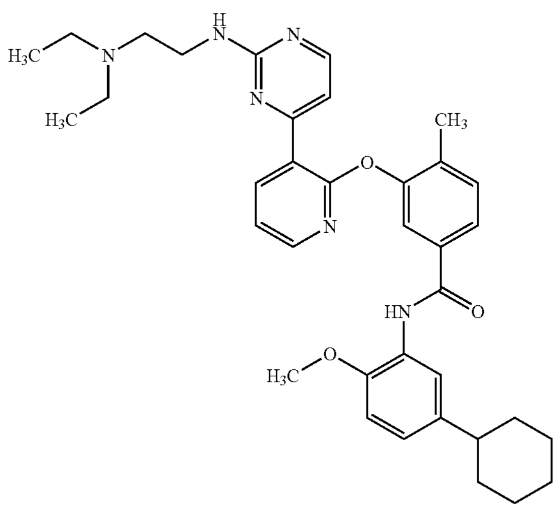 | 608.78 | 609 |
| 288 | 4-methyl-3-((3-(2-(methylamino)-4-pyrimidinyl)-2-pyridinyl)oxy)-N-((3-(trifluoromethyl)phenyl)methyl)benzamide | 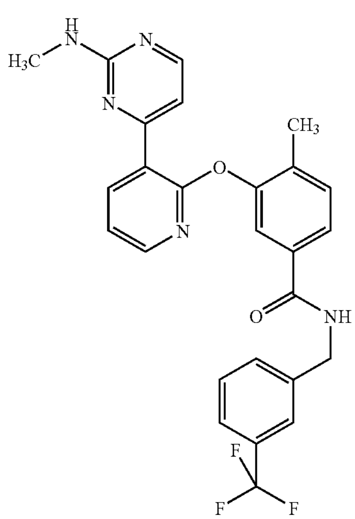 | 493.49 | 494 |

| Ex. No. | Structure Name | Structure | MW | MS Data |
|---|---|---|---|---|
| 289 | 4-methyl-3-((3-(2-(methylamino)-4-pyrimidinyl)-2-pyridinyl)oxy)-N-(2,2,3,3,3-pentafluoropropyl)benzamide | 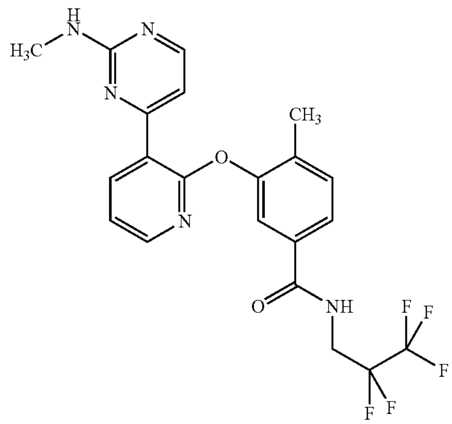 | 467.4 | 468 |
| 290 | N-(2,2,3,3,4,4,4-heptafluorobutyl)-4-methyl-3-((3-(2-(methylamino)-4-pyrimidinyl)-2-pyridinyl)oxy)benzamide | 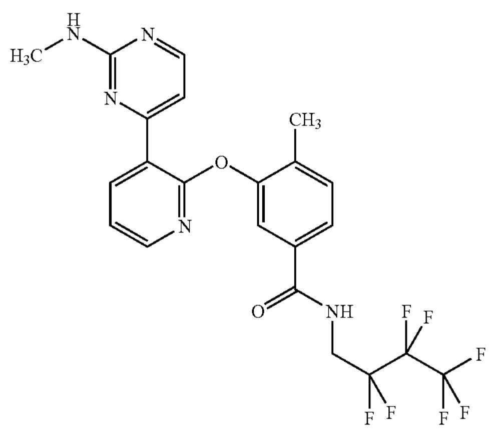 | 517.4 | 518 |
| 291 | N-((1S)-1-cyclohexylethyl)-4-methyl-3-((3-(2-(methylamino)-4-pyrimidinyl)-2-pyridinyl)oxy)benzamide | 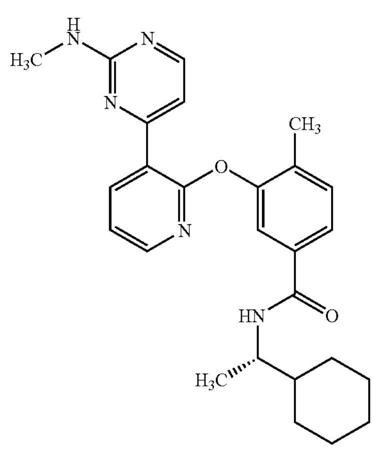 | 445.56 | 446 |

-continued

| Ex. No. | Structure Name | Structure | MW | MS Data |
|---|---|---|---|---|
| 292 | N-((1R)-1-cyclohexylethyl)-4-methyl-3-((3-(2-(methylamino)-4-pyrimidinyl)-2-pyridinyl)oxy)benzamide | 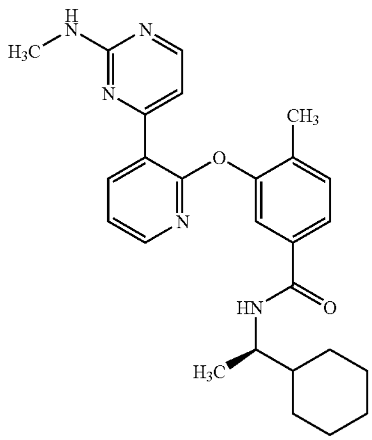 | 445.56 | 446 |
| 293 | N-(5-(1,1-dimethylethyl)-2-(methyloxy)phenyl)-4-methyl-3-((3-(2-(methylamino)-4-pyrimidinyl)-2-pyridinyl)oxy)benzamide | 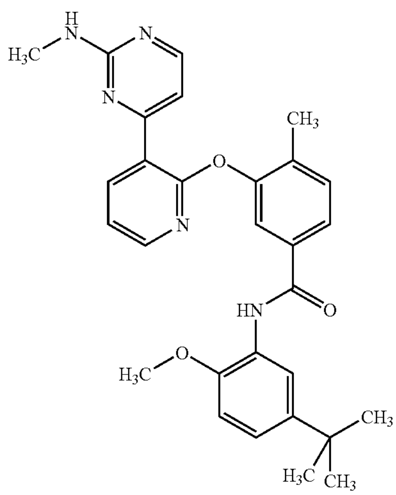 | 497.6 | 498 |
| 294 | 3-((3-(2-((2-(diethylamino)ethyl)amino)-4-pyrimidinyl)-2-pyridinyl)oxy)-4-methyl-N-(2-(4-morpholinyl)-5-(trifluoromethyl)phenyl)benzamide | 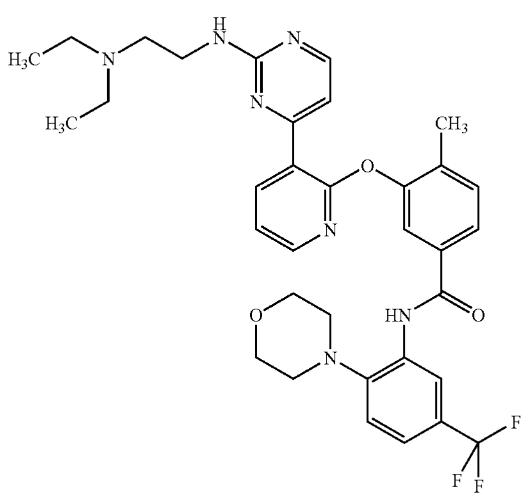 | 649.71 | 650 |

| Ex. No. | Structure Name | Structure | MW | MS Data |
|---|---|---|---|---|
| 295 | N-(5-(1,1-dimethylpropyl)-2-(methyloxy)phenyl)-4-methyl-3-((3-(2-(methylamino)-4-pyrimidinyl)-2-pyridinyl)oxy)benzamide | 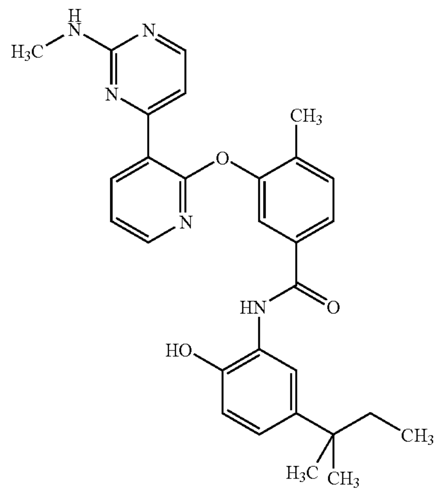 | 511.62 | 512 |
| 296 | N-butyl-4-methyl-3-((3-(2-(methylamino)-4-pyrimidinyl)-2-pyridinyl)oxy)benzamide | 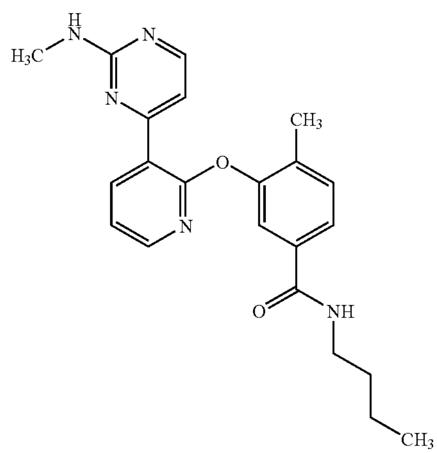 | 391.47 | 392 |
| 297 | 4-methyl-3-((3-(2-(methylamino)-4-pyrimidinyl)-2-pyridinyl)oxy)-N-pentylbenzamide | 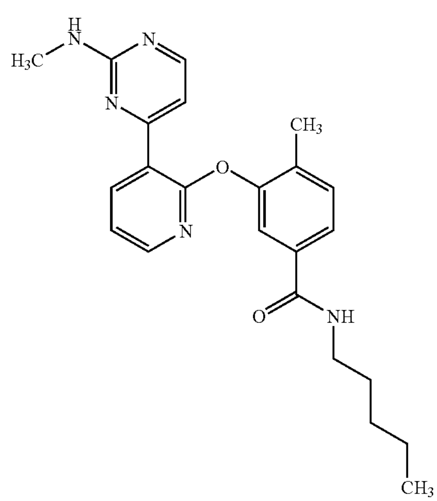 | 405.5 | 406 |

-continued

| Ex. No. | Structure Name | Structure | MW | MS Data |
|---|---|---|---|---|
| 298 | 3-((3-(2-(methylamino)-4-pyrimidinyl)-2-pyridinyl)oxy)-N-phenylbenzamide | 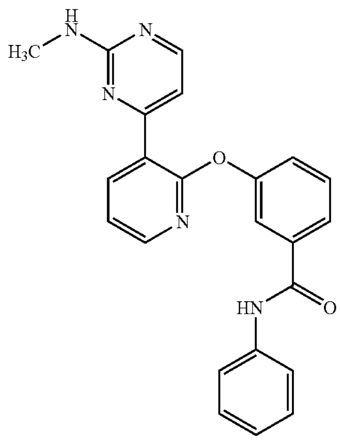 | 397.44 | 398 |
| 299 | 3-((3-(2-(methylamino)-4-pyrimidinyl)-2-pyridinyl)oxy)-N-(3-(trifluoromethyl)phenyl)benzamide | 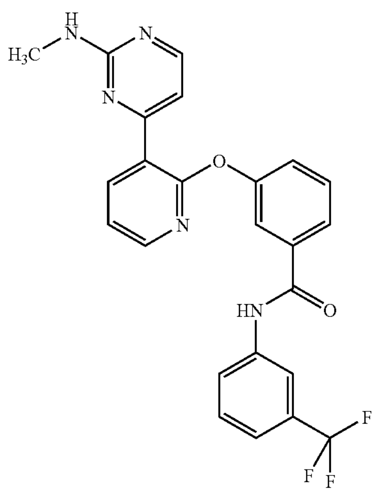 | 465.43 | 466 |
| 300 | 3-((3-(2-(methylamino)-4-pyrimidinyl)-2-pyridinyl)oxy)-N-(2-(1-piperidinyl)-5-(trifluoromethyl)phenyl)benzamide | 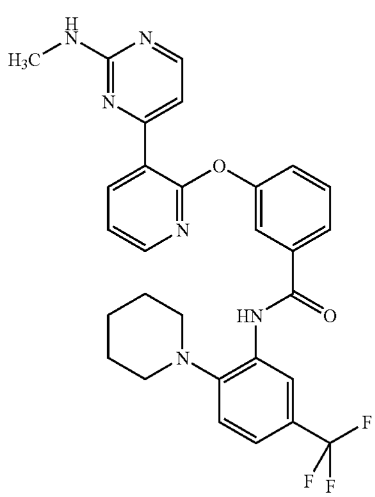 | 548.57 | 549 |

-continued

| Ex. No. | Structure Name | Structure | MW | MS Data |
|---|---|---|---|---|
| 301 | N-(5-cyclohexyl-2-(methyloxy)phenyl)-3-((3-(2-(methylamino)-4-pyrimidinyl)-2-pyridinyl)oxy)benzamide | 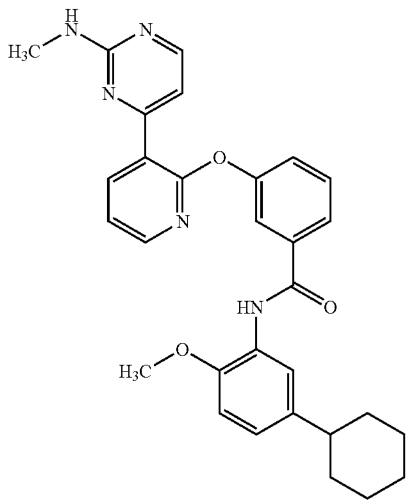 | 509.61 | 510 |
| 302 | 3-((3-(2-(methylamino)-4-pyrimidinyl)-2-pyridinyl)oxy)-N-(3-((((2S)-1-methyl-2-pyrrolidinyl)methyl)oxy)-5-(trifluoromethyl)phenyl benzamide | 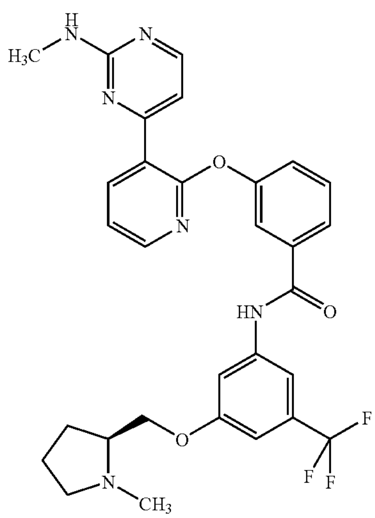 | 578.59 | 579 |
| 303 | 3-((3-(2-(methylamino)-4-pyrimidinyl)-2-pyridinyl)oxy)-N-(2-(methyloxy)phenyl)benzamide | 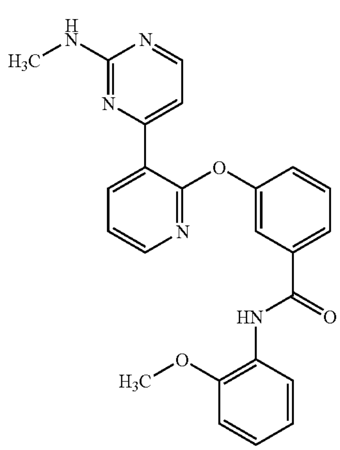 | 427.46 | 428 |

| Ex. No. | Structure Name | Structure | MW | MS Data |
|---|---|---|---|---|
| 304 | 3-((3-(2-(methylamino)-4-pyrimidinyl)-2-pyridinyl)oxy)-N-(4-(1-methylethyl)phenyl)benzamide | 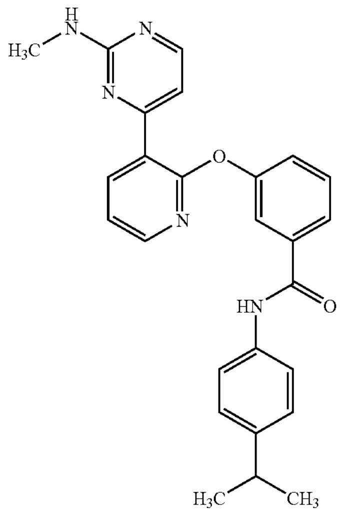 | 439.52 | 440 |
| 305 | 3-((3-(2-(methylamino)-4-pyrimidinyl)-2-pyridinyl)oxy)-N-(2-methyl-3-(trifluoromethyl)phenyl)benzamide | 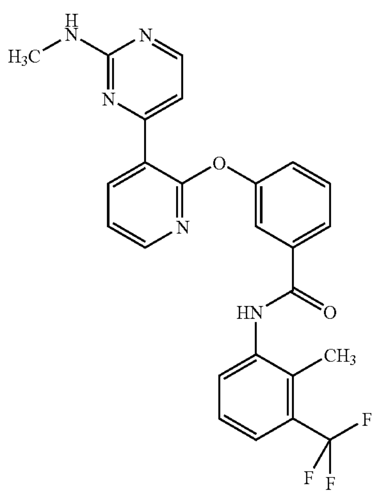 | 479.46 | 480 |
| 306 | 4-chloro-3-((3-(2-(methylamino)-4-pyrimidinyl)-2-pyridinyl)oxy)-N-phenylbenzamide | 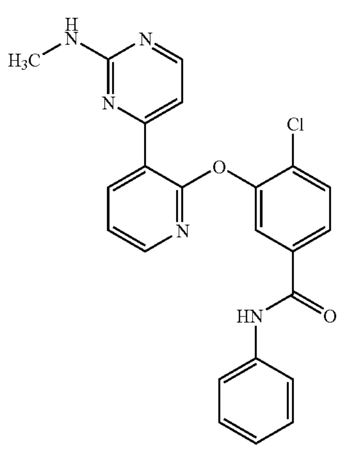 | 431.88 | 432 |

-continued

| Ex. No. | Structure Name | Structure | MW | MS Data |
|---|---|---|---|---|
| 307 | 4-chloro-3-((3-(2-(methylamino)-4-pyrimidinyl)-2-pyridinyl)oxy)-N-(3-(trifluoromethyl)phenyl)benzamide | 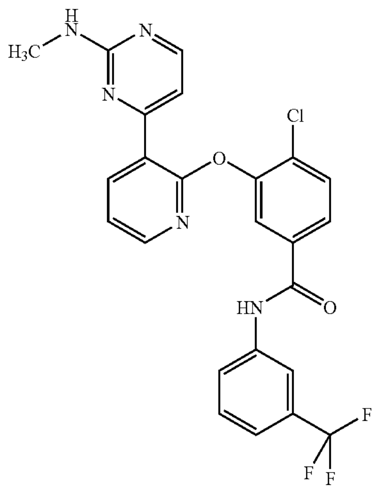 | 499.88 | 500 |
| 308 | 4-chloro-3-((3-(2-(methylamino)-4-pyrimidinyl)-2-pyridinyl)oxy)-N-(2-(1-piperidinyl)-5-trifluoromethyl)phenyl benzamide | 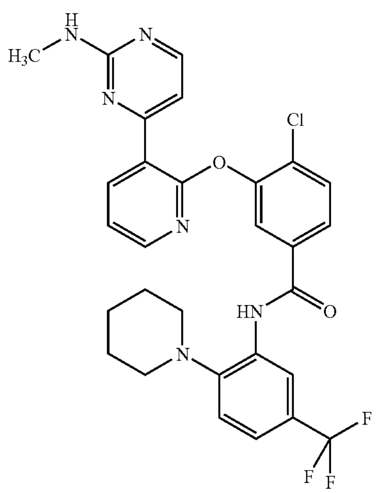 | 583.01 | 583 |
| 309 | 4-chloro-N-(5-cyclohexyl-2-(methyloxy)phenyl)-3-((3-(2-(methylamino)-4-pyrimidinyl)-2-pyridinyl)oxy)benzamide | 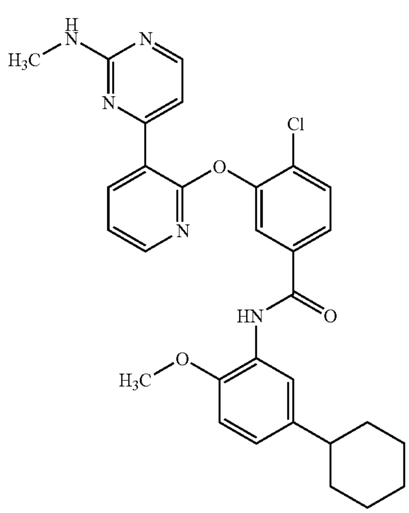 | 544.05 | 544 |

| Ex. No. | Structure Name | Structure | MW | MS Data |
|---|---|---|---|---|
| 310 | 4-chloro-3-((3-(2-(methylamino)-4-pyrimidinyl)-2-pyridinyl)oxy)-N-(3-((((2S)-1-methyl-2-pyrrolidinyl)methyl)oxy)-5-(trifluoromethyl)phenyl)benzamide | 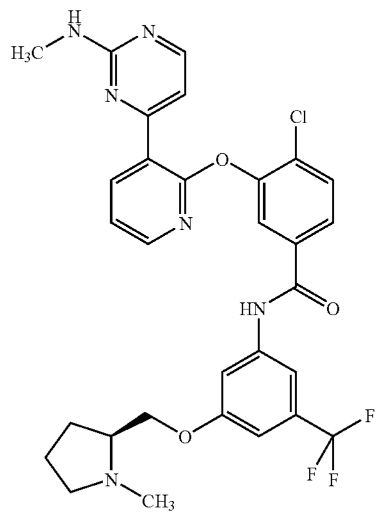 | 613.04 | 613 |
| 311 | 4-chloro-3-((3-(2-(methylamino)-4-pyrimidinyl)-2-pyridinyl)oxy)-N-(2-(methyloxy)phenyl)benzamide | 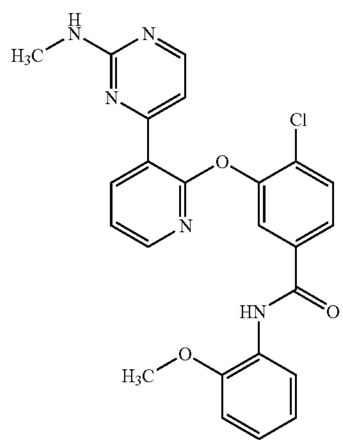 | 461.91 | 462 |
| 312 | 4-chloro-3-((3-(2-(methylamino)-4-pyrimidinyl)-2-pyridinyl)oxy)-N-(4-(1-methylethyl)phenyl)benzamide | 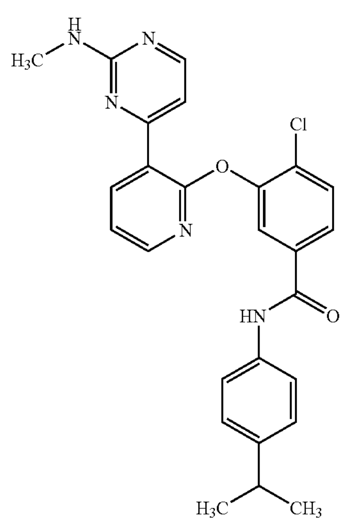 | 473.96 | 474 |

-continued

| Ex. No. | Structure Name | Structure | MW | MS Data |
|---|---|---|---|---|
| 313 | 4-chloro-3-((3-(2-(methylamino)-4-pyrimidinyl)-2-pyridinyl)oxy)-N-(2-methyl-3-(trifluoromethyl)phenyl)benzamide | 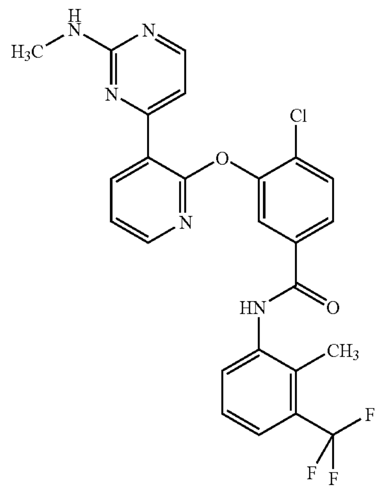 | 513.9 | 514 |
| 314 | 4-fluoro-3-((3-(2-(methylamino)-4-pyrimidinyl)-2-pyridinyl)oxy)-N-phenylbenzamide | 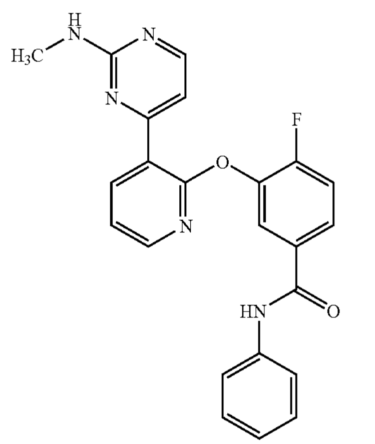 | 415.43 | 416 |
| 315 | 4-fluoro-3-((3-(2-(methylamino)-4-pyrimidinyl)-2-pyridinyl)oxy)-N-(3-(trifluoromethyl)phenyl)benzamide | 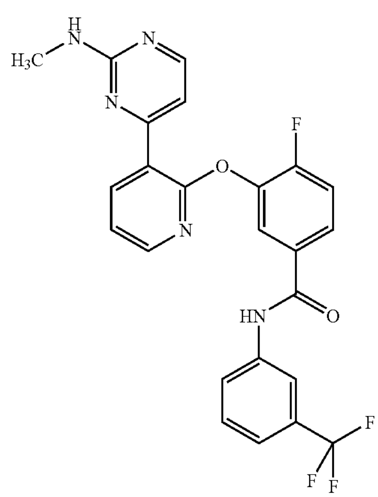 | 483.42 | 484 |

-continued

| Ex. No. | Structure Name | Structure | MW | MS Data |
|---|---|---|---|---|
| 316 | 4-fluoro-3-((3-(2-(methylamino)-4-pyrimidinyl)-2-pyridinyl)oxy)-N-(2-(1-piperidinyl)-5-trifluoromethyl)phenyl)benzamide | 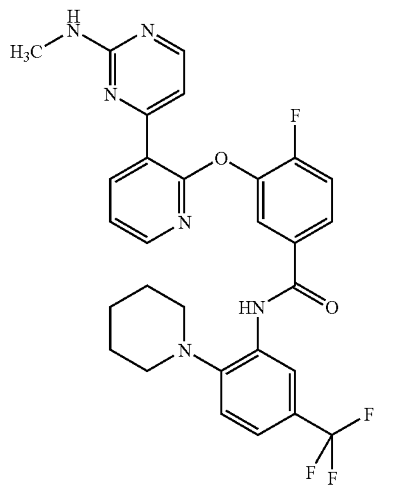 | 566.56 | 567 |
| 317 | N-(5-cyclohexyl-2-(methyloxy)phenyl)-4-fluoro-3-((3-(2-(methylamino)-4-pyrimidinyl)-2-pyridinyl)oxy)benzamide | 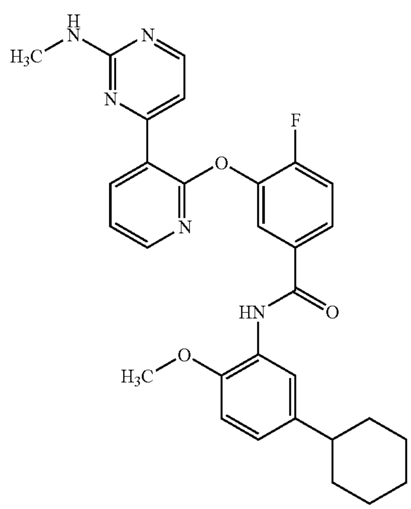 | 527.6 | 528 |
| 318 | 4-fluoro-3-((3-(2-(methylamino)-4-pyrimidinyl)-2-pyridinyl)oxy)-N-(3-((((2S)-1-methyl-2-pyrrolidinyl)methyl)oxy)-5-(trifluoromethyl)phenyl)benzamide | 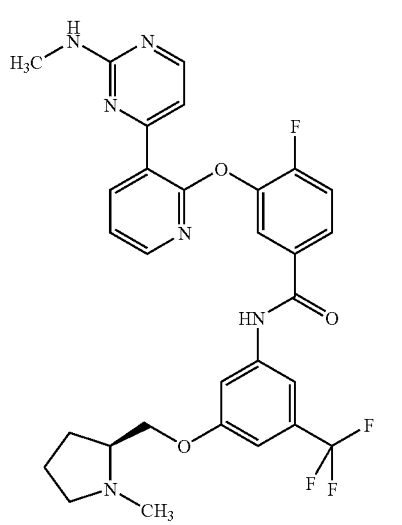 | 596.58 | 597 |

| Ex. No. | Structure Name | Structure | MW | MS Data |
|---|---|---|---|---|
| 319 | 4-fluoro-3-((3-(2-(methylamino)-4-pyrimidinyl)-2-pyridinyl)oxy)-N-(2-(methyloxy)phenyl)benzamide | 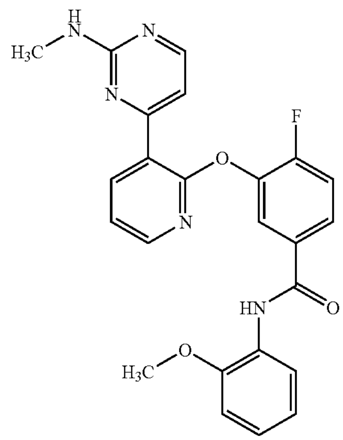 | 445.45 | 446 |
| 320 | 4-fluoro-3-((3-(2-(methylamino)-4-pyrimidinyl)-2-pyridinyl)oxy)-N-(4-(1-methylethyl)phenyl)benzamide | 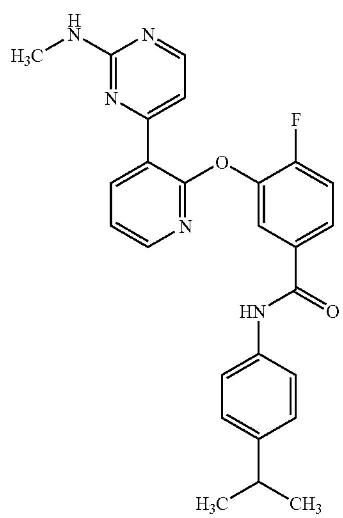 | 457.51 | 458 |
| 321 | 4-fluoro-3-((3-(2-(methylamino)-4-pyrimidinyl)-2-pyridinyl)oxy)-N-(2-methyl-3-trifluoromethyl)phenyl)benzamide | 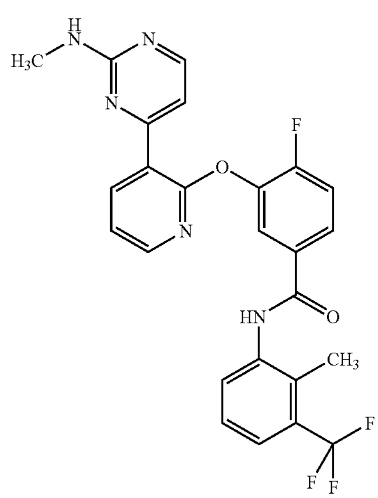 | 497.45 | 498 |

-continued

| Ex. No. | Structure Name | Structure | MW | MS Data |
|---|---|---|---|---|
| 322 | 2-methyl-3-((3-(2-(methylamino)-4-pyrimidinyl)-2-pyridinyl)oxy)-N-phenylbenzamide | 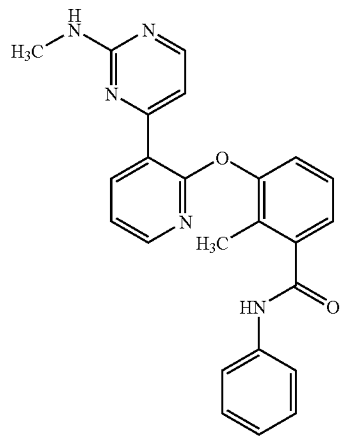 | 411.46 | 412 |
| 323 | 2-methyl-3-((3-(2-(methylamino)-4-pyrimidinyl)-2-pyridinyl)oxy)-N-(3-(trifluoromethyl)phenyl)benzamide | 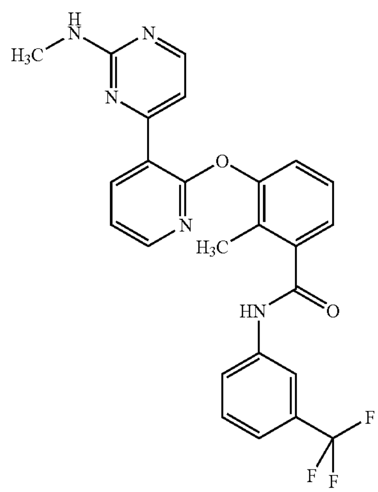 | 479.46 | 480 |
| 324 | 2-methyl-3-((3-(2-(methylamino)-4-pyrimidinyl)-2-pyridinyl)oxy)-N-(2-(1-piperidinyl)-5-trifluoromethyl)phenyl)benzamide | 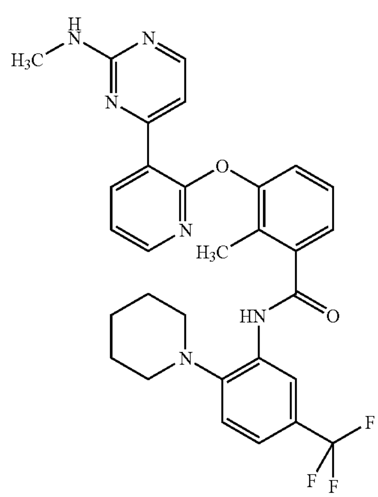 | 562.59 | 563 |

| Ex. No. | Structure Name | Structure | MW | MS Data |
|---|---|---|---|---|
| 325 | N-(5-cyclohexyl-2-(methyloxy)phenyl)-2-methyl-3-((3-(2-(methylamino)-4-pyrimidinyl)-2-pyridinyl)oxy)benzamide | 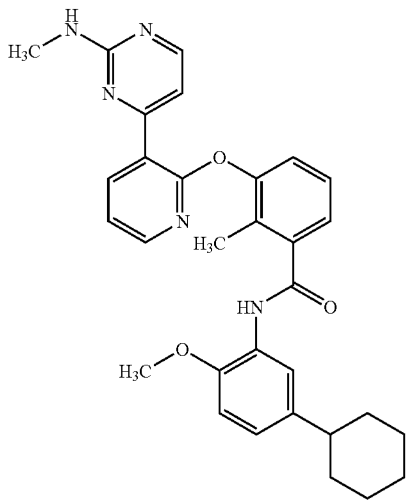 | 523.63 | 524 |
| 326 | 2-methyl-3-((3-(2-(methylamino)-4-pyrimidinyl)-2-pyridinyl)oxy)-N-(3-((((2S)-1-methyl-2-pyrrolidinyl)methyl)oxy)-5-(trifluoromethyl)phenyl)benzamide | 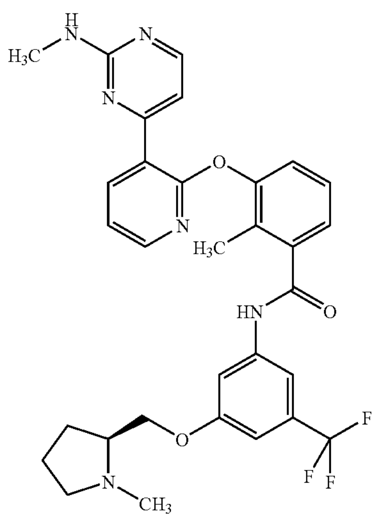 | 592.62 | 593 |
| 327 | 2-methyl-3-((3-(2-(methylamino)-4-pyrimidinyl)-2-pyridinyl)oxy)-N-(2-(methyloxy)phenyl)benzamide | 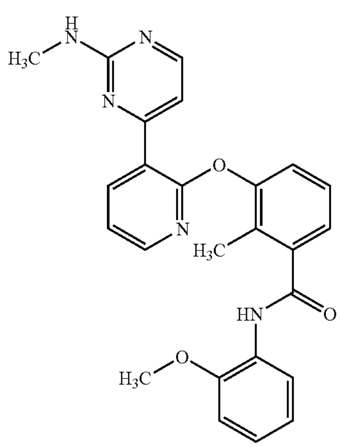 | 441.49 | 442 |

| Ex. No. | Structure Name | Structure | MW | MS Data |
|---|---|---|---|---|
| 328 | 2-methyl-3-((3-(2-(methylamino)-4-pyrimidinyl)-2-pyridinyl)oxy)-N-(4-(1-methylethyl)phenyl)benzamide | 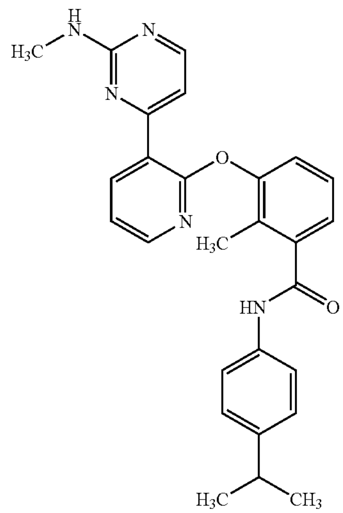 | 453.54 | 454 |
| 329 | 2-methyl-3-((3-(2-(methylamino)-4-pyrimidinyl)-2-pyridinyl)oxy)-N-(2-methyl-3-(trifluoromethyl)phenyl)benzamide | 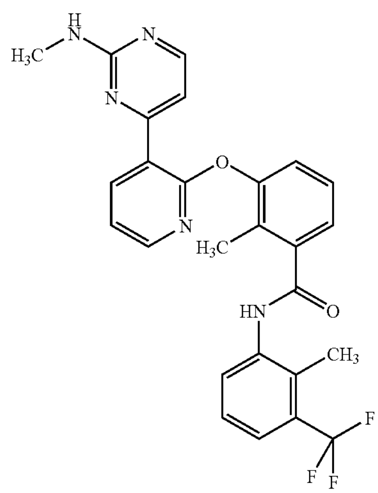 | 493.49 | 494 |
| 330 | 2-fluoro-3-((3-(2-(methylamino)-4-pyrimidinyl)-2-pyridinyl)oxy)-N-phenylbenzamide | 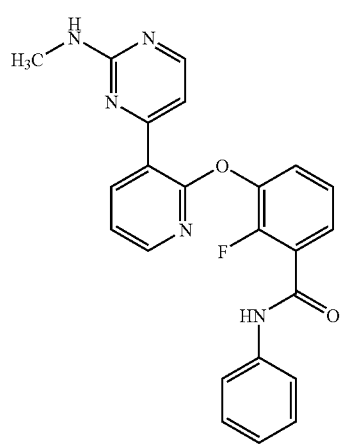 | 415.43 | 416 |

-continued

| Ex. No. | Structure Name | Structure | MW | MS Data |
|---|---|---|---|---|
| 331 | 2-fluoro-3-((3-(2-(methylamino)-4-pyrimidinyl)-2-pyridinyl)oxy)-N-(3-(trifluoromethyl)phenyl)benzamide | 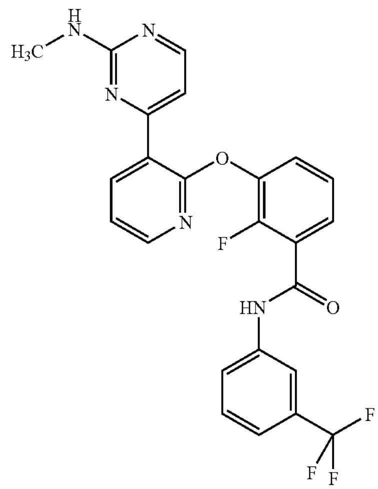 | 483.42 | 484 |
| 332 | 2-fluoro-3-((3-(2-(methylamino)-4-pyrimidinyl)-2-pyridinyl)oxy)-N-(2-(1-piperidinyl)-5-trifluoromethyl)phenyl)benzamide | 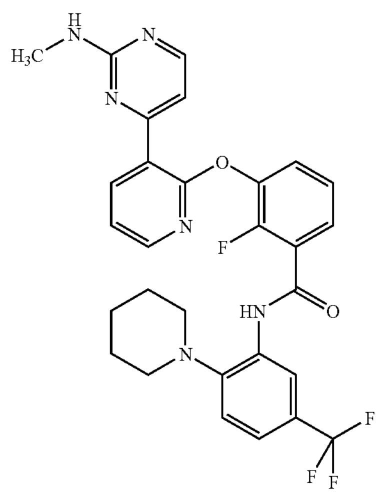 | 566.56 | 567 |
| 333 | N-(5-cyclohexyl-2-(methyloxy)phenyl)-2-fluoro-5-((3-(2-(methylamino)-4-pyrimidinyl)-2-pyridinyl)oxy)benzamide | 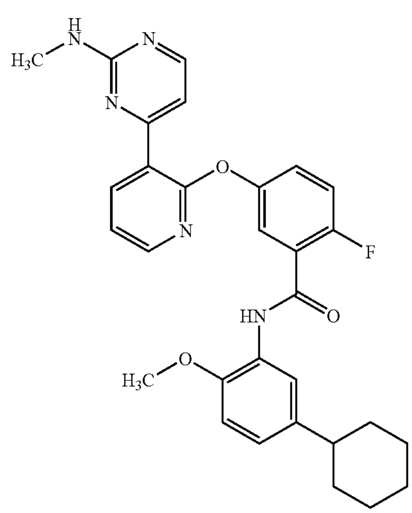 | 527.6 | 528 |

-continued

| Ex. No. | Structure Name | Structure | MW | MS Data |
|---|---|---|---|---|
| 334 | 2-fluoro-5-((3-(2-(methylamino)-4-pyrimidinyl)-2-pyridinyl)oxy)-N-(3-((((2S)-1-methyl-2-pyrrolidinyl)methyl)oxy)-5-(trifluoromethyl)phenyl)benzamide | 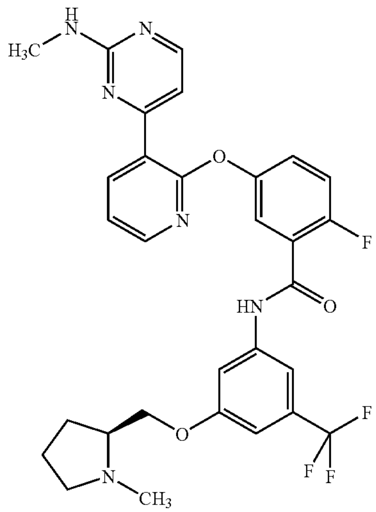 | 596.58 | 597 |
| 335 | 2-fluoro-5-((3-(2-(methylamino)-4-pyrimidinyl)-2-pyridinyl)oxy)-N-(2-(methyloxy)phenyl)benzamide | 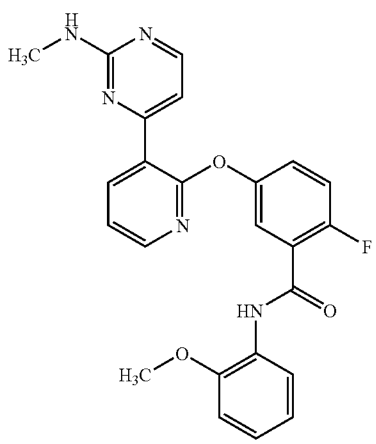 | 445.45 | 446 |
| 336 | 2-fluoro-5-((3-(2-(methylamino)-4-pyrimidinyl)-2-pyridinyl)oxy)-N-(4-(1-methylethyl)phenyl)benzamide | 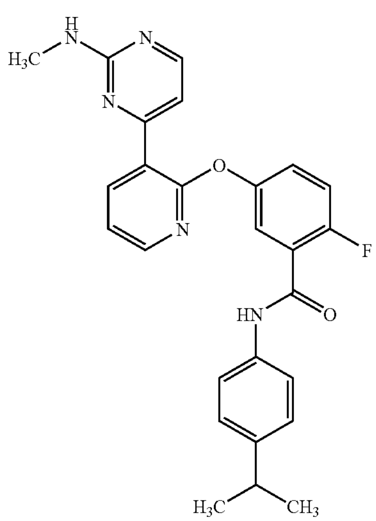 | 457.51 | 458 |

-continued

| Ex. No. | Structure Name | Structure | MW | MS Data |
|---|---|---|---|---|
| 337 | 2-fluoro-5-((3-(2-(methylamino)-4-pyrimidinyl)-2-pyridinyl)oxy)-N-(2-methyl-3-(trifluoromethyl)phenyl)benzamide | 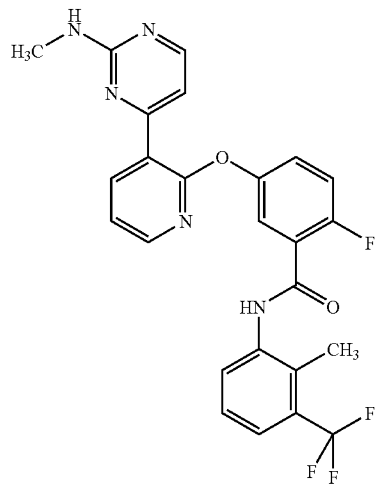 | 497.45 | 498 |
| 338 | N-(2-((2-(dimethylamino)ethyl)(methyl)amino)-5-(trifluoromethyl)phenyl)-4-methyl-3-((3-(2-(methylamino)-4-pyrimidinyl)-2-pyridinyl)oxy)benzamide | 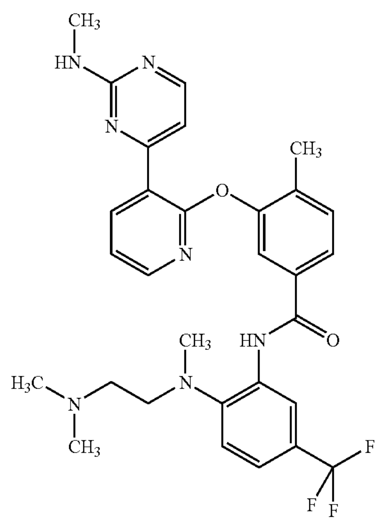 | 579.62 | 580 |
| 339 | 4-methyl-3-((3-(2-(methylamino)-4-pyrimidinyl)-2-pyridinyl)oxy)-N-(2-(4-methyl-1-piperazinyl)-(trifluoromethyl)phenyl)benzamide | 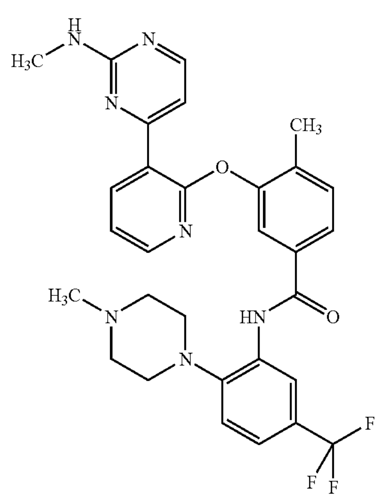 | 577.61 | 578 |

-continued

| Ex. No. | Structure Name | Structure | MW | MS Data |
|---|---|---|---|---|
| 340 | N-(2-((3-(dimethylamino)propyl)(methyl)amino)-5-(trifluoromethyl)phenyl)-4-methyl-3-((3-(2-(methylamino)-4-pyrimidinyl)-2-pyridinyl)oxy)benzamide | 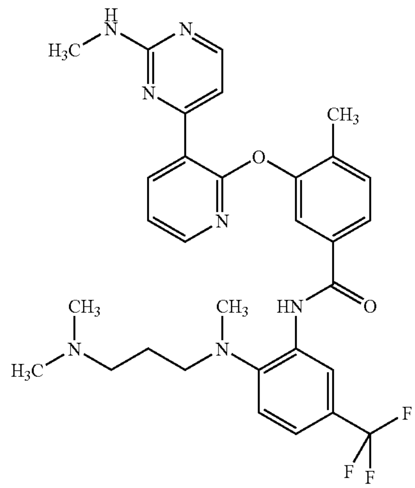 | 593.65 | 594 |
| 341 | N-(2-((2-(dimethylamino)ethyl)(methyl)amino)-5-(trifluoromethyl)phenyl)-4-methyl-3-((3-(4-(methylamino)-1,3,5-triazin-2-yl)-2-pyridinyl)oxy)benzamide | 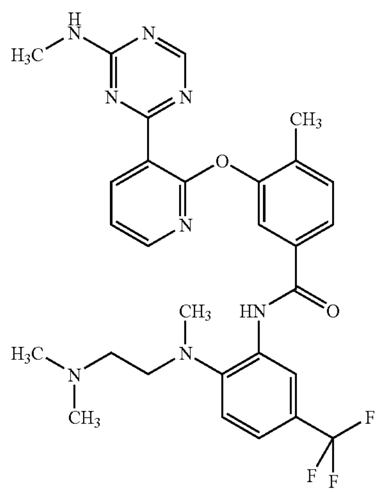 | 580.61 | 581 |
| 342 | 3-((3-(2-(methylamino)-4-pyrimidinyl)-2-pyridinyl)sulfanyl)-N-(3-(trifluoromethyl)phenyl)benzamide | 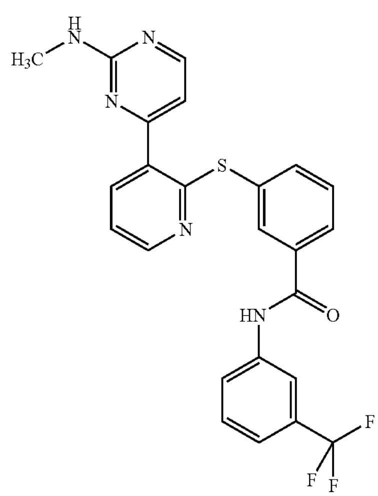 | 481.50 | 482 |

| Ex. No. | Structure Name | Structure | MW | MS Data |
|---|---|---|---|---|
| 343 | 3-((3-(2-(methylamino)-4-pyrimidinyl)-2-pyridinyl)sulfanyl)-N-(2-(1-piperidinyl)-5-(trifluoromethyl)phenyl)benzamide | 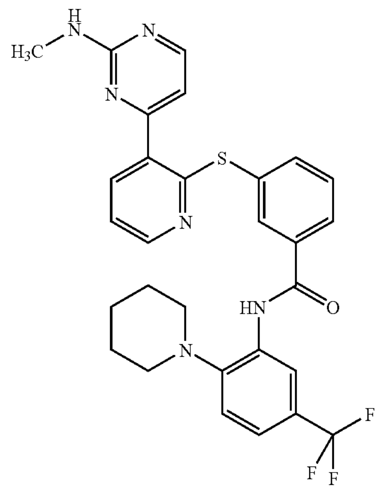 | 564.63 | 565 |
| 344 | N-(3-(1,1-dimethylethyl)-1-phenyl-1H-pyrazol-5-yl)-4-methyl-3-((2'-(methylamino)-3,4'-bipyridin-2-yl)oxy)benzamide | 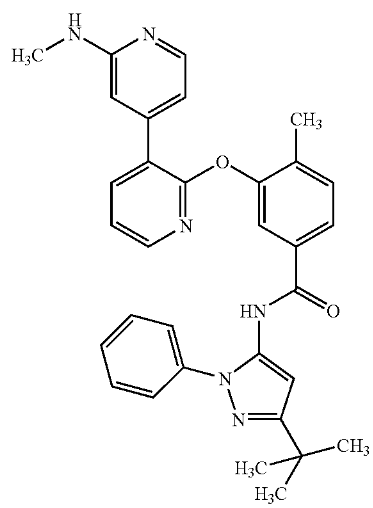 | 532.64 | 533 |
| 345 | N-(2-((3-(dimethylamino)propyl)(methyl)amino)-5-(trifluoromethyl)phenyl)-4-methyl-3-((3-(4-(methylamino)-1,3,5-triazin-2-yl)-2-pyridinyl)oxy)benzamide | 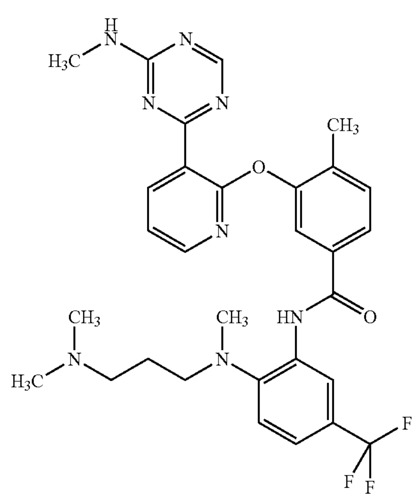 | 594.64 | 595 |

-continued

| Ex. No. | Structure Name | Structure | MW | MS Data |
|---|---|---|---|---|
| 346 | N-(5-(1,1-dimethylpropyl)-2-hydroxyphenyl)-4-methyl-3-((2'-(methylamino)-3,4'-bipyridin-2-yl)oxy)benzamide | 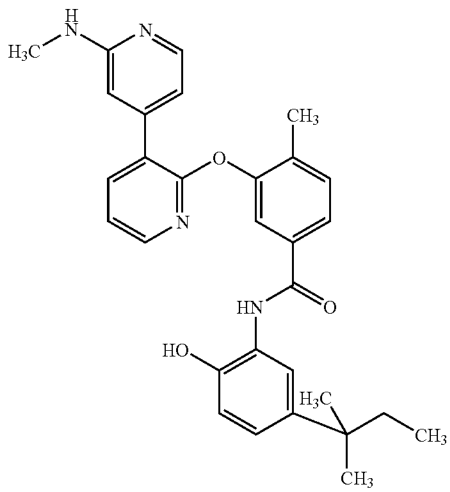 | 496.61 | 497 |
| 347 | 4-methyl-3-((3-(4-(methylamino)-1,3,5-triazin-2-yl)-2-pyridinyl)oxy)-N-(2-(4-methyl-1-piperazinyl)-5-(trifluoromethyl)phenyl)benzamide | 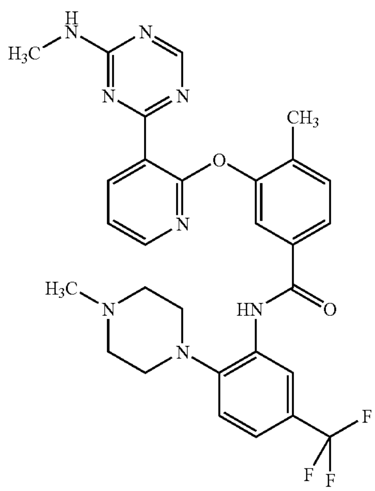 | 578.6 | 579 |
| 348 | 3-((3-(2-(methylamino)-4-pyrimidinyl)-2-pyridinyl)sulfanyl)-N-(4-(1-methylethyl)phenyl)benzamide | 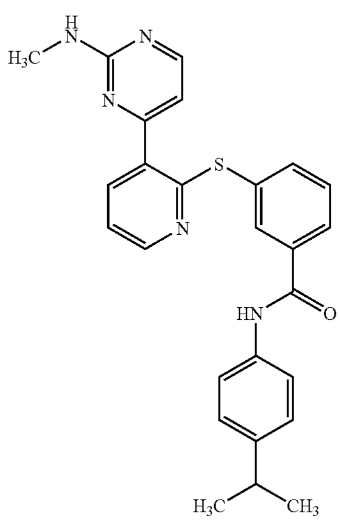 | 455.58 | 456 |

-continued

| Ex. No. | Structure Name | Structure | MW | MS Data |
|---|---|---|---|---|
| 349 | 3-((3-(2-(methylamino)-4-pyrimidinyl)-2-pyridinyl)sulfanyl)-N-(2-(methyloxy)phenyl)benzamide | 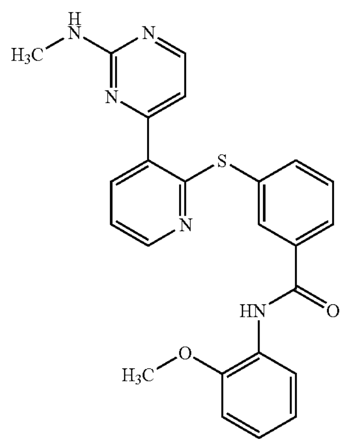 | 443.53 | 444 |
| 350 | 4-methyl-3-((2'-(methylamino)-3,4'-bipyridin-2-yl)oxy)-N-(2-(4-methyl-1-piperazinyl)-5-(trifluoromethyl)phenyl benzamide | 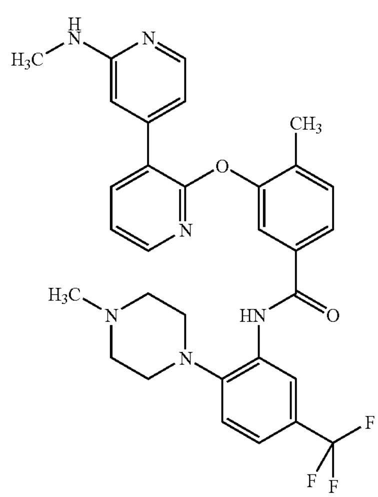 | 576.62 | 577 |
| 351 | N-(2-((2-(dimethylamino)ethyl)(methyl)amino)-5-(trifluoromethyl)phenyl)-4-methyl-3-((2'-(methylamino) 3,4'-bipyridin-2-yl)oxy)benzamide | 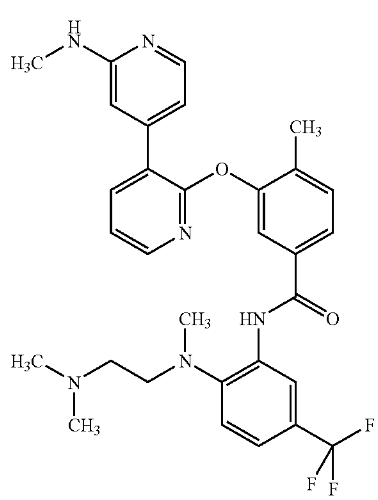 | 578.64 | 579 |

-continued

| Ex. No. | Structure Name | Structure | MW | MS Data |
|---|---|---|---|---|
| 352 | N-(2-((3-(dimethylamino)propyl)(methyl)amino)-5-(trifluoromethyl)phenyl)-4-methyl-3-((2'-(methylamino)-3,4'-bipyridin-2-yl)oxy)benzamide | 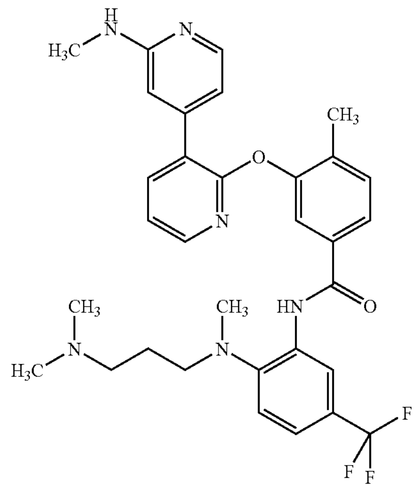 | 592.66 | 593 |
| 353 | N,4-dimethyl-3-((3-(2-(methylamino)-4-pyrimidinyl)-2-pyridinyl)oxy)-N-(3-(trifluoromethyl)phenyl)benzamide | 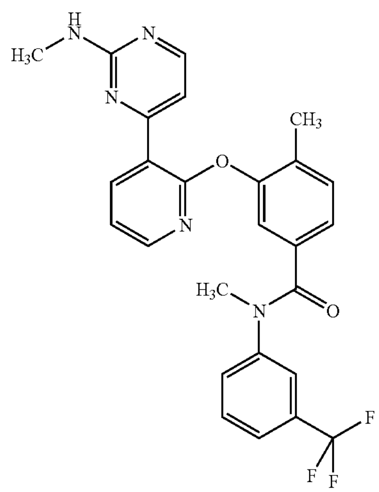 | 493.49 | 494 |
| 354 | N,4-dimethyl-3-((3-(4-(methylamino)-1,3,5-triazin-2-yl)-2-pyridinyl)oxy)-N-(3-(trifluoromethyl)phenyl)benzamide | 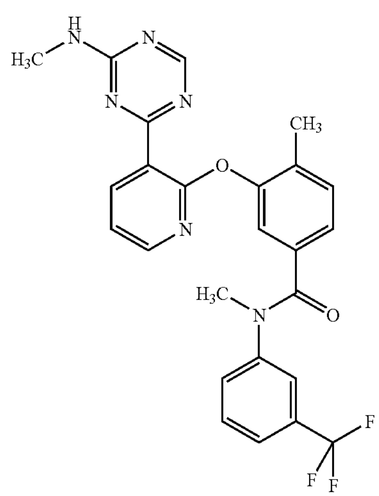 | 494.48 | 495 |

-continued

| Ex. No. | Structure Name | Structure | MW | MS Data |
|---|---|---|---|---|
| 355 | 4-methyl-3-((3-(4-(methylamino)-1,3,5-triazin-2-yl)-2-pyridinyl)oxy)-N-(3-((((2S)-1-methyl-2-pyrrolidinyl)methyl)oxy)-5-(trifluoromethyl)phenyl benzamide | 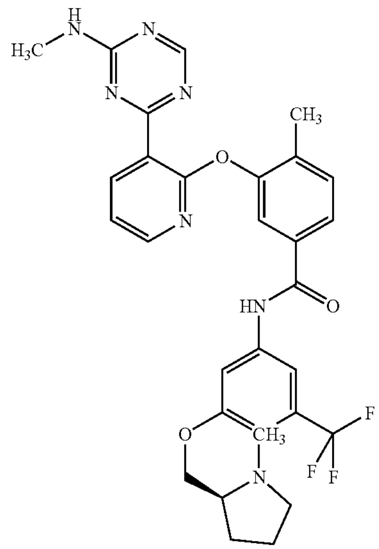 | 593.61 | 594 |
| 356 | 4-methyl-3-((3-(2-(methylamino)-4-pyrimidinyl)-2-pyridinyl)oxy)-N-(2-((2-(1-pyrrolidinyl)ethyl)oxy)-5-(trifluoromethyl)phenyl) benzamide | 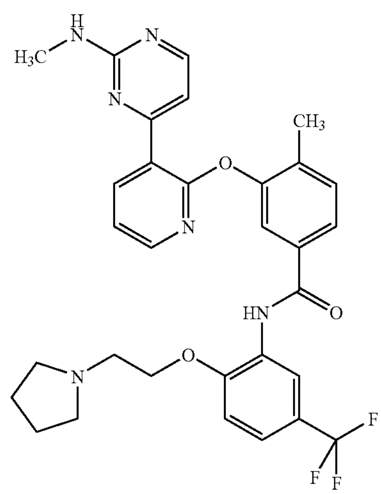 | 592.62 | 593 |
| 357 | 4-methyl-3-((3-(4-(methylamino)-1,3,5-triazin-2-yl)-2-pyridinyl)oxy)-N-(2-(1-piperidinyl)-5-(trifluoromethyl)phenyl) benzamide | 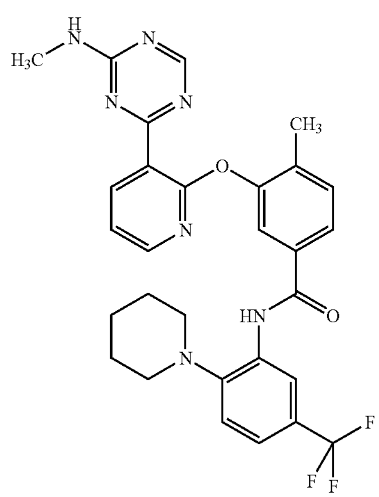 | 563.58 | 564 |

-continued

| Ex. No. | Structure Name | Structure | MW | MS Data |
|---|---|---|---|---|
| 358 | 4-methyl-3-((2'-(methylamino)-3,4'-bipyridin-2-yl)oxy)-N-(2-(1-piperidinyl)-5-(trifluoromethyl)phenyl)benzamide | 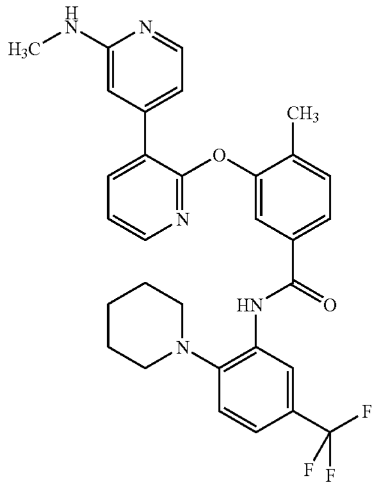 | 561.61 | 562 |
| 359 | 4-fluoro-3-((3-(4-(methylamino)-1,3,5-triazin-2-yl)-2-pyridinyl)oxy)-N-(2-(1-piperidinyl)-5-trifluoromethyl)phenyl)benzamide | 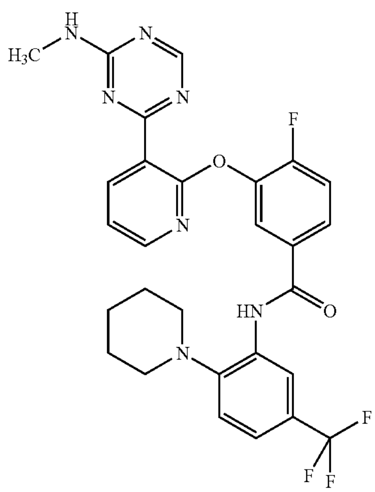 | 567.54 | 568 |
| 360 | 4-fluoro-3-((3-(4-(methylamino)-1,3,5-triazin-2-yl)-2-pyridinyl)oxy)-N-(3-(trifluoromethyl)phenyl)benzamide | 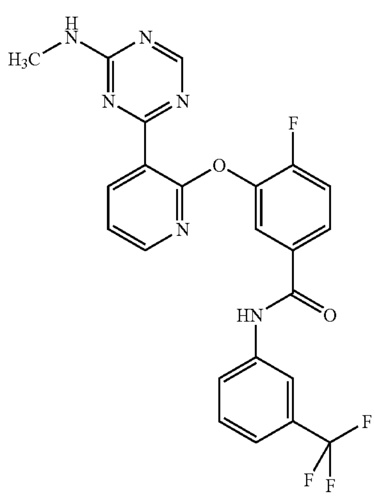 | 484.41 | 485 |

| Ex. No. | Structure Name | Structure | MW | MS Data |
|---|---|---|---|---|
| 361 | N-(2-((2-(dimethylamino)ethyl)(methyl)amino)-5-(trifluoromethyl)phenyl)-4-fluoro-3-((3-(4-(methylamino)-1,3,5-triazin-2-yl)-2-pyridinyl)oxy)benzamide | 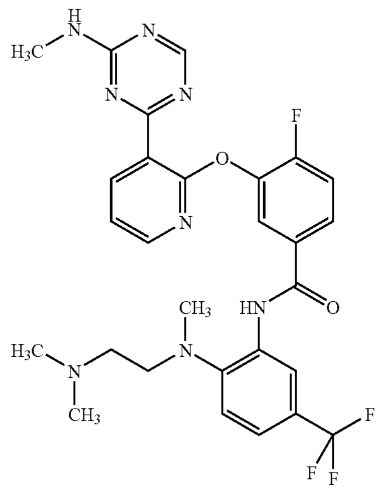 | 584.58 | 585 |
| 362 | N-(2-((3-(dimethylamino)propyl)(methyl)amino)-5-(trifluoromethyl)phenyl)-4-fluoro-3-((3-(4-(methylamino)-1,3,5-triazin-2-yl)-2-pyridinyl)oxy)benzamide | 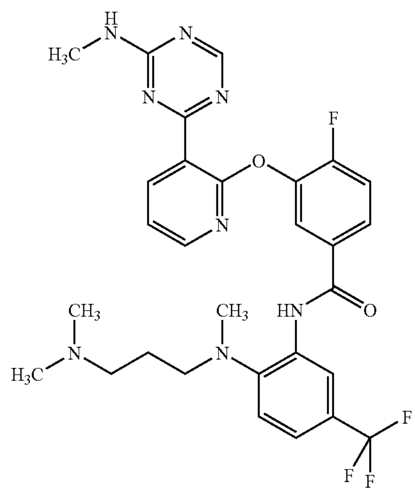 | 598.6 | 599 |
| 363 | 4-fluoro-3-((3-(4-(methylamino)-1,3,5-triazin-2-yl)-2-pyridinyl)oxy)-N-(2-(4-methyl-1-piperazinyl)-5-(trifluoromethyl)phenyl)benzamide | 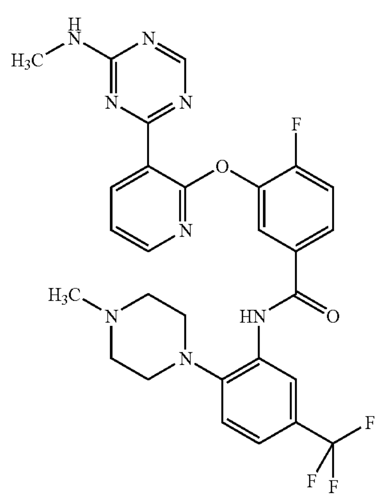 | 582.56 | 593 |

-continued

| Ex. No. | Structure Name | Structure | MW | MS Data |
|---|---|---|---|---|
| 364 | N-methyl-4-(2-((2-methyl-5-((6-(trifluoromethyl)-2,3-dihydro-1H-indol-1-yl)carbonyl)phenyl)oxy)-3-pyridinyl)-2-pyrimidinamine | 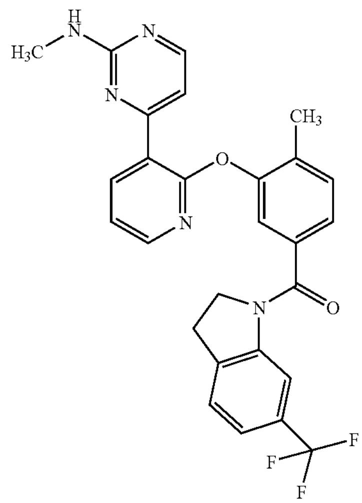 | 505.5 | 506 |
| 365 | N-methyl-4-(2-((2-methyl-5-((7-(trifluoromethyl)-3,4-dihydro-1(2H)-quinolinyl)carbonyl)phenyl)oxy)-3-pyridinyl)-2-pyrimidinamine | 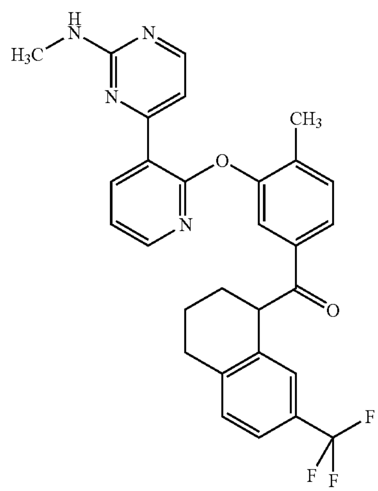 | 519.52 | 520 |
| 366 | 4-fluoro-3-((3-(4-(methylamino)-1,3,5-triazin-2-yl)-2-pyridinyl)oxy)-N-(2-((2-(1-pyrrolidinyl)ethyl)oxy)-5-(trifluoromethyl)phenyl)benzamide | 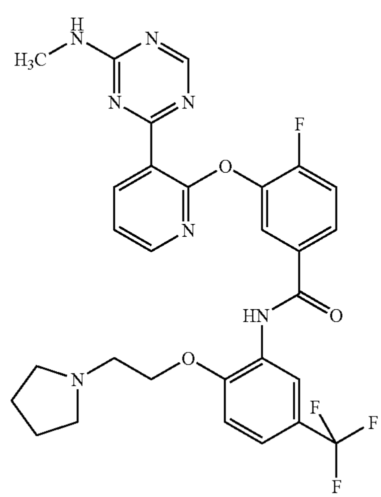 | 597.57 | 598 |

| Ex. No. | Structure Name | Structure | MW | MS Data |
|---|---|---|---|---|
| 367 | 2-flouro-5-((3-(4-(methylamino)-1,3,5-triazin-2-yl)-2-pyridinyl)oxy)-N-(2-((2-(1-pyrrolidinyl)ethyl)oxy)-5-(trifluoromethyl)phenyl)benzamide | 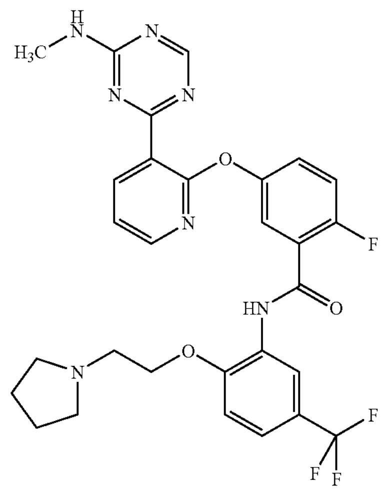 | 597.57 | 598 |
| 368 | 2-fluoro-5-((3-(4-(methylamino)-1,3,5-triazin-2-yl)-2-pyridinyl)oxy)-N-(2-(4-methyl-1-piperazinyl)-5-(trifluoromethyl)phenyl)benzamide | 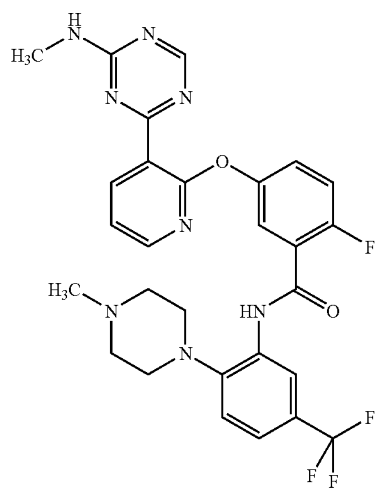 | 582.56 | 583 |
| 369 | N-(2-((3-(dimethylamino)propyl)(methyl)amino)-5-(trifluoromethyl)phenyl)-2-fluoro-5-((3-(4-(methylamino)-1,3,5-triazin-2-yl)-2-pyridinyl)oxy)benzamide | 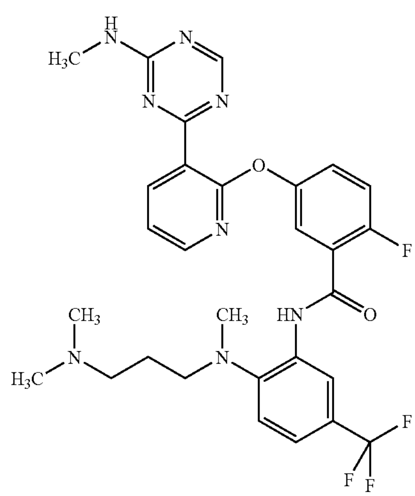 | 598.6 | 599 |

| Ex. No. | Structure Name | Structure | MW | MS Data |
|---|---|---|---|---|
| 370 | 2-fluoro-5-((3-(4-(methylamino)-1,3,5-triazin-2-yl)-2-pyridinyl)oxy)-N-(3-(trifluoromethyl)phenyl)benzamide | 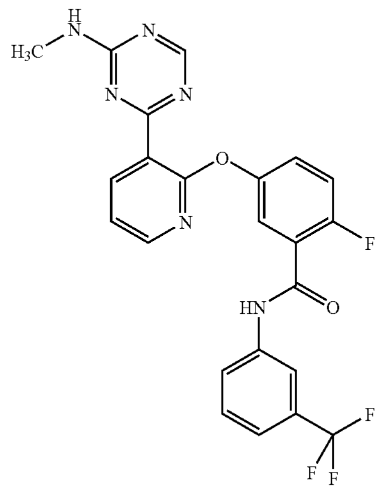 | 484.41 | 485 |
| 371 | 2-fluoro-5-((3-(4-(methylamino)-1,3,5-triazin-2-yl)-2-pyridinyl)oxy)-N-(2-(methyloxy)-5-(trifluoromethyl)phenyl)benzamide | 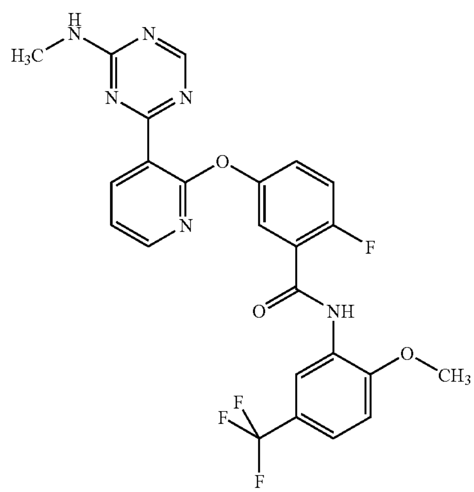 | 514.44 | 515 |
| 372 | N-((1R)-1-cyclohexylethyl)-2-fluoro-5-((3-(4-(methylamino)-1,3,5-triazin-2-yl)-2-pyridinyl)oxy)benzamide | 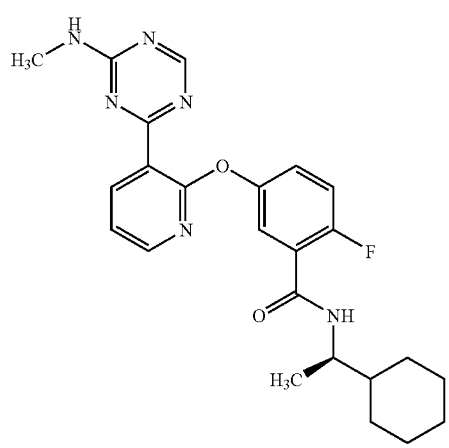 | 450.51 | 451 |

-continued

| Ex. No. | Structure Name | Structure | MW | MS Data |
|---|---|---|---|---|
| 373 | 2-fluoro-5-((3-(4-(methylamino)-1,3,5-triazin-2-yl)-2-pyridinyl)oxy)-N-(2-(1-piperidinyl)-5-(trifluoromethyl)phenyl)benzamide | 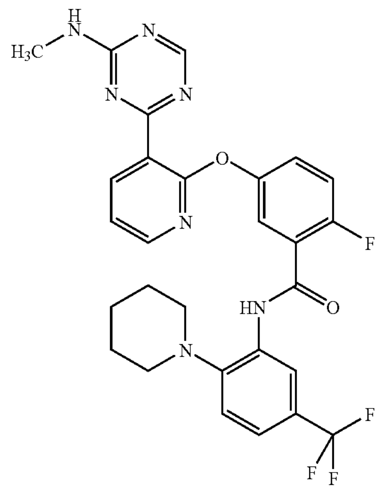 | 567.54 | 568 |
| 374 | 2-fluoro-5-((3-(2-(methylamino)-4-pyrimidinyl)-2-pyridinyl)oxy)-N-(2-(1-pyrrolidinyl)-5-(trifluoromethyl)phenyl)benzamide | 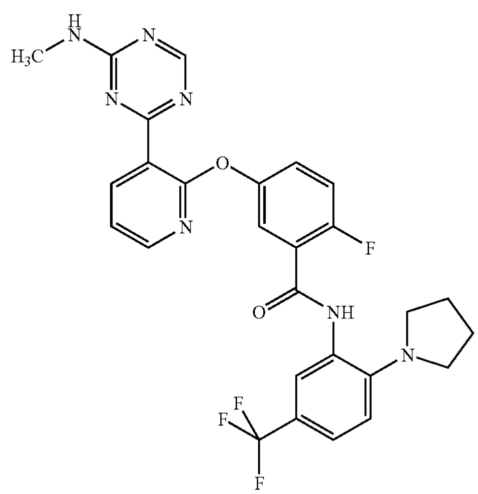 | 552.53 | 553 |
| 375 | 2-fluoro-5-((3-(4-(methylamino)-1,3,5-triazin-2-yl)-2-pyridinyl)oxy)-N-(3-((trifluoromethyl)oxy)phenyl)benzamide | 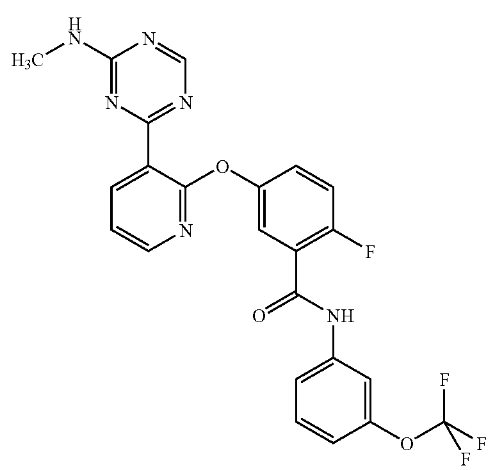 | 500.41 | 501 |

-continued

| Ex. No. | Structure Name | Structure | MW | MS Data |
|---|---|---|---|---|
| 376 | 4-(2-((4-fluoro-3-((6-(trifluoromethyl)-2,3-dihydro-1H-indol-1-yl)carbonyl)phenyl)oxy)-3-pyridinyl)-N-methyl-1,3,5-triazin-2-amine | 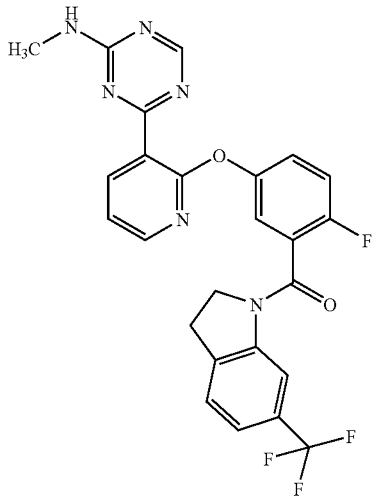 | 510.45 | 511 |
| 377 | 4-(2-((2-fluoro-5-((6-(trifluoromethyl)-2,3-dihydro-1H-indol-1-yl)carbonyl)phenyl)oxy)-3-pyridinyl)-N-methyl-1,3,5-triazin-2-amine | 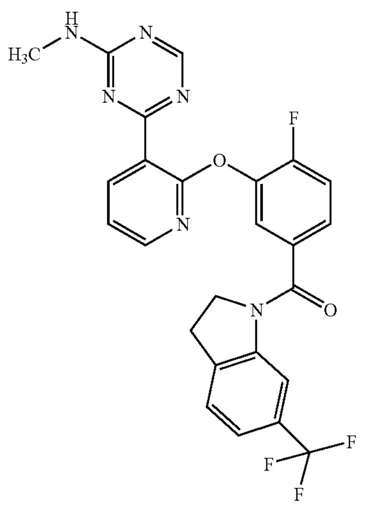 | 510.45 | 511 |
| 378 | 4-fluoro-3-((3-(4-(methylamino)-1,3,5-triazin-2-yl)-2-pyridinyl)oxy)-N-(3-((trifluoromethyl)oxy)phenyl)benzamide | 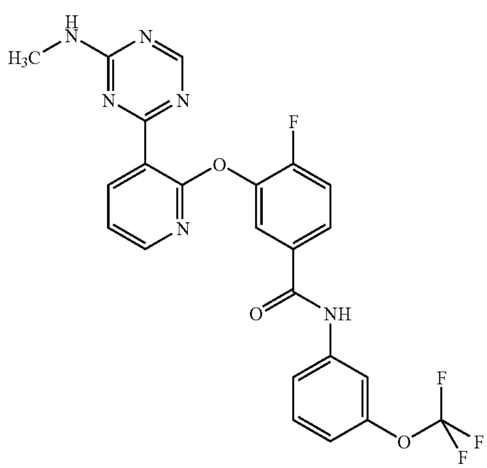 | 500.41 | 501 |

| Ex. No. | Structure Name | Structure | MW | MS Data |
|---|---|---|---|---|
| 379 | 4-methyl-3-((3-(4-(methylamino)-1,3,5-triazin-2-yl)-2-pyridinyl)oxy)-N-phenylbenzamide | 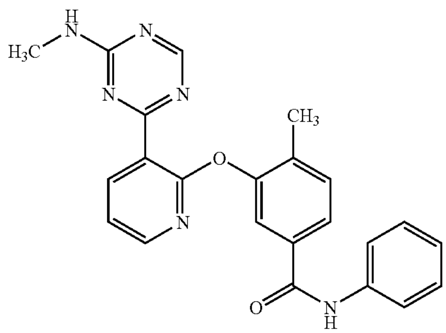 | 412.45 | 413 |
| 380 | 4-methyl-3-((3-(4-(methylamino)-1,3,5-triazin-2-yl)-2-pyridinyl)oxy)-N-(2-(methyloxy)phenyl)benzamide | 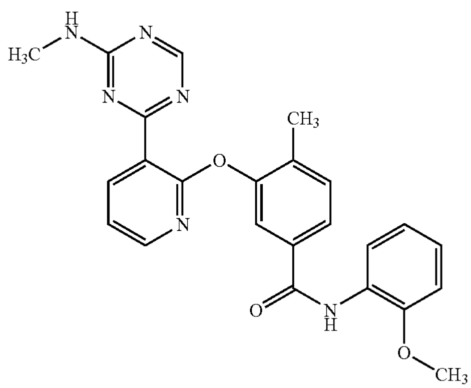 | 442.48 | 443 |
| 381 | 4-methyl-3-((3-(4-(methylamino)-1,3,5-triazin-2-yl)-2-pyridinyl)oxy)-N-(4-(1-methlethyl)phenyl)benzamide | 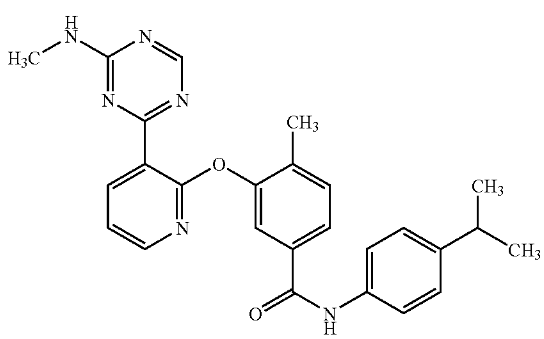 | 454.53 | 455 |
| 382 | N-(4-fluoro-3-(trifluoromethyl)phenyl)-4-methyl-3-((3-(4-(methylamino)-1,3,5-triazin-2-yl)-2-pyridinyl)oxy)benzamide | 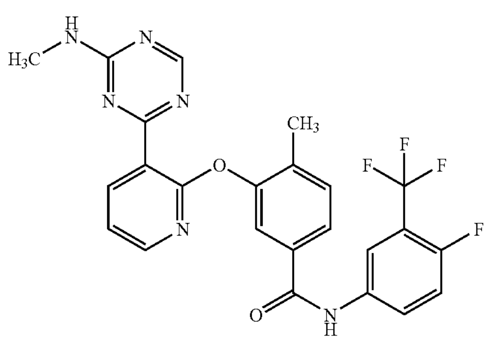 | 498.44 | 499 |

| Ex. No. | Structure Name | Structure | MW | MS Data |
|---|---|---|---|---|
| 383 | 4-methyl-3-((3-(4-(methylamino)-1,3,5-triazin-2-yl)-2-pyridinyl)oxy)-N-(2-methyl-3-(trifluoromethyl)phenyl)benzamide | 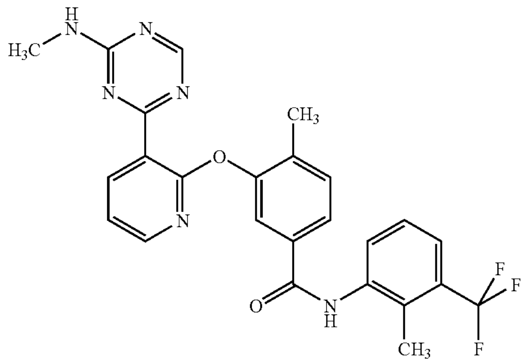 | 494.48 | 495 |
| 384 | 4-methyl-3-((3-(4-(methylamino)-1,3,5-triazin-2-yl)-2-pyridinyl)oxy)-N-(3-(methyloxy)-5-(trifluoromethyl)phenyl)benzamide | 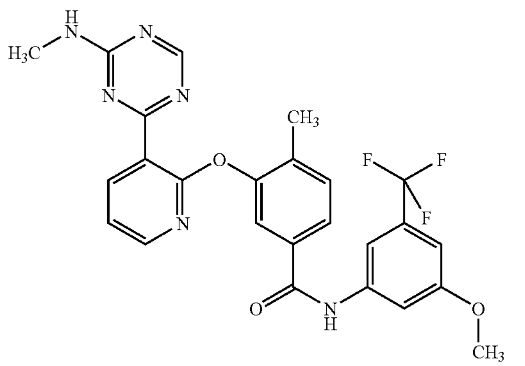 | 510.47 | 511 |
| 385 | 4-methyl-3-((3-(4-(methylamino)-1,3,5-triazin-2-yl)-2-pyridinyl)oxy)-N-(2-(1-pyrrolidinyl)-5-(trifluoromethyl)phenyl benzamide | 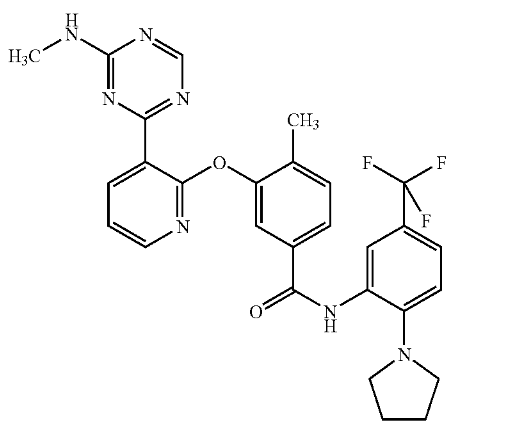 | 549.55 | 550 |
| 386 | 4-methyl-3-((3-(4-(methylamino)-1,3,5-triazin-2-yl)-2-pyridinyl)oxy)-N-(2-(methyloxy)-5-(phenyloxy)phenyl)benzamide | 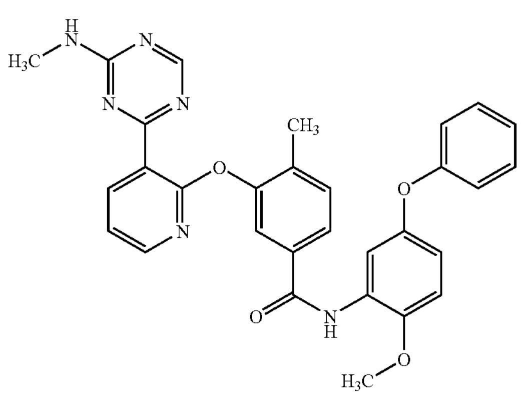 | 534.57 | 535 |

-continued

| Ex. No. | Structure Name | Structure | MW | MS Data |
|---|---|---|---|---|
| 387 | 4-methyl-3-((3-(4-(methylamino)-1,3,5-triazin-2-yl)-2-pyridinyl)oxy)-N-(4-(methyloxy)-1,1'-biphenyl-3-yl)benzamide | 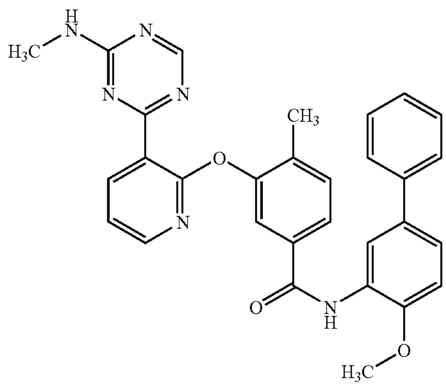 | 518.57 | 519 |
| 388 | N-(5-(1,1-dimethylethyl)-2-(methyloxy)phenyl)-4-methyl-3-((3-(4-(methylamino)-1,3,5-triazin-2-yl)-2-pyridinyl)oxy)benzamide | 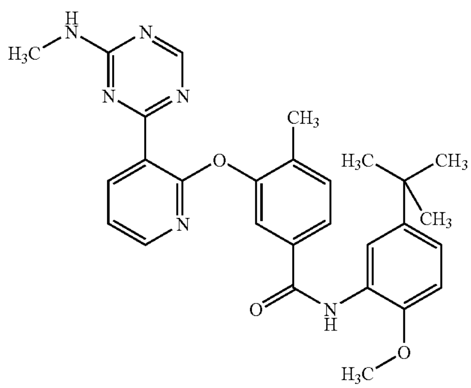 | 498.58 | 499 |
| 389 | N-(2,5-bis(ethyloxy)phenyl)-4-methyl-3-((3-(4-(methylamino)-1,3,5-triazin-2-yl)-2-pyridinyl)oxy)benzamide | 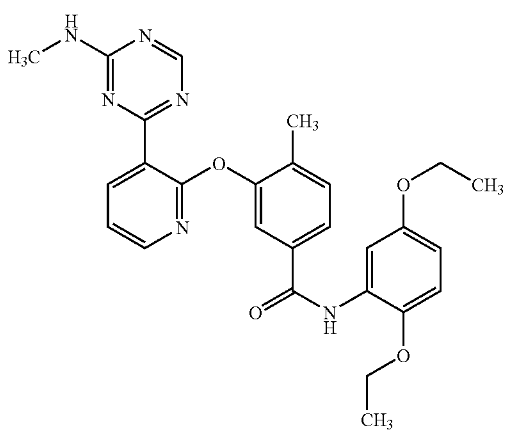 | 500.56 | 501 |
| 390 | 4-methyl-3-((3-(4-(methylamino)-1,3,5-triazin-2-yl)-2-pyridinyl)oxy)-N-(2-methyl-5-(1-methylethyl)phenyl)benzamide | 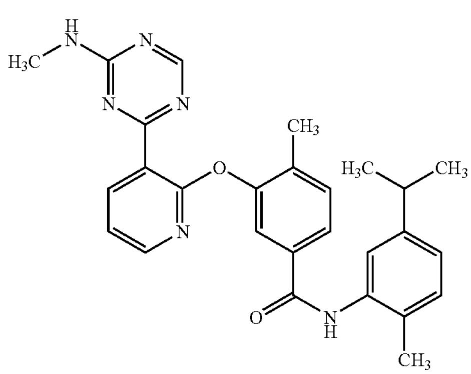 | 468.56 | 469 |

| Ex. No. | Structure Name | Structure | MW | MS Data |
|---|---|---|---|---|
| 391 | 4-methyl-3-((3-(4-(methylamino)-1,3,5-triazin-2-yl)-2-pyridinyl)oxy)-N-(3-((phenylmethyl)oxy)phenyl)benzamide | 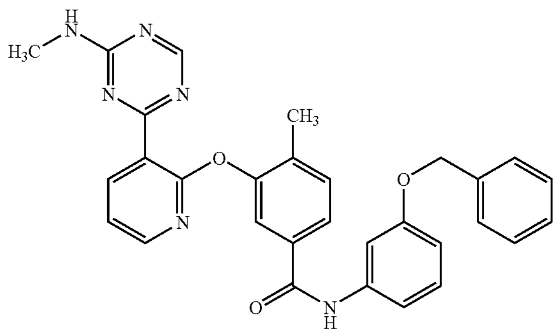 | 518.57 | 519 |
| 392 | N-(1,1'-biphenyl-3-yl)-4-methyl-3-((3-(4-(methylamino)-1,3,5-triazin-2-yl)-2-pyridinyl)oxy)benzamide | 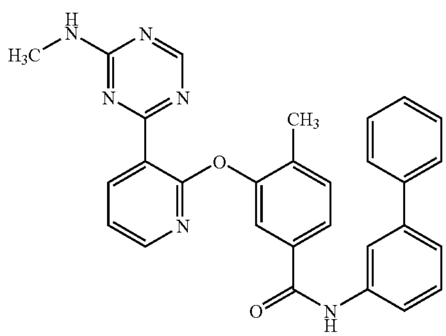 | 488.55 | 489 |
| 393 | N-(3-(ethyloxy)phenyl)-4-methyl-3-((3-(4-(methylamino)-1,3,5-triazin-2-yl)-2-pyridinyl)oxy)benzamide | 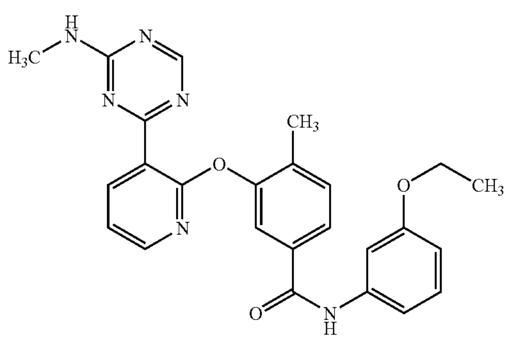 | 456.5 | 457 |
| 394 | 4-methyl-3-((3-(4-(methylamino)-1,3,5-triazin-2-yl)-2-pyridinyl)oxy)-N-(3-((1-methylethyl)oxy)phenyl)benzamide | 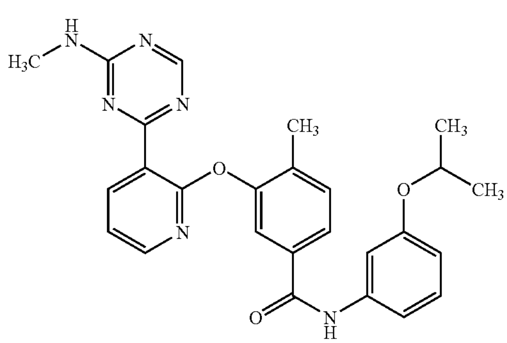 | 470.53 | 471 |

| Ex. No. | Structure Name | Structure | MW | MS Data |
|---|---|---|---|---|
| 395 | 4-methyl-3-((3-(4-(methylamino)-1,3,5-triazin-2-yl)-2-pyridinyl)oxy)-N-(3-(trifluoromethyl)phenyl)benzamide | 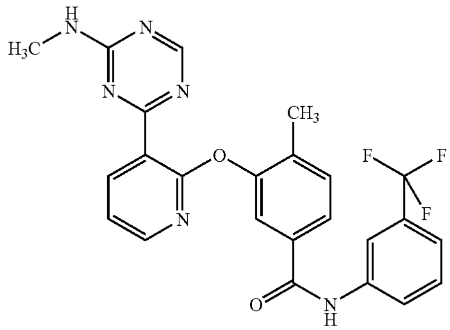 | 480.45 | 481 |
| 396 | 4-methyl-3-((3-(4-(methylamino)-1,3,5-triazin-2-yl)-2-pyridinyl)oxy)-N-(3-((trifluoromethyl)oxy)phenyl)benzamide | 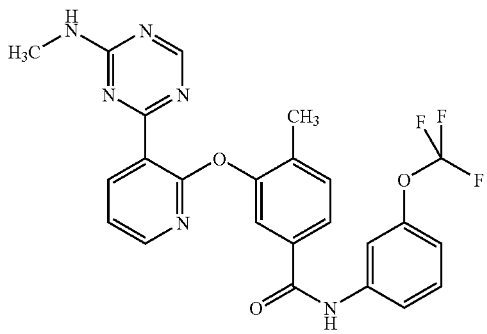 | 496.45 | 497 |
| 397 | 4-methyl-3-((3-(4-(methylamino)-1,3,5-triazin-2-yl)-2-pyridinyl)oxy)-N-(3-((1,1,2,2-tetrafluoroethyl)oxy)phenyl)benzamide | 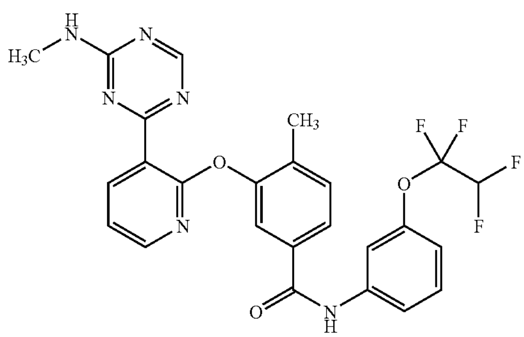 | 528.46 | 529 |
| 398 | N-(3-(hexyloxy)phenyl)-4-methyl-3-((3-(4-(methylamino)-1,3,5-triazin-2-yl)-2-pyridinyl)oxy)benzamide | 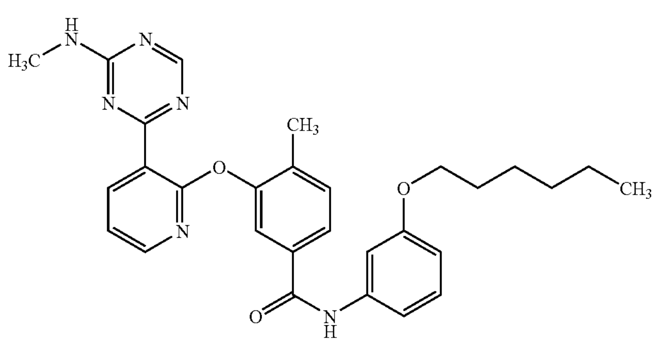 | 512.61 | 513 |

| Ex. No. | Structure Name | Structure | MW | MS Data |
|---|---|---|---|---|
| 399 | N-(3-(2,5-dimethyl-1H-pyrrol-1-yl)phenyl)-4-methyl-3-((3-(4-(methylamino)-1,3,5-triazin-2-yl)-2-pyridinyl)oxy)benzamide | 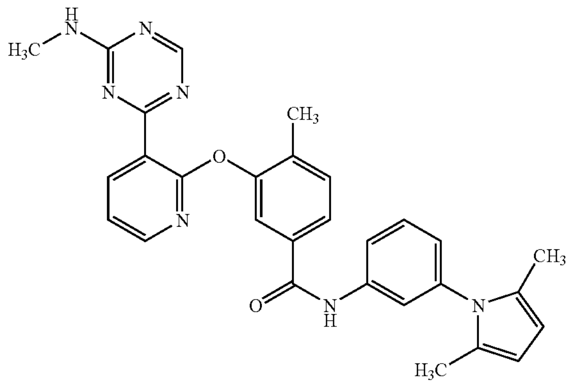 | 505.58 | 506 |
| 400 | N-(5-(1,1-dimethylethyl)-3-isoxazolyl)-4-methyl-3-((3-(4-(methylamino)-1,3,5-triazin-2-yl)-2-pyridinyl)oxy)benzamide | 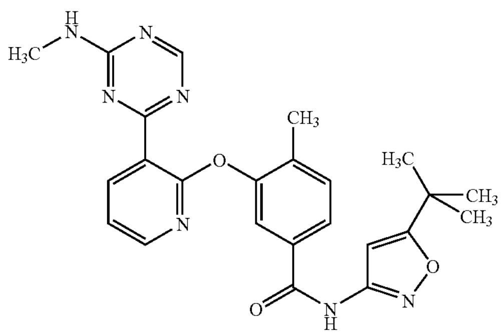 | 459.51 | 460 |
| 401 | N-methyl-4-(2-((2-methyl-5-((6-(trifluoromethyl)-1H-indol-1-yl)carbonyl)phenyl)oxy)-3-pyridinyl)-1,3,5-triazin-2-amine | 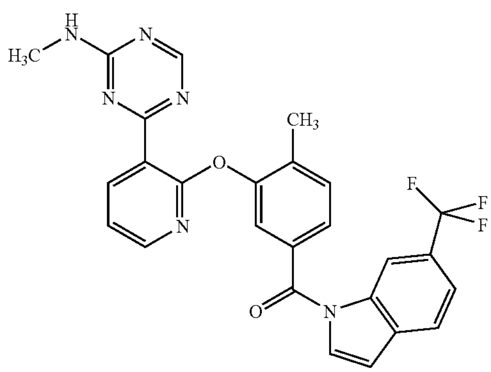 | 504.47 | 505 |
| 402 | N-(cyclohexylmethyl)-4-methyl-3-((3-(4-(methylamino)-1,3,5-triazin-2-yl)-2-pyridinyl)oxy)benzamide | 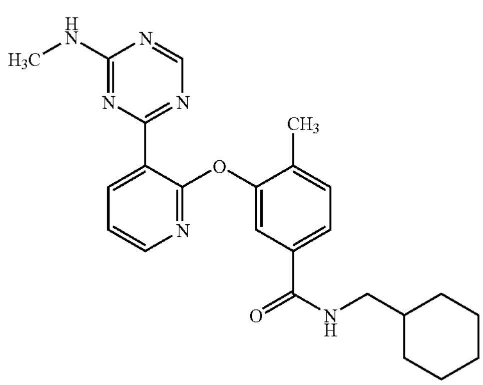 | 432.52 | 433 |

-continued

| Ex. No. | Structure Name | Structure | MW | MS Data |
|---|---|---|---|---|
| 403 | N-((1R)-1-cyclohexylethyl)-4-methyl-3-((3-(4-(methylamino)-1,3,5-triazin-2-yl)-2-pyridinyl)oxy)benzamide | 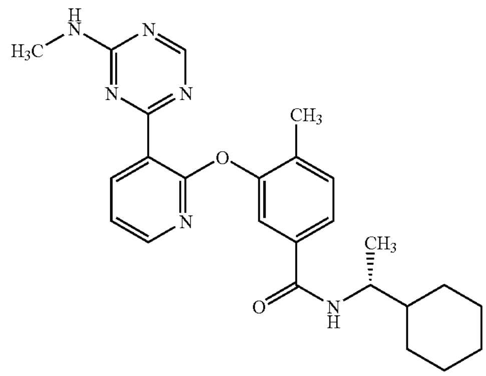 | 446.55 | 447 |
| 404 | N-((1S)-1-cyclohexylethyl)-4-methyl-3-((3-(4-(methylamino)-1,3,5-triazin-2-yl)-2-pyridinyl)oxy)benzamide | 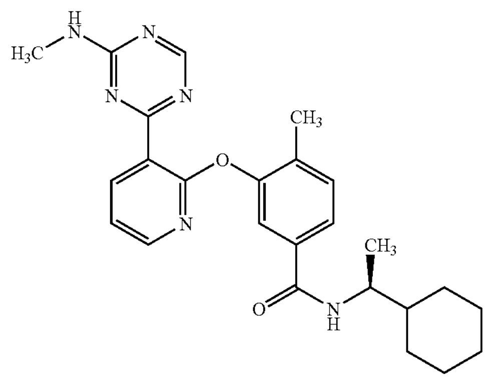 | 446.55 | 447 |
| 405 | 4-methyl-3-((3-(4-(methylamino)-1,3,5-triazin-2-yl)-2-pyridinyl)oxy)-N-((3-(trifluoromethyl)phenyl)methyl)benzamide | 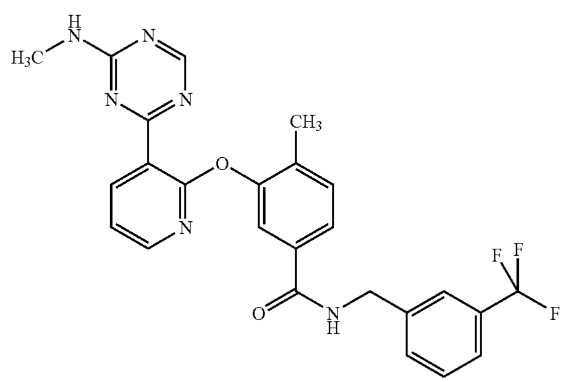 | 494.48 | 495 |
| 406 | N-(3,3-dimethylbutyl)-4-methyl-3-((3-(4-(methylamino)-1,3,5-triazin-2-yl)-2-pyridinyl)oxy)benzamide | 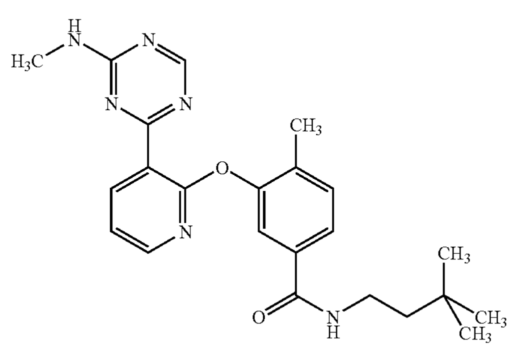 | 420.51 | 421 |

-continued

| Ex. No. | Structure Name | Structure | MW | MS Data |
|---|---|---|---|---|
| 407 | N-(2-fluoro-5-(trifluoromethyl)phenyl)-4-methyl-3-((3-(4-(methylamino)-1,3,5-triazin-2-yl)-2-pyridinyl)oxy)benzamide | 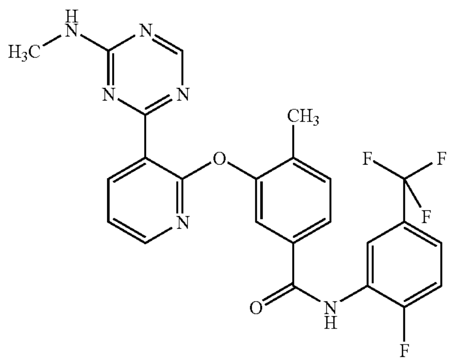 | 498.44 | 499 |
| 408 | N-(2,2,3,3,4,4,4-heptafluorobutyl)-4-methyl-3-((3-(4-(methylamino)-1,3,5-triazin-2-yl)-2-pyridinyl)oxy)benzamide | 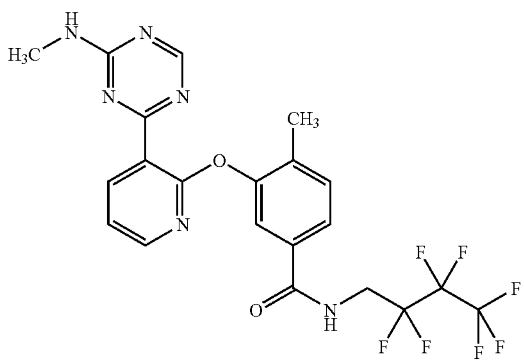 | 518.39 | 519 |
| 409 | N-(3,5-dichlorophenyl)-4-methyl-3-((3-(4-(methylamino)-1,3,5-triazin-2-yl)-2-pyridinyl)oxy)benzamide | 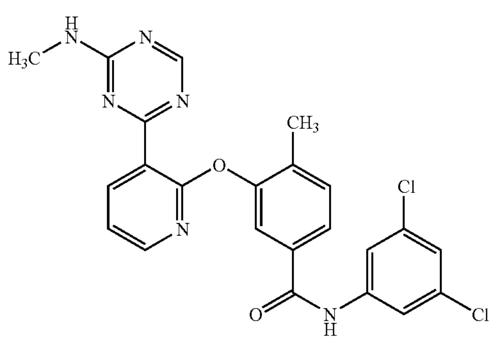 | 481.34 | 481 |
| 410 | N-(2,3-dichlorophenyl)-4-methyl-3-((3-(4-(methylamino)-1,3,5-triazin-2-yl)-2-pyridinyl)oxy)benzamide | 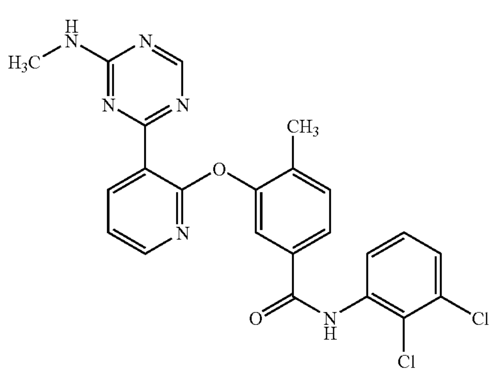 | 481.34 | 481 |

| Ex. No. | Structure Name | Structure | MW | MS Data |
|---|---|---|---|---|
| 411 | 2-fluoro-5-((3-(4-(methylamino)-1,3,5-triazin-2-yl)-2-pyridinyl)oxy)-N-(2-((4-methyl-1-piperazinyl)methyl)-5-(trifluoromethyl)phenyl benzamide | 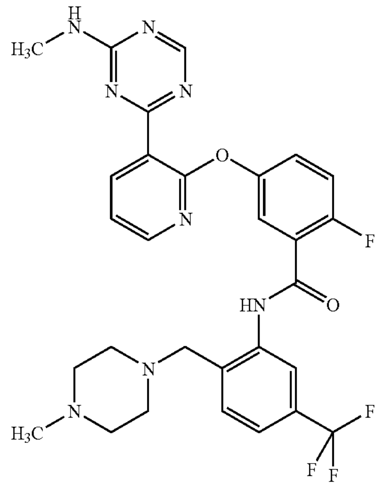 | 596.59 | 597 |
| 412 | 2-fluoro-5-((3-(2-(methylamino)-4-pyrimidinyl)-2-pyridinyl)oxy)-N-(2-((4-methyl-1-piperazinyl)methyl)-5-(trifluoromethyl)phenyl) benzamide | 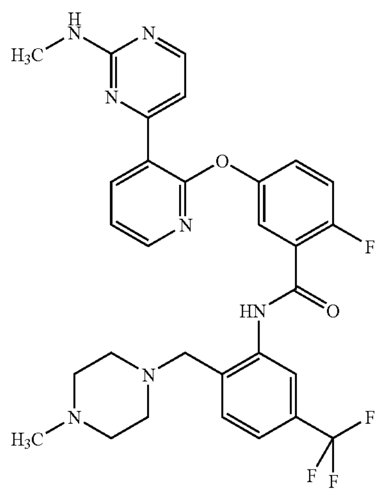 | 595.6 | 596 |
| 413 | 2-fluoro-5-((3-(4-(methylamino)-1,3,5-triazin-2-y1)-2-pyridinyl)oxy)-N-(2-(1-piperazinyl)-5-trifluoromethyl)phenyl) benzamide | 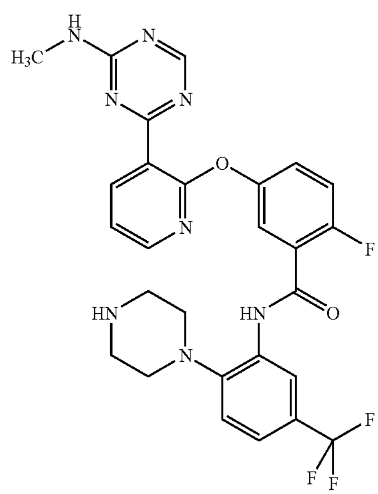 | 568.53 | 569 |

-continued

| Ex. No. | Structure Name | Structure | MW | MS Data |
|---|---|---|---|---|
| 414 | N-(3,5-bis((2,2,2-trifluoroethyl)oxy)phenyl)-4-methyl-3-((3-(4-(methylamino)-1,3,5-triazin-2-yl)-2-pyridinyl)oxy)benzamide | 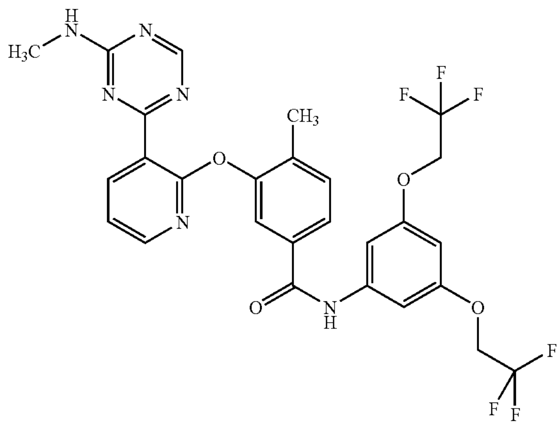 | 608.5 | 609 |
| 415 | 4-methyl-3-((3-(4-(methylamino)-1,3,5-triazin-2-yl)-2-pyridinyl)oxy)-N-(2-(4-morpholinyl)-5-(trifluoromethyl)phenyl)benzamide | 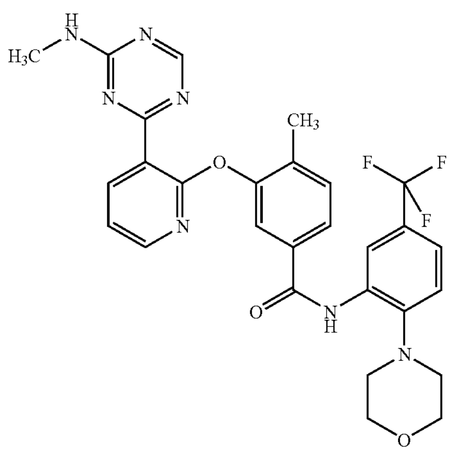 | 565.55 | 566 |
| 416 | N-(2-chloro-5-(trifluoromethyl)phenyl 4-methyl-3-((3-(4-(methylamino)-1,3,5-triazin-2-yl)-2-pyridinyl)oxy)benzamide | 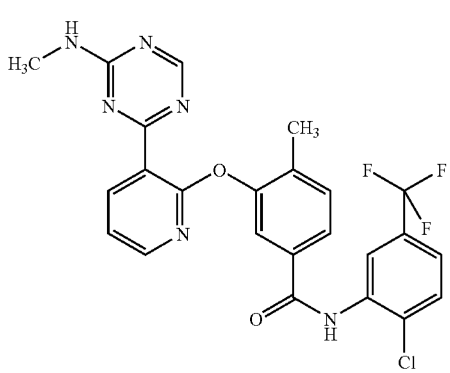 | 514.89 | 515 |

| Ex. No. | Structure Name | Structure | MW | MS Data |
|---|---|---|---|---|
| 417 | N-(1,3-diphenyl-1H-pyrazol-5-yl)-4-methyl-3-((3-(4-(methylamino)-1,3,5-triazin-2-yl)-2-pyridinyl)oxy)benzamide | 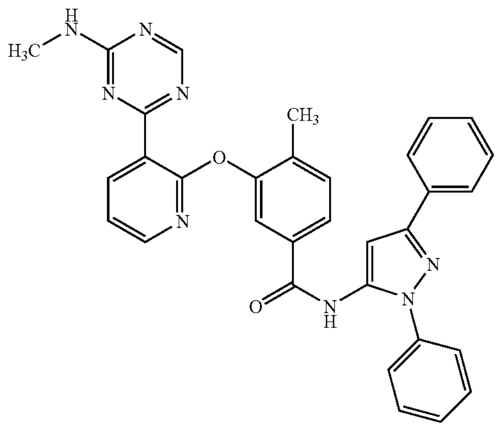 | 554.61 | 555 |
| 418 | 4-methyl-3-((2'-(methylamino)-3,4'-bipyridin-2-yl)oxy)-N-phenylbenzamide | 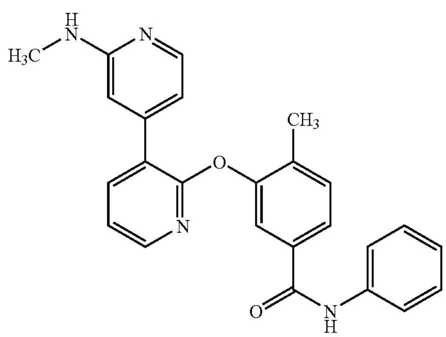 | 410.48 | 411 |
| 419 | 4-methyl-3-((2'-(methylamino)-3,4'-bipyridin-2-yl)oxy)-N-(2-(methyloxy)phenyl)benzamide | 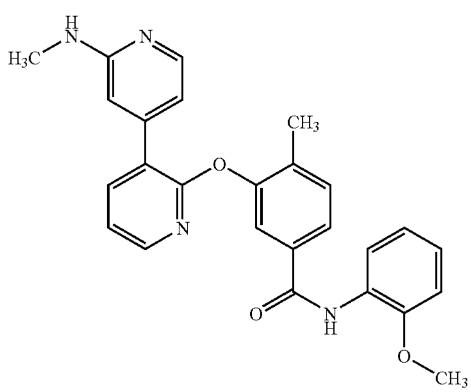 | 440.5 | 441 |
| 420 | 4-methyl-3-((2'-(methylamino)-3,4'-bipyridin-2-yl)oxy)-N-(4-(1-methylethyl)phenyl)benzamide | 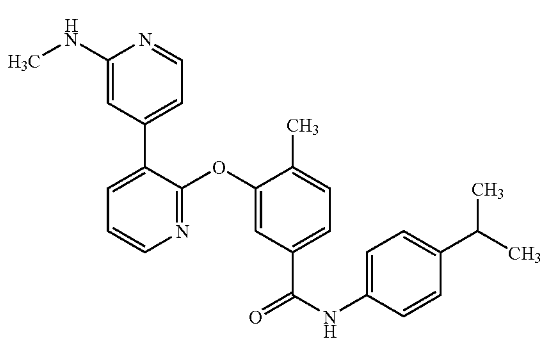 | 452.56 | 453 |

-continued

| Ex. No. | Structure Name | Structure | MW | MS Data |
|---|---|---|---|---|
| 421 | N-(4-fluoro-3-(trifluoromethyl)phenyl)-4-methyl-3-((2'-(methylamino)-3,4'-bipyridin-2-yl)oxy)benzamide | 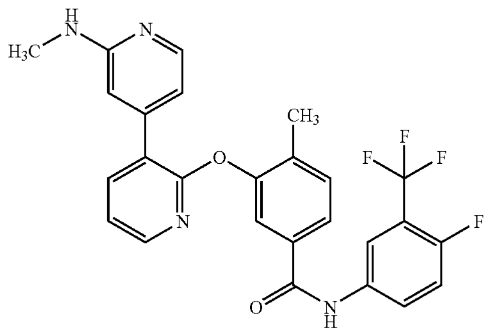 | 496.46 | 497 |
| 422 | 4-methyl-3-((2'-(methylamino)-3,4-bipyridin-2-yl)oxy)-N-(2-methyl-3-(trifluoromethyl)phenyl)benzamide | 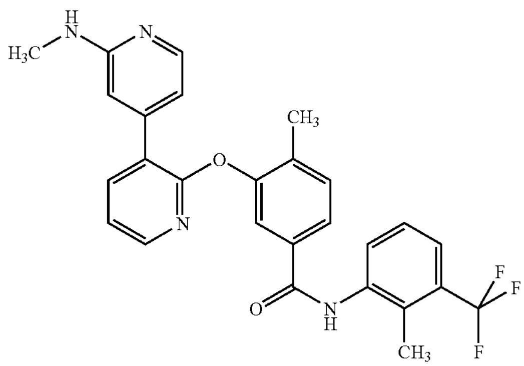 | 492.5 | 493 |
| 423 | 4-methyl-3-((2'-(methylamino)-3,4-bipyridin-2-yl)oxy)-N-(3-(methyloxy)-5-(trifluoromethyl)phenyl)benzamide | 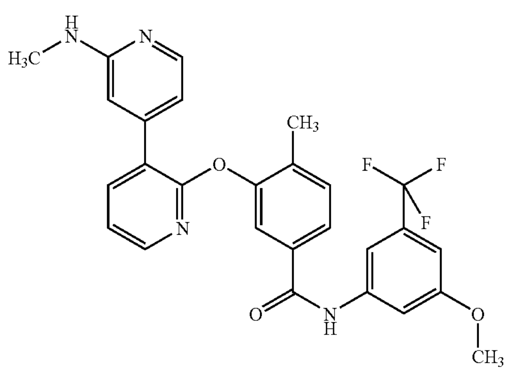 | 508.5 | 509 |
| 424 | N-(3,5-bis((2,2,2-trifluoroethyl)oxy)phenyl)-4-methyl-3-((2'-(methylamino)-3,4'-bipyridin-2-yl)oxy)benzamide | 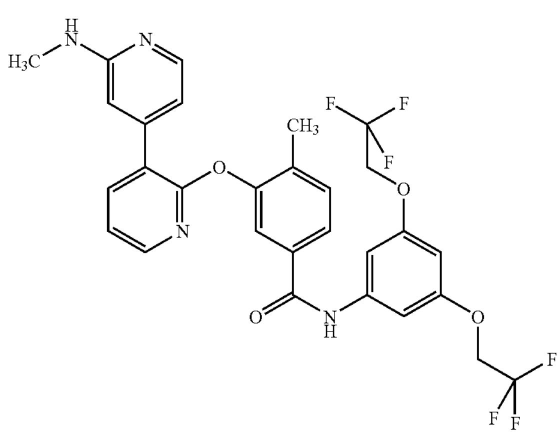 | 606.52 | 607 |

-continued

| Ex. No. | Structure Name | Structure | MW | MS Data |
|---|---|---|---|---|
| 425 | 4-methyl-3-((2'-(methylamino)-3,4'-bipyridin-2-yl)oxy)-N-(2-(4-morpholinyl)-5-(trifluoromethyl)phenyl)benzamide | 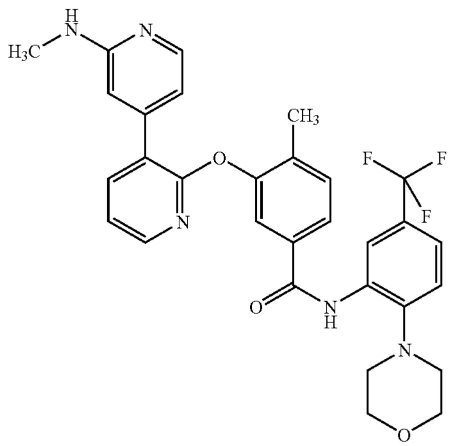 | 563.58 | 564 |
| 426 | 4-methyl-3-((2'-(methylamino)-3,4'-bipyridin-2-yl)oxy)-N-(2-(1-pyrrolidinyl)-5-(trifluoromethyl)phenyl)benzamide | 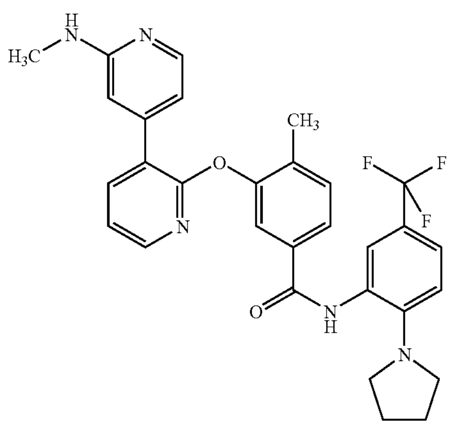 | 547.58 | 548 |
| 427 | N-(2-chloro-5-(trifluoromethyl)phenyl)-4-methyl-3-((2'-(methylamino)-3,4'-bipyridin-2-yl)oxy)benzamide | 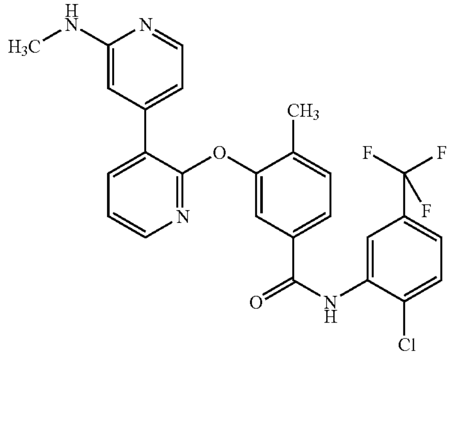 | 512.92 | 513 |

| Ex. No. | Structure Name | Structure | MW | MS Data |
|---|---|---|---|---|
| 428 | 4-methyl-3-((2'-(methylamino)-3,4'-bipyridin-2-yl)oxy)-N-(2-(methyloxy)-5-(phenyloxy)phenyl)benzamide | 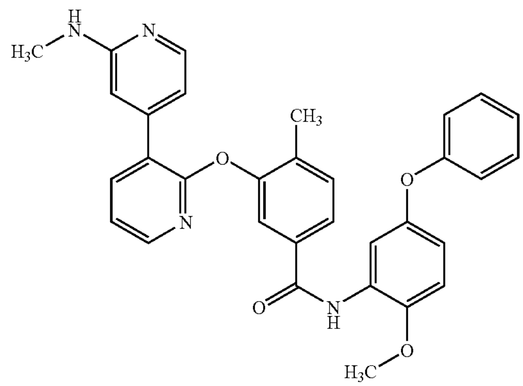 | 532.6 | 533 |
| 429 | 4-methyl-3-((2'-(methylamino)-3,4'-bipyridin-2-yl)oxy)-N-(4-(methyloxy)-1,1'-biphenyl-3-yl)benzamide | 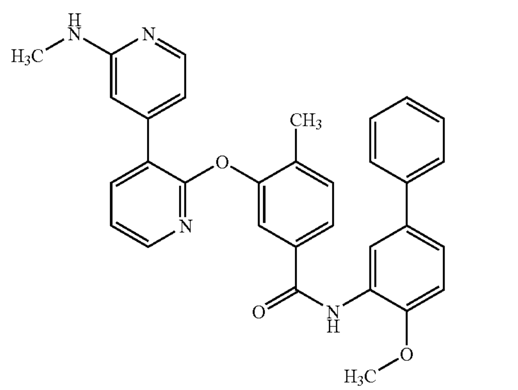 | 516.6 | 517 |
| 430 | N-(5-(1,1-dimethylethyl)-2-(methyloxy)phenyl)-4-methyl-3-((2'-(methylamino)-3,4'-bipyridin-2-yl)oxy)benzamide | 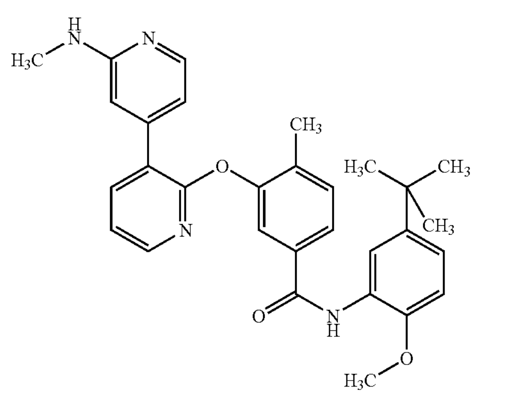 | 496.61 | 497 |

-continued
| Ex. No. | Structure Name | Structure | MW | MS Data |
|---|---|---|---|---|
| 431 | N-(2,5-bis(ethyloxy)phenyl)-4-methyl-3-((2'-(methylamino)-3,4'-bipyridin-2-yl)oxy)benzamide | 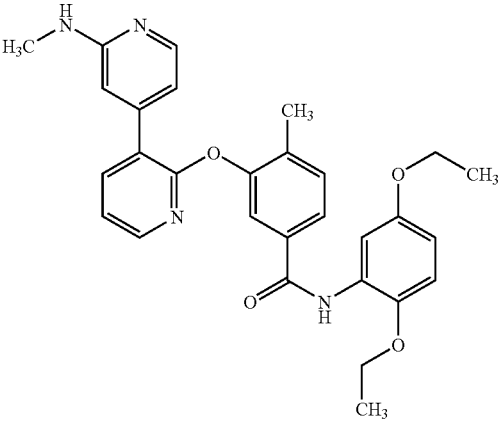 | 498.58 | 499 |
| 432 | 4-methyl-3-((2'-(methylamino)-3,4'-bipyridin-2-yl)oxy)-N-(2-methyl-5-(1-methylethyl)phenyl)benzamide | 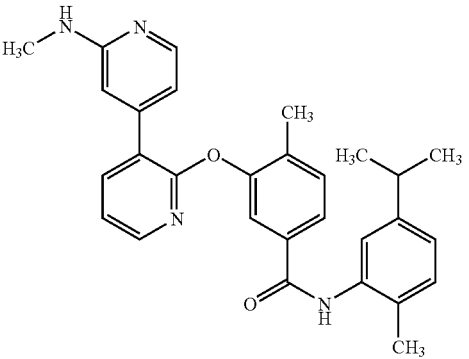 | 466.58 | 467 |
| 433 | 4-methyl-3-((2'-(methylamino)-3,4'-bipyridin-2-yl)oxy)-N-(3-((phenylmethyl)oxy)phenyl)benzamide | 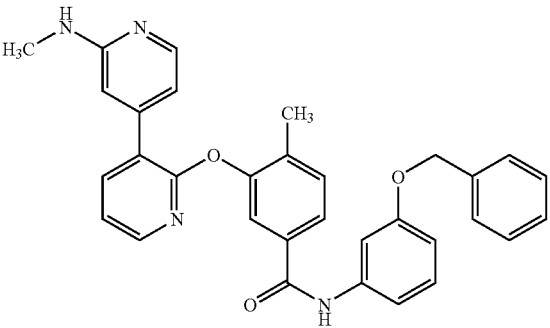 | 516.6 | 517 |
| 434 | N-(1,1'-biphenyl-3-yl)-4-methyl-3-((2'-(methylamino)-3,4'-bipyridin-2-yl)oxy)benzamide | 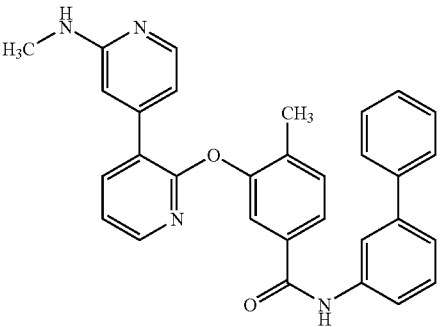 | 486.57 | 487 |

-continued

| Ex. No. | Structure Name | Structure | MW | MS Data |
|---|---|---|---|---|
| 435 | N-(3-(ethyloxy)phenyl)-4-methyl-3-((2'-(methylamino)-3,4'-bipyridin-2-yl)oxy)benzamide | 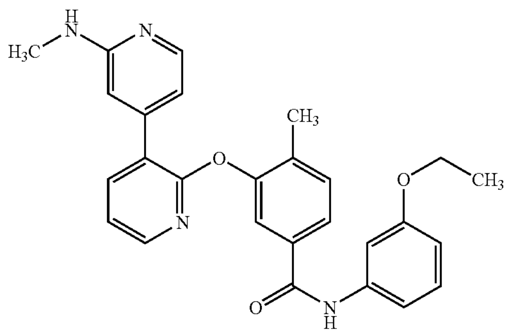 | 454.53 | 455 |
| 436 | 4-methyl-3-((2'-(methylamino)-3,4'-bipyridin-2-yl)oxy)-N-(3-((1-methylethyl)oxy)phenyl)benzamide | 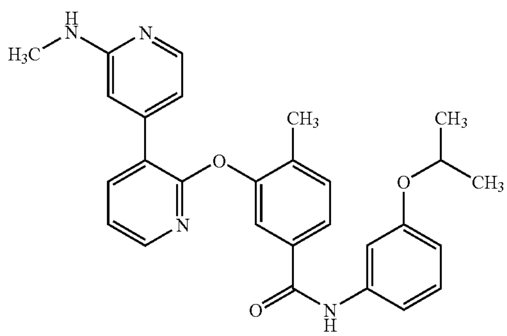 | 468.55 | 469 |
| 437 | 4-methyl-3-((2'-(methylamino)-3,4'-bipyridin-2-yl)oxy)-N-(3-(trifluoromethyl)phenyl)benzamide | 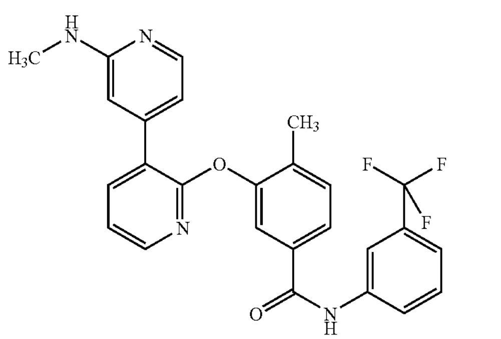 | 478.47 | 479 |
| 438 | 4-methyl-3-((2'-(methylamino)-3,4'-bipyridin-2-yl)oxy)-N-(3-((trifluoromethyl)oxy)phenyl)benzamide | 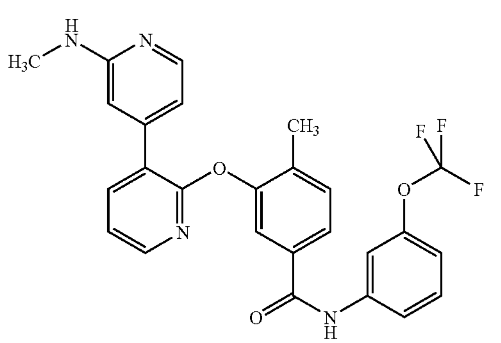 | 494.47 | 495 |

| Ex. No. | Structure Name | Structure | MW | MS Data |
|---|---|---|---|---|
| 439 | 4-methyl-3-((2'-(methylamino)-3,4'-bipyridin-2-yl)oxy)-N-(3-((1,1,2,2-tetrafluoroethyl)oxy)phenyl)benzamide | 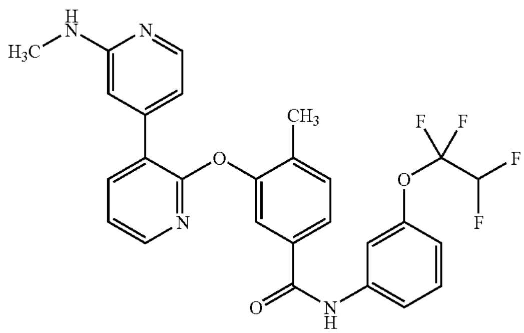 | 526.49 | 527 |
| 440 | N-(3-(hexyloxy)phenyl)-4-methyl-3-((2'-(methylamino)-3,4'-bipyridin-2-yl)oxy)benzamide | 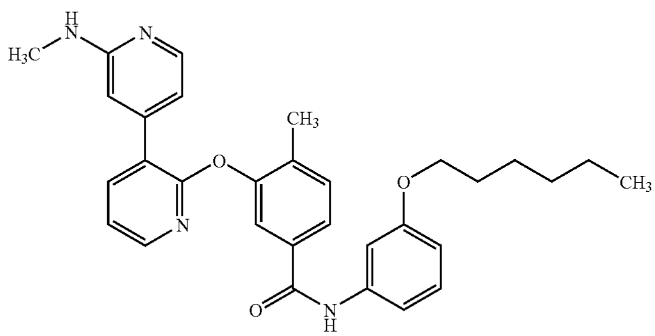 | 510.63 | 511 |
| 441 | N-(3-(2,5-dimethyl-1H-pyrrol-1-yl)phenyl)-4-methyl-3-((2'-(methylamino)-3,4'-bipyridin-2-yl)oxy)benzamide | 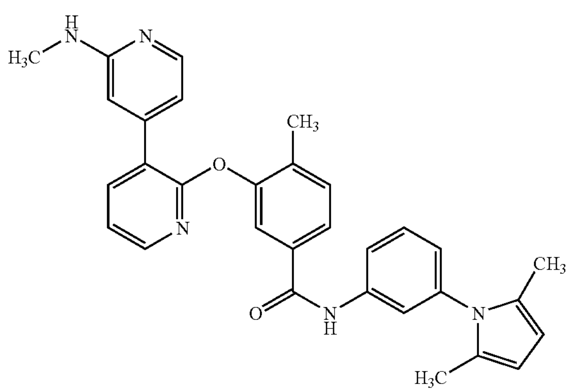 | 503.6 | 504 |
| 442 | N-(5-(1,1-dimethylethyl)-3-isoxazolyl)-4-methyl-3-((2'-(methylamino)-3,4'-bipyridin-2-yl)oxy)benzamide | 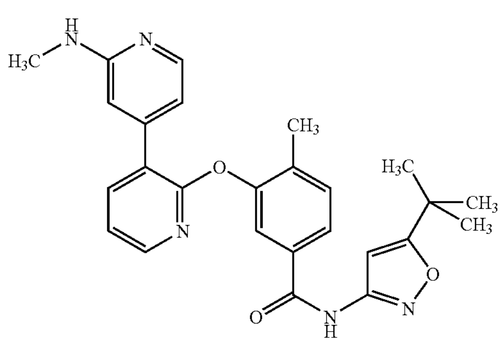 | 457.53 | 458 |

-continued

| Ex. No. | Structure Name | Structure | MW | MS Data |
|---|---|---|---|---|
| 443 | N-(1,3-diphenyl-1H-pyrazol-5-yl)-4-methyl-3-((2'-(methylamino)-3,4'-bipyridin-2-yl)oxy)benzamide | 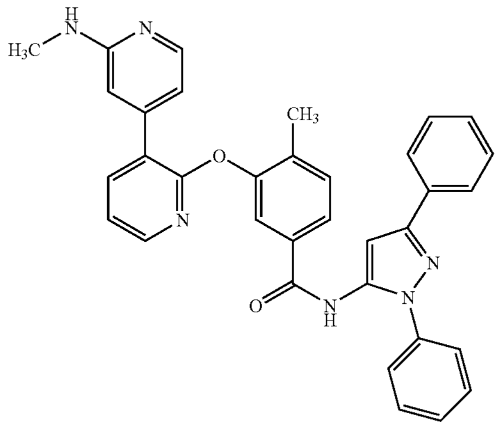 | 552.63 | 553 |
| 444 | N-methyl-2-((2-methyl-5-((6-(trifluoromethyl)-1H-indol-1-yl)carbonyl)phenyl)oxy)-3,4'-bipyridin-2'-amine | 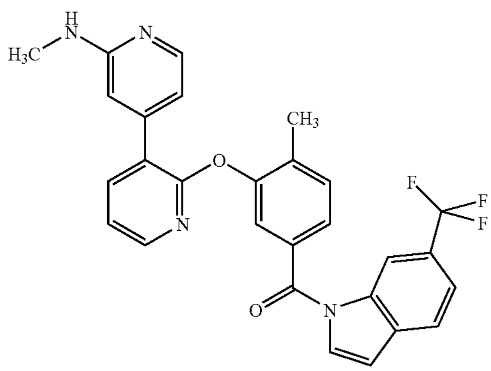 | 502.49 | 503 |
| 445 | N-(cyclohexylmethyl)-4-methyl-3-((2'-(methylamino)-3,4'-bipyridin-2-yl)oxy)benzamide | 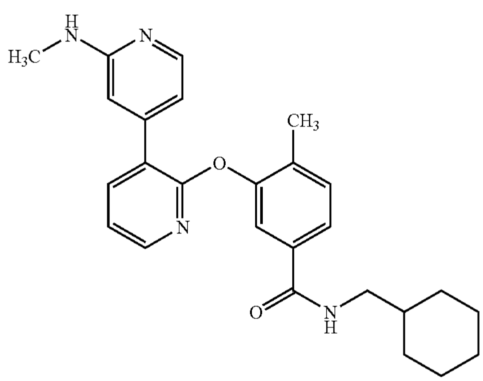 | 430.55 | 431 |
| 446 | N-((1R)-1-cyclohexylethyl)-4-methyl-3-((2'-(methylamino)-3,4'-bipyridin-2-yl)oxy)benzamide | 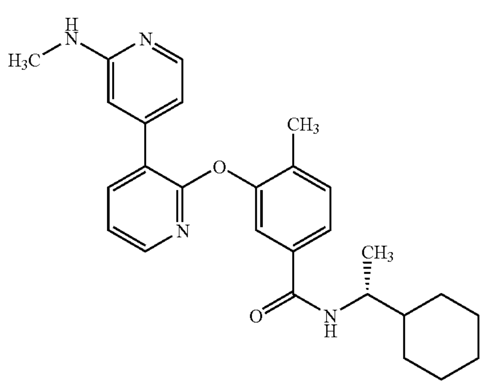 | 444.58 | 445 |

| Ex. No. | Structure Name | Structure | MW | MS Data |
|---|---|---|---|---|
| 447 | N-((1S)-1-cyclohexylethyl)-4-methyl-3-((2'-(methylamino)-3,4'-bipyridin-2-yl)oxy)benzamide | 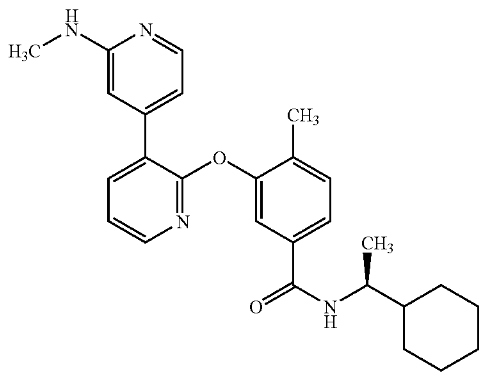 | 444.58 | 445 |
| 448 | 4-methyl-3-((2'-(methylamino)-3,4'-bipyridin-2-yl)oxy)-N-((3-(trifluoromethyl)phenyl)methyl)benzamide | 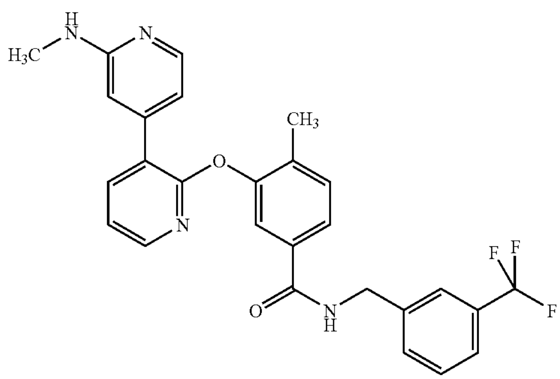 | 492.5 | 493 |
| 449 | N-(3,3-dimethylbutyl)-4-methyl-3-((2'-(methylamino)-3,4'-bipyridin-2-yl)oxy)benzamide | 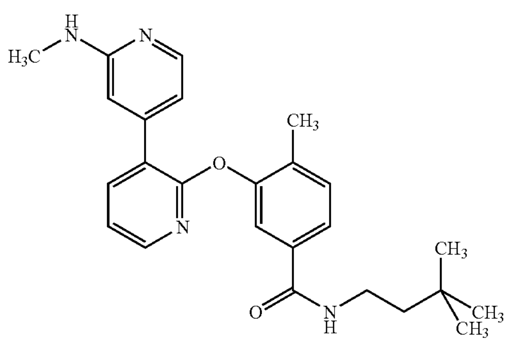 | 418.54 | 419 |
| 450 | N-(2-fluoro-5-(trifluoromethyl)phenyl)-4-methyl-3-((2'-(methylamino)-3,4'-bipyridin-2-yl)oxy)benzamide | 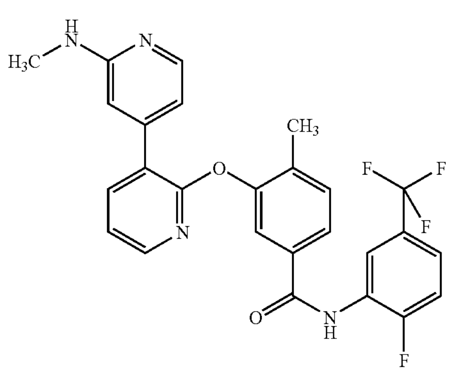 | 496.46 | 497 |

-continued

| Ex. No. | Structure Name | Structure | MW | MS Data |
|---|---|---|---|---|
| 451 | N-(2,2,3,3,4,4,4-heptafluorobutyl)-4-methyl-3-((2'-(methylamino)-3,4'-bipyridin-2-yl)oxy)benzamide | 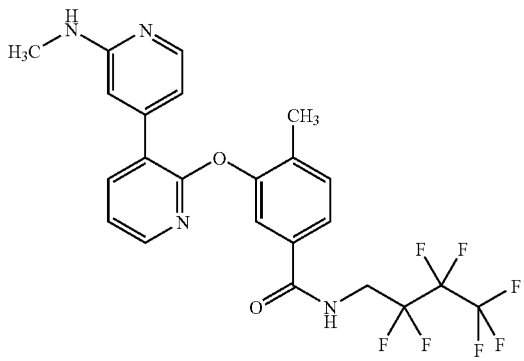 | 516.41 | 517 |
| 452 | N-(3,5-dichlorophenyl)-4-methyl-3-((2'-(methylamino)-3,4'-bipyridin-2-yl)oxy)benzamide | 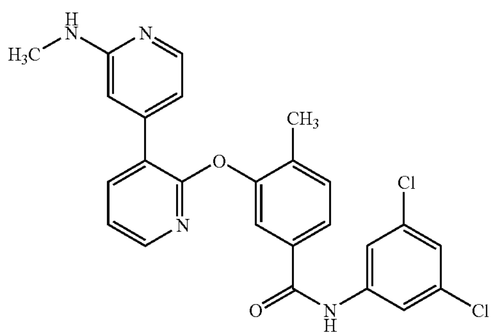 | 479.37 | 479 |
| 453 | N-(2,3-dichlorophenyl)-4-methyl-3-((2'-(methylamino)-3,4'-bipyridin-2-yl)oxy)benzamide | 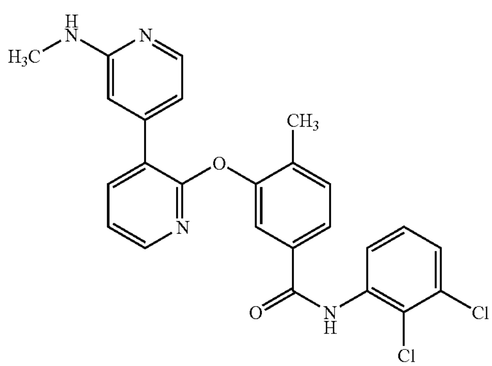 | 479.37 | 479 |
| 454 | 2-fluoro-5-((3-(4-(methylamino)-1,3,5-triazin-2-yl)-2-pyridinyl)oxy)-N-(3-((1-methylethyl)oxy)phenyl)benzamide | 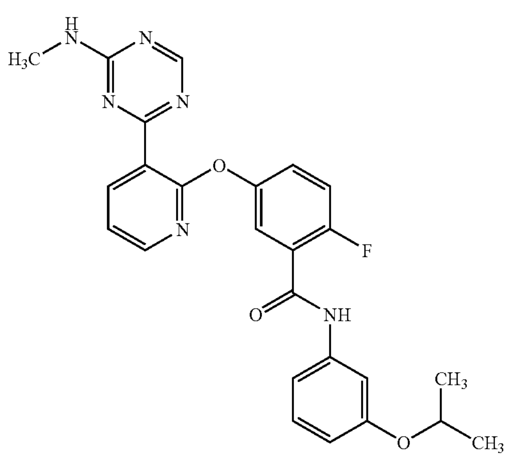 | 474.49 | 475 |

-continued

| Ex. No. | Structure Name | Structure | MW | MS Data |
|---|---|---|---|---|
| 455 | N-(2-((3-(dimethylamino)propyl)(methyl)amino)-5-(trifluoromethyl)phenyl)-2-fluoro-5-((3-(2-(methylamino)-4-pyrimidinyl)-2-pyridinyl)oxy)benzamide | 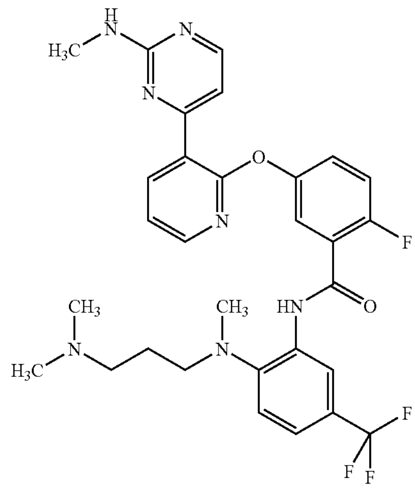 | 597.61 | 589 |
| 456 | 2-fluoro-5-((3-(2-(methylamino)-4-pyrimidinyl)-2-pyridinyl)oxy)-N-(2-(4-methyl-1-piperazinyl)-5-(trifluoromethyl)phenyl)benzamide | 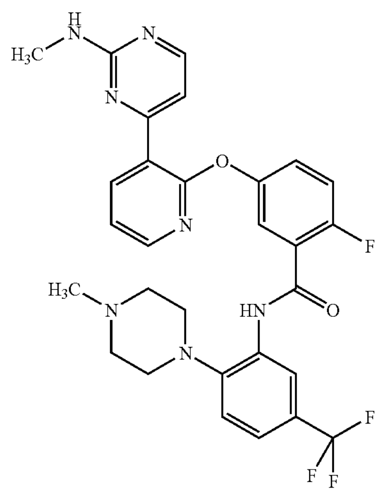 | 581.57 | 582 |
| 457 | 2-fluoro-5-((3-(2-(methylamino)-4-pyrimidinyl)-2-pyridinyl)oxy)-N-(3-((trifluoromethyl)oxy)phenyl)benzamide | 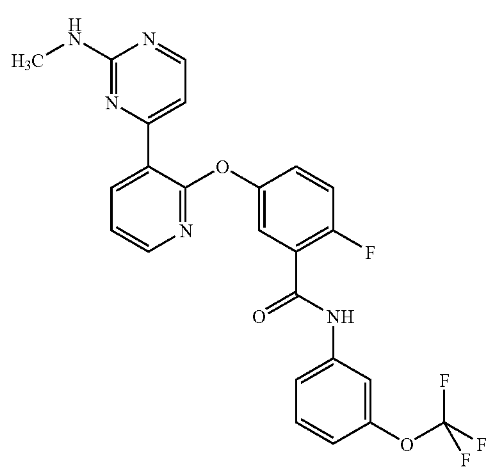 | 499.42 | 500 |

| Ex. No. | Structure Name | Structure | MW | MS Data |
|---|---|---|---|---|
| 458 | 2-fluoro-5-((3-(2-(methylamino)-4-pyrimidinyl)-2-pyridinyl)oxy)-N-(3-((1-methylethyl)oxy)phenyl)benzamide | 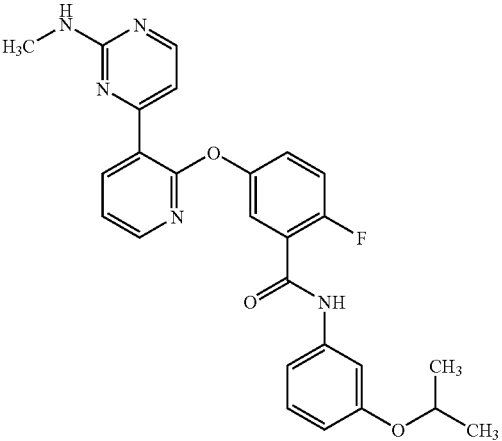 | 473.51 | 474 |
| 459 | N-(2-((3R)-3-(dimethylamino)-1-pyrrolidinyl)-5-(trifluoromethyl)phenyl)-2-fluoro-5-((3-(2-(methylamino)-4-pyrimidinyl)-2-pyridinyl)oxy)benzamide | 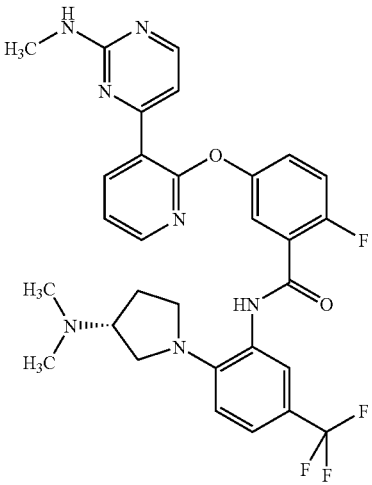 | 595.6 | 596 |
| 460 | N-(2-((2-(dimethylamino)ethyl)(methyl)amino)-5-(trifluoromethyl)phenyl)-2-fluoro-5-((3-(2-(methylamino)-4-pyrimidinyl)-2-pyridinyl)oxy)benzamide | 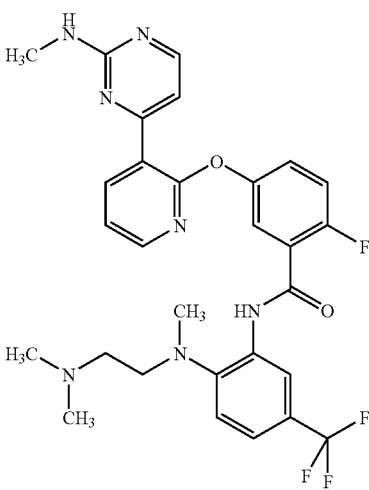 | 583.59 | 584 |

-continued

| Ex. No. | Structure Name | Structure | MW | MS Data |
|---|---|---|---|---|
| 461 | N-(2-((3S)-3-(dimethylamino)-1-pyrrolidinyl)-5-(trifluoromethyl)phenyl)-2-fluoro-5-((3-(2-(methylamino)-4-pyrimidinyl)-2-pyridinyl)oxy)benzamide | 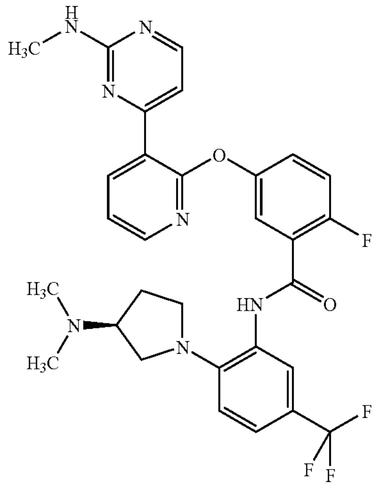 | 595.6 | 596 |
| 462 | 2-fluoro-5-((3-(4-(methylamino)-1,3,5-triazin-2-yl)-2-pyridinyl)oxy)-N-(3-((((2S)-1-methyl-2-pyrrolidinyl)methyl)oxy)-5-(trifluoromethyl)phenyl) benzamide | 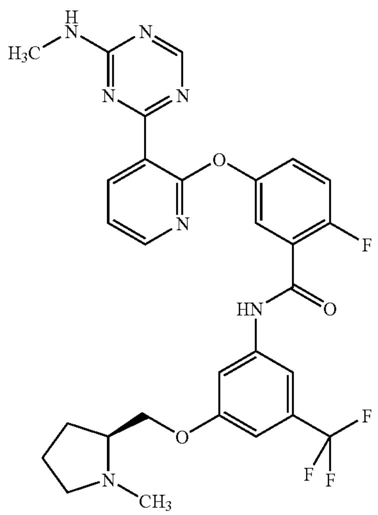 | 597.57 | 598 |
| 463 | 2-fluoro-5-((2'-(methylamino)-3,4'-bipyridin-2-yl)oxy)-N-(3-((1-methylethyl)oxy)phenyl) benzamide | 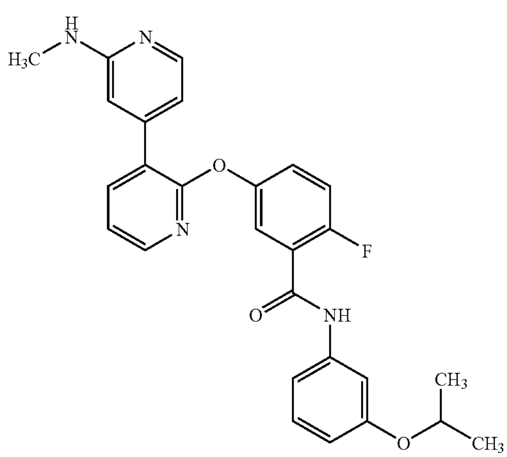 | 472.52 | 473 |

| Ex. No. | Structure Name | Structure | MW | MS Data |
|---|---|---|---|---|
| 464 | N-(2-((2-(dimethylamino)ethyl)(methyl)amino)-5-(trifluoromethyl)phenyl)-2-fluoro-5-((2'-(methylamino)-3,4'-bipyridin-2-yl)oxy)benzamide | 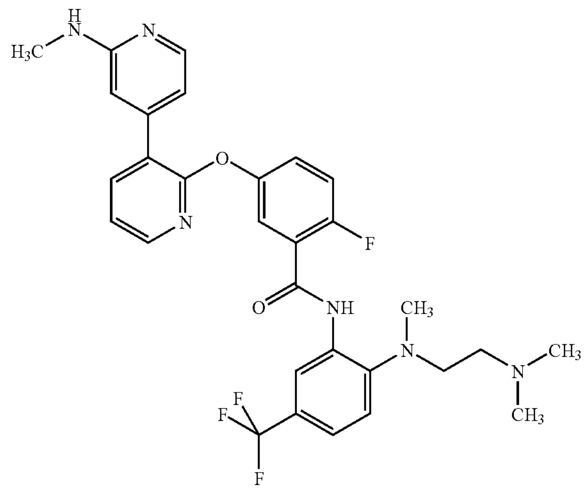 | 582.6 | 583 |
| 465 | N-(2-((3R)-3-(dimethylamino)-1-pyrrolidinyl)-5-(trifluoromethyl)phenyl)-2-fluoro-5-((3-(4-(methylamino)-1,3,5-triazin-2-yl)-2-pyridinyl)oxy)benzamide | 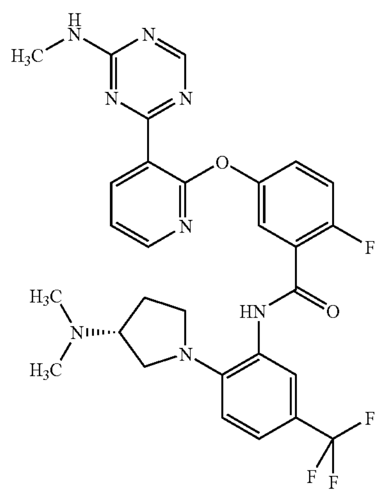 | 596.59 | 597 |
| 466 | N-(2-((3S)-3-(dimethylamino)-1-pyrrolidinyl)-5-(trifluoromethyl)phenyl)-2-fluoro-5-((3-(4-(methylamino)-1,3,5-triazin-2-yl)-2-pyridinyl)oxy)benzamide | 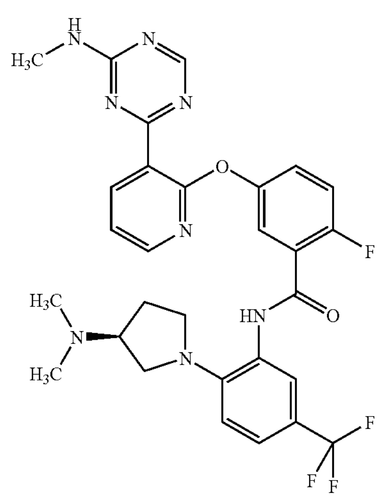 | 596.59 | 597 |

| Ex. No. | Structure Name | Structure | MW | MS Data |
|---|---|---|---|---|
| 467 | N-(2-((3R)-3-(dimethylamino)-1-pyrrolidinyl)-5-(trifluoromethyl)phenyl)-4-methyl-3-((3-(2-(methylamino)-4-pyrimidinyl)-2-pyridinyl)oxy)benzamide | 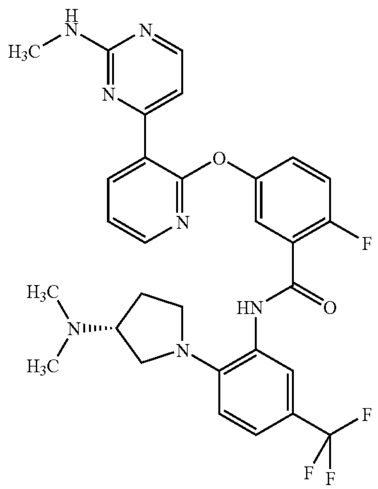 | 591.63 | 592 |
| 468 | N-(2-((3S)-3-(dimethylamino)-1-pyrrolidinyl)-5-(trifluoromethyl)phenyl)-4-methyl-3-((3-(2-(methylamino)-4-pyrimidinyl)-2-pyridinyl)oxy)benzamide | 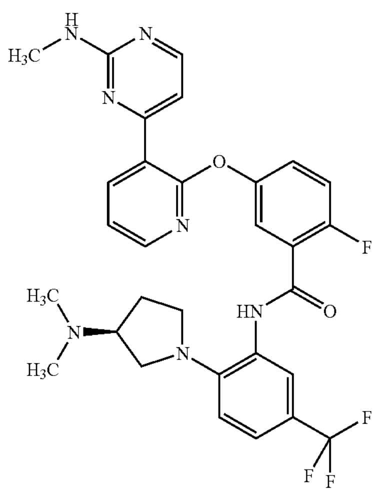 | 591.63 | 592 |
| 469 | N-(3-(ethyloxy)phenyl)-2-fluoro-5-((3-(4-(methylamino)-1,3,5-triazin-2-yl)-2-pyridinyl)oxy)benzamide | 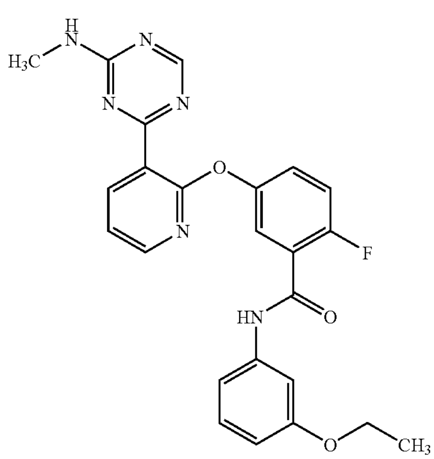 | 460.47 | 461 |

-continued

| Ex. No. | Structure Name | Structure | MW | MS Data |
|---|---|---|---|---|
| 470 | 2-fluoro-5-((3-(4-(methylamino)-1,3,5-triazin-2-yl)-2-pyridinyl)oxy)-N-(3-(phenyloxy)phenyl)benzamide | 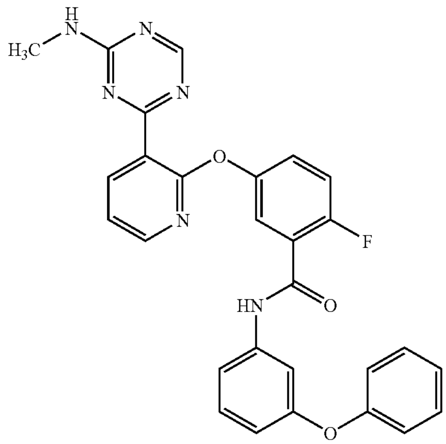 | 508.51 | 509 |
| 471 | 2-fluoro-5-((2'-(methylamino)-3,4'-bipyridin-2-yl)oxy)-N-(2-((4-methyl-1-piperazinyl)methyl)-5-(trifluoromethyl)phenyl)benzamide | 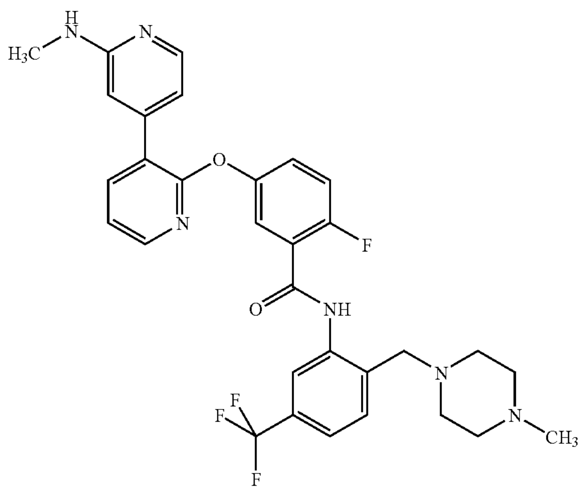 | 594.61 | 595 |
| 472 | N-(2-(((3R)-3-(dimethylamino)-1-pyrrolidinyl)methyl)-5-(trifluoromethyl)phenyl)-2-fluoro-5-((3-(2-(methylamino)-4-pyrimidinyl)-2-pyridinyl)oxy)benzamide | 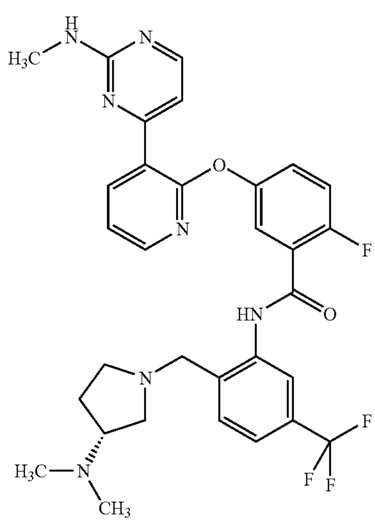 | 609.63 | 610 |

| Ex. No. | Structure Name | Structure | MW | MS Data |
|---|---|---|---|---|
| 473 | N-(2-(((3R)-3-(dimethylamino)-1-pyrrolidinyl)methyl)-5-(trifluoromethyl)phenyl)-2-fluoro-5-((3-(4-(methylamino)-1,3,5-triazin-2-yl)-2-pyridinyl)oxy)benzamide | 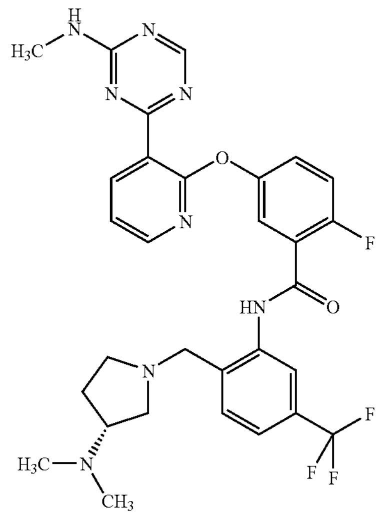 | 610.61 | 611 |
| 474 | N-(2-(((3S)-3-(dimethylamino)-1-pyrrolidinyl)methyl)-5-(trifluoromethyl)phenyl)-2-fluoro-5-((3-(4-(methylamino)-1,3,5-triazin-2-yl)-2-pyridinyl)oxy)benzamide | 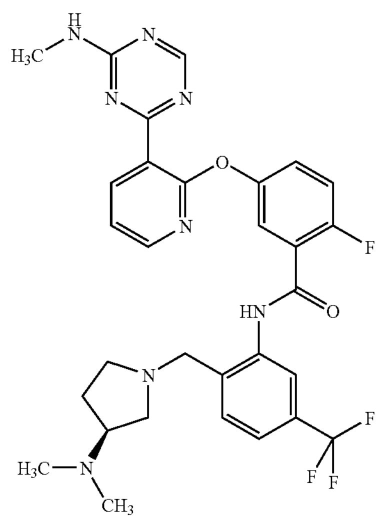 | 610.61 | 611 |
| 475 | N-(2-(((3S)-3-(dimethylamino)-1-pyrrolidinyl)methyl)-5-trifluoromethyl)phenyl)-2-fluoro-5-((3-(2-(methylamino)-4-pyrimidinyl)-2-pyridinyl)oxy)benzamide | 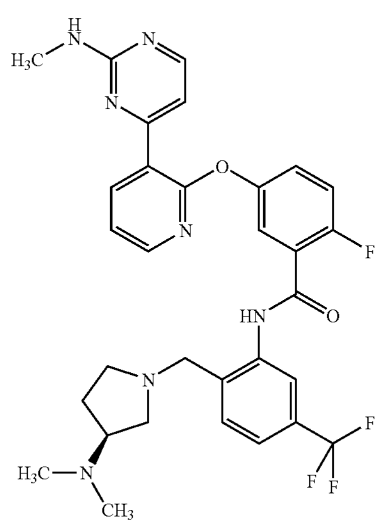 | 609.63 | 610 |

-continued

| Ex. No. | Structure Name | Structure | MW | MS Data |
|---|---|---|---|---|
| 476 | 2-fluoro-5-((3-(2-(methylamino)-4-pyrimidinyl)-2-pyridinyl)oxy)-N-(2-(methyl(1-methyl-3-pyrrolidinyl)amino)-5-(trifluoromethyl)phenyl)benzamide | | 595.6 | 596 |
| 477 | N-(3-(ethyloxy)phenyl)-2-fluoro-5-((2'-(methylamino)-3,4'-bipyridin-2-yl)oxy)benzamide | 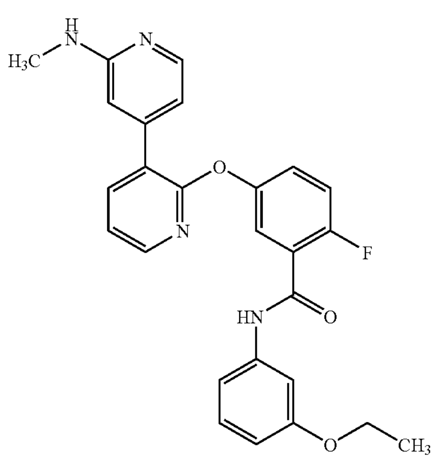 | 458.49 | 459 |

| Ex. No. | Structure Name | Structure | MW | MS Data |
|---|---|---|---|---|
| 478 | 2-fluoro-5-((3-(4-(methylamino)-1,3,5-triazin-2-yl)-2-pyridinyl)oxy)-N-(2-(methyl(1-methyl-3-pyrrolidinyl)amino)-5-(trifluoromethyl)phenyl)benzamide | 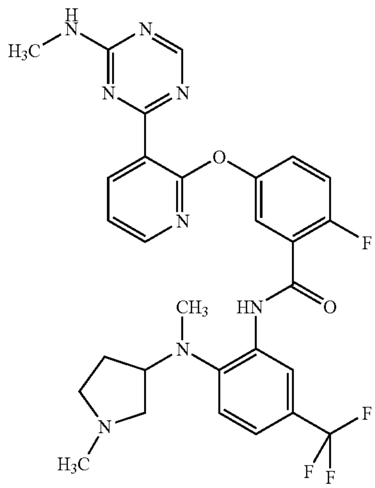 | 596.59 | 597 |
| 479 | 2-methyl-6-((3-(2-(methylamino)-4-pyrimidinyl)-2-pyridinyl)oxy)-N-(3-(1-methylethyl)phenyl)-4-pyridinecarboxamide | 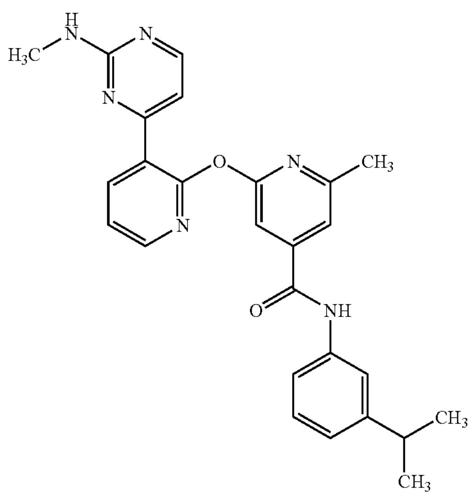 | 454.53 | 455 |
| 480 | 2-methyl-6-((3-(2-(methylamino)-4-pyrimidinyl)-2-pyridinyl)oxy)-N-(3-(methyloxy)-5-(trifluoromethyl)phenyl)-4-pyridinecarboxamide | 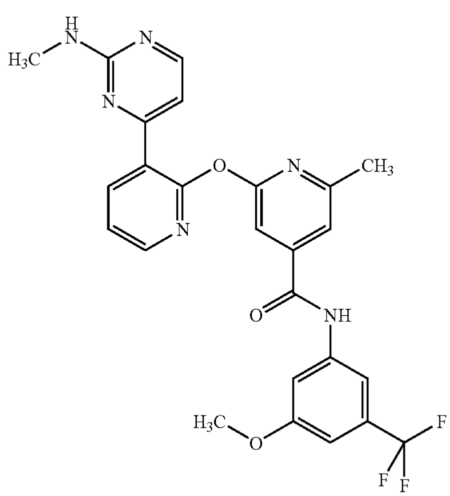 | 510.47 | 511 |

-continued

| Ex. No. | Structure Name | Structure | MW | MS Data |
|---|---|---|---|---|
| 481 | N-(2-((3-(dimethylamino)propyl)methyl)amino)-5-(trifluoromethyl)phenyl)-2-fluoro-4-methyl-5-((3-(2-(methylamino)-4-pyrimidinyl)-2-pyridinyl)oxy)benzamide | 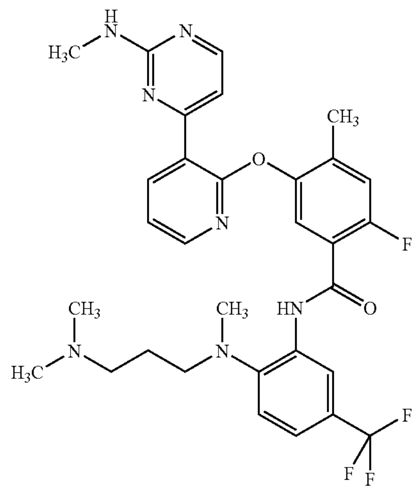 | 611.64 | 612 |
| 482 | N-(2-((3R)-3-(dimethylamino)-1-pyrrolidinyl)-5-(trifluoromethyl)phenyl)-2-fluoro-4-methyl-5-((3-(2-(methylamino)-4-pyrimidinyl)-2-pyridinyl)oxy)benzamide | 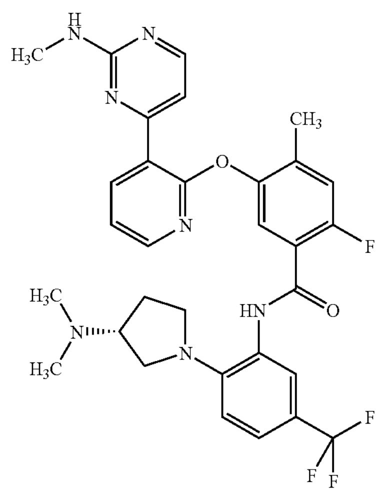 | 609.63 | 610 |
| 483 | 2-fluoro-4-methyl-5-((3-(4-(methylamino)-1,3,5-triazin-2-yl)-2-pyridinyl)oxy)-N-(3-(1-methylethyl)phenyl)benzamide | 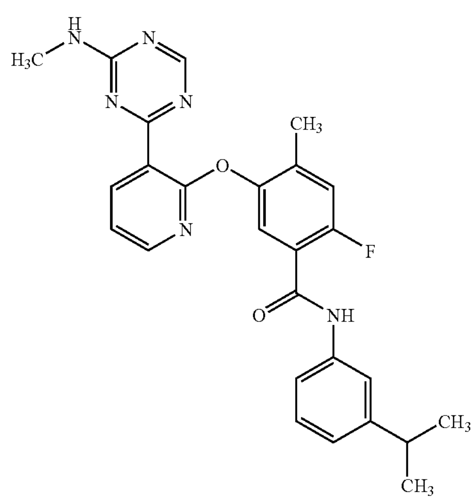 | 472.52 | 473 |

| Ex. No. | Structure Name | Structure | MW | MS Data |
|---|---|---|---|---|
| 484 | 2-fluoro-5-((3-(4-(methylamino)-1,3,5-triazin-2-yl)-2-pyridinyl)oxy)-N-(2-(methyl(1-methyl-4-piperidinyl)amino)-5-(trifluoromethyl)phenyl)benzamide | 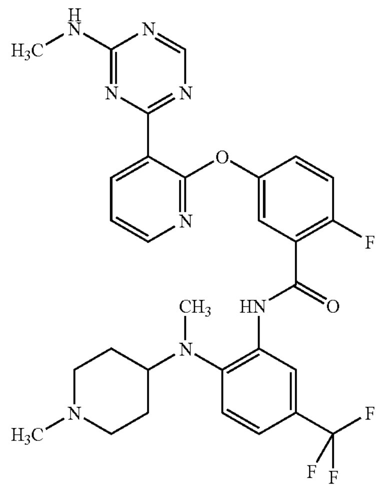 | 610.61 | 611 |
| 485 | 2-fluoro-5-((3-(2-(methylamino)-4-pyrlinidinyl)-2-pyridinyl)oxy)-N-(2-(methyl(1-methyl-4-piperidinyl)amino)-5-(trifluoromethyl)phenyl)benzamide | 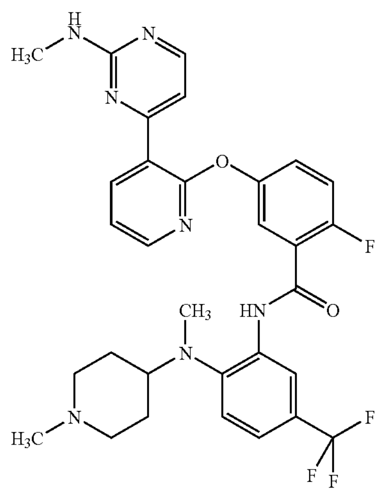 | 609.63 | 610 |
| 486 | 3-bromo-5-((3-(2-(methylamino)-4-pyrimidinyl)-2-pyridinyl)oxy)-N-(3-(1-methylethyl)phenyl)benzamide | 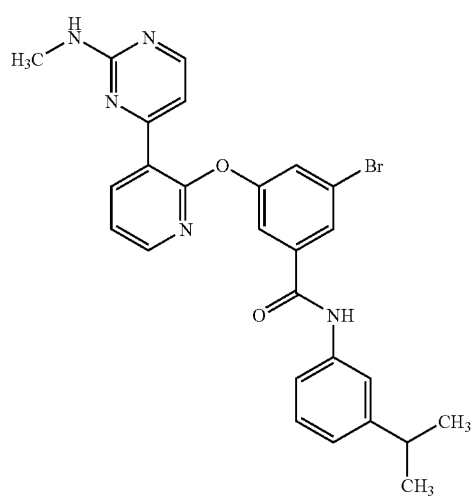 | 518.41 | 518 |

-continued

| Ex. No. | Structure Name | Structure | MW | MS Data |
|---|---|---|---|---|
| 487 | 3-bromo-5-((3-(2-(methylamino)-4-pyrimidinyl)-2-pyridinyl)oxy)-N-(3-(methyloxy)-5-(trifluoromethyl)phenyl)benzamide | 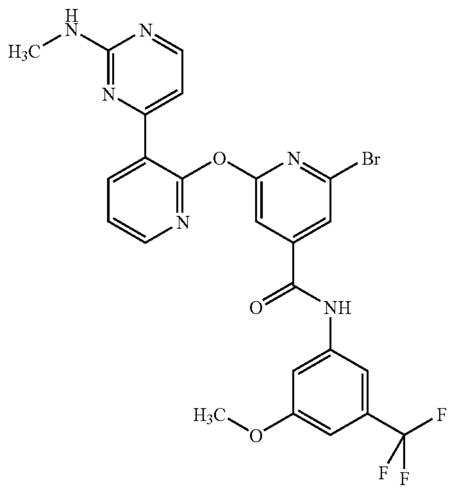 | 574.36 | 574 |
| 488 | 2-fluoro-4-methyl-5-((3-(2-(methylamino)-4-pyrimidinyl)-2-pyridinyl)oxy)-N-(2-(methyl(1-methyl-4-piperidinyl)amino)-5-(trifluoromethyl)phenyl)benzamide | 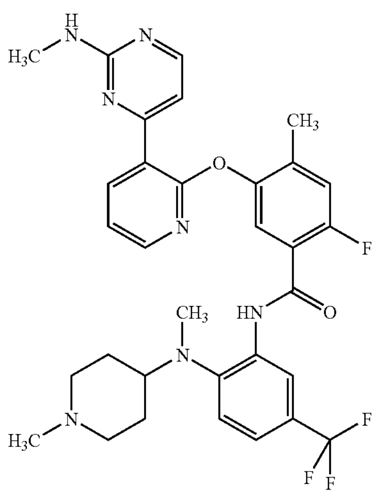 | 623.65 | 624 |
| 489 | 2-fluoro-4-methyl-5-((3-(4-(methylamino)-1,3,5-triazin-2-yl)-2-pyridinyl)oxy)-N-(2-(methyl(1-methyl-4-piperidinyl)amino)-5-(trifluoromethyl)phenyl)benzamide | 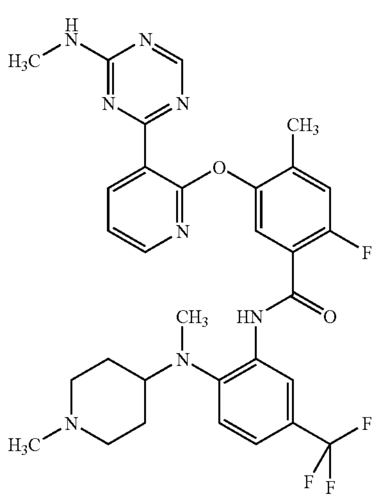 | 624.64 | 625 |

| Ex. No. | Structure Name | Structure | MW | MS Data |
|---|---|---|---|---|
| 490 | 3-bromo-N-(2-((3-(dimethylamino)propyl)methyl)amino)-5-(trifluoromethyl)phenyl)-5-((3-(2-(methylamino)-4-pyrimidinyl)-2-pyridinyl)oxy)benzamide | 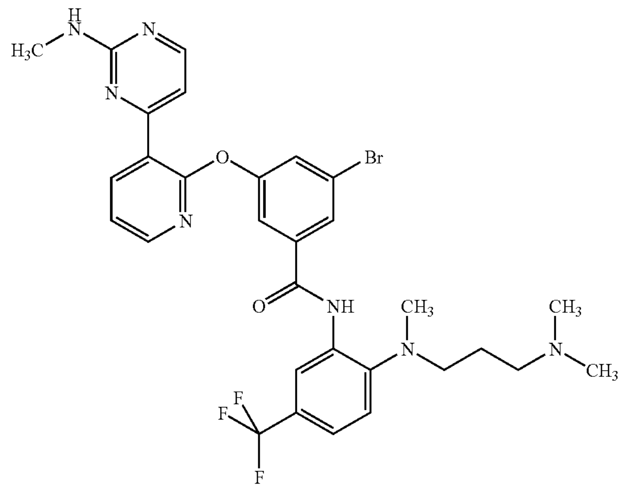 | 658.52 | 658 |
| 491 | 3-bromo-5-((3-(2-(methylamino)-4-pyrimidinyl)-2-pyridinyl)oxy)-N-(2-(methyl((1-methyl-3-pyrrolidinyl)amino)-5-(trifluoromethyl)phenyl benzamide | | 656.51 | 656 |

| Ex. No. | Structure Name | Structure | MW | MS Data |
|---|---|---|---|---|
| 492 | 3-fluoro-5-((3-(2-(methylamino)-4-pyrimidinyl)-2-pyridinyl)oxy)-N-(3-(1-methylethyl)phenyl)benzamide | 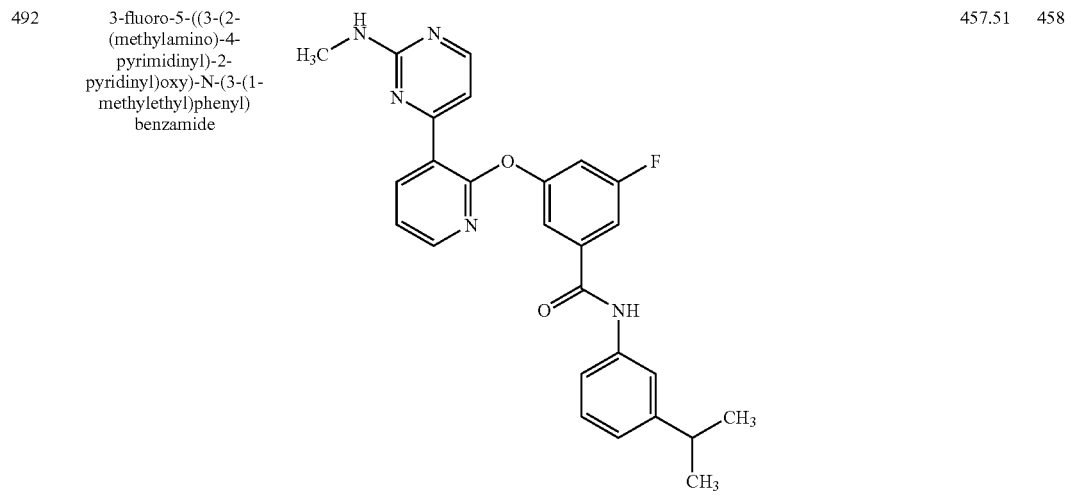 | 457.51 | 458 |
| 493 | 3-((3-(2-(methylamino)-4-pyrimidinyl)-2-pyridinyl)oxy)-N-(3-(1-methylethyl)phenyl)benzamide | 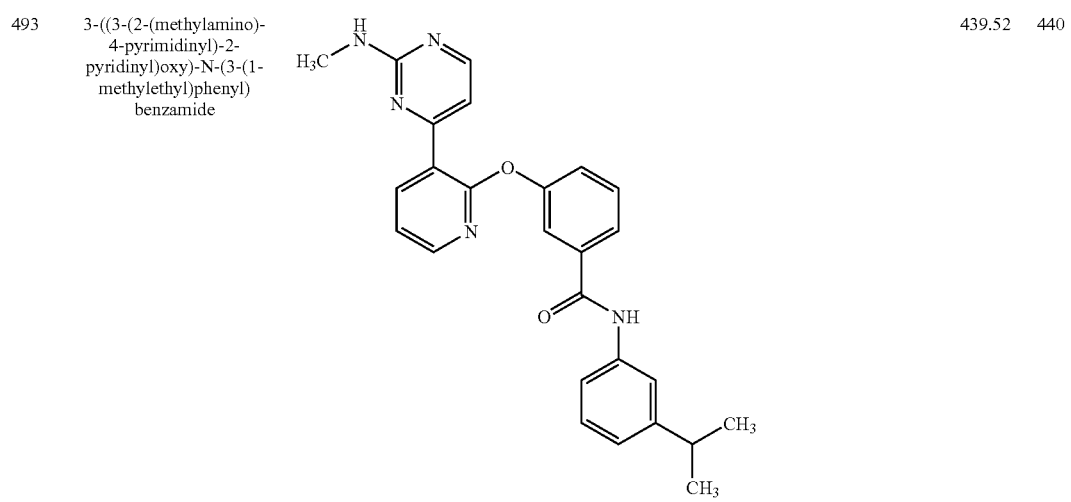 | 439.52 | 440 |

-continued

| Ex. No. | Structure Name | Structure | MW | MS Data |
|---|---|---|---|---|
| 494 | 2-fluoro-3-((3-(2-(methylamino)-4-pyrimidinyl)-2-pyridinyl)oxy)-N-(3-(1-methylethyl)phenyl)benzamide | 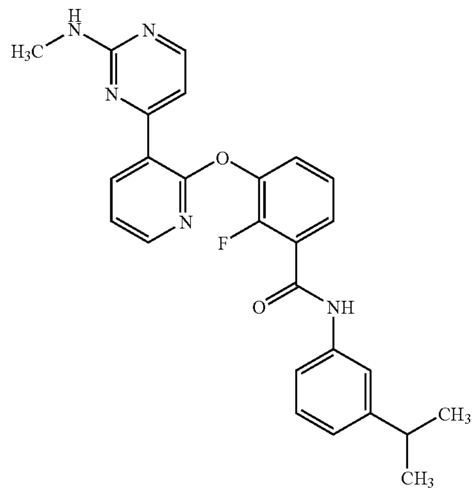 | 457.51 | 458 |
| 495 | 2-fluoro-4-methyl-5-((3-(2-(methylamino)-4-pyrimidinyl)-2-pyridinyl)oxy)-N-(2-(methyl(1-methyl-3-pyrrolidinyl)amino)-5-(trifluoromethyl)phenyl)benzamide | | 609.63 | 610 |

| Ex. No. | Structure Name | Structure | MW | MS Data |
|---|---|---|---|---|
| 496 | 2-fluoro-4-methyl-5-((3-(4-(methylamino)-1,3,5-triazin-2-yl)-2-pyridinyl)oxy)-N-(2-(methyl(1-methyl-3-pyrrolidinyl)amino)-5-(trifluoromethyl)phenyl) benzamide | | 610.62 | 611 |
| 497 | 3-fluoro-5-((3-(2-(methylamino)-4-pyrimidinyl)-2-pyridinyl)oxy)-N-(3-(tri(methyloxy)-5-fluoromethyl)phenyl benzamide | 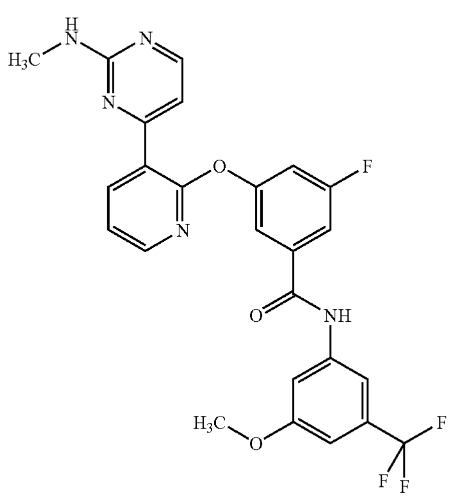 | 513.45 | 514 |

| Ex. No. | Structure Name | Structure | MW | MS Data |
|---|---|---|---|---|
| 498 | 3-fluoro-5-((3-(4-(methylamino)-1,3,5-triazin-2-yl)-2-pyridinyl)oxy)-N-(3-(1-methylethyl)phenyl)benzamide | 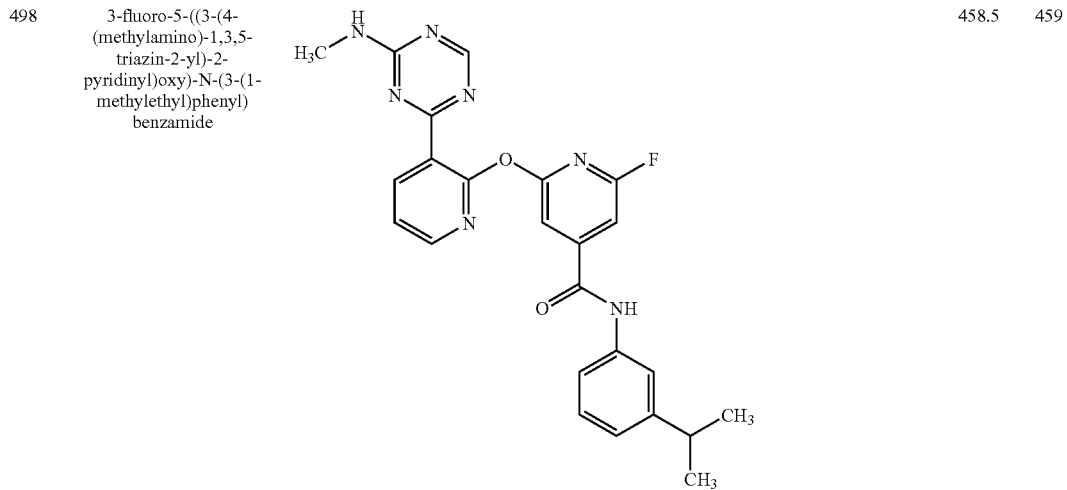 | 458.5 | 459 |
| 499 | N-(2-((3-(dimethylamino)propyl)(methyl)amino)-5-(trifluoromethyl)phenyl)-2-fluoro-4-methyl-5-((3-(4-(methylamino)-1,3,5-triazin-2-yl)-2-pyridinyl)oxy)benzamide | 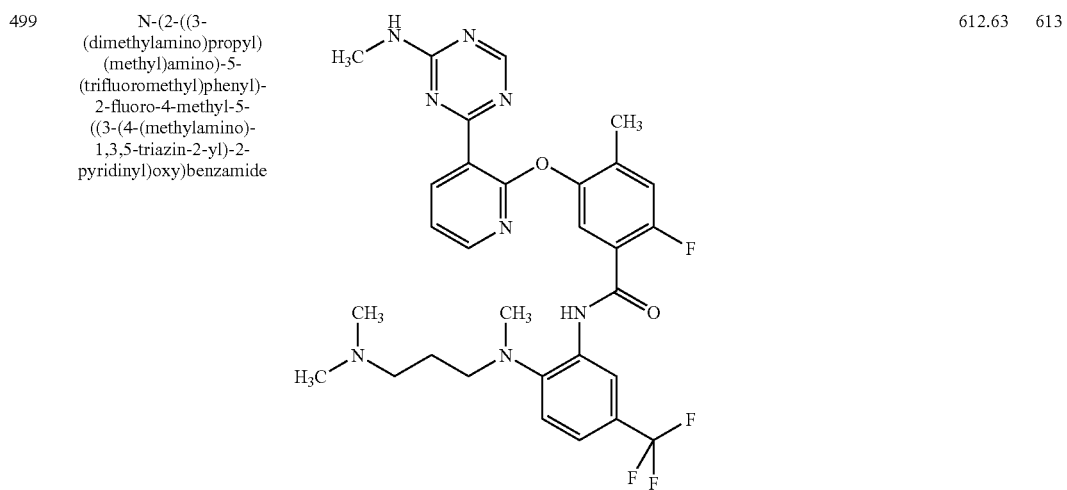 | 612.63 | 613 |

-continued

| Ex. No. | Structure Name | Structure | MW | MS Data |
|---|---|---|---|---|
| 500 | 3-fluoro-5-((3-(2-(methylamino)-4-pyrimidinyl)-2-pyridinyl)oxy)-N-(2-(methyl(1-methyl-3-pyrrolidinyl)amino)-5-(trifluoromethyl)phenyl)benzamide | | 595.6 | 596 |
| 501 | N-(2-((3-(dimethylamino)propyl)methyl)amino)-5-(1-methylethyl)phenyl)-2-fluoro-5-((3-(4-(methylamino)-1,3,5-triazin-2-yl)-2-pyridinyl)oxy)benzamide | 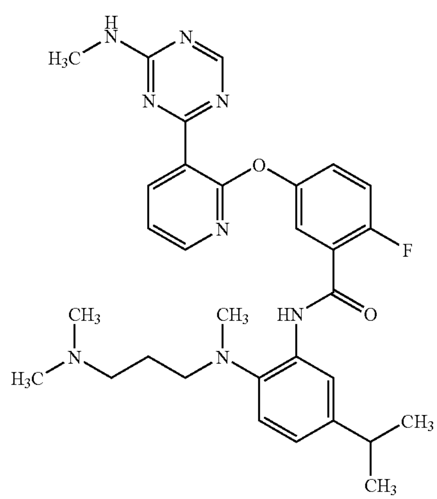 | 572.68 | 573 |

-continued

| Ex. No. | Structure Name | Structure | MW | MS Data |
|---|---|---|---|---|
| 502 | N-(2-((3-(dimethylamino)propyl)(methyl)amino)-5-(trifluoromethyl)phenyl)-3-fluoro-5-((3-(2-(methylamino)-4-pyrimidinyl)-2-pyridinyl)oxy)benzamide | 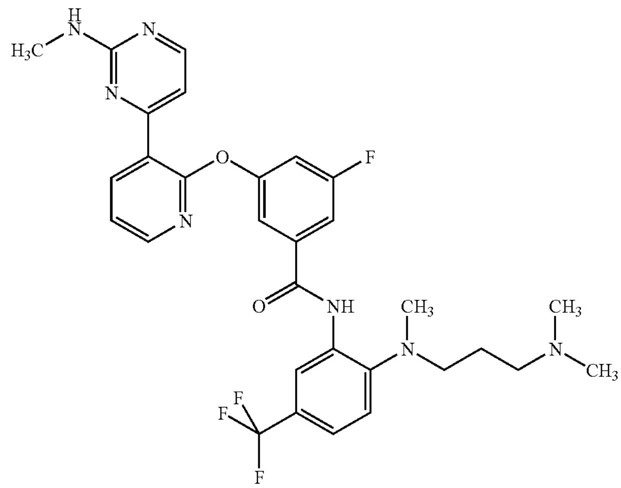 | 597.61 | 598 |
| 503 | N-(2-((3-(dimethylamino)propyl)(methyl)amino)-5-(1-methylethyl)phenyl)-2-fluoro-5-((3-(2-(methylamino)-4-pyrimidinyl)-2-pyridinyl)oxy)benzamide | 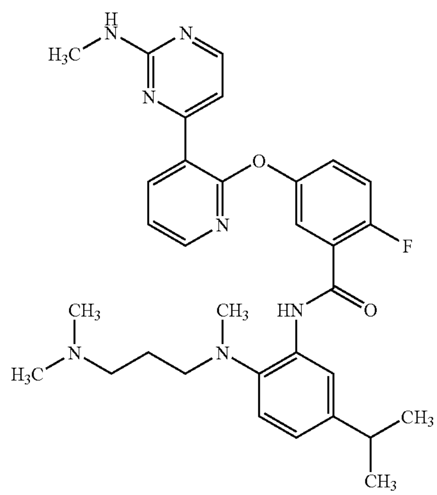 | 571.7 | 572 |
| 504 | 2-fluoro-5-((3-(4-(methylamino)-1,3,5-triazin-2-yl)-2-pyridinyl)oxy)-N-(3-(1-methylethyl)phenyl)benzamide | 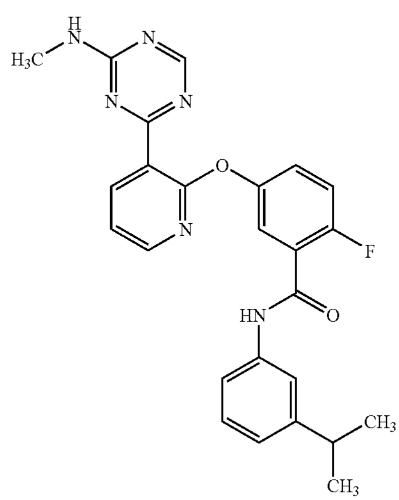 | 458.5 | 459 |

| Ex. No. | Structure Name | Structure | MW | MS Data |
|---|---|---|---|---|
| 505 | 2-fluoro-5-((3-(2-(methylamino)-4-pyrimidinyl)-2-pyridinyl)oxy)-N-(3-(1-methylethyl)phenyl) benzamide | 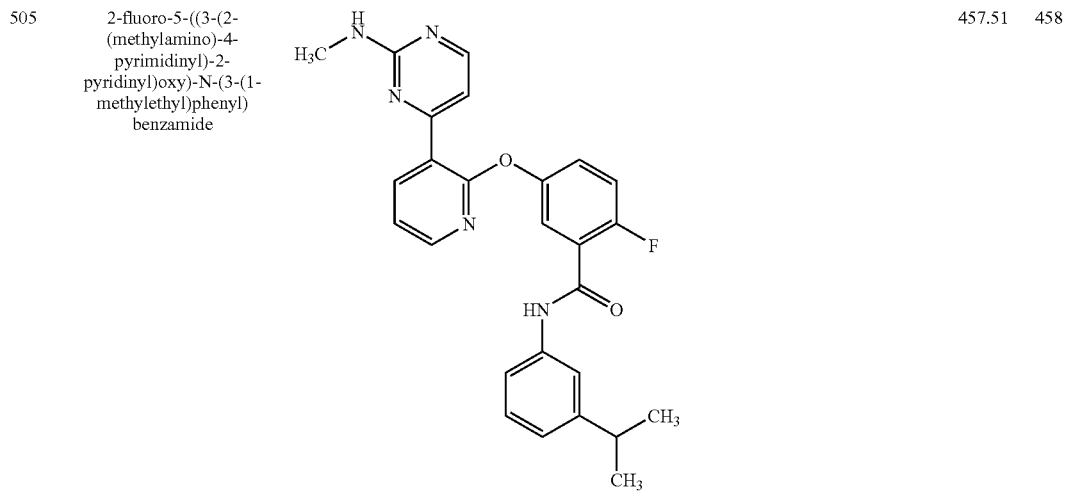 | 457.51 | 458 |
| 506 | N-(2-((3-(dimethylamino)propyl) (methyl)amino)-5-(trifluoromethyl)phenyl)-3-fluoro-5-((3-(4-(methylamino)-1,3,5-triazin-2-yl)-2-pyridinyl)oxy)benzamide | 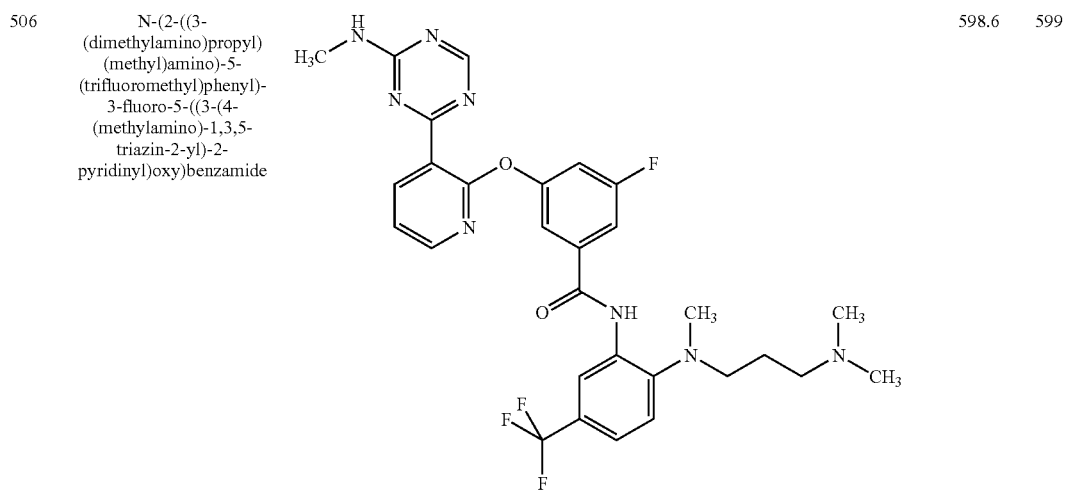 | 598.6 | 599 |

| Ex. No. | Structure Name | Structure | MW | MS Data |
|---|---|---|---|---|
| 507 | 3-fluoro-5-((3-(4-(methylamino)-1,3,5-triazin-2-yl)-2-pyridinyl)oxy)-N-(2-(methyl(1-methyl-3-pyrrolidinyl)amino)-5-(trifluoromethyl)phenyl benzamide | | 596.59 | 597 |
| 508 | 2-fluoro-5-((3-(2-(methylamino)-4-pyrimidinyl)-2-pyridinyl)oxy)-N-(2-(methyl((3R)-1-methyl-3-pyrrolidinyl)amino)-5-(trifluoromethyl)phenyl)benzamide | 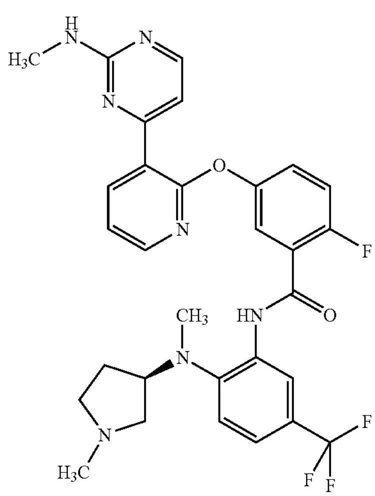 | 595.6 | 596 |

| Ex. No. | Structure Name | Structure | MW | MS Data |
|---|---|---|---|---|
| 509 | 2-fluoro-5-((3-(2-(methylamino)-4-pyrimidinyl)-2-pyridinyl)oxy)-N-(2-(methyl(1-methyl-3-pyrrolidinyl)amino)-5-(trifluoromethyl)phenyl)benzamide | 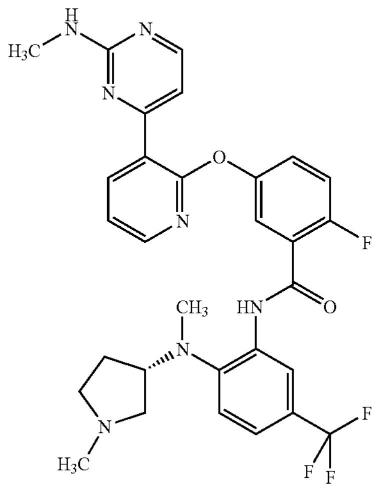 | 595.6 | 596 |
| 510 | N-(2-((3-(dimethylamino)propyl)methyl)amino)-5-(1,1-dimethylethyl)phenyl)-2-fluoro-5-((3-(4-(methylamino)-1,3,5-triazin-2-yl)-2-pyridinyl)oxy)benzamide | 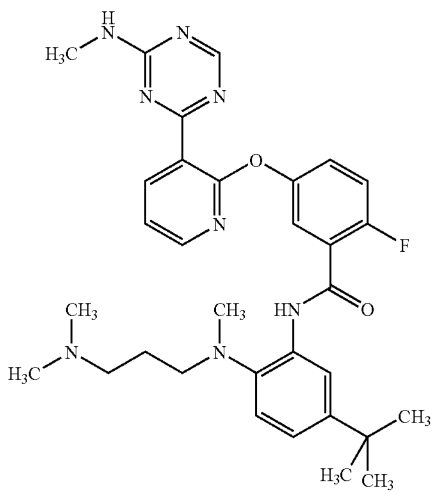 | 586.71 | 587 |
| 511 | N-(2-(2-(dimethylamino)-1,1-dimethylethyl)-5-(trifluoromethyl)phenyl)-2-fluoro-5-((3-(2-(methylamino)-4-pyrimidinyl)-2-pyridinyl)oxy)benzamide | 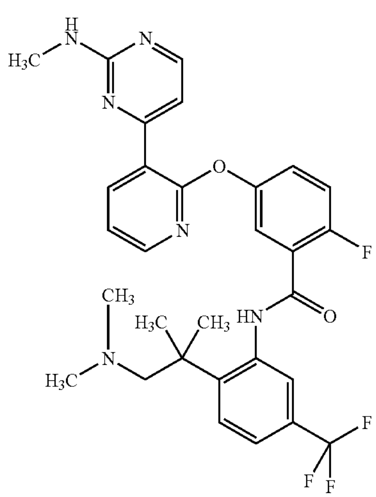 | 582.6 | 583 |

| Ex. No. | Structure Name | Structure | MW | MS Data |
|---|---|---|---|---|
| 512 | 2-fluoro-5-((2'-(methylamino)-3,4'-bipyridin-2-yl)oxy)-N-(2-(methyl(1-methyl-3-pyrrolidinyl)amino)-5-(trifluoromethyl)phenyl)benzamide | 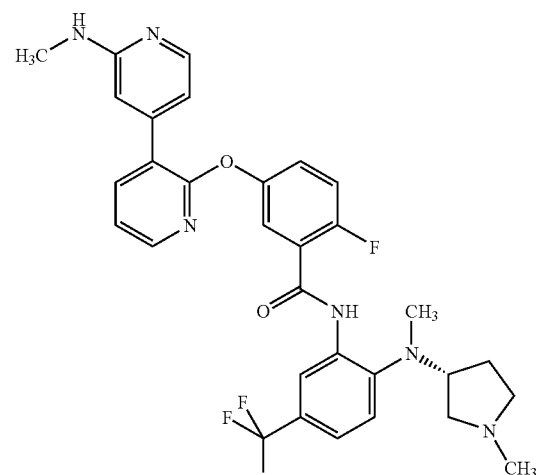 | 594.61 | 595 |
| 513 | N-(2-((3-(dimethylamino)propyl)(methyl)amino)-5-(1,1-dimethylethyl)phenyl)-2-fluoro-5-((3-(2-(methylamino)-4-pyrimidinyl)-2-pyridinyl)oxy)benzamide | 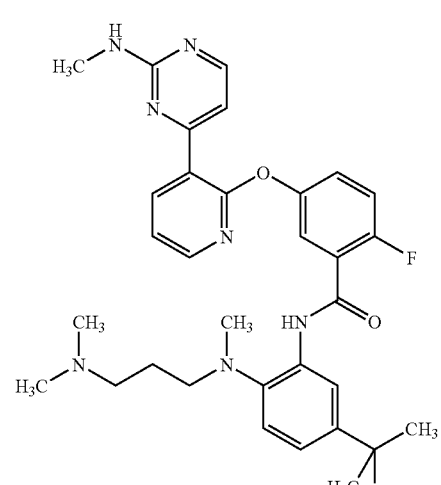 | 585.72 | 586 |

-continued

| Ex. No. | Structure Name | Structure | MW | MS Data |
|---|---|---|---|---|
| 514 | N-phenyl-4-((3-(4-pyrimidinyl)-2-pyridinyl)oxy)benzamide | 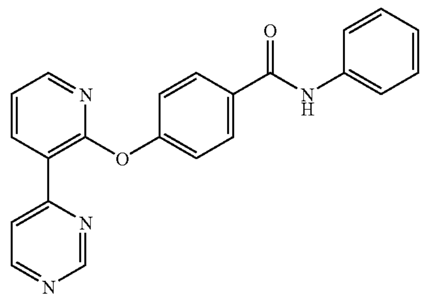 | 368.39 | 369 |
| 515 | N-(2-((3R)-3-(dimethylamino)-1-pyrrolidinyl)-5-(trifluoromethyl)phenyl)-2-fluoro-5-((2'-(methylamino)-3,4'-bipyridin-2-yl)oxy)benzamide | 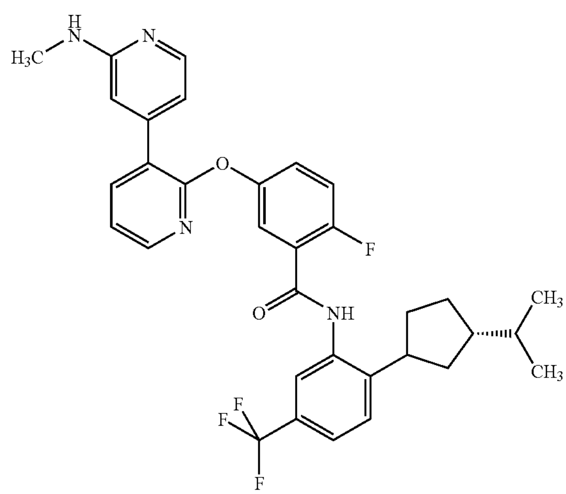 | 594.61 | 595 |
| 516 | N-(2-fluorophenyl)-4-((3-(4-pyrimidinyl)-2-pyridinyl)oxy)benzamide | 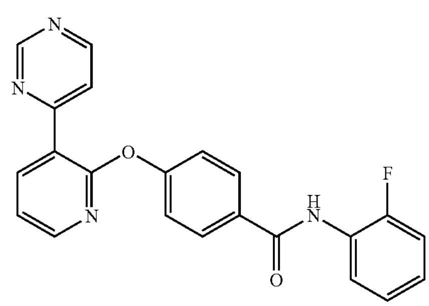 | 386.38 | 387 |
| 517 | N-(3-fluoro-2-(methyloxy)phenyl)-4-((3-(4-pyrimidinyl)-2-pyridinyl)oxy)benzamide | 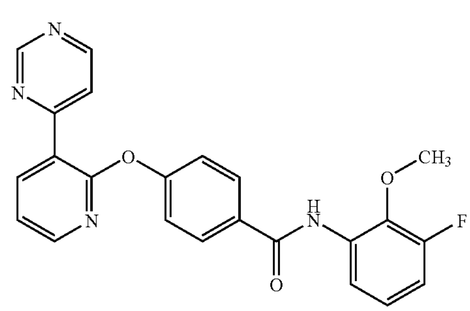 | 416.41 | 417 |

| Ex. No. | Structure Name | Structure | MW | MS Data |
|---|---|---|---|---|
| 518 | N-(2-((3-(dimethylamino)propyl)(methyl)amino)-5-ethynylphenyl)-2-fluoro-5-((3-(2-(methylamino)-4-pyrimidinyl)-2-pyridinyl)oxy)benzamide | 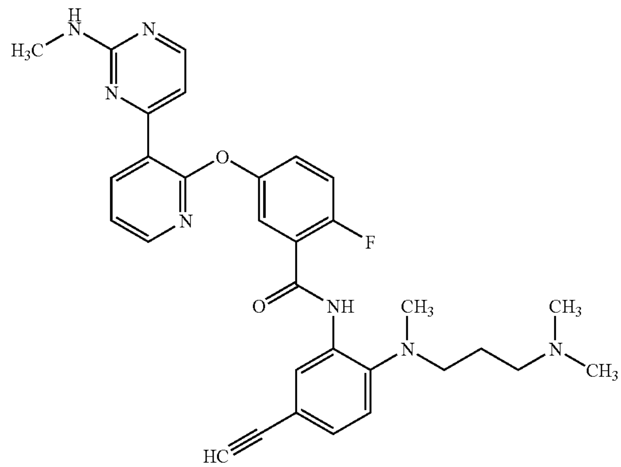 | 553.64 | 554 |
| 519 | N-(2-((3-(dimethylamino)propyl)(methyl)amino)-5-ethynylphenyl)-2-fluoro-5-((3-(4-(methylamino)-1,3,5-triazin-2-yl)-2-pyridinyl)oxy)benzamide | 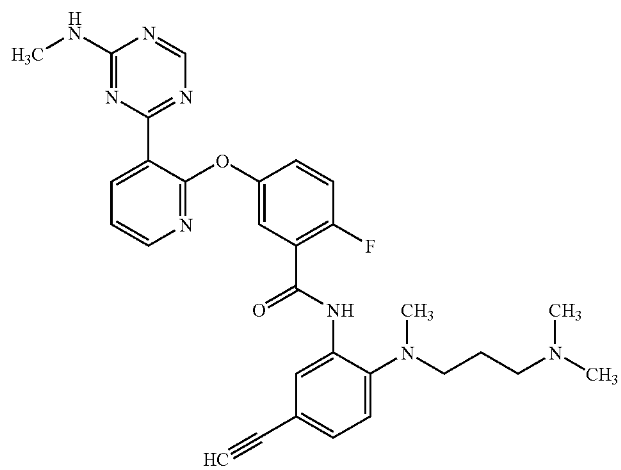 | 554.63 | 555 |
| 520 | N-(2-((3-(dimethylamino)propyl)(methyl)amino)-5-(pentafluoroethyl)phenyl)-2-fluoro-5-((3-(2-(methylamino)-4-pyrimidinyl)-2-pyridinyl)oxy)benzamide | 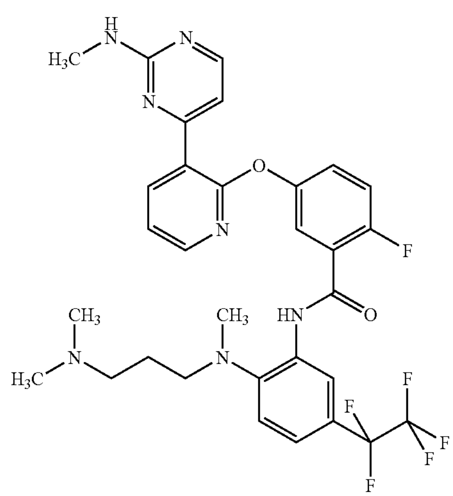 | 647.62 | 648 |

-continued

| Ex. No. | Structure Name | Structure | MW | MS Data |
|---|---|---|---|---|
| 521 | N-(2-((3-(dimethylamino)propyl)(methyl)amino)-5-(pentafluoroethyl)phenyl)-2-fluoro-5-((3-(4-(methylamino)-1,3,5-triazin-2-yl)-2-pyridinyl)oxy)benzamide | 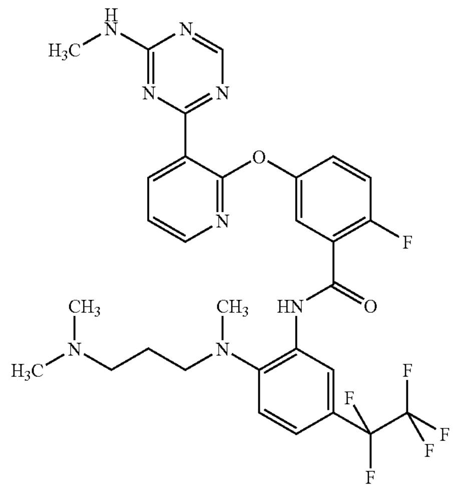 | 648.61 | 649 |
| 522 | N-(2-((3-(dimethylamino)propyl)(methyl)amino)-5-(trifluoromethyl)phenyl)-2-fluoro-5-((2'-(methylamino)-3,4-bipyridin-2-yl)oxy)benzamide | 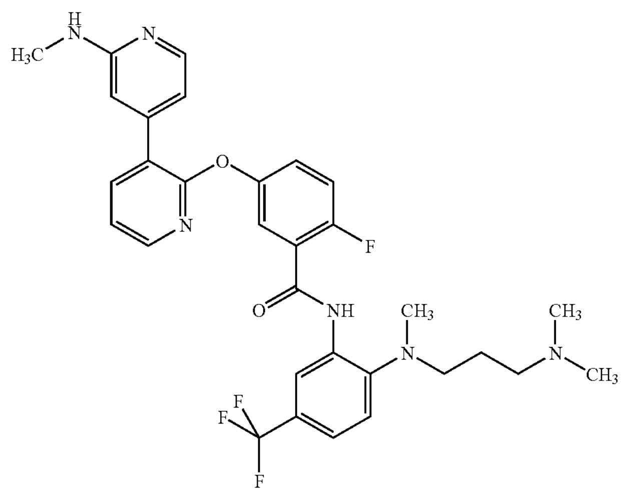 | 596.63 | 597 |
| 523 | N-(2-((3-(dimethylamino)propyl)(methyl)amino)-5-(1,1-dimethylethyl)phenyl)-2-fluoro-5-((2'-(methylamino)-3,4'-bipyridin-2-yl)oxy)benzamide | 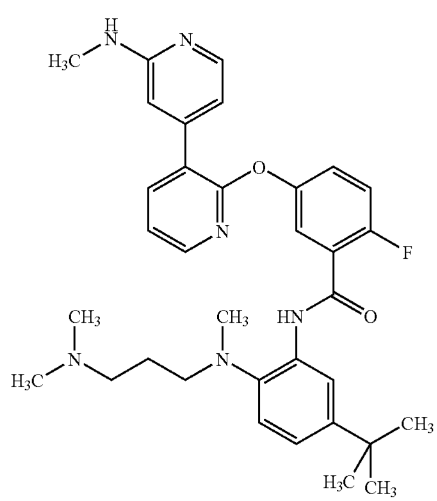 | 584.74 | 585 |

| Ex. No. | Structure Name | Structure | MW | MS Data |
|---|---|---|---|---|
| 524 | N-(5-bromo-2-((3-(dimethylamino)propyl)(methyl)amino)phenyl)-2-fluoro-5-((3-(2-(methylamino)-4-pyrimidinyl)-2-pyridinyl)oxy)benzamide | 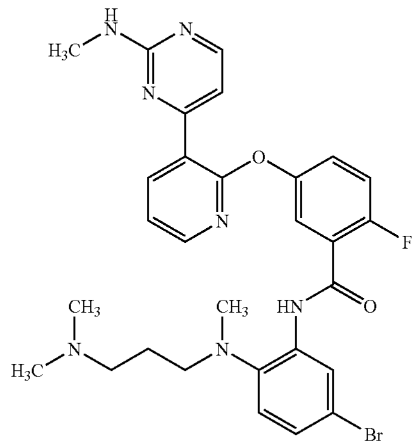 | 608.51 | 610 |
| 525 | N-(3-chloro-2-((3-(dimethylamino)propyl)(methyl)amino)-5-(trifluoromethyl)phenyl)-2-fluoro-5-((3-(2-(methylamino)-4-pyrimidinyl)-2-pyridinyl)oxy)benzamide | 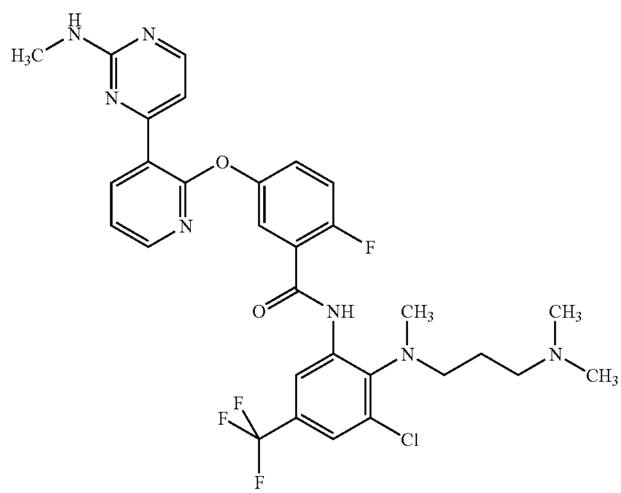 | 632.06 | 632 |
| 526 | N-(3-chloro-2-((3-(dimethylamino)propyl)(methyl)amino)-5-(trifluoromethyl)phenyl)-2-fluoro-5-((3-(4-(methylamino)-1,3,5-triazin-2-yl)-2-pyridinyl)oxy)benzamide | 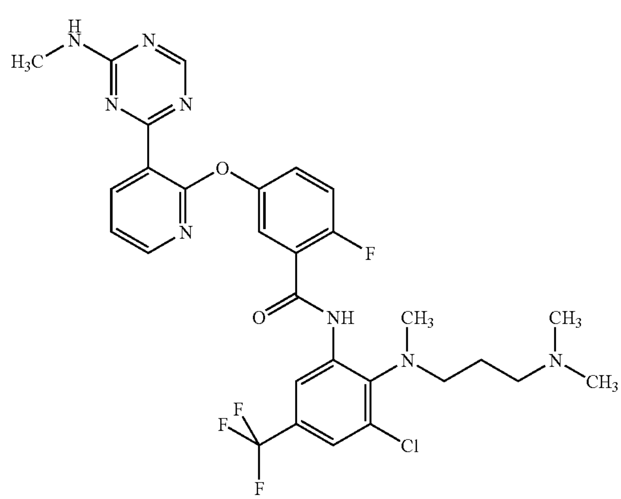 | 633.05 | 633 |

| Ex. No. | Structure Name | Structure | MW | MS Data |
|---|---|---|---|---|
| 527 | N-(5-chloro-2-((3-(dimethylamino)propyl)(methyl)amino)phenyl)-2-fluoro-5-((3-(2-(methylamino)-4-pyrimidinyl)-2-pyridinyl)oxy)benzamide | 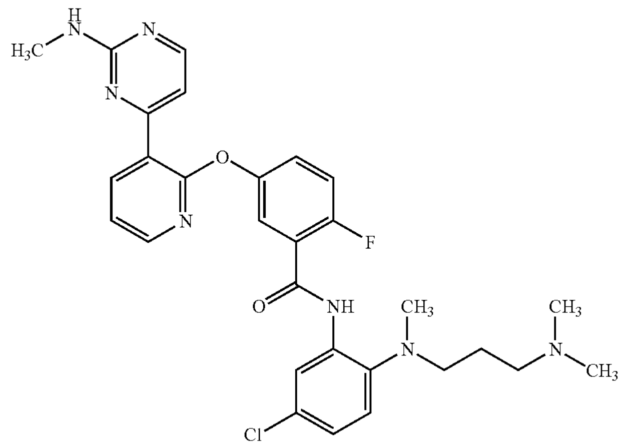 | 564.06 | 564 |
| 528 | 2-fluoro-5-((3-(4-(methylamino)-1,3,5-triazin-2-yl)-2-pyridinyl)oxy)-N-(3-(1-methyl-4-piperidinyl)-5-(trifluoromethyl)phenyl)benzamide | 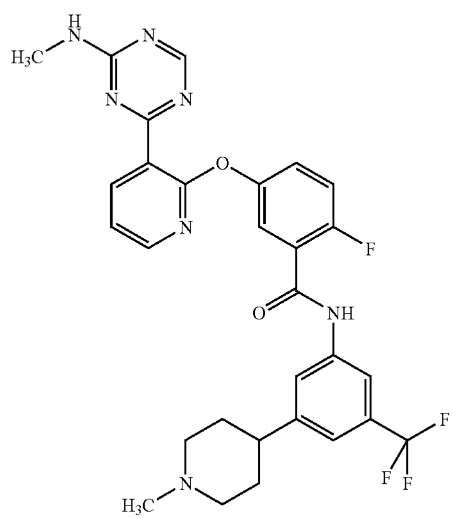 | 581.57 | 582 |
| 529 | N-(5-bromo-2-((3-(dimethylamino)propyl)(methyl)amino)phenyl)-2-fluoro-5-((3-(4-(methylamino)-1,3,5-triazin-2-yl)-2-pyridinyl)oxy)benzamide | 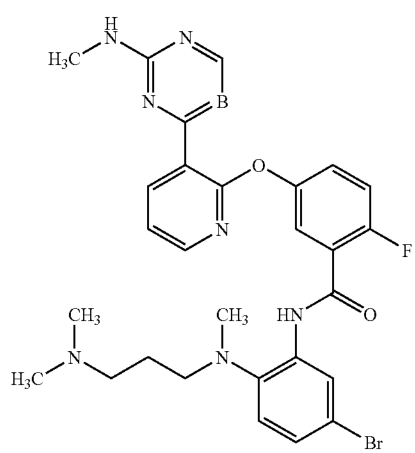 | 609.5 | 609 |

| Ex. No. | Structure Name | Structure | MW | MS Data |
|---|---|---|---|---|
| 530 | N-(5-cyclopropyl-2-((3-(dimethylamino)propyl)(methyl)amino)phenyl)-2-fluoro-5-((3-(2-(methylamino)-4-pyrimidinyl)-2-pyridinyl)oxy)benzamide | 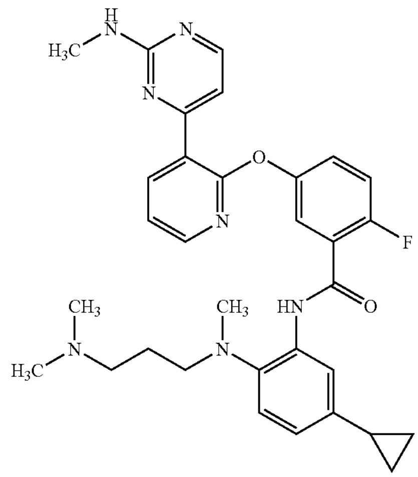 | 569.68 | 570 |
| 531 | N-(5-cyclopropyl-2-((3-(dimethylamino)propyl)(methyl)amino)phenyl)-2-fluoro-5-((3-(4-(methylamino)-1,3,5-triazin-2-yl)-2-pyridinyl)oxy)benzamide | 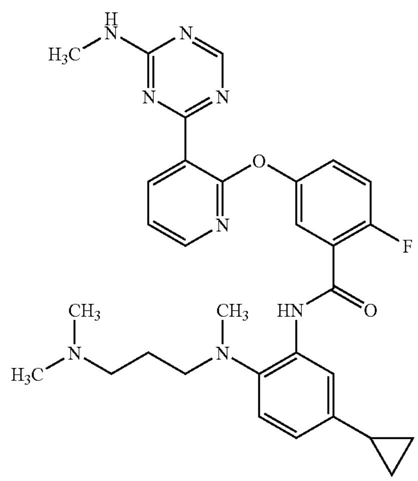 | 570.67 | 571 |
| 532 | N-(5-chloro-2-((3-(dimethylamino)propyl)(methyl)amino)phenyl)-2-fluoro-5-((3-(4-(methylamino)-1,3,5-triazin-2-yl)-2-pyridinyl)oxy)benzamide | 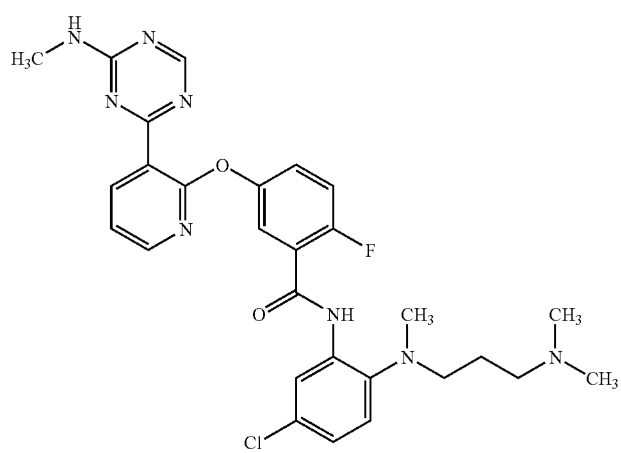 | 565.05 | 565 |

-continued

| Ex. No. | Structure Name | Structure | MW | MS Data |
|---|---|---|---|---|
| 533 | N-(5-chloro-2-(methyl(1-methyl-3-pyrrolidinyl)amino)phenyl)-2-fluoro-5-((3-(2-(methylamino)-4-pyrimidinyl)-2-pyridinyl)oxy)benzamide | | 562.04 | 562 |
| 534 | N-(2-((dimethylamino)methyl)-5-(trifluoromethyl)phenyl)-2-fluoro-5-((3-(2-(methylamino)-4-pyrimidinyl)-2-pyridinyl)oxy)benzamide | 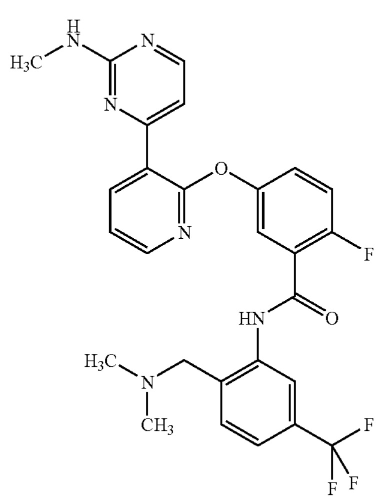 | 540.52 | 541 |

-continued

| Ex. No. | Structure Name | Structure | MW | MS Data |
|---|---|---|---|---|
| 535 | N-(2-((dimethylamino)methyl)-5-(trifluoromethyl)phenyl)-2-fluoro-5-((3-(4-(methylamino)-1,3,5-triazin-2-yl)-2-pyridinyl)oxy)benzamide | 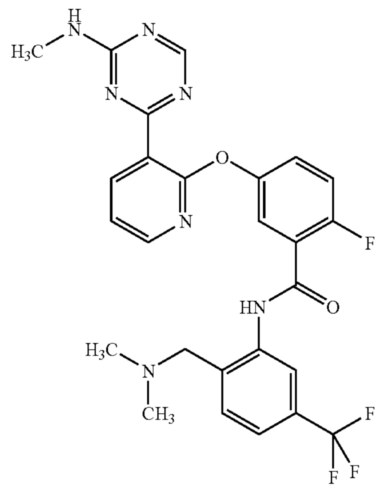 | 541.51 | 542 |
| 536 | 2-fluoro-5-((3-(2-(methylamino)-4-pyrimidinyl)-2-pyridinyl)oxy)-N-(3-((4-methyl-1-piperazinyl)methyl)-5-(trifluoromethyl)phenyl)benzamide | 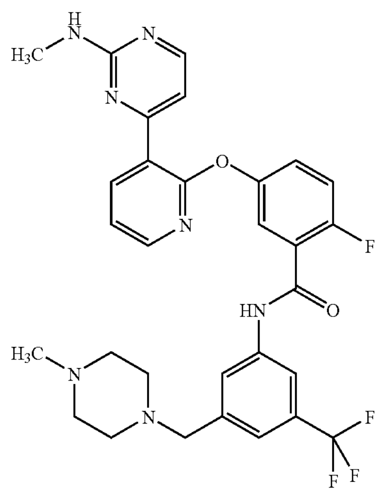 | 595.6 | 596 |
| 537 | N-(3-((1,1-dioxido-4-thiomorpholinyl)carbonyl)-5-(trifluoromethyl)phenyl)-2-fluoro-5-((3-(2-(methylamino)-4-pyrimidinyl)-2-pyridinyl)oxy)benzamide | 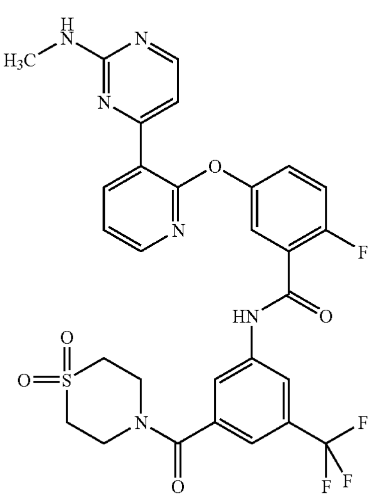 | 644.6 | 645 |

| Ex. No. | Structure Name | Structure | MW | MS Data |
|---|---|---|---|---|
| 538 | 2-fluoro-5-((3-(2-(methylamino)-4-pyrimidinyl)-2-pyridinyl)oxy)-N-(2-(1H-1,2,4-triazol-1-yl)-5-(trifluoromethyl)phenyl)benzamide | 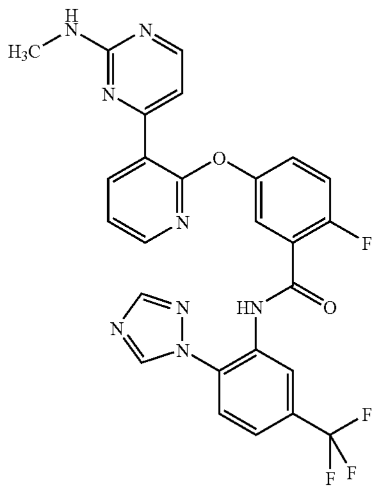 | 550.47 | 551 |
| 539 | 4-methyl-3-((3-(2-(methylamino)-4-pyrimidinyl)-2-pyridinyl)oxy)-N-(3-((4-methyl-1-piperazinyl)methyl)-5-(trifluoromethyl)phenyl)benzamide | 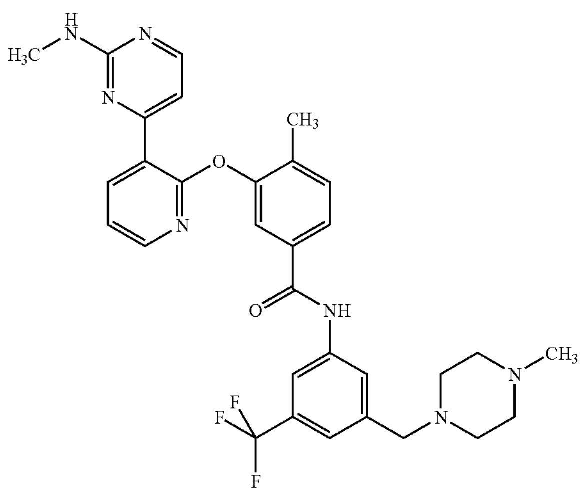 | 591.63 | 592 |
| 540 | 2-fluoro-N-(2-((2-imino-1,3-oxazolidin-3-yl)methyl)-5-(trifluoromethyl)phenyl)-5-((3-(2-(methylamino)-4-pyrimidinyl)-2-pyridinyl)oxy)benzamide | 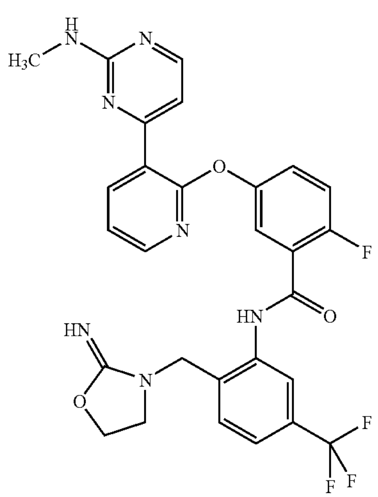 | 581.53 | 582 |

| Ex. No. | Structure Name | Structure | MW | MS Data |
|---|---|---|---|---|
| 541 | 2-fluoro-N-(2-((2-imino-1,3-oxazolidin-3-yl)methyl)-5-(trifluoromethyl)phenyl)-5-((3-(4-(methylamino)-1,3,5-triazin-2-yl)-2-pyridinyl)oxy)benzamide | 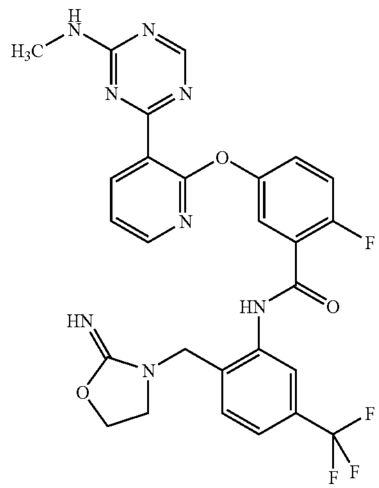 | 582.52 | 583 |
| 542 | N-(3-bromophenyl)-2-(4-((3-(2-(methylamino)-4-pyrimidinyl)-2-pyridinyl)oxy)phenyl)acetamide | 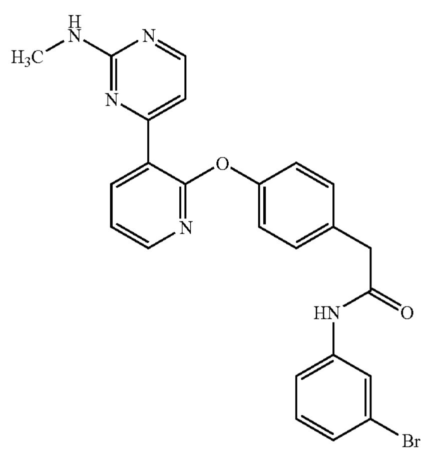 | 490.36 | 490 |
| 543 | N-(3-fluorophenyl)-2-(4-((3-(2-(methylamino)-4-pyrimidinyl)-2-pyridinyl)oxy)phenyl)acetamide | 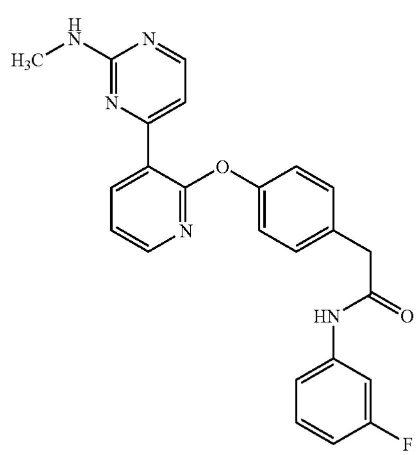 | 429.45 | 430 |

-continued

| Ex. No. | Structure Name | Structure | MW | MS Data |
|---|---|---|---|---|
| 544 | N-(3-fluoro-5-(trifluoromethyl)phenyl)-2-(4-((3-(2-(methylamino)-4-pyrimidinyl)-2-pyridinyl)oxy)phenyl)acetamide | 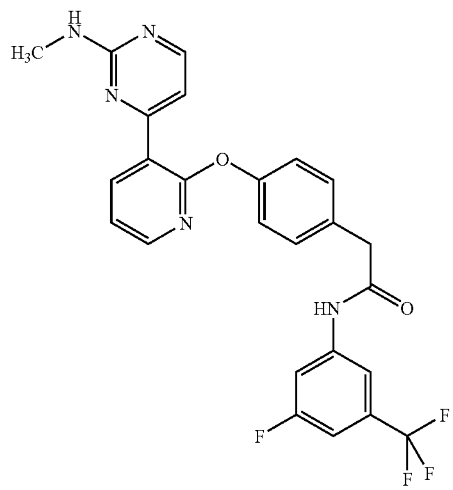 | 497.45 | 498 |
| 545 | 3-(((4-((3-(2-(methylamino)-4-pyrimidinyl)-2-pyridinyl)oxy)phenyl)acetyl)amino)benzamide | 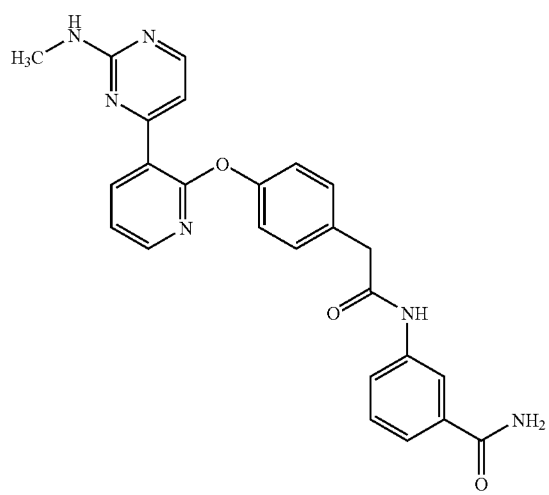 | 454.49 | 455 |
| 546 | 2-(4-((3-(2-(methylamino)-4-pyrimidinyl)-2-pyridinyl)oxy)phenyl)-N-(5-methyl-3-isoxazolyl)acetamide | 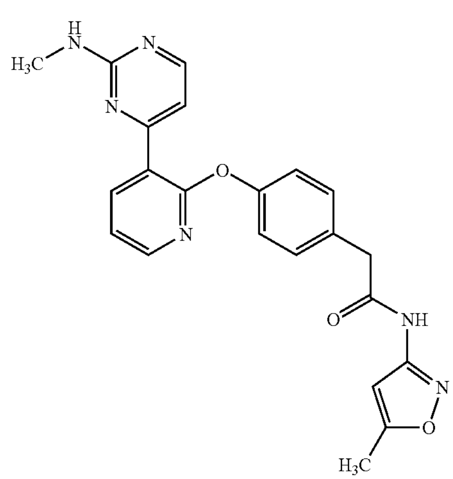 | 416.44 | 417 |

-continued

| Ex. No. | Structure Name | Structure | MW | MS Data |
|---|---|---|---|---|
| 547 | N-(3-isoxazolyl)-2-(4-((3-(2-(methylamino)-4-pyrimidinyl)-2-pyridinyl)oxy)phenyl)acetamide | 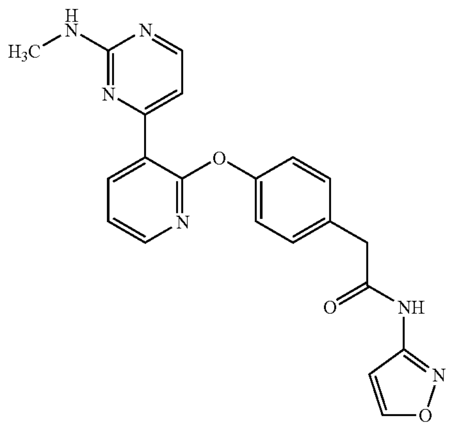 | 402.41 | 403 |
| 548 | 2-(4-((3-(2-(methylamino)-4-pyrimidinyl)-2-pyridinyl)oxy)phenyl)-N-(5-methyl-1H-pyrazol-3-yl)acetamide | 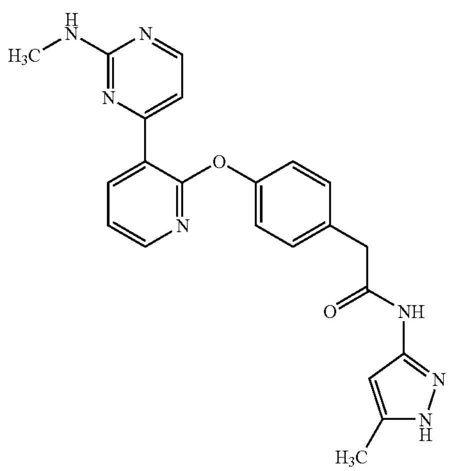 | 415.45 | 416 |
| 549 | 2-(4-((3-(2-(methylamino)-4-pyrimidinyl)-2-pyridinyl)oxy)phenyl)-N-(3-pyridinyl)acetamide | 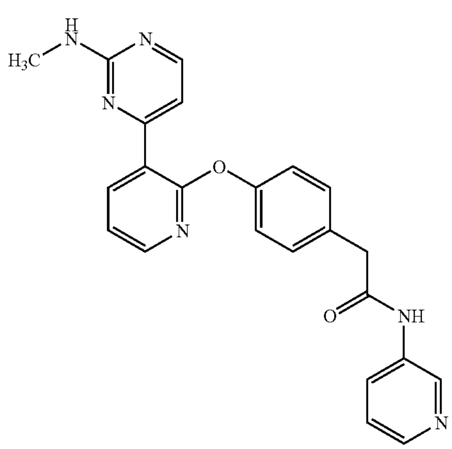 | 412.45 | 413 |

-continued

| Ex. No. | Structure Name | Structure | MW | MS Data |
|---|---|---|---|---|
| 550 | 2-(4-((3-(2-(methylamino)-4-pyrimidinyl)-2-pyridinyl)oxy)phenyl)-N-(4-pyridinyl)acetamide | 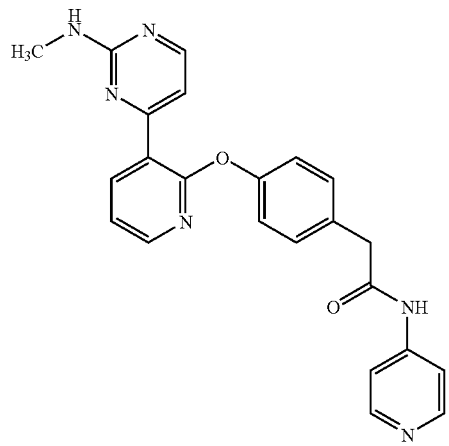 | 412.45 | 413 |
| 551 | N-methyl-3-(((4-((3-(2-(methylamino)-4-pyrimidinyl)-2-pyridinyl)oxy)phenyl)acetyl)amino)benzamide | 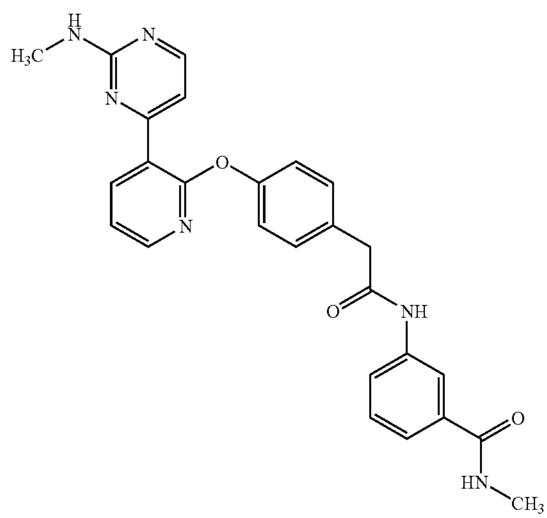 | 468.51 | 469 |
| 552 | N-(4-chlorophenyl)-2-(4-((3-(2-(methylamino)-4-pyrimidinyl)-2-pyridinyl)oxy)phenyl)acetamide | 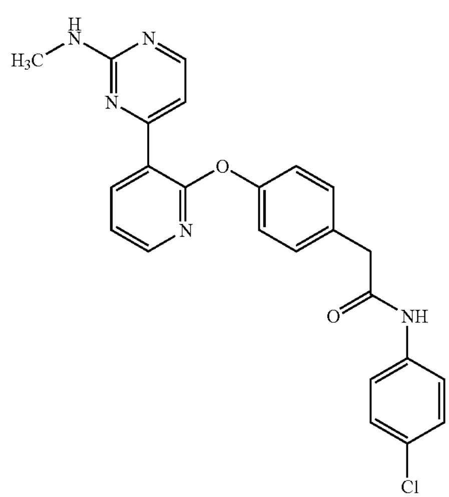 | 445.91 | 446 |

| Ex. No. | Structure Name | Structure | MW | MS Data |
|---|---|---|---|---|
| 553 | N-cyclopropyl-4-methyl-3-((3-(2-methylamino)-4-pyrimidinyl)-2-pyridinyl)oxy)benzamide | 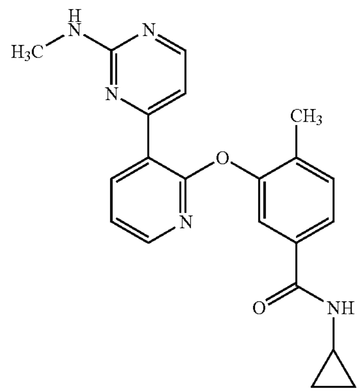 | 375.43 | 376 |
| 554 | N-(4-(1,1-dimethylethyl)phenyl)-3-((3-(4-pyrimidinyl)-2-pyridinyl)oxy)benzamide | 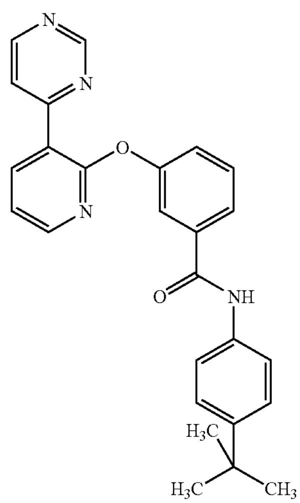 | 424.5 | 425 |
| 555 | N-(3-(1,1-dimethylethyl)-1-methyl-1H-pyrazol-5-yl)-3-((3-(4-pyrimidinyl)-2-pyridinyl)oxy)benzamide | 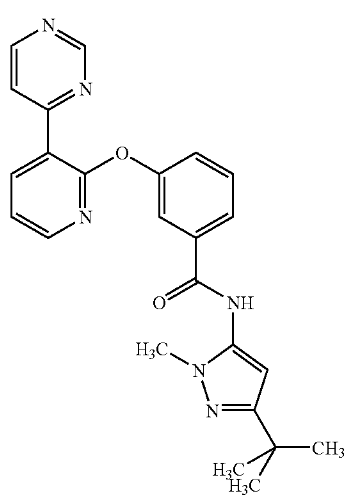 | 428.49 | 429 |

-continued

| Ex. No. | Structure Name | Structure | MW | MS Data |
|---|---|---|---|---|
| 556 | N-(5-(1,1-dimethylethyl)-3-isoxazolyl)-3-((3-(4-pyrimidinyl)-2-pyridinyl)oxy)benzamide | 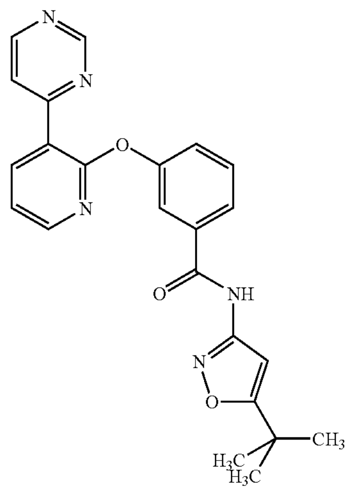 | 415.45 | 416 |
| 557 | 3-((3-(4-pyrimidinyl)-2-pyridinyl)oxy)-N-(4-(trifluoromethyl)phenyl)benzamide | 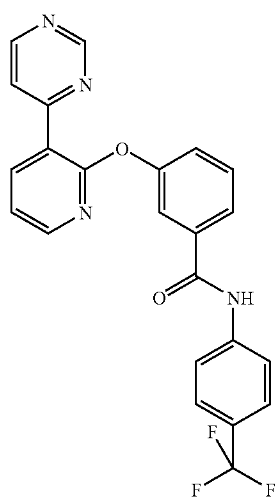 | 436.39 | 437 |
| 558 | N-(3-chlorophenyl)-3-((3-(4-pyrimidinyl)-2-pyridinyl)oxy)benzamide | 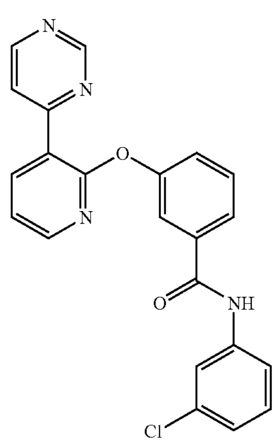 | 402.84 | 403 |

-continued

| Ex. No. | Structure Name | Structure | MW | MS Data |
|---|---|---|---|---|
| 559 | N-(2,3-dihydro-1H-inden-5-yl)-3-((3-(4-pyrimidinyl)-2-pyridinyl)oxy)benzamide | 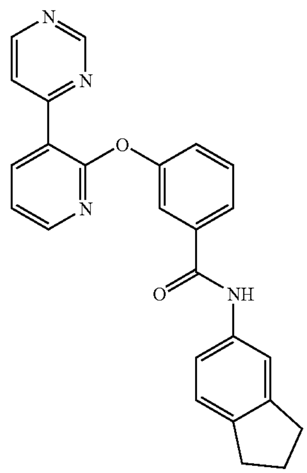 | 408.46 | 409 |
| 560 | 3-((3-(4-pyrimidinyl)-2-pyridinyl)oxy)-N-((3-(trifluoromethyl)phenyl(methyl)benzamide | 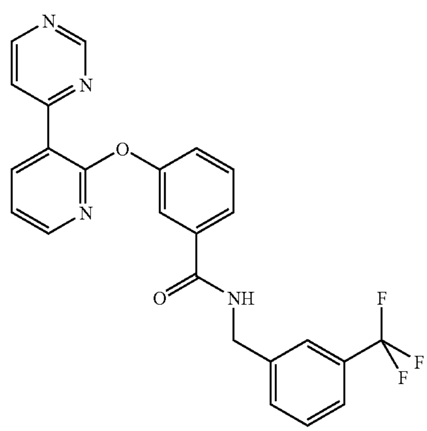 | 450.42 | 451 |
| 561 | N-(1H-indazol-5-yl)-3-((3-(4-pyrimidinyl)-2-pyridinyl)oxy)benzamide | 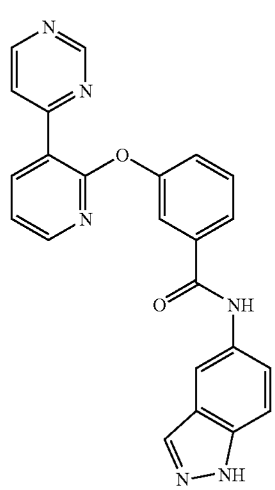 | 408.42 | 409 |

-continued

| Ex. No. | Structure Name | Structure | MW | MS Data |
|---|---|---|---|---|
| 562 | N-(1H-indazol-6-yl)-3-((3-(4-pyrimidinyl)-2-pyridinyl)oxy)benzamide | 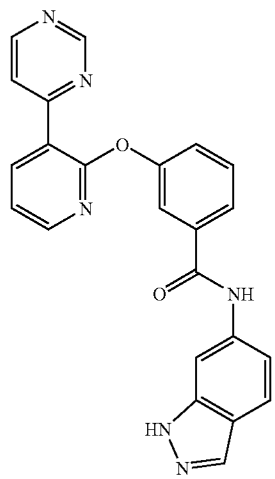 | 408.42 | 409 |
| 563 | 3-((3-(4-pyrimidinyl)-2-pyridinyl)oxy)-N-(3-(trifluoromethyl)phenyl)benzamide | 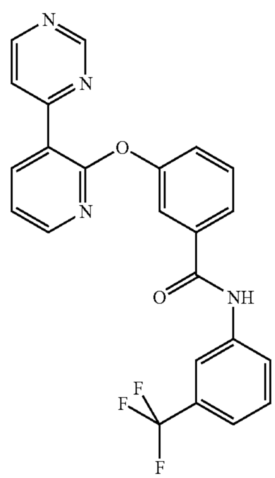 | 436.39 | 437 |
| 564 | N-(4-(1,1-dimethylethyl)phenyl)-4-methyl-3-((3-(4-pyrimidinyl)-2-pyridinyl)oxy)benzamide | 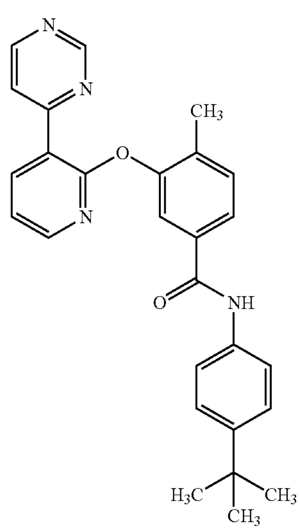 | 438.53 | 439 |

-continued

| Ex. No. | Structure Name | Structure | MW | MS Data |
|---|---|---|---|---|
| 565 | N-(3-(1,1-dimethylethyl)-1-methyl-1H-pyrazol-5-yl)-4-methyl-3-((3-(4-pyrimidinyl)-2-pyridinyl)oxy)benzamide | 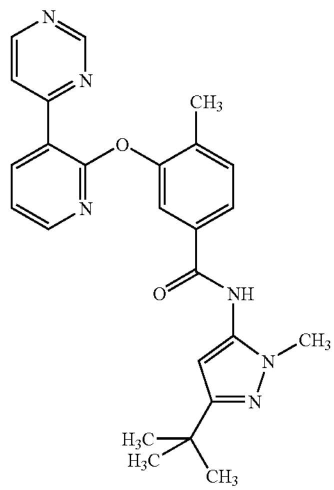 | 442.52 | 443 |
| 566 | 4-methyl-3-((3-(4-pyrimidinyl)-2-pyridinyl)oxy)-N-(4-(trifluoromethyl)phenyl)benzamide | 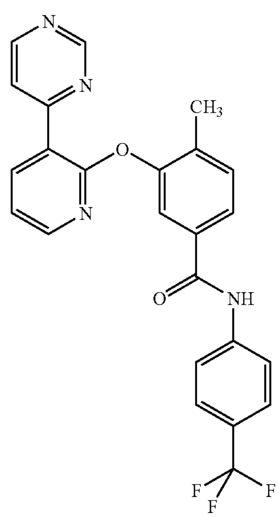 | 450.42 | 451 |
| 567 | N-(2,3-dihydro-1H-inden-5-yl)-4-methyl-3-((3-(4-pyrimidinyl)-2-pyridinyl)oxy)benzamide | 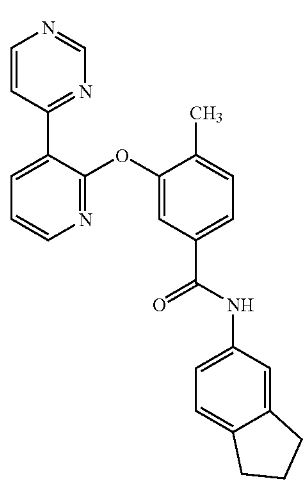 | 422.49 | 423 |

-continued

| Ex. No. | Structure Name | Structure | MW | MS Data |
|---|---|---|---|---|
| 568 | 4-methyl-3-((3-(4-pyrimidinyl)-2-pyridinyl)oxy)-N-((3-(trifluoromethyl)phenyl)methyl)benzamide | 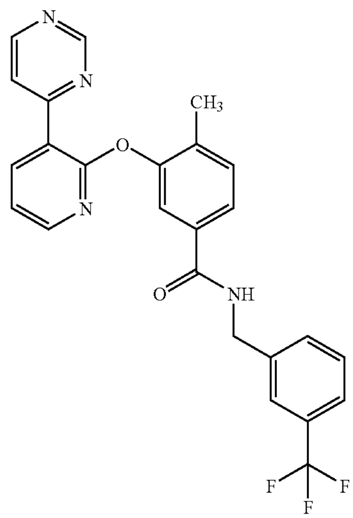 | 464.44 | 465 |
| 569 | N-(1H-indazol-5-yl)-4-methyl-3-((3-(4-pyrimidinyl)-2-pyridinyl)oxy)benzamide | 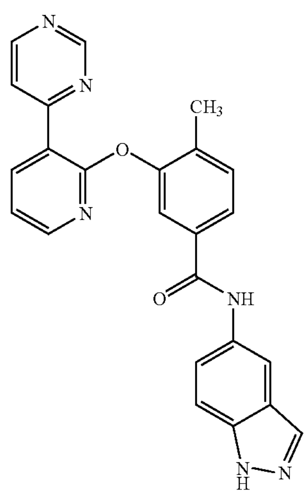 | 422.45 | 423 |
| 570 | N-(1H-indazol-6-yl)-4-methyl-3-((3-(4-pyrimidinyl)-2-pyridinyl)oxy)benzamide | 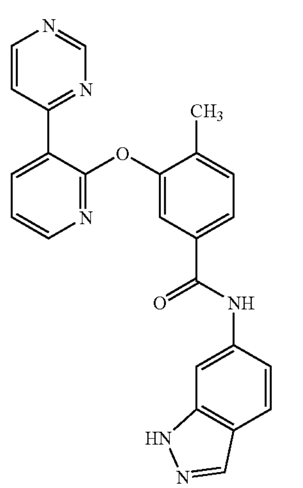 | 422.45 | 423 |

-continued

| Ex. No. | Structure Name | Structure | MW | MS Data |
|---|---|---|---|---|
| 571 | N-((1S)-1-cyclohexylethyl)-3-((3-(4-pyrimidinyl)-2-pyridinyl)oxy)benzamide | 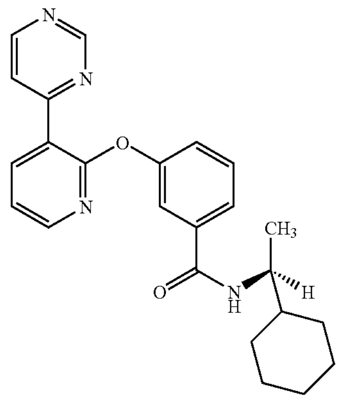 | 402.5 | 403 |
| 572 | N-(3-(dimethylamino)phenyl)-3-((3-(4-pyrimidinyl)-2-pyridinyl)oxy)benzamide | 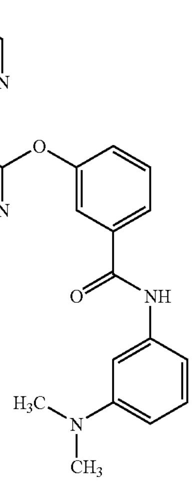 | 411.46 | 412 |
| 573 | N-(4-chloro-3-(trifluoromethyl)phenyl)-3-((3-(4-pyrimidinyl)-2-pyridinyl)oxy)benzamide | 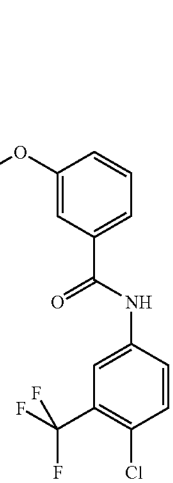 | 470.84 | 471 |

| Ex. No. | Structure Name | Structure | MW | MS Data |
|---|---|---|---|---|
| 574 | N-(3-amino-5-(trifluoromethyl)phenyl)-3-((3-(4-pyrimidinyl)-2-pyridinyl)oxy)benzamide | 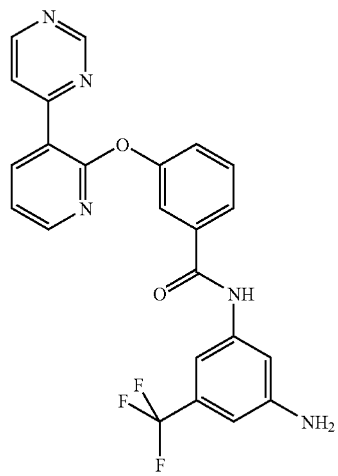 | 451.41 | 452 |
| 575 | 3-((3-(4-pyrimidinyl)-2-pyridinyl)oxy)-N-((2-(trifluoromethyl)phenyl)methyl)benzamide | 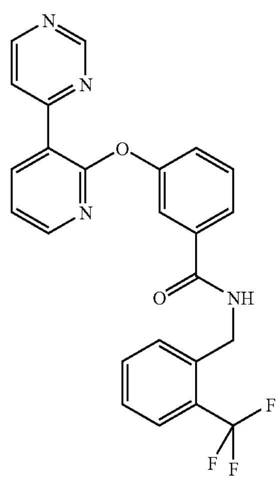 | 450.42 | 451 |
| 576 | N-(3-(hydroxymethyl)phenyl)-3-((3-(4-pyrimidinyl)-2-pyridinyl)oxy)benzamide | 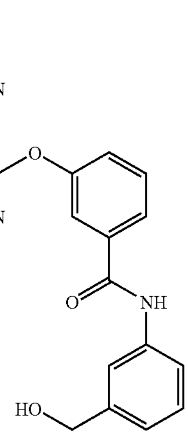 | 398.42 | 399 |

| Ex. No. | Structure Name | Structure | MW | MS Data |
|---|---|---|---|---|
| 577 | N-(3,4-dimethyphenyl)-3-((3-(4-pyrimidinyl)-2-pyridinyl)oxy)benzamide | 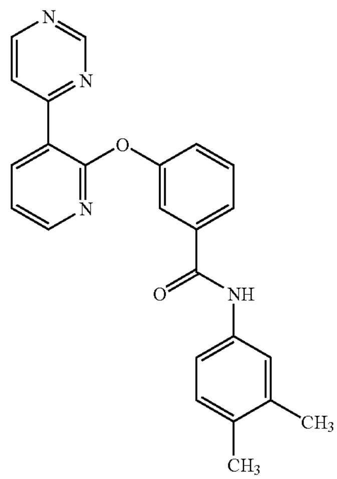 | 396.45 | 397 |
| 578 | 3-((3-(4-pyrimidinyl)-2-pyridinyl)oxy)-N-((4-(trifluoromethyl)phenyl)methyl)benzamide | 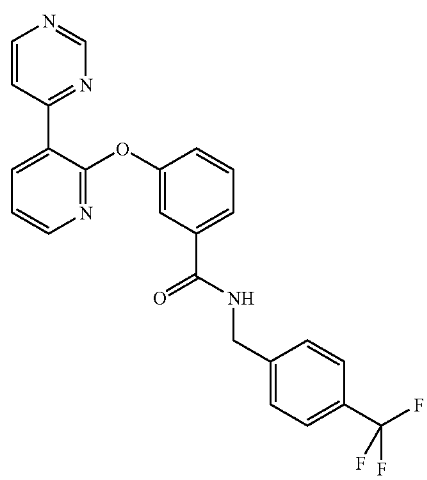 | 450.42 | 451 |
| 579 | N-(4-(aminocarbonyl)phenyl)-3-((3-(4-pyrimidinyl)-2-pyridinyl)oxy)benzamide | 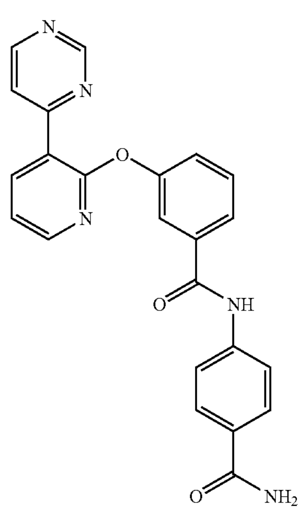 | 411.42 | 412 |

-continued

| Ex. No. | Structure Name | Structure | MW | MS Data |
|---|---|---|---|---|
| 580 | N-(3-(1,1-dimethylethyl)phenyl)-3-((3-(4-pyrimidinyl)-2-pyridinyl)oxy)benzamide | 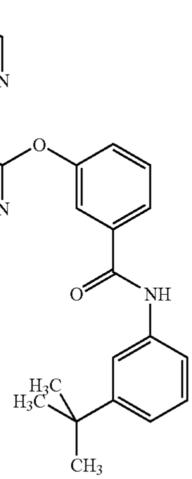 | 424.5 | 425 |
| 581 | N-(1-naphthalenyl)-3-((3-(4-pyrimidinyl)-2-pyridinyl)oxy)benzamide | 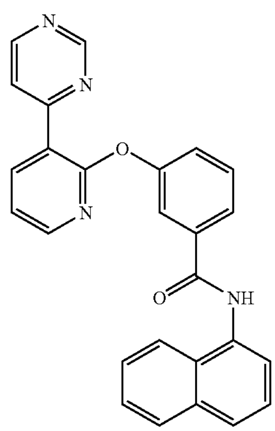 | 418.45 | 419 |
| 582 | N-phenyl-3-((3-(4-pyrimidinyl)-2-pyridinyl)oxy)benzamide | 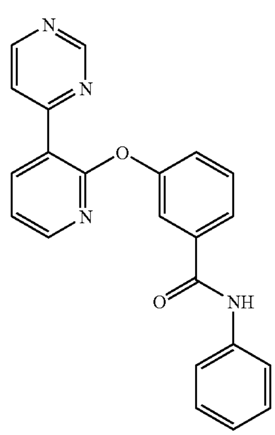 | 368.39 | 369 |

-continued

| Ex. No. | Structure Name | Structure | MW | MS Data |
|---|---|---|---|---|
| 583 | N-(3,3-dimethylbutyl)-3-((3-(4-pyrimidinyl)-2-pyridinyl)oxy)benzamide | 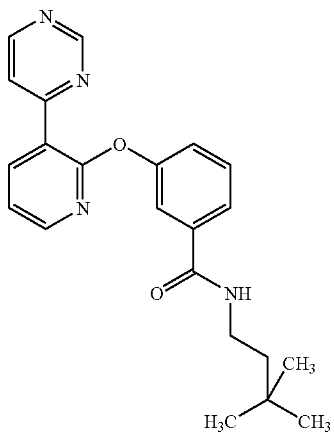 | 376.46 | 377 |
| 584 | N-(3-chlorophenyl)-4-methyl-3-((3-(4-pyrimidinyl)-2-pyridinyl)oxy)benzamide | 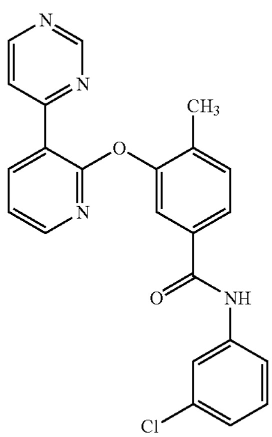 | 416.87 | 417 |
| 585 | N-(3-(dimethylamino)phenyl)-4-methyl-3-((3-(4-pyrimidinyl)-2-pyridinyl)oxy)benzamide | 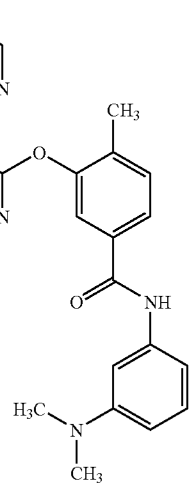 | 425.49 | 426 |

| Ex. No. | Structure Name | Structure | MW | MS Data |
|---|---|---|---|---|
| 586 | N-(4-chloro-3-(trifluoromethyl)phenyl)-4-methyl-3-((3-(4-pyrimidinyl)-2-pyridinyl)oxy)benzamide | 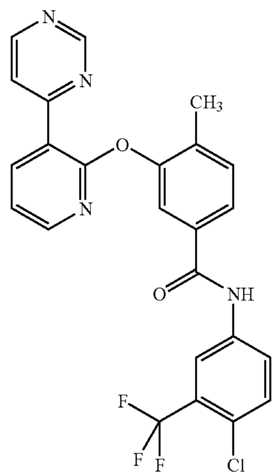 | 484.86 | 485 |
| 587 | N-((1S)-1-cyclohexylethyl)-4-methyl-3-((3-(4-pyrimidinyl)-2-pyridinyl)oxy)benzamide | 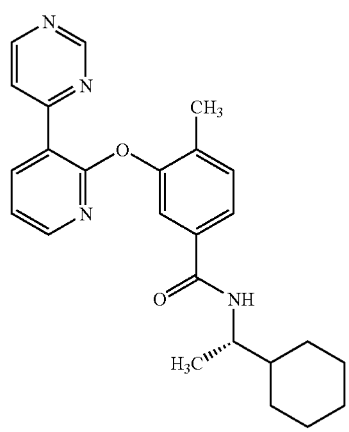 | 416.52 | 417 |
| 588 | 4-methyl-3-((3-(4-pyrimidinyl)-2-pyridinyl)oxy)-N-((2-(trifluoromethyl)phenyl)methyl)benzamide | 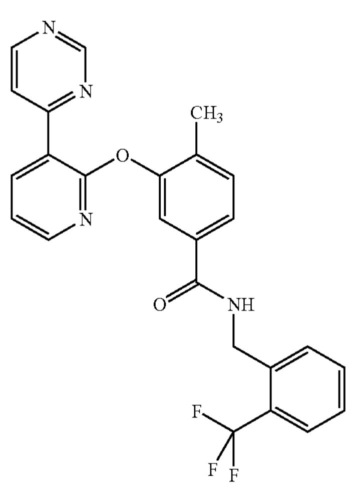 | 464.44 | 465 |

| Ex. No. | Structure Name | Structure | MW | MS Data |
|---|---|---|---|---|
| 589 | N-(3,5-dichlorophenyl)-3-((3-(4-pyrimidinyl)-2-pyridinyl)oxy)benzamide | 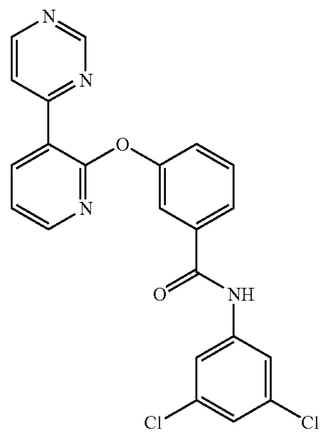 | 437.29 | 437 |
| 590 | N-(2-fluoro-5-(trifluoromethyl)phenyl)-3-((3-(4-pyrimidinyl)-2-pyridinyl)oxy)benzamide | 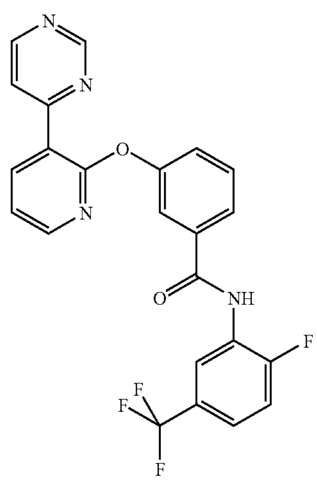 | 454.38 | 455 |
| 591 | N-(2-methyl-5-(trifluoromethyl)phenyl)-3-((3-(4-pyrimidinyl)-2-pyridinyl)oxy)benzamide | 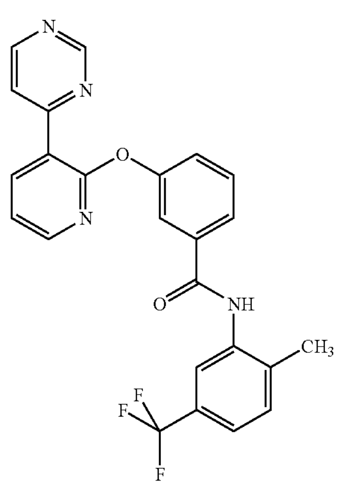 | 450.42 | 451 |

| Ex. No. | Structure Name | Structure | MW | MS Data |
|---|---|---|---|---|
| 592 | N-(3,5-dimethylphenyl)-3-((3-(4-pyrimidinyl)-2-pyridinyl)oxy)benzamide | 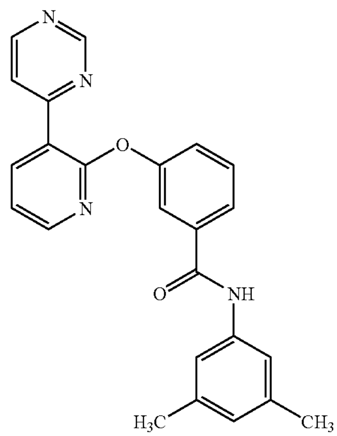 | 396.45 | 397 |
| 593 | N-(3-(1-methylethyl)phenyl)-3-((3-(4-pyrimidinyl)-2-pyridinyl)oxy)benzamide | 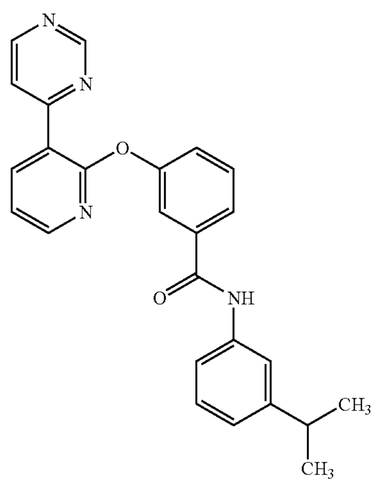 | 410.48 | 411 |
| 594 | N-(4-fluoro-3-(trifluoromethyl)phenyl)-3-((3-(4-pyrimidinyl)-2-pyridinyl)oxy)benzamide | 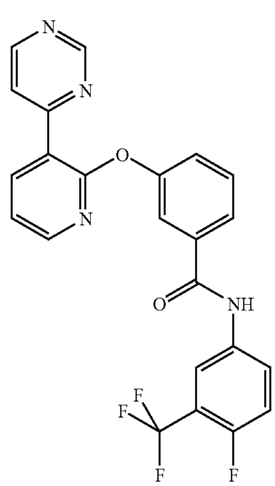 | 454.38 | 455 |

| Ex. No. | Structure Name | Structure | MW | MS Data |
|---|---|---|---|---|
| 595 | N-(3-chloro-4-fluorophenyl)-3-((3-(4-pyrimidinyl)-2-pyridinyl)oxy)benzamide | 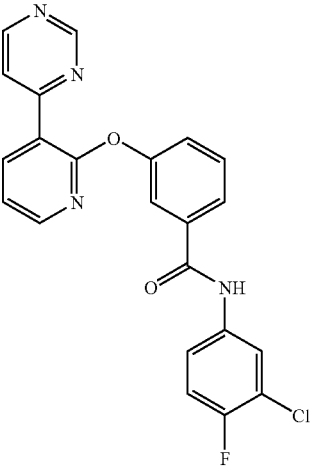 | 420.83 | 421 |
| 596 | N-(4-(methyloxy)-3-(trifluoromethyl)phenyl)-3-((3-(4-pyrimidinyl)-2-pyridinyl)oxy)benzamide | 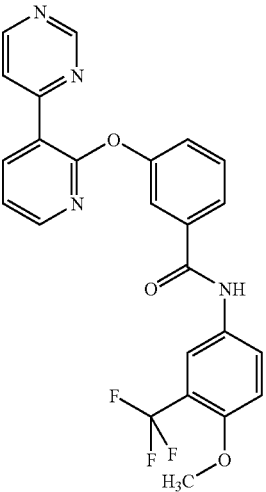 | 466.42 | 467 |
| 597 | N-(3-(ethyloxy)phenyl)-3-((3-(4-pyrimidinyl)-2-pyridinyl)oxy)benzamide | 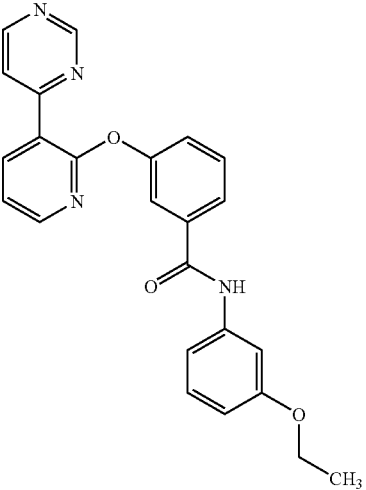 | 412.45 | 413 |

-continued

| Ex. No. | Structure Name | Structure | MW | MS Data |
|---|---|---|---|---|
| 598 | N-(2,3-dihydro-1H-inden-4-yl)-3-((3-(4-pyrimidinyl)-2-pyridinyl)oxy)benzamide | 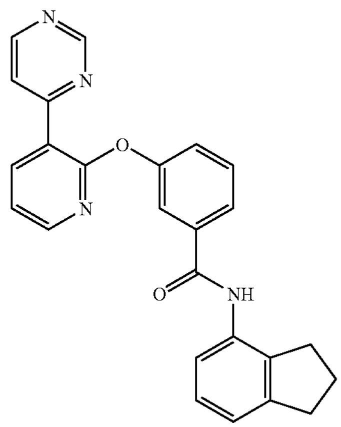 | 408.46 | 409 |
| 599 | N-(3-((1-methylethyl)oxy)phenyl)-3-((3-(4-pyrimidinyl)-2-pyridinyl)oxy)benzamide | 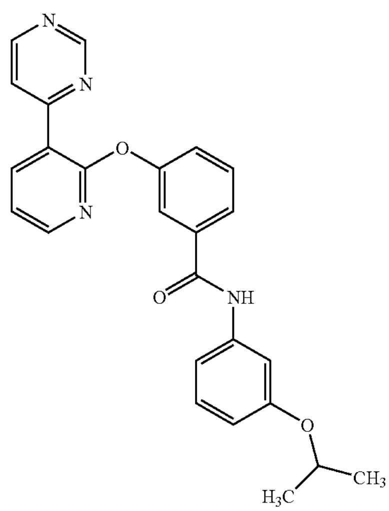 | 426.47 | 427 |
| 600 | N-(4-nitro-3-(trifluoromethyl)phenyl)-3-((3-(4-pyrimidinyl)-2-pyridinyl)oxy)benzamide | 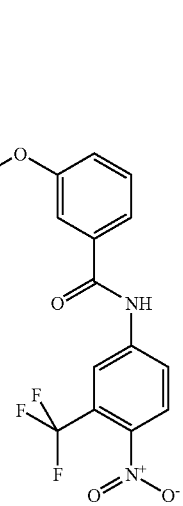 | 481.39 | 482 |

-continued

| Ex. No. | Structure Name | Structure | MW | MS Data |
|---|---|---|---|---|
| 601 | N-(3-(methyloxy)-5-(trifluoromethyl)phenyl)-3-((3-(4-pyrimidinyl)-2-pyridinyl)oxy)benzamide | 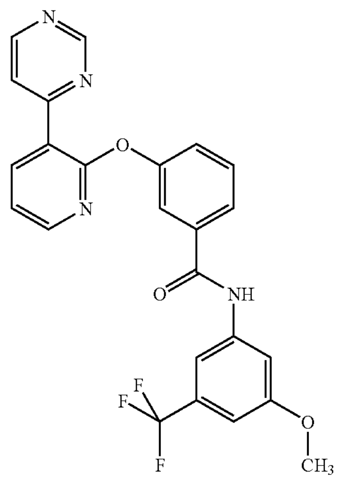 | 466.42 | 467 |
| 602 | 4-(2-((5-((((2R, 6S)-2,6-dimethyl-1-piperidinyl)carbonyl)-2-methylphenyl)oxy)-3-pyridinyl)pyrimidine | 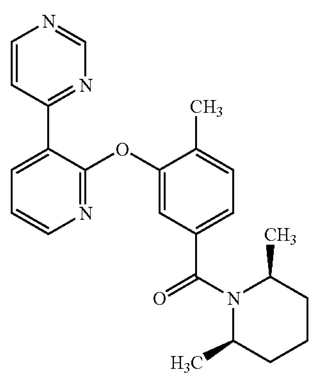 | 402.5 | 403 |
| 603 | N-(3,5-dimethylphenyl)-4-methyl-3-((3-(4-pyrimidinyl)-2-pyridinyl)oxy)benzamide | 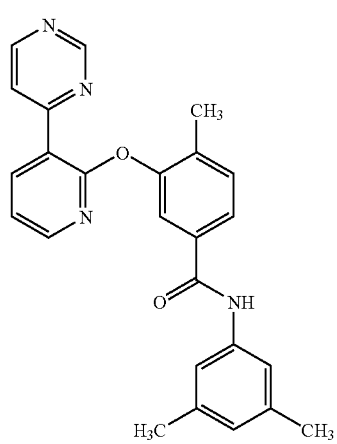 | 410.48 | 411 |

-continued

| Ex. No. | Structure Name | Structure | MW | MS Data |
|---|---|---|---|---|
| 604 | N-(3-(1,1-dimethylethyl)phenyl)-4-methyl-3-((3-(4-pyrimidinyl)-2-pyridinyl)oxy)benzamide | 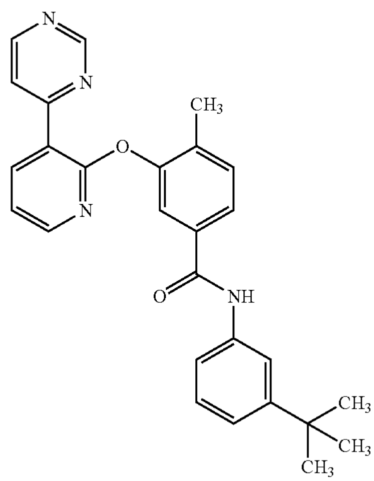 | 438.53 | 439 |
| 605 | 4-methyl-N-phenyl-3-((3-(4-pyrimidinyl)-2-pyridinyl)oxy)benzamide | 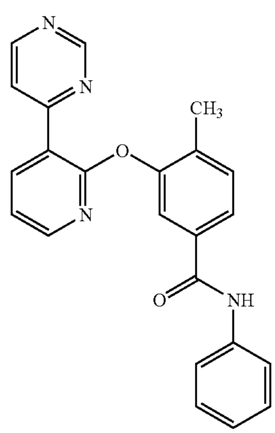 | 382.42 | 383 |
| 606 | 4-methyl-N-(3-(1-methylethyl)phenyl)-3-((3-(4-pyrimidinyl)-2-pyridinyl)oxy)benzamide | 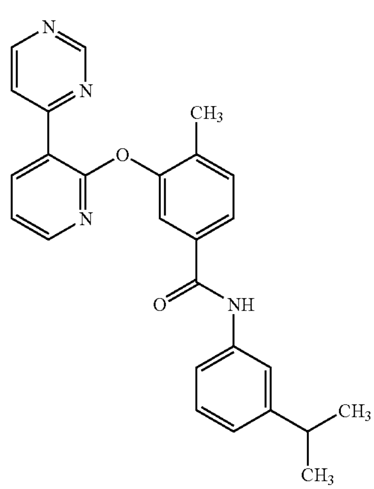 | 424.5 | 425 |

-continued

| Ex. No. | Structure Name | Structure | MW | MS Data |
|---|---|---|---|---|
| 607 | N-(3-(ethyloxy)phenyl)-4-methyl-3-((3-(4-pyrimidinyl)-2-pyridinyl)oxy)benzamide | 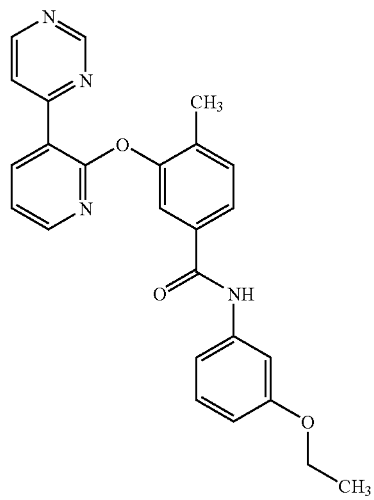 | 426.47 | 427 |
| 608 | N-(2,3-dihydro-1H-inden-4-yl)-4-methyl-3-((3-(4-pyrimidinyl)-2-pyridinyl)oxy)benzamide | 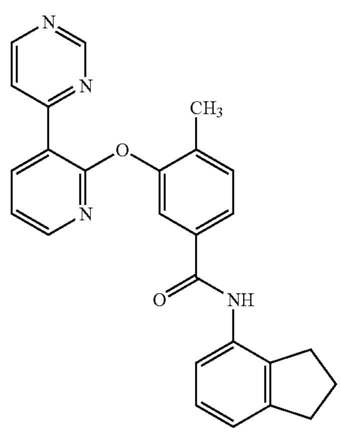 | 422.49 | 423 |
| 609 | N-(3-(4-morpholinylmethyl)phenyl)-3-((3-(4-pyrimidinyl)-2-pyridinyl)oxy)benzamide | 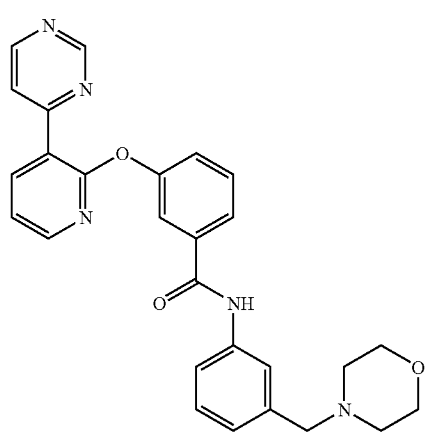 | 467.53 | |

-continued

| Ex. No. | Structure Name | Structure | MW | MS Data |
|---|---|---|---|---|
| 610 | N-(3,4-dimethylphenyl)-4-methyl-3-((3-(4-pyrimidinyl)-2-pyridinyl)oxy)benzamide | 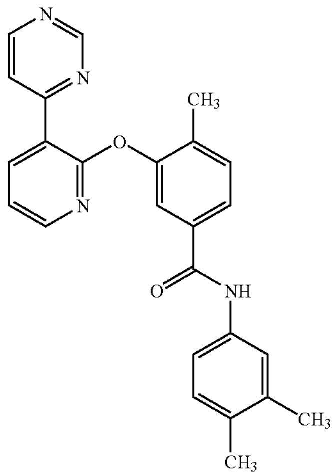 | 410.48 | 411 |
| 611 | 4-methyl-3-((3-(4-pyrimidinyl)-2-pyridinyl)oxy)-N-((4-(trifluoromethyl)phenyl)methyl)benzamide | 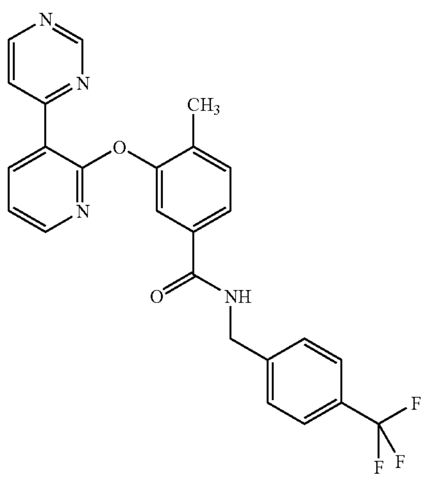 | 464.44 | 465 |
| 612 | N-(3-(aminocarbonyl)phenyl)-4-methyl-3-((3-(4-pyrimidinyl)-2-pyridinyl)oxy)benzamide | 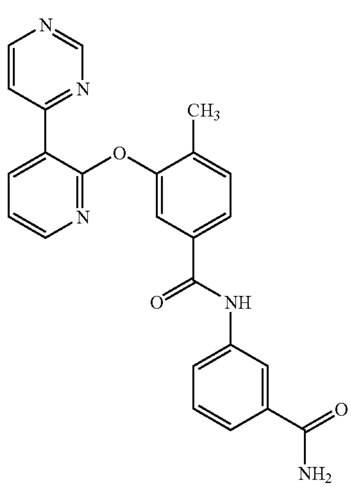 | 425.45 | 426 |

-continued

| Ex. No. | Structure Name | Structure | MW | MS Data |
|---|---|---|---|---|
| 613 | 4-methyl-N-(1-naphthalenyl)-3-((3-(4-pyrimidinyl)-2-pyridinyl)oxy)benzamide | 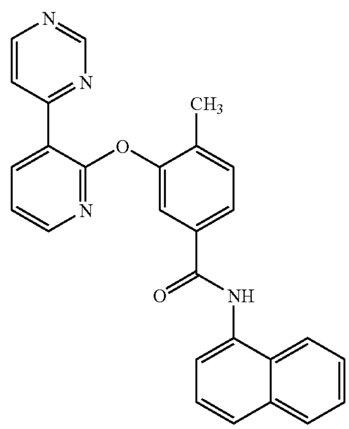 | 432.48 | 433 |
| 614 | N-(4-fluoro-3-(trifluoromethyl)phenyl)-4-methyl-3-((3-(4-pyrimidinyl)-2-pyridinyl)oxy)benzamide | 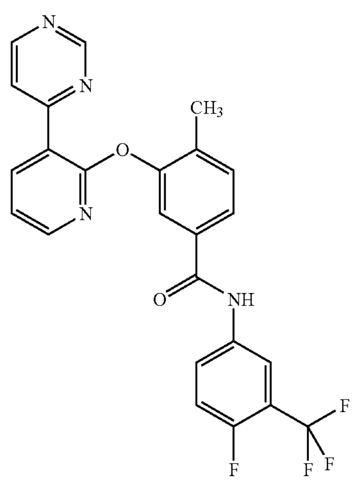 | 468.41 | 469 |
| 615 | 4-methyl-N-(3-((1-methylethyl)oxy)phenyl)-3-((3-(4-pyrimidinyl)-2-pyridinyl)oxy)benzamide | 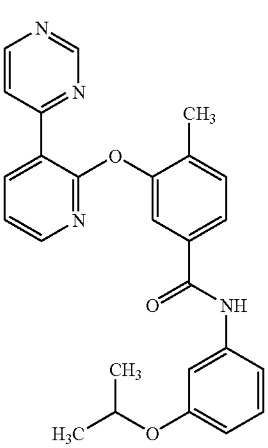 | 440.5 | 441 |

-continued
| Ex. No. | Structure Name | Structure | MW | MS Data |
|---|---|---|---|---|
| 616 | 4-methyl-N-(4-(4-morpholinyl)phenyl)-3-((3-(4-pyrimidinyl)-2-pyridinyl)oxy)benzamide | 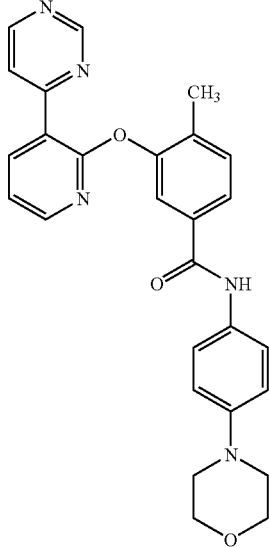 | 467.53 | 468 |
| 617 | N-(4-(diethylamino)phenyl)-4-methyl-3-((3-(4-pyrimidinyl)-2-pyridinyl)oxy)benzamide | 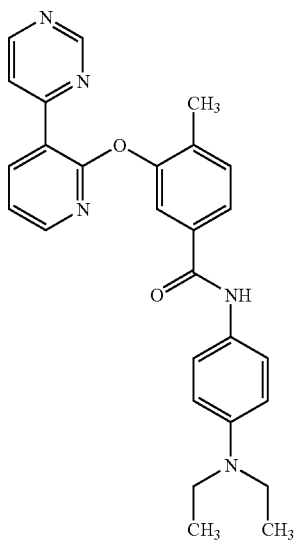 | 453.54 | 454 |

| Ex. No. | Structure Name | Structure | MW | MS Data |
|---|---|---|---|---|
| 618 | 4-methyl-N-(4-(1-piperidinyl)phenyl)-3-((3-(4-pyrimidinyl)-2-pyridinyl)oxy)benzamide | 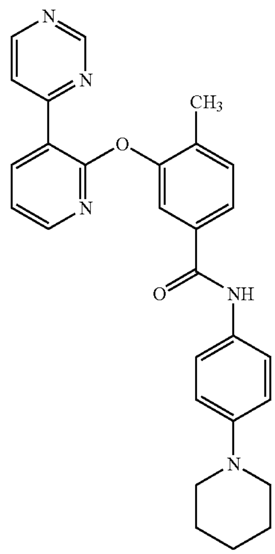 | 465.55 | 466 |
| 619 | N-(4-(1H-imidazol-1-yl)phenyl)-4-methyl-3-((3-(4-pyrimidinyl)-2-pyridinyl)oxy)benzamide | 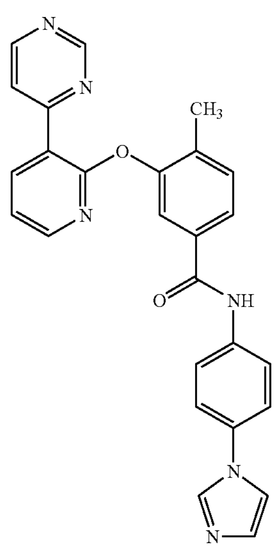 | 448.48 | 449 |

| Ex. No. | Structure Name | Structure | MW | MS Data |
|---|---|---|---|---|
| 620 | 4-methyl-N-(4-(4-methyl-1-piperazinyl)phenyl)-3-((3-(4-pyrimidinyl)-2-pyridinyl)oxy)benzamide | 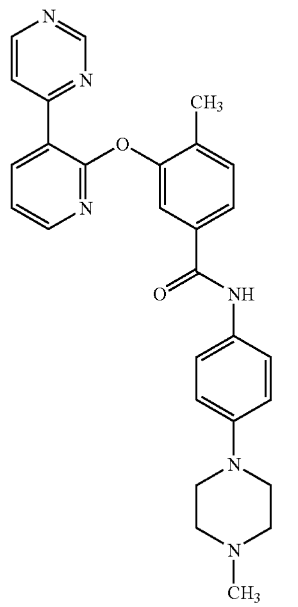 | 480.57 | 481 |
| 621 | N-(4-(acetyl(methyl)amino)phenyl)-4-methyl-3-((3-(4-pyrimidinyl)-2-pyridinyl)oxy)benzamide | 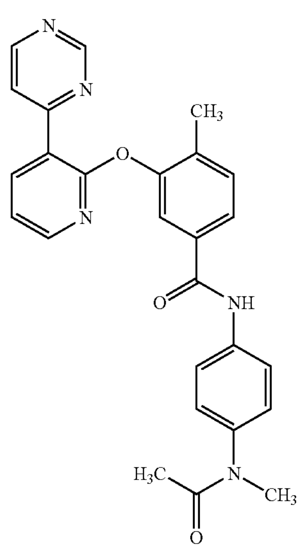 | 453.5 | 454 |

| Ex. No. | Structure Name | Structure | MW | MS Data |
|---|---|---|---|---|
| 622 | 4-methyl-3-((3-(4-pyrimidinyl)-2-pyridinyl)oxy)-N-(4-(1H-1,2,4-triazol-1-yl)phenyl)benzamide | 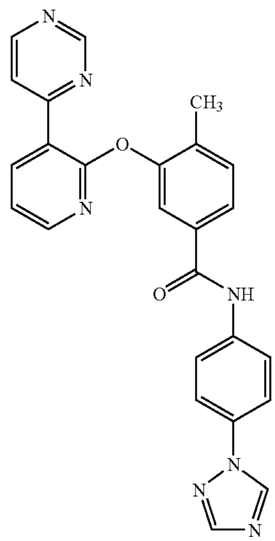 | 449.47 | 450 |
| 623 | 4-methyl-N-(4-pyridinyl)-3-((3-(4-pyrimidinyl)-2-pyridinyl)oxy)benzamide | 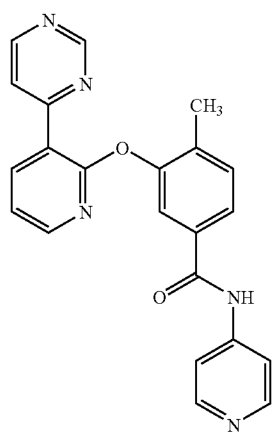 | 383.41 | 384 |
| 624 | N-(4-hydroxyphenyl)-4-methyl-3-((3-(4-pyrimidinyl)-2-pyridinyl)oxy)benzamide | 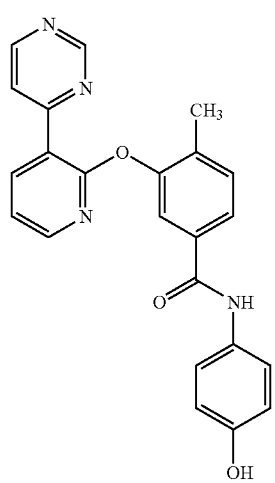 | 398.42 | 399 |

-continued

| Ex. No. | Structure Name | Structure | MW | MS Data |
|---|---|---|---|---|
| 625 | 4-methyl-N-(3-(piperidin-4-yloxy)-5-(trifluoromethyl)phenyl)-3-(3-(pyrimidin-4-yl)pyridin-2-yloxy)benzamide | 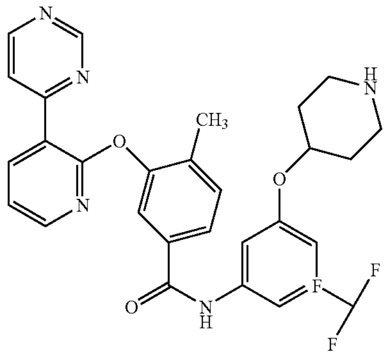 | 549.55 | 549 |
| 626 | tert-butyl- 4-(3-(4-methyl-3-(3-(pyrimidin-4-yl)pyridin-2-yloxy)benzamido)-5-(trifluoromethyl)phenoxy)piperidine-1-carboxylate | 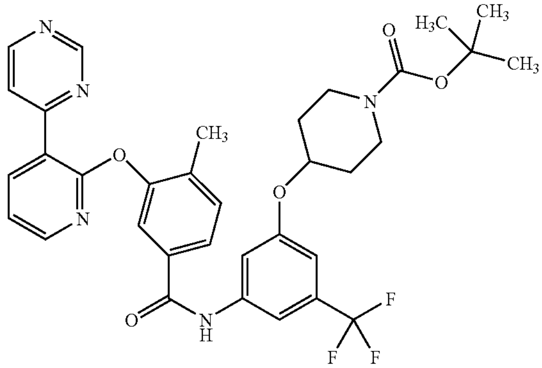 | 649.67 | 649 |
| 627 | N-(2-((3-(dimethylamino)propyl)(methyl)amino)-5-(trifluoromethyl)phenyl)-2-methoxy-5-(3-(4-(methylamino)-1,3,5-triazin-2-yl)pyridin-2-yloxy)benzamide | 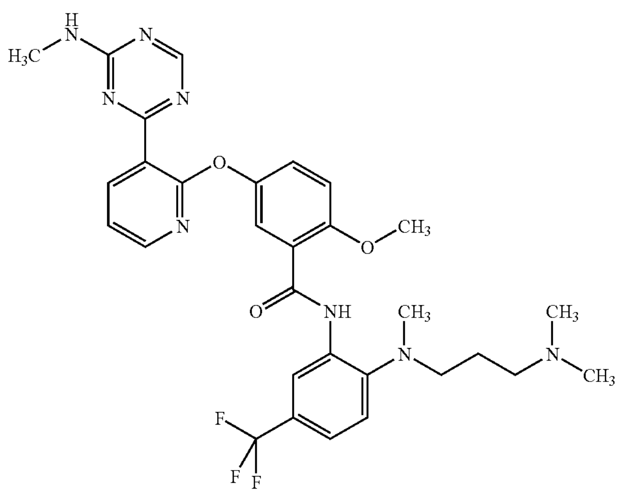 | 610.64 | 611 |
| 628 | 4-(3-(2-(methylamino)pyrimidin-4-yl)pyridin-2-yloxy)-N-(3-(trifluoromethyl)phenyl)benzamide | 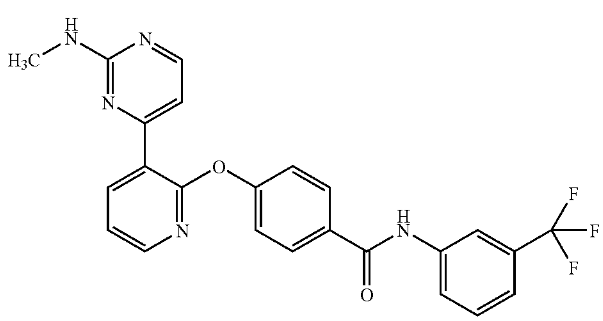 | 465.43 | 466 |

METHOD I

EXAMPLE 629

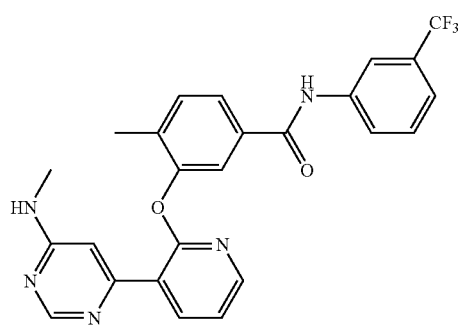

Synthesis of 4-Methyl-3-((3-(6-(methylamino)-4-pyrimidinyl)-2-pyridinyl)oxy)-N-(3-(trifluoromethyl)phenyl)benzamide Step 1. Preparation of [6-(2-chloro-pyridin-3-yl)-pyrimidin-4-yl]-methyl-amine 4-Chloro-6-(2-chloro-pyridin-3-yl)-pyrimidine (450 mg, 1.99 mmol), methylamine hydrochloride (202 mg, 2.99 mmol), $K_2CO_3$ (550 mg, 3.98 mmol) and DMSO (3.0 mL) were combined. The mixture was heated overnight at 80° C. in a sealed tube. The cooled mixture was diluted with water (300 mL) and the resulting solid was filtered, washed with water and dried to yield the title compound. MS m/z=221 [M+1]$^+$. Calc'd for $C_{10}H_9ClN_4$: 220.66.

Step 2. Preparation of 4-methyl-3-((3-(6-(methylamino)-4-pyrimidinyl)-2-pyridinyl)oxy)-N-(3-(trifluoromethyl)phenyl)benzamide

[6-(2-Chloro-pyridin-3-yl)-pyrimidin-4-yl]-methyl-amine (55 mg, 0.25 mmol), 3-hydroxy-4-methyl-N-(3-trifluoromethyl-phenyl)-benzamide (81 mg, 0.27 mmol), $Cs_2CO_3$ (162 mg, 0.50 mmol) and DMSO (0.8 mL) were combined. The mixture was heated overnight at 125° C. in a sealed tube. The resulting mixture was cooled to RT, diluted with water and extracted with EtOAc. The aqueous layer was neutralized (pH~7) with TFA and extracted with EtOAc. The organic layer was dried over $Na_2SO_4$, filtered and concentrated to yield the title compound. MS m/z=480 [M+1]$^+$. Calc'd for $C_{25}H_{20}F_3N_5O_2$: 479.47.

| Ex. No. | Structure Name | Structure | MW | MS Data |
|---|---|---|---|---|
| 630 | 3-((5-chloro-3-(2-(methylamino)-4-pyrimidinyl)-2-pyridinyl)oxy)-4-methyl-N-(3-(1-methylethyl)phenyl)benzamide | 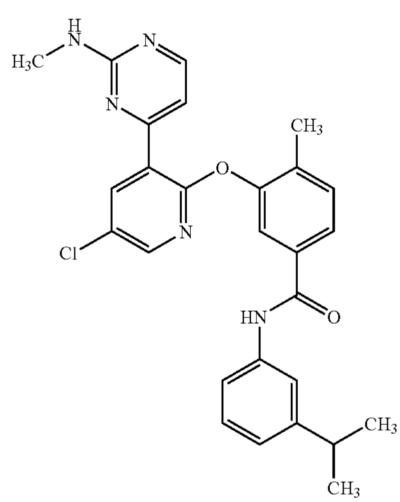 | 487.99 | 488 |

| Ex. No. | Structure Name | Structure | MW | MS Data |
|---|---|---|---|---|
| 631 | 3-((3-(4-((4-(dimethylamino)butyl)amino)-1,3,5-triazin-2-yl)-2-pyridinyl)oxy)-4-methyl-N-(3-(1-methylethyl)phenyl)benzamide | 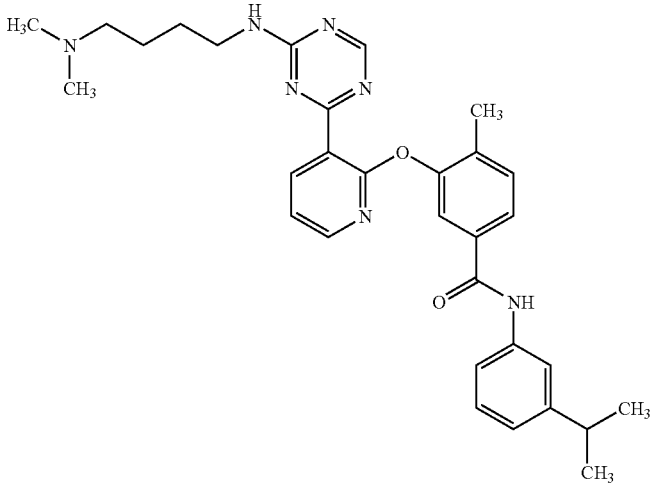 | 539.68 | 540 |
| 632 | 4-methyl-N-(3-(1-methylethyl)phenyl)-3-((3-(4-((3-(4-morpholinyl)propyl)amino)-1,3,5-triazin-2-yl)-2-pyridinyl)oxy)benzamide | 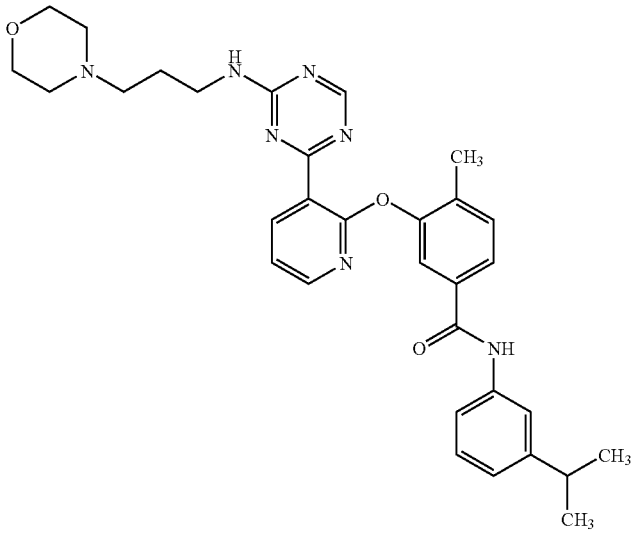 | 567.69 | 568 |
| 633 | 4-methyl-N-(3-(1-methylethyl)phenyl)-3-((3-(4-((2-(4-morpholinyl)ethyl)amino)-1,3,5-triazin-2-yl)-2-pyridinyl)oxy)benzamide | 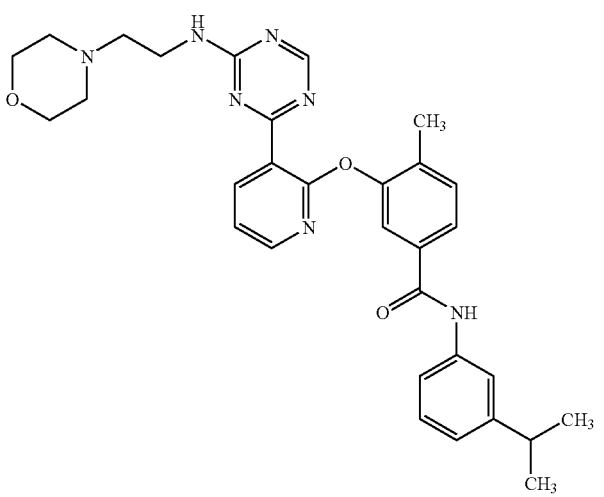 | 553.66 | 554 |

-continued

| Ex. No. | Structure Name | Structure | MW | MS Data |
|---|---|---|---|---|
| 634 | N-(5-cyclohexyl-2-(methyloxy)phenyl)-4-methyl-3-((3-(4-((3-(4-morpholinyl)propyl)amino)-1,3,5-triazin-2-yl)-2-pyridinyl)oxy)benzamide | 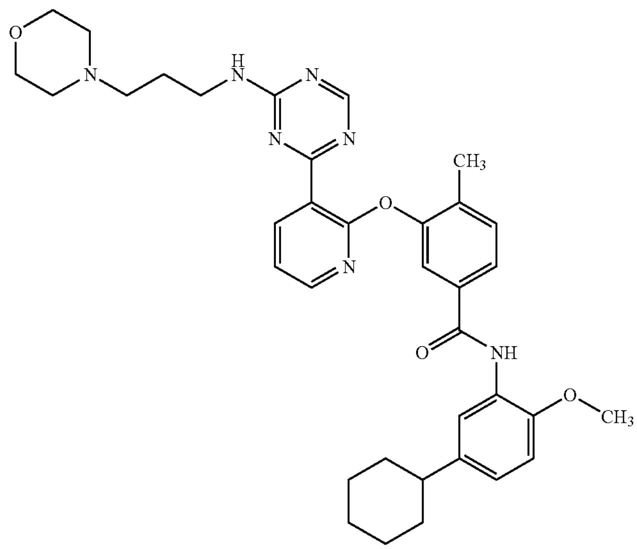 | 637.78 | 638 |
| 635 | N-(5-cyclohexyl-2-(methyloxy)phenyl)-3-((3-(4-((4-(dimethylamino)butyl)amino)-1,3,5-triazin-2-yl)-2-pyridinyl)oxy)-4-methylbenzamide | 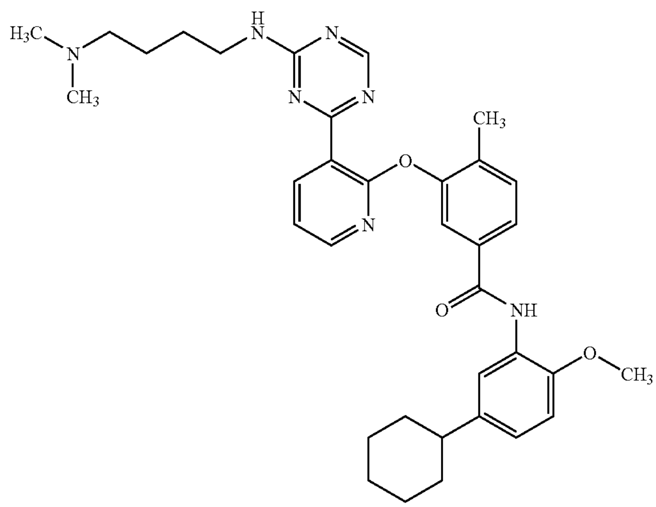 | 609.77 | 610 |
| 636 | N-(5-cyclohexyl-2-(methyloxy)phenyl)-4-methyl-3-((3-(4-((2-(4-morpholinyl)ethyl)amino)-1,3,5-triazin-2-yl)-2-pyridinyl)oxy)benzamide | 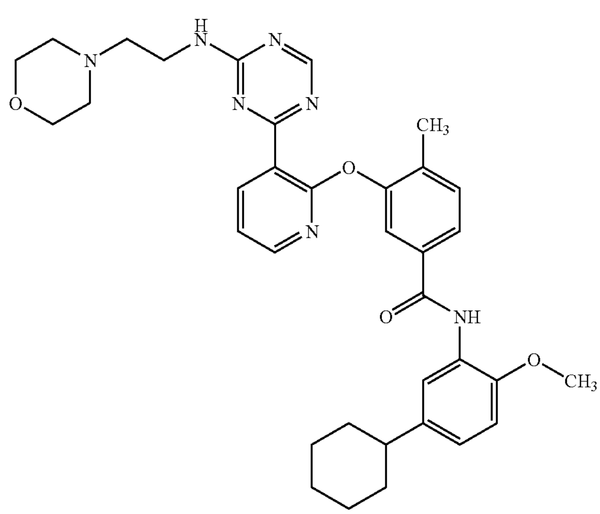 | 623.75 | 624 |

-continued

| Ex. No. | Structure Name | Structure | MW | MS Data |
|---|---|---|---|---|
| 637 | 4-methyl-N-(3-(1-methylethyl)phenyl)-3-((3-(4-quinolinyl)-2-pyridinyl)oxy)benzamide | 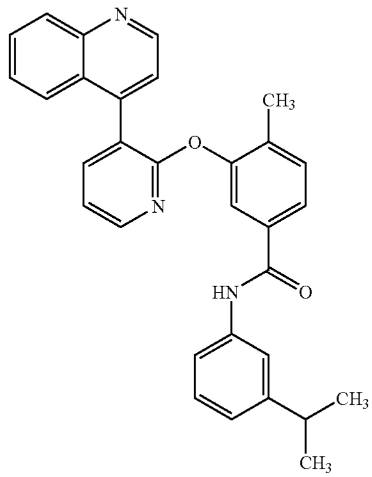 | 473.57 | 474 |
| 638 | 4-methyl-N-(3-(1-methylethyl)phenyl)-3-((2'-((3-(4-morpholinyl)propyl)amino)-3,4'-bipyridin-2-yl)oxy)benzamide | 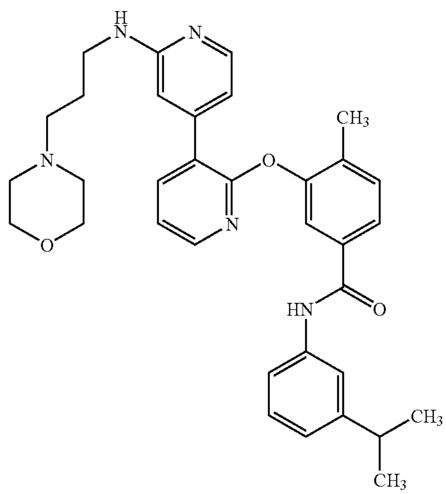 | 565.71 | 566 |
| 639 | N-(5-cyclohexyl-2-(methyloxy)phenyl)-4-methyl-3-((3-(4-quinolinyl)-2-pyridinyl)oxy)benzamide | 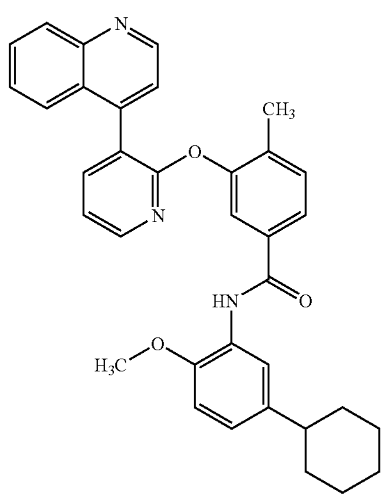 | 543.66 | 544 |

| Ex. No. | Structure Name | Structure | MW | MS Data |
|---|---|---|---|---|
| 640 | 3-((3-(6,7-bis(methyloxy)-4-quinazolinyl)-2-pyridinyl)oxy)-4-methyl-N-(3-(1-methylethyl)phenyl)benzamide | 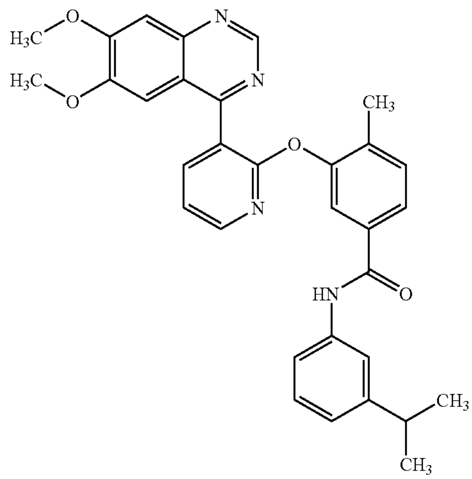 | 534.61 | 535 |
| 641 | N-(5-cyclohexyl-2-(methyloxy)phenyl)-4-methyl-3-((2'-((3-(4-morpholinyl)propyl)amino)-3,4'-bipyridin-2-yl)oxy)benzamide | 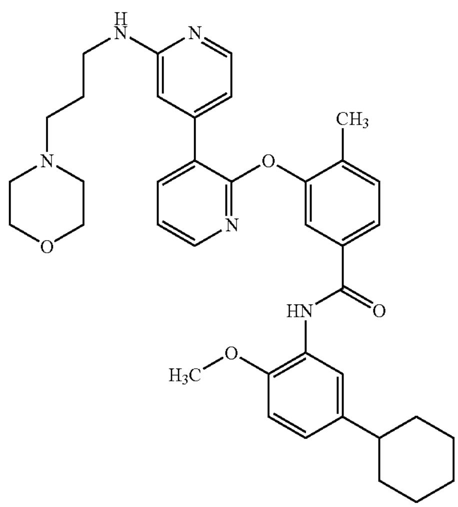 | 635.8 | 636 |
| 642 | 4-methyl-3-((3-(4-(methylamino)-1,3,5-triazin-2-yl)-2-pyridinyl)oxy)-N-(3-(1-methylethyl)phenyl)benzamide | 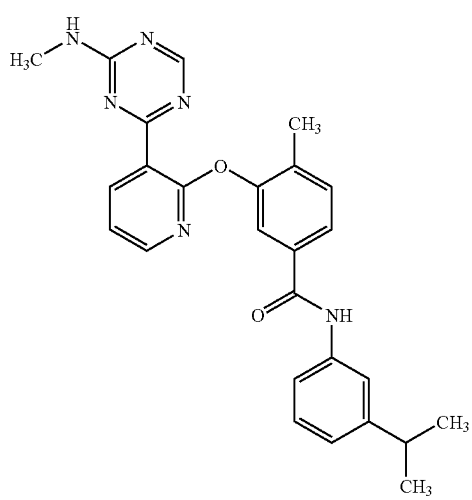 | 454.53 | 455 |

| Ex. No. | Structure Name | Structure | MW | MS Data |
|---|---|---|---|---|
| 643 | N-(5-cyclohexyl-2-(methyloxy)phenyl)-4-methyl-3-((3-(4-(methylamino)-1,3,5-triazin-2-yl)-2-pyridinyl)oxy)benzamide | 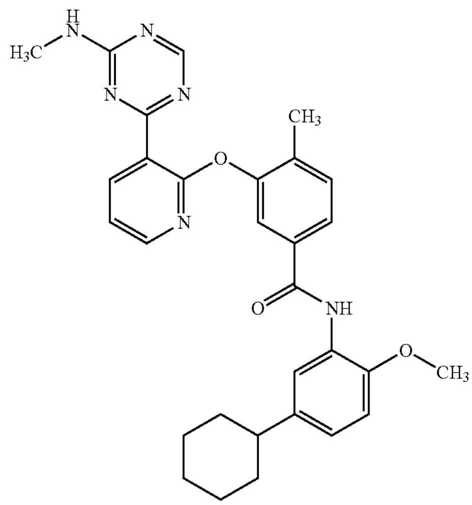 | 524.62 | 525 |
| 644 | 4-methyl-N-(3-(1-methylethyl)phenyl)-3-((3-(4-((2-(1-pyrrolidinyl)ethyl)amino)-1,3,5-triazin-2-yl)-2-pyridinyl)oxy)benzamide | 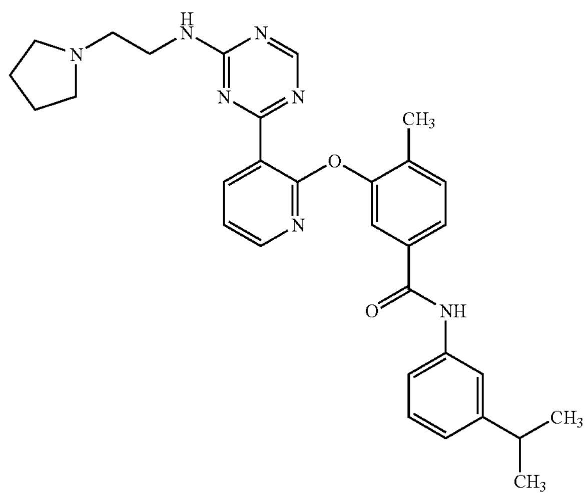 | 537.66 | 538 |
| 645 | 3-((3-(4-(ethylamino)-1,3,5-triazin-2-yl)-2-pyridinyl)oxy)-4-methyl-N-(3-(1-methylethyl)phenyl)benzamide | 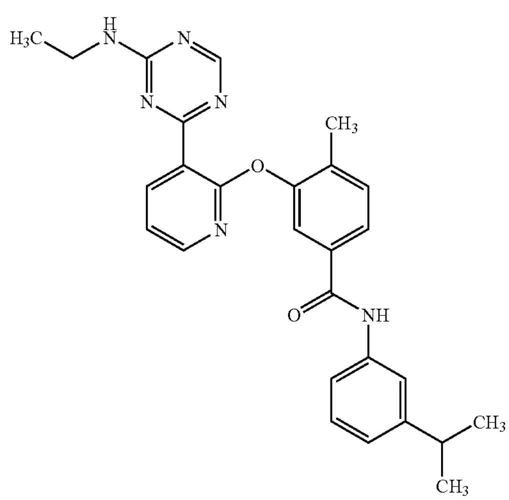 | 468.56 | 469 |

-continued

| Ex. No. | Structure Name | Structure | MW | MS Data |
|---|---|---|---|---|
| 646 | 4-methyl-N-(3-(1-methylethyl)phenyl)-3-((3-(4-(propylamino)-1,3,5-triazin-2-yl)-2-pyridinyl)oxy)benzamide | 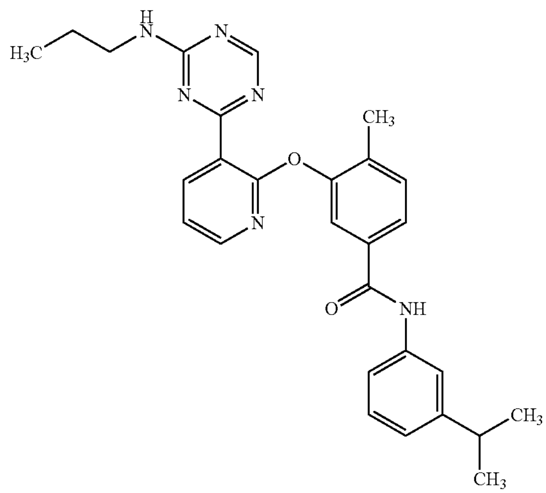 | 482.58 | 483 |
| 647 | N-(5-cyclohexyl-2-(methyloxy)phenyl)-4-methyl-3-((3-(4-((2-(1-pyrrolidinyl)ethyl)amino)-1,3,5-triazin-2-yl)-2-pyridinyl)oxy)benzamide | 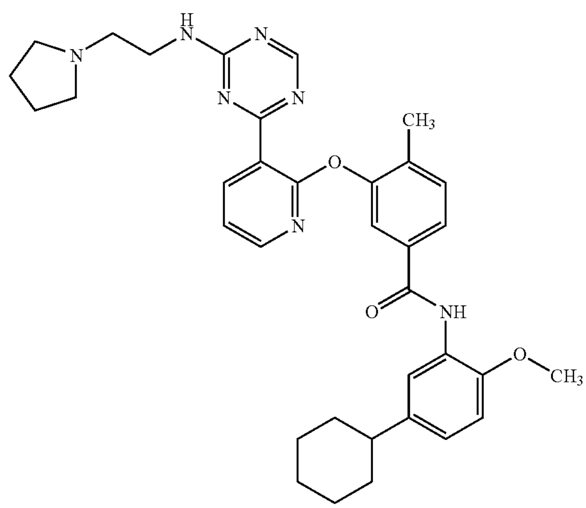 | 607.76 | 608 |
| 648 | N-(5-cyclohexyl-2-(methyloxy)phenyl)-3-((3-(4-(ethylamino)-1,3,5-triazin-2-yl)-2-pyridinyl)oxy)-4-methylbenzamide | 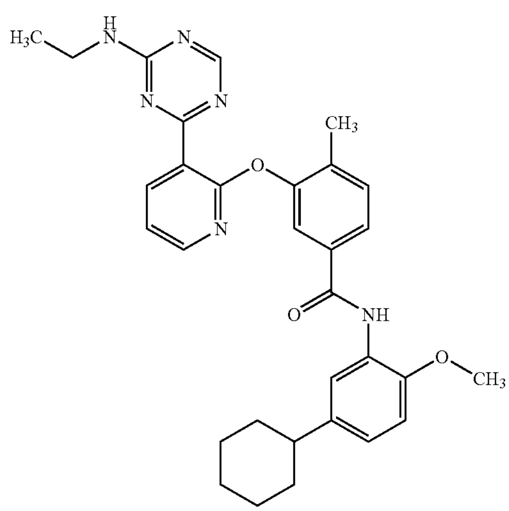 | 538.65 | 539 |

-continued

| Ex. No. | Structure Name | Structure | MW | MS Data |
|---|---|---|---|---|
| 649 | N-(5-cyclohexyl-2-(methyloxy)phenyl)-4-methyl-3-((3-(4-(propylamino)-1,3,5-triazin-2-yl)-2-pyridinyl)oxy)benzamide | 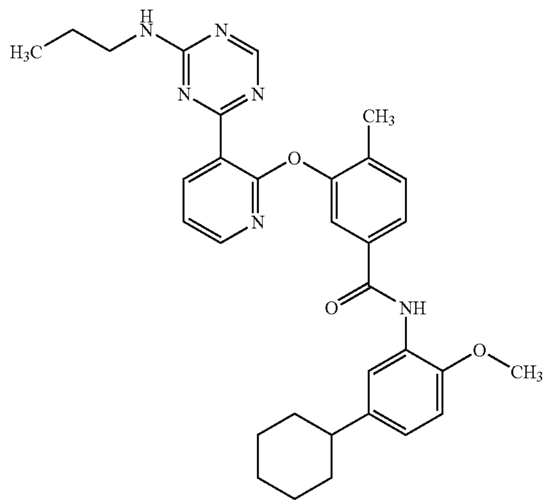 | 552.67 | 553 |
| 650 | 3-((3-(6,7-bis(methyloxy)-4-quinazolinyl)-2-pyridinyl)oxy)-N-(5-cyclohexyl-2-(methyloxy)phenyl)-4-methylbenzamide | 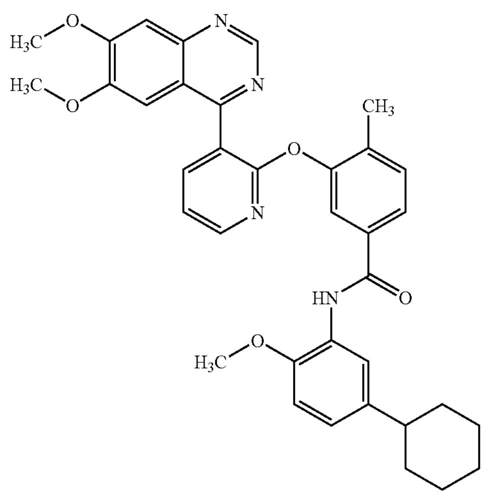 | 604.7 | 605 |
| 651 | 3-((3-(5-fluoro-2-((2-(1-pyrrolidinyl)ethyl)amino)-4-pyrimidinyl)-2-pyridinyl)oxy)-4-methyl-N-(3-(1-methylethyl)phenyl)benzamide | 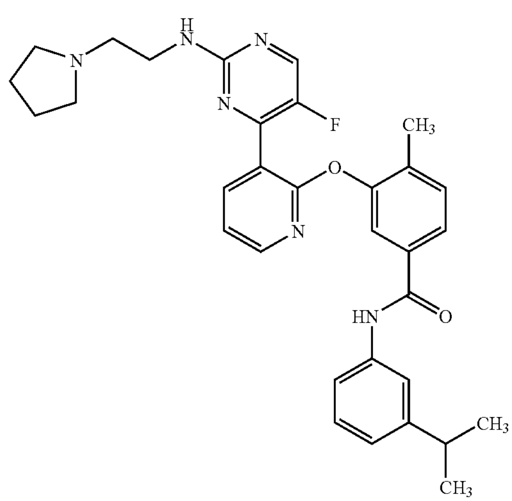 | 554.67 | 555 |

-continued
| Ex. No. | Structure Name | Structure | MW | MS Data |
|---|---|---|---|---|
| 652 | 4-methyl-3-((2'-((3-(4-morpholinyl)propyl)amino)-3,4'-bipyridin-2-yl)oxy)-N-(2-(4-morpholinyl)-5-trifluoromethyl)phenyl)benzamide | 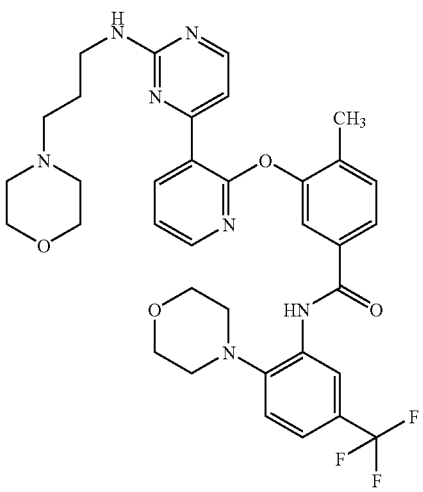 | 676.74 | 677 |
| 653 | N-(5-cyclohexyl-2-(methyloxy)phenyl)-3-((3-(5-fluoro-2-((2-(1-pyrrolidinyl)ethyl)amino)-4-pyrimidinyl)-2-pyridinyl)oxy)-4-methylbenzamide | 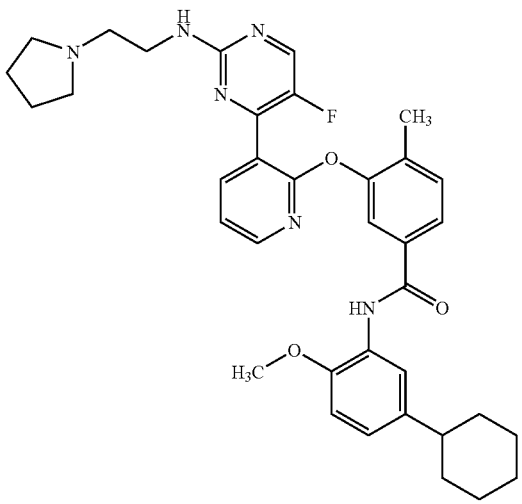 | 624.76 | 625 |
| 654 | 3-((3-(4-(butylamino)-1,3,5-triazin-2-yl)-2-pyridinyl)oxy)-N-(5-cyclohexyl-2-(methyloxy)phenyl)-4-methylbenzamide | 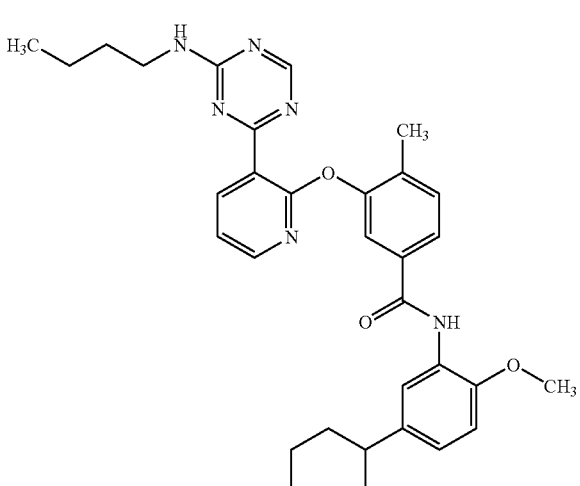 | 566.7 | 567 |

| Ex. No. | Structure Name | Structure | MW | MS Data |
|---|---|---|---|---|
| 655 | N-(5-cyclohexyl-2-(methyloxy)phenyl)-3-((3-(4-((2-hydroxyethyl)amino)-1,3,5-triazin-2-yl)-2-pyridinyl)oxy)-4-methylbenzamide | 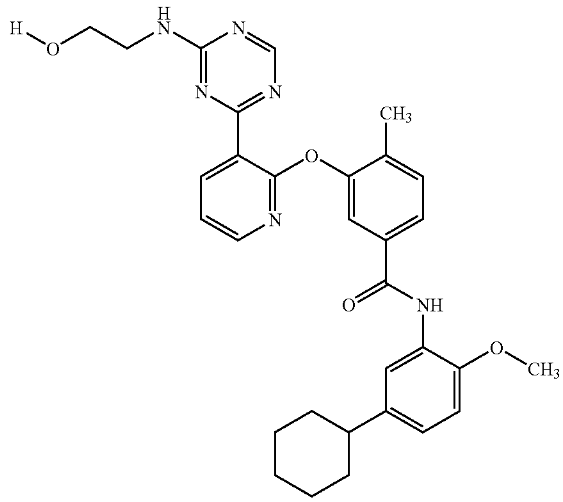 | 554.65 | 555 |
| 656 | 3-((3-(5-fluoro-2-(methylamino)-4-pyrimidinyl)-2-pyridinyl)oxy)-4-methyl-N-(3-(1-methylethyl)phenyl)benzamide | 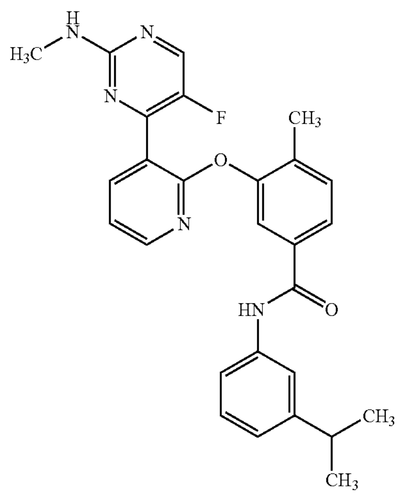 | 471.53 | 472 |
| 657 | N-(5-cyclohexyl-2-(methyloxy)phenyl)-3-((3-(5-fluoro-2-(methylamino)-4-pyrimidinyl)-2-pyridinyl)oxy)-4-methylbenzamide | 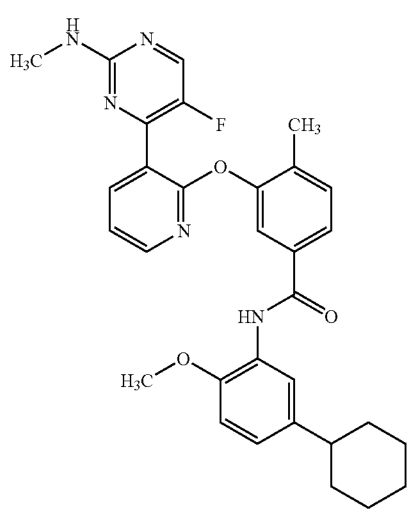 | 541.62 | 542 |

| Ex. No. | Structure Name | Structure | MW | MS Data |
|---|---|---|---|---|
| 658 | N-(5-cyclohexyl-2-(methyloxy)phenyl)-4-methyl-3-((2'-(methylamino)-3,4'-bipyridin-2-yl)oxy)benzamide | 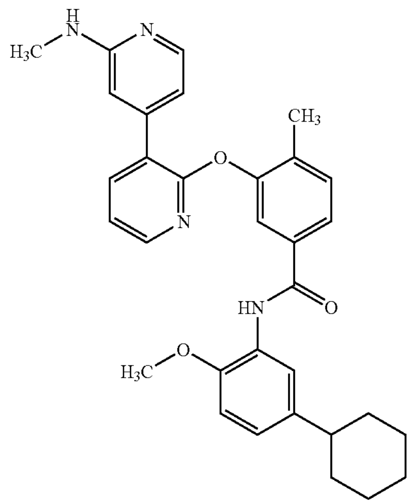 | 522.68 | 523 |
| 659 | 4-methyl-3-((3-(2-(methylamino)-4-pyrimidinyl)-2-pyridinyl)oxy)-N-(3-(1-methylethyl)phenyl)benzamide | 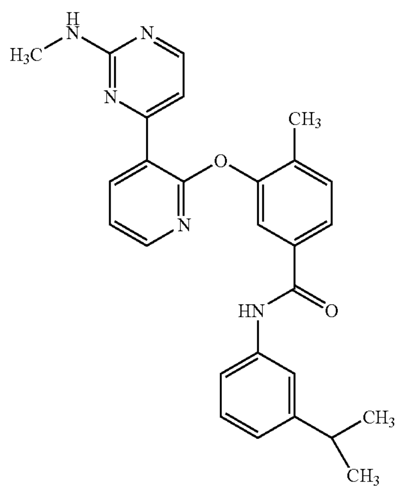 | 453.54 | 454 |
| 660 | 2-fluoro-5-((2'-(methylamino)-3,4'-bipyridin-2-yl)oxy)-N-(2-(1-piperidinyl)-5-(trifluoromethyl)phenyl)benzamide | 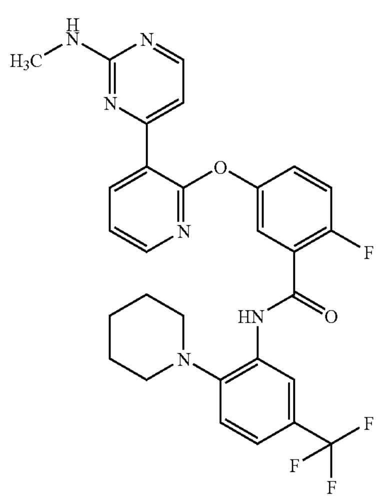 | 565.57 | 566 |

| Ex. No. | Structure Name | Structure | MW | MS Data |
|---|---|---|---|---|
| 661 | 4-methyl-3-((2'-(methyloxy)-3,4'-bipyridin-2-yl)oxy)-N-(3-(trifluoromethyl)phenyl)benzamide | 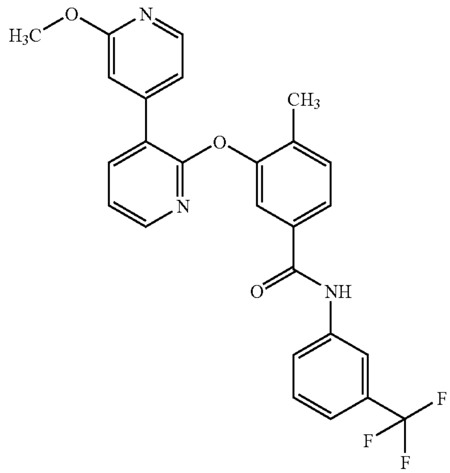 | 479.46 | 480 |
| 662 | 3-((5-bromo-3-(4-pyrimidinyl)-2-pyridinyl)oxy)-4-methyl-N-(3-(trifluoromethyl)phenyl)benzamide | 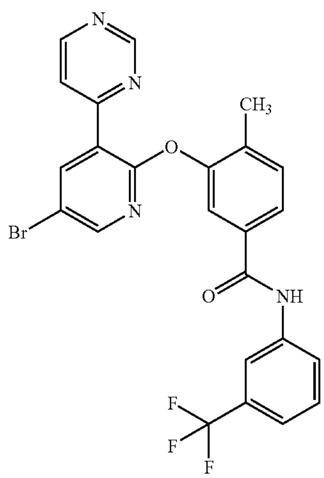 | 529.31 | 530 |

METHOD J

EXAMPLE 663

Synthesis of N-(3-Methyl-4-((3-(4-pyrimidinyl)-2-pyridinyl)oxy)phenyl)-2-(3-(trifluoromethyl)phenyl)acetamide

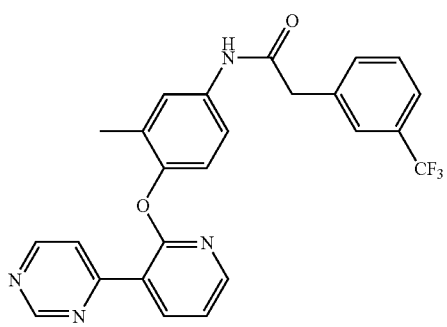

To 3-methyl-4-(3-pyrimidin-4-yl-pyridin-2-yloxy)-phenylamine (30 mg, 0.11 mmol), (3-trifluoromethyl-phenyl)-acetic acid (27 mg, 0.13 mmol), and EDC (41 mg, 0.22 mmol) was added $CH_2Cl_2$ (2.0 mL). The mixture was stirred for 6 h at RT, concentrated, diluted with EtOAc, and extracted with saturated $NaHCO_3$. The organic layer was dried over $Na_2SO_4$, filtered, concentrated and purified by reverse-phase HPLC to yield N-(3-Methyl-4-((3-(4-pyrimidinyl)-2-pyridinyl)oxy)phenyl)-2-(3-(trifluoromethyl)phenyl)acetamide. MS m/z=465 [M+1]$^+$. Calc'd for $C_{25}H_{19}F_3N_4O_2$: 464.45.

EXAMPLE 664

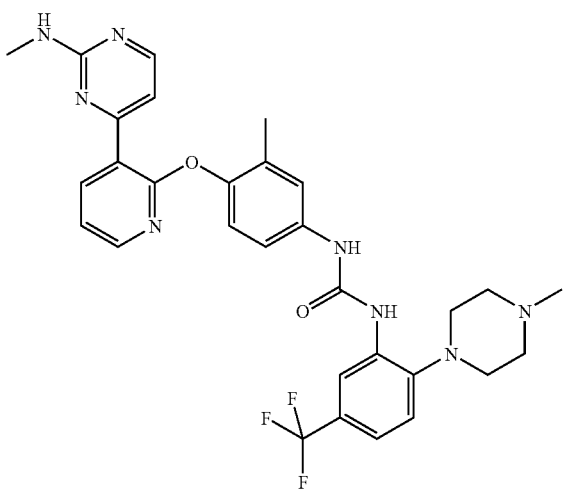

Synthesis of N-(3-methyl-4-((3-(2-(methylamino)-4-pyrimidinyl)-2-pyridinyl)oxy)phenyl)-N'-(2-(4-methyl-1-piperazinyl)-5-(trifluoromethyl)phenyl)urea Step 1. Preparation of phenyl 3-methyl-4-(3-(2-(methylamino)pyrimidin-4-yl)pyridin-2-yloxy)phenylcarbamate To 4-(2-(4-amino-2-methylphenoxy)pyridin-3-yl)-N-methylpyrimidin-2-amine (200 mg, 0.65 mmol) in THF (4 mL) was added diisopropylethylamine (0.097 mL, 0.72 mmol) and phenyl chloroformate (102 mg, 0.65 mmol). The mixture was stirred for 3.5 hours at RT and used without purification.

Step 2. Preparation of N-(3-methyl-4-((3-(2-(methylamino)-4-pyrimidinyl)-2-pyridinyl)oxy)phenyl)-N'-(2-(4-methyl-1-piperazinyl)-5-(trifluoromethyl)phenyl)urea To phenyl 3-methyl-4-(3-(2-(methylamino)pyrimidin-4-yl)pyridin-2-yloxy)phenylcarbamate (59 mg, 0.14 mmol) in THF (1 mL) was added 2-(4-methylpiperazin-1-yl)-5-(trifluoromethyl)benzenamine (30 mg, 0.12 mmol). The mixture was stirred for 40 hours at 80° C. The crude material was purified by silica gel chromatography (0-20% MeOH/$CH_2Cl_2$) to yield the title compound as a light yellow solid. MS m/z=593 [M+H]$^+$. Calc'd for $C_{30}H_{31}F_3N_8O_2$: 592.63.

EXAMPLE 665

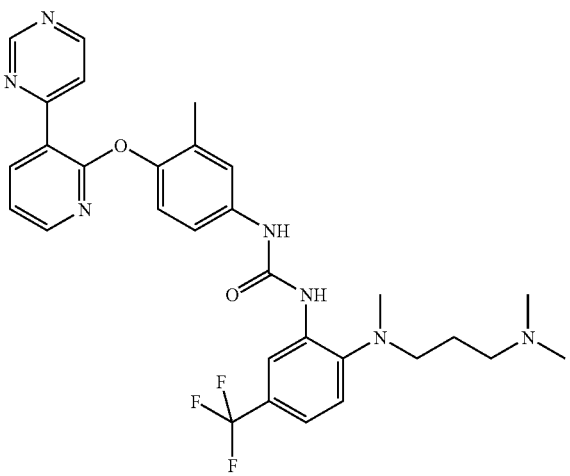

Synthesis of N-(2-((3-(dimethylamino)propyl)(methyl)amino)-5-(trifluoromethyl)phenyl)-N'-(3-methyl-4-((3-(4-pyrimidinyl)-2-pyridinyl)oxy)phenyl)urea Step 1. Preparation of 4-(2-(4-isocyanato-2-methylphenoxy)pyridin-3-yl)pyrimidine To 3-methyl-4-(3-(pyrimidin-4-yl)pyridin-2-yloxy)benzenamine (93 mg, 0.33 mmol) in $CH_2Cl_2$ (8 mL) was added saturated sodium bicarbonate (4 mL) followed 5 minutes later by phosgene (20% solution in toluene, 0.27 mL, 0.50 mmol). The mixture was stirred for 15 minutes at RT, diluted with $CH_2Cl_2$ and extracted with water. The organic layer was dried over sodium sulfate, filtered, concentrated and used without purification.

Step 2. Preparation of N-(2-((3-(dimethylamino)propyl)(methyl)amino)-5-(trifluoromethyl)phenyl)-N'-(3-methyl-4-((3-(4-pyrimidinyl)-2-pyridinyl)oxy)phenyl)urea To 4-(2-(4-isocyanato-2-methylphenoxy)pyridin-3-yl)pyrimidine (93 mg, 0.33 mmol) in toluene (3 mL) was added $N^1$-(3-(dimethylamino)propyl)-$N^1$-methyl-4-(trifluoromethyl)benzene-1,2-diamine (82 mg, 0.30 mmol).

The mixture was stirred for 2.5 days at RT, then concentrated and purified by semi-preparative HPLC (Gilson, acidic mobile phase) to yield the title compound as an off-white solid. MS m/z=580 [M+H]$^+$. Calc'd for $C_{30}H_{32}F_3N_7O_2$: 579.63.

EXAMPLE 666

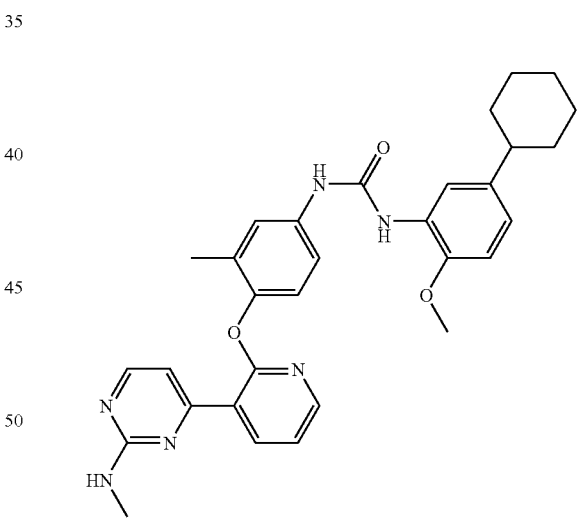

Synthesis of N-(5-Cyclohexyl-2-(methyloxy)phenyl)-N'-(3-methyl-4-((3-(2-(methylamino)-4-pyrimidnyl)-2-pyridinyl)oxy)phenyl)urea Step 1. Preparation of 4-cyclohexyl-2-isocyanato-1-methoxy-benzene To 5-cyclohexyl-2-methoxy-phenylamine (106 mg, 0.49 mmol), $CH_2Cl_2$ (10 mL) and saturated $NaHCO_3$ (5 mL) was added a 20% solution of $COCl_2$ in toluene (0.39 mL) directly to the organic layer. The mixture was stirred for 15 min at RT, diluted with CH$_2$Cl$_2$ and extracted with water. The organic layer was dried over Na$_2$SO$_4$, filtered and concentrated to yield 4-cyclohexyl-2-isocyanato-1-methoxy-benzene.

Step 2. Preparation of {4-[2-(4-amino-2-methyl-phenoxy)-pyridin-3-yl]-pyrimidin-2-yl}-methyl-amine 4-Amino-2-methyl-phenol (84 mg, 0.68 mmol), Cs$_2$CO$_3$ (665 mg, 2.04 mmol) and NMP (2.5 mL) were combined. The mixture was heated for 5 minutes at 100° C., cooled to RT and [4-(2-chloro-pyridin-3-yl)-pyrimidin-2-yl]-methyl-amine (150 mg, 0.68 mmol) was added. The mixture was heated in the microwave to 210° C. for 20 minutes, cooled, filtered through a plug of cotton and purified by reverse-phase HPLC (Gilson, acidic mobile phase) to yield the title compound. MS m/z=308 [M+1]$^+$. Calc'd for C$_{17}$H$_{17}$N$_5$O: 307.36.

Step 3. Preparation of N-(5-cyclohexyl-2-(methyloxy)phenyl)-N'-(3-methyl-4-((3-(2-(methylamino)-4-pyrimidnyl)-2-pyridinyl)oxy)phenyl)urea To 4-cyclohexyl-2-isocyanato-1-methoxy-benzene (56 mg, 0.24 mmol) in toluene (3.0 mL) was added {4-[2-(4-amino-2-methyl-phenoxy)-pyridin-3-yl]-pyrimidin-2-yl}-methyl-amine (46 mg, 0.15 mmol). The mixture was stirred overnight at RT, concentrated and purified by preparative TLC (50% EtOAc/CH$_2$Cl$_2$) to yield N-(5-cyclohexyl-2-(methyloxy)phenyl)-N'-(3-methyl-4-((3-(2-(methylamino)-4-pyrimidinyl)-2-pyridinyl)oxy)phenyl)urea. MS m/z=539 [M+1]$^+$. Calc'd for C$_{31}$H$_{34}$N$_6$O$_3$: 538.66.

[Note: there are many commercially available isocyanates which may also be reacted in a manner analogous that described in method J, and sulfonyl chlorides can also be added in an analogous fashion to that described in Method C.]

| Ex. No. | Structure Name | Structure | MW | MS Data |
|---|---|---|---|---|
| 667 | N-(2-fluoro-5-(trifluoromethyl)phenyl)-N'-(3-methyl-4-((3-(4-pyrimidinyl)-2-pyridinyl)oxy)phenyl)urea | 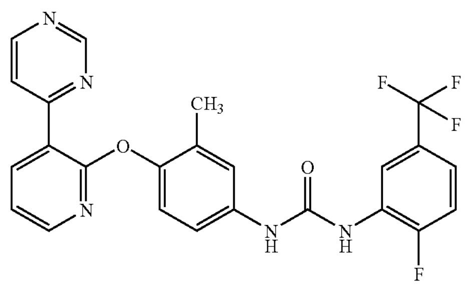 | 483.42 | 484 |
| 668 | N-(2-fluoro-3-(trifluoromethyl)phenyl)-N'-(3-methyl-4-((3-(4-pyrimidinyl)-2-pyridinyl)oxy)phenyl)urea | 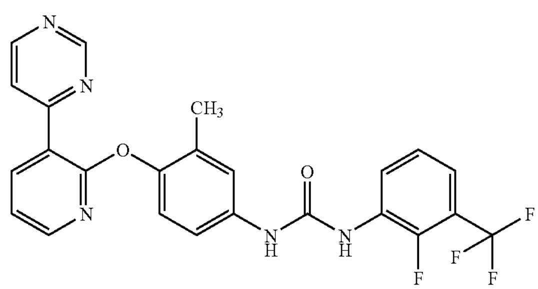 | 483.42 | 484 |
| 669 | N-(4-((3-(4-pyrimidinyl)-2-pyridinyl)oxy)-1-naphthalenyl)-N'-(3-(trifluoromethyl)phenyl)urea | 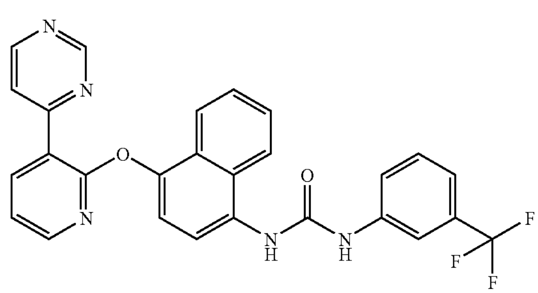 | 501.47 | 502 |

| Ex. No. | Structure Name | Structure | MW | MS Data |
|---|---|---|---|---|
| 670 | N-phenyl-N'-(4-((3-(4-pyrimidinyl)-2-pyridinyl)oxy)-1-naphthalenyl)urea | 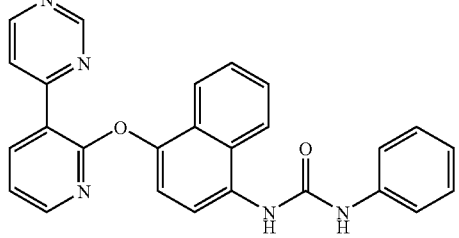 | 433.47 | 434 |
| 671 | N-(2,5-dimethyl-4-((3-(4-pyrimidinyl)-2-pyridinyl)oxy)phenyl)-N'-(3-(trifluoromethyl)phenyl)urea | 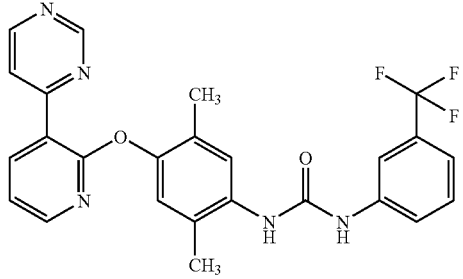 | 479.46 | 480 |
| 672 | N-(2,5-dimethyl-4-((3-(4-pyrimidinyl)-2-pyridinyl)oxy)phenyl)-N'-phenylurea | 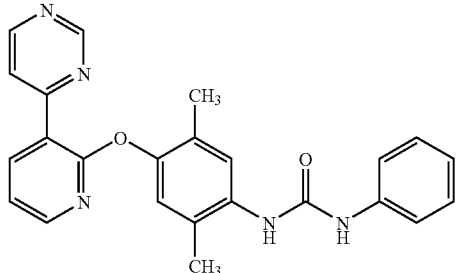 | 411.46 | 412 |
| 673 | N-(3-methyl-4-((3-(4-pyrimidinyl)-2-pyridinyl)oxy)phenyl)-3-(trifluoromethyl)benzenesulfonamide | 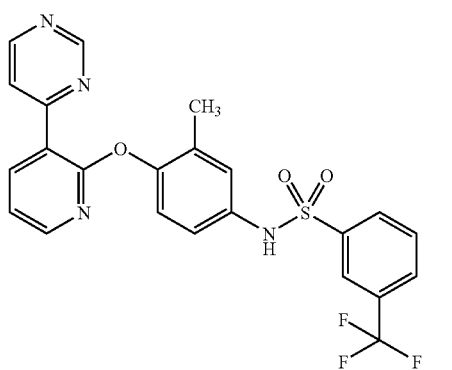 | 486.47 | 487 |
| 674 | N-(3-methyl-4-((3-(4-pyrimidinyl)-2-pyridinyl)oxy)phenyl)benzenesulfonamide | 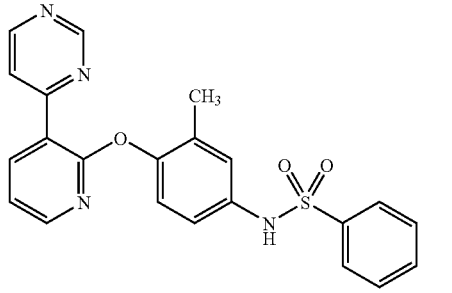 | 418.48 | 419 |

| Ex. No. | Structure Name | Structure | MW | MS Data |
|---|---|---|---|---|
| 675 | N-(2-chloro-5-(trifluoromethyl)phenyl)-N'-(3-methyl-4-((3-(4-pyrimidinyl)-2-pyridinyl)oxy)phenyl)urea | 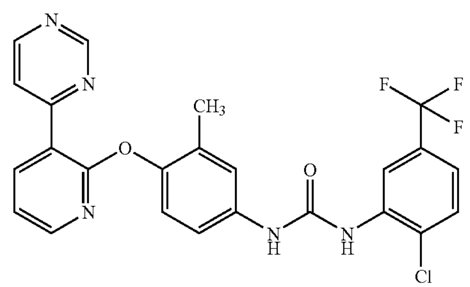 | 499.88 | 500 |
| 676 | N-(5-chloro-2-(methyloxy)phenyl)-N'-(3-methyl-4-((3-(4-pyrimidinyl)-2-pyridinyl)oxy)phenyl)urea | 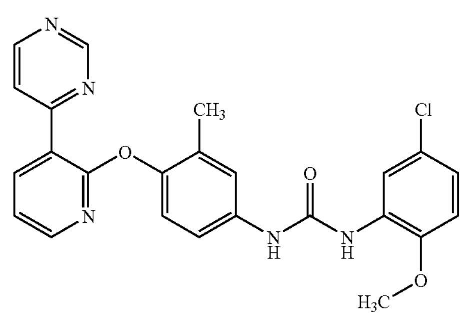 | 461.91 | 462 |
| 677 | N-(3,5-bis(trifluoromethyl)phenyl)-N'-(3-methyl-4-((3-(4-pyrimidinyl)-2-pyridinyl)oxy)phenyl)urea | 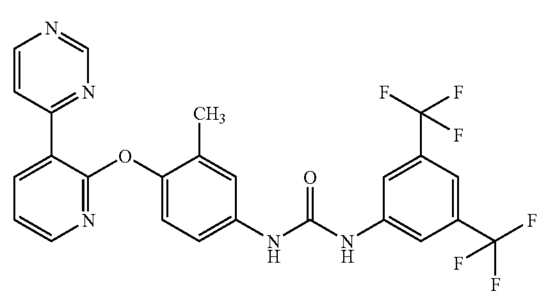 | 533.43 | 534 |
| 678 | 2,3-dichloro-N-(4-((3-(4-pyrimidinyl)-2-pyridinyl)oxy)-1-naphthalenyl)benzenesulfonamide | 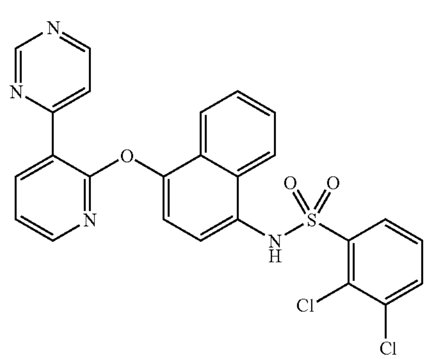 | 523.4 | 524 |

-continued

| Ex. No. | Structure Name | Structure | MW | MS Data |
|---|---|---|---|---|
| 679 | N-(4-((3-(4-pyrimidinyl)-2-pyridinyl)oxy)-1-naphthalenyl)-3-(trifluoromethyl)benzenesulfonamide | 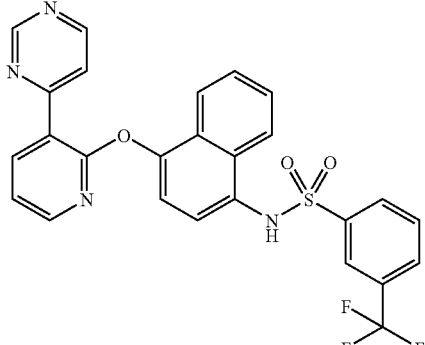 | 522.51 | 523 |
| 680 | N-(2-fluoro-4-((3-(4-pyrimidinyl)-2-pyridinyl)oxy)phenyl)-N'-(3-(trifluoromethyl)phenyl)urea | 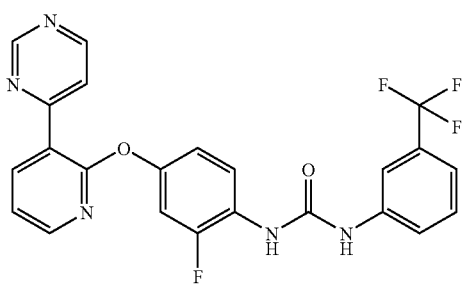 | 469.4 | 470 |
| 681 | N-(4-((3-(4-pyrimidinyl)-2-pyridinyl)oxy)phenyl)-N'-(3-(trifluoromethyl)phenyl)urea | 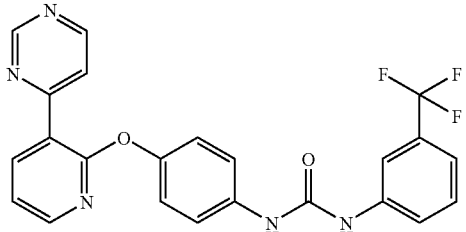 | 451.41 | 452 |
| 682 | N-phenyl-N'-(4-((3-(4-pyrimidinyl)-2-pyridinyl)oxy)phenyl)urea | 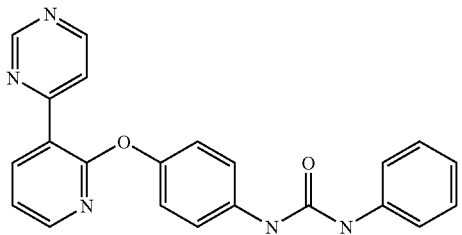 | 383.41 | 384 |
| 683 | 2,3-dichloro-N-(4-((3-(4-pyriinidinyl)-2-pyridinyl)oxy)phenyl)benzenesulfonamide | 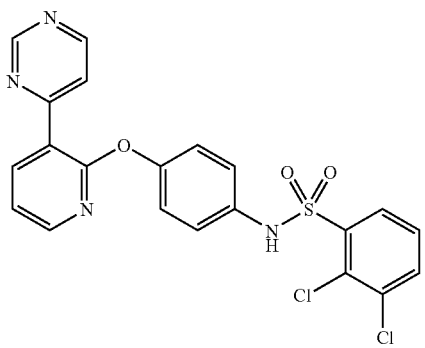 | 473.34 | 473 |

-continued

| Ex. No. | Structure Name | Structure | MW | MS Data |
|---|---|---|---|---|
| 684 | N-(2-fluoro-5-(trifluoromethyl)phenyl)-N'-(4-((3-(4-pyrimidinyl)-2-pyridinyl)oxy)-1-naphthalenyl)urea | 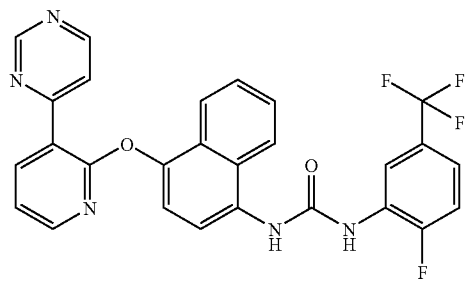 | 519.46 | 520 |
| 685 | N-(3-methyl-4-((3-(4-pyrimidinyl)-2-pyridinyl)oxy)phenyl)-1H-indole-2-carboxamide | 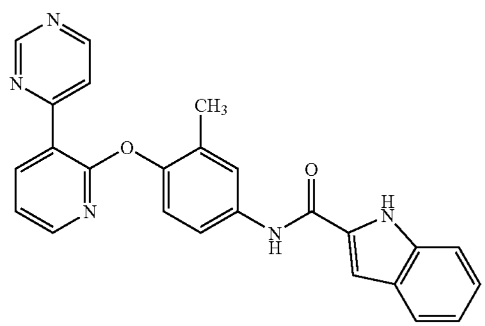 | 421.46 | 422 |
| 686 | N-(3,5-dichloro-4-((3-(4-pyrimidinyl)-2-pyridinyl)oxy)phenyl)-N'-(3-(trifluoromethyl)phenyl)urea | 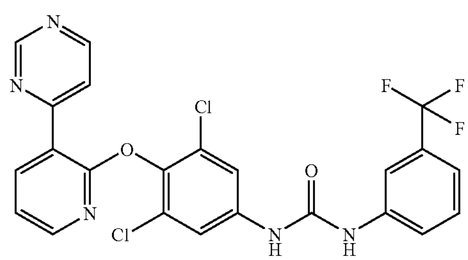 | 520.3 | 520 |
| 687 | N-(2-chloro-5-(trifluoromethyl)phenyl)-N'-(4-((3-(4-pyrimidinyl)-2-pyridinyl)oxy)-1-naphthalenyl)urea | 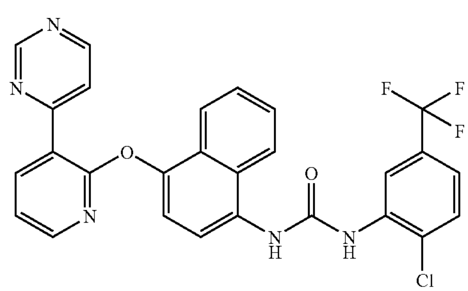 | 535.91 | 558 |
| 688 | N-(8-((3-(4-pyrimidinyl)-2-pyridinyl)oxy)-5-quinouinyl)-N'-(3-(trifluoromethyl)phenyl)urea | 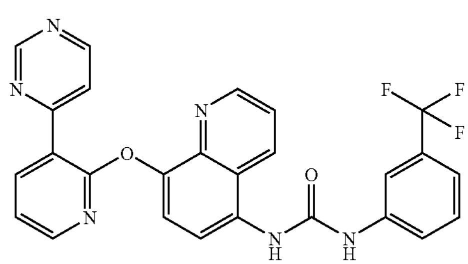 | 502.45 | 503 |

-continued

| Ex. No. | Structure Name | Structure | MW | MS Data |
|---|---|---|---|---|
| 689 | N-(2-chloro-5-(trifluoromethyl)phenyl)-N'-(8-((3-(4-pyrimidinyl)-2-pyridinyl)oxy)-5-quinolinyl)urea | 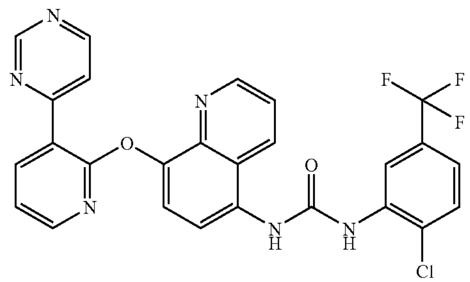 | 536.9 | 537 |
| 690 | 3,5-dichloro-N-(4-methyl-3-((3-(4-pyrimidinyl)-2-pyridinyl)oxy)phenyl)benzamide | 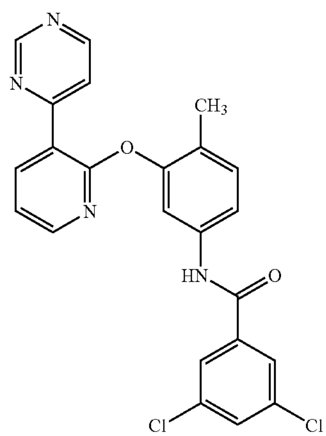 | 451.31 | 473 |
| 691 | 3-chloro-2-fluoro-N-(4-methyl-3-((3-(4-pyrimidinyl)-2-pyridinyl)oxy)phenyl)-5-(trifluoromethyl)benzamide | 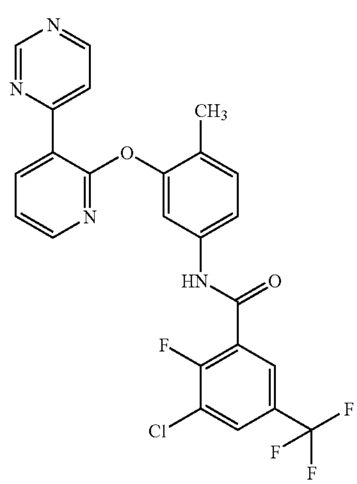 | 502.85 | 503 |

-continued

| Ex. No. | Structure Name | Structure | MW | MS Data |
|---|---|---|---|---|
| 692 | 2-chloro-N-(4-methyl-3-((3-(4-pyrimidinyl)-2-pyridinyl)oxy)phenyl)-5-(trifluoromethyl)benzamide | 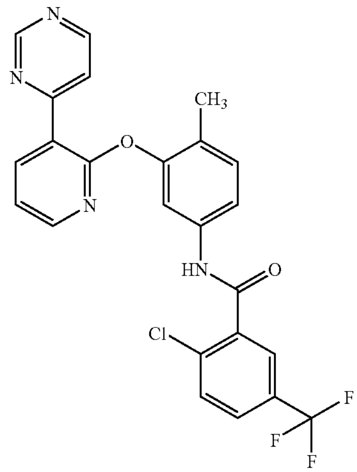 | 484.86 | 485 |
| 693 | 3-(1,1-dimethylethyl)-1-methyl-N-(4-methyl-3-((3-(4-pyrimidinyl)-2-pyridinyl)oxy)phenyl)-1H-pyrazole-5-carboxamide | 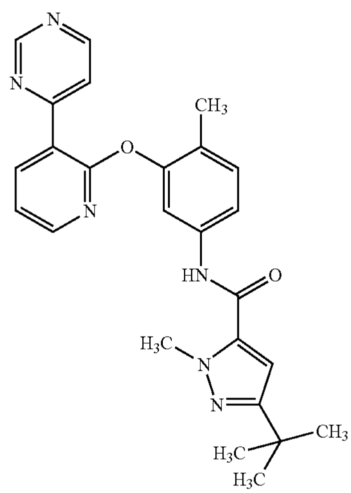 | 442.52 | 443 |
| 694 | N-(4-methyl-3-((3-(4-pyrimidinyl)-2-pyridinyl)oxy)phenyl)-3-((trifluoromethyl)oxy)benzamide | 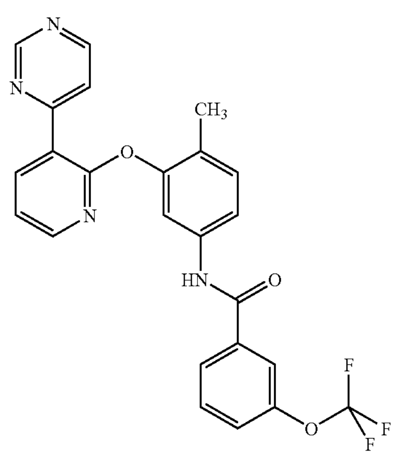 | 466.42 | 467 |

-continued

| Ex. No. | Structure Name | Structure | MW | MS Data |
|---|---|---|---|---|
| 695 | N-(4-methyl-3-((3-(4-pyrimidinyl)-2-pyridinyl)oxy)phenyl)-3,5-bis(trifluoromethyl)benzamide | 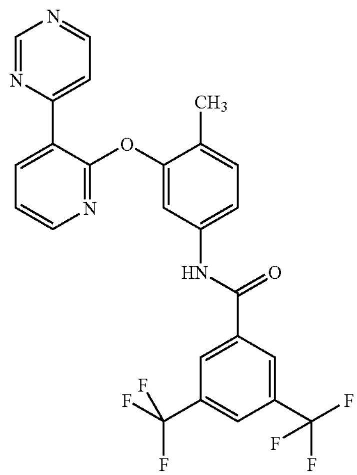 | 518.41 | 519 |
| 696 | N-(3,5-bis(trifluoromethyl)phenyl)-N'-(8-((3-(4-pyrimidinyl)-2-pyridinyl)oxy)-5-quinolinyl)urea | 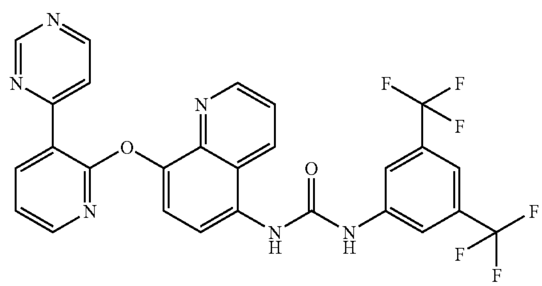 | 570.45 | 571 |
| 697 | N-(8-((3-(4-pyrimidinyl)-2-pyridinyl)oxy)-5-quinolinyl)-N'-(4-(trifluoromethyl)phenyl)urea | 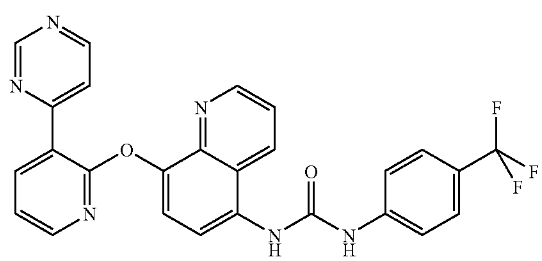 | 502.45 | 503 |
| 698 | N-(8-((3-(4-pyrimidinyl)-2-pyridinyl)oxy)-5-quinolinyl)-2-(3-(trifluoromethyl)phenyl)acetamide | 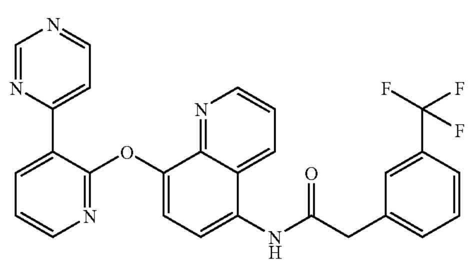 | 501.47 | 502 |
| 699 | N-(3-methyl-4-((3-(4-pyrimidinyl)-2-pyridinyl)oxy)phenyl)-N'-(3-((trifluoromethyl)sulfanyl)phenyl)urea | 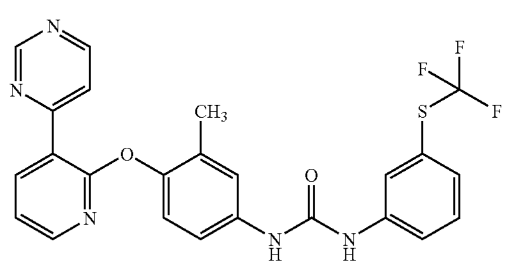 | 497.5 | 498 |

-continued

| Ex. No. | Structure Name | Structure | MW | MS Data |
|---|---|---|---|---|
| 700 | N-(3-bromophenyl)-N'-(3-methyl-4-((3-(4-pyrimidinyl)-2-pyridinyl)oxy)phenyl)urea | 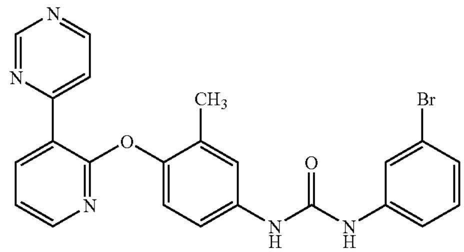 | 476.33 | 476 |
| 701 | N-(2-fluoro-5-(trifluoromethyl)phenyl)-N'-(3-methyl-4-((3-(2-(methylamino)-4-pyrimidinyl)-2-pyridinyl)oxy)phenyl)urea | 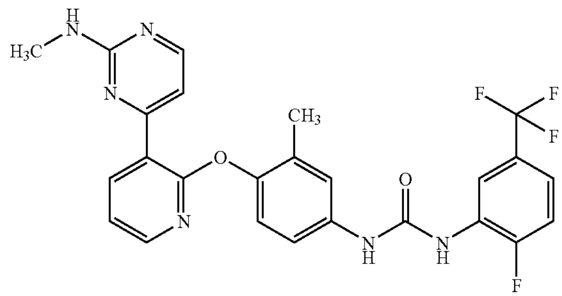 | 512.47 | 513 |
| 702 | N-(3-methyl-4-((3-(2-(methylamino)-4-pyrimidinyl)-2-pyridinyl)oxy)phenyl)-N'-(3-(trifluoroinethyl)phenyl)urea | 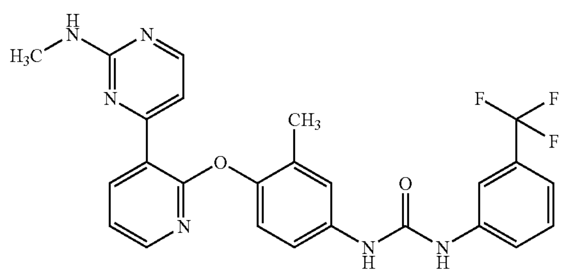 | 494.48 | 495 |
| 703 | N-(5-cyclohexyl-2-(methyloxy)phenyl)-N'-(3-methyl-4-((3-(4-pyrimidinyl)-2-pyridinyl)oxy)phenyl)urea | 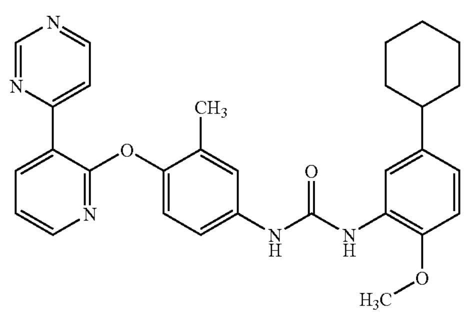 | 509.61 | 510 |
| 704 | N-(4-((3-(4-pyrimidinyl)-2-pyridinyl)oxy)-1-naphthalenyl)benzamide | 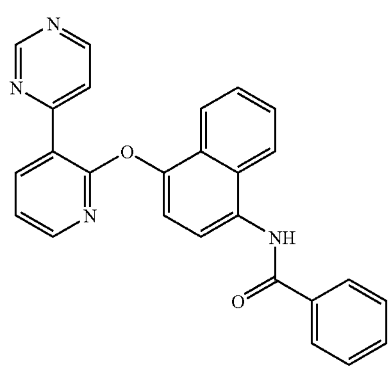 | 418.45 | 419 |

-continued

| Ex. No. | Structure Name | Structure | MW | MS Data |
|---|---|---|---|---|
| 705 | N-(2-fluoro-5-(trifluoromethyl)phenyl)-N'-(4-((3-(2-(methylamino)-4-pyrimidinyl)-2-pyridinyl)oxy)-1-naphthalenyl)urea | 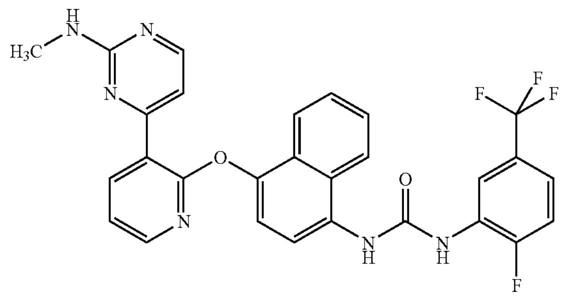 | 548.5 | 549 |
| 706 | N-(2,3-dimethyl-4-((3-(2-methylamino)-4-pyrimidinyl)-2-pyridinyl)oxy)phenyl)-N'-(3-(trifluoromethyl)phenyl)urea | 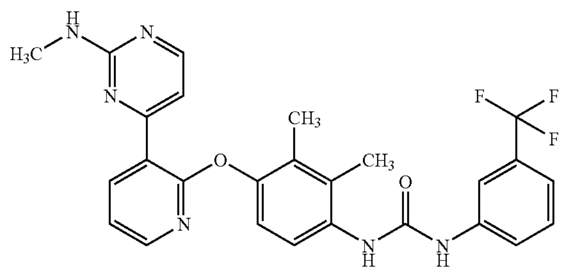 | 508.5 | 509 |
| 707 | N-(2,3-dimethyl-4-((3-(2-(methylamino)-4-pyrimidinyl)-2-pyridinyl)oxy)phenyl)-N'-(2-fluoro-5-(trifluoromethyl)phenyl)urea | 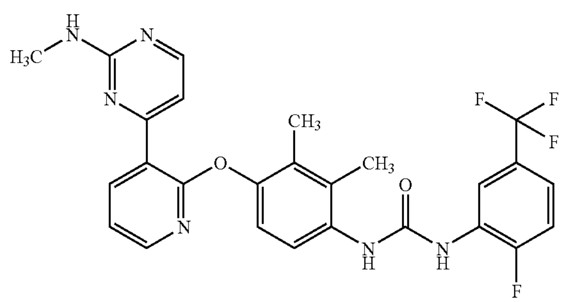 | 526.49 | 527 |
| 708 | N-(3,5-bis(trifluoromethyl)phenyl)-N'-(2,3-dimethyl-4-((3-(2-(methylamino)-4-pyrimidinyl)-2-pyridinyl)oxy)phenyl)urea | 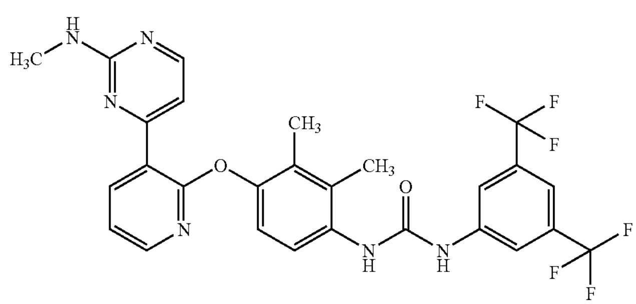 | 576.5 | 577 |
| 709 | N-butyl-N'-(3-methyl-4-((3-(4-pyrimidinyl)-2-pyridinyl)oxy)phenyl)urea | 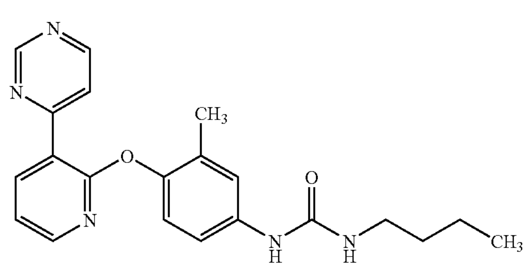 | 377.45 | 378 |

-continued

| Ex. No. | Structure Name | Structure | MW | MS Data |
|---|---|---|---|---|
| 710 | N-(2-fluoro-5-(trifluoromethyl)phenyl)-N'-(4-((3-(4-(methylamino)-1,3,5-triazin-2-yl)-2-pyridinyl)oxy)-1-naphthalenyl)urea | 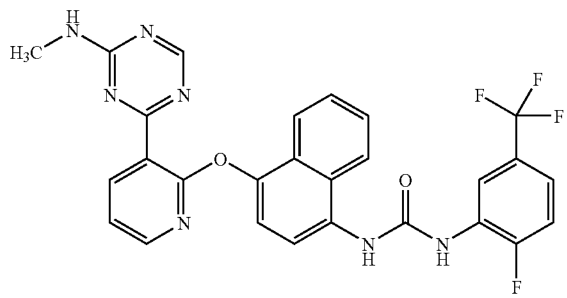 | 549.49 | 550 |
| 711 | 5-(1,1-dimethylethyl)-2-(methyloxy)-N-(4-methyl-3-((3-(4-pyrimidinyl)-2-pyridinyl)oxy)phenyl)benzamide | 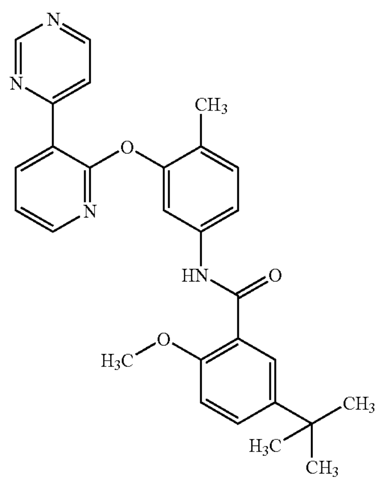 | 468.55 | 469 |
| 712 | 5-(1,1-dimethylethyl)-N-(4-methyl-3-((3-(2-(methylamino)-4-pyrimidinyl)-2-pyridinyl)oxy)phenyl)-2-(methyloxy)benzamide | 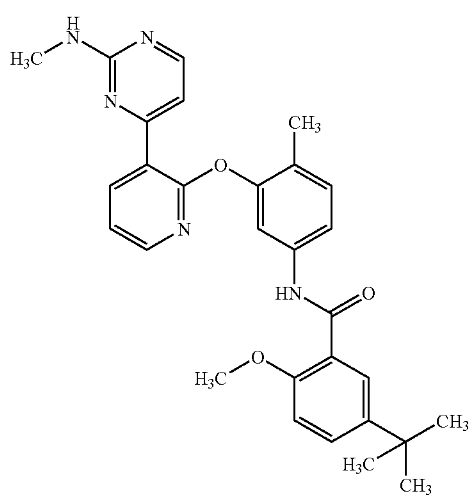 | 497.6 | 498 |

-continued

| Ex. No. | Structure Name | Structure | MW | MS Data |
|---|---|---|---|---|
| 713 | N-(4-methyl-3-((3-(2-(methylamino)-4-pyrimidinyl)-2-pyridinyl)oxy)phenyl)-3-((trifluoromethyl)oxy)benzamide | 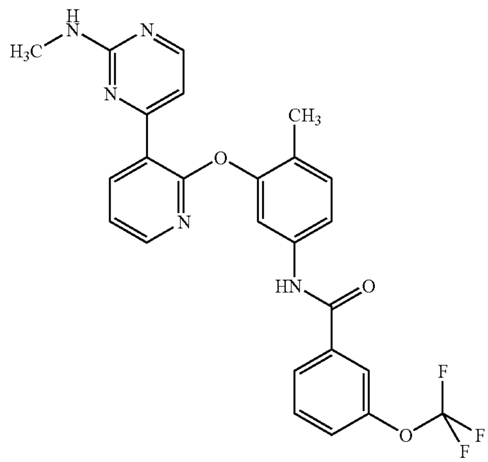 | 495.46 | 496 |
| 714 | N-(4-methyl-3-((3-(4-(methylamino)-1,3,5-triazin-2-yl)-2-pyridinyl)oxy)phenyl)-3-((trifluoromethyl)oxy)benzamide | 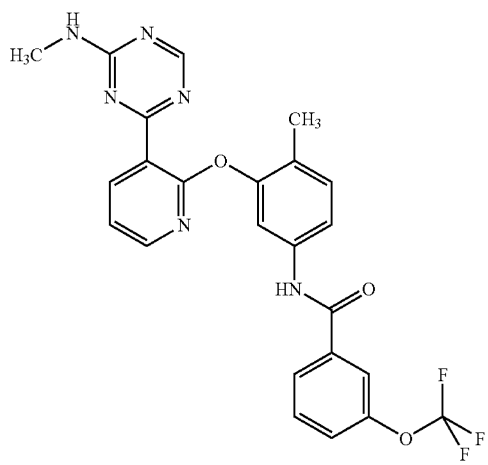 | 496.45 | 497 |
| 715 | 5-(1,1-dimethylethyl)-N-(4-methyl-3-((3-(4-(methylamino)-1,3,5-triazin-2-yl)-2-pyridinyl)oxy)phenyl)-2-(methyloxy)benzamide | 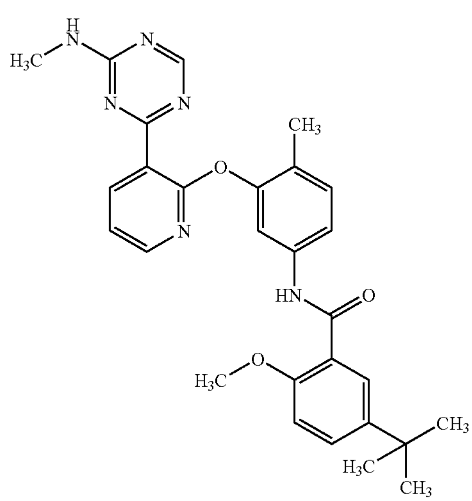 | 498.58 | 499 |

| Ex. No. | Structure Name | Structure | MW | MS Data |
|---|---|---|---|---|
| 716 | N-(4-methyl-3-((3-(2-(methylamino)-4-pyrimidinyl)-2-pyridinyl)oxy)phenyl)-3-((1,1,2,2-tetrafluoroethyl)oxy)benzamide | 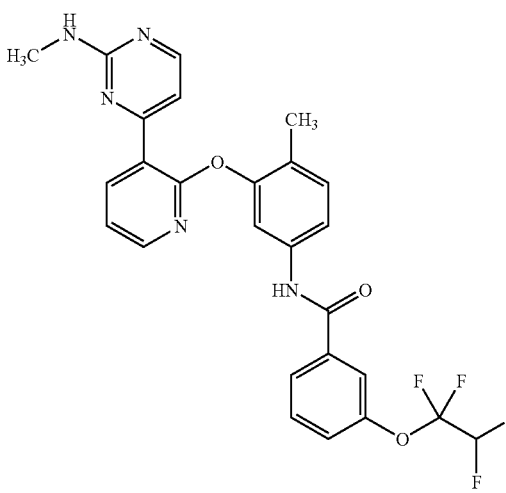 | 527.48 | 528 |
| 717 | N-(4-methyl-3-((3-(4-(methylamino)-1,3,5-triazin-2-yl)-2-pyridinyl)oxy)phenyl)-3-((1,1,2,2-tetrafluoroethyl)oxy)benzamide | 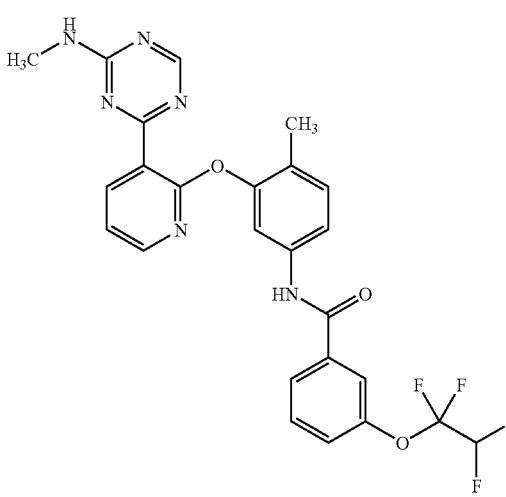 | 528.46 | 529 |
| 718 | N-(4-methyl-3-((3-(2-(methylamino)-4-pyrimidinyl)-2-pyridinyl)oxy)phenyl)-3-(trifluoromethyl)benzenesulfonamide | 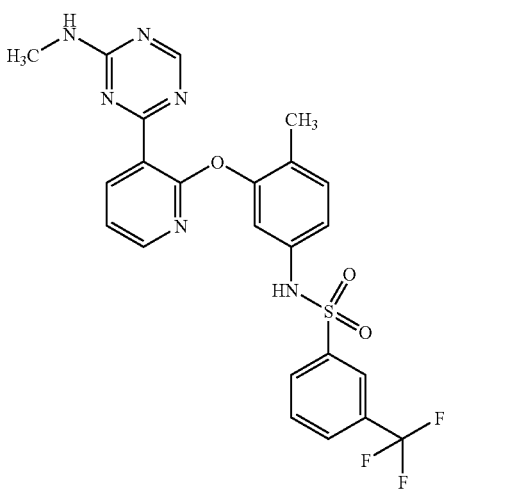 | 515.51 | 516 |

-continued

| Ex. No. | Structure Name | Structure | MW | MS Data |
|---|---|---|---|---|
| 719 | 2,3-dichloro-N-(4-methyl-3-((3-(2-(methylamino)-4-pyrimidinyl)-2-pyridinyl)oxy)phenyl)benzenesulfonamide | 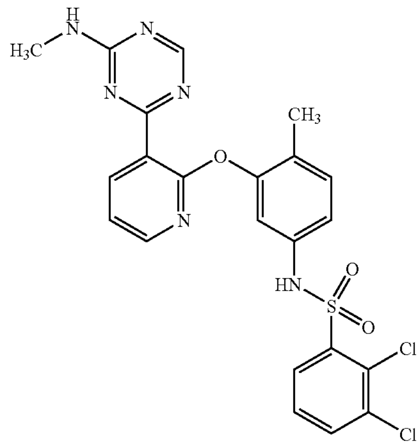 | 516.41 | 516 |
| 720 | 2-chloro-N-(4-methyl-3-((3-(2-(methylamino)-4-pyrimidinyl)-2-pyridinyl)oxy)phenyl)-5-(trifluoromethyl)benzamide | 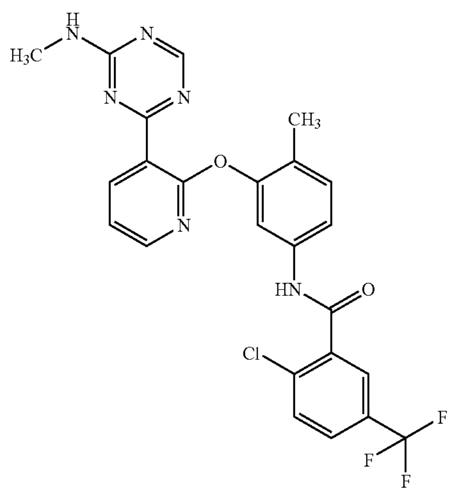 | 513.9 | 514 |
| 721 | 3-(1,1-dimethylethyl)-1-methyl-N-(4-methyl-3-((3-(2-(methylamino)-4-pyrimidinyl)-2-pyridinyl)oxy)phenyl)-1H-pyrazole-5-carboxamide | 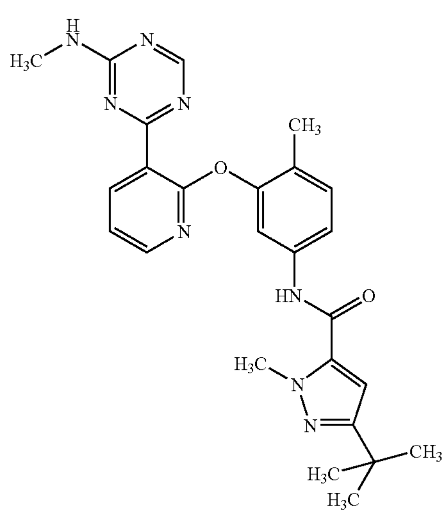 | 471.56 | 472 |

| Ex. No. | Structure Name | Structure | MW | MS Data |
|---|---|---|---|---|
| 722 | N-(4-methyl-3-((3-(4-(methylamino)-1,3,5-triazin-2-yl)-2-pyridinyl)oxy)phenyl)-3-(trifluoromethyl)benzamide | 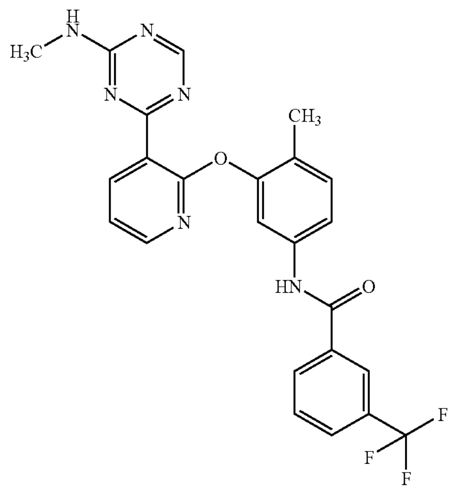 | 480.45 | 481 |
| 723 | 2-fluoro-N-(4-methyl-3-((3-(4-(methylamino)-1,3,5-triazin-2-yl)-2-pyridinyl)oxy)phenyl)-5-(trifluoromethyl)benzamide | 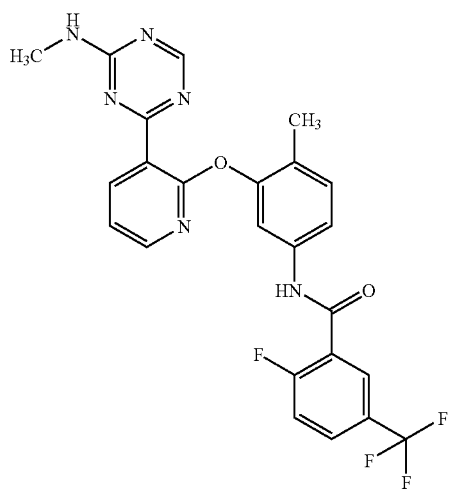 | 498.44 | 499 |
| 724 | N-(4-methyl-3-((3-(4-(methylamino)-1,3,5-triazin-2-yl)-2-pyridinyl)oxy)phenyl)-3-(1H-pyrrol-1-yl)benzamide | 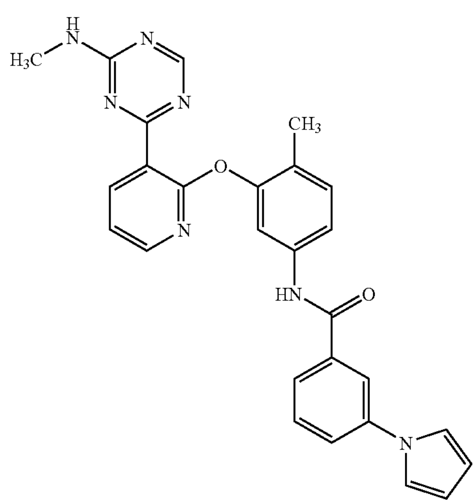 | 477.53 | 478 |

-continued

| Ex. No. | Structure Name | Structure | MW | MS Data |
|---|---|---|---|---|
| 725 | N-(4-methyl-3-((3-(4-(methylamino)-1,3,5-triazin-2-yl)-2-pyridinyl)oxy)phenyl)-2-(3-(trifluoromethyl)phenyl)acetamide | 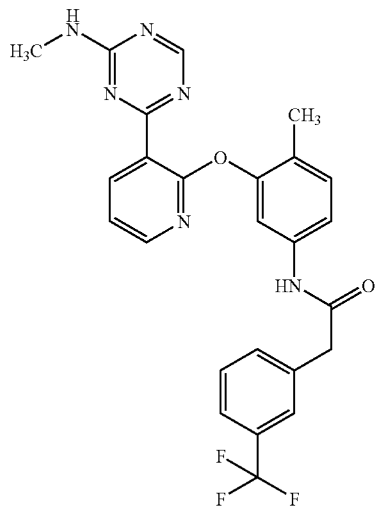 | 494.48 | 495 |
| 726 | N-(2-chloro-5-((3-(4-(methylamino)-1,3,5-triazin-2-yl)-2-pyridinyl)oxy)phenyl)-N'-(3-(trifluoromethyl)phenyl)urea | 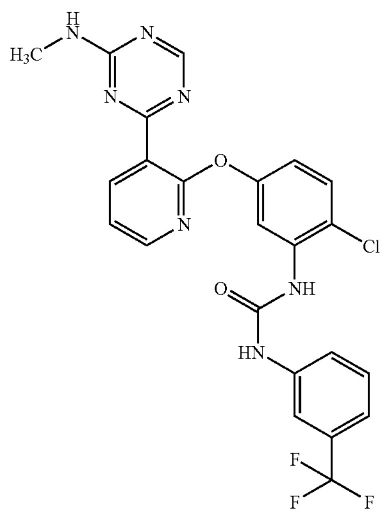 | 515.88 | 515 |
| 727 | N-(2-chloro-5-((3-(4-(methylamino)-1,3,5-triazin-2-yl)-2-pyridinyl)oxy)phenyl)-3-(trifluoromethyl)benzamide | 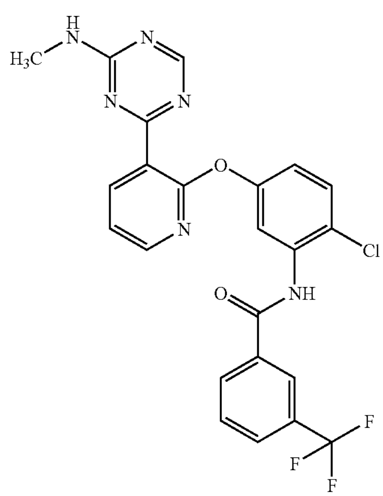 | 500.87 | 500 |

| Ex. No. | Structure Name | Structure | MW | MS Data |
|---|---|---|---|---|
| 728 | N-(4-methyl-3-((3-(4-(methylamino)-1,3,5-triazin-2-yl)-2-pyridinyl)oxy)phenyl)-3-(phenyloxy)benzamide | 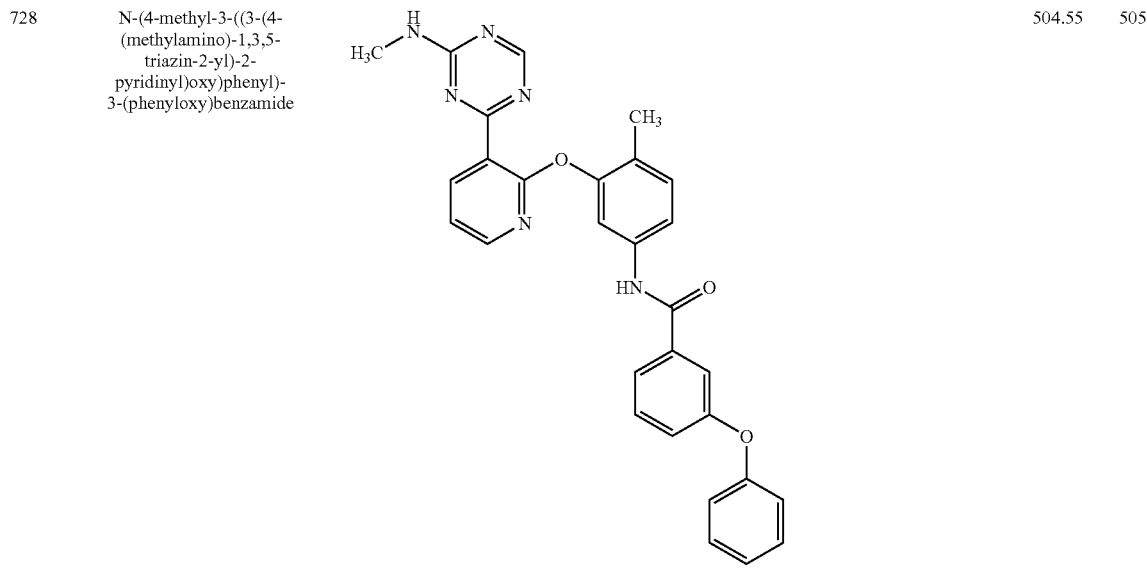 | 504.55 | 505 |
| 729 | N-(2-chloro-5-((3-(2-(methylamino)-4-pyrimidinyl)-2-pyridinyl)oxy)phenyl)-3-((1,1,2,2-tetrafluoroethyl)oxy)benzamide | 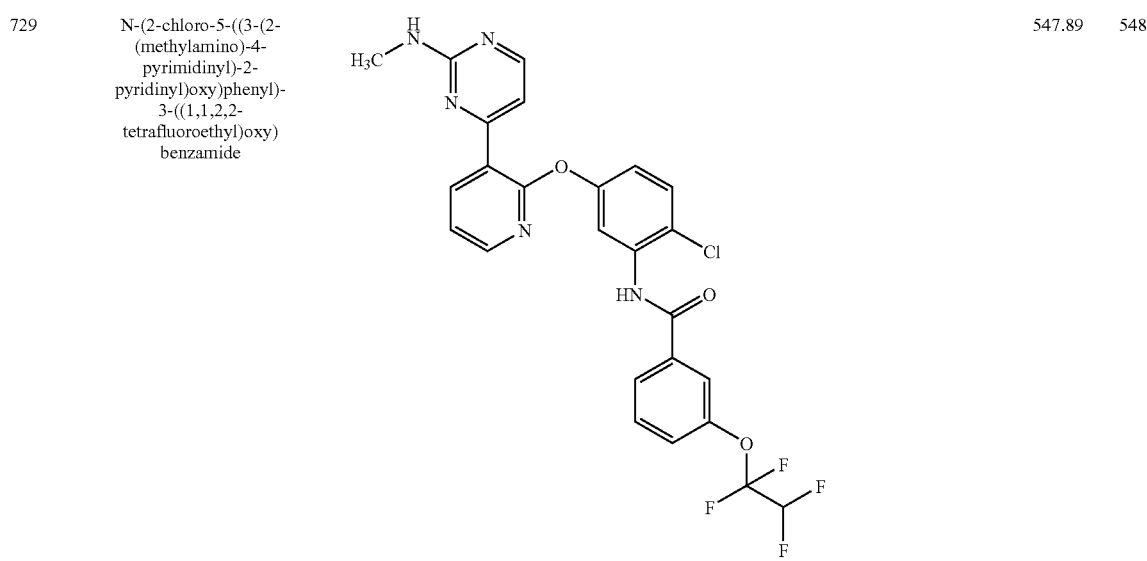 | 547.89 | 548 |

| Ex. No. | Structure Name | Structure | MW | MS Data |
|---|---|---|---|---|
| 730 | 2-bromo-N-(4-methyl-3-((3-(2-(methylamino)-4-pyrimidinyl)-2-pyridinyl)oxy)phenyl)-5-(methyloxy)benzamide | 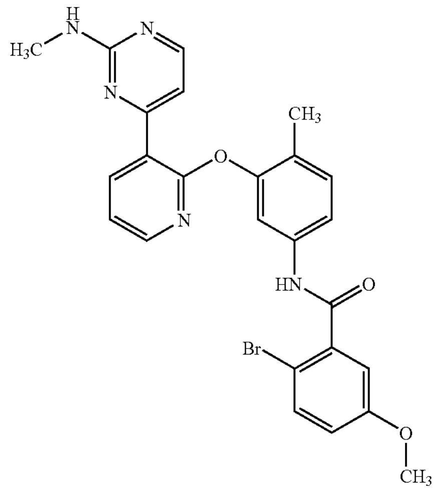 | 520.38 | 520 |
| 731 | N-(2-chloro-5-((3-(4-(methylamino)-1,3,5-triazin-2-yl)-2-pyridinyl)oxy)phenyl)-3-((1,1,2,2-tetrafluoroethyl)oxy)benzamide | 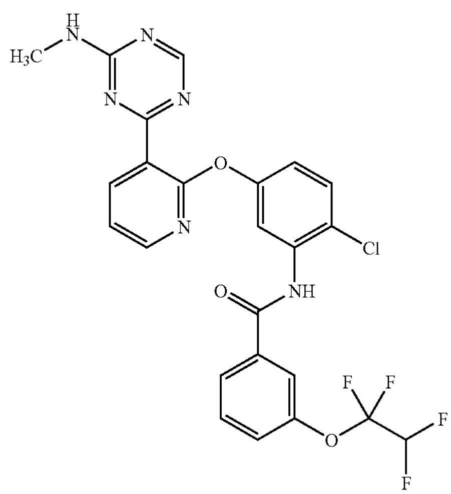 | 548.88 | 549 |
| 732 | 2-chloro-N-(2-chloro-5-((3-(4-(methylamino)-1,3,5-triazin-2-yl)-2-pyridinyl)oxy)phenyl)-5-(trifluoromethyl)benzamide | 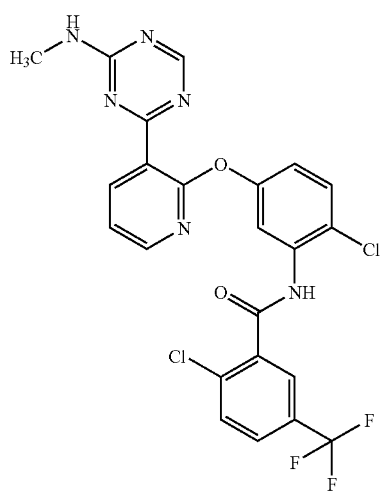 | 535.31 | 535 |

-continued

| Ex. No. | Structure Name | Structure | MW | MS Data |
|---|---|---|---|---|
| 733 | N-(2-chloro-5-((3-(2-(methylamino)-4-pyrimidinyl)-2-pyridinyl)oxy)phenyl)-3-(trifluoromethyl)benzamide | 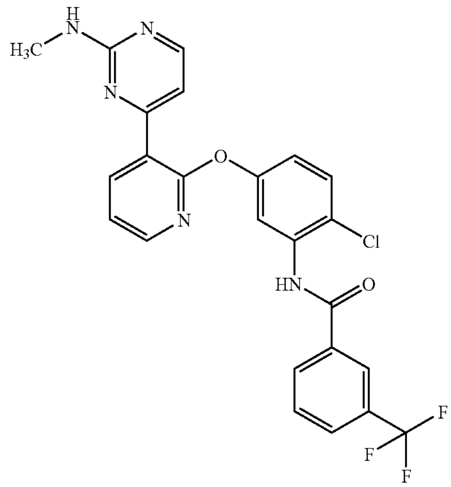 | 499.88 | 500 |
| 734 | N-(2-chloro-5-((3-(4-(methylamino)-1,3,5-triazin-2-yl)-2-pyridinyl)oxy)phenyl)-N'-(4-(trifluoromethyl)phenyl)urea | 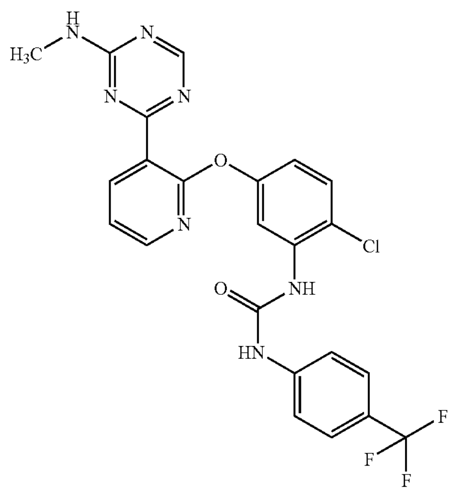 | 515.88 | 516 |
| 735 | 2-chloro-N-(2-chloro-5-((3-(2-(methylamino)-4-pyrimidinyl)-2-pyridinyl)oxy)phenyl)-5-(trifluoromethyl)benzamide | 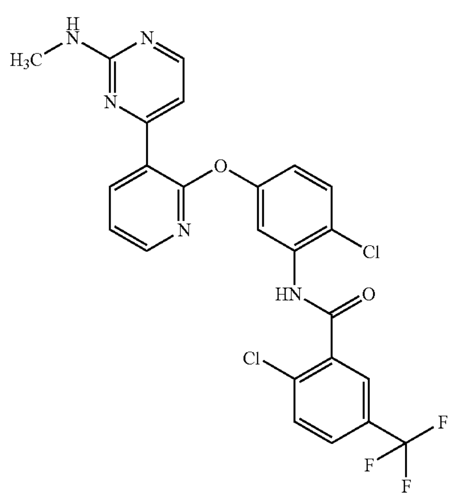 | 534.32 | 534 |

-continued

| Ex. No. | Structure Name | Structure | MW | MS Data |
|---|---|---|---|---|
| 736 | N-(3-((3-(4-(methylamino)-1,3,5-triazin-2-yl)-2-pyridinyl)oxy)phenyl)-3-(1H-pyrrol-1-yl)benzamide | 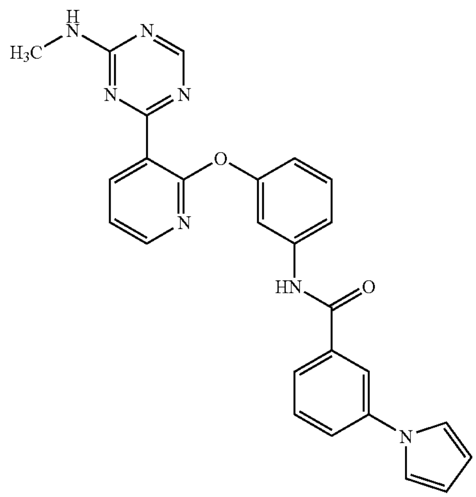 | 463.5 | 464 |
| 737 | N-(3-((3-(4-(methylamino)-1,3,5-triazin-2-yl)-2-pyridinyl)oxy)phenyl)-3-(trifluoromethyl)benzamide | 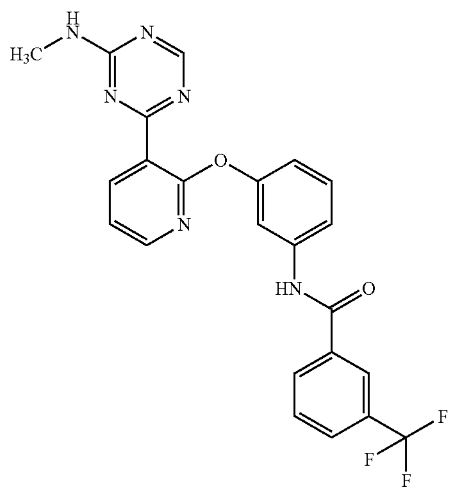 | 466.42 | 467 |
| 738 | N-(2,4-dichloro-5-((3-(2-(methylamino)-4-pyrimidinyl)-2-pyridinyl)oxy)phenyl)-3-((1,1,2,2-tetrafluoroethyl)oxy)benzamide | 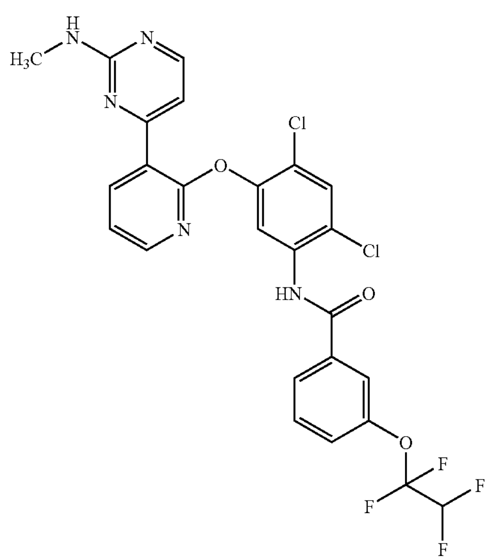 | 582.34 | 582 |

| Ex. No. | Structure Name | Structure | MW | MS Data |
|---|---|---|---|---|
| 739 | 2-bromo-N-(2-chloro-5-((3-(2-(methylamino)-4-pyrimidinyl)-2-pyridinyl)oxy)phenyl)-5-(methyloxy)benzamide | 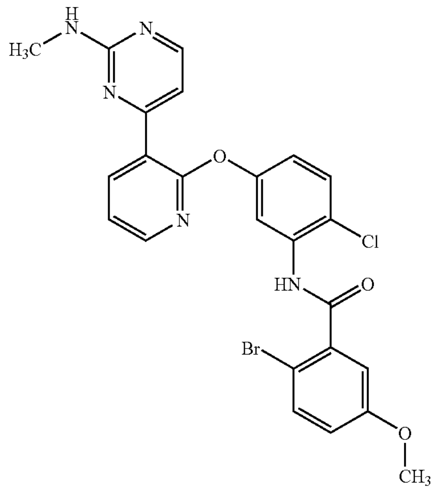 | 540.8 | 542 |
| 740 | 5-(1,1-dimethylethyl)-N-(3-((3-(4-(methylamino)-1,3,5-triazin-2-yl)-2-pyridinyl)oxy)phenyl)-2-(methyloxy)benzamide | 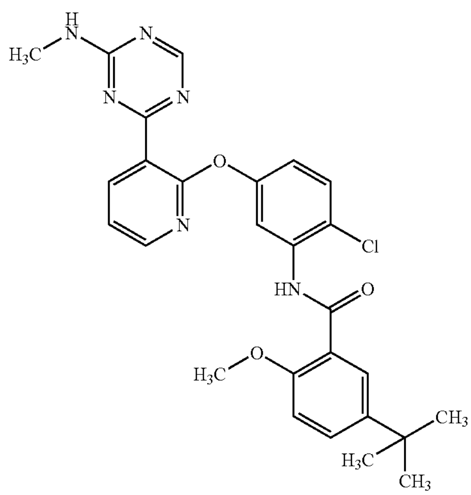 | 484.56 | 485 |
| 741 | 2-fluoro-N-(3-((3-(4-(methylamino)-1,3,5-triazin-2-yl)-2-pyridinyl)oxy)phenyl)-5-(trifluoromethyl)benzamide | 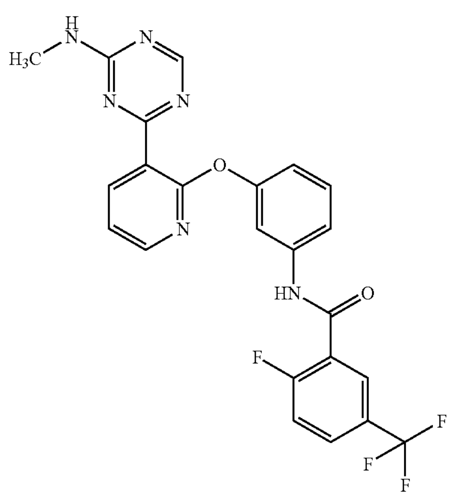 | 484.41 | 485 |

-continued

| Ex. No. | Structure Name | Structure | MW | MS Data |
|---|---|---|---|---|
| 742 | N-(2-methyl-3-((3-(2-(methylamino)-4-pyrimidinyl)-2-pyridinyl)oxy)phenyl)-3-((1,1,2,2-tetrafluoroethyl)oxy)benzamide | 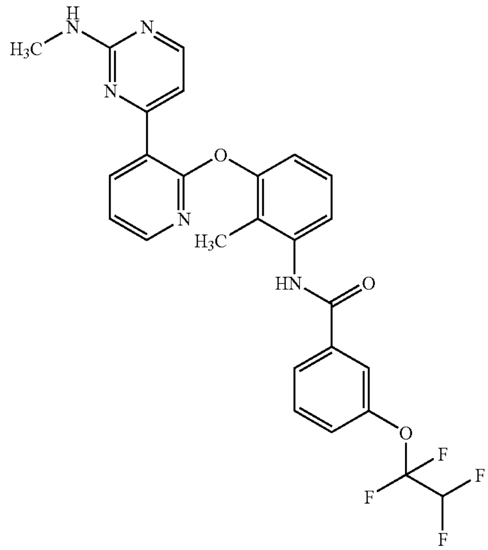 | 527.48 | 528 |
| 743 | 2-chloro-N-(2-methyl-3-((3-(2-(methylamino)-4-pyrimidinyl)-2-pyridinyl)oxy)phenyl)-5-(trifluoromethyl)benzamide | 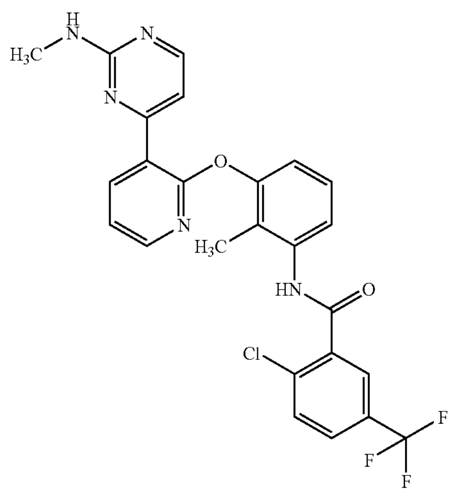 | 513.9 | 514 |
| 744 | N-(4-methyl-3-((2'-(methylamino)-3,4'-bipyridin-2-yl)oxy)phenyl)-3-((1,1,2,2-tetrafluoroethyl)oxy)benzamide | 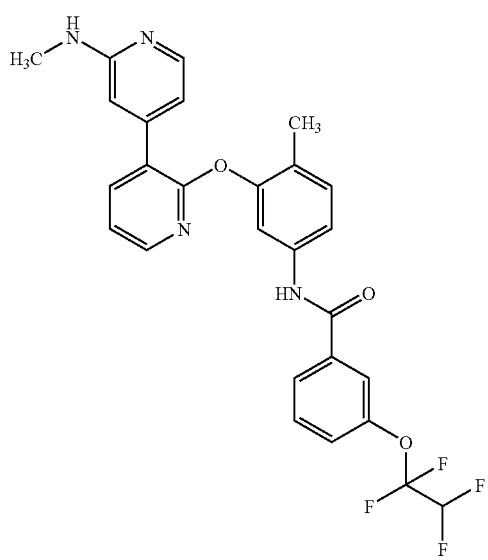 | 526.49 | 527 |

| Ex. No. | Structure Name | Structure | MW | MS Data |
|---|---|---|---|---|
| 745 | 5-(1,1-dimethylethyl)-N-(4-methyl-3-((2'-(methylamino)-3,4'-bipyridin-2-yl)oxy)phenyl)-2-(methyloxy)benzamide | 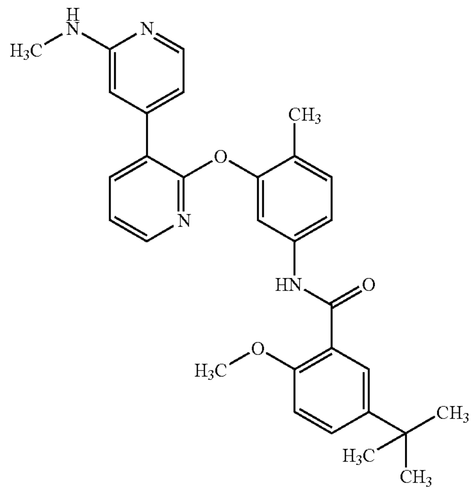 | 496.61 | 497 |
| 746 | 2-chloro-N-(2,4-dichloro-5-((3-(2-(methylamino)-4-pyrimidinyl)-2-pyridinyl)oxy)phenyl)-5-(trifluoromethyl)benzamide | 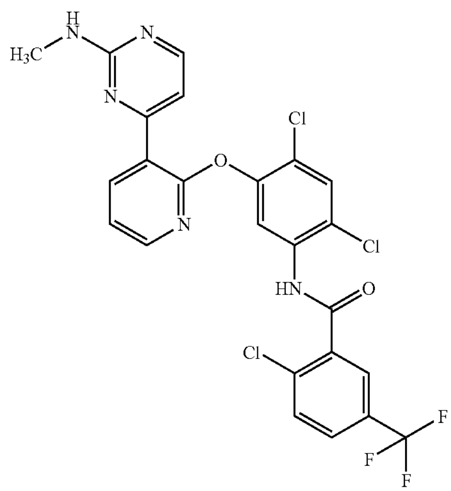 | 568.77 | 567 |
| 747 | N-(4-methyl-3-((3-(4-(methylamino)-1,3,5-triazin-2-yl)-2-pyridinyl)oxy)phenyl)-2-(4-(trifluoromethyl)phenyl)acetamide | 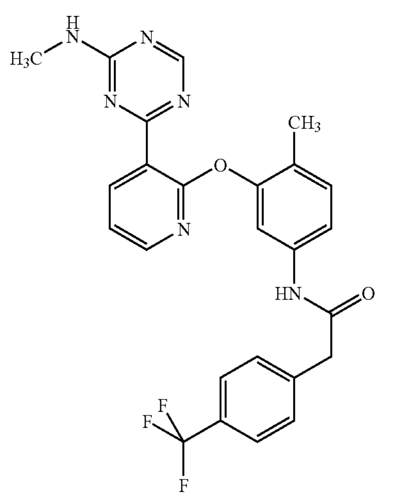 | 494.48 | 495 |

-continued

| Ex. No. | Structure Name | Structure | MW | MS Data |
|---|---|---|---|---|
| 748 | N-(4-methyl-3-((3-(4-(methylamino)-1,3,5-triazin-2-yl)-2-pyridinyl)oxy)phenyl)-2-(2-(trifluoromethyl)phenyl) acetamide | 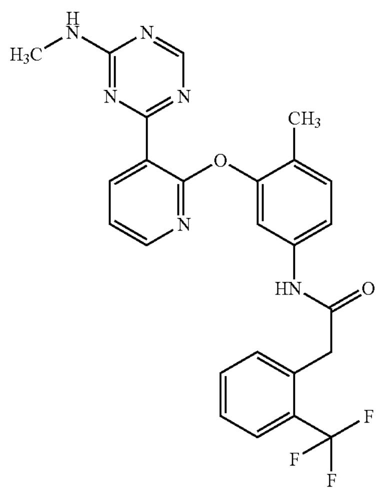 | 494.48 | 495 |
| 749 | 5-(1,1-dimethylethyl)-N-(3-((2'-(methylamino)-3,4'-bipyridin-2-yl)oxy)phenyl)-2-(methyloxy)benzamide | 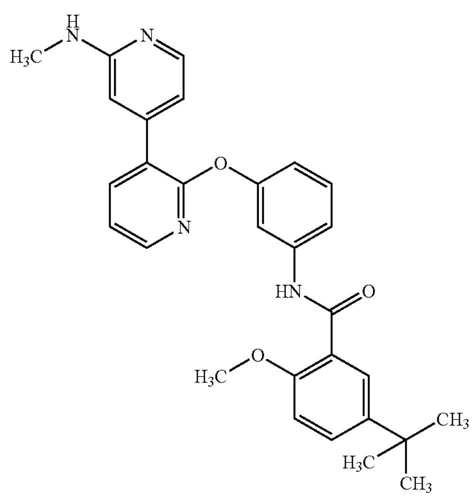 | 482.58 | 483 |
| 750 | N-(3-((2'-(methylamino)-3,4'-bipyridin-2-yl)oxy)phenyl)-3-((1,1,2,2-tetrafluoroethyl)oxy) benzamide | 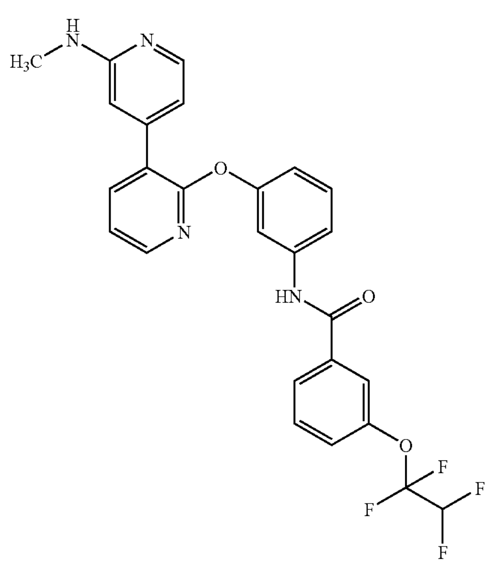 | 512.46 | 513 |

| Ex. No. | Structure Name | Structure | MW | MS Data |
|---|---|---|---|---|
| 751 | 3,5-dichloro-N-(4-methyl-3-((3-(2-(methylamino)-4-pyrimidinyl)-2-pyridinyl)oxy)phenyl)benzamide | 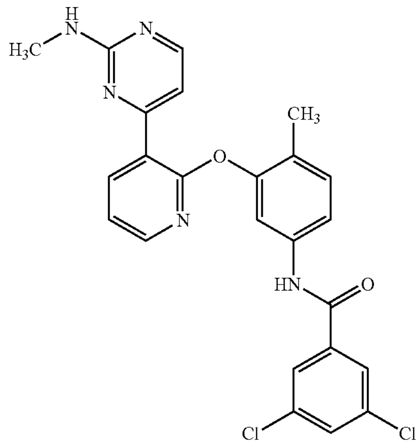 | 480.35 | 481 |
| 752 | 5-(1,1-dimethylethyl)-N-(3-((3-(2-(methylamino)-4-pyrimidinyl)-2-pyridinyl)oxy)-5-(trifluoromethyl)phenyl)-2-(methyloxy)benzamide | 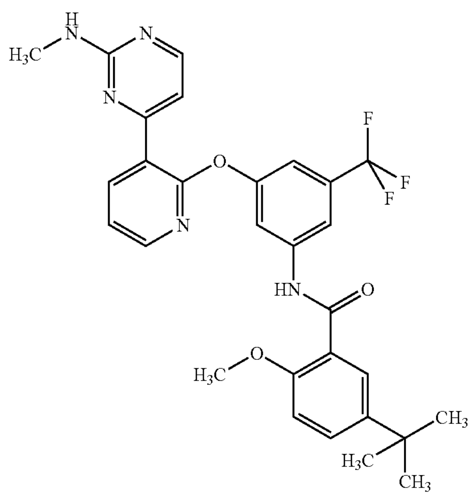 | 551.57 | 552 |
| 753 | N-(3-((3-(2-(methylamino)-4-pyrimidinyl)-2-pyridinyl)oxy)-5-(trifluoromethyl)phenyl)-3-((1,1,2,2,-tetrafluoroethyl)oxy)benzamide | 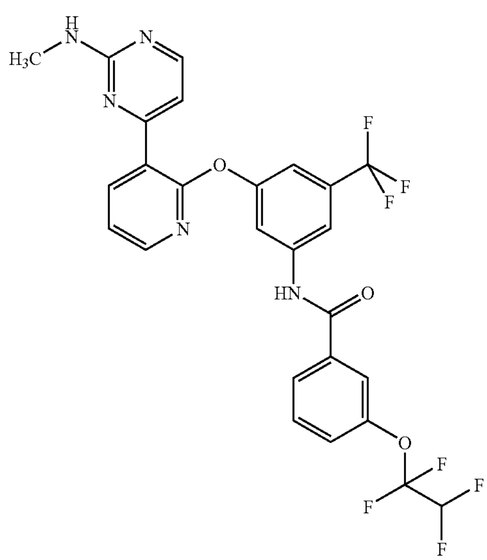 | 581.45 | 582 |

-continued

| Ex. No. | Structure Name | Structure | MW | MS Data |
|---|---|---|---|---|
| 754 | 3,5-dichloro-N-(3-((3-(2-(methylamino)-4-pyrimidinyl)-2-pyridinyl)oxy)-5-(trifluoromethyl)phenyl)benzamide | 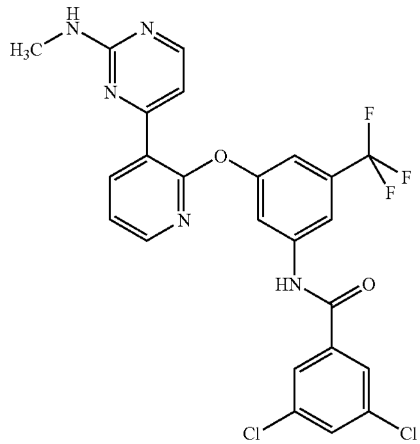 | 534.32 | 534 |
| 755 | N-(3-((3-(2-(methylamino)-4-pyrimidinyl)-2-pyridinyl)oxy)-5-(trifluoromethyl)phenyl)-3-(trifluoromethyl)benzamide | 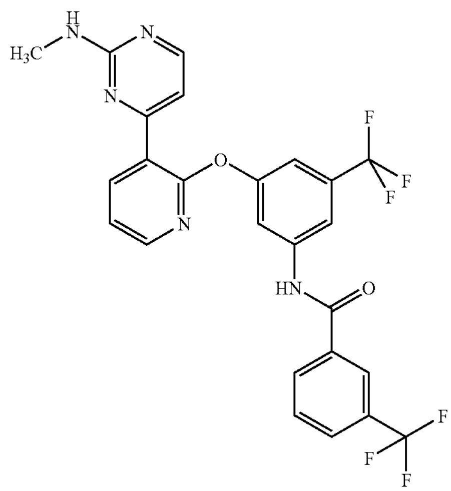 | 533.43 | 534 |
| 756 | 3-(1-methylethyl)-N-(4-methyl-3-((2'-(methylamino)-3,4'-bipyridin-2-yl)oxy)phenyl)benzamide | 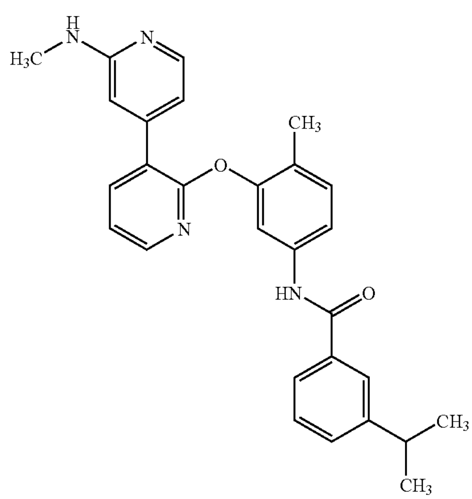 | 452.56 | 453 |

| Ex. No. | Structure Name | Structure | MW | MS Data |
|---|---|---|---|---|
| 757 | N-(3-((3-(4-(methylamino)-1,3,5-triazin-2-yl)-2-pyridinyl)oxy)phenyl)-3-(trifluoromethyl)benzamide | 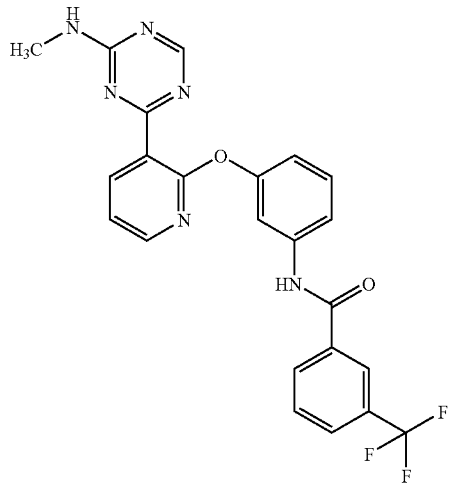 | 466.42 | 467 |
| 758 | N-(3-((3-(2-(methylamino)-4-pyrimidinyl)-2-pyridinyl)oxy)-5-(trifluoromethyl)phenyl)-3-(1-methylethyl)benzamide | 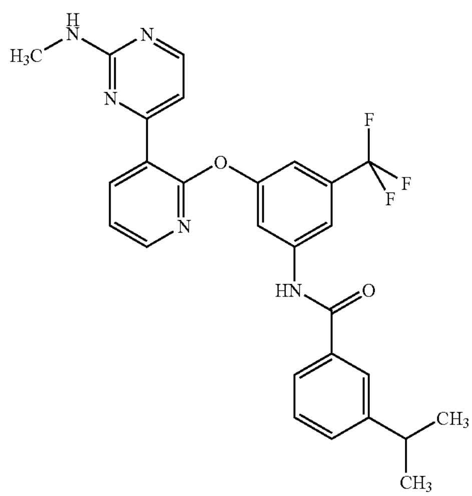 | 507.51 | 508 |
| 759 | N-(2-chloro-5-((2'-(methylamino)-3,4'-bipyridin-2-yl)oxy)phenyl)-2-fluoro-5-(trifluoromethyl)benzamide | 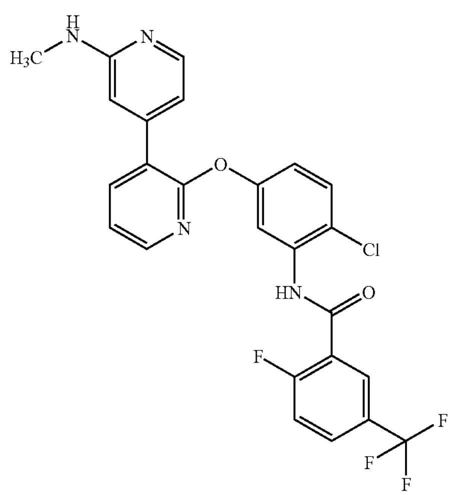 | 516.88 | 517 |

| Ex. No. | Structure Name | Structure | MW | MS Data |
|---|---|---|---|---|
| 760 | N-(3-((2'-(methylamino)-3,4'-bipyridin-2-yl)oxy)phenyl)-3-(1-methylethyl)benzamide | 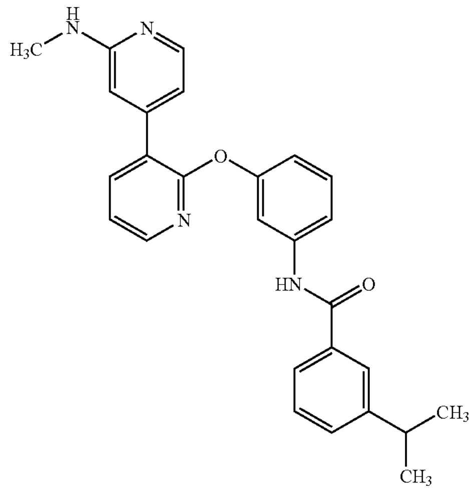 | 438.53 | 439 |
| 761 | N-(3-((3-(4-(methylamino)-1,3,5-triazin-2-yl)-2-pyridinyl)oxy)phenyl)-3-(1-methylethyl)benzamide | 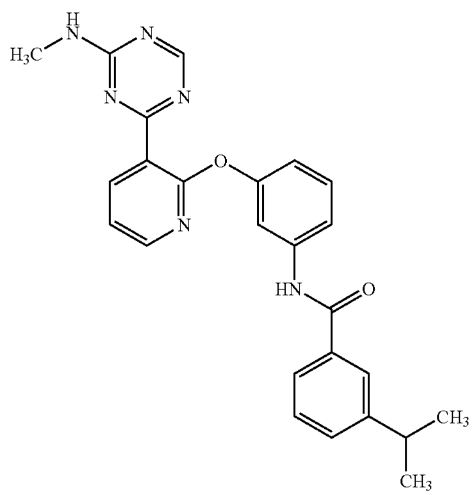 | 440.51 | 441 |
| 762 | N-(3-((3-(4-(methylamino)-1,3,5-triazin-2-yl)-2-pyridinyl)oxy)-5-(trifluoromethyl)phenyl)-3-(1-methylethyl)benzamide | 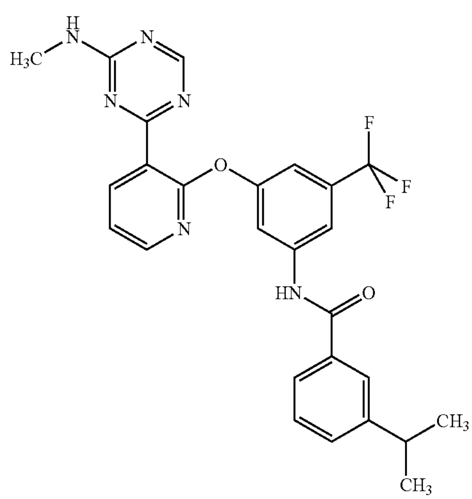 | 508.5 | 509 |

-continued

| Ex. No. | Structure Name | Structure | MW | MS Data |
|---|---|---|---|---|
| 763 | 3-(1-methylethyl)-N-(4-methyl-3-((3-(2-(methylamino)-4-pyrimidinyl)-2-pyridinyl)oxy)phenyl)benzamide | 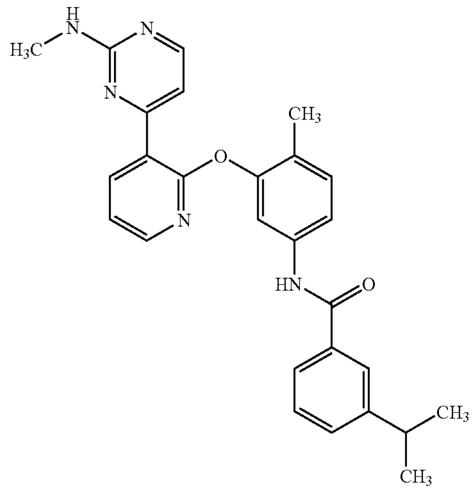 | 453.54 | 454 |
| 764 | 3-(1-methylethyl)-N-(4-methyl-3-((3-(4-(methylamino)-1,3,5-triazin-2-yl)-2-pyridinyl)oxy)phenyl)benzamide | 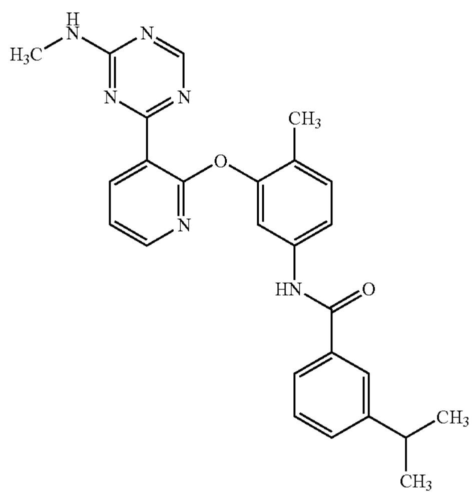 | 454.53 | 455 |
| 765 | N-(3-((3-(2-(methylamino)-4-pyrimidinyl)-2-pyridinyl)oxy)phenyl)-3-(1-methylethyl)benzamide | 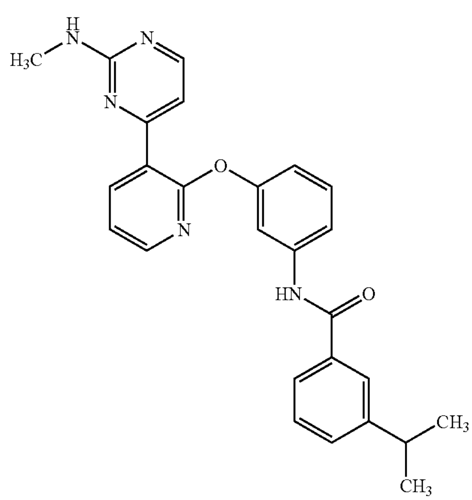 | 439.52 | 440 |

-continued

| Ex. No. | Structure Name | Structure | MW | MS Data |
|---|---|---|---|---|
| 766 | 5-(1,1-dimethylethyl)-N-(3-((3-(2-(methylamino)-4-pyrimidinyl)-2-pyridinyl)oxy)phenyl)-2-(methyloxy)benzamide | 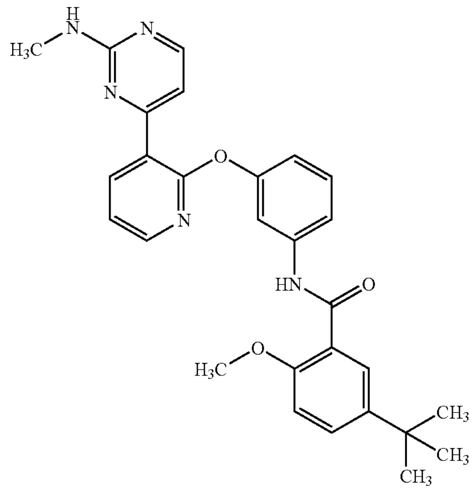 | 483.57 | 484 |
| 767 | N-(3-((3-(2-(methylamino)-4-pyrimidinyl)-2-pyridinyl)oxy)phenyl)-3-((1,1,2,2-tetrafluoroethyl)oxy)benzamide | 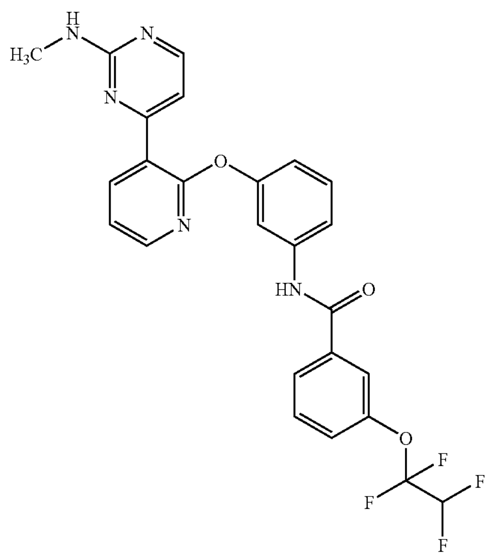 | 513.45 | 514 |
| 768 | 3,5-dichloro-N-(3-((3-(2-(methylamino)-4-pyrimidinyl)-2-pyridinyl)oxy)phenyl)benzamide | 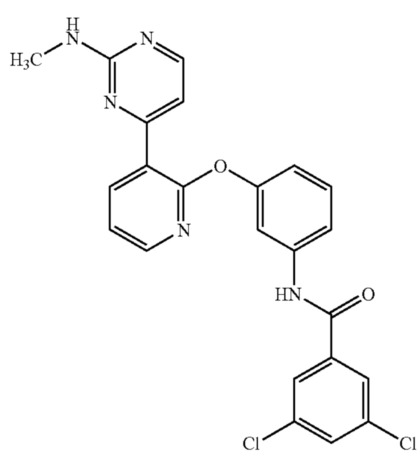 | 466.33 | 466 |

-continued

| Ex. No. | Structure Name | Structure | MW | MS Data |
|---|---|---|---|---|
| 769 | N-(3-((2'-(methylamino)-3,4'-bipyridin-2-yl)oxy)-5-(trifluoromethyl)phenyl)-3-(1-methylethyl)benzamide | 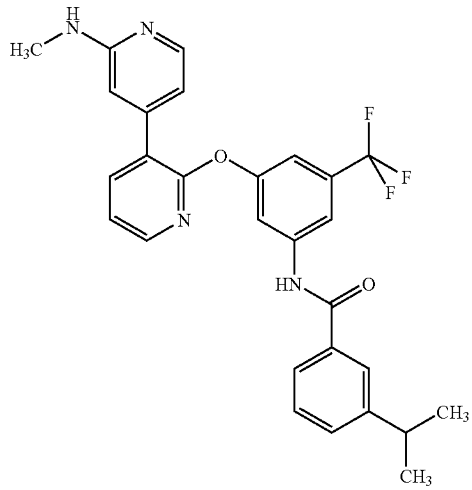 | 506.53 | 506 |
| 770 | 3-(dimethylamino)-N-(4-methyl-3-((2'-(methylamino)-3,4'-bipyridin-2-yl)oxy)phenyl)benzamide | 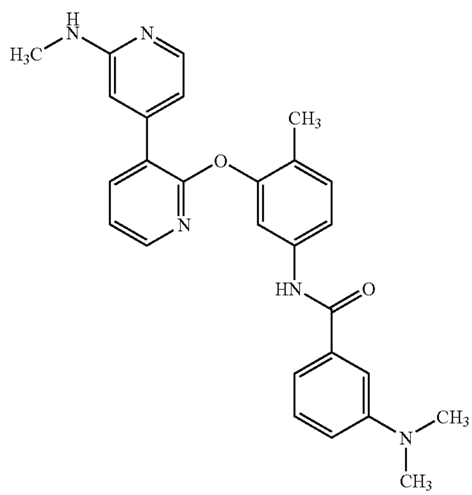 | 453.54 | 454 |
| 771 | 3-(dimethylamino)-N-(3-((3-(2-(methylamino)-4-pyrimidinyl)-2-pyridinyl)oxy)-5-(trifluoromethyl)phenyl)benzamide | 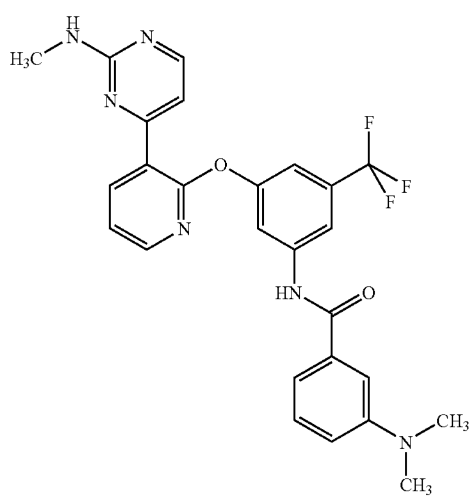 | 508.5 | 509 |

| Ex. No. | Structure Name | Structure | MW | MS Data |
|---|---|---|---|---|
| 772 | N-(2-chloro-5-((2'-(methylamino)-3,4'-bipyridin-2-yl)oxy)phenyl)-3-(1-methylethyl)benzamide | 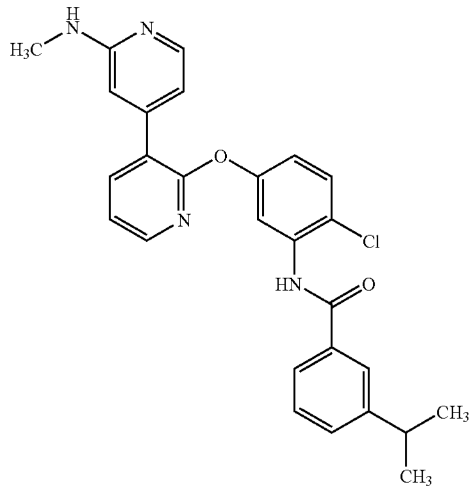 | 472.97 | 473 |
| 773 | N-(2-chloro-5-((3-(2-(methylamino)-4-pyrimidinyl)-2-pyridinyl)oxy)phenyl)-3-(1-methylethyl)benzamide | 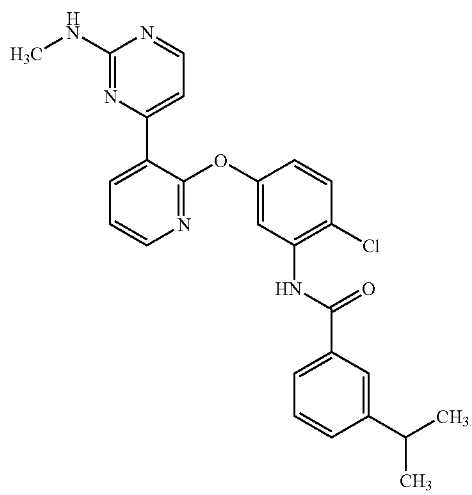 | 473.96 | 474 |
| 774 | N-(4-fluoro-3-((3-(4-(methylamino)-1,3,5-triazin-2-yl)-2-pyridinyl)oxy)phenyl)-3-(1-methylethyl)benzamide | 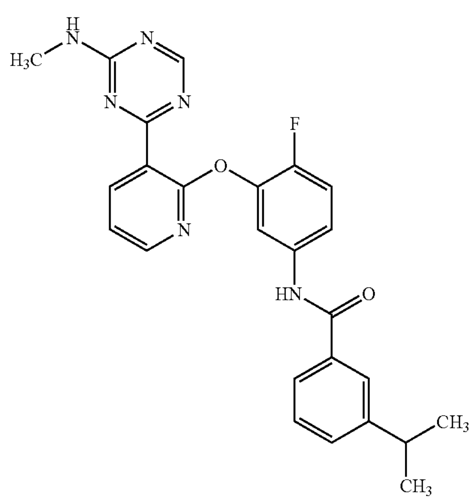 | 458.5 | 459 |

-continued

| Ex. No. | Structure Name | Structure | MW | MS Data |
|---|---|---|---|---|
| 775 | N-(3-(1,1-dimethylethyl)phenyl)-2-fluoro-5-((3-(4-(methylamino)-1,3,5-triazin-2-yl)-2-pyridinyl)oxy)benzamide | 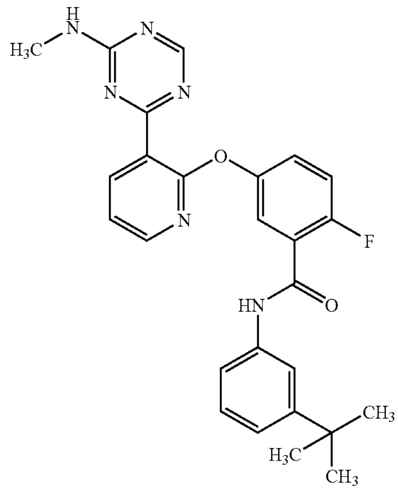 | 472.52 | 473 |
| 776 | N-(3-methyl-4-((3-(2-(methylamino)-4-pyrimidinyl)-2-pyridinyl)oxy)phenyl)-N'-phenylurea | 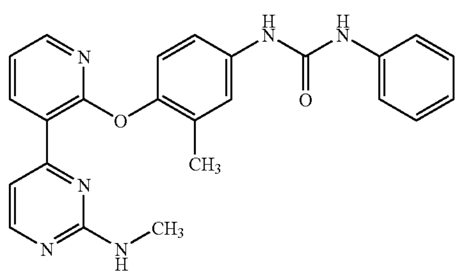 | 426.48 | 427 |
| 777 | N-(3-methyl-4-((3-(2-(methylamino)-4-pyrimidinyl)-2-pyridinyl)oxy)phenyl)-2-phenylacetamide | 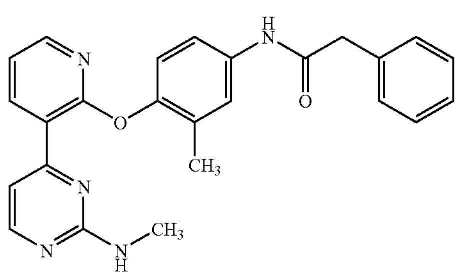 | 425.49 | 426 |
| 778 | phenyl 3-methyl-4-((3-(2-(methylamino)-4-pyrimidinyl)-2-pyridinyl)oxy)phenylcarbamate | 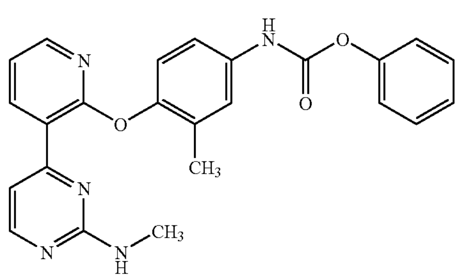 | 427.46 | 428 |

-continued

| Ex. No. | Structure Name | Structure | MW | MS Data |
|---|---|---|---|---|
| 779 | N-(3-methyl-4-((3-(2-(methylamino)-4-pyrimidinyl)-2-pyridinyl)oxy)phenyl)benzamide | 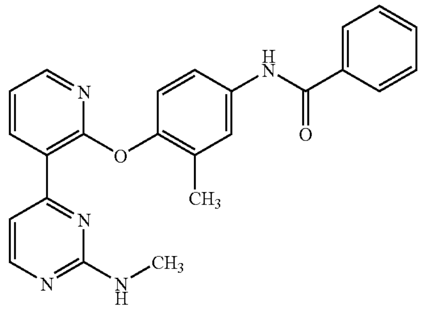 | 411.46 | 412 |
| 780 | N-(3-chlorophenyl)-N'-(3-methyl-4-((3-(2-(methylamino)-4-pyrimidinyl)-2-pyridinyl)oxy)phenyl)urea | 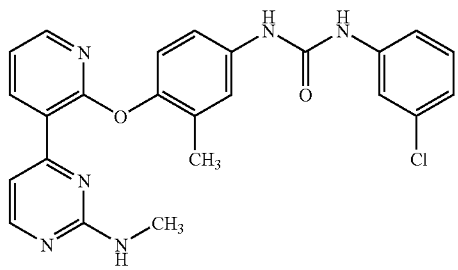 | 460.92 | 461 |
| 781 | N-(2-chlorophenyl)-N'-(3-methyl-4-((3-(2-(methylamino)-4-pyrimidinyl)-2-pyridinyl)oxy)phenyl)urea | 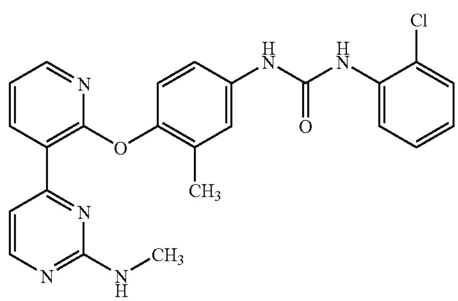 | 460.92 | 461 |
| 782 | N-(4-chlorophenyl)-N'-(3-methyl-4-((3-(2-(methylamino)-4-pyrimidinyl)-2-pyridinyl)oxy)phenyl)urea | 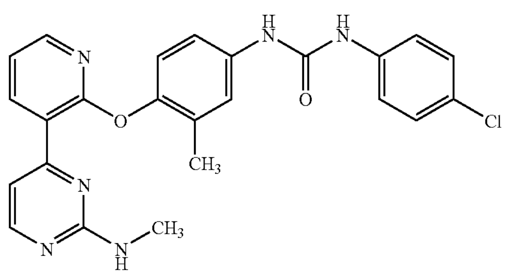 | 460.92 | 461 |
| 783 | N-(3-methyl-4-((3-(2-(methylamino)-4-pyrimidinyl)-2-pyridinyl)oxy)phenyl)-N'-(3-methylphenyl)urea | 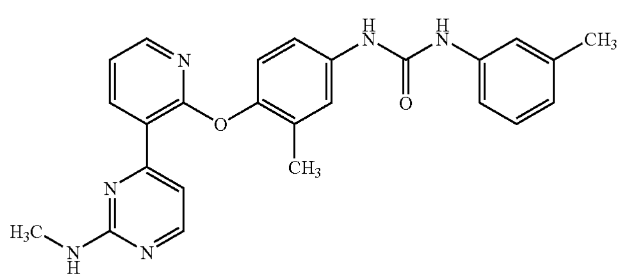 | 440.51 | 441 |

-continued

| Ex. No. | Structure Name | Structure | MW | MS Data |
|---|---|---|---|---|
| 784 | N-(3-methyl-4-((3-(2-(methylamino)-4-pyrimidinyl)-2-pyridinyl)oxy)phenyl)-N'-(3-(methyloxy)phenyl)urea | 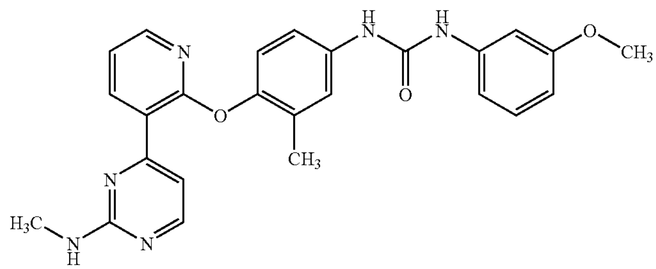 | 456.5 | 457 |
| 785 | N-(3-cyanophenyl)-N'-(3-methyl-4-((3-(2-(methylamino)-4-pyrimidinyl)-2-pyridinyl)oxy)phenyl)urea | 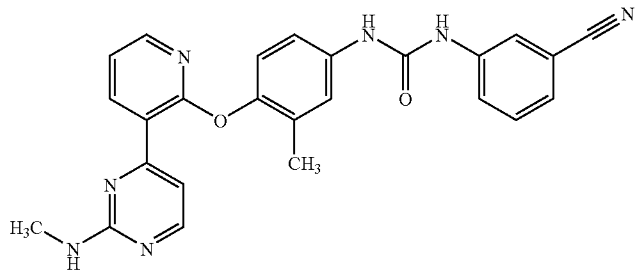 | 451.49 | 452 |
| 786 | N-ethyl-N'-(3-methyl-4-((3-(2-(methylamino)-4-pyrimidinyl)-2-pyridinyl)oxy)phenyl)urea | 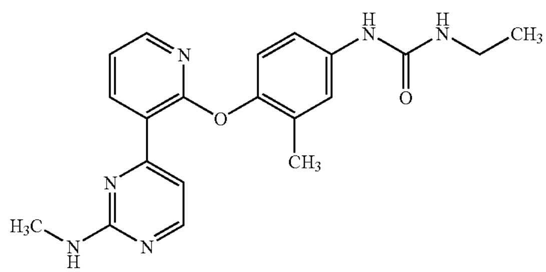 | 378.43 | 379 |
| 787 | N-cyclohexyl-N'-(3-methyl-4-((3-(2-(methylamino)-4-pyrimidinyl)-2-pyridinyl)oxy)phenyl)urea | 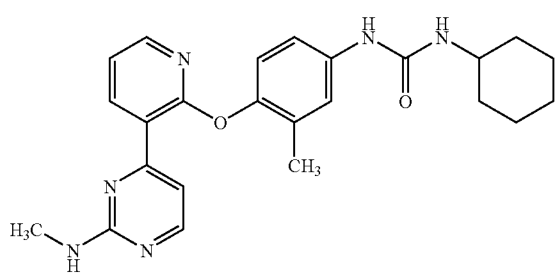 | 432.52 | 433 |
| 788 | N-cyclopentyl-N'-(3-methyl-4-((3-(2-(methylamino)-4-pyrimidinyl)-2-pyridinyl)oxy)phenyl)urea | 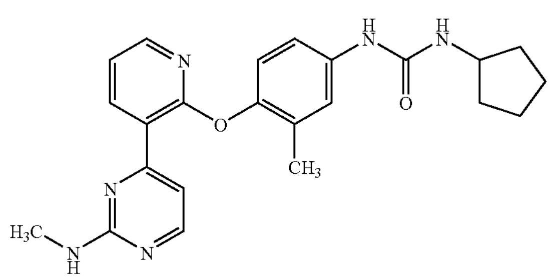 | 418.5 | 419 |

-continued

| Ex. No. | Structure Name | Structure | MW | MS Data |
|---|---|---|---|---|
| 789 | N-(3-methyl-4-((3-(2-(methylamino)-4-pyrimidinyl)-2-pyridinyl)oxy)phenyl)-N'-(phenylmethyl)urea | 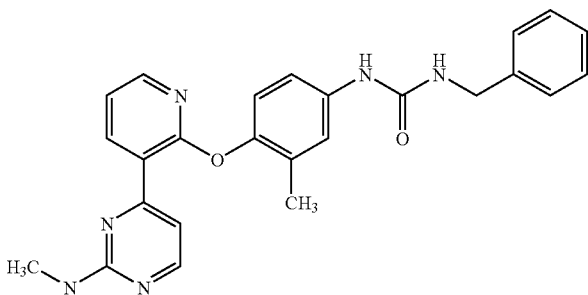 | 440.51 | 441 |
| 790 | N-(3-fluorophenyl)-N'-(3-methyl-4-((3-(2-(methylamino)-4-pyrimidinyl)-2-pyridinyl)oxy)phenyl)urea | 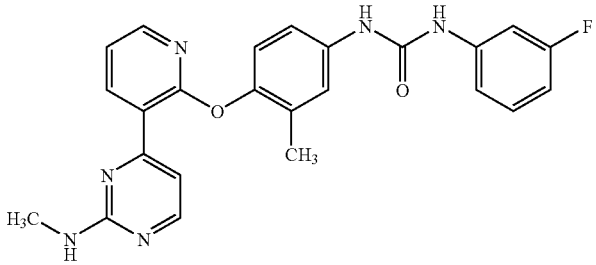 | 444.47 | 445 |
| 791 | N-(3-methyl-4-((3-(2-(methylamino)-4-pyrimidinyl)-2-pyridinyl)oxy)phenyl)-N'-(3-(trifluoromethyl)phenyl)thiourea | 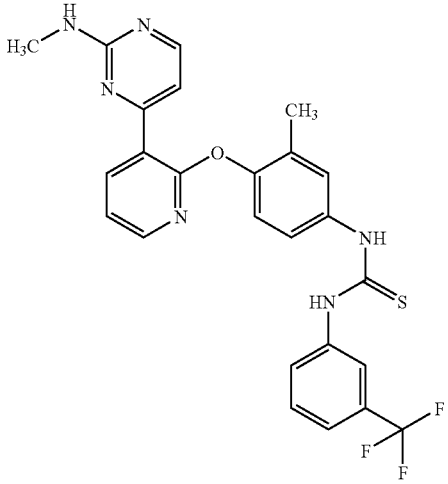 | 510.54 | 511 |
| 792 | N-(2-chloro-5-(trifluoromethyl)phenyl)-N'-(3-methyl-4-((3-(2-(methylamino)-4-pyrimidinyl)-2-pyridinyl)oxy)phenyl)urea | 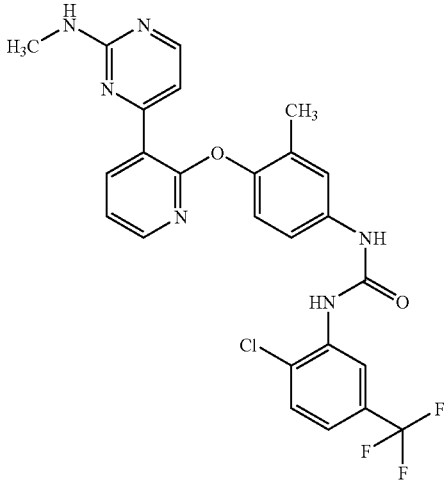 | 528.92 | 529 |

| Ex. No. | Structure Name | Structure | MW | MS Data |
|---|---|---|---|---|
| 793 | N-(5-chloro-2-(methyloxy)phenyl)-N'-(3-methyl-4-((3-(2-(methylamino)-4-pyrimidinyl)-2-pyridinyl)oxy)phenyl)urea | 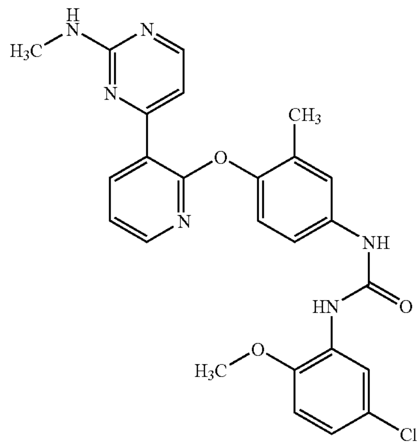 | 490.95 | 491 |
| 794 | N-(3-fluoro-5-(trifluoromethyl)phenyl)-N'-(3-methyl-4-((3-(2-(methylamino)-4-pyrimidinyl)-2-pyridinyl)oxy)phenyl)urea | 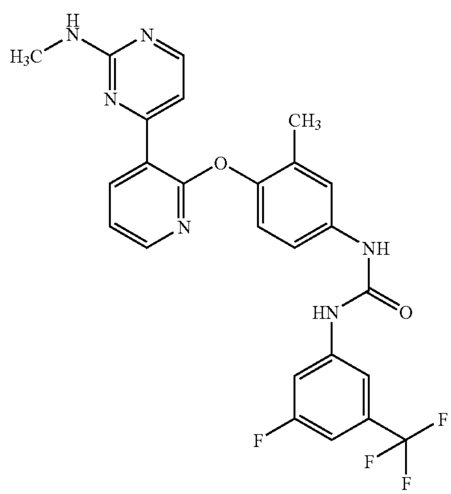 | 512.47 | 513 |
| 795 | N-(3,5-bis(methyloxy)phenyl)-N'-(3-methyl-4-((3-(2-(methylamino)-4-pyrimidinyl)-2-pyridinyl)oxy)phenyl)urea | 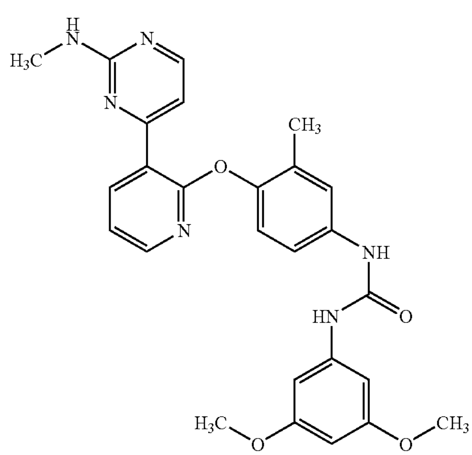 | 486.53 | 487 |

-continued

| Ex. No. | Structure Name | Structure | MW | MS Data |
|---|---|---|---|---|
| 796 | N-(3-methyl-4-((3-(2-(methylamino)-4-pyrimidinyl)-2-pyridinyl)oxy)phenyl)-N'-phenylthiourea | 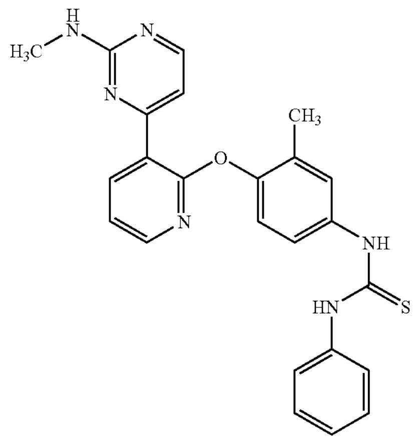 | 442.55 | 443 |
| 797 | N-(3-methyl-4-((3-(4-pyrimidinyl)-2-pyridinyl)oxy)phenyl)-N'-(3-(trifluoromethyl)phenyl)thiourea | 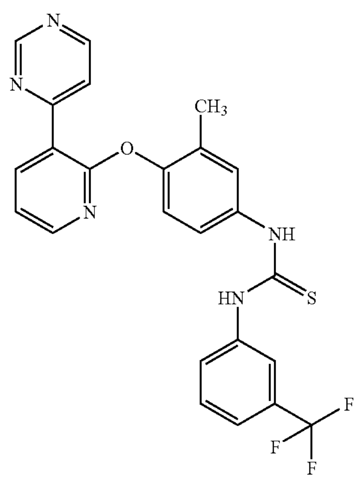 | 481.5 | 482 |
| 798 | N-(2-((3S)-3-(dimethylamino)-1-pyrrolidinyl)-5-(trifluoromethyl)phenyl)-N'-(4-((3-(4-(methylamino)-1,3,5-triazin-2-yl)-2-pyridinyl)oxy)-1-naphthalenyl)urea | 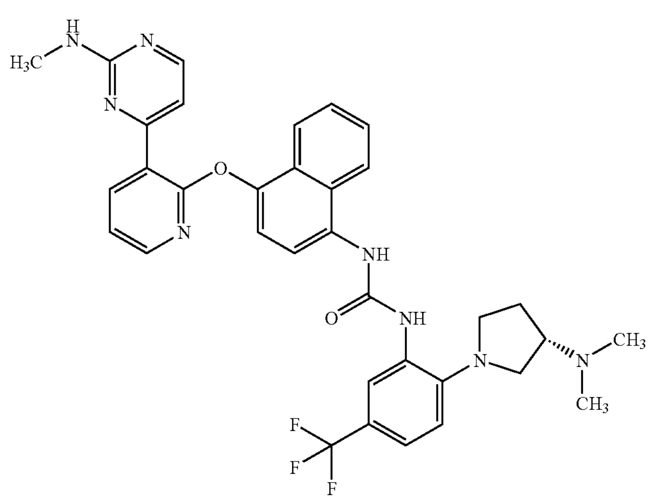 | 643.67 | 644 |

-continued

| Ex. No. | Structure Name | Structure | MW | MS Data |
|---|---|---|---|---|
| 799 | N-(4-((3-(4-(methylamino)-1,3,5-triazin-2-yl)-2-pyridinyl)oxy)-1-naphthalenyl)-N'-(3-(trifluoromethyl)phenyl) urea | 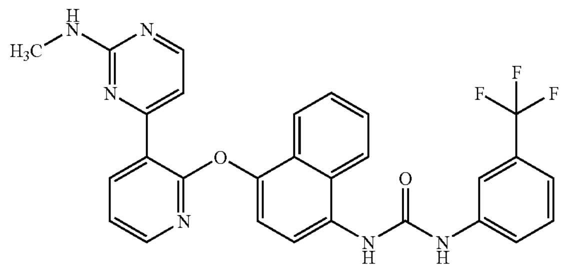 | 531.5 | 532 |
| 800 | N-(2-((3-(dimethylamino)propyl)(methyl)amino)-5-(trifluoromethyl)phenyl)-N'-(4-((3-(4-(methylamino)-1,3,5-triazin-2-yl)-2-pyridinyl)oxy)-1-naphthalenyl)urea | 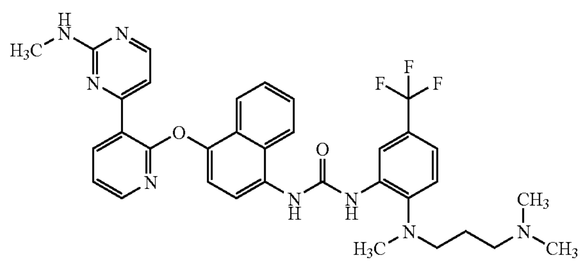 | 645.69 | 646 |
| 801 | N-(4-((3-(4-(methylamino)-1,3,5-triazin-2-yl)-2-pyridinyl)oxy)-1-naphthalenyl)-N'-(2-(methyl(1-methyl-3-pyrrolidinyl)amino)-5-(trifluoromethyl)phenyl) urea | | 643.67 | 644 |
| 802 | N-(2-(((3R)-3-(dimethylamino)-1-pyrrolidinyl)methyl)-5-(trifluoromethyl)phenyl)-N'-(4-((3-(4-(methylamino)-1,3,5-triazin-2-yl)-2-pyridinyl)oxy)-1-naphthalenyl)urea | 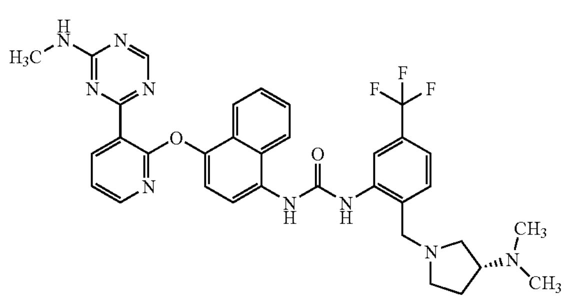 | 657.7 | 658 |

-continued

| Ex. No. | Structure Name | Structure | MW | MS Data |
|---|---|---|---|---|
| 803 | N-(3-bromophenyl)-N'-(3-methyl-4-((3-(2-(methylamino)-4-pyrimidinyl)-2-pyridinyl)oxy)phenyl)urea | 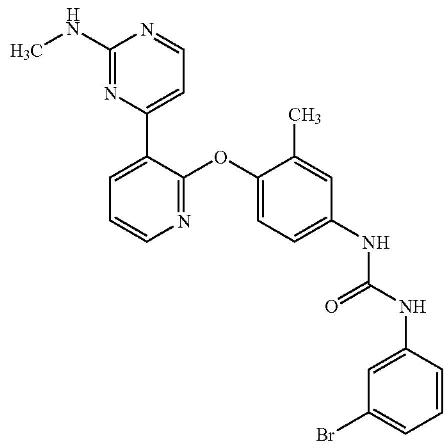 | 505.37 | 505 |
| 804 | N-(1,3-benzodioxol-5-yl)-N'-(3-methyl-4-((3-(2-(methylamino)-4-pyrimidinyl)-2-pyridinyl)oxy)phenyl)urea | 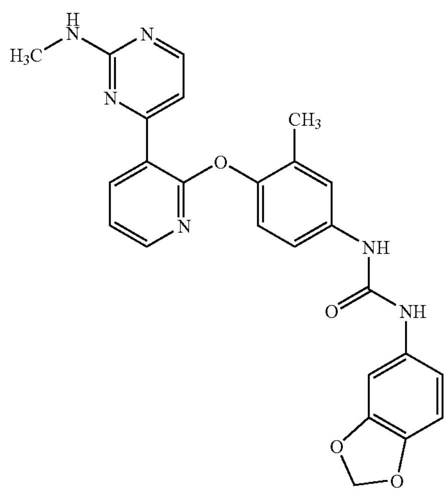 | 407.49 | 471 |
| 805 | N-(3-methyl-4-((3-(2-(methylamino)-4-pyrimidinyl)-2-pyridinyl)oxy)phenyl)-1H-indole-2-carboxamide | 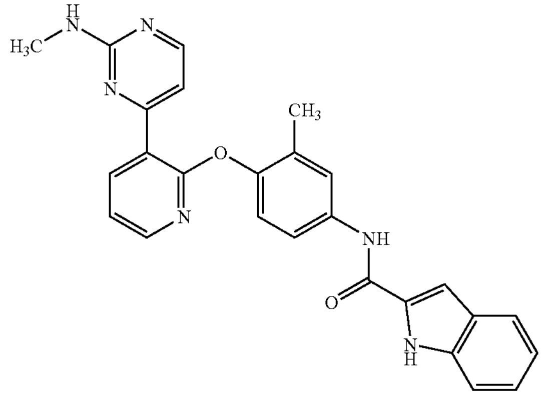 | 450.5 | 451 |

| Ex. No. | Structure Name | Structure | MW | MS Data |
|---|---|---|---|---|
| 806 | N-(2,5-dichlorophenyl)-N'-(3-methyl-4-((3-(2-(methylamino)-4-pyrimidinyl)-2-pyridinyl)oxy)phenyl)urea | 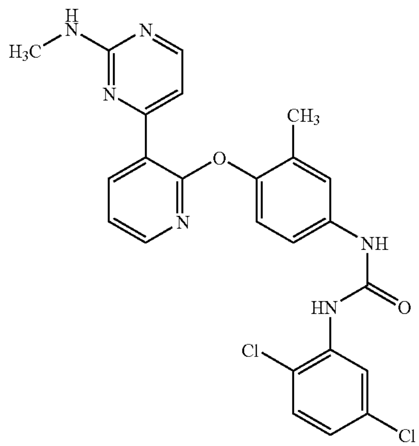 | 495.37 | 495 |
| 807 | N-(3,5-dichlorophenyl)-N'-(3-methyl-4-((3-(2-(methylamino)-4-pyrimidinyl)-2-pyridinyl)oxy)phenyl)urea | 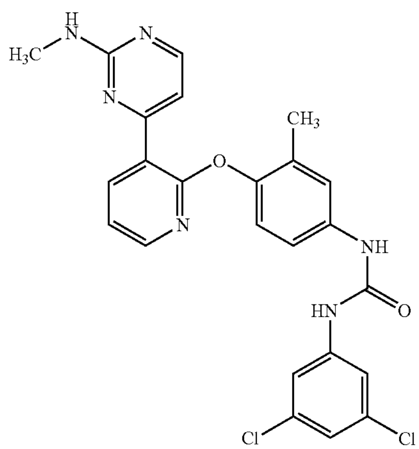 | 495.37 | 495 |
| 808 | N-(5-chloro-2-methylphenyl)-N'-(3-methyl-4-((3-(2-(methylamino)-4-pyrimidinyl)-2-pyridinyl)oxy)phenyl)urea | 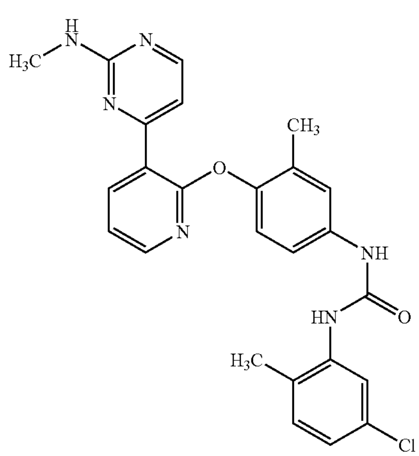 | 474.95 | 475 |

-continued

| Ex. No. | Structure Name | Structure | MW | MS Data |
|---|---|---|---|---|
| 809 | N-(3-methyl-4-((3-(2-(methylamino)-4-pyrimidinyl)-2-pyridinyl)oxy)phenyl)-2-(3-(trifluoromethyl)phenyl)acetamide | 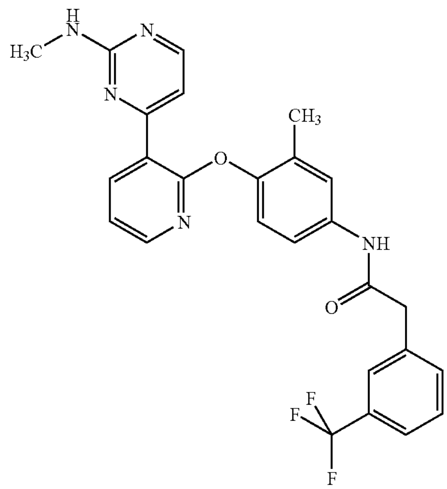 | 493.49 | 494 |
| 810 | N-(3-methyl-4-((3-(2-(methylamino)-4-pyrimidinyl)-2-pyridinyl)oxy)phenyl)-3-(trifluoromethyl)benzamide | 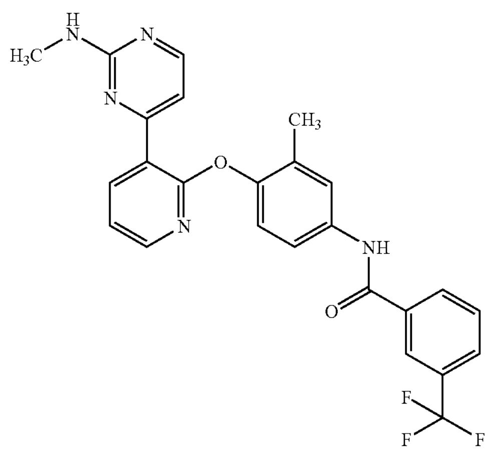 | 479.46 | 480 |
| 811 | 5-chloro-N-(3-methyl-4-((3-(2-(methylamino)-4-pyrimidinyl)-2-pyridinyl)oxy)phenyl)-1H-indole-2-carboxamide | 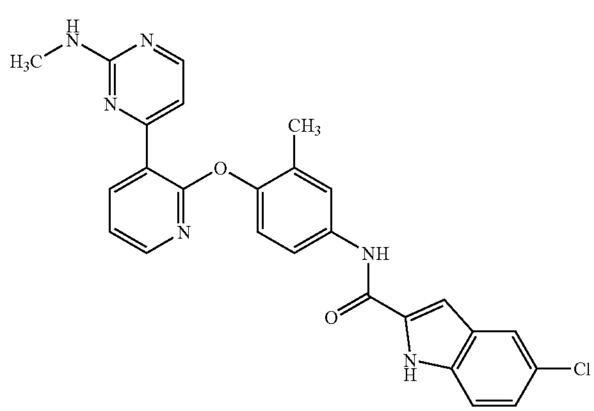 | 484.94 | 485 |

| Ex. No. | Structure Name | Structure | MW | MS Data |
|---|---|---|---|---|
| 812 | N-(2-((3-(dimethylamino)propyl)(methyl)amino)-5-(trifluoromethyl)phenyl)-N'-(3-methyl-4-((3-(2-(methylamino)-4-pyrimidinyl)-2-pyridinyl)oxy)phenyl)urea | 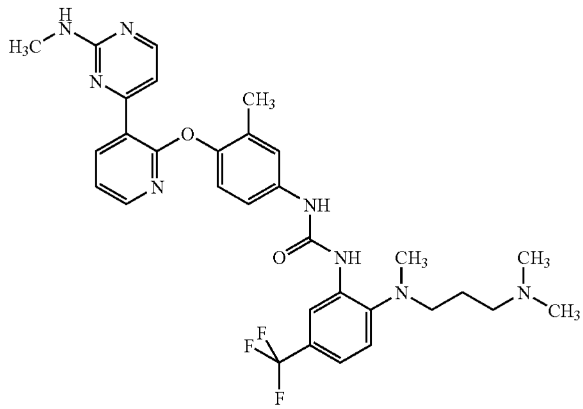 | 608.67 | 609 |
| 813 | N-(3-methyl-4-((3-(2-(methylamino)-4-pyrimidinyl)-2-pyridinyl)oxy)phenyl)-N'-(2-((2-(1-pyrrolidinyl)ethyl)oxy)-5-(trifluoromethyl)phenyl)urea | 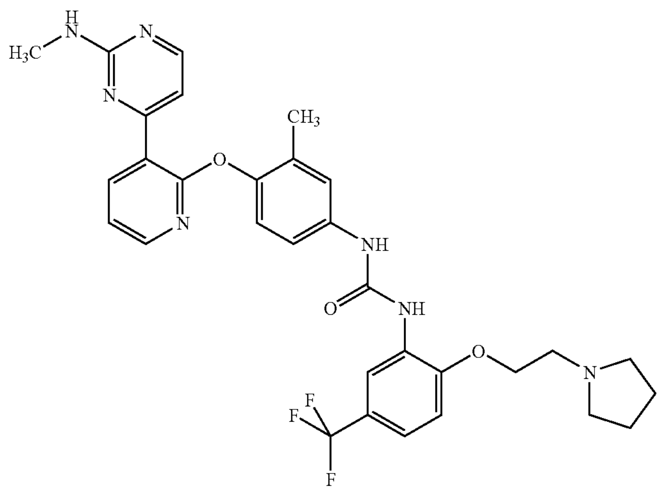 | 607.63 | 608 |
| 814 | N-(3-methyl-4-((3-(2-(methylamino)-4-pyrimidinyl)-2-pyridinyl)oxy)phenyl)-N'-(2-(methyl(1-methyl-3-pyrrolidinyl)amino)-5-(trifluoromethyl)phenyl)urea | | 606.65 | 607 |

-continued

| Ex. No. | Structure Name | Structure | MW | MS Data |
|---|---|---|---|---|
| 815 | N-(3-methyl-4-((3-(2-(methylamino)-4-pyrimidinyl)-2-pyridinyl)oxy)phenyl)-N'-(2-((4-methyl-1-piperazinyl)methyl)-5-(trifluoromethyl)phenyl)urea | 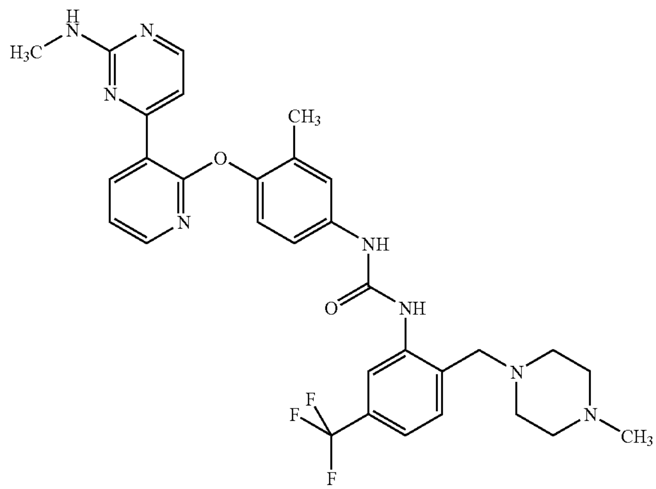 | 606.65 | 607 |
| 816 | N-(3-(ethyloxy)phenyl)-N'-(3-methyl-4-((3-(2-(methylamino)-4-pyrimidinyl)-2-pyridinyl)oxy)phenyl)urea | 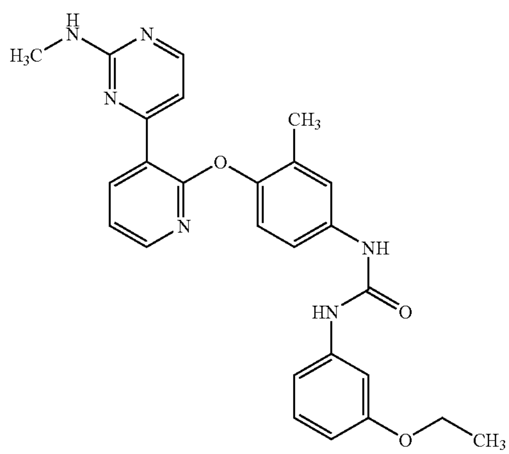 | 470.53 | 471 |
| 817 | N-(2,5-bis(1,1-dimethylethyl)phenyl)-N'-(3-methyl-4-((3-(2-(methylamino)-4-pyrimidinyl)-2-pyridinyl)oxy)phenyl)urea | 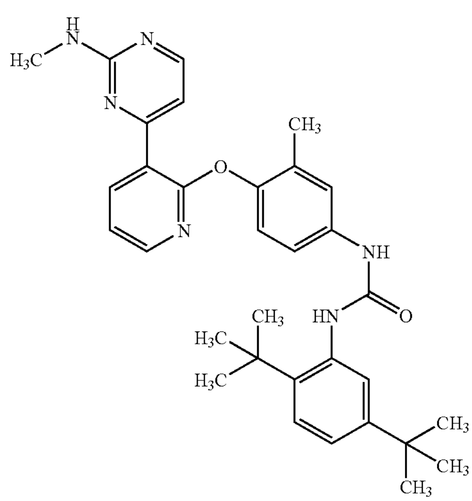 | 538.69 | 539 |

-continued

| Ex. No. | Structure Name | Structure | MW | MS Data |
|---|---|---|---|---|
| 818 | N-(5-(1,1-dimethylethyl)-2-(methyloxy)phenyl)-N'-(3-methyl-4-((3-(2-(methylamino)-4-pyrimidinyl)-2-pyridinyl)oxy)phenyl)urea | 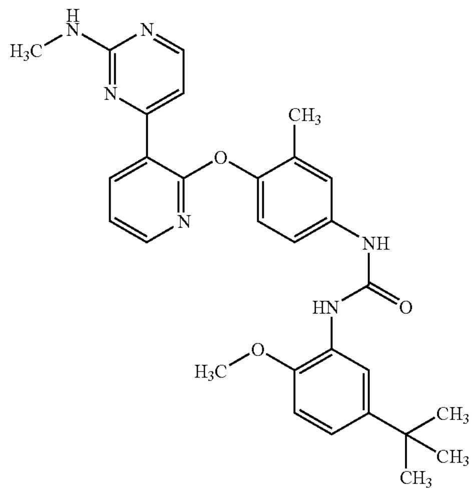 | 512.61 | 513 |
| 819 | N-(5-chloro-2-((3-(dimethylamino)propyl)(methyl)amino)phenyl)-N'-(3-methyl-4-((3-(2-(methylamino)-4-pyrimidinyl)-2-pyridinyl)oxy)phenyl)urea | 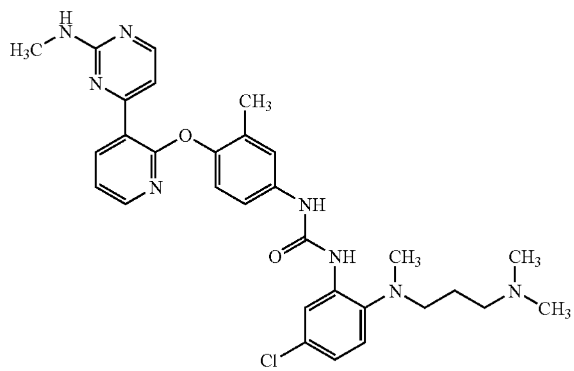 | 575.11 | 575 |
| 820 | N-(3-methyl-4-((3-(2-(methylamino)-4-pyrimidinyl)-2-pyridinyl)oxy)phenyl)-N'-((3-methylphenyl)methyl)urea | 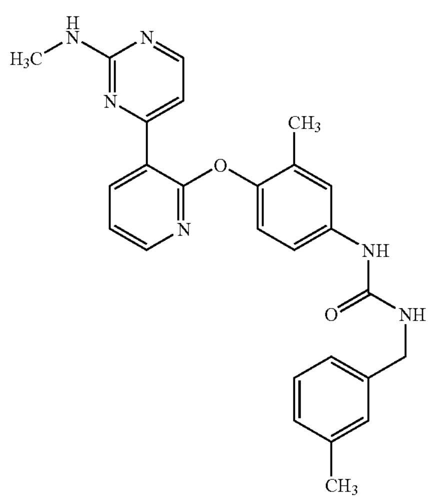 | 454.53 | 455 |

-continued

| Ex. No. | Structure Name | Structure | MW | MS Data |
|---|---|---|---|---|
| 821 | N-(5-bromo-2-((3-(dimethylamino)propyl)(methyl)amino)phenyl)-N'-(3-methyl-4-((3-(2-(methylamino)-4-pyrimidinyl)-2-pyridinyl)oxy)phenyl)urea | 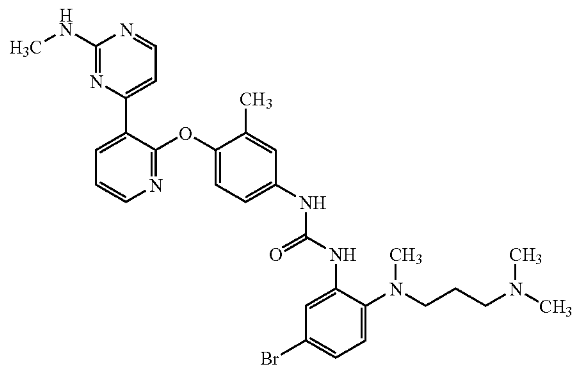 | 619.57 | 620 |
| 822 | N-(2-((3-(dimethylamino)propyl)oxy)-5-(trifluoromethyl)phenyl)-N'-(3-methyl-4-((3-(2-(methylamino)-4-pyrimidinyl)-2-pyridinyl)oxy)phenyl)urea | 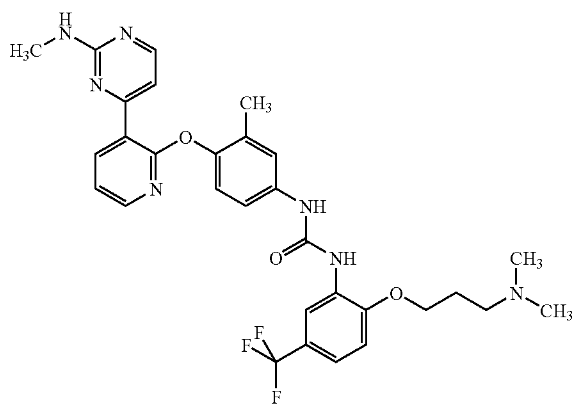 | 595.62 | 596 |
| 823 | N-(3-methyl-4-((3-(2-(methylamino)-4-pyrimidinyl)-2-pyridinyl)oxy)phenyl)-N'-(3-(1-methyl-4-piperidinyl)-5-(trifluoromethyl)phenyl)urea | 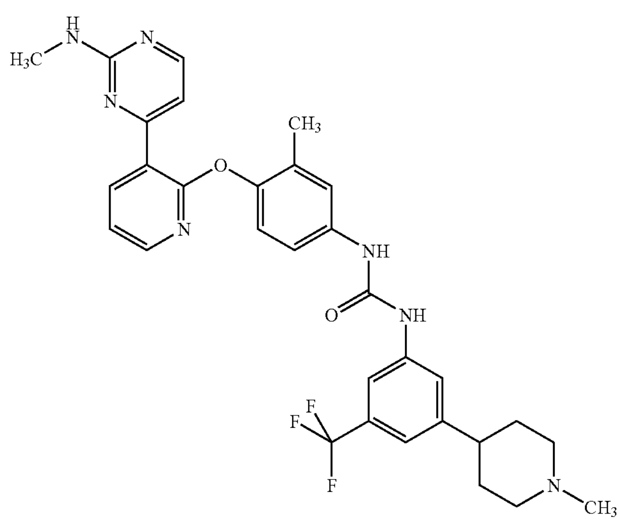 | 591.63 | 592 |

-continued

| Ex. No. | Structure Name | Structure | MW | MS Data |
|---|---|---|---|---|
| 824 | N-(5-chloro-2-(methyl(1-methyl-3-pyrrolidinyl)amino)phenyl)-N'-(3-methyl-4-((3-(2-(methylamino)-4-pyrimidinyl)-2-pyridinyl)oxy)phenyl)urea | | 573.1 | 573 |
| 825 | N-(3-methyl-4-((3-(2-(methylamino)-4-pyrimidinyl)-2-pyridinyl)oxy)phenyl)-N'-(5-methyl-2-(methyloxy)phenyl)urea | 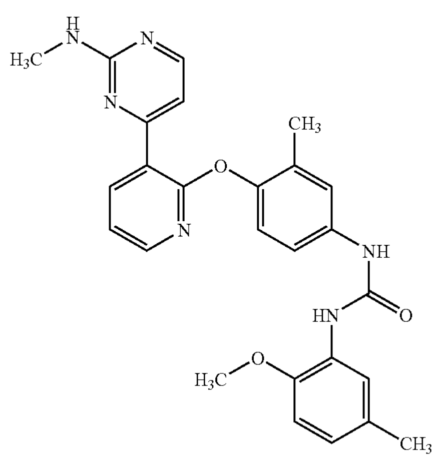 | 470.53 | 471 |

-continued

| Ex. No. | Structure Name | Structure | MW | MS Data |
|---|---|---|---|---|
| 826 | N-(2,5-dimethylphenyl)-N'-(3-methyl-4-((3-(2-(methylamino)-4-pyrimidinyl)-2-pyridinyl)oxy)phenyl)urea | 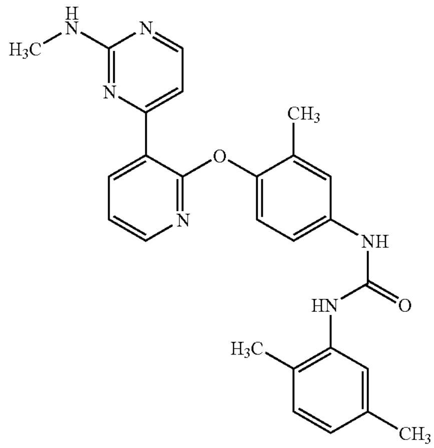 | 454.53 | 455 |
| 827 | N-(3-ethylphenyl)-N'-(3-methyl-4-((3-(2-(methylamino)-4-pyrimidinyl)-2-pyridinyl)oxy)phenyl)urea | 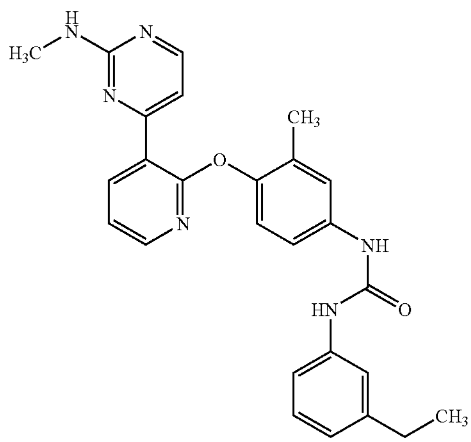 | 454.53 | 455 |
| 828 | N-(2-fluoro-5-(trifluoromethyl)phenyl)-N'-(4-((3-(4-(methylamino)-1,3,5-triazin-2-yl)-2-pyridinyl)oxy)-1-naphthalenyl)thiourea | 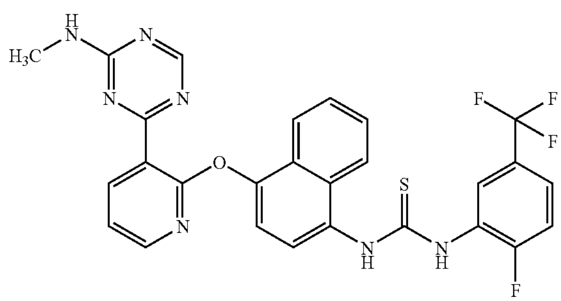 | 565.55 | 566 |
| 829 | N-(5-(1,1-dimethylethyl)-2-(methyloxy)phenyl)-N'-(4-((3-(4-(methylamino)-1,3,5-triazin-2-yl)-2-pyridinyl)oxy)-1-naphthalenyl)urea | 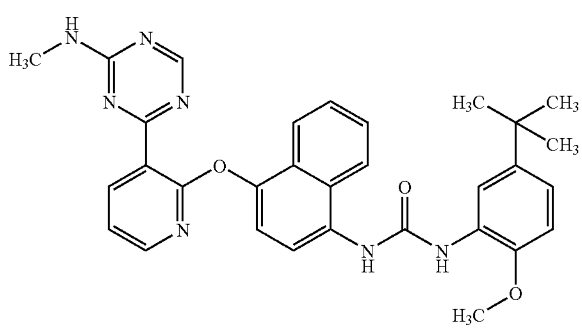 | 549.63 | 550 |

-continued

| Ex. No. | Structure Name | Structure | MW | MS Data |
|---|---|---|---|---|
| 830 | N-(3,5-bis(trifluoromethyl) phenyl)-N'-(4-((3-(4-(methylamino)-1,3,5-triazin-2-yl)-2-pyridinyl)oxy)-1-naphthalenyl)urea | 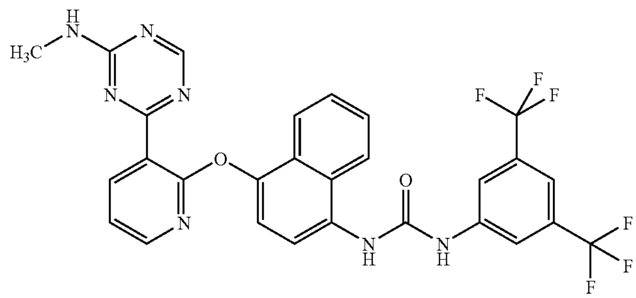 | 599.49 | 600 |
| 831 | N-(4-((3-(4-(methylamino)-1,3,5-triazin-2-yl)-2-pyridinyl)oxy)-1-naphthalenyl)-N'-(3-((trifluoromethyl)sulfanyl)phenyl)thiourea | 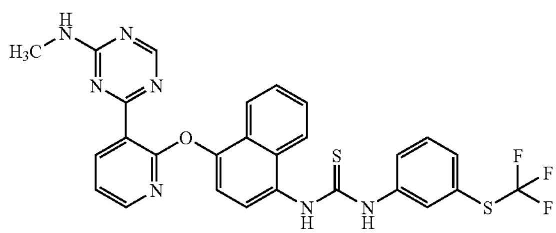 | 579.63 | 580 |
| 832 | N-(3-ethylphenyl)-N'-(4-((3-(4-(methylamino)-1,3,5-triazin-2-yl)-2-pyridinyl)oxy)-1-naphthalenyl)urea | 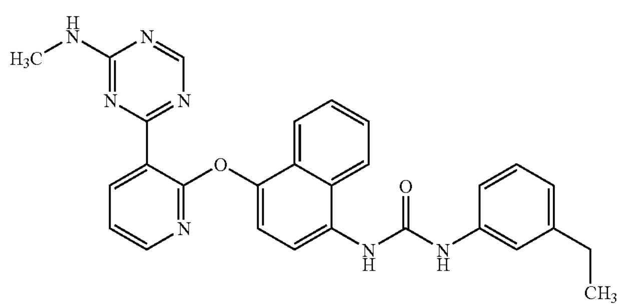 | 491.55 | 492 |
| 833 | N-(3,5-bis(trifluoromethyl) phenyl)-N'(4-((3-(4-(methylamino)-1,3,5-triazin-2-yl)-2-pyridinyl)oxy)-1-naphthalenyl)thiourea | 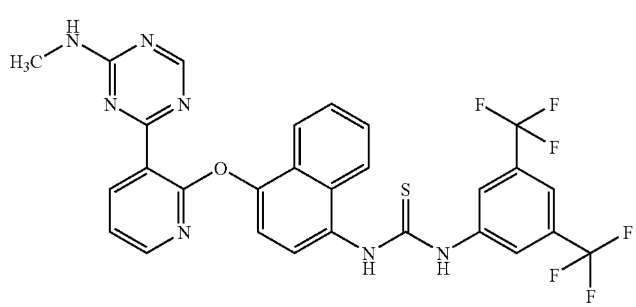 | 615.56 | 616 |

| Ex. No. | Structure Name | Structure | MW | MS Data |
|---|---|---|---|---|
| 834 | N-(3-chloro-4-((3-(2-(methylamino)-4-pyrimidinyl)-2-pyridinyl)oxy)phenyl)-N'-(5-chloro-2-(methyloxy)phenyl)urea | 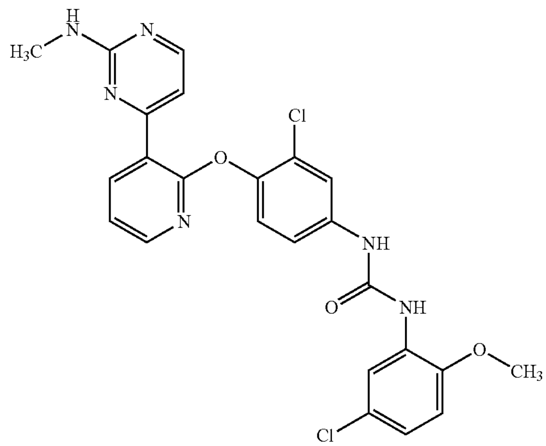 | 511.37 | 511 |
| 835 | N-(3-chloro-4-((3-(2-(methylamino)-4-pyrimidinyl)-2-pyridinyl)oxy)phenyl)-N'-(2-fluoro-5-(trifluoromethyl)phenyl)urea | 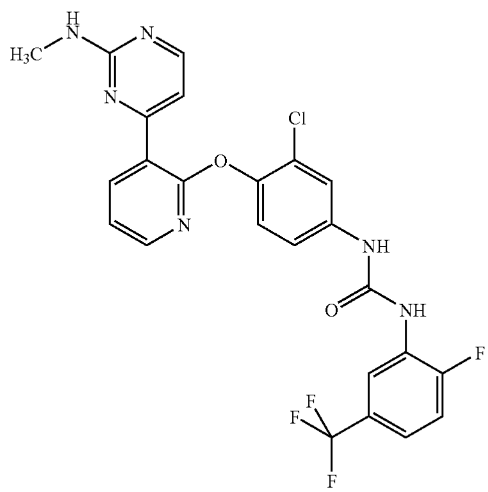 | 532.88 | 533 |
| 836 | N-(3-chloro-4-((3-(2-(methylamino)-4-pyrimidinyl)-2-pyridinyl)oxy)phenyl)-N'-(3-fluoro-5-(trifluoromethyl)phenyl)urea | 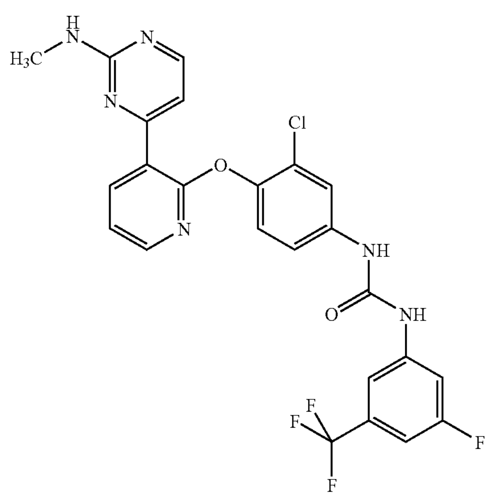 | 532.88 | 533 |

-continued

| Ex. No. | Structure Name | Structure | MW | MS Data |
|---|---|---|---|---|
| 837 | N-(3-chloro-4-((3-(2-(methylamino)-4-pyrimidinyl)-2-pyridinyl)oxy)phenyl)-N'-(3-(trifluoromethyl)phenyl)urea | 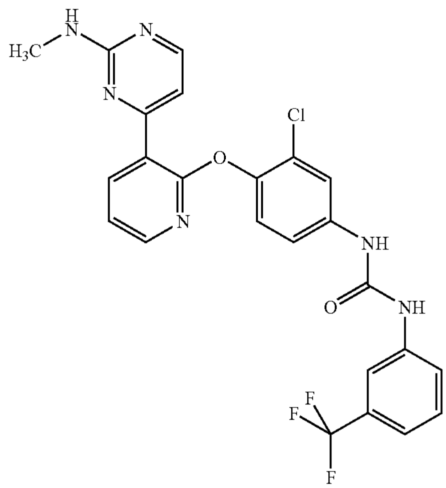 | 514.89 | 515 |
| 838 | N-(3-methyl-4-((3-(2-(methylamino)-4-pyrimidinyl)-2-pyridinyl)oxy)phenyl)-N'-(3-((4-methyl-1-piperazinyl)methyl)-5-(trifluoromethyl)phenyl)urea | 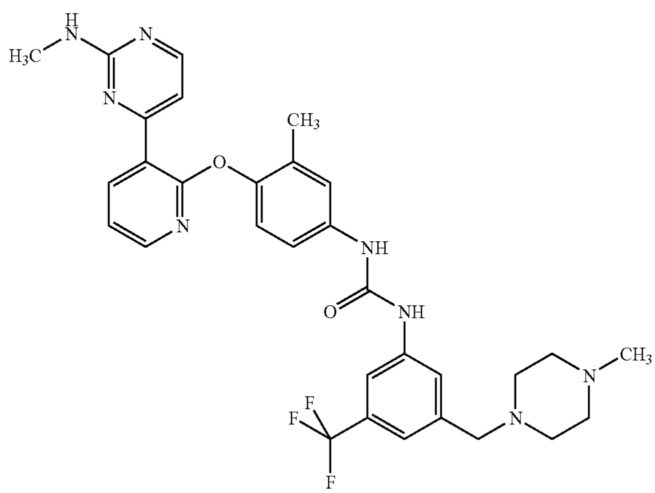 | 606.65 | 607 |
| 839 | N-(3-methyl-4-((3-(2-(methylamino)-4-pyrimidinyl)-2-pyridinyl)oxy)phenyl)-N'-(3-((4-methyl-1-piperazinyl)carbonyl)-5-(trifluoromethyl)phenyl)urea | 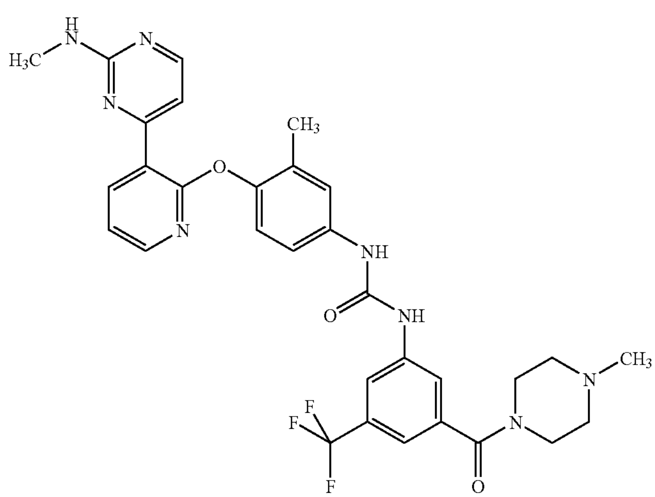 | 620.63 | 621 |

| Ex. No. | Structure Name | Structure | MW | MS Data |
|---|---|---|---|---|
| 840 | N-(3-chloro-2-((3-(dimethylamino)propyl)(methyl)amino)-5-(trifluoromethyl)phenyl)-N'-(3-methyl-4-((3-(2-(methylamino)-4-pyridinyl)-2-pyridinyl)oxy)phenyl)urea | 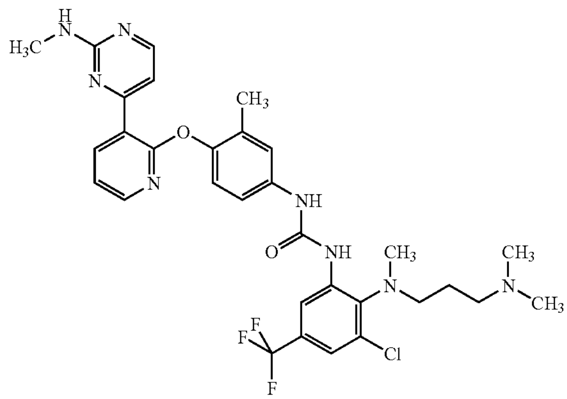 | 643.11 | 643 |
| 841 | N-(5-(1,1-dimethylethyl)-3-isoxazolyl)-N'-(3-methyl-4-((3-(2-(methylamino)-4-pyrimidinyl)-2-pyridinyl)oxy)phenyl)urea | 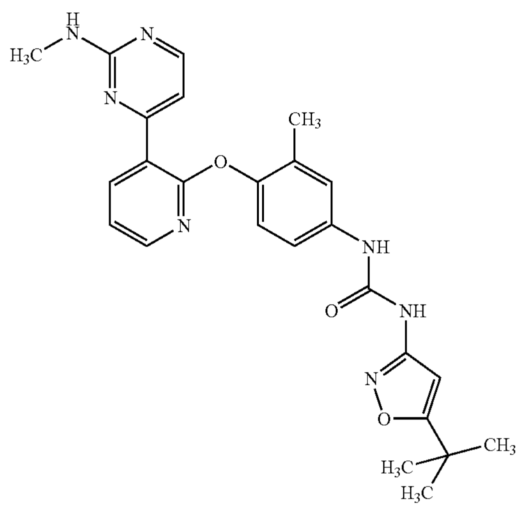 | 473.53 | 474 |
| 842 | N-(3-methyl-4-((3-(2-(methylamino)-4-pyrimidinyl)-2-pyridinyl)oxy)phenyl)-N'-(2-(4-morpholinyl)-5-(trifluoromethyl)phenyl)urea | 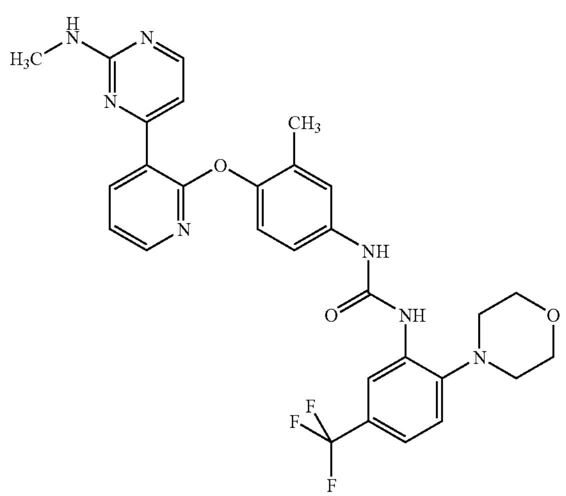 | 579.58 | 580 |

| Ex. No. | Structure Name | Structure | MW | MS Data |
|---|---|---|---|---|
| 843 | N-(4-ethyl-2-pyridinyl)-N'-(3-methyl-4-((3-(2-(methylamino)-4-pyrimidinyl)-2-pyridinyl)oxy)phenyl)urea | 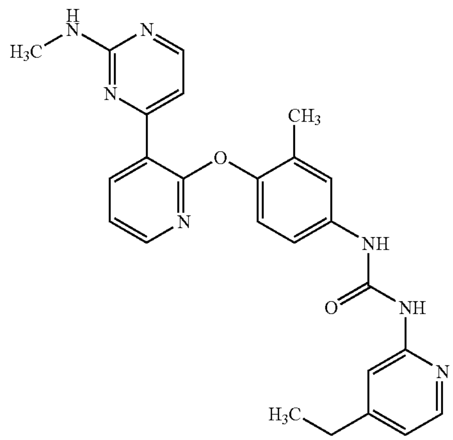 | 455.52 | 456 |
| 844 | N-(3-methyl-4-((3-(2-(methylamino)-4-pyrimidinyl)-2-pyridinyl)oxy)phenyl)-7-(trifluoromethyl)-3,4-dihydro-1(2H)-quinolinecarboxamide | 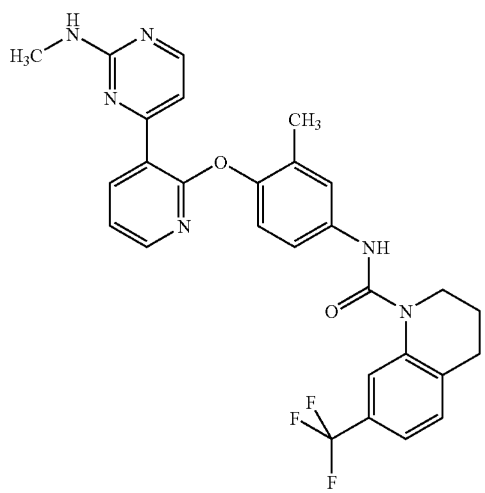 | 534.54 | 535 |
| 845 | N-(4-((3-(4-(methylamino)-1,3,5-triazin-2-yl)-2-pyridinyl)oxy)-1-naphthalenyl)-N'-(2-(methyloxy)phenyl)urea | 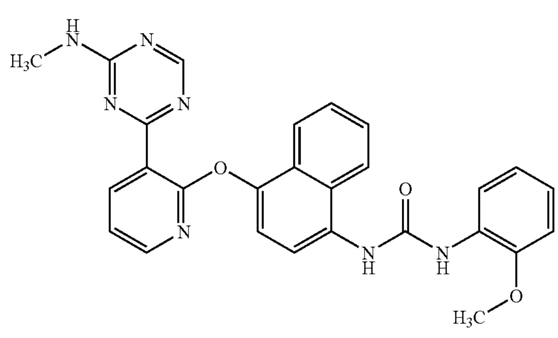 | 493.52 | 494 |

| Ex. No. | Structure Name | Structure | MW | MS Data |
|---|---|---|---|---|
| 846 | N-(5-chloro-2-(methyloxy)phenyl)-N'-(4-((3-(4-(methylamino)-1,3,5-triazin-2-yl)-2-pyridinyl)oxy)-1-naphthalenyl)urea | 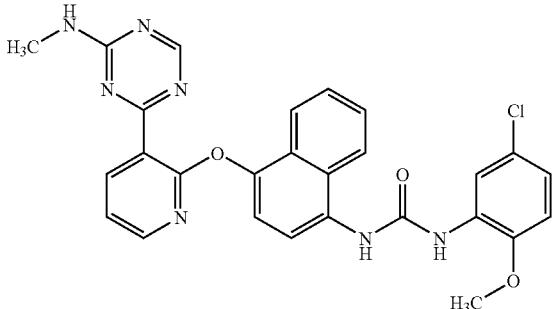 | 527.97 | 528 |
| 847 | N-(3,5-bis(methyloxy)phenyl)-N'-(4-((3-(4-(methylamino)-1,3,5-triazin-2-yl)-2-pyridinyl)oxy)-1-naphthalenyl)urea | 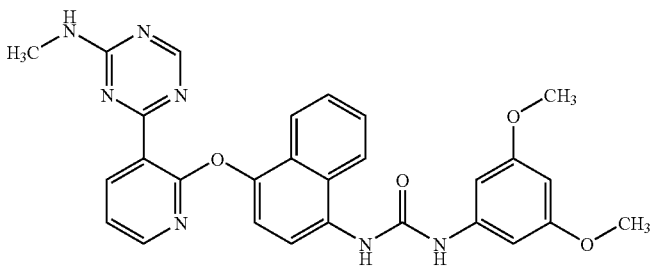 | 523.55 | 524 |
| 848 | N-(3-methyl-4-((3-(4-(methylamino)-1,3,5-triazin-2-yl)-2-pyridinyl)oxy)phenyl)-N'-(2-(methyloxy)phenyl)urea | 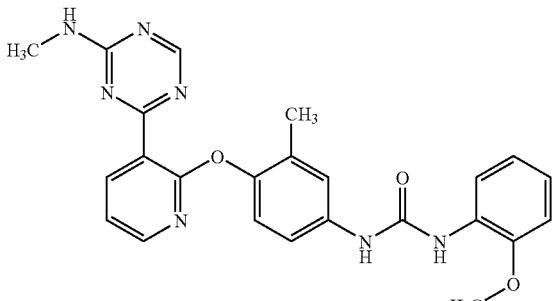 | 457.49 | 458 |
| 849 | N-(5-chloro-2-(methyloxy)phenyl)-N'-(3-methyl-4-((3-(4-(methylamino)-1,3,5-triazin-2-yl)-2-pyridinyl)oxy)phenyl)urea | 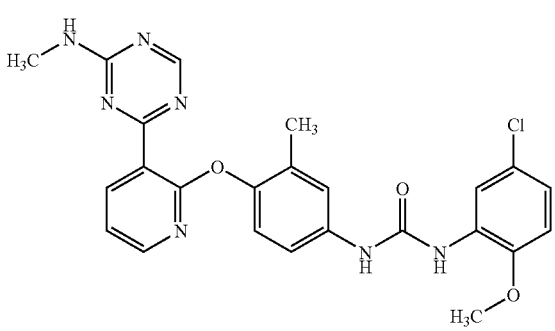 | 491.94 | 492 |
| 850 | N-(3,5-bis(methyloxy)phenyl)-N'-(3-methyl-4-((3-(4-(methylamino)-1,3,5-triazin-2-yl)-2-pyridinyl)oxy)phenyl)urea | 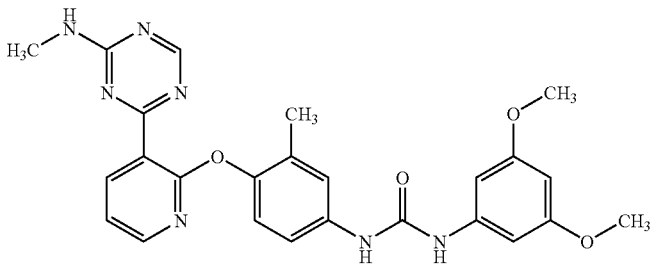 | 487.52 | 488 |

| Ex. No. | Structure Name | Structure | MW | MS Data |
|---|---|---|---|---|
| 851 | N-(3,4-dimethyl-5-isoxazolyl)-N'-(3-methyl-4-((3-(2-(methylamino)-4-pyrimidinyl)-2-pyridinyl)oxy)phenyl)urea | 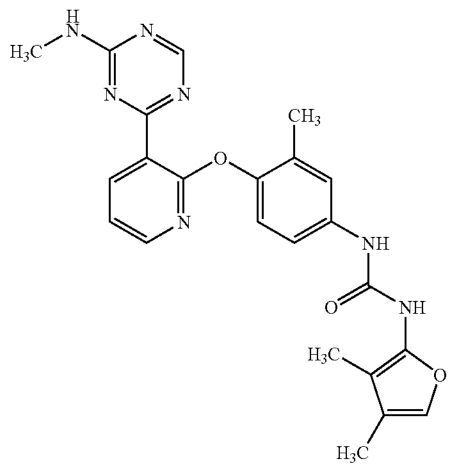 | 445.48 | 446 |
| 852 | N-(2-((dimethylamino)methyl)-5-(trifluoromethyl)phenyl)-N'-(3-methyl-4-((3-(2-(methylamino)-pyrimidinyl)-2-pyridinyl)oxy)phenyl)urea | 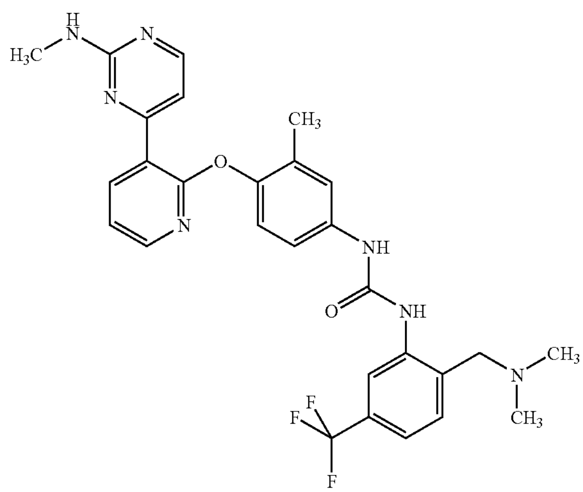 | 551.57 | 552 |
| 853 | N-(2-chloro-5-(trifluoromethyl)phenyl)-N'-(3-methyl-4-((3-(4-(methylamino)-1,3,5-triazin-2-yl)-2-pyridinyl)oxy)phenyl)urea | 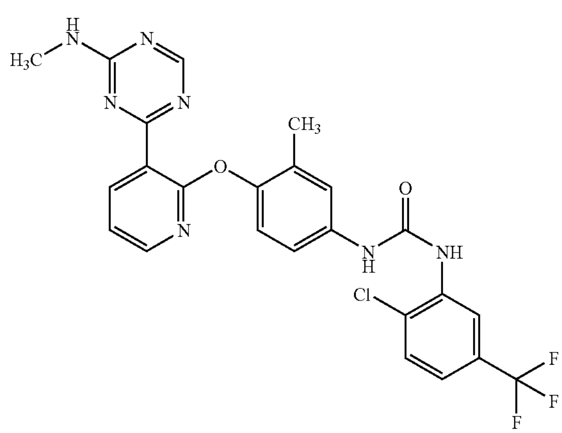 | 529.91 | 530 |

| Ex. No. | Structure Name | Structure | MW | MS Data |
|---|---|---|---|---|
| 854 | N-(2,4-bis(methyloxy)phenyl)-N'-(3-methyl-4-((3-(4-(methylamino)-1,3,5-triazin-2-yl)-2-pyridinyl)oxy)phenyl)urea | 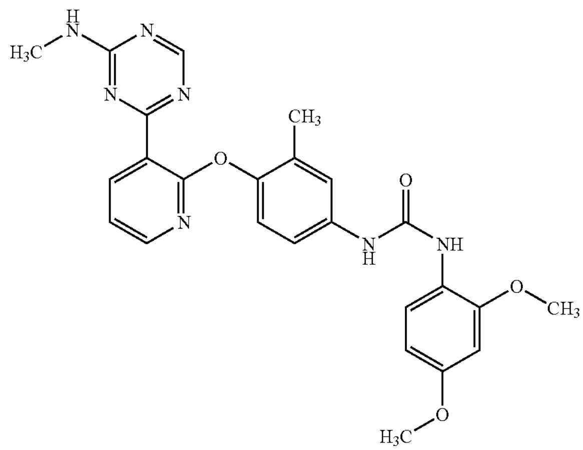 | 487.52 | 488 |
| 855 | N-(5-chloro-2,4-bis(methyloxy)phenyl)-N'-(3-methyl-4-((3-(4-(methylamino)-1,3,5-triazin-2-yl)-2-pyridinyl)oxy)phenyl)urea | 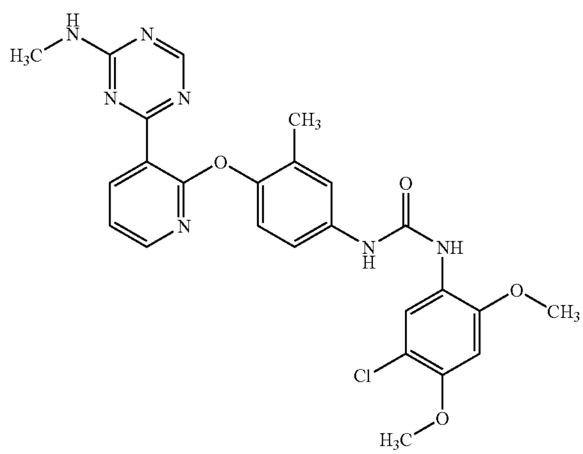 | 521.96 | 523 |
| 856 | N-(2-chloro-5-(trifluoromethyl)phenyl)-N'-(4-((3-(4-(methylamino)-1,3,5-triazin-2-yl)-2-pyridinyl)oxy)-1-naphthalenyl)urea | 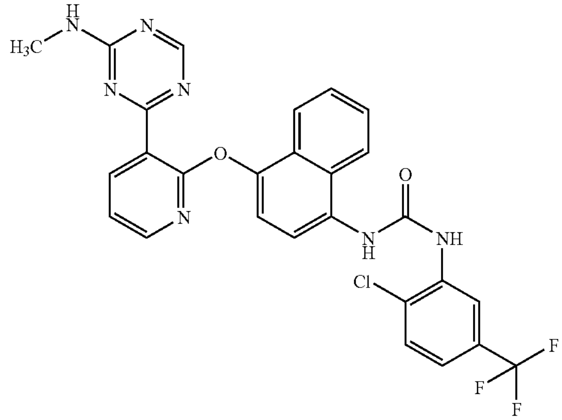 | 565.94 | 567 |

| Ex. No. | Structure Name | Structure | MW | MS Data |
|---|---|---|---|---|
| 857 | N-(2,4-bis(methyloxy)phenyl)-N'-(4-((3-(4-(methylamino)-1,3,5-triazin-2-yl)-2-pyridinyl)oxy)-1-naphthalenyl)urea | 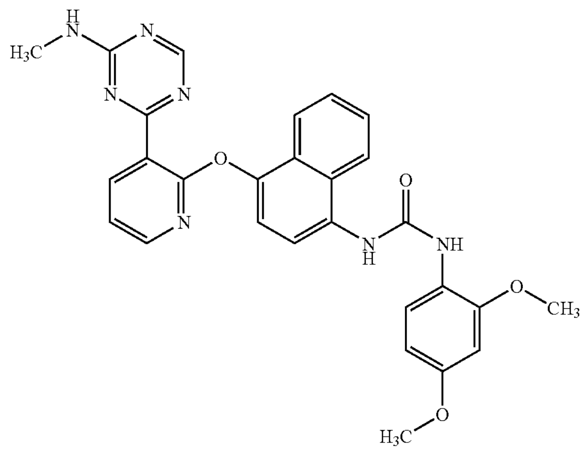 | 523.55 | 525 |
| 858 | N-(5-chloro-2,4-bis(methyloxy)phenyl)-N'-(4-((3-(4-(methylamino)-1,3,5-triazin-2-yl)-2-pyridinyl)oxy)-1-naphthalenyl)urea | 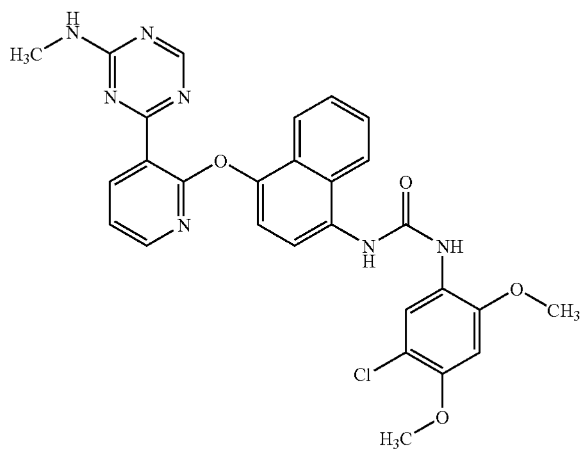 | 558 | 558 |
| 859 | N-(2-((3-(dimethylamino)propyl)(methyl)amino)-5-ethynylphenyl)-N'-(3-methyl-4-((3-(2-(methylamino)-4-pyrimidinyl)-2-pyridinyl)oxy)phenyl)urea | 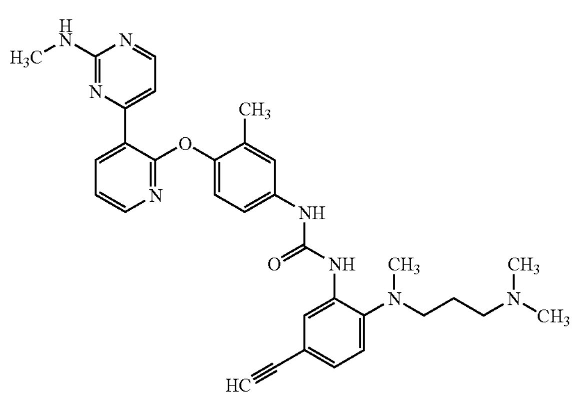 | 564.69 | 565 |

-continued

| Ex. No. | Structure Name | Structure | MW | MS Data |
|---|---|---|---|---|
| 860 | N-(3-((1,1-dioxido-4-thiomorpholinyl)carbonyl)-5-(trifluoromethyl)phenyl)-N'-(3-methyl-4-((3-(2-(methylamino)-4-pyrimidinyl)-2-pyridinyl)oxy)phenyl)urea | 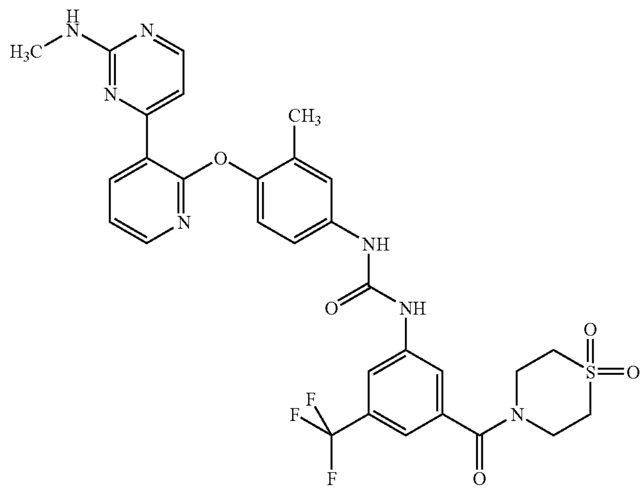 | 655.65 | 656 |
| 861 | N-(2-((3-(dimethylamino)propyl)oxy)-5-(trifluoromethyl)phenyl)-N'-(3-methyl-4-((3-(4-pyrimidinyl)-2-pyridinyl)oxy)phenyl)urea | 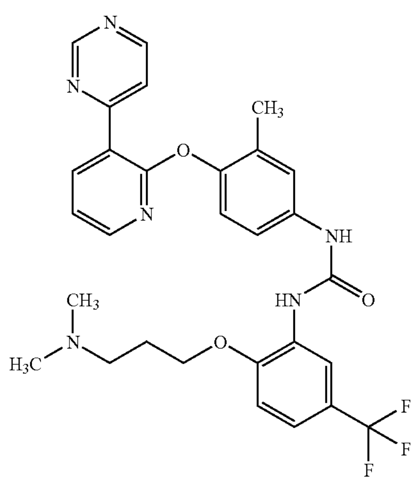 | 566.58 | 567 |
| 862 | N-(2,3-dimethylphenyl)-N'-(3-methyl-4-((3-(2-(methylamino)-4-pyrimidinyl)-2-pyridinyl)oxy)phenyl)urea | 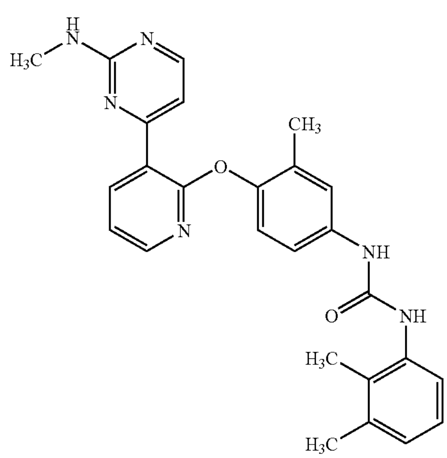 | 454.53 | 455 |

-continued

| Ex. No. | Structure Name | Structure | MW | MS Data |
|---|---|---|---|---|
| 863 | N-(2-chloro-4-(trifluoromethyl)phenyl)-N'-(3-methyl-4-((3-(2-(methylamino)-4-pyrimidinyl)-2-pyridinyl)oxy)phenyl)urea | 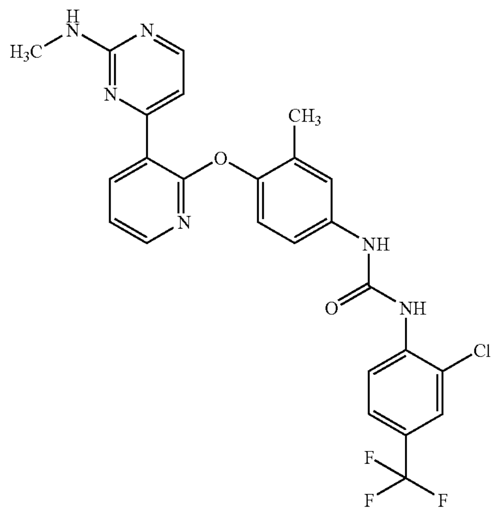 | 528.92 | 529 |
| 864 | N-(4-chloro-3-(trifluoromethyl)phenyl)-N'-(3-methyl-4-((3-(2-(methylamino)-4-pyrimidinyl)-2-pyridinyl)oxy)phenyl)urea | 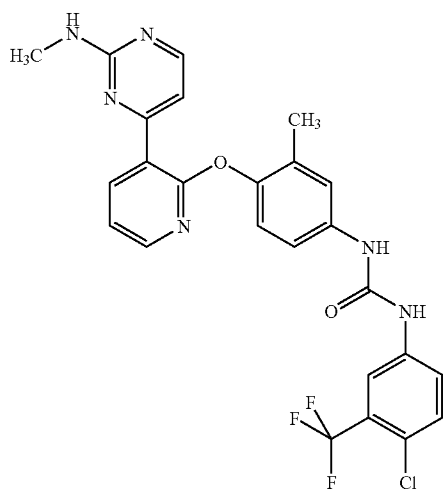 | 528.92 | 529 |
| 865 | N-(3-chloro-2-((3-(dimethylamino)propyl)(methyl)amino)-5-(trifluoromethyl)phenyl)-N'-(3-methyl-4-((3-(4-pyrimidinyl)-2-pyridinyl)oxy)phenyl)urea | 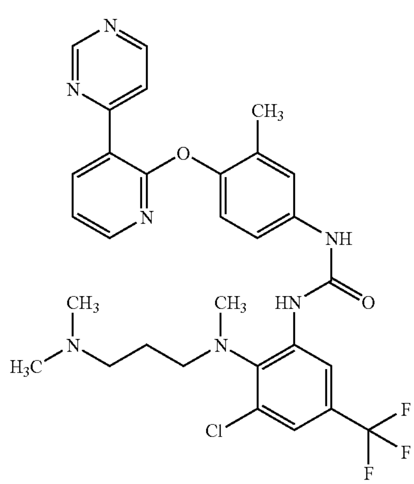 | 614.07 | 614 |

-continued

| Ex. No. | Structure Name | Structure | MW | MS Data |
|---|---|---|---|---|
| 866 | N-(5-chloro-2-((3-(dimethylamino)propyl)(methyl)amino)phenyl)-N'-(3-methyl-4-((3-(4-pyrimidinyl)-2-pyridinyl)oxy)phenyl)urea | 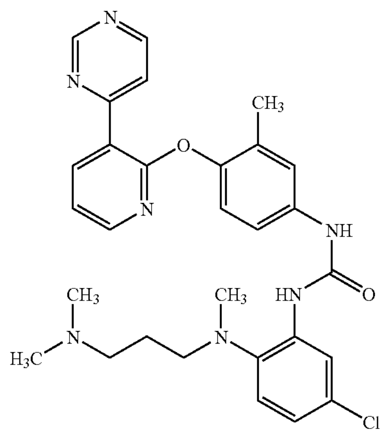 | 546.07 | 546 |
| 867 | N-(5-chloro-2,4-bis(methyloxy)phenyl)-N'-(3-methyl-4-((3-(2-(methylamino)-4-pyrimidinyl)-2-pyridinyl)oxy)phenyl)urea | 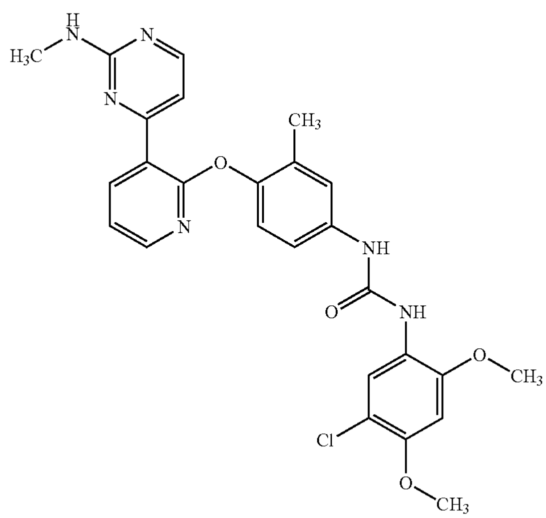 | 520.97 | 521 |
| 868 | N-(5-chloro-2-methylphenyl)-N'-(3-methyl-4-((3-(4-(methylamino)-1,3,5-triazin-2-yl)-2-pyridinyl)oxy)phenyl)urea | 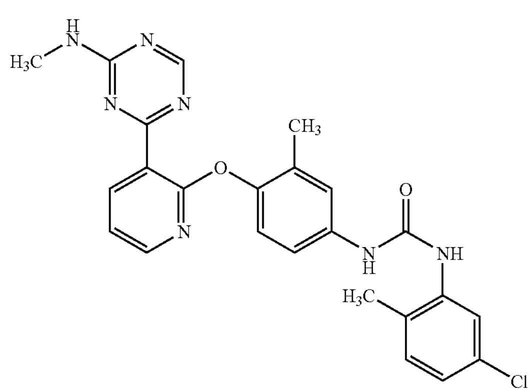 | 475.94 | 476 |

| Ex. No. | Structure Name | Structure | MW | MS Data |
|---|---|---|---|---|
| 869 | N-(3-(ethyloxy)phenyl)-N'-(3-methyl-4-((3-(4-(methylamino)-1,3,5-triazin-2-yl)-2-pyridinyl)oxy)phenyl)urea | 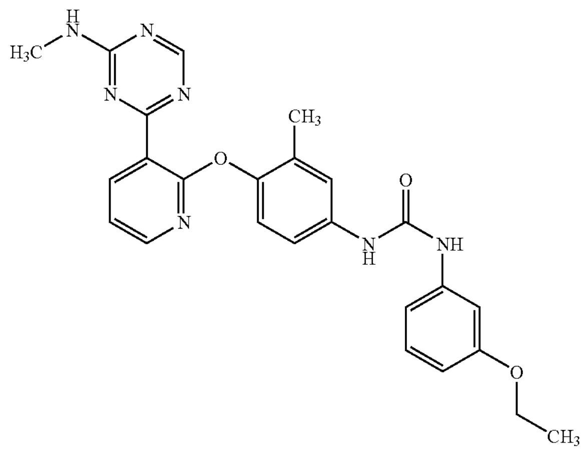 | 471.52 | 472 |
| 870 | N-(3-ethylphenyl)-N'-(3-methyl-4-((3-(4-(methylamino)-1,3,5-triazin-2-yl)-2-pyridinyl)oxy)phenyl)urea | 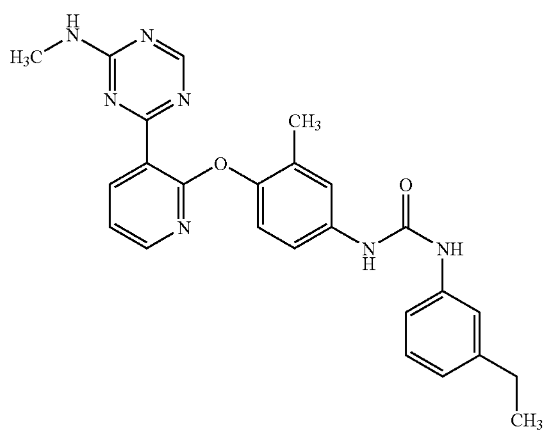 | 455.52 | 456 |
| 871 | N-(2,5-dimethylphenyl)-N'-(3-methyl-4-((3-(4-(methylamino)-1,3,5-triazin-2-yl)-2-pyridinyl)oxy)phenyl)urea | 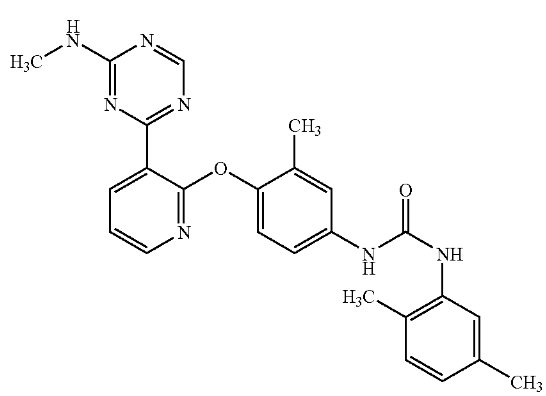 | 455.52 | 456 |

-continued

| Ex. No. | Structure Name | Structure | MW | MS Data |
|---|---|---|---|---|
| 872 | N-(2,5-bis(methyloxy)phenyl)-N'-(3-methyl-4-((3-(4-(methylamino)-1,3,5-triazin-2-yl)-2-pyridinyl)oxy)phenyl)urea | 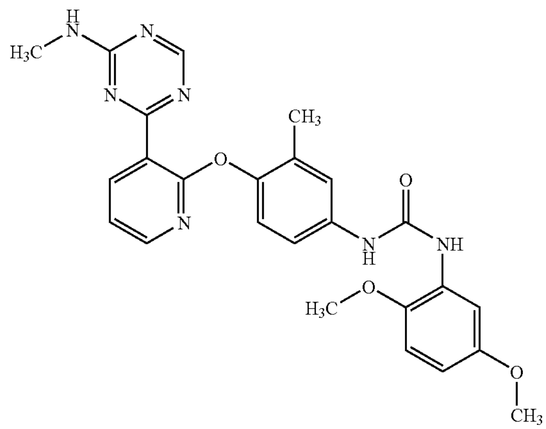 | 487.52 | 488 |
| 873 | N-(2,5-dichlorophenyl)-N'-(3-methyl-4-((3-(4-(methylamino)-1,3,5-triazin-2-yl)-2-pyridinyl)oxy)phenyl)urea | 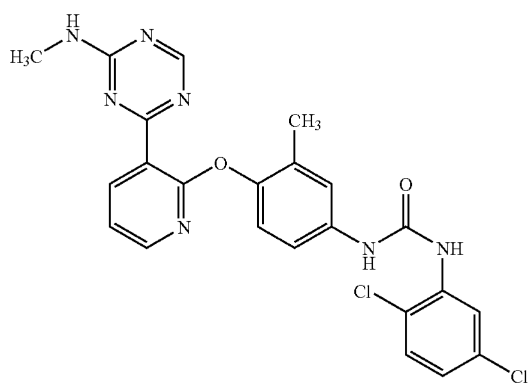 | 496.36 | 496 |
| 874 | 1-(3-chloro-4-(3-(4-(methylamino)-1,3,5-triazin-2-yl)pyridin-2-yloxy)phenyl)-3-(3-ethoxyphenyl)urea | 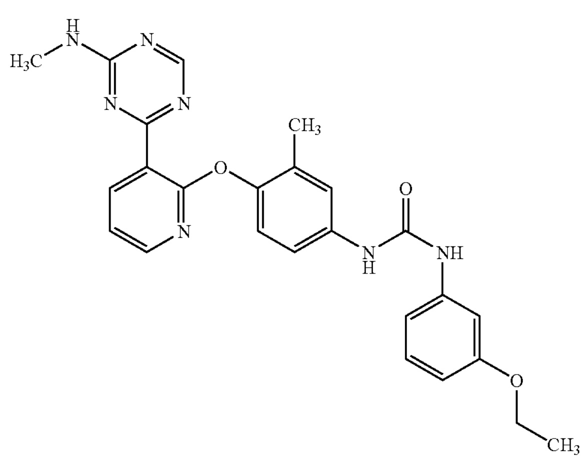 | 491.94 | 492 |

-continued
| Ex. No. | Structure Name | Structure | MW | MS Data |
|---|---|---|---|---|
| 875 | N-(3-chloro-4-((3-(4-(methylamino)-1,3,5-triazin-2-yl)-2-pyridinyl)oxy)phenyl)-N'-(3-ethylphenyl)urea | 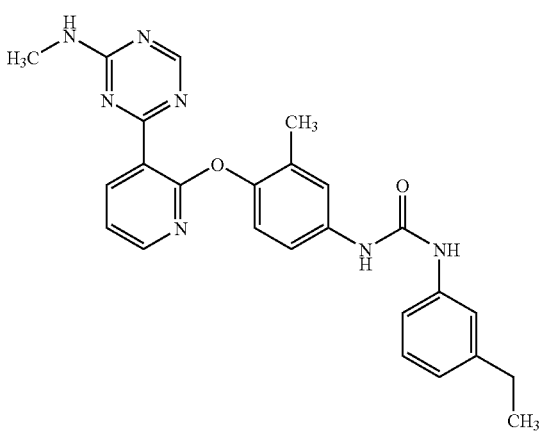 | 475.94 | 476 |
| 876 | N-(3-chloro-4-((3-(4-(methylamino)-1,3,5-triazin-2-yl)-2-pyridinyl)oxy)phenyl)-N'-(5-chloro-2-(methyloxy)phenyl)urea | 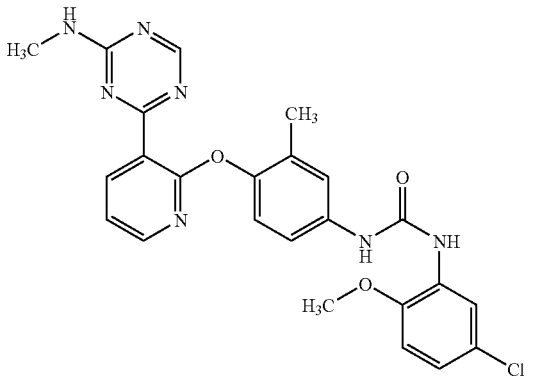 | 512.36 | 513 |
| 877 | N-(3,5-bis(methyloxy)phenyl)-N'-(3-chloro-4-((3-(4-(methylamino)-1,3,5-triazin-2-yl)-2-pyridinyl)oxy)phenyl)urea | 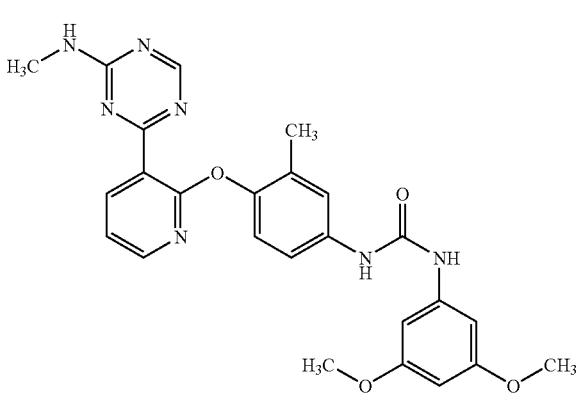 | 507.94 | 508 |

|Ex. No.|Structure Name|Structure|MW|MS Data|
|---|---|---|---|---|
|878|N-(2,5-bis(methyloxy)phenyl)-N'-(3-methyl-4-((3-(2-(methylamino)-4-pyrimidinyl)-2-pyridinyl)oxy)phenyl)urea| 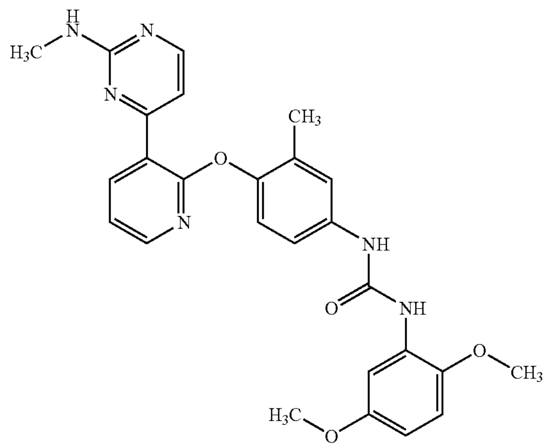 |486.53|487|
|879|N-(5-cyclopropyl-2-((3-(dimethylamino)propyl)(methyl)amino)phenyl)-N'-(3-methyl-4-((3-(4-pyrimidinyl)-2-pyridinyl)oxy)phenyl)urea| 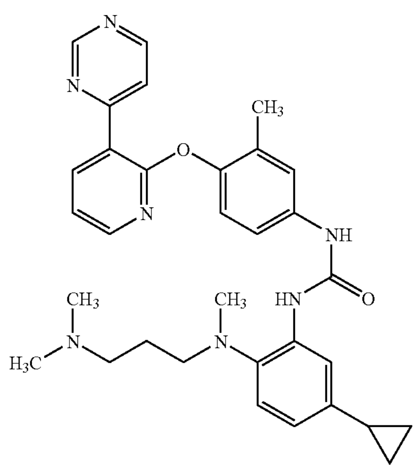 |551.69|552|
|880|N-(5-cyclopropyl-2-((3-(dimethylamino)propyl)(methyl)amino)phenyl)-N'-(3-methyl-4-((3-(2-(methylamino)-4-pyrimidinyl)-2-pyridinyl)oxy)phenyl)urea| 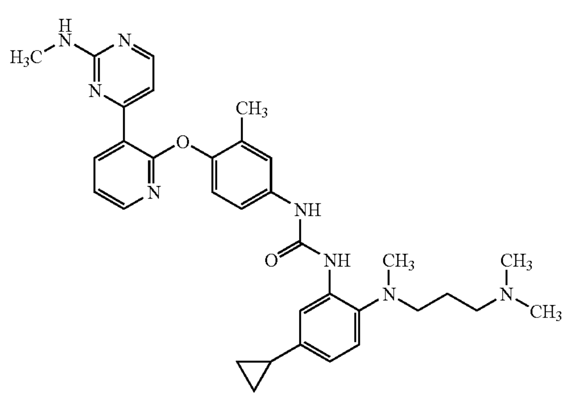 |580.73|581|

-continued

| Ex. No. | Structure Name | Structure | MW | MS Data |
|---|---|---|---|---|
| 881 | N-(5-chloro-2-(methyloxy)phenyl)-N'-(3-methyl-4-((3-(2-((3-(4-morpholinyl)propyl)amino)-4-pyrimidinyl)-2-pyridinyl)oxy)phenyl)urea | 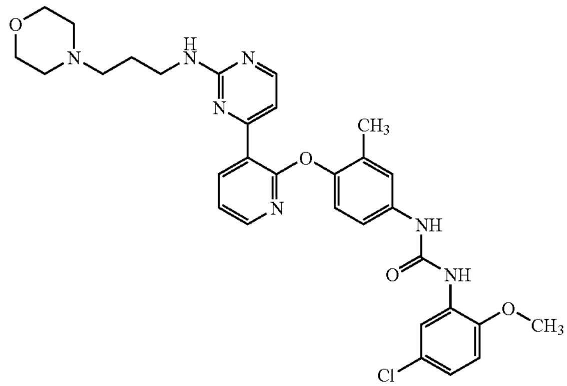 | 604.11 | 604 |
| 882 | N-(3-chloro-4-fluorophenyl)-N'-(3-methyl-4-((3-(2-(methylamino)-4-pyrimidinyl)-2-pyridinyl)oxy)phenyl)urea | 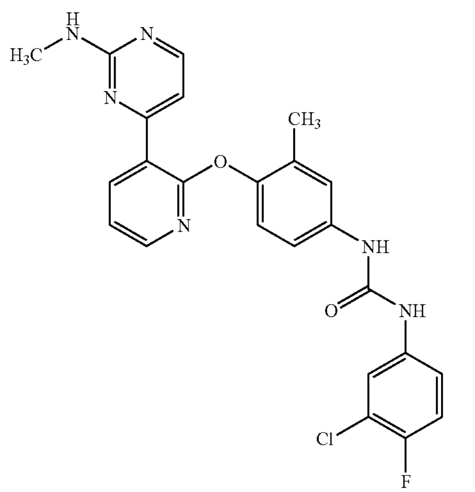 | 478.91 | 479 |
| 883 | N-(5-fluoro-2-methylphenyl)-N'-(3-methyl-4-((3-(2-(methylamino)-4-pyrimidinyl)-2-pyridinyl)oxy)phenyl)urea | 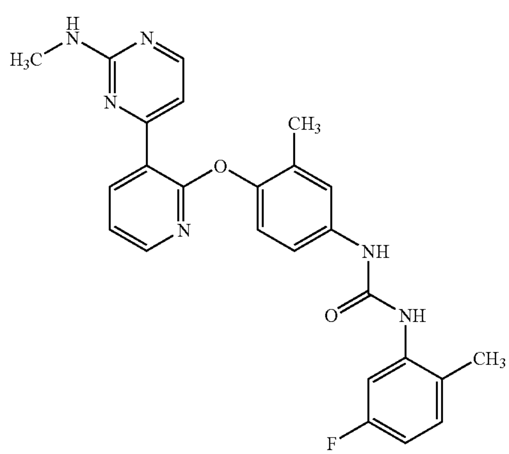 | 458.5 | 459 |

| Ex. No. | Structure Name | Structure | MW | MS Data |
|---|---|---|---|---|
| 884 | N-(3-methyl-4-((3-(2-(methylamino)-4-pyrimidinyl)-2-pyridinyl)oxy)phenyl)-N'-(2,4,5-trichlorophenyl)urea | 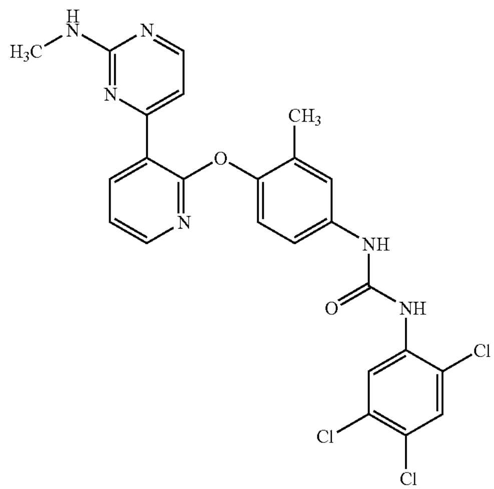 | 529.81 | 529 |
| 885 | N-(5-chloro-2-(methyloxy)phenyl)-N'-(3-methyl-4-((3-(2-((3-(2-oxo-1-pyrrolidinyl)propyl)amino)-4-pyrimidinyl)-2-pyridinyl)oxy)phenyl)urea | 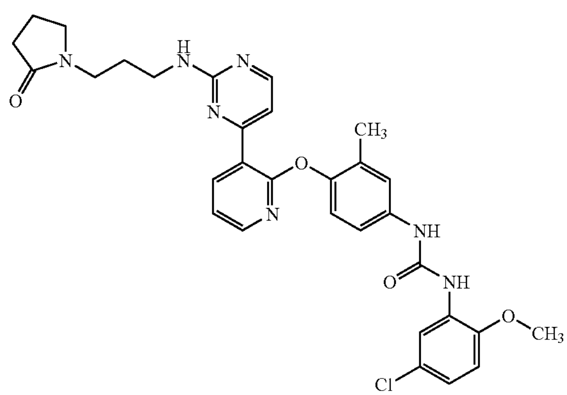 | 602.09 | 602 |
| 886 | N-(3-methyl-4-((3-(2-((3-(2-oxo-1-pyrrolidinyl)propyl)amino)-4-pyrimidinyl)-2-pyridinyl)oxy)phenyl)-N'-(3-(trifluoromethyl)phenyl)urea | 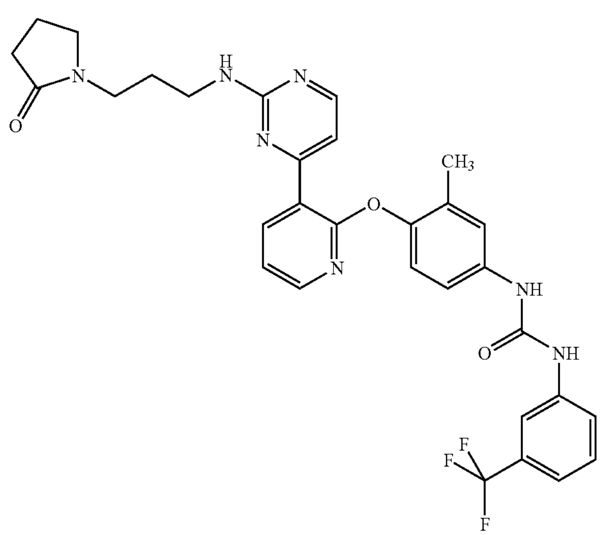 | 605.62 | 606 |

| Ex. No. | Structure Name | Structure | MW | MS Data |
|---|---|---|---|---|
| 887 | N-(3-methyl-4-((3-(2-(methylamino)-4-pyrimidinyl)-2-pyridinyl)oxy)phenyl)-N'-(3-((trifluoromethyl)sulfanyl)phenyl)urea | 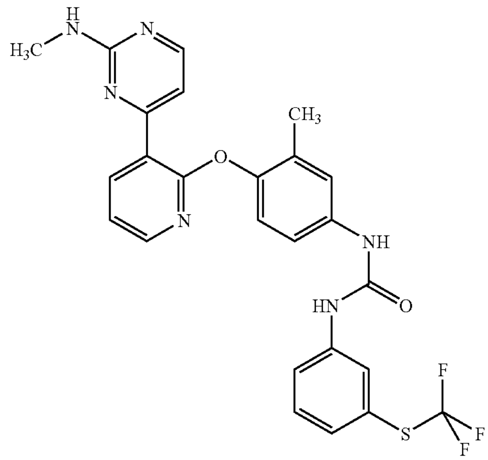 | 526.54 | 527 |
| 888 | N-(3-methyl-4-((3-(2-(methylamino)-4-pyrimidinyl)-2-pyridinyl)oxy)phenyl)-N'-(3-((trifluoromethyl)sulfanyl)phenyl)thiourea | 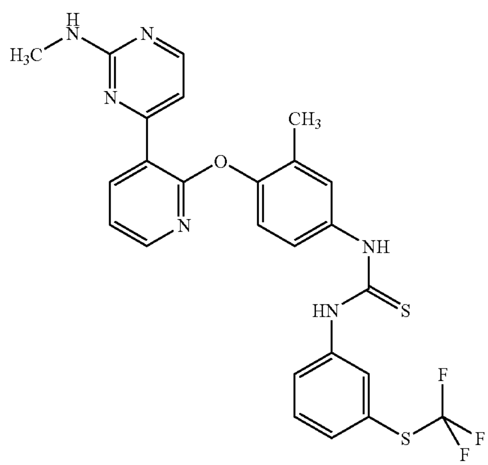 | 542.61 | 543 |
| 889 | N-(5-chloro-2-(methyloxy)phenyl)-N'-(2,3-dimethyl-4-((3-(2-(methylamino)-4-pyrimidinyl)-2-pyridinyl)oxy)phenyl)urea | 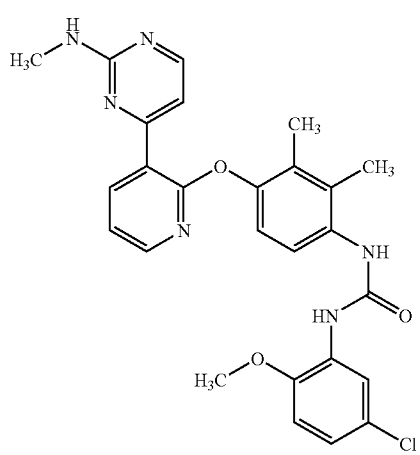 | 504.98 | 505 |

| Ex. No. | Structure Name | Structure | MW | MS Data |
|---|---|---|---|---|
| 890 | N-(3-chlorophenyl)-N'-(2,3-dimethyl-4-((3-(2-(methylamino)-4-pyrimidinyl)-2-pyridinyl)oxy)phenyl)urea | 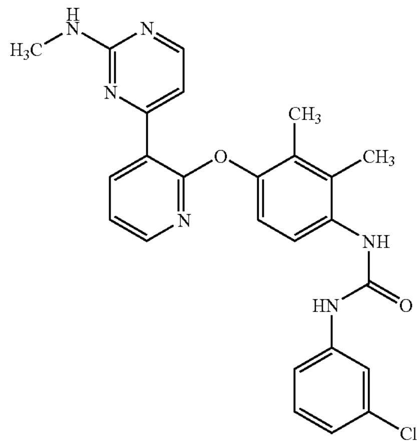 | 474.95 | 475 |
| 891 | N-(2,3-dimethyl-4-((3-(2-(methylamino)-4-pyrimidinyl)-2-pyridinyl)oxy)phenyl)-N'-(3-fluoro-5-(trifluoromethyl)phenyl)urea | 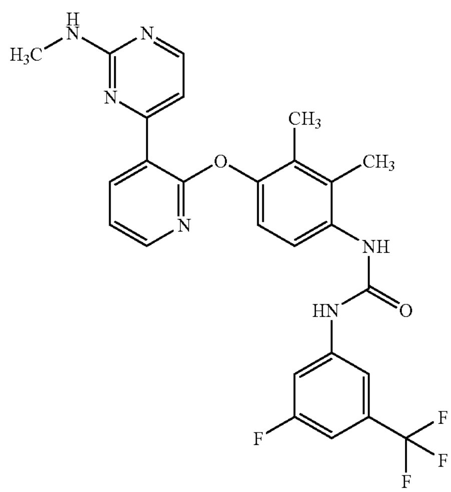 | 526.49 | 527 |
| 892 | N-(2-chloro-5-(trifluoromethyl)phenyl)-N'-(2,3-dimethyl-4-((3-(2-(methylamino)-4-pyrimidinyl)-2-pyridinyl)oxy)phenyl)urea | 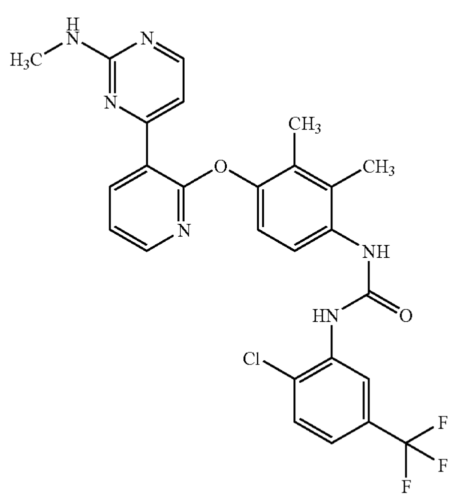 | 542.95 | 543 |

| Ex. No. | Structure Name | Structure | MW | MS Data |
|---|---|---|---|---|
| 893 | N-(5-chloro-2,4-bis(methyloxy)phenyl)-N'-(2,3-dimethyl-4-((3-(2-(methylamino)-4-pyrimidinyl)-2-pyridinyl)oxy)phenyl)urea | 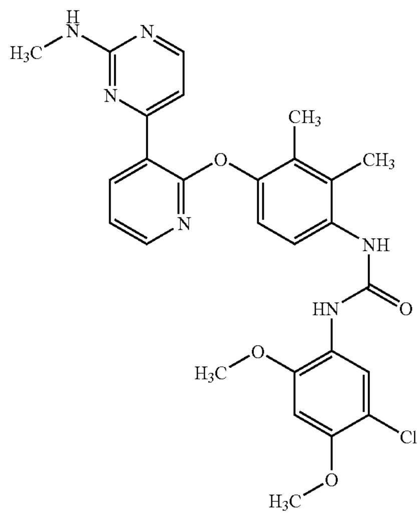 | 535 | 535 |
| 894 | N-(3-methyl-4-((3-(2-(methylamino)-4-pyrimidinyl)-2-pyridinyl)oxy)phenyl)-N'-(2-(1H-1,2,4-triazol-1-yl)-5-(trifluoromethyl)phenyl)urea | 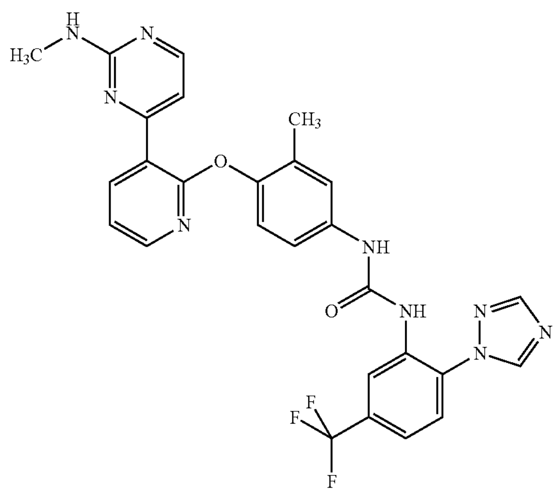 | 561.53 | 562 |
| 895 | N-(3-methyl-4-((3-(2-(methylamino)-4-pyrimidinyl)-2-pyridinyl)oxy)phenyl)-N'-(4-(trifluoromethyl)-2-pyridinyl)urea | 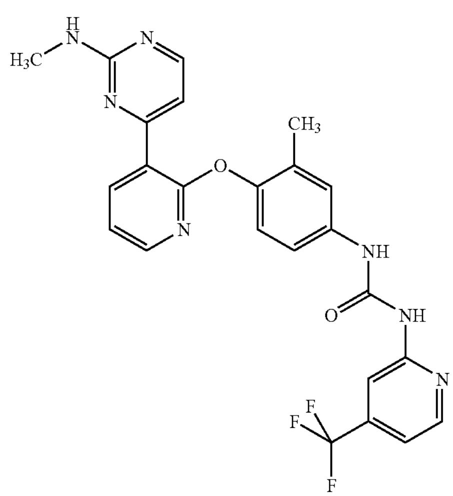 | 495.46 | 496 |

-continued

| Ex. No. | Structure Name | Structure | MW | MS Data |
|---|---|---|---|---|
| 896 | N-(3-methyl-4-((3-(2-(methylamino)-4-pyrimidinyl)-2-pyridinyl)oxy)phenyl)-N'-(2-(methyloxy)-5-(trifluoromethyl)phenyl)urea | 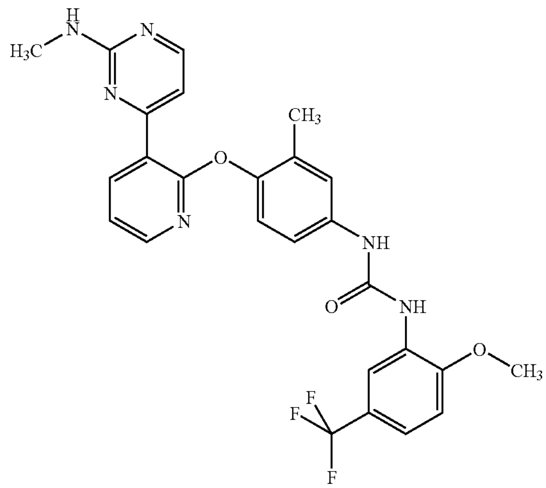 | 524.5 | 525 |
| 897 | N-(2,3-dimethyl-4-((3-(2-(methylamino)-4-pyrimidinyl)-2-pyridinyl)oxy)phenyl)-N'-(2-(methyloxy)-5-(trifluoromethyl)phenyl)urea | 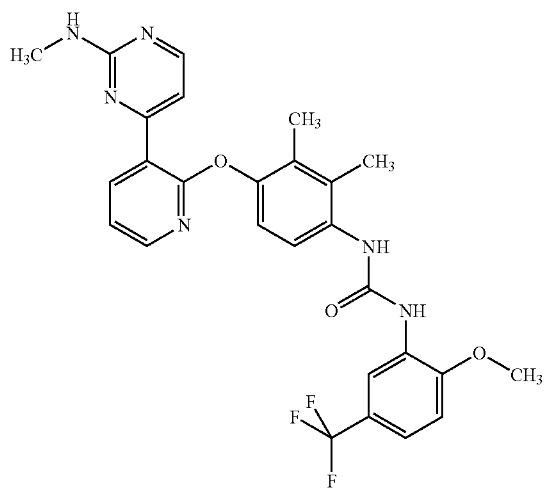 | 538.53 | 539 |
| 898 | N-(2,3-dimethyl-4-((3-(2-(methylamino)-4-pyrimidinyl)-2-pyridinyl)oxy)phenyl)-N'-(3-fluorophenyl)urea | 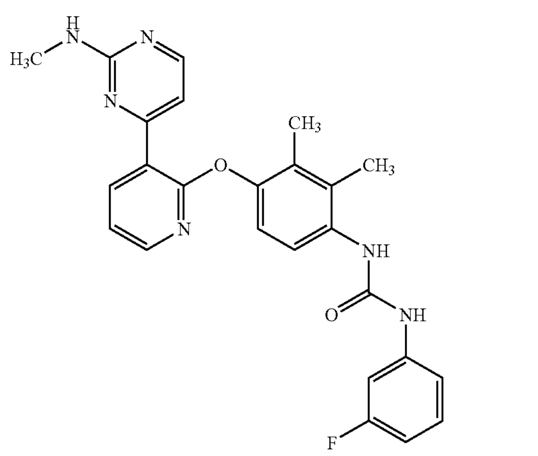 | 458.5 | 459 |

-continued

| Ex. No. | Structure Name | Structure | MW | MS Data |
|---|---|---|---|---|
| 899 | N-(3-fluorophenyl)-N'-(4-((3-(2-(methylamino)-4-pyrimidinyl)-2-pyridinyl)oxy)phenyl)urea | 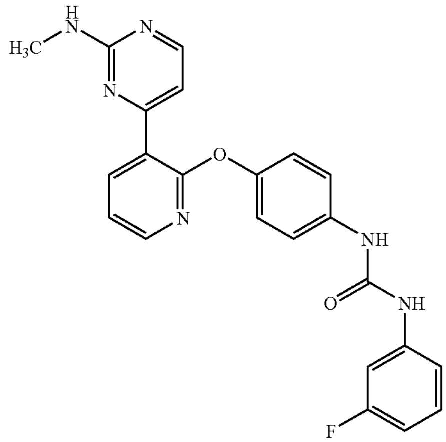 | 430.44 | 431 |
| 900 | N-cyclopropyl-N'-(3-methyl-4-((3-(2-(methylamino)-4-pyrimidinyl)-2-pyridinyl)oxy)phenyl)urea | 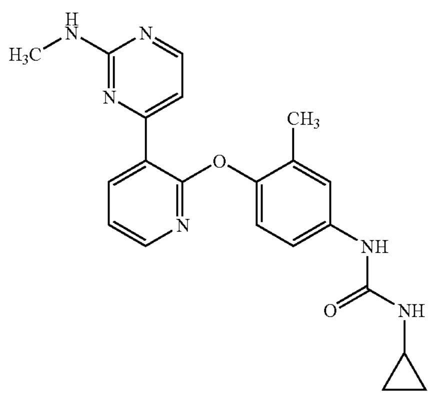 | 390.44 | 391 |
| 901 | N-(5-chloro-2-(methyloxy)phenyl)-N'-(4-((3-(2-(methylamino)-4-pyrimidinyl)-2-pyridinyl)oxy)phenyl)urea | 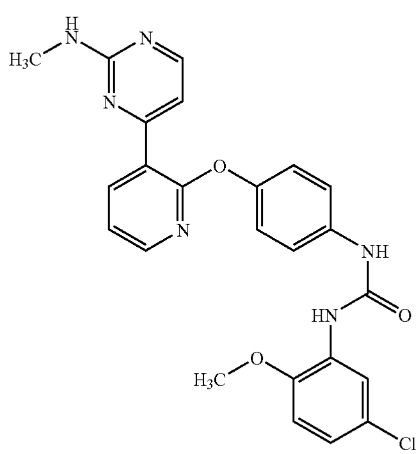 | 476.92 | 477 |

| Ex. No. | Structure Name | Structure | MW | MS Data |
|---|---|---|---|---|
| 902 | N-(5-chloro-2,4-bis(methyloxy)phenyl)-N'-(4-((3-(2-(methylamino)-4-pyrimidinyl)-2-pyridinyl)oxy)phenyl)urea | 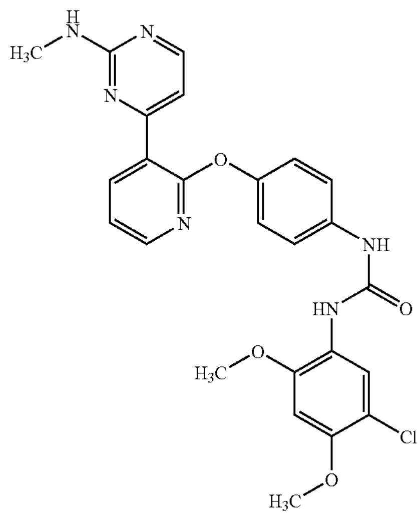 | 506.95 | 507 |
| 903 | N-(3-bromophenyl)-N'-(4-((3-(2-(methylamino)-4-pyrimidinyl)-2-pyridinyl)oxy)phenyl)urea | 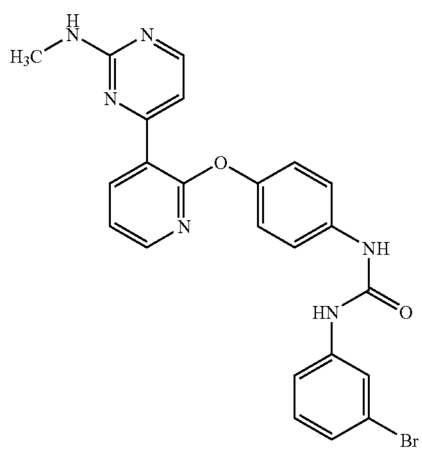 | 491.35 | 491 |
| 904 | N-(2-chloro-5-(trifluoromethyl)phenyl)-N'-(4-((3-(2-(methylamino)-4-pyrimidinyl)-2-pyridinyl)oxy)phenyl)urea | 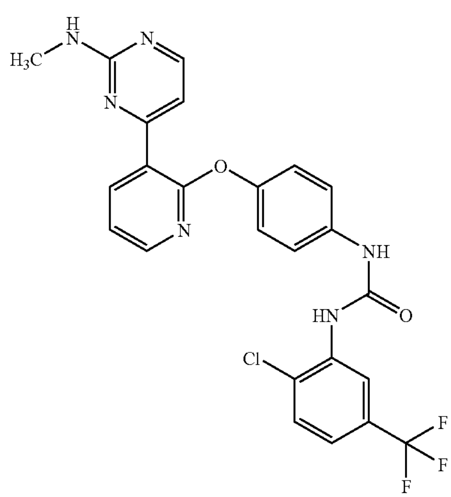 | 514.89 | 515 |

| Ex. No. | Structure Name | Structure | MW | MS Data |
|---|---|---|---|---|
| 905 | N-(3-chlorophenyl)-N'-(4-((3-(2-(methylamino)-4-pyrimidinyl)-2-pyridinyl)oxy)phenyl)urea | 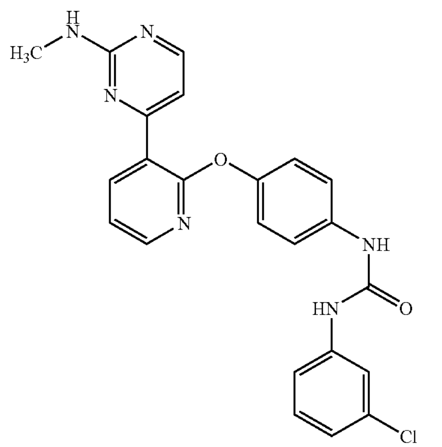 | 446.9 | 447 |
| 906 | N-(3-fluoro-5-(trifluoromethyl)phenyl)-N'-(4-((3-(2-(methylamino)-4-pyrimidinyl)-2-pyridinyl)oxy)phenyl)urea | 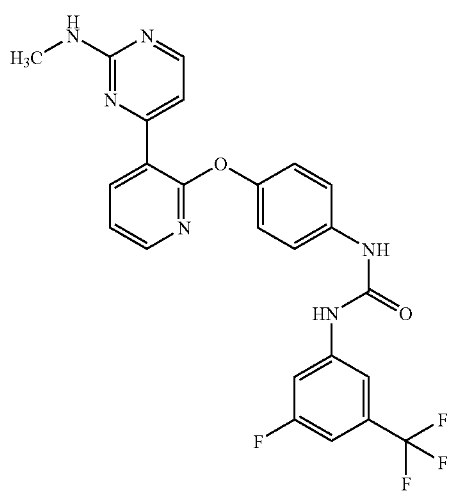 | 498.44 | 499 |
| 907 | N-(3-methyl-4-((3-(2-(methylamino)-4-pyrimidinyl)-2-pyridinyl)oxy)phenyl)-N'-(2-(methyl((2S)-1-methyl-2-pyrrolidinyl)amino)-5-(trifluoromethyl)phenyl) urea | 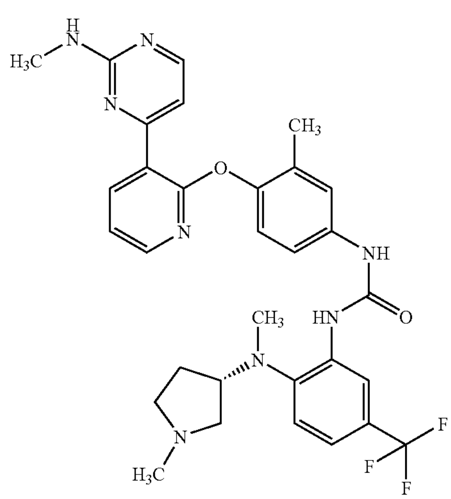 | 606.65 | 607 |

| Ex. No. | Structure Name | Structure | MW | MS Data |
|---|---|---|---|---|
| 908 | N-(3-methyl-4-((3-(2-(methylamino)-4-pyrimidinyl)-2-pyridinyl)oxy)phenyl)-N'-(2-(methyl((3R)-1-methyl-3-pyrrolidinyl)amino)-5-(trifluoromethyl)phenyl)urea | 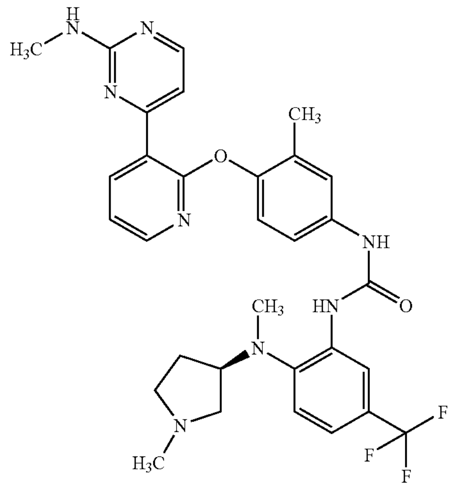 | 606.65 | 607 |
| 909 | N-(5-chloro-2-(methyloxy)phenyl)-N'-(4-((3-(2-(methylamino)-4-pyrimidinyl)-2-pyridinyl)sulfanyl)phenyl)urea | 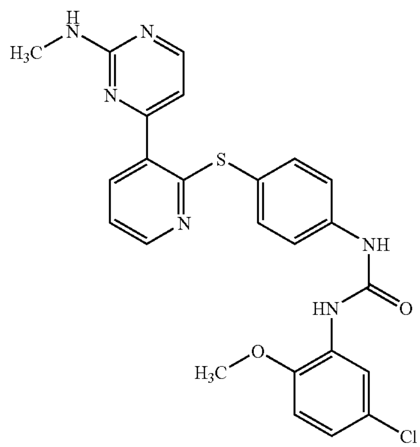 | 492.99 | 493 |
| 910 | N-(3-chlorophenyl)-N'-(4-((3-(2-(methylamino)-4-pyrimidinyl)-2-pyridinyl)sulfanyl)phenyl)urea | 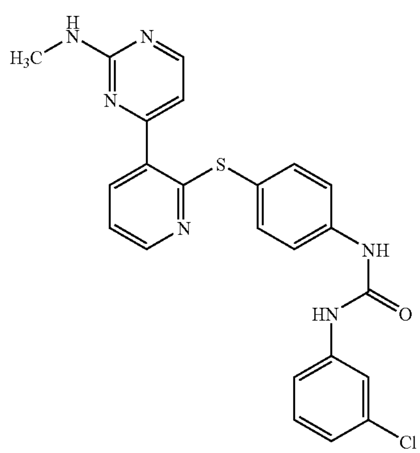 | 462.96 | 463 |

| Ex. No. | Structure Name | Structure | MW | MS Data |
|---|---|---|---|---|
| 911 | N-(3-fluoro-5-(trifluoromethyl)phenyl)-N'-(4-((3-(2-(methylamino)-4-pyrimidinyl)-2-pyridinyl)sulfanyl)phenyl)urea | 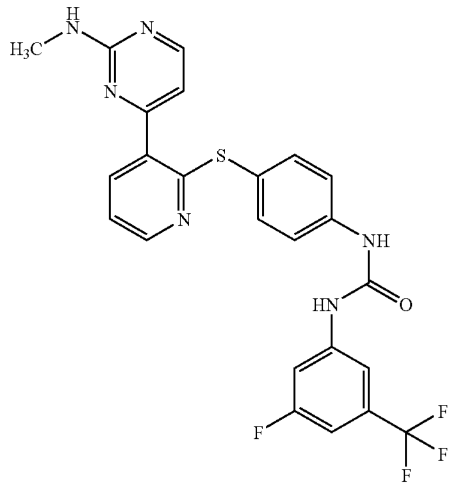 | 514.51 | 515 |
| 912 | N-(3-bromophenyl)-N'-(4-((3-(2-(methylamino)-4-pyrimidinyl)-2-pyridinyl)sulfanyl)phenyl)urea | 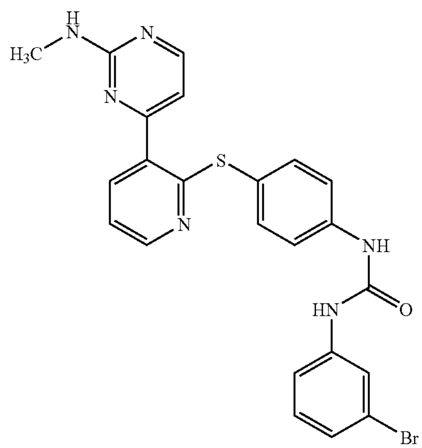 | 507.41 | 509 |
| 913 | N-(3-fluorophenyl)-N'-(4-((3-(2-(methylamino)-4-pyrimidinyl)-2-pyridinyl)sulfanyl)phenyl)urea | 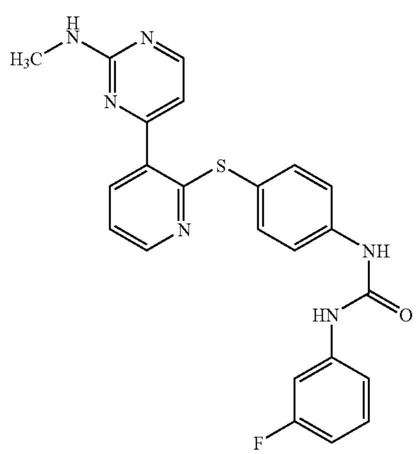 | 446.51 | 447 |

-continued

| Ex. No. | Structure Name | Structure | MW | MS Data |
|---|---|---|---|---|
| 914 | N-(4-((3-(2-(methylamino)-4-pyrimidinyl)-2-pyridinyl)oxy)phenyl)-N'-phenylurea | 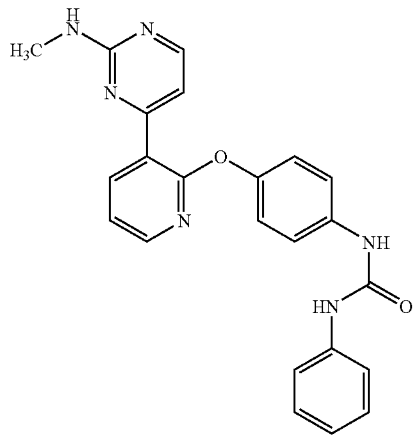 | 412.45 | 413 |
| 915 | N-(4-((3-(2-(methylamino)-4-pyrimidinyl)-2-pyridinyl)sulfanyl)phenyl)-N'-phenylurea | 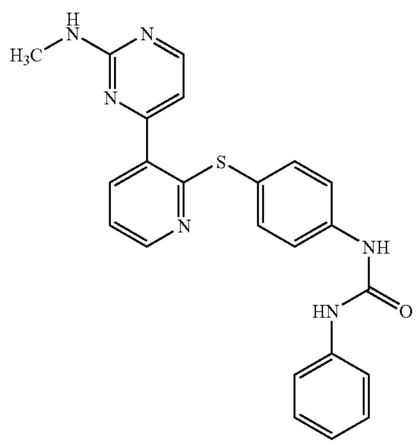 | 428.52 | 429 |
| 916 | N-(4-((3-(2-(methylamino)-4-pyrimidinyl)-2-pyridinyl)oxy)phenyl)benzamide | 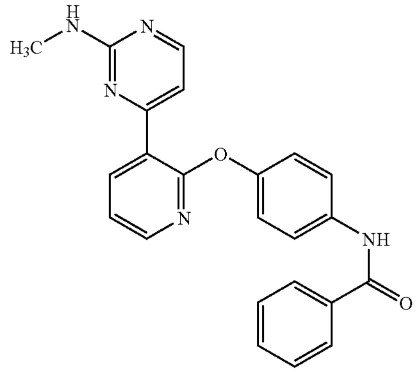 | 397.44 | 398 |

-continued

| Ex. No. | Structure Name | Structure | MW | MS Data |
|---|---|---|---|---|
| 917 | 3-bromo-N-(4-((3-(2-(methylamino)-4-pyrimidinyl)-2-pyridinyl)oxy)phenyl)benzamide | 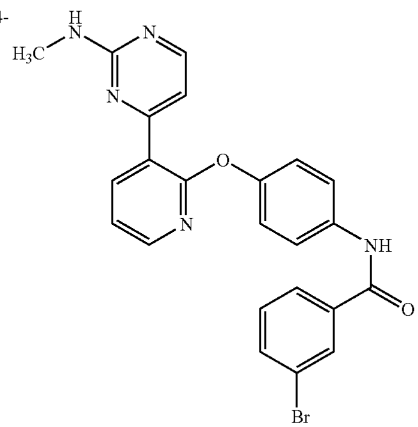 | 476.33 | 478 |
| 918 | N-(4-((3-(2-(methylamino)-4-pyrimidinyl)-2-pyridinyl)oxy)phenyl)-3-(trifluoromethyl)benzamide | 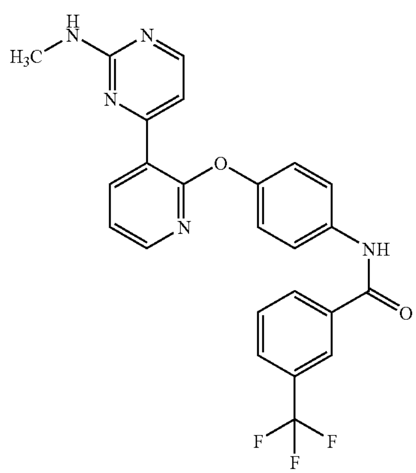 | 465.43 | 466 |
| 919 | N-(4-((3-(6,7-bis(methyloxy)-4-quinazolinyl)-2-pyridinyl)oxy)phenyl)-N'-(3-fluorophenyl)urea | 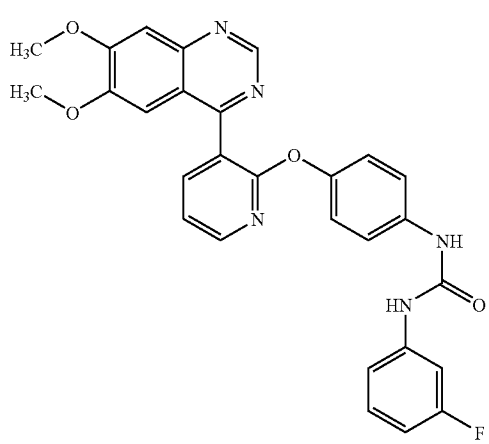 | 511.51 | 512 |

-continued

| Ex. No. | Structure Name | Structure | MW | MS Data |
|---|---|---|---|---|
| 920 | N-(5-chloro-2-(methyloxy)phenyl)-N'-(4-((2'-(methylamino)-3,4'-bipyridin-2-yl)oxy)phenyl)urea | 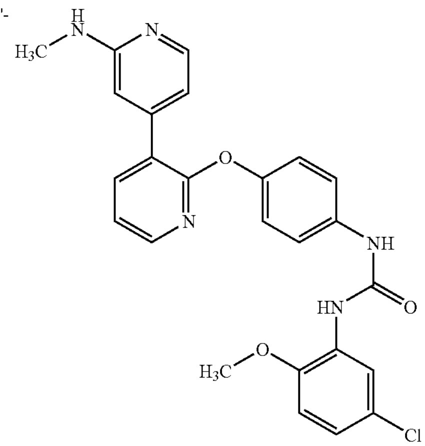 | 475.93 | 476 |
| 921 | N-(2,4-bis(methyloxy)phenyl)-N'-(4-((2'-(methylamino)-3,4'-bipyridin-2-yl)oxy)phenyl)urea | 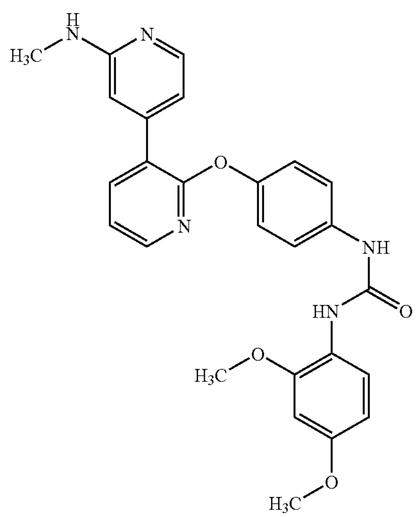 | 471.51 | 472 |
| 922 | N-(2,5-bis(1,1-dimethylethyl)phenyl)-N'-(4-((3-(2-(methylamino)-4-pyrimidinyl)-2-pyridinyl)sulfanyl)phenyl)urea | 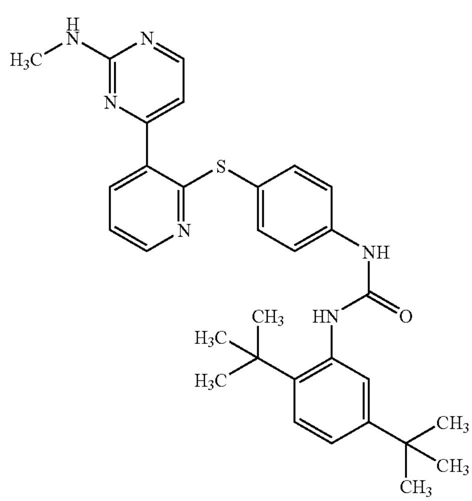 | 540.73 | 541 |

-continued

| Ex. No. | Structure Name | Structure | MW | MS Data |
|---|---|---|---|---|
| 923 | N-(2-chloro-5-(trifluoromethyl)phenyl)-N'-(4-((3-(2-(methylamino)-4-pyrimidinyl)-2-pyridinyl)sulfanyl)phenyl)urea | 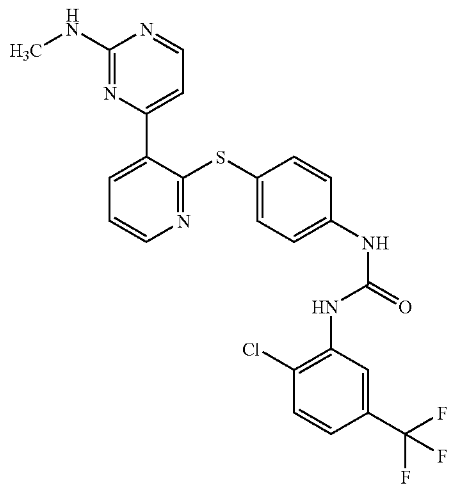 | 530.96 | 531 |
| 924 | N-(3-methyl-4-((3-(2-(methylamino)-4-pyrimidinyl)-2-pyridinyl)oxy)phenyl)-2-thiophenecarboxamide | 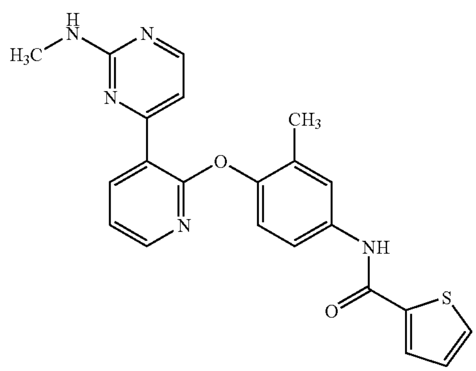 | 417.49 | 418 |
| 925 | N-(3-methyl-4-((3-(2-(methylamino)-4-pyrimidinyl)-2-pyridinyl)oxy)phenyl)-2-furancarboxamide | 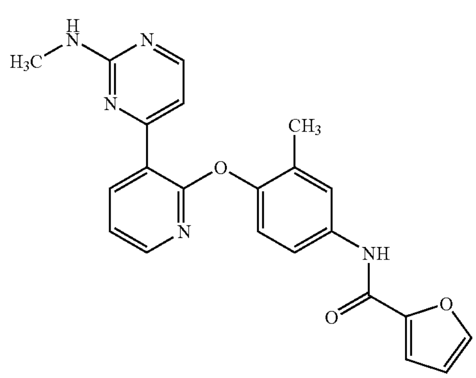 | 401.42 | 402 |

-continued

| Ex. No. | Structure Name | Structure | MW | MS Data |
|---|---|---|---|---|
| 926 | N-(2-fluorophenyl)-N'-(4-((3-(2-(methylamino)-4-pyrimidinyl)-2-pyridinyl)oxy)phenyl)urea | 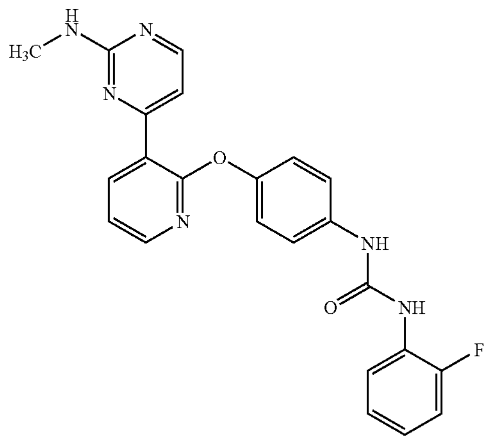 | 430.44 | 431 |
| 927 | N-(2-fluorophenyl)-N'-(4-((3-(2-(methylamino)-4-pyrimidinyl)-2-pyridinyl)sulfanyl)phenyl)urea | 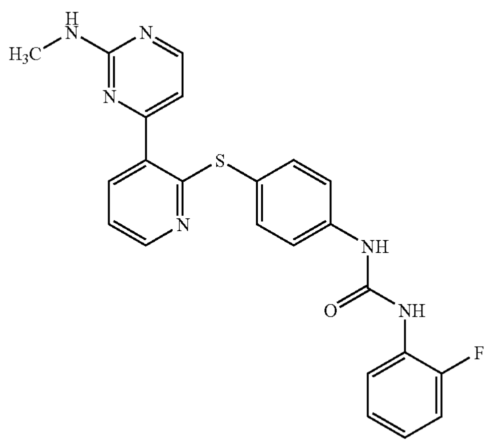 | 446.51 | 447 |
| 928 | N-(4-((3-(2-(methylamino)-4-pyrimidinyl)-2-pyridinyl)oxy)phenyl)-N'-(3-(trifluoromethyl)phenyl)urea | 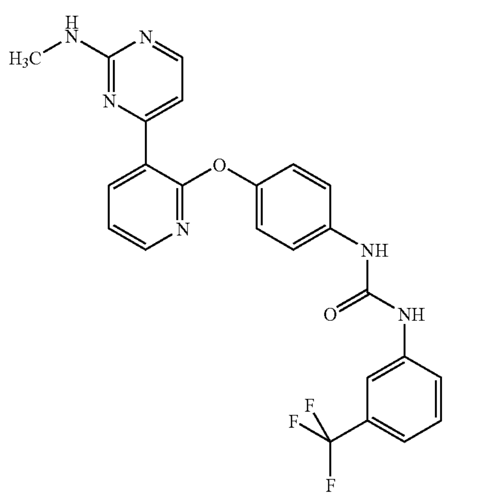 | 480.45 | 481 |

| Ex. No. | Structure Name | Structure | MW | MS Data |
|---|---|---|---|---|
| 929 | N-(4-((3-(2-(methylamino)-4-pyrimidinyl)-2-pyridinyl)sulfanyl)phenyl)-N'-(3-(trifluoromethyl)phenyl)urea | 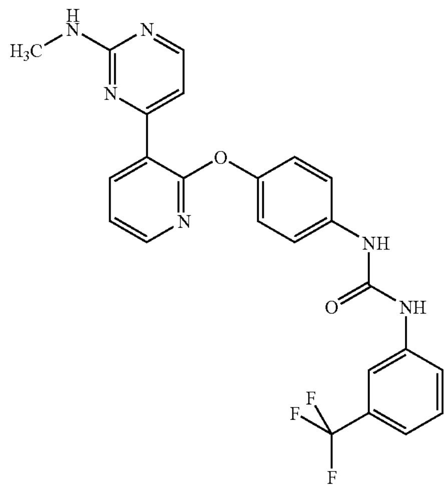 | 496.51 | 497 |
| 930 | N-(4-((3-(5-fluoro-2-(methylamino)-4-pyrimidinyl)-2-pyridinyl)oxy)phenyl)-N'-phenylurea | 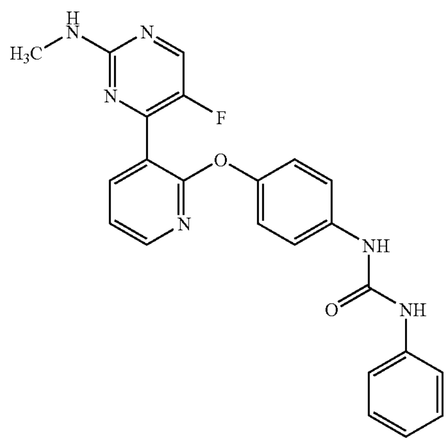 | 430.44 | 431 |
| 931 | N-(4-((3-(2-(methylamino)-4-pyrimidinyl)-2-pyridinyl)oxy)phenyl)-N'-(3-((trifluoromethyl)sulfanyl)phenyl)urea | 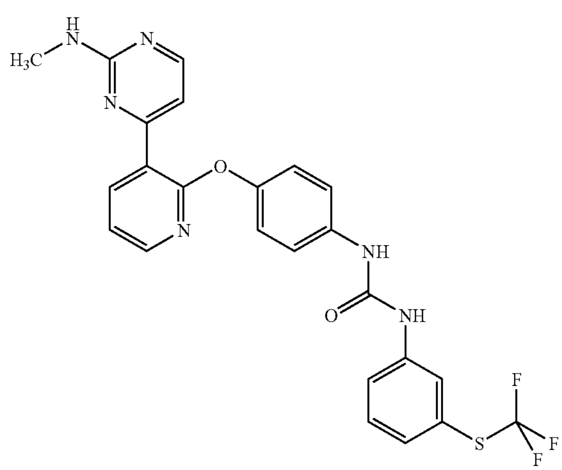 | 512.51 | 513 |

| Ex. No. | Structure Name | Structure | MW | MS Data |
|---|---|---|---|---|
| 932 | N-(3-cyanophenyl)-N'-(4-((3-(2-(methylamino)-4-pyrimidinyl)-2-pyridinyl)oxy)phenyl)urea | 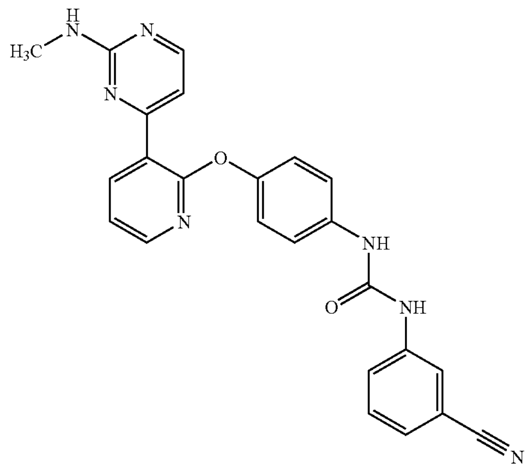 | 437.46 | 438 |
| 933 | ethyl 3-((((4-((3-(2-(methylamino)-4-pyrimidinyl)-2-pyridinyl)oxy)phenyl)amino)carbonyl)amino)benzoate | 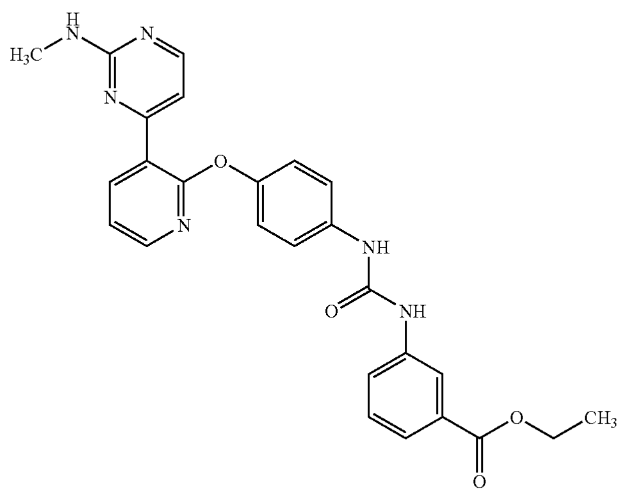 | 484.51 | 485 |
| 934 | ethyl 4-((((4-((3-(2-(methylamino)-4-pyrimidinyl)-2-pyridinyl)oxy)phenyl)amino)carbonyl)amino)benzoate | 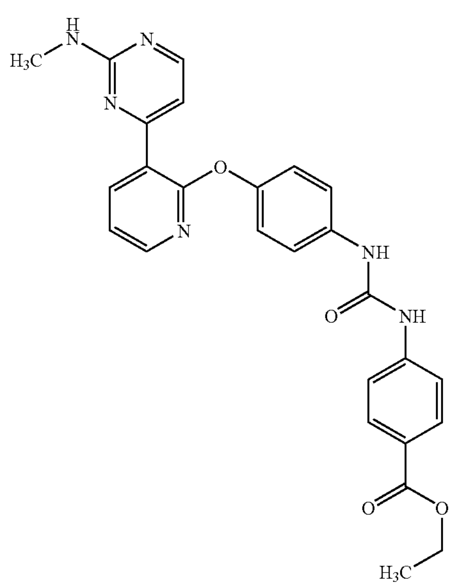 | 484.51 | 485 |

| Ex. No. | Structure Name | Structure | MW | MS Data |
|---|---|---|---|---|
| 935 | N-(2-bromophenyl)-N'-(4-((3-(2-(methylamino)-4-pyrimidinyl)-2-pyridinyl)oxy)phenyl)urea | 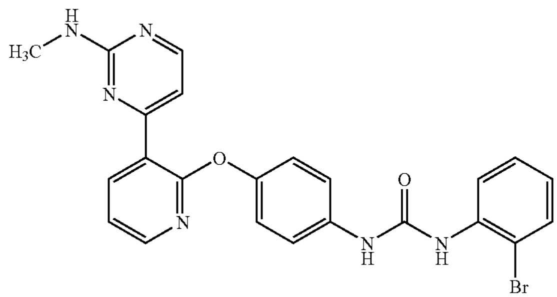 | 491.35 | 491 |
| 936 | N-(2-(ethyloxy)phenyl)-N'-(4-((3-(2-(methylamino)-4-pyrimidinyl)-2-pyridinyl)oxy)phenyl)urea | 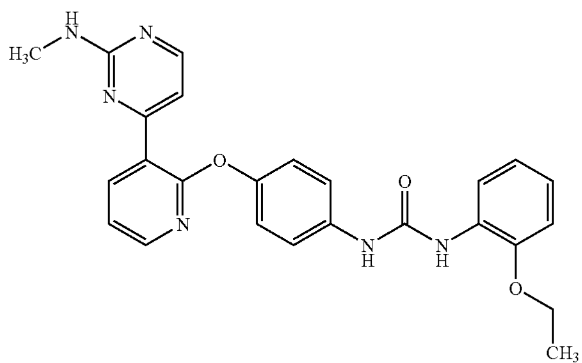 | 456.5 | 457 |
| 937 | N-(2-bromophenyl)-N'-(4-((3-(2-(methylamino)-4-pyrimidinyl)-2-pyridinyl)sulfanyl)phenyl)urea | 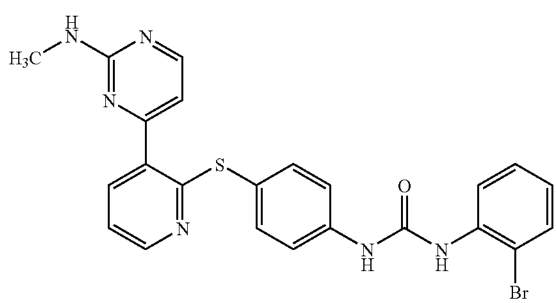 | 507.41 | 507 |
| 938 | N-(2-(ethyloxy)phenyl)-N'-(4-((3-(2-(methylamino)-4-pyrimidinyl)-2-pyridinyl)sulfanyl)phenyl)urea | 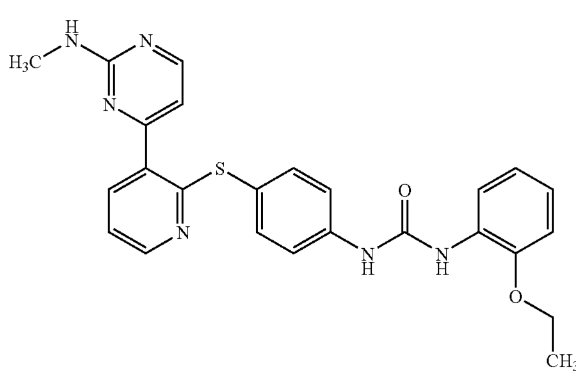 | 472.57 | 473 |

-continued

| Ex. No. | Structure Name | Structure | MW | MS Data |
|---|---|---|---|---|
| 939 | N-(4-((3-(5-fluoro-2-(methylamino)-4-pyrimidinyl)-2-pyridinyl)oxy)phenyl)-N'-(3-(trifluoromethyl)phenyl)urea | 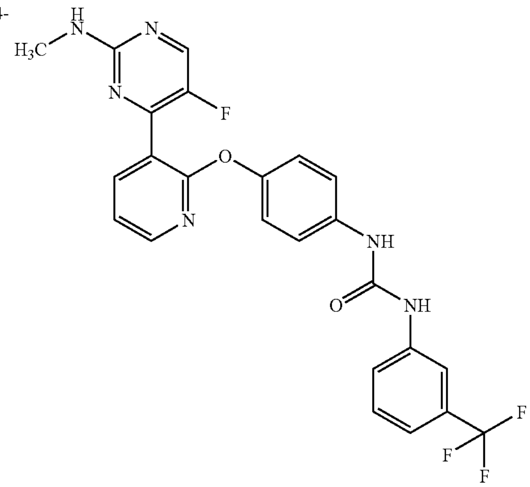 | 498.44 | 499 |
| 940 | N-(4-((2'-(methylamino)-3,4'-bipyridin-2-yl)oxy)phenyl)-N'-phenylurea | 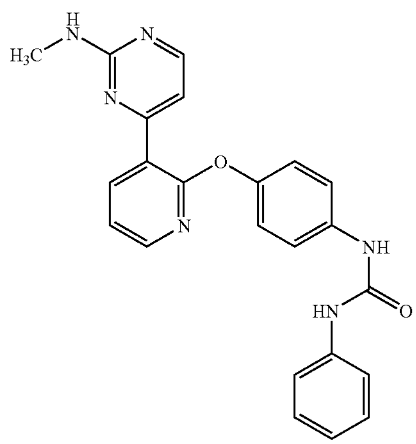 | 411.46 | 412 |
| 941 | 2-chloro-N-(3-methyl-4-((3-(2-(methylamino)-4-pyrimidinyl)-2-pyridinyl)oxy)phenyl)benzamide | 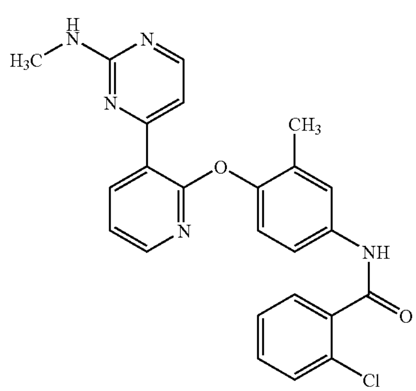 | 445.91 | 446 |

-continued

| Ex. No. | Structure Name | Structure | MW | MS Data |
|---|---|---|---|---|
| 942 | 3-chloro-N-(3-methyl-4-((3-(2-(methylamino)-4-pyrimidinyl)-2-pyridinyl)oxy)phenyl)benzamide | 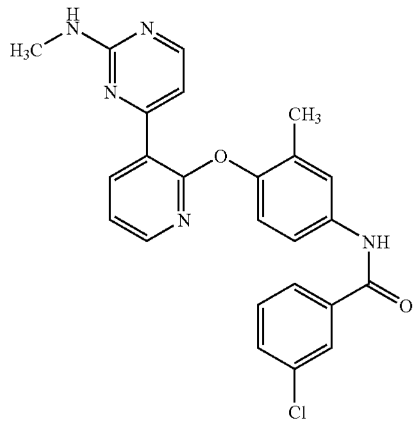 | 445.91 | 446 |
| 943 | 4-chloro-N-(3-methyl-4-((3-(2-(methylamino)-4-pyrimidinyl)-2-pyridinyl)oxy)phenyl)benzamide | 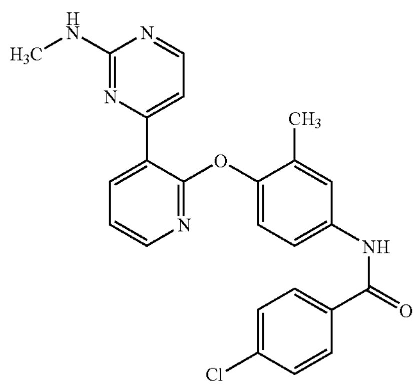 | 445.91 | 446 |
| 944 | N-(2-chlorophenyl)-N'-(4-((3-(2-(methylamino)-pyrimidinyl)-2-pyridinyl)oxy)phenyl)urea | 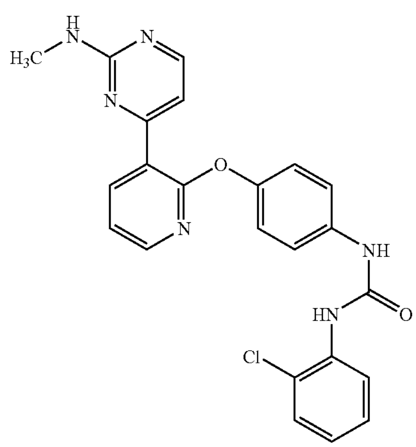 | 446.9 | 447 |

| Ex. No. | Structure Name | Structure | MW | MS Data |
|---|---|---|---|---|
| 945 | N-(4-chlorophenyl)-N'-(4-((3-(2-(methylamino)-4-pyrimidinyl)-2-pyridinyl)oxy)phenyl)urea | 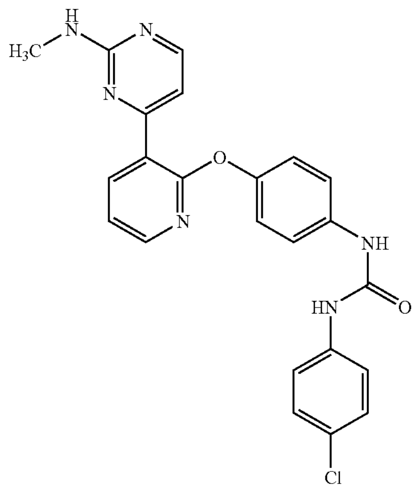 | 446.9 | 447 |
| 946 | N-(4-((3-(2-(methylamino)-4-pyrimidinyl)-2-pyridinyl)oxy)-1-naphthalenyl)-3-(trifluoromethyl)benzamide | 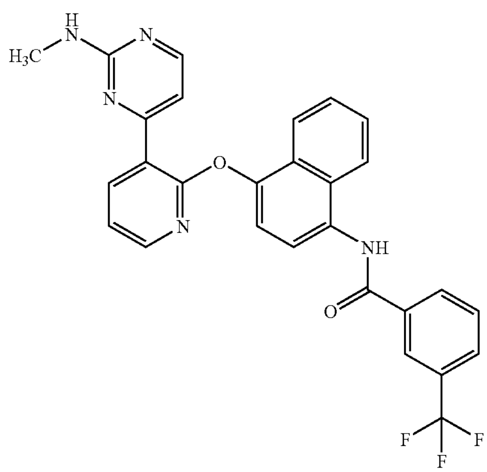 | 515.49 | 516 |
| 947 | 3-chloro-N-(3-methyl-4-((3-(2-(methylamino)-4-pyrimidinyl)-2-pyridinyl)oxy)phenyl)-2-thiophenecarboxamide | 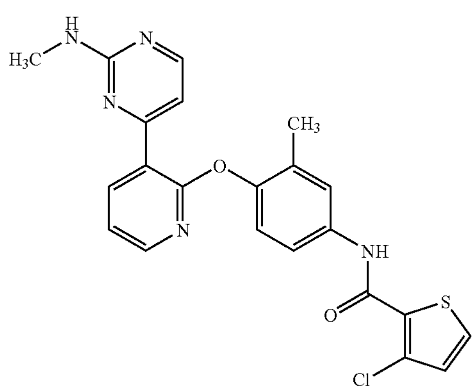 | 451.94 | 452 |

-continued

| Ex. No. | Structure Name | Structure | MW | MS Data |
|---|---|---|---|---|
| 948 | N-(3-methyl-4-((3-(2-(methylamino)-4-pyrimidinyl)-2-pyridinyl)oxy)phenyl)-1-benzothiophene-2-carboxamide | 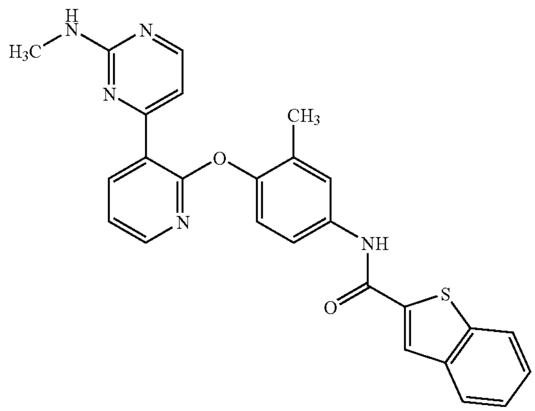 | 467.55 | 468 |
| 949 | 3-chloro-N-(3-methyl-4-((3-(2-(methylamino)-4-pyrimidinyl)-2-pyridinyl)oxy)phenyl)-1-benzothiophene-2-carboxamide | 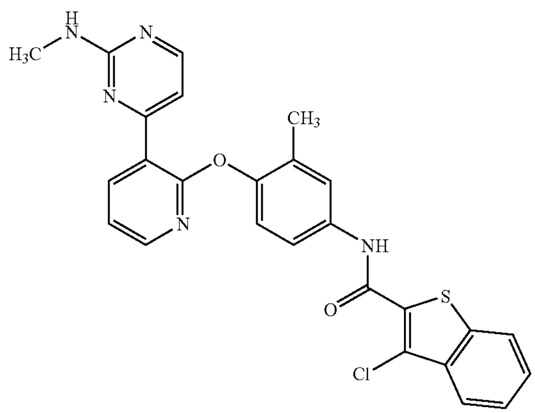 | 502 | 502 |
| 950 | 3-(1,1-dimethylethyl)-1-methyl-N-(3-methyl-4-((3-(2-(methylamino)-4-pyrimidinyl)-2-pyridinyl)oxy)phenyl)-1H-pyrazole-5-carboxamide | 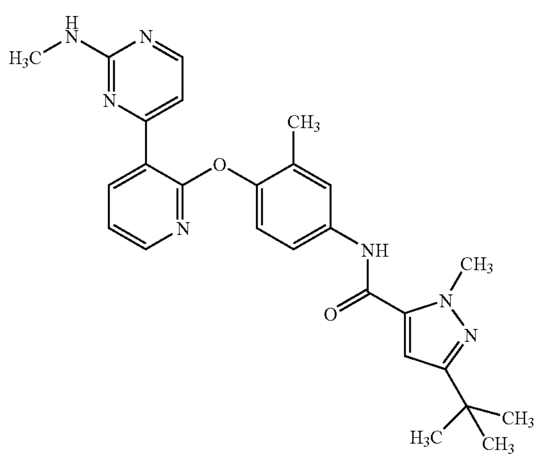 | 471.56 | 472 |

-continued

| Ex. No. | Structure Name | Structure | MW | MS Data |
|---|---|---|---|---|
| 951 | 3-methyl-N-(3-methyl-4-((3-(2-(methylamino)-4-pyrimidinyl)-2-pyridinyl)oxy)phenyl)-2-thiophenecarboxamide | 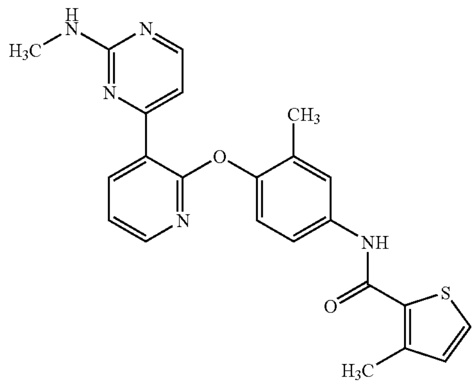 | 431.52 | 432 |
| 952 | 5-chloro-N-(3-methyl-4-((3-(2-(methylamino)-4-pyrimidinyl)-2-pyridinyl)oxy)phenyl)-2-thiophenecarboxamide | 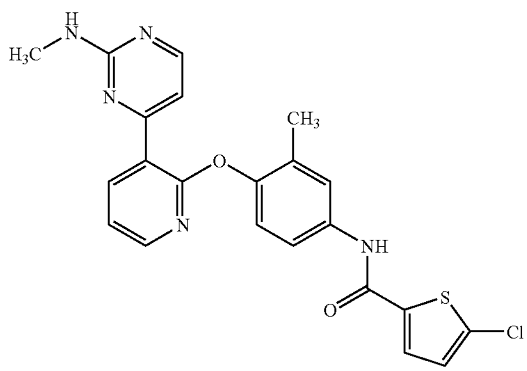 | 451.94 | 452 |
| 953 | 5-methyl-N-(3-methyl-4-((3-(2-(methylamino)-4-pyrimidinyl)-2-pyridinyl)oxy)phenyl)-2-thiophenecarboxamide | 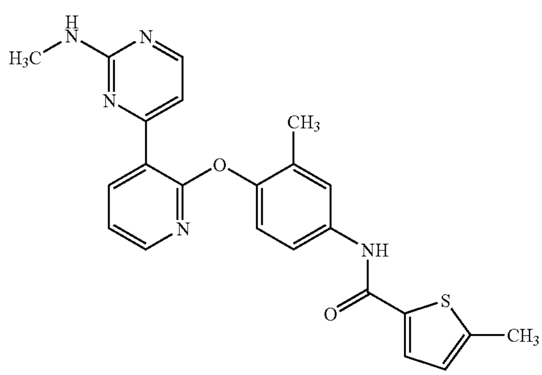 | 431.52 | 432 |
| 954 | N-(3-methyl-4-((3-(2-(methylamino)-4-pyrimidinyl)-2-pyridinyl)oxy)phenyl)-4-quinolinecarboxamide | 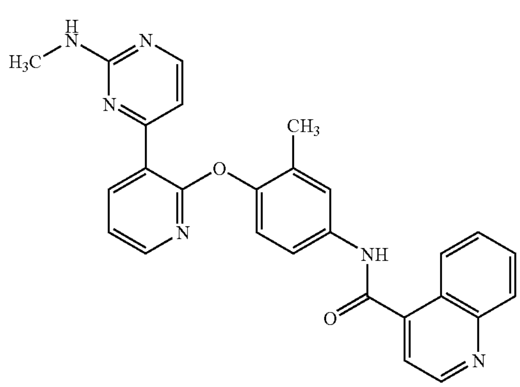 | 462.51 | 463 |

-continued

| Ex. No. | Structure Name | Structure | MW | MS Data |
|---|---|---|---|---|
| 955 | N-(3-methyl-4-((3-(2-(methylamino)-4-pyrimidinyl)-2-pyridinyl)oxy)phenyl)-4-pyridinecarboxamide | 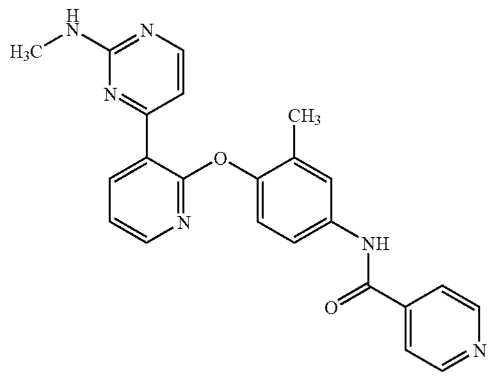 | 412.45 | 413 |
| 956 | 3-bromo-N-(3-methyl-4-((3-(2-(methylamino)-4-pyrimidinyl)-2-pyridinyl)oxy)phenyl)benzamide | 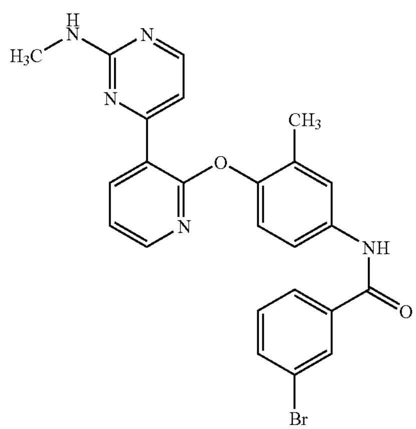 | 490.36 | 492 |
| 957 | N-(4-((3-(2-(methylamino)-4-pyrimidinyl)-2-pyridinyl)oxy)phenyl)-N'-(2-(trifluoromethyl)phenyl)urea | 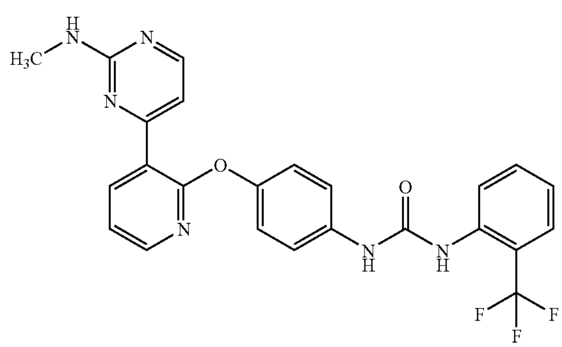 | 480.45 | 481 |
| 958 | N-(3-chloro-4-fluorophenyl)-N'-(4-((3-(2-(methylamino)-4-pyrimidinyl)-2-pyridinyl)oxy)phenyl)urea | 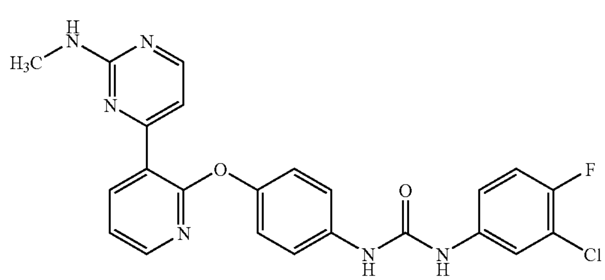 | 464.89 | 465 |

| Ex. No. | Structure Name | Structure | MW | MS Data |
|---|---|---|---|---|
| 959 | N-(3,4-difluorophenyl)-N'-(4-((3-(2-(methylamino)-4-pyrimidinyl)-2-pyridinyl)oxy)phenyl)urea | 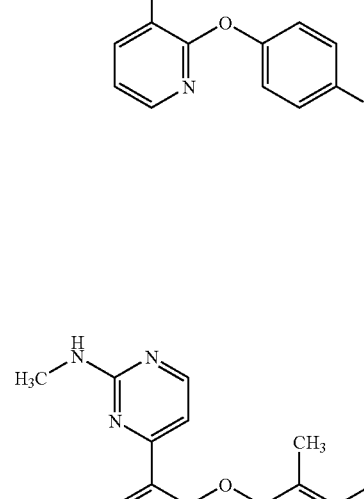 | 448.43 | 449 |
| 960 | N-(2,3-dimethyl-4-((3-(2-(methylamino)-4-pyrimidinyl)-2-pyridinyl)oxy)phenyl)-N'-phenylurea | 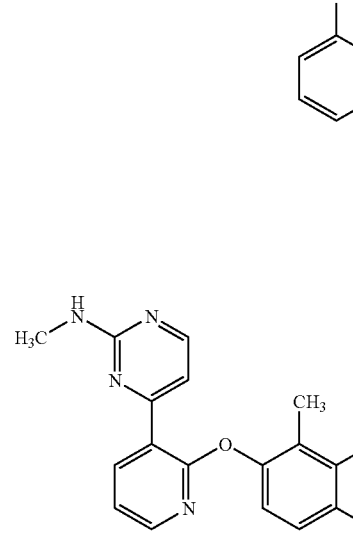 | 440.51 | 441 |
| 961 | N-(4-chlorophenyl)-N'-(2,3-dimethyl-4-((3-(2-(methylamino)-4-pyrimidinyl)-2-pyridinyl)oxy)phenyl)urea | 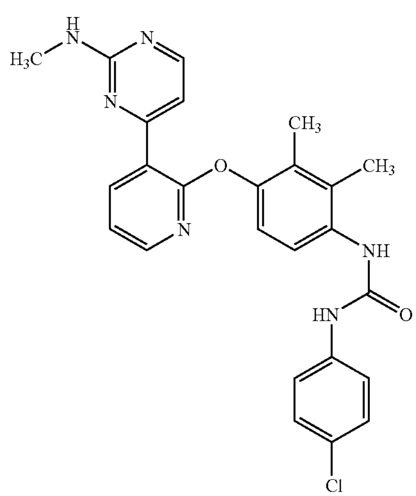 | 474.95 | 475 |

-continued

| Ex. No. | Structure Name | Structure | MW | MS Data |
|---|---|---|---|---|
| 962 | N-(4-((3-(4-(methylamino)-1,3,5-triazin-2-yl)-2-pyridinyl)oxy)phenyl)-N'-phenylurea | 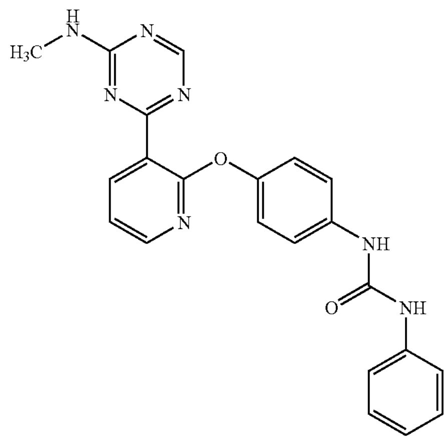 | 413.44 | 414 |
| 963 | N-(4-((3-(4-(methylamino)-1,3,5-triazin-2-yl)-2-pyridinyl)oxy)phenyl)-N'-(3-(trifluoromethyl)phenyl)urea | 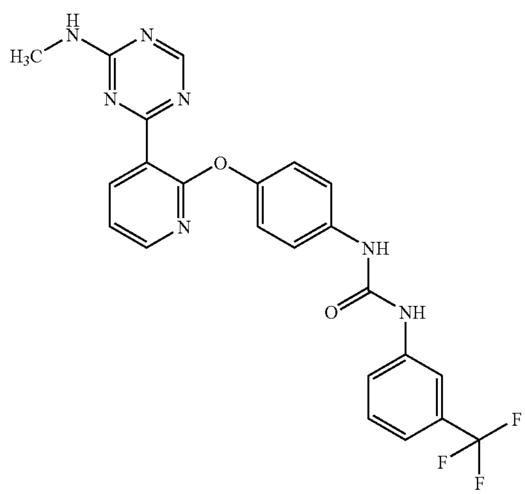 | 481.44 | 482 |
| 964 | N-(2-methyl-4-((3-(2-(methylamino)-4-pyrimidinyl)-2-pyridinyl)oxy)phenyl)-3-(trifluoromethyl)benzamide | 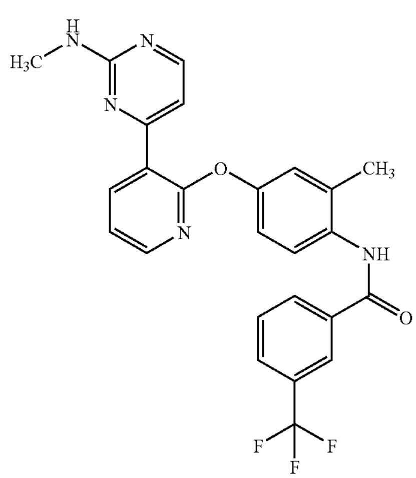 | 479.46 | 480 |

| Ex. No. | Structure Name | Structure | MW | MS Data |
|---|---|---|---|---|
| 965 | 3-bromo-N-(2-methyl-4-((3-(2-(methylamino)-4-pyrimidinyl)-2-pyridinyl)oxy)phenyl) benzamide | 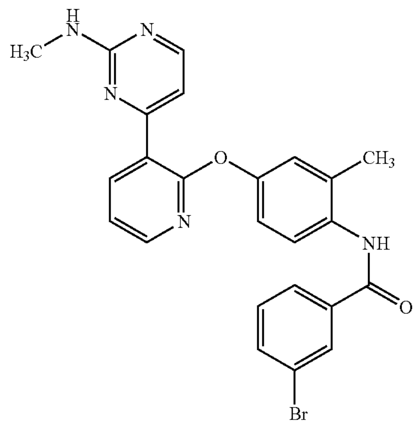 | 490.36 | 490 |
| 966 | N-(2-methyl-4-((3-(2-(methylamino)-4-pyrimidinyl)-2-pyridinyl)oxy)phenyl)-N'-(3-(trifluoromethyl)phenyl) urea | 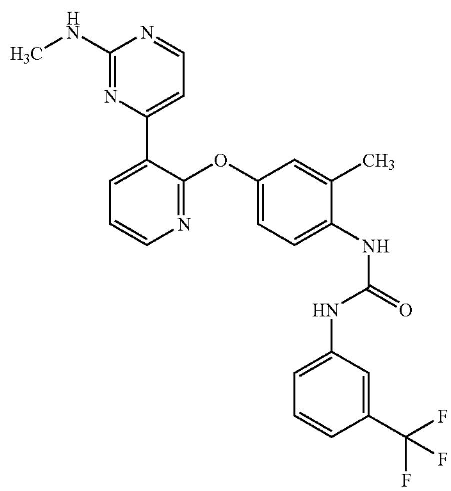 | 494.48 | 495 |
| 967 | N-(4-((3-(4-(methylamino)-1,3,5-triazin-2-yl)-2-pyridinyl)oxy)-1-naphthalenyl)-N'-(2-(methyl((3R)-1-methyl-3-pyrrolidinyl)amino)-5-(trifluoromethyl)phenyl) urea | 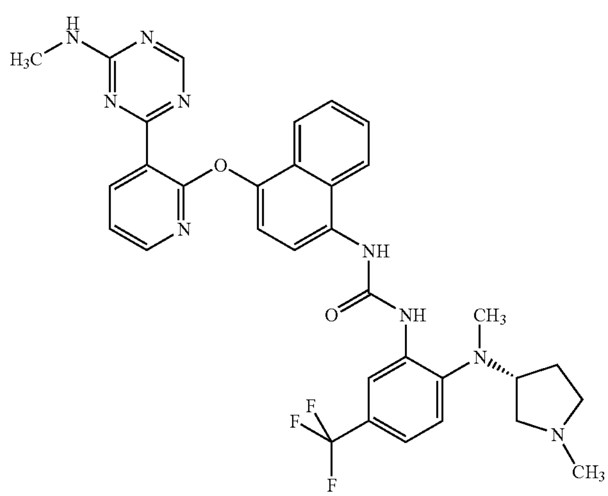 | 643.67 | 644 |

-continued
| Ex. No. | Structure Name | Structure | MW | MS Data |
|---|---|---|---|---|
| 968 | N-(3-methyl-4-((3-(2-(methylamino)-4-pyrimidinyl)-2-pyridinyl)oxy)phenyl)-2-naphthalenecarboxamide | 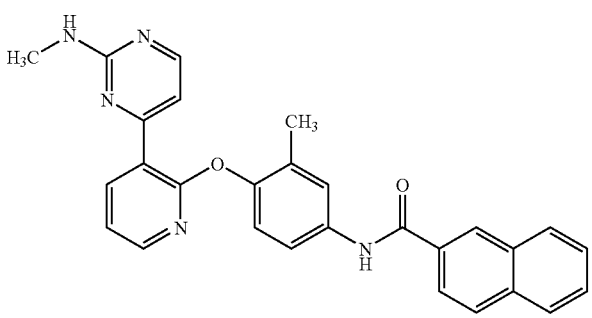 | 461.52 | |
| 969 | N-(2-methyl-4-((3-(2-(methylamino)-4-pyrimidinyl)-2-pyridinyl)oxy)phenyl)-N'-phenylurea | 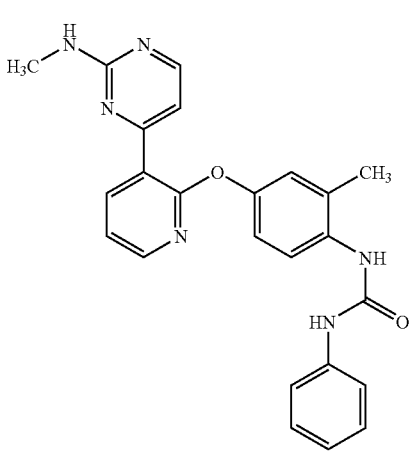 | 426.48 | 427 |
| 970 | N-(4-chlorophenyl)-N'-(2-methyl-4-((3-(2-(methylamino)-4-pyrimidinyl)-2-pyridinyl)oxy)phenyl)urea | 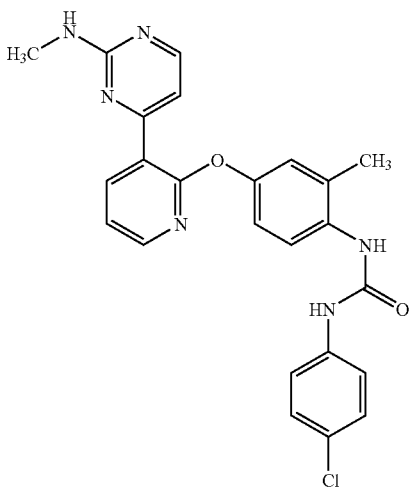 | 460.92 | 461 |

| Ex. No. | Structure Name | Structure | MW | MS Data |
|---|---|---|---|---|
| 971 | N-(3-methyl-4-((3-(2-(methylamino)-4-pyrimidinyl)-2-pyridinyl)oxy)phenyl)-3-thiophenecarboxamide | 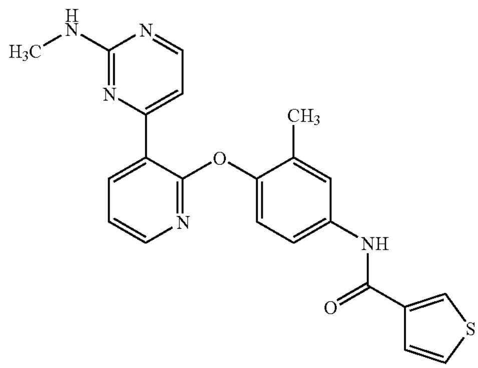 | 417.49 | 418 |
| 972 | N-(4-((3-(2-(methylamino)-4-pyrimidinyl)-2-pyridinyl)oxy)phenyl)-N'-(4-((trifluoromethyl)sulfanyl)phenyl)urea | 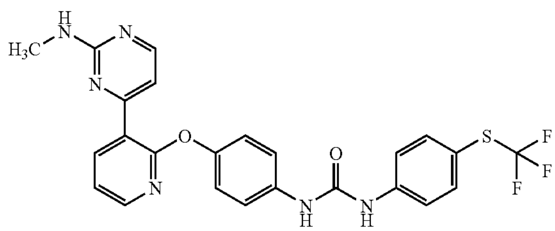 | 512.51 | 513 |
| 973 | N-(4-fluorophenyl)-N'-(4-((3-(2-(methylamino)-4-pyrimidinyl)-2-pyridinyl)oxy)phenyl)urea | 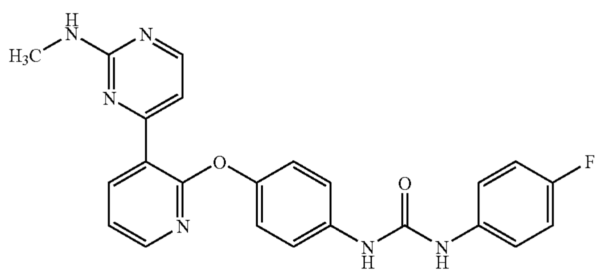 | 430.44 | 431 |
| 974 | N-(3-fluoro-4-methylphenyl)-N'(4-((3-(2-(methylamino)-4-pyrimidinyl)-2-pyridinyl)oxy)phenyl)urea | 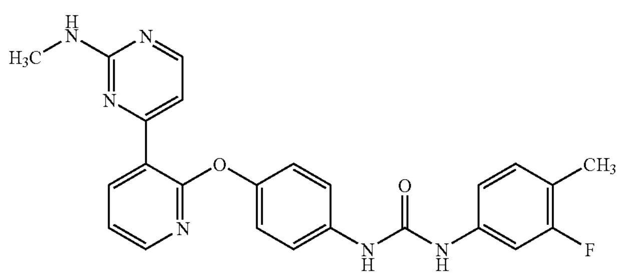 | 444.47 | 445 |
| 975 | N-(4-((3-(2-(methylamino)-pyrimidinyl)-2-pyridinyl)oxy)phenyl)-N'-(4-(1-methylethyl)phenyl)urea | 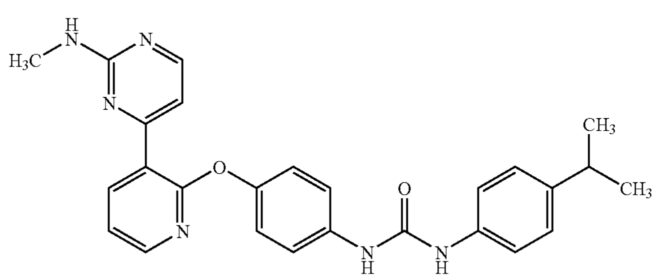 | 454.53 | 455 |

| Ex. No. | Structure Name | Structure | MW | MS Data |
|---|---|---|---|---|
| 976 | 3-(1,1-dimethylethyl)-1-methyl-N-(4-((3-(2-(methylamino)-4-pyrimidinyl)-2-pyridinyl)oxy)phenyl)-1H-pyrazole-5-carboxamide | 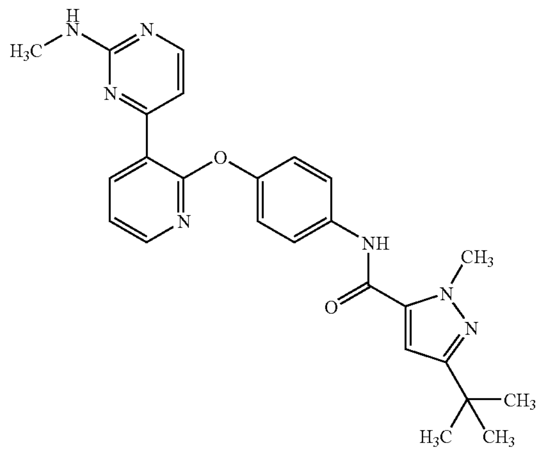 | 457.54 | 458 |
| 977 | N-(4-cyanophenyl)-N'-(4-((3-(2-(methylamino)-4-pyrimidinyl)-2-pyridinyl)oxy)phenyl)urea | 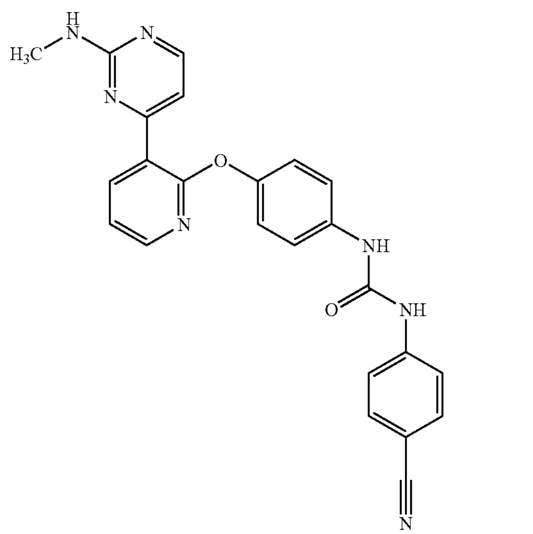 | 437.46 | 438 |
| 978 | N-(4-bromophenyl)-N'-(4-((3-(2-(methylamino)-4-pyrimidinyl)-2-pyridinyl)oxy)phenyl)urea | 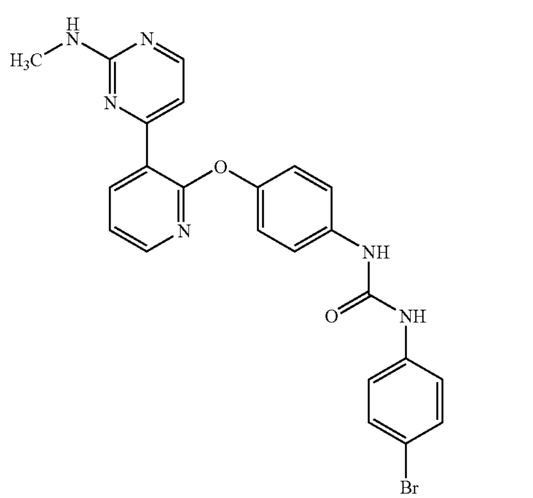 | 491.35 | 493 |

| Ex. No. | Structure Name | Structure | MW | MS Data |
|---|---|---|---|---|
| 979 | N-(4-((3-(2-(methylamino)-4-pyrimidinyl)-2-pyridinyl)oxy)phenyl)-N'-(4-(phenyloxy)phenyl)urea | 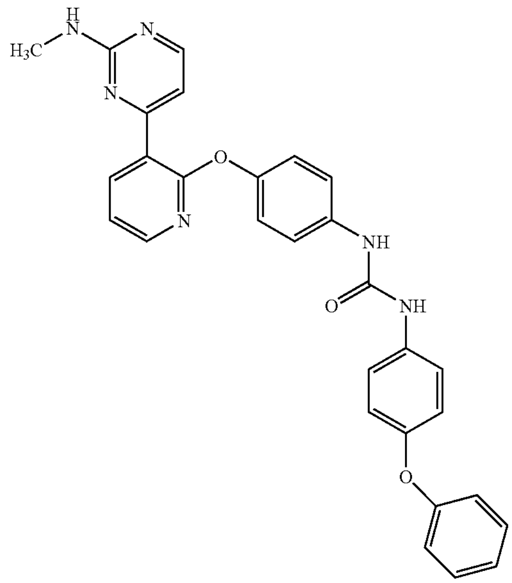 | 504.55 | 505 |
| 980 | N-(4-((3-(2-(methylamino)-4-pyrimidinyl)-2-pyridinyl)oxy)phenyl)-N'-(3,4,5-tris(methyloxy)phenyl)urea | 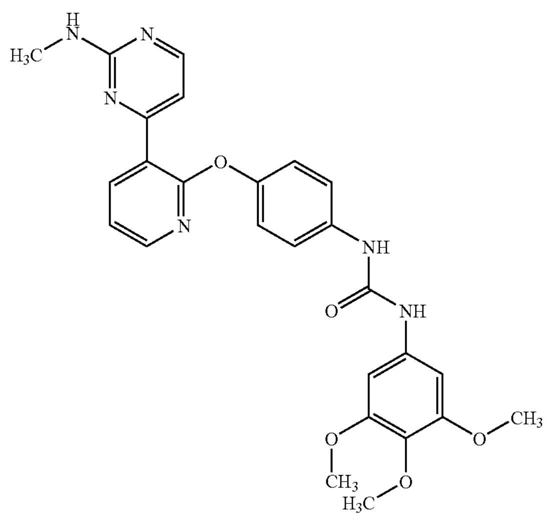 | 502.53 | 503 |
| 981 | N-(2-fluoro-3-(trifluoromethyl)phenyl)-N'-(4-((3-(2-(methylamino)-4-pyrimidinyl)-2-pyridinyl)oxy)phenyl)urea | 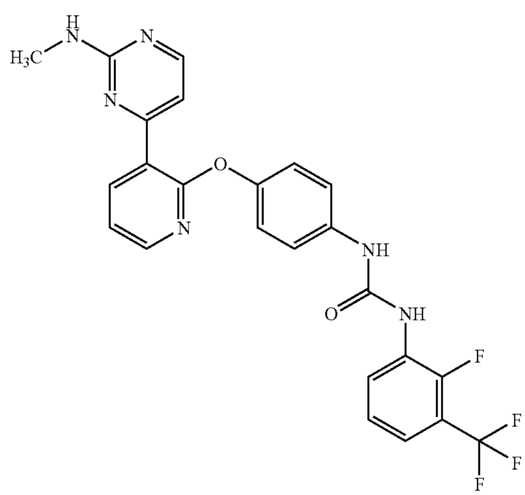 | 498.44 | 499 |

| Ex. No. | Structure Name | Structure | MW | MS Data |
|---|---|---|---|---|
| 982 | N-(4-((3-(2-(methylamino)-4-pyrimidinyl)-2-pyridinyl)oxy)phenyl)-2-oxo-2-phenylacetamide | 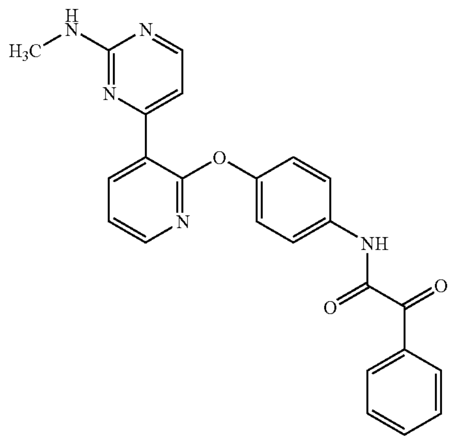 | 425.45 | 426 |
| 983 | N-(3-methyl-4-((3-(2-(methylamino)-4-pyrimidinyl)-2-pyridinyl)oxy)phenyl)-1H-benzimidazole-5-carboxamide | 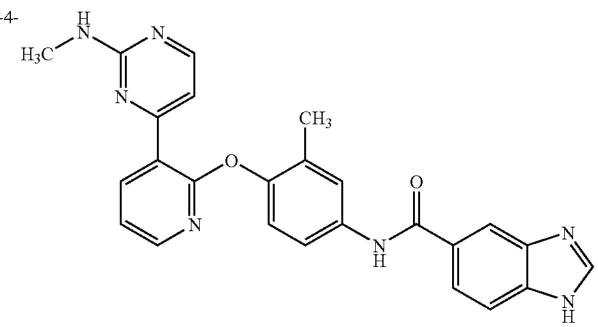 | 451.49 | |
| 984 | N-(3-methyl-4-((3-(2-(methylamino)-4-pyrimidinyl)-2-pyridinyl)oxy)phenyl)-1H-1,2,3-benzotriazole-5-carboxamide | 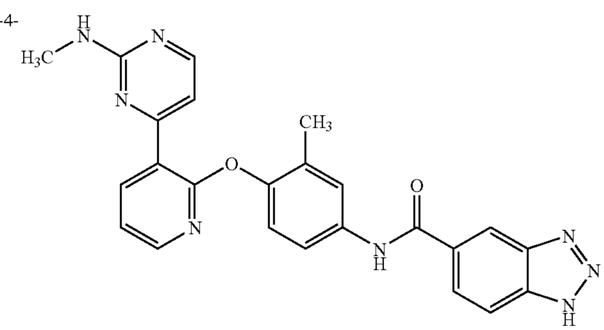 | 452.48 | |
| 985 | 6-hydroxy-N-(3-methyl-4-((3-(2-(methylamino)-4-pyrimidinyl)-2-pyridinyl)oxy)phenyl)-3-pyridmecarboxamide | 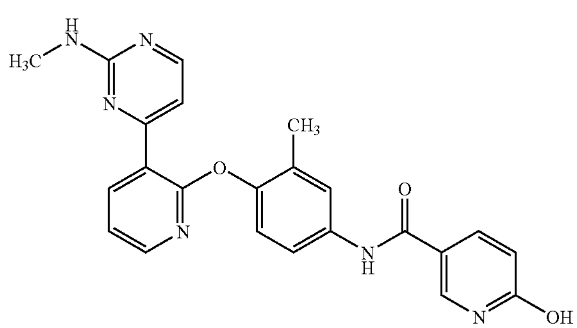 | 428.45 | |

| Ex. No. | Structure Name | Structure | MW | MS Data |
|---|---|---|---|---|
| 986 | N-(3-methyl-4-((3-(2-(methylamino)-4-pyrimidinyl)-2-pyridinyl)oxy)phenyl)-3-pyridinecarboxamide | 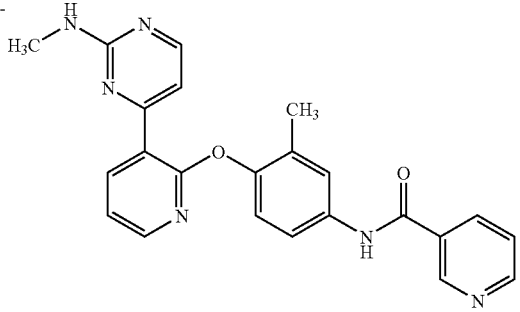 | 412.45 | |
| 987 | N-(3-methyl-4-((3-(2-(methylamino)-4-pyrimidinyl)-2-pyridinyl)oxy)phenyl)-1-naphthalenecarboxamide | 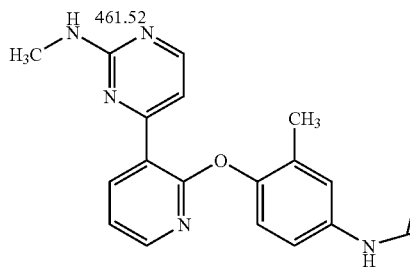 | 461.52 | |
| 988 | 2-methyl-N-(3-methyl-4-((3-(2-(methylamino)-4-pyrimidinyl)-2-pyridinyl)oxy)phenyl)-1H-benzimidazole-5-carboxamide | 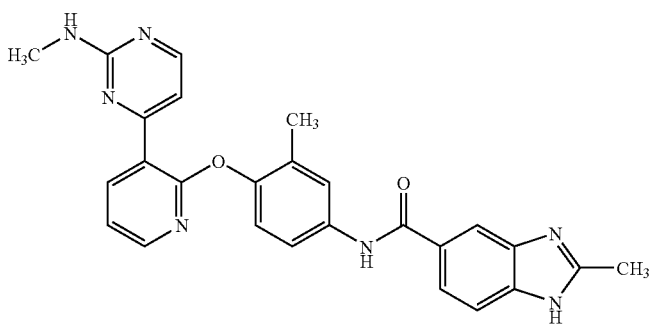 | 465.51 | |
| 989 | N-(3-methyl-4-((3-(2-(methylamino)-4-pyrimidinyl)-2-pyridinyl)oxy)phenyl)-6-quinolinecarboxamide | 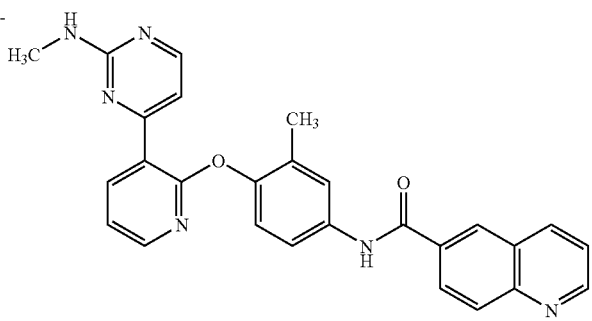 | 462.51 | |

-continued

| Ex. No. | Structure Name | Structure | MW | MS Data |
|---|---|---|---|---|
| 990 | N-(3-methyl-4-((3-(2-(methylamino)-4-pyrimidinyl)-2-pyridinyl)oxy)phenyl)-1H-indole-5-carboxamide | 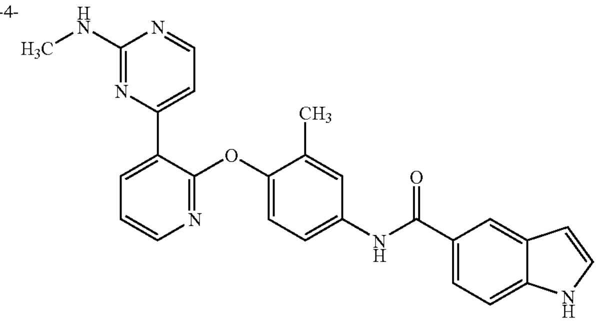 | 450.5 | |
| 991 | N-(3-methyl-4-((3-(2-(methylamino)-4-pyrimidinyl)-2-pyridinyl)oxy)phenyl)-1H-indole-6-carboxamide | 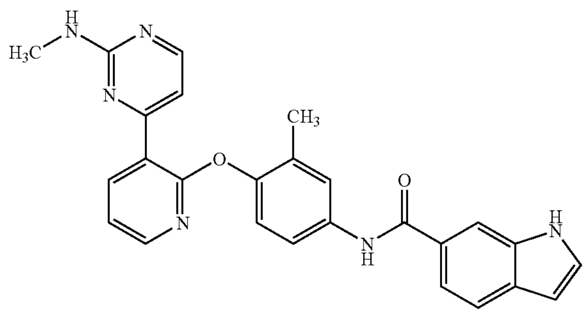 | 450.5 | |
| 992 | N-(4-chloro-3-(trifluoromethyl)phenyl)-N'-(4-((3-(2-(methylamino)-4-pyrimidinyl)-2-pyridinyl)oxy)phenyl)urea | 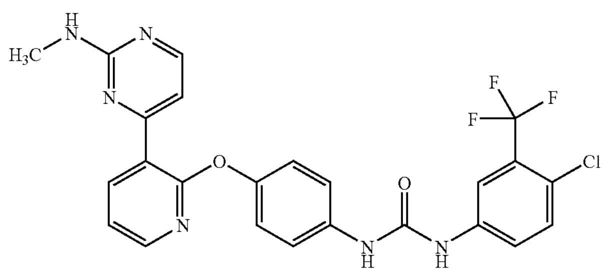 | 514.89 | 515 |
| 993 | N-(4-(dimethylamino)phenyl)-N'-(4-((3-(2-(methylamino)-4-pyrimidinyl)-2-pyridinyl)oxy)phenyl)urea | 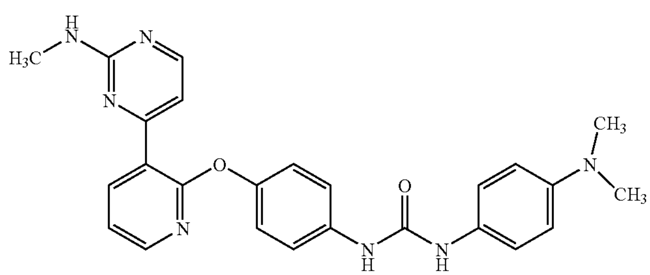 | 455.52 | 456 |
| 994 | N-(3-methyl-4-((3-(2-(methylamino)-4-pyrimidinyl)-2-pyridinyl)oxy)phenyl)-3-(1H-pyrrol-1-yl)benzamide | 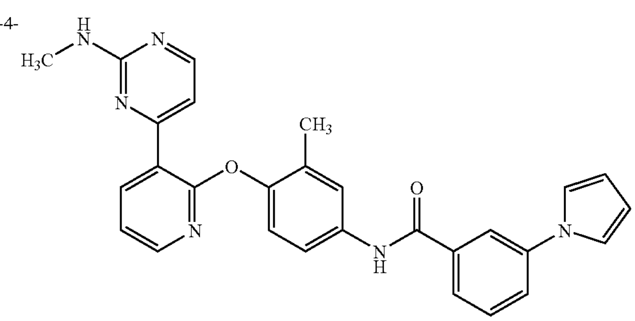 | 476.54 | 477 |

-continued

| Ex. No. | Structure Name | Structure | MW | MS Data |
|---|---|---|---|---|
| 995 | N-(3-methyl-4-((3-(2-(methylamino)-4-pyrimidinyl)-2-pyridinyl)oxy)phenyl)-3-(phenyloxy)benzamide | 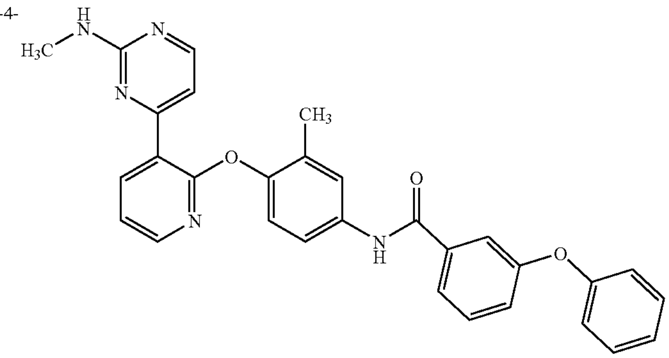 | 503.56 | 504 |
| 996 | N-(3-chloro-4-(methyloxy)phenyl)-N'-(4-((3-(2-(methylamino)-4-pyrimidinyl)-2-pyridinyl)oxy)phenyl)urea | 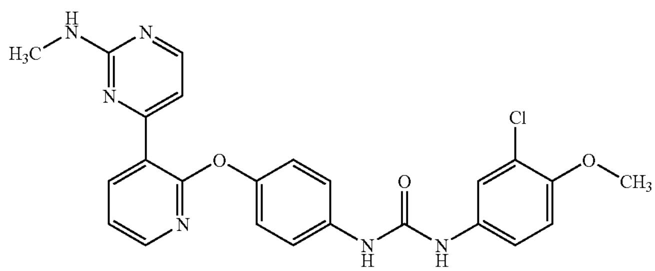 | 476.92 | 477 |
| 997 | N-(3,5-dichlorophenyl)-N'-(4-((3-(2-(methylamino)-4-pyrimidinyl)-2-pyridinyl)oxy)phenyl)urea | 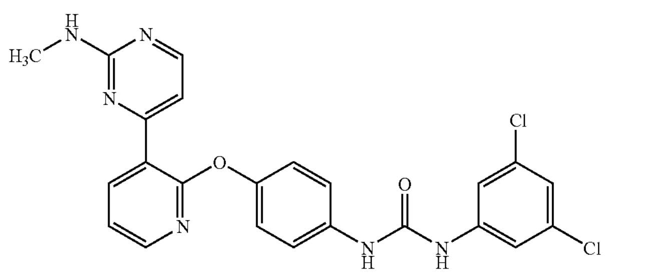 | 481.34 | 481 |
| 998 | N-(4-fluoro-3-(trifluoromethyl)phenyl)-N'-(4-((3-(2-(methylamino)-4-pyrimidinyl)-2-pyridinyl)oxy)phenyl)urea | 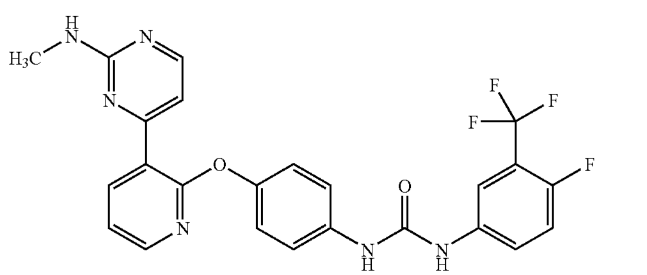 | 498.44 | 499 |
| 999 | N-(3-methyl-4-((3-(2-(methylamino)-4-pyrimidinyl)-2-pyridinyl)oxy)phenyl)-4-(phenyloxy)benzamide | 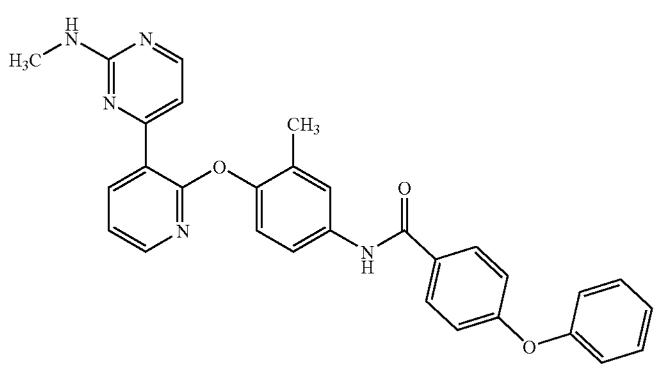 | 503.56 | 504 |

-continued

| Ex. No. | Structure Name | Structure | MW | MS Data |
|---|---|---|---|---|
| 1000 | N-(4-chlorophenyl)-N'-(4-((3-(2-(methylamino)-4-pyrimidinyl)-2-pyridinyl)sulfanyl)phenyl)urea | 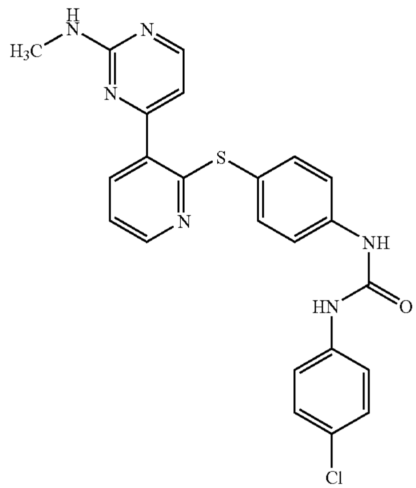 | 462.96 | 463 |
| 1001 | N-(4-((3-(2-(methylamino)-4-pyrimidinyl)-2-pyridinyl)sulfanyl)phenyl)-N'-(4-(1-methylethyl)phenyl)urea | 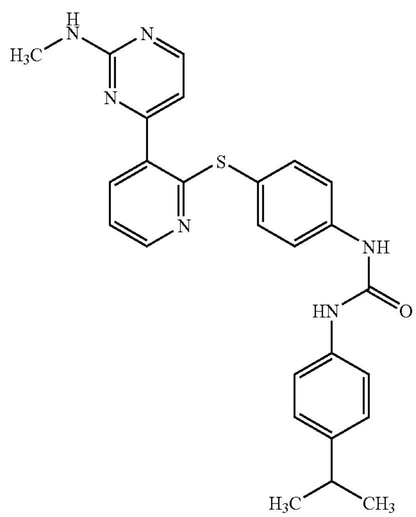 | 470.60 | 471 |
| 1002 | N-(4-((3-(2-(methylamino)-4-pyrimidinyl)-2-pyridinyl)oxy)phenyl)-3-(1H-pyrrol-1-yl)benzamide | 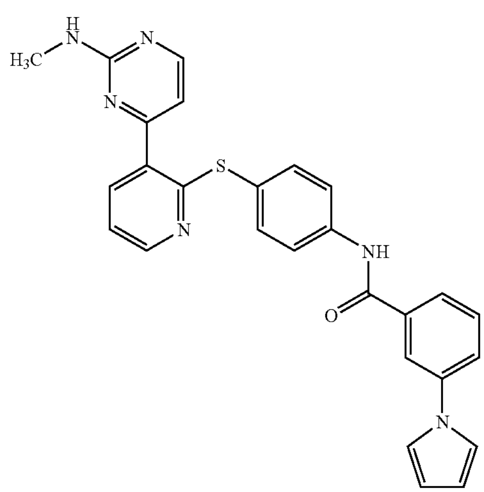 | 462.51 | 463 |

| Ex. No. | Structure Name | Structure | MW | MS Data |
|---|---|---|---|---|
| 1003 | 1-methyl-N-(3-methyl-4-((3-(2-(methylamino)-4-pyrimidinyl)-2-pyridinyl)oxy)phenyl)-1H-indole-2-carboxamide | 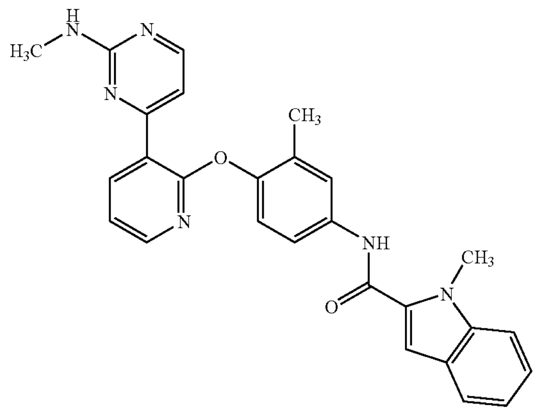 | 464.53 | 465 |
| 1004 | 1-ethyl-3-methyl-N-(3-methyl-4-((3-(2-(methylamino)-4-pyrimidinyl)-2-pyridinyl)oxy)phenyl)-1H-pyrazole-5-carboxamide | 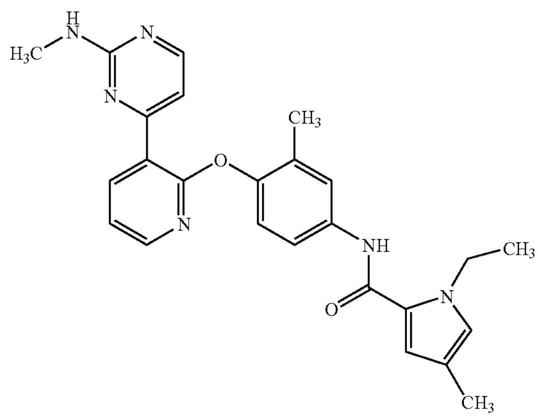 | 443.51 | 444 |
| 1005 | N-(3-methyl-4-((3-(2-(methylamino)-4-pyrimidinyl)-2-pyridinyl)oxy)phenyl)-1-benzothiophene-3-carboxamide | 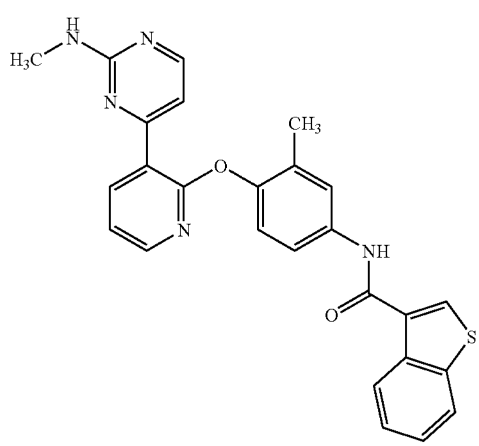 | 467.55 | 468 |

-continued

| Ex. No. | Structure Name | Structure | MW | MS Data |
|---|---|---|---|---|
| 1006 | 4-cyclohexyl-N-(3-methyl-4-((3-(2-(methylamino)-4-pyrimidinyl)-2-pyridinyl)oxy)phenyl)benzamide | 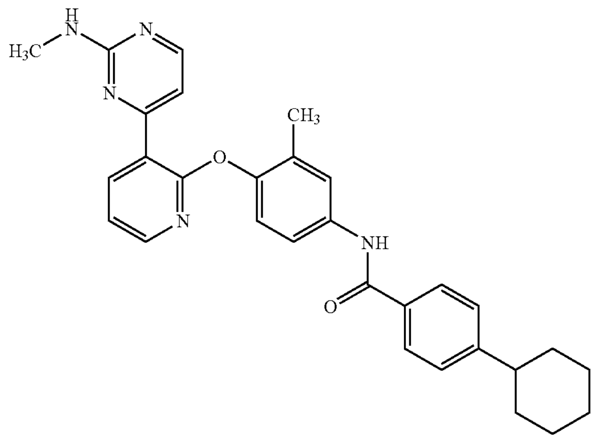 | 493.61 | 494 |
| 1007 | N-(4-((3-(2-(methylamino)-4-pyrimidinyl)-2-pyridinyl)oxy)phenyl)-N'-phenylthiourea | 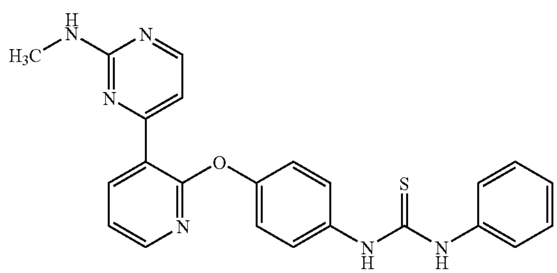 | 428.52 | 429 |
| 1008 | N-(3-ethylphenyl)-N'-(4-((3-(2-(methylamino)-4-pyrimidinyl)-2-pyridinyl)oxy)phenyl)urea | 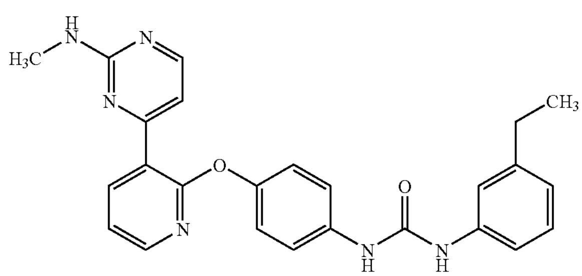 | 440.51 | 441 |
| 1009 | (3-chloro-4-((3-(2-(methylamino)-4-pyrimidinyl)-2-pyridinyl)oxy)phenyl)-N'-(3-fluoro-4-methylphenyl)urea | 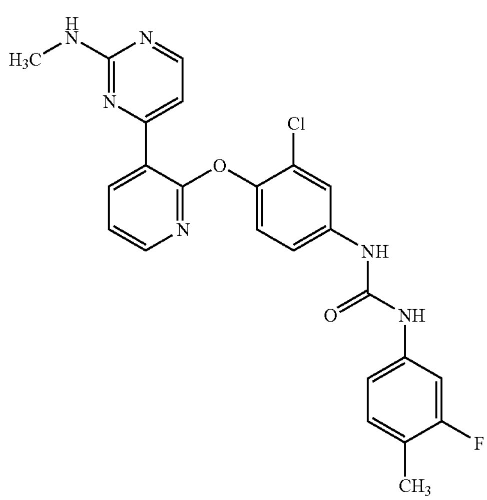 | 478.91 | 479 |

-continued

| Ex. No. | Structure Name | Structure | MW | MS Data |
|---|---|---|---|---|
| 1010 | N-(3-methyl-4-((3-(2-(methylamino)-4-pyrimidinyl)-2-pyridinyl)oxy)phenyl)-2-oxo-2-phenylacetamide | 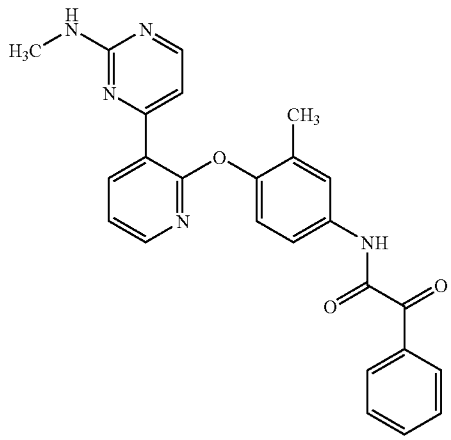 | 439.47 | 440 |
| 1011 | N-(4-(1,1-dimethylethyl)phenyl)-N'-(4-((3-(2-(methylamino)-4-pyrimidinyl)-2-pyridinyl)oxy)phenyl)urea | 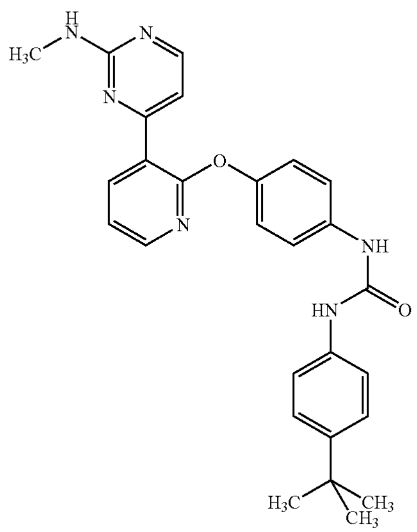 | 468.56 | 469 |
| 1012 | N-(4-(ethyloxy)phenyl)-N'-(4-((3-(2-(methylamino)-4-pyrimidinyl)-2-pyridinyl)oxy)phenyl)urea | 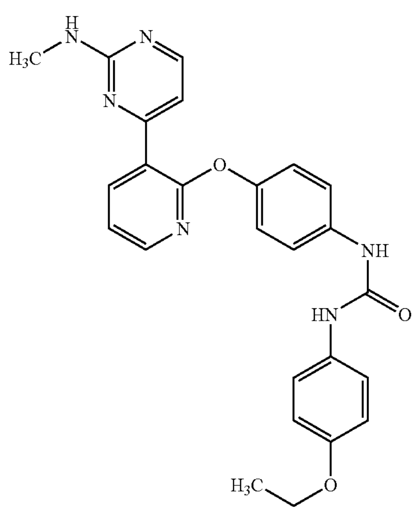 | 456.5 | 457 |

-continued

| Ex. No. | Structure Name | Structure | MW | MS Data |
|---|---|---|---|---|
| 1013 | N-(4-((3-(2-(methylamino)-4-pyrimidinyl)-2-pyridinyl)oxy)phenyl)-N'-(2,4,5-trichlorophenyl)urea | 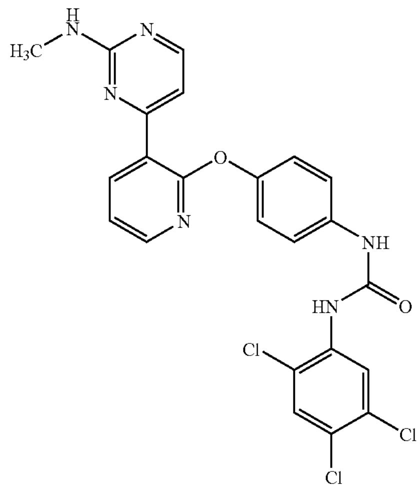 | 515.79 | 515 |
| 1014 | N-(2,3-dihydro-1,4-benzodioxin-6-yl)-N'-(4-((3-(2-(methylamino)-4-pyrimidinyl)-2-pyridinyl)oxy)phenyl)urea | 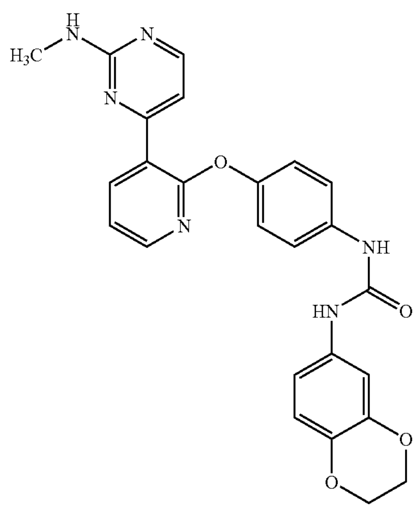 | 470.49 | 471 |
| 1015 | N-(3-methyl-4-((3-(2-(methylamino)-4-pyrimidinyl)-2-pyridinyl)oxy)phenyl)-2-(phenyloxy)benzamide | 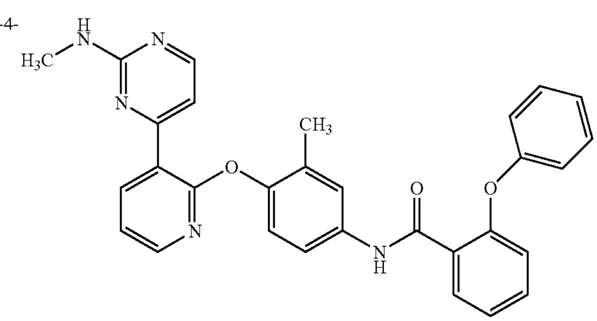 | 503.56 | 504 |

| Ex. No. | Structure Name | Structure | MW | MS Data |
|---|---|---|---|---|
| 1016 | 1,1-dimethylethyl 2-((3-methyl-4-((3-(2-(methylamino)-4-pyrimidinyl)-2-pyridinyl)oxy)phenyl)amino)-2-oxo-1-phenylethylcarbamate | | 540.62 | 541 |
| 1017 | N-(3-fluoro-4-(methyloxy)phenyl)-N'-(4-((3-(2-(methylamino)-4-pyrimidinyl)-2-pyridinyl)oxy)phenyl)urea | 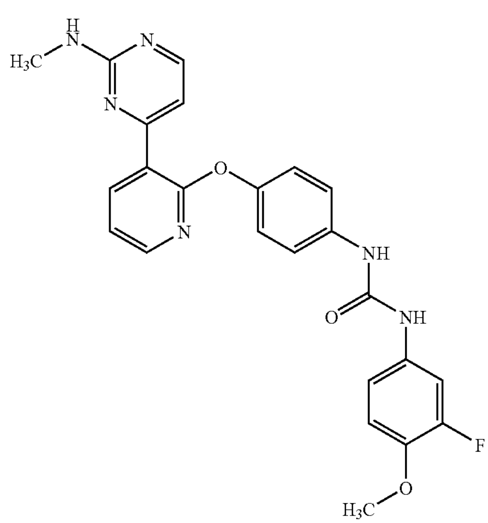 | 460.47 | 461 |

-continued

| Ex. No. | Structure Name | Structure | MW | MS Data |
|---|---|---|---|---|
| 1018 | N-(3-fluoro-4-(methyloxy)phenyl)-N'-(3-methyl-4-((3-(2-(methylamino)-4-pyrimidinyl)-2-pyridinyl)oxy)phenyl)urea | 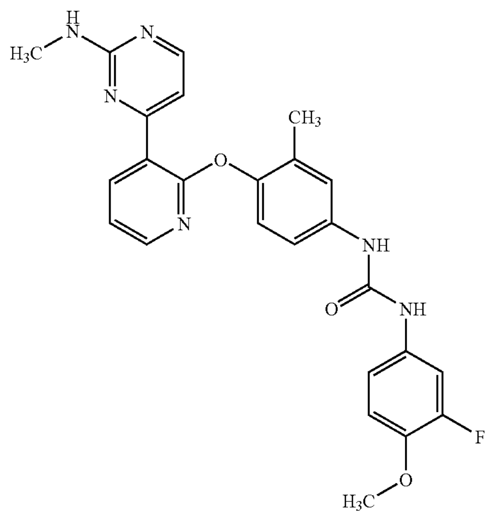 | 474.49 | 475 |
| 1019 | 4-chloro-N-(4-methyl-3-((3-(4-pyrimidinyl)-2-pyridinyl)oxy)phenyl)-3-((trifluoromethyl)oxy)benzamide | 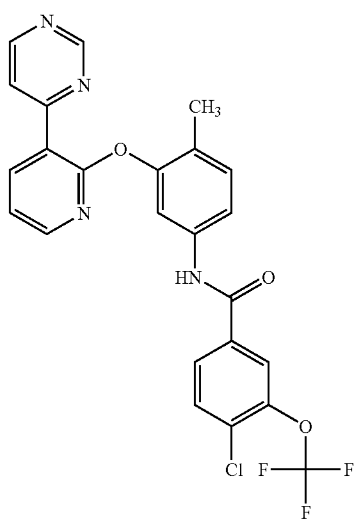 | 500.86 | 501 |
| 1020 | N-(4-methyl-3-((3-(4-pyrimidinyl)-2-pyridinyl)oxy)phenyl)-3-(trifluoromethyl)benzamide | 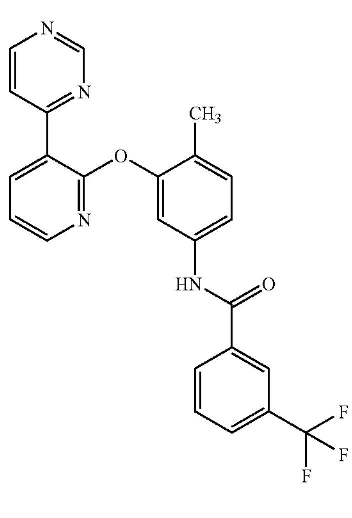 | 450.42 | 451 |

-continued

| Ex. No. | Structure Name | Structure | MW | MS Data |
|---|---|---|---|---|
| 1021 | N-(4-methyl-3-((3-(4-pyrimidinyl)-2-pyridinyl)oxy)phenyl)-4-((phenylmethyl)oxy)benzamide | 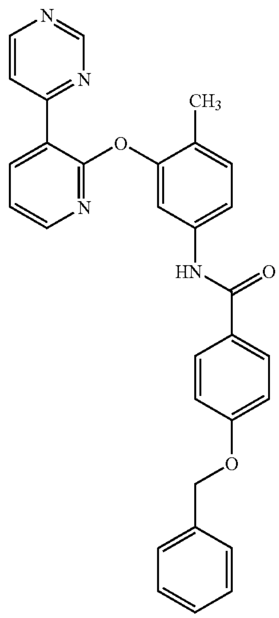 | 488.55 | 489 |
| 1022 | 2-cyclohexyl-N-(4-methyl-3-((3-(4-pyrimidinyl)-2-pyridinyl)oxy)phenyl)acetamide | 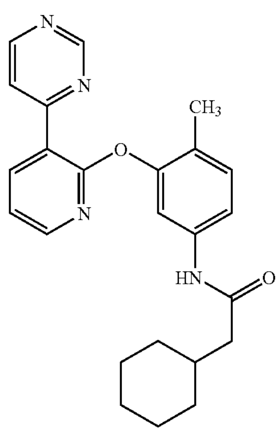 | 402.5 | 403 |
| 1023 | N-(4-methyl-3-((3-(4-pyrimidinyl)-2-pyridinyl)oxy)phenyl)hexanamide | 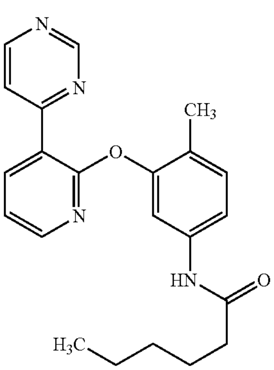 | 376.46 | 377 |

-continued

| Ex. No. | Structure Name | Structure | MW | MS Data |
|---|---|---|---|---|
| 1024 | N-(3-methyl-4-((3-(2-(methylamino)-4-pyrimidinyl)-2-pyridinyl)oxy)phenyl)-3-(3-thienyl)benzamide | 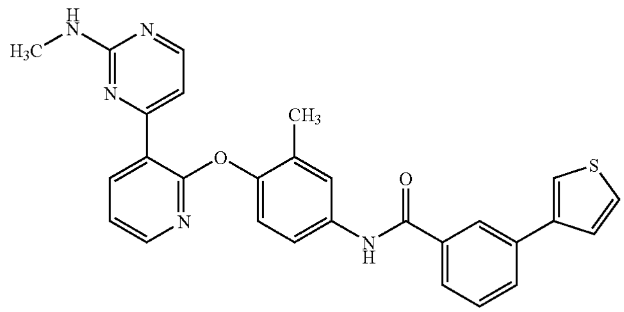 | 493.59 | |
| 1025 | N-(4-((3-(2-(methylamino)-4-pyrimidinyl)-2-pyridinyl)oxy)phenyl)-N'-(5-methyl-1H-pyrazol-3-yl)urea | 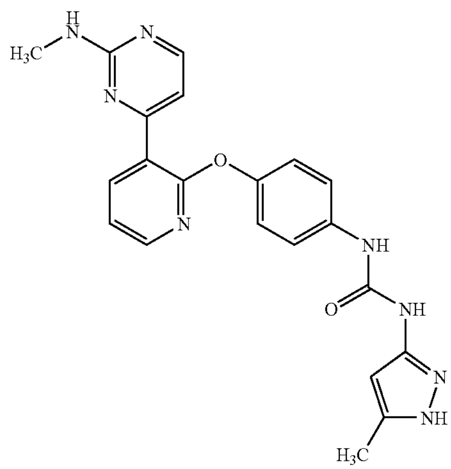 | 416.44 | 417 |
| 1026 | N-(1-ethyl-1H-pyrazol-5-yl)-N'-(4-((3-(2-(methylamino)-4-pyrimidinyl)-2-pyridinyl)oxy)phenyl)urea | 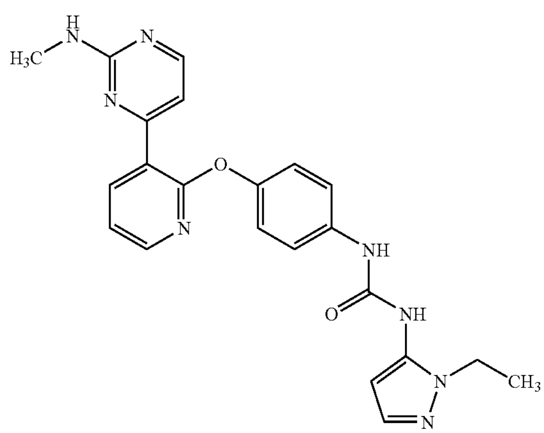 | 430.47 | 431 |

-continued

| Ex. No. | Structure Name | Structure | MW | MS Data |
|---|---|---|---|---|
| 1027 | N-(4-bromo-3-fluorophenyl)-N'-(4-((3-(2-methylamino)-4-pyrimidinyl)-2-pyridinyl)oxy)phenyl)urea | 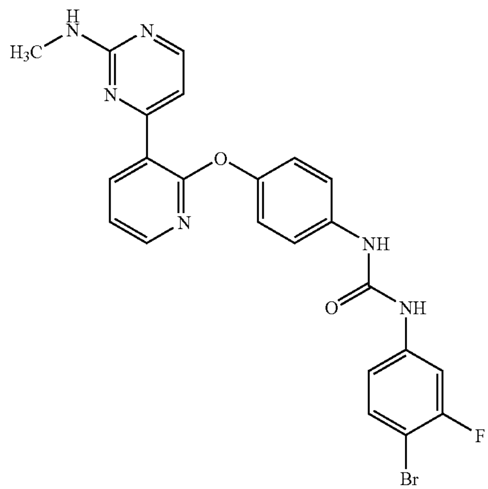 | 509.34 | 509 |
| 1028 | N-(4-bromo-3-fluorophenyl)-N'-(3-methyl-4-((3-(2-(methylamino)-4-pyrimidinyl)-2-pyridinyl)oxy)phenyl)urea | 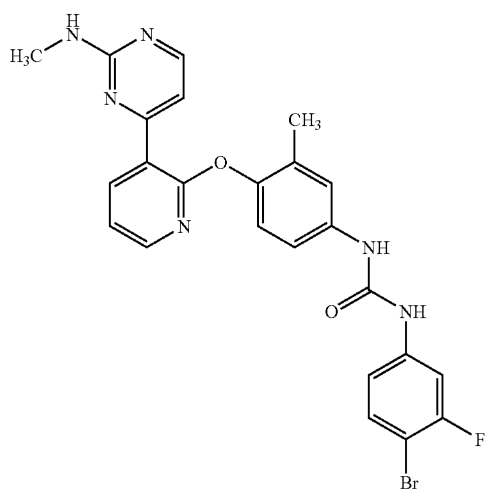 | 523.36 | 523 |
| 1029 | N-(3-fluoro-4-((3-(4-methyl-1-piperazinyl)propyl)oxy)phenyl)-N'-(4-((3-(2-(methylamino)-4-pyrimidinyl)-2-pyridinyl)oxy)phenyl)urea | 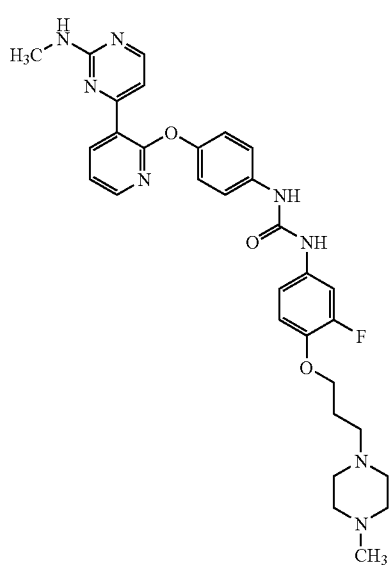 | 586.67 | 587 |

-continued

| Ex. No. | Structure Name | Structure | MW | MS Data |
|---|---|---|---|---|
| 1030 | N-(3-methyl-4-((3-(2-(methylamino)-4-pyrimidinyl)-2-pyridinyl)oxy)phenyl)-3-(1-pyrrolidinyl)benzamide | 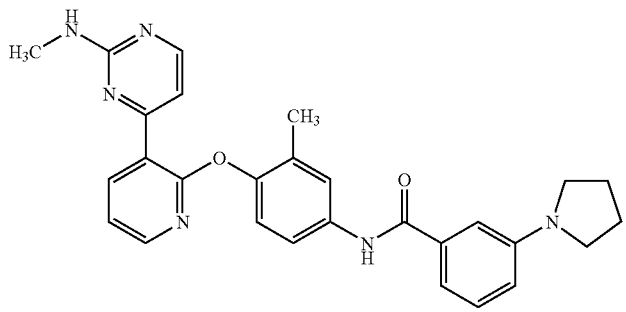 | 480.57 | 481 |
| 1031 | N-(3-methyl-4-((3-(2-(methylamino)-4-pyrimidinyl)-2-pyridinyl)oxy)phenyl)-3-(2-thienyl)benzamide | 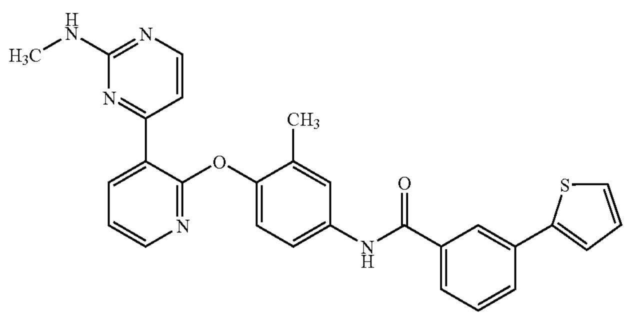 | 493.59 | 494 |
| 1032 | N-(2-(diethylamino)ethyl)-2-fluoro-4-((((4-((3-(2-(methylamino)-4-pyrimidinyl)-2-pyridinyl)oxy)phenyl)amino)carbonyl)amino)benzamide | 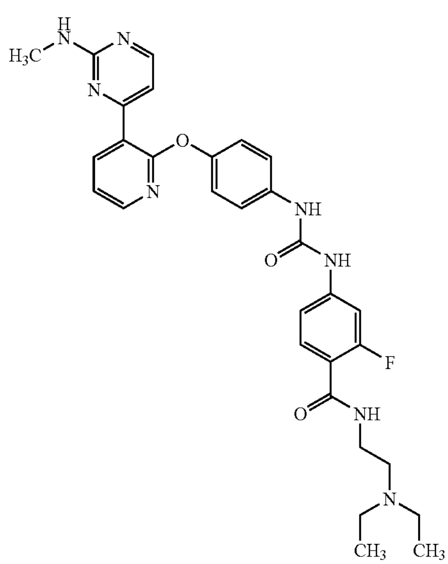 | 572.64 | 573 |

-continued

| Ex. No. | Structure Name | Structure | MW | MS Data |
|---|---|---|---|---|
| 1033 | N-(3-methyl-4-((3-(2-(methylamino)-4-pyrimidinyl)-2-pyridinyl)oxy)phenyl)-4-(phenylmethyl)-2-morpholinecarboxamide | | 510.6 | 511 |
| 1034 | 3-fluoro-N-(3-methyl-4-((3-(2-(methylamino)-4-pyrimidinyl)-2-pyridinyl)oxy)phenyl)-5-(trifluoromethyl)benzamide | 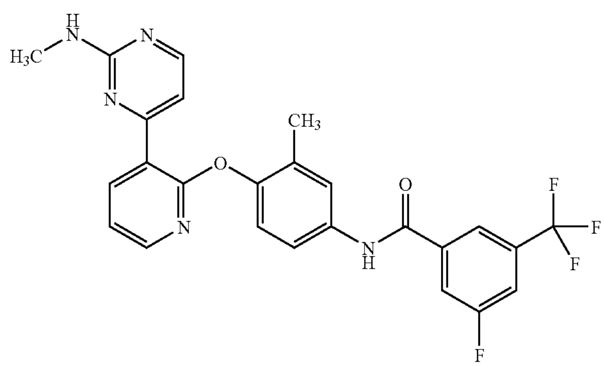 | 497.45 | 498 |
| 1035 | 4-fluoro-N-(3-methyl-4-((3-(2-(methylamino)-4-pyrimidinyl)-2-pyridinyl)oxy)phenyl)-3-(trifluoromethyl)benzamide | 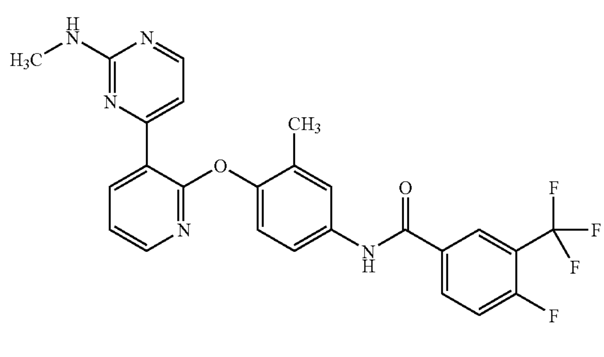 | 497.45 | 498 |
| 1036 | N-(4-chlorophenyl)-N'-(4-((3-(2-(methylamino)-4-pyrimidinyl)-2-pyridinyl)sulfinyl)phenyl)urea | 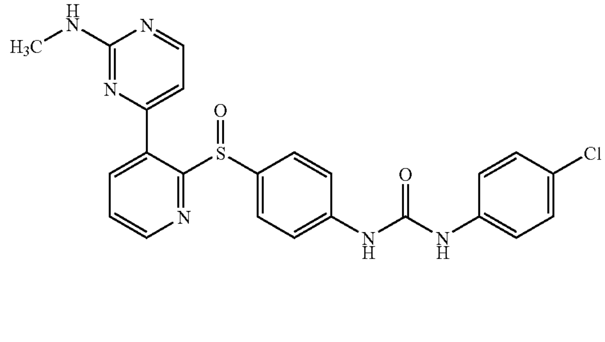 | 478.96 | 479 |

-continued

| Ex. No. | Structure Name | Structure | MW | MS Data |
|---|---|---|---|---|
| 1037 | N-(1,1'-biphenyl-4-yl)-N'-(4-((3-(2-(methylamino)-4-pyrimidinyl)-2-pyridinyl)oxy)phenyl)urea | 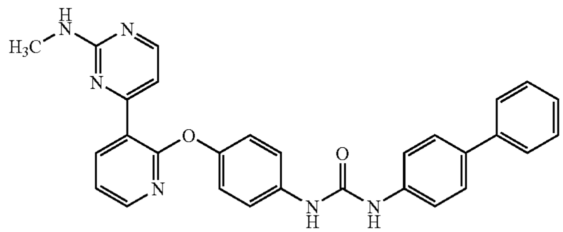 | 488.55 | 489 |
| 1038 | N-(4-((3-(2-(methylamino)-4-pyrimidinyl)-2-pyridinyl)oxy)phenyl)-N'-(4-((1-methyl-4-piperidinyl)oxy)phenyl)urea | 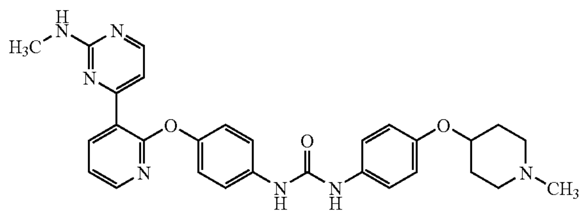 | 525.61 | 526 |
| 1039 | N-(4-(2-(3,4-dimethyl-1-piperazinyl)ethyl)phenyl)-N'-(4-((3-(2-(methylamino)-4-pyrimidinyl)-2-pyridinyl)oxy)phenyl)urea | 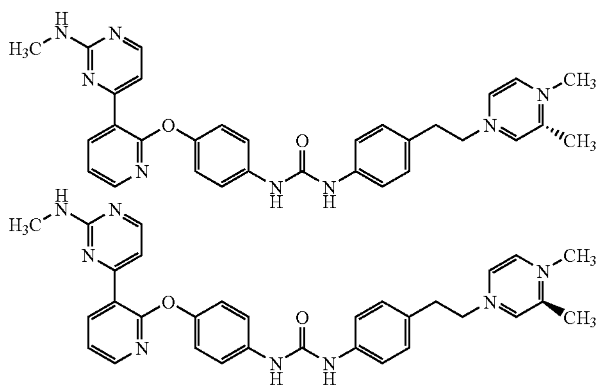 | 552.68 | 553 |
| 1040 | N-(3-fluoro-4-((3-(1H-imidazol-1-yl)propyl)oxy)phenyl)-N'-(4-((3-(2-(methylamino)-4-pyrimidinyl)-2-pyridinyl)oxy)phenyl)urea | 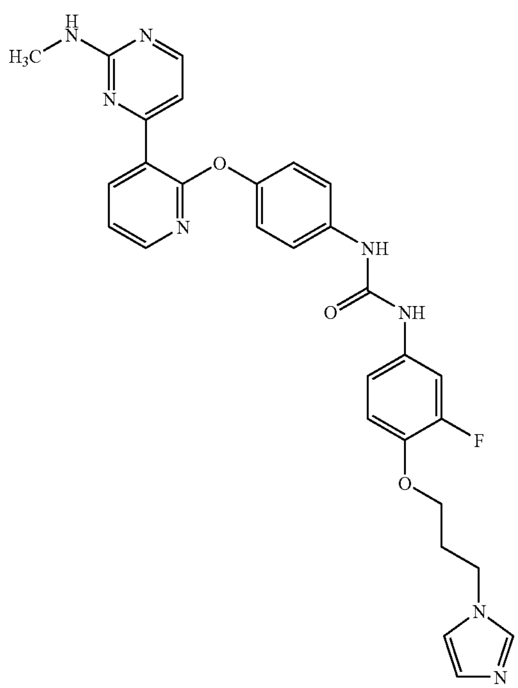 | 554.58 | 555 |

| Ex. No. | Structure Name | Structure | MW | MS Data |
|---|---|---|---|---|
| 1041 | N-(3-ethyl-4-methylphenyl)-N'-(4-((3-(2-(methylamino)-4-pyrimidinyl)-2-pyridinyl)oxy)phenyl)urea | 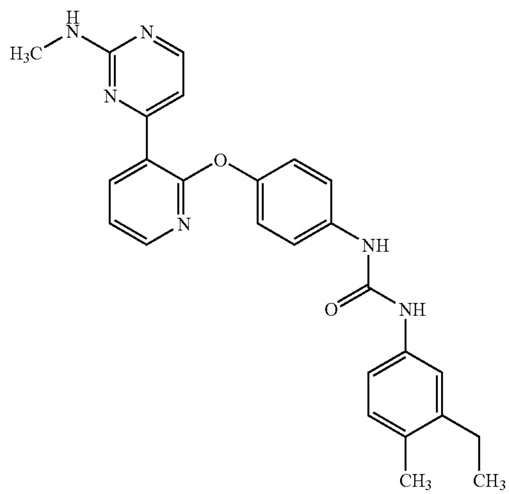 | 454.53 | 455 |
| 1042 | N-(3-ethyl-4-methylphenyl)-N'-(3-methyl-4-((3-(2-(methylamino)-4-pyrimidinyl)-2-pyridinyl)oxy)phenyl)urea | 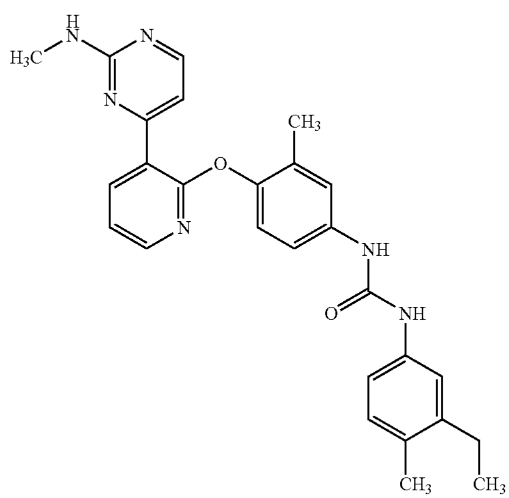 | 468.56 | 469 |
| 1043 | N-(3-fluoro-4-methylphenyl)-N'-(2-methyl-4-((3-(2-(methylamino)-4-pyrimidinyl)-2-pyridinyl)oxy)phenyl)urea | 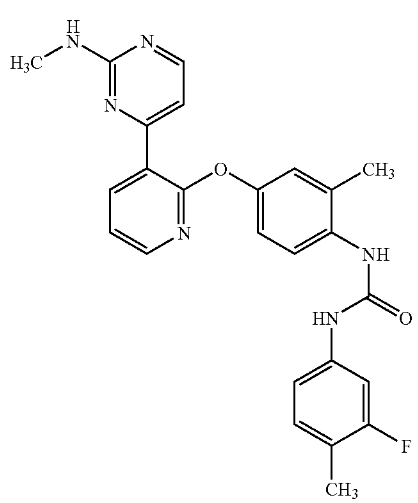 | 458.5 | 459 |

-continued

| Ex. No. | Structure Name | Structure | MW | MS Data |
|---|---|---|---|---|
| 1044 | N-(4-bromophenyl)-N'-(2-methyl-4-((3-(2-(methylamino)-4-pyrimidinyl)-2-pyridinyl)oxy)phenyl)urea | 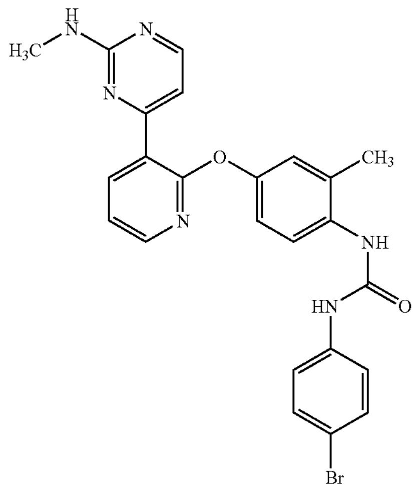 | 505.37 | 505 |
| 1045 | N-(3-fluoro-4-(methyloxy)phenyl)-N'-(2-methyl-4-((3-(2-(methylamino)-4-pyrimidinyl)-2-pyridinyl)oxy)phenyl)urea | 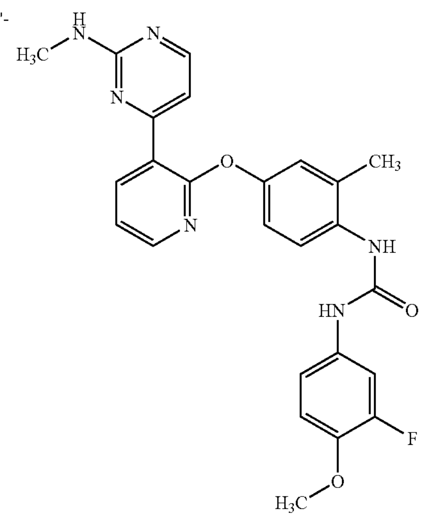 | 474.49 | 475 |
| 1046 | N-(4-bromo-3-fluorophenyl)-N'-(2-methyl-4-((3-(2-(methylamino)-4-pyrimidinyl)-2-pyridinyl)oxy)phenyl)urea | 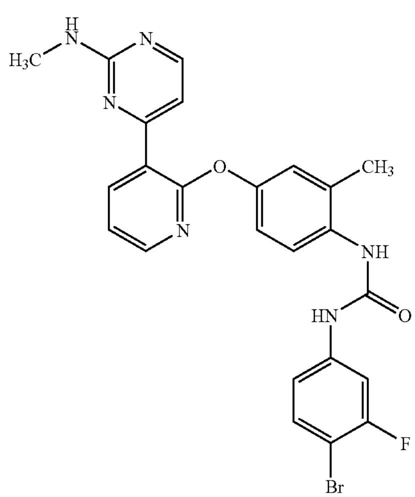 | 523.36 | 525 |

-continued

| Ex. No. | Structure Name | Structure | MW | MS Data |
|---|---|---|---|---|
| 1047 | N-(4-chloro-3-fluorophenyl)-N'-(4-((3-(2-(methylamino)-4-pyrimidinyl)-2-pyridinyl)oxy)phenyl)urea | 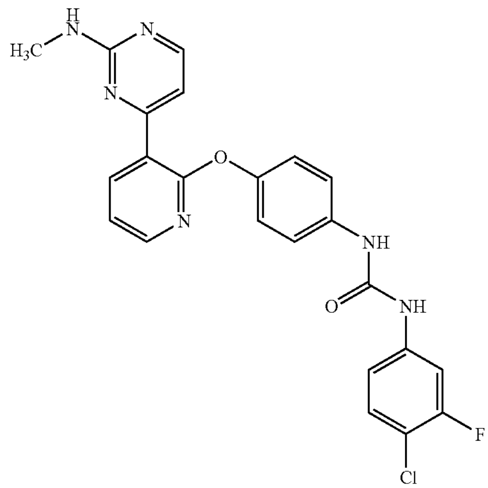 | 464.89 | 465 |
| 1048 | N-(4-chloro-3-fluorophenyl)-N'-(3-methyl-4-((3-(2-(methylamino)-4-pyrimidinyl)-2-pyridinyl)oxy)phenyl)urea | 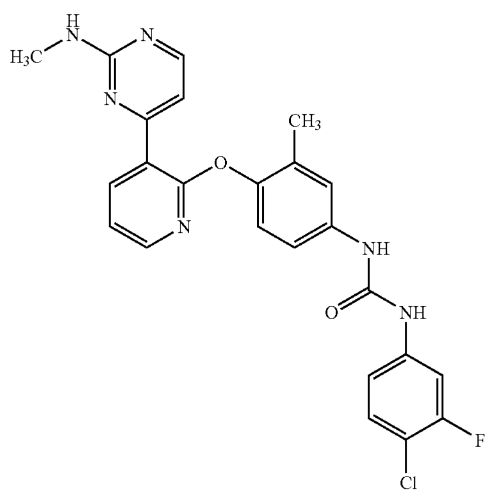 | 478.91 | 479 |
| 1049 | 3-((3S)-3-(dimethylamino)-1-pyrrolidinyl)-N-(3-methyl-4-((3-(2-(methylamino)-4-pyrimidinyl)-2-pyridinyl)oxy)phenyl)benzamide | 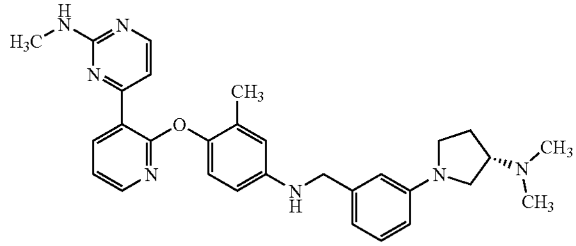 | 523.64 | 524 |

-continued

| Ex. No. | Structure Name | Structure | MW | MS Data |
|---|---|---|---|---|
| 1050 | N-(4-((3-(2-(methylamino)-4-pyrimidinyl)-2-pyridinyl)oxy)-1-naphthalenyl)-N'-phenylurea | 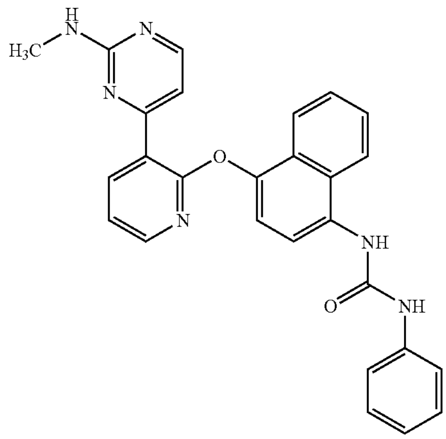 | 462.51 | 463 |
| 1051 | N-(3-methyl-4-((3-(2-(methylamino)-4-pyrimidinyl)-2-pyridinyl)oxy)phenyl)-4-(4-methyl-1-piperazinyl)benzamide | 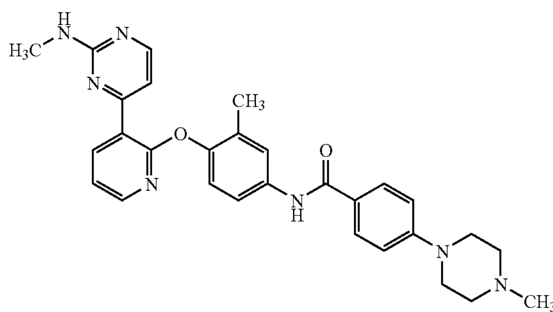 | 509.61 | 510 |
| 1052 | N-(3-methyl-4-((3-(2-(methylamino)-4-pyrimidinyl)-2-pyridinyl)oxy)phenyl)-1H-indole-7-carboxamide | 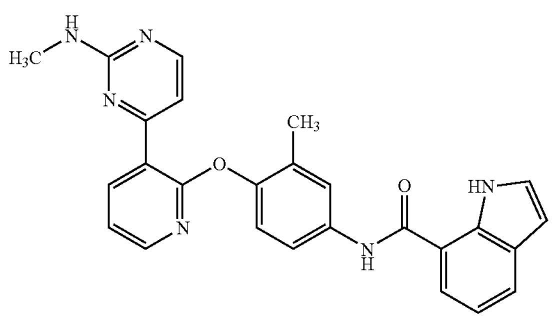 | 450.5 | 451 |
| 1053 | N-(2,3-dihydro-1H-inden-5-yl)-N'-(4-((3-(2-(methylamino)-4-pyrimidinyl)-2-pyridinyl)oxy)phenyl)urea | 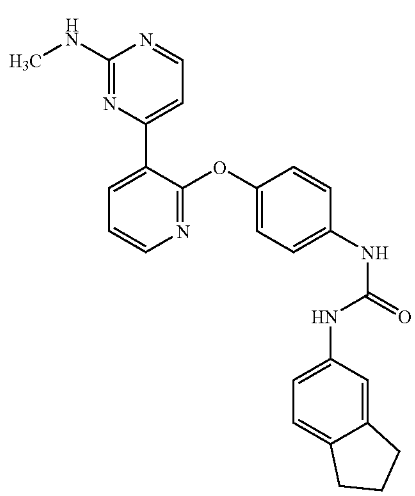 | 452.52 | 453 |

-continued

| Ex. No. | Structure Name | Structure | MW | MS Data |
|---|---|---|---|---|
| 1054 | (9H-fluoren-2-yl)-N'-(3-methyl-4-((3-(2-(methylamino)-4-pyrimidinyl)-2-pyridinyl)oxy)phenyl)urea | 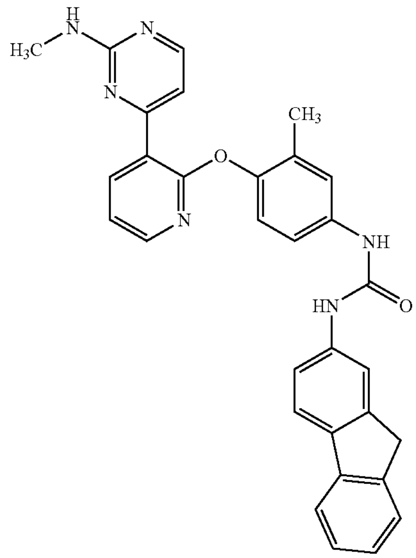 | 514.59 | 515 |
| 1055 | N-(2,3-dihydro-1H-inden-5-yl)-N'-(3-methyl-4-((3-(2-(methylamino)-4-pyrimidinyl)-2-pyridinyl)oxy)phenyl)urea | 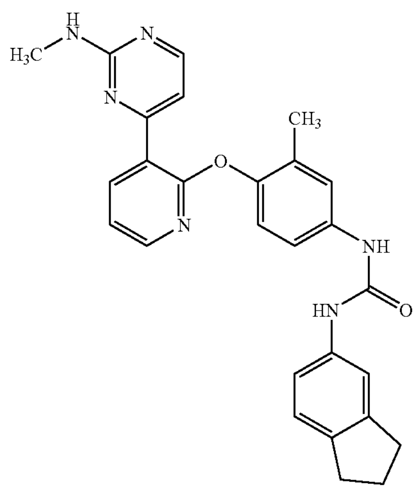 | 466.54 | 467 |
| 1056 | N-(4-((3-(2-(methylamino)-4-pyrimidinyl)-2-pyridinyl)oxy)phenyl)-N'-(4-(trifluoromethyl)phenyl)urea | 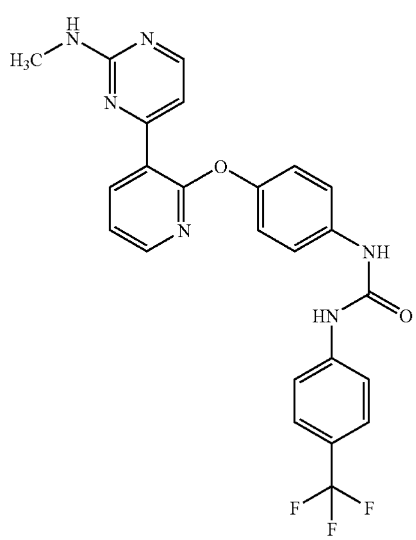 | 480.45 | 481 |

-continued
| Ex. No. | Structure Name | Structure | MW | MS Data |
|---|---|---|---|---|
| 1057 | N-(3-methyl-4-((3-(2-(methylamino)-4-pyrimidinyl)-2-pyridinyl)oxy)phenyl)-N'-(4-(trifluoromethyl)phenyl) urea | 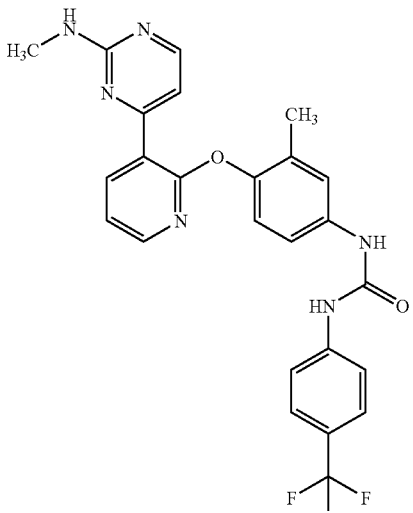 | 494.48 | 495 |
| 1058 | N-(3-fluoro-4-methylphenyl)-N'-(3-methyl-4-((3-(2-(methylamino)-4-pyrimidinyl)-2-pyridinyl)oxy)phenyl)urea | 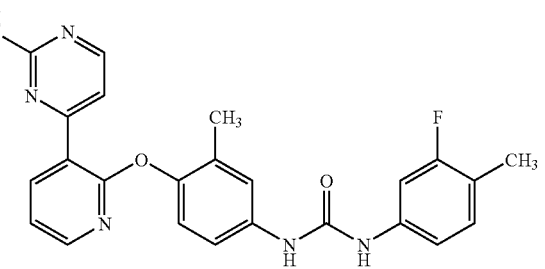 | 458.5 | 459 |
| 1059 | N-(3-((3-(4-pyrimidinyl)-2-pyridinyl)oxy)phenyl)-3-((trifluoromethyl)oxy) benzamide | 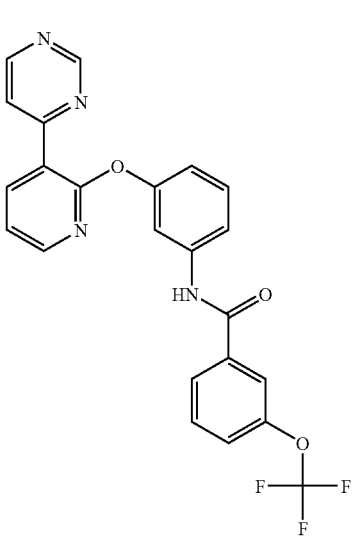 | 452.39 | 453 |

| Ex. No. | Structure Name | Structure | MW | MS Data |
|---|---|---|---|---|
| 1060 | 4-chloro-N-(3-((3-(4-pyrimidinyl)-2-pyridinyl)oxy)phenyl)-3-((trifluoromethyl)oxy)benzamide | 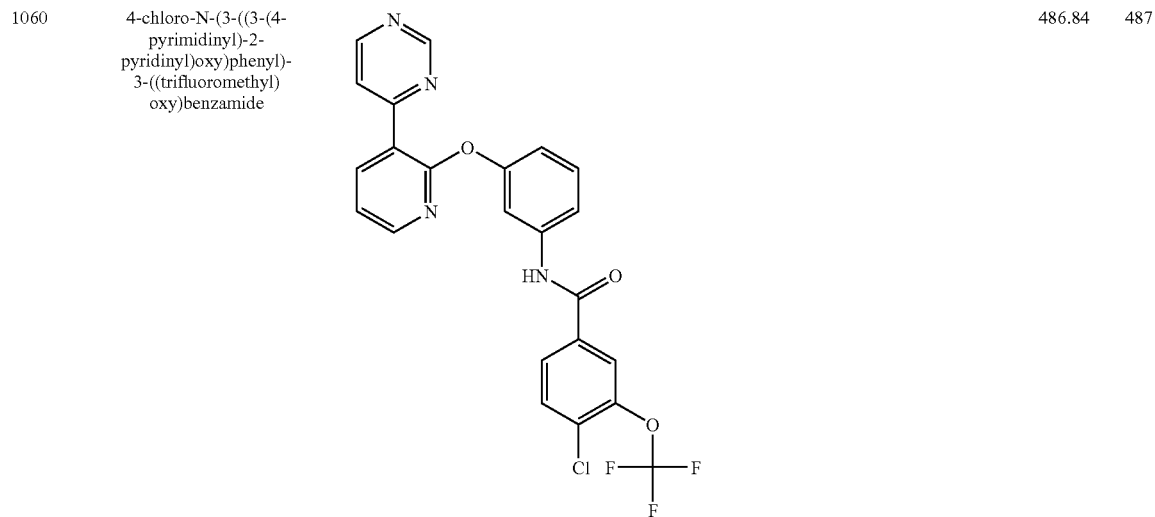 | 486.84 | 487 |
| 1061 | N-(3-((3-(4-pyrimidinyl)-2-pyridinyl)oxy)phenyl)-3-(trifluoromethyl)benzamide | 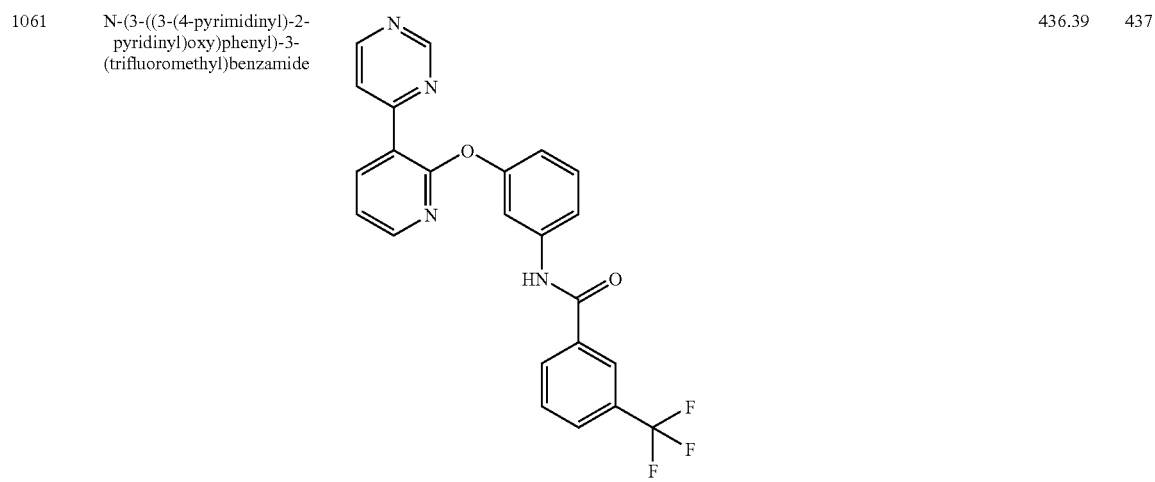 | 436.39 | 437 |

| Ex. No. | Structure Name | Structure | MW | MS Data |
|---|---|---|---|---|
| 1062 | 4-((phenylmethyl)oxy)-N-(3-((3-(4-pyrimidinyl)-2-pyridinyl)oxy)phenyl)benzamide | 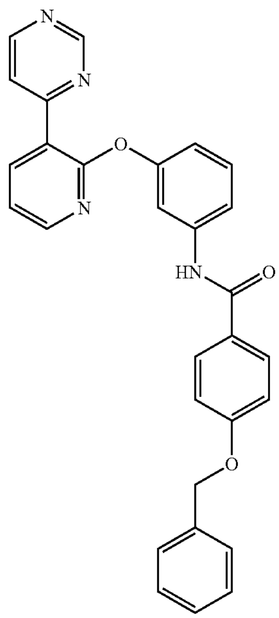 | 474.52 | 475 |
| 1063 | 2-cyclohexyl-N-(3-((3-(4-pyrimidinyl)-2-pyridinyl)oxy)phenyl)acetamide | 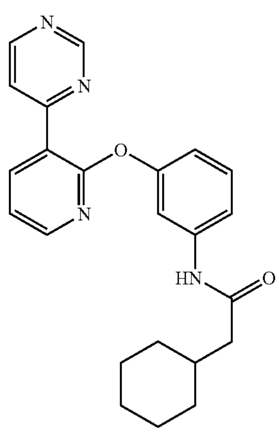 | 388.47 | 389 |
| 1064 | N-(3-((3-(4-pyrimidinyl)-2-pyridinyl)oxy)phenyl)hexanamide | 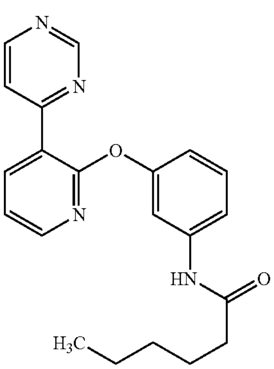 | 362.43 | 363 |

-continued

| Ex. No. | Structure Name | Structure | MW | MS Data |
|---|---|---|---|---|
| 1065 | 4-(dimethylamino)-N-(3-((3-(4-pyrimidinyl)-2-pyridinyl)oxy)phenyl) benzamide | 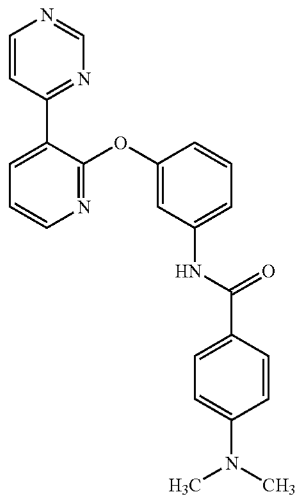 | 411.46 | 412 |
| 1066 | 3-(1,1-dimethylethyl)-1-methyl-N-(3-((3-(4-pyrimidinyl)-2-pyridinyl)oxy)phenyl)-1H-pyrazole-5-carboxamide | 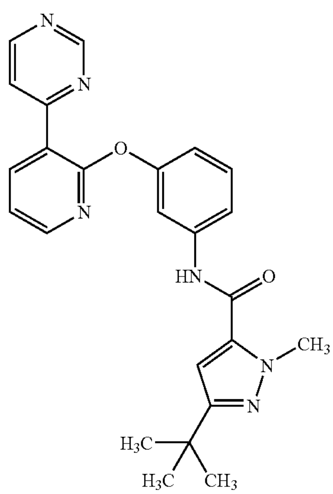 | 428.49 | 429 |
| 1067 | 4,4-dimethyl-N-(3-((3-(4-pyrimidinyl)-2-pyridinyl)oxy)phenyl) pentanamide | 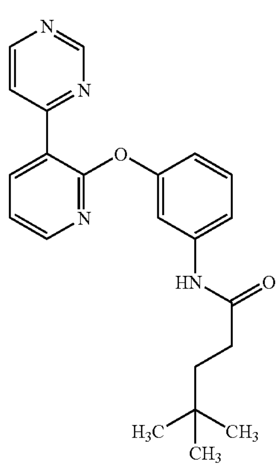 | 376.46 | 377 |

| Ex. No. | Structure Name | Structure | MW | MS Data |
|---|---|---|---|---|
| 1068 | 4,4-dimethyl-N-(4-methyl-3-((3-(4-pyrimidinyl)-2-pyridinyl)oxy)phenyl)pentanamide | 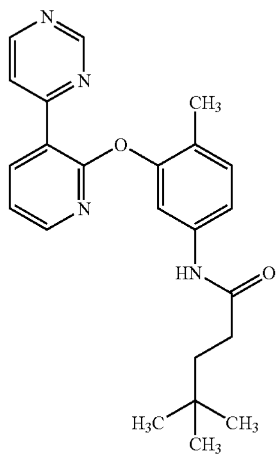 | 390.48 | 391 |
| 1069 | 4-((4-methyl-1-piperazinyl)methyl)-N-(3-((3-(4-pyrimidinyl)-2-pyridinyl)oxy)phenyl)benzamide | 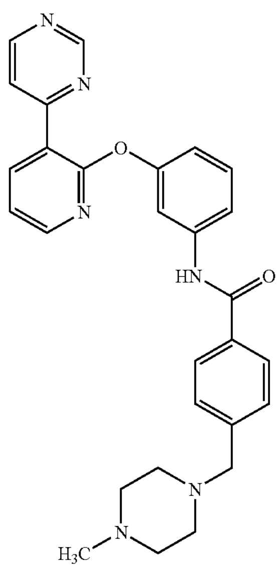 | 480.57 | 481 |
| 1070 | N-(9H-fluoren-2-yl)-N'-(4-((3-(2-(methylamino)-4-pyrimidinyl)-2-pyridinyl)oxy)phenyl)urea | 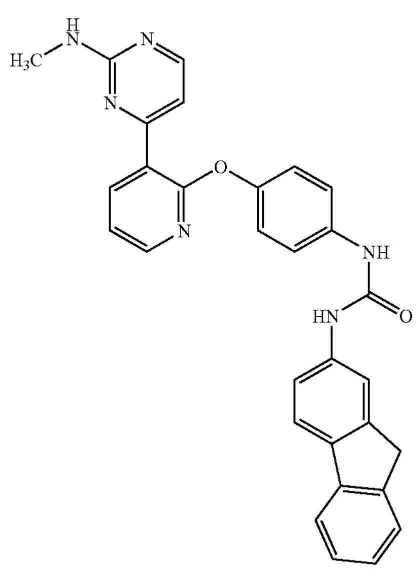 | 500.56 | 501 |

-continued

| Ex. No. | Structure Name | Structure | MW | MS Data |
|---|---|---|---|---|
| 1071 | N-(1-acetyl-3,3-dimethyl-2,3-dihydro-1H-indol-6-yl)-N'-(4-((3-(2-(methylamino)-4-pyrimidinyl)-2-pyridinyl)oxy)phenyl)urea | 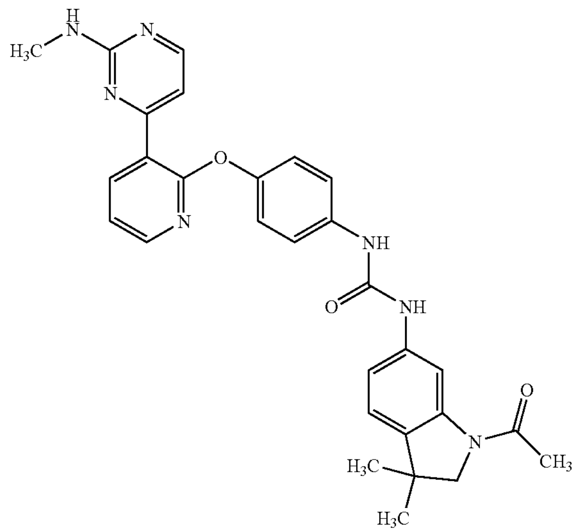 | 523.59 | 524 |
| 1072 | N-(1-acetyl-3,3-dimethyl-2,3-dihydro-1H-indol-6-yl)-N'-(3-methyl-4-((3-(2-(methylamino)-4-pyrimidinyl)-2-pyridinyl)oxy)phenyl)urea | 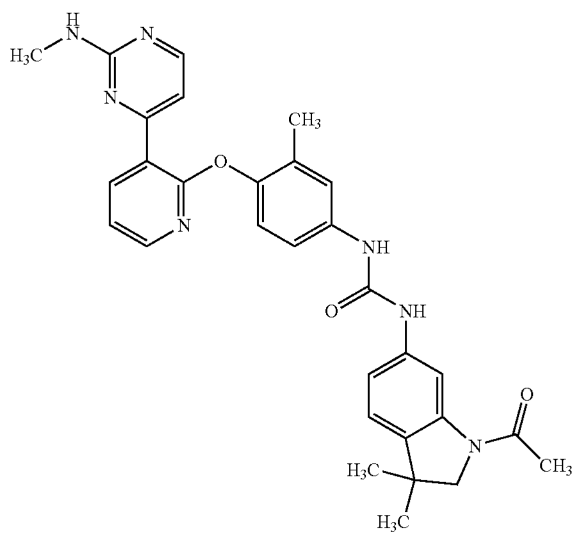 | 537.62 | 538 |
| 1073 | N-(3-(1,1-dimethylethyl)phenyl)-N'-(4-((3-(2-(methylamino)-4-pyrimidinyl)-2-pyridinyl)oxy)phenyl)urea | 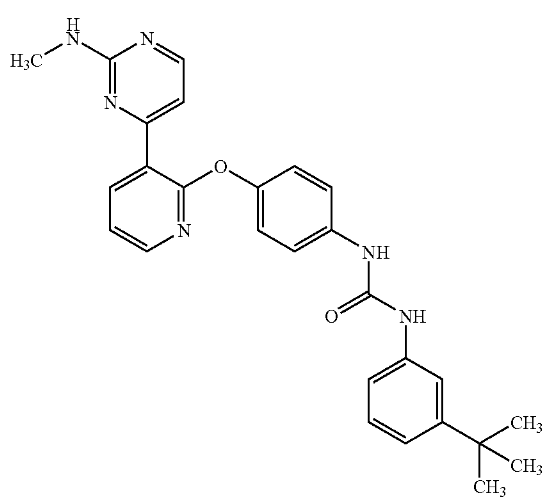 | 468.56 | 469 |

-continued

| Ex. No. | Structure Name | Structure | MW | MS Data |
|---|---|---|---|---|
| 1074 | N-(3-(1,1-dimethylethyl)phenyl)-N'-(3-methyl-4-((3-(2-(methylamino)-4-pyrimidinyl)-2-pyridinyl)oxy)phenyl)urea | 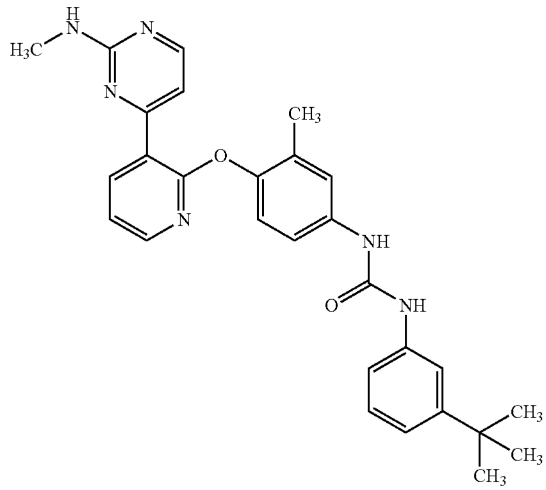 | 482.58 | 483 |
| 1075 | N-(3-(1,1-dimethylethyl)phenyl)-N'-(2-methyl-4-((3-(2-(methylamino)-4-pyrimidinyl)-2-pyridinyl)oxy)phenyl)urea | 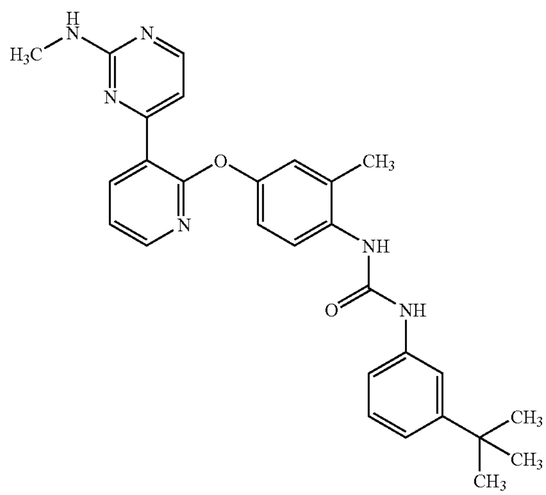 | 482.58 | 483 |
| 1076 | N-(3-(1,1-dimethylethyl)phenyl)-N'-(2,3-dimethyl-4-((3-(2-(methylamino)-4-pyrimidinyl)-2-pyridinyl)oxy)phenyl)urea | 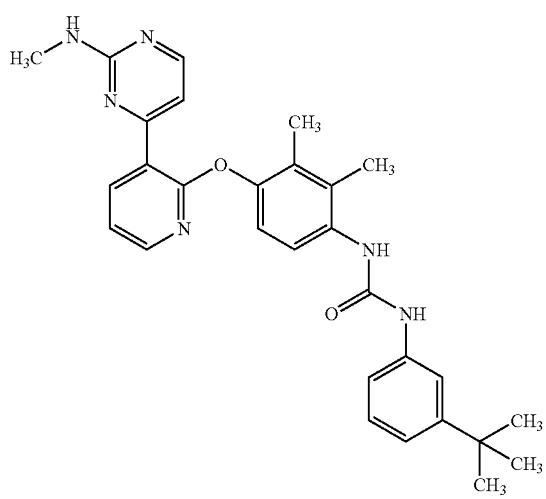 | 496.61 | 497 |

-continued

| Ex. No. | Structure Name | Structure | MW | MS Data |
|---|---|---|---|---|
| 1077 | N-(1,1-dimethylethyl)-N'-(3-methyl-4-((3-(2-(methylamino)-4-pyrimidinyl)-2-pyridinyl)oxy)phenyl)urea | 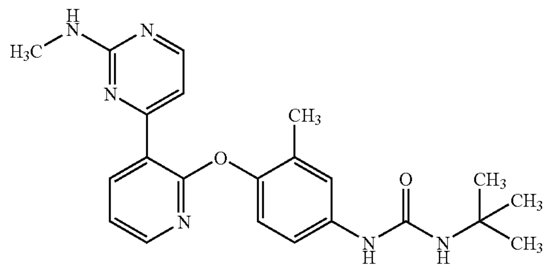 | 406.49 | 407 |
| 1078 | N-(3-fluoro-4-methylphenyl)-N'-(4-((3-(2-(methylamino)-4-pyrimidinyl)-2-pyridinyl)oxy)-1-naphthalenyl)urea | 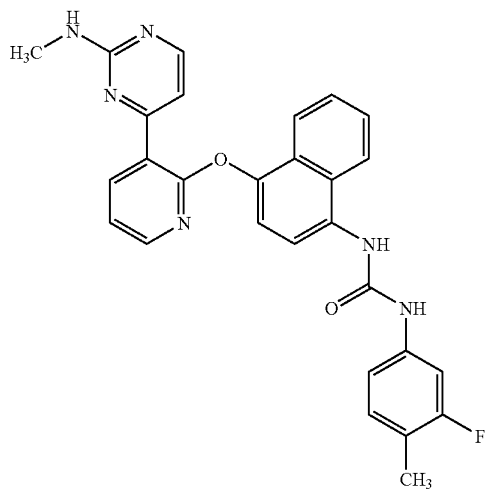 | 494.53 | 495 |
| 1079 | N-(4-(1,1-dimethylethyl)phenyl)-N'-(4-((3-(2-(methylamino)-4-pyrimidinyl)-2-pyridinyl)oxy)-1-naphthalenyl)urea | 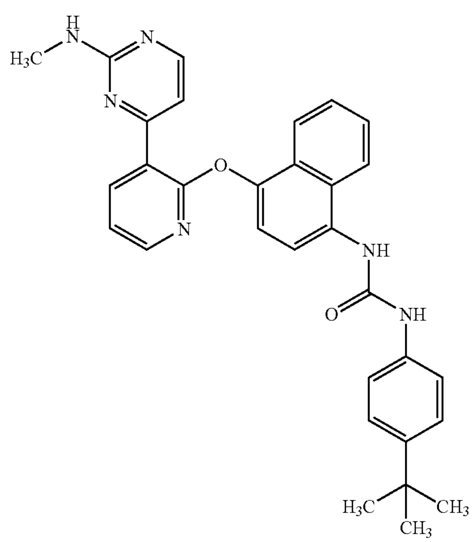 | 518.62 | 519 |

-continued

| Ex. No. | Structure Name | Structure | MW | MS Data |
|---|---|---|---|---|
| 1080 | N-(4-((3-(2-(phenylamino)-4-pyrimidinyl)-2-pyridinyl)oxy)phenyl)-3-(trifluoromethyl)benzamide | 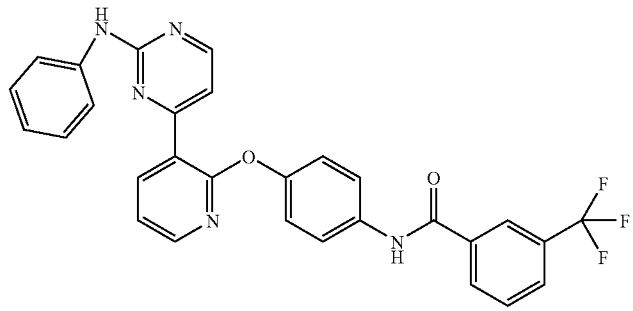 | 527.5 | 528 |
| 1081 | N-(3-methyl-4-((3-(2-((4-(4-methyl-1-piperazinyl)phenyl)amino)-4-pyrimidinyl)-2-pyridinyl)oxy)phenyl)acetamide | 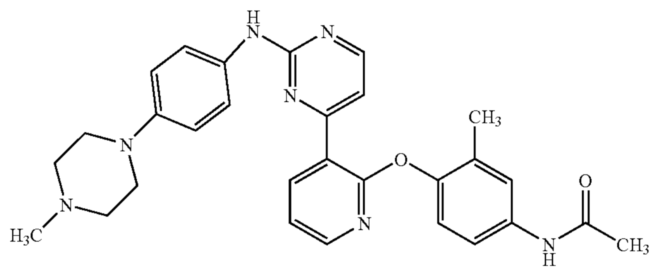 | 509.61 | 510 |
| 1082 | N-(4-((3-(2-(methylamino)-4-pyrimidinyl)-2-pyridinyl)oxy)phenyl)-N'-(4-methylphenyl)urea | 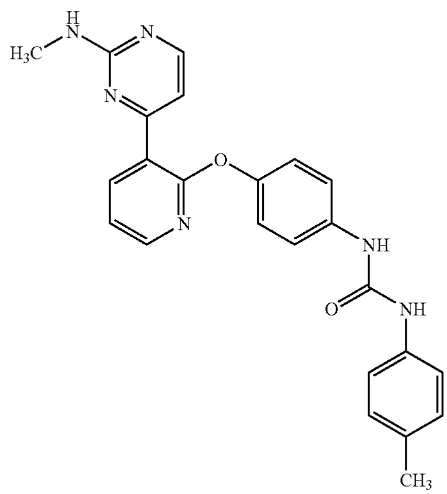 | 426.48 | 427 |
| 1083 | N-(3-methyl-4-((3-(2-(methylamino)-4-pyrimidinyl)-2-pyridinyl)oxy)phenyl)-N'-(4-methylphenyl)urea | 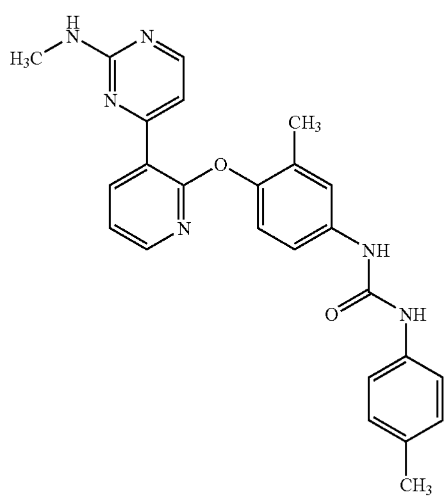 | 440.51 | 441 |

-continued

| Ex. No. | Structure Name | Structure | MW | MS Data |
|---|---|---|---|---|
| 1084 | N-(2-methyl-4-((3-(2-(methylamino)-4-pyrimidinyl)-2-pyridinyl)oxy)phenyl)-N'-(4-methylphenyl)urea | 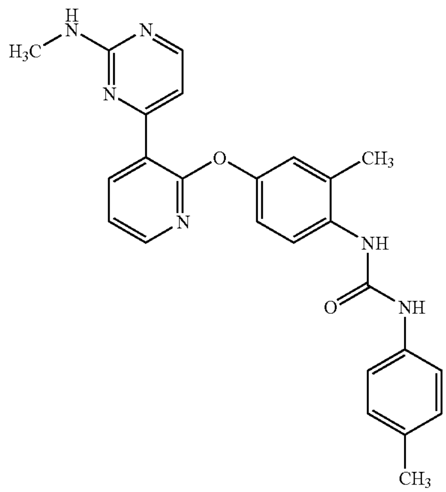 | 440.51 | 441 |
| 1085 | N-(2,3-dimethyl-4-((3-(2-(methylamino)-4-pyrimidinyl)-2-pyridinyl)oxy)phenyl)-N'-(4-methylphenyl)urea | 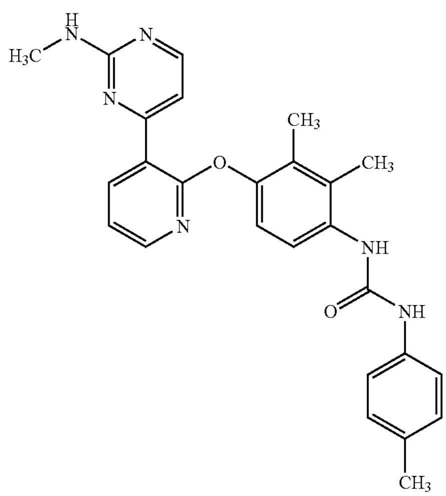 | 454.53 | 455 |
| 1086 | N-(4-((3-(2-((4-(4-methyl-1-piperazinyl)phenyl)amino)-4-pyrimidinyl)-2-pyridinyl)sulfanyl)phenyl)-3-(trifluoromethyl)benzamide | 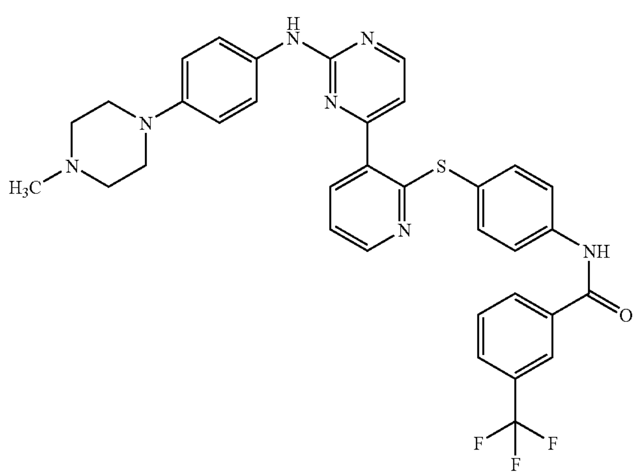 | 641.72 | 642 |

-continued

| Ex. No. | Structure Name | Structure | MW | MS Data |
|---|---|---|---|---|
| 1087 | N-(4-((3-(2-(methylamino)-4-pyrimidinyl)-2-pyridinyl)oxy)phenyl)-N'-(phenylmethyl)urea | 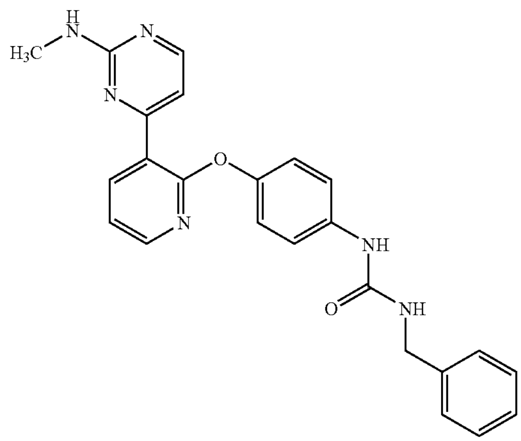 | 426.48 | 427 |
| 1088 | N-(2-methyl-4-((3-(2-(methylamino)-4-pyrimidinyl)-2-pyridinyl)oxy)phenyl)-N'-(phenylmethyl)urea | 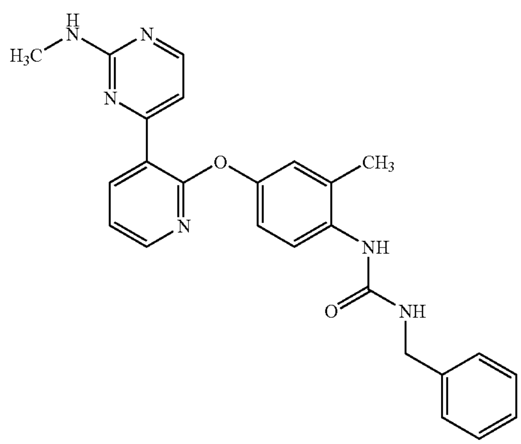 | 440.51 | 441 |
| 1089 | N-(2,3-dimethyl-4-((3-(2-(methylamino)-4-pyrimidinyl)-2-pyridinyl)oxy)phenyl)-N'-(phenylmethyl)urea | 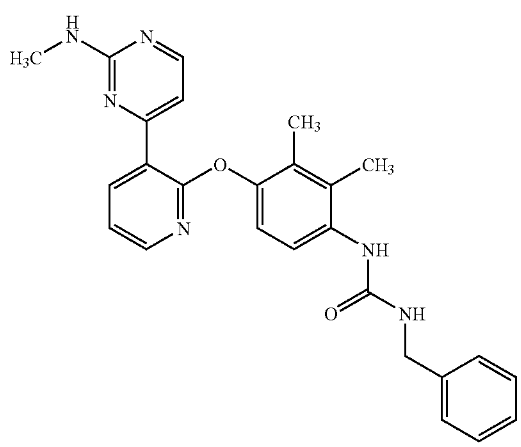 | 454.53 | 455 |

| Ex. No. | Structure Name | Structure | MW | MS Data |
|---|---|---|---|---|
| 1090 | N-(4-((3-(2-(methylamino)-4-pyrimidinyl)-2-pyridinyl)oxy)-1-naphthalenyl)-N'-(phenylmethyl)urea | 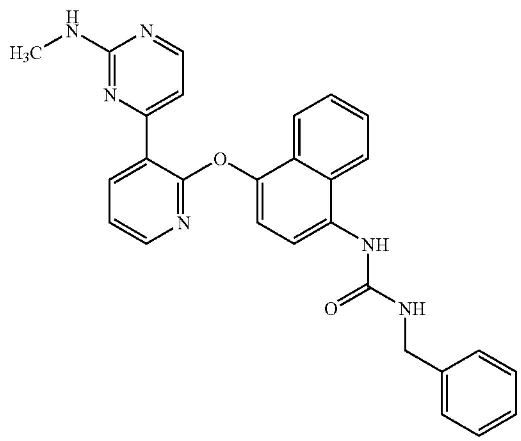 | 476.54 | 477 |
| 1091 | N-(4-((3-(2-(methylamino)-4-pyrimidinyl)-2-pyridinyl)oxy)phenyl)-N'-((3-methylphenyl)methyl)urea | 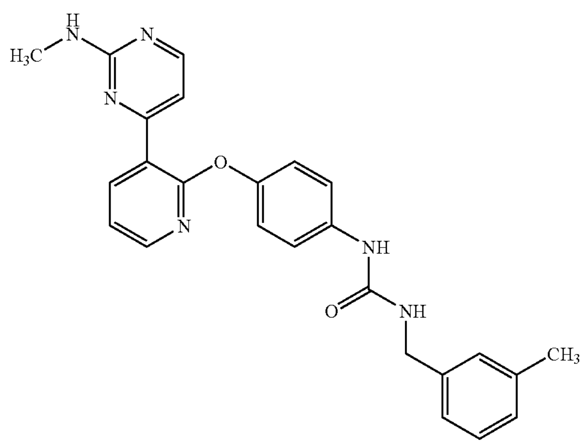 | 440.51 | 441 |
| 1092 | N-(3-methyl-4-((3-(2-(methylamino)-4-pyrimidinyl)-2-pyridinyl)oxy)phenyl)-N'-((2-methylphenyl)methyl)urea | 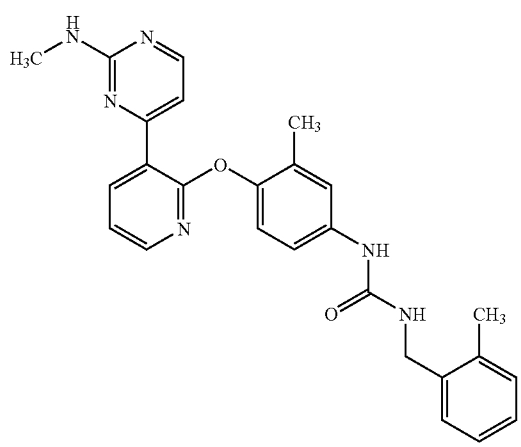 | 454.53 | 455 |

-continued

| Ex. No. | Structure Name | Structure | MW | MS Data |
|---|---|---|---|---|
| 1093 | N-(4-((3-(2-(methylamino)-4-pyrimidinyl)-2-pyridinyl)oxy)phenyl)-N'-((2-methylphenyl)methyl)urea | 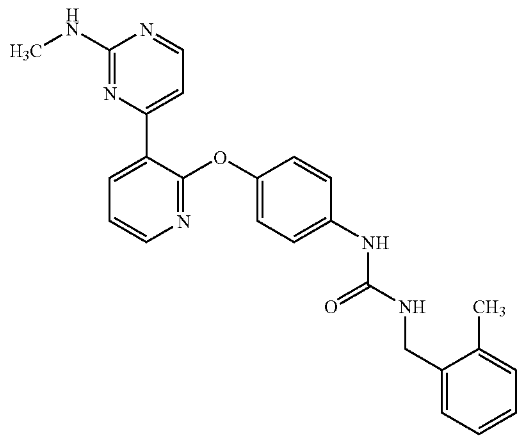 | 440.51 | 441 |
| 1094 | N-(4-((3-(2-(methylamino)-4-pyrimidinyl)-2-pyridinyl)oxy)phenyl)-N'-((4-methylphenyl)methyl)urea | 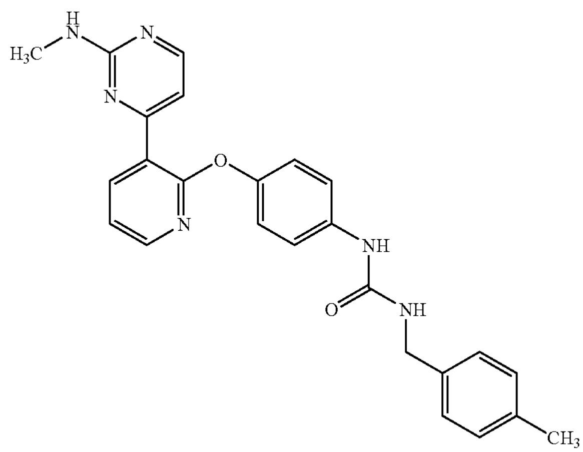 | 440.51 | 441 |
| 1095 | N-(3-methyl-4-((3-(2-(methylamino)-4-pyrimidinyl)-2-pyridinyl)oxy)phenyl)-N'-((4-methylphenyl)methyl)urea | 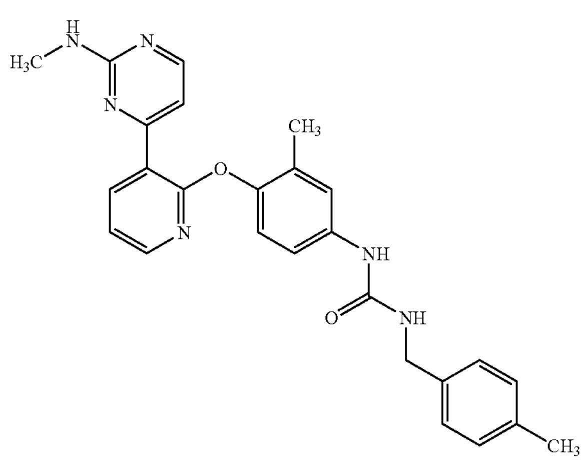 | 454.53 | 455 |

-continued

| Ex. No. | Structure Name | Structure | MW | MS Data |
|---|---|---|---|---|
| 1096 | N-(4-chlorophenyl)-N'-(4-((3-(2-((3-(4-morpholinyl)propyl)amino)-4-pyrimidinyl)-2-pyridinyl)oxy)phenyl)urea | 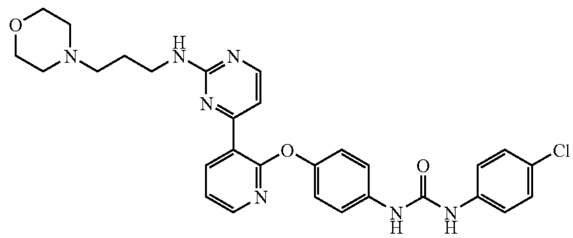 | 560.05 | 560 |
| 1097 | 1-(1-acetylindolin-6-yl)-3-(3-methyl-4-(3-(2-(methylamino)pyrimidin-4-yl)pyridin-2-yloxy)phenyl)urea | 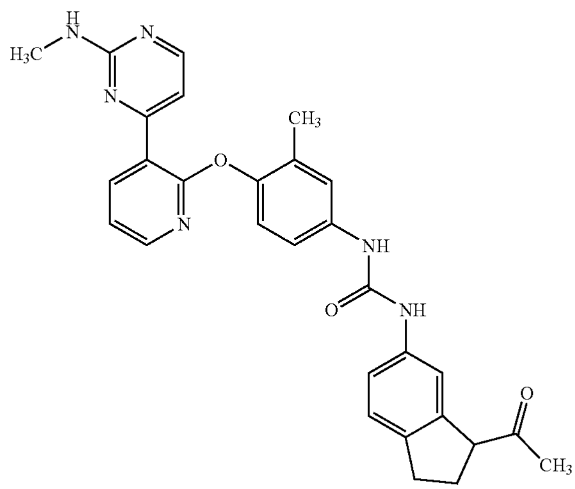 | 509.57 | 510 |
| 1098 | 1-(4-tert-butylphenyl)-3-(3-methyl-4-(3-(2-(methylamino)pyrimidin-4-yl)pyridin-2-yloxy)phenyl)urea | 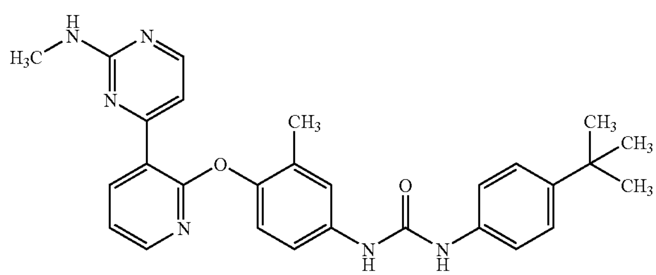 | 482.58 | 483 |
| 1099 | 1-(4-isopropylphenyl)-3-(3-methyl-4-(3-(2-(methylamino)pyrimidin-4-yl)pyridin-2-yloxy)phenyl)urea | 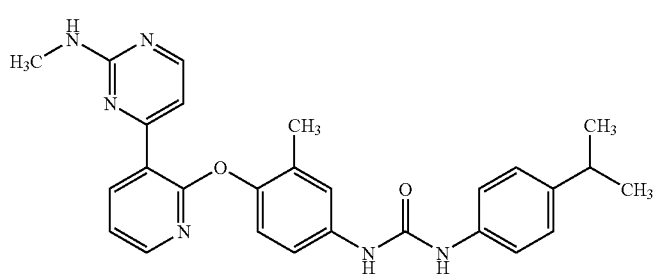 | 468.56 | 469 |

| Ex. No. | Structure Name | Structure | MW | MS Data |
|---|---|---|---|---|
| 1100 | 1-(2,3-dihydro-1H-inden-5-yl)-3-(4-(3-(2-(methylamino)pyrimidin-4-yl)pyridin-2-yloxy)naphthalen-1-yl)urea | 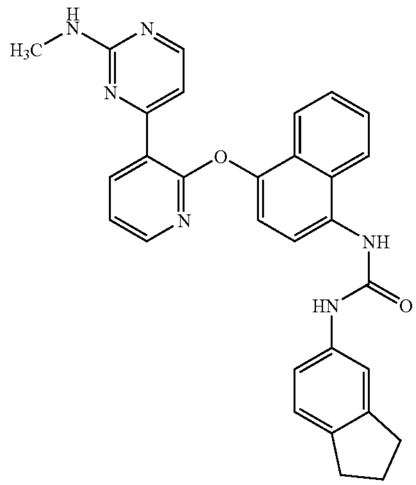 | 502.57 | 503 |
| 1101 | 1-(2,3-dihydro-1H-inden-5-yl)-3-(4-(3-(2-(3-morpholinopropylamino)pyrimidin-4-yl)pyridin-2-yloxy)phenyl)urea | 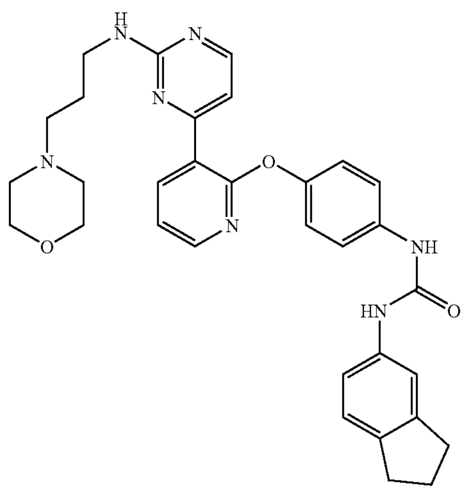 | 565.67 | 566 |
| 1102 | 1-(3-fluoro-4-methylphenyl)-3-(4-(3-(2-(3-morpholinopropylamino)pyrimidin-4-yl)pyridin-2-yloxy)phenyl)urea | 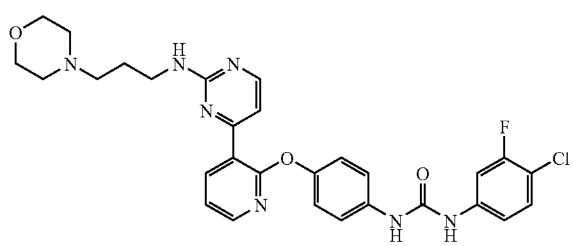 | 557.63 | 558 |
| 1103 | 1-(4-(3-(4-(methylamino)-1,3,5-triazin-2-yl)pyridin-2-yloxy)naphthalen-1-yl)-3-phenylurea | 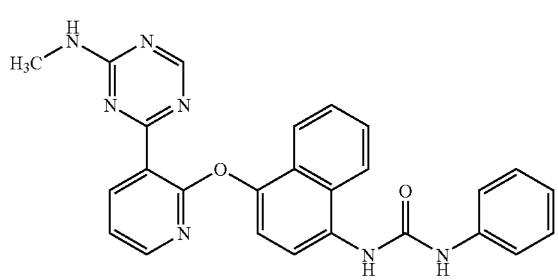 | 463.5 | 464 |

-continued

| Ex. No. | Structure Name | Structure | MW | MS Data |
|---|---|---|---|---|
| 1104 | 1-(3-methyl-4-(3-(2-(4-(4-methylpiperazin-1-yl)phenylamino)pyrimidin-4-yl)pyridin-2-yloxy)phenyl)-3-phenylurea | 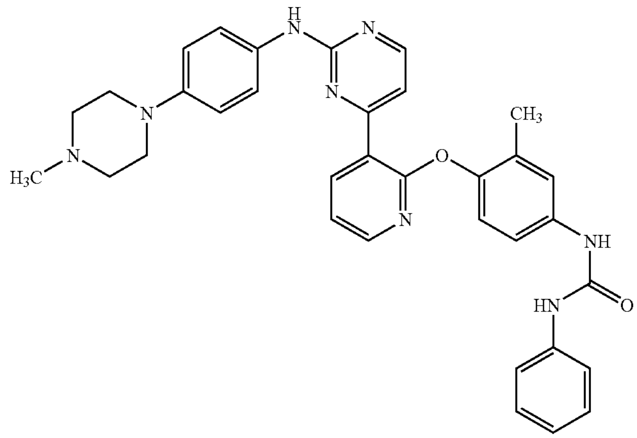 | 586.7 | 587 |
| 1105 | 1-(3-methyl-4-(3-(2-(4-(4-methylpiperazin-1-yl)phenylamino)pyrimidin-4-yl)pyridin-2-yloxy)phenyl)-3-(4-methylbenzyl)urea | 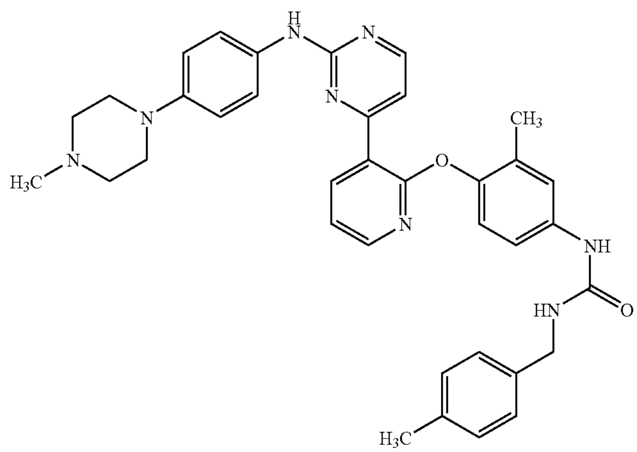 | 614.75 | 615 |
| 1106 | N-(3-methyl-4-(3-(2-(4-(4-methylpiperazin-1-yl)phenylamino)pyrimidin-4-yl)pyridin-2-yloxy)phenyl)-3-(thiophen-2-yl)benzamide | 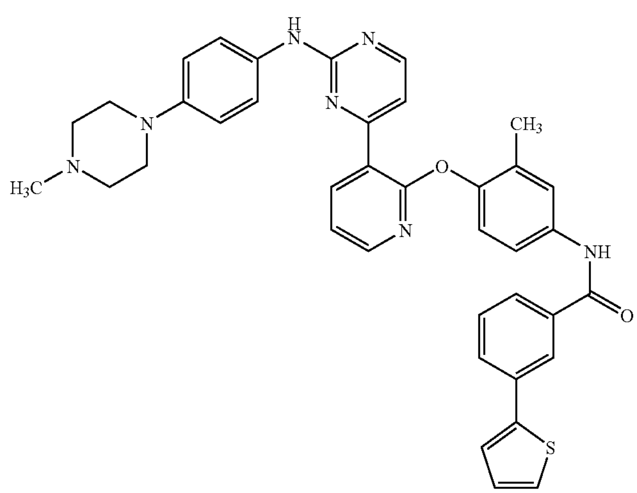 | 653.81 | 654 |

| Ex. No. | Structure Name | Structure | MW | MS Data |
|---|---|---|---|---|
| 1107 | 1-(4-(3-(4-(methylamino)-1,3,5-triazin-2-yl)pyridin-2-yloxy)naphthalen-1-yl)-3-(2-((4-methylpiperazin-1-yl)methyl)-5-(trifluoromethyl)phenyl)urea | 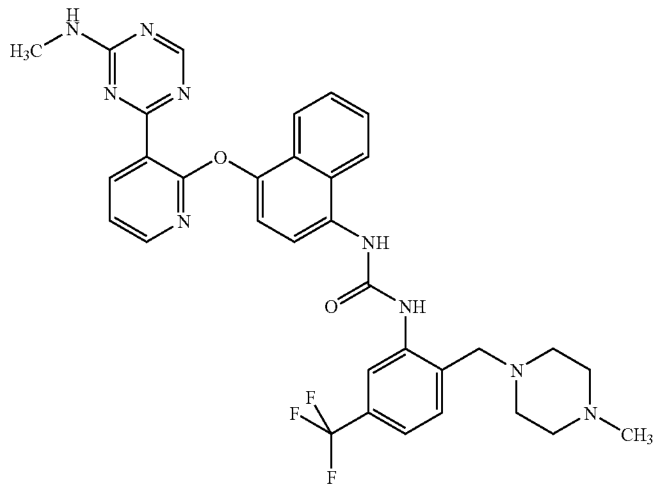 | 643.67 | 644 |
| 1108 | N-(1,1-dimethylethyl)-N'-(3-methyl-4-((3-(2-((4-(4-methyl-1-piperazinyl)phenyl)amino)-4-pyrimidinyl)-2-pyridinyl)oxy)phenyl)urea | 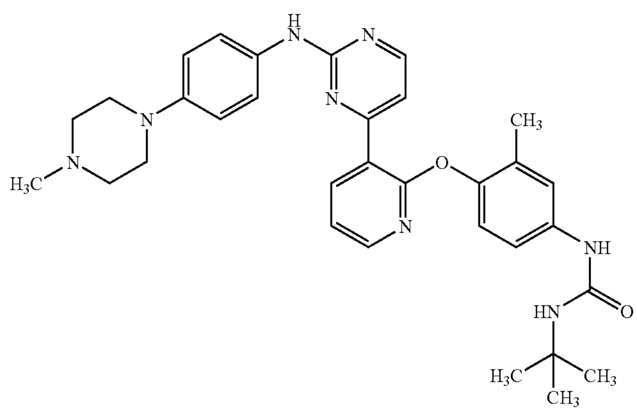 | 566.71 | 567 |
| 1109 | N-ethyl-N'-(4-((3-(2-(methylamino)-4-pyrimidinyl)-2-pyridinyl)oxy)-1-naphthalenyl)urea | 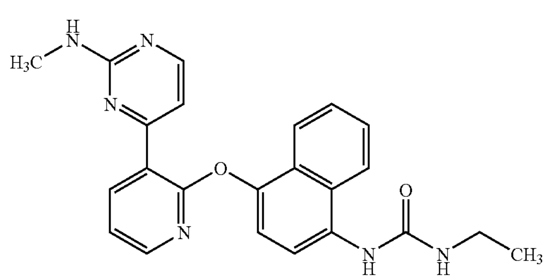 | 414.47 | 415 |

-continued

| Ex. No. | Structure Name | Structure | MW | MS Data |
|---|---|---|---|---|
| 1110 | N-(2-(1H-imidazol-1-ylmethyl)-5-(trifluoromethyl)phenyl) N'-(4-((3-(4-(methylamino)-1,3,5-triazin-2-yl)-2-pyridinyl)oxy)-1-naphthalenyl)urea | 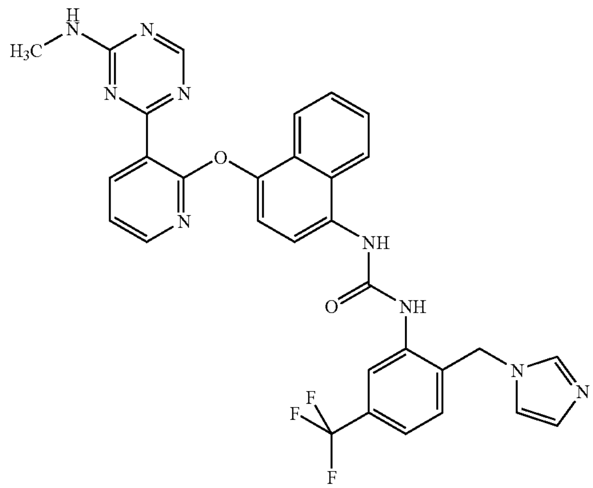 | 611.59 | 612 |
| 1111 | N-(3-methyl-4-((3-(2-((4-(4-methyl-1-piperazinyl)phenyl)amino)-4-pyrimidinyl)-2-pyridinyl)oxy)phenyl)cyclopropanecarboxamide | 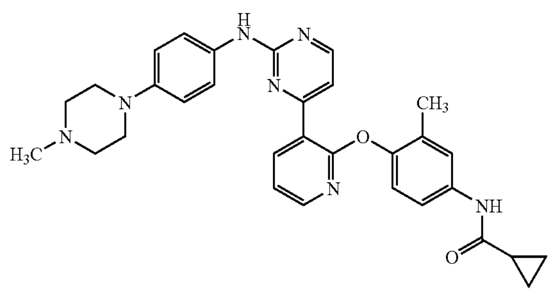 | 535.65 | 536 |
| 1112 | N-(4-chlorophenyl)-N'-(3-methyl-4-((3-(2-((4-(4-methyl-1-piperazinyl)phenyl)amino)-4-pyrimidinyl)-2-pyridinyl)oxy)phenyl)urea | 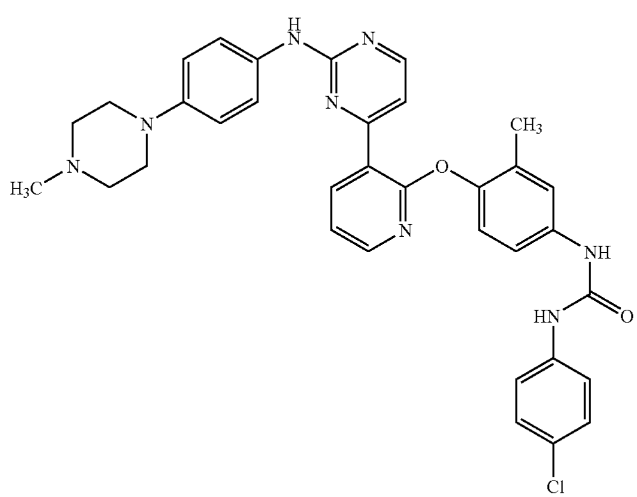 | 621.14 | 621 |

-continued

| Ex. No. | Structure Name | Structure | MW | MS Data |
|---|---|---|---|---|
| 1113 | N-(4-((3-(4-(methylamino)-1,3,5-triazin-2-yl)-2-pyridinyl)oxy)-1-naphthalenyl)-N'-(2-(1-pyrrolidinylmethyl)-5-(trifluoromethyl)phenyl) urea | 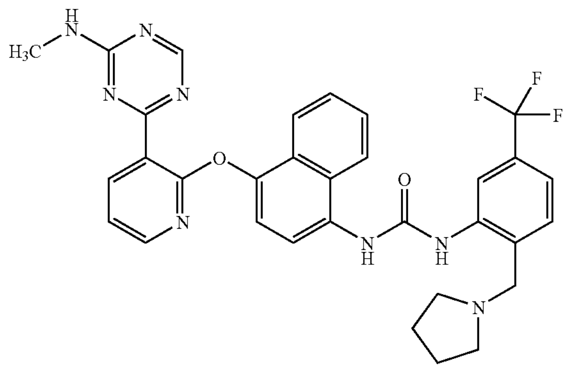 | 614.63 | 615 |
| 1114 | 1-tert-butyl-3-(4-(3-(2-(methylamino)pyrimidin-4-yl)pyridin-2-yloxy)naphthalen-1-yl)urea | 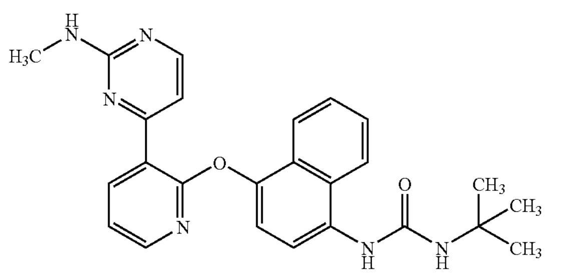 | 442.52 | 443 |
| 1115 | 1-(4-(3-(2-(4-(4-methylpiperazin-1-yl)phenylamino)pyrimidin-4-yl)pyridin-2-yloxy)phenyl)-3-phenylurea | 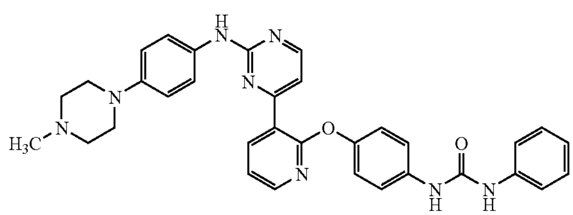 | 572.67 | 573 |
| 1116 | 1-(2-(methyl(1-methylpiperidin-4-yl)amino)-5-(trifluoromethyl)phenyl)-3-(4-(3-(4-(methylamino)-1,3,5-triazin-2-yl)pyridin-2-yloxy)naphthalen-1-yl)urea | 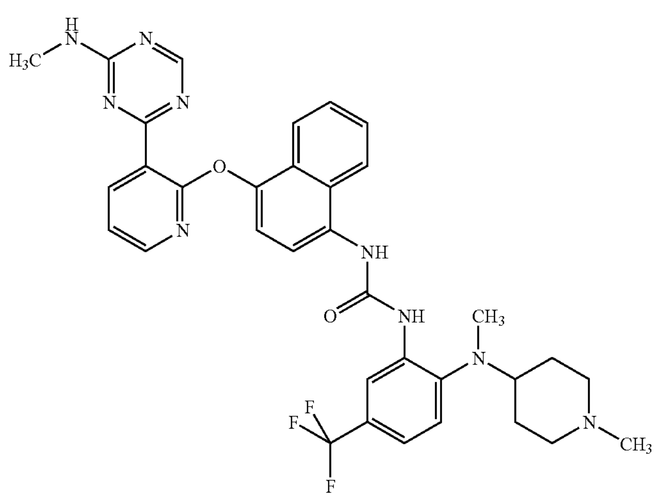 | 657.7 | 658 |

-continued

| Ex. No. | Structure Name | Structure | MW | MS Data |
|---|---|---|---|---|
| 1117 | 1-(5-chloro-2-((3-(dimethylamino)propyl)(methyl)amino)phenyl)-3-(4-(3-(4-(methylamino)-1,3,5-triazin-2-yl)pyridin-2-yloxy)naphthalen-1-yl)urea | 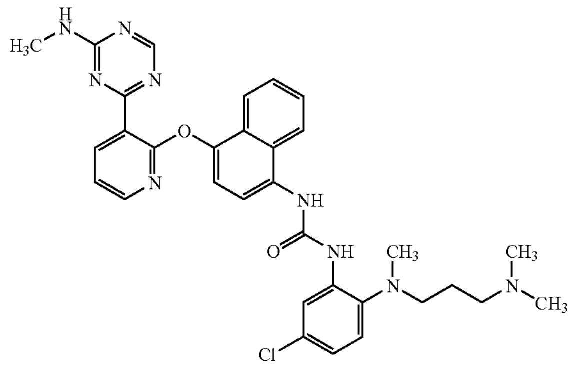 | 612.13 | 612 |
| 1118 | 3-formyl-N-(3-methyl-4-(3-(2-(methylamino)pyrimidin-4-yl)pyridin-2-yloxy)phenyl)benzamide | 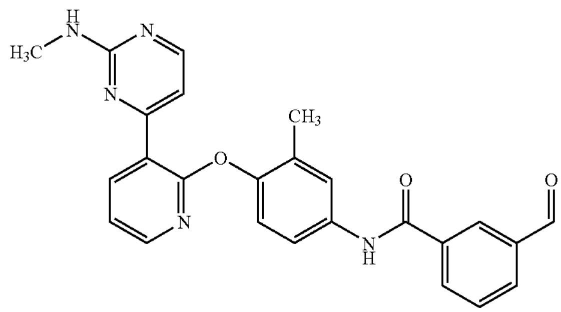 | 439.47 | 440 |
| 1119 | 1-(2-((2-(dimethylamino)ethyl)(methyl)amino)-5-(trifluoromethyl)phenyl)-3-(4-(3-(4-(methylamino)-1,3,5-triazin-2-yl)pyridin-2-yloxy)naphthalen-1-yl)urea | 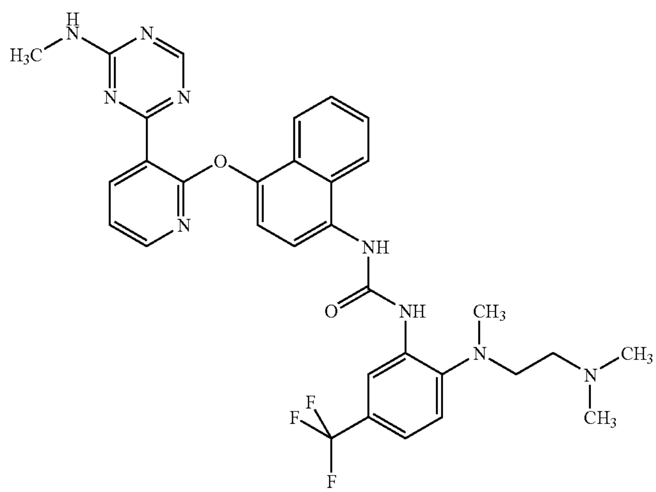 | 631.66 | 632 |
| 1120 | 1-(5-cyclopropyl-2-((3-(dimethylamino)propyl)(methyl)amino)phenyl)-3-(4-(3-(4-(methylamino)-1,3,5-triazin-2-yl)pyridin-2-yloxy)naphthalen-1-yl)urea | 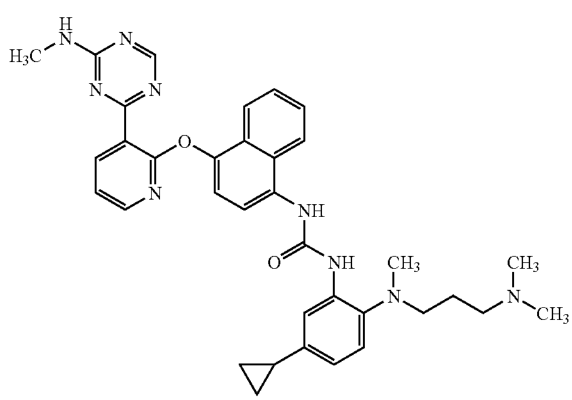 | 617.75 | 617 |

-continued

| Ex. No. | Structure Name | Structure | MW | MS Data |
|---|---|---|---|---|
| 1121 | N-(3-fluoro-4-methylphenyl)-N'-(4-((3-(4-quinolinyl)-2-pyridinyl)oxy)phenyl)urea | 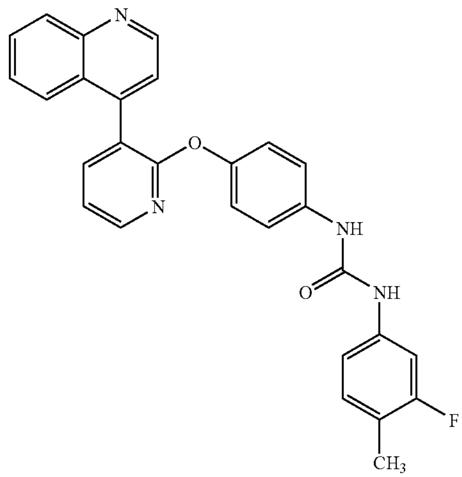 | 464.5 | 465 |
| 1122 | N-(4-chlorophenyl)-N'-(4-((3-(4-quinolinyl)-2-pyridinyl)oxy)phenyl)urea | 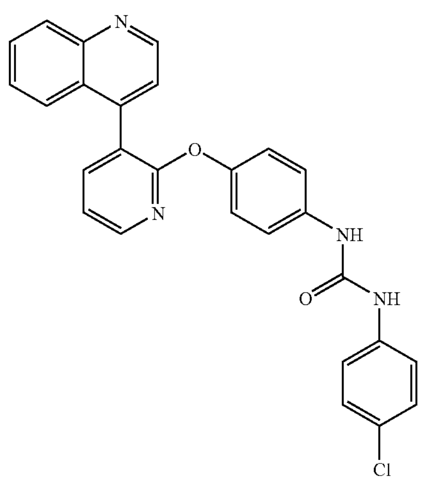 | 466.93 | 467 |
| 1123 | 1-(4-(3-(6,7-dimethoxyquinolin-4-yl)pyridin-2-yloxy)phenyl)-3-(3-fluoro-4-methylphenyl)urea | 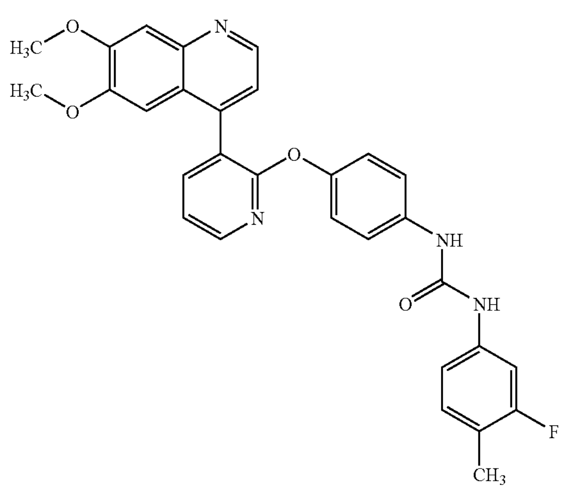 | 524.55 | 525 |

-continued

| Ex. No. | Structure Name | MW | MS Data |
|---|---|---|---|
| 1124 | 1-(4-chlorophenyl)-3-(4-(3-(6,7-dimethoxyquinolin-4-yl)pyridin-2-yloxy)phenyl)urea | 526.98 | 527 |
| 1125 | 1-(4-(3-(1H-pyrrolo[2,3-b]pyridin-4-yl)pyridin-2-yloxy)phenyl)-3-tert-butylurea | 401.47 | 402 |
| 1126 | 1-(4-(3-(1H-pyrrolo[2,3-b]pyridin-4-yl)pyridin-2-yloxy)phenyl)-3-(3-fluoro-2-methylphenyl)urea | 453.48 | 454 |
| 1127 | 1-(4-(3-(1H-pyrrolo[2,3-b]pyridin-4-yl)pyridin-2-yloxy)phenyl)-3-phenylurea | 421.46 | 422 |
| 1128 | 1-(4-(3-(1H-pyrrolo[2,3-b]pyridin-4-yl)pyridin-2-yloxy)phenyl)-3-(4-chlorophenyl)urea | 455.9 | 456 |

-continued

| Ex. No. | Structure Name | Structure | MW | MS Data |
|---|---|---|---|---|
| 1129 | N-(4-(3-(1H-pyrrolo[2,3-b]pyridin-4-yl)pyridin-2-yloxy)phenyl)benzamide | 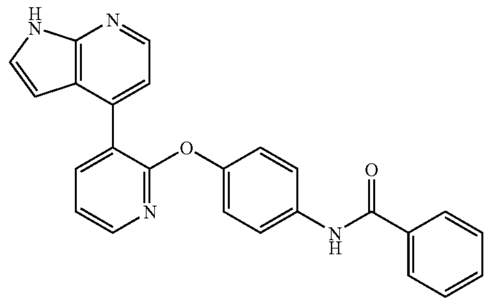 | 406.44 | 407 |
| 1130 | N-(4-(3-(1H-pyrrolo[2,3-b]pyridin-4-yl)pyridin-2-yloxy)phenyl)-3-(trifluoromethyl)benzamide | 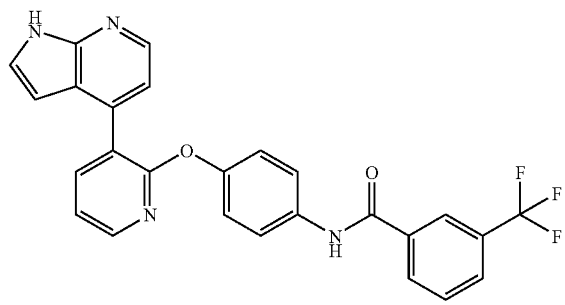 | 474.44 | 475 |
| 1131 | 1-(2-((S)-3-(dimethylamino)piperidin-1-yl)-5-(trifluoromethyl)phenyl)-3-(4-(3-(4-(methylamino)-1,3,5-triazin-2-yl)pyridin-2-yloxy)naphthalen-1-yl)urea | 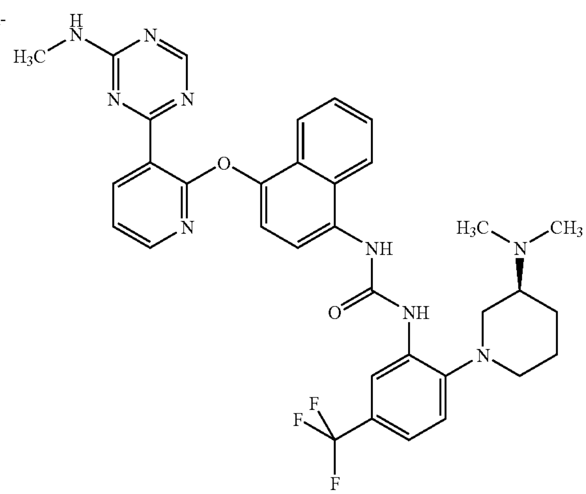 | 657.7 | 658 |
| 1132 | 1-(3-methyl-4-(3-(2-(4-(4-methylpiperazin-1-yl)phenylamino)pyrimidin-4-yl)pyridin-2-yloxy)phenyl)-3-(5-methylisoxazol-3-yl)urea | 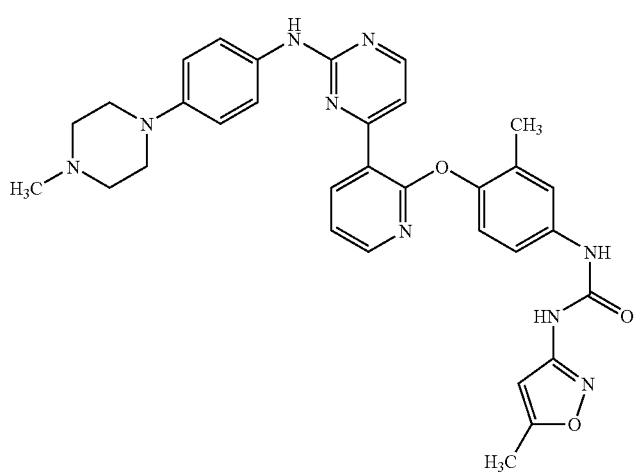 | 591.67 | 592 |

-continued

| Ex. No. | Structure Name | Structure | MW | MS Data |
|---|---|---|---|---|
| 1133 | 1-(3-methyl-4-(3-(2-(4-(4-methylpiperazin-1-yl)phenylamino)pyrimidin-4-yl)pyridin-2-yloxy)phenyl)-3-(thiazol-2-yl)urea | 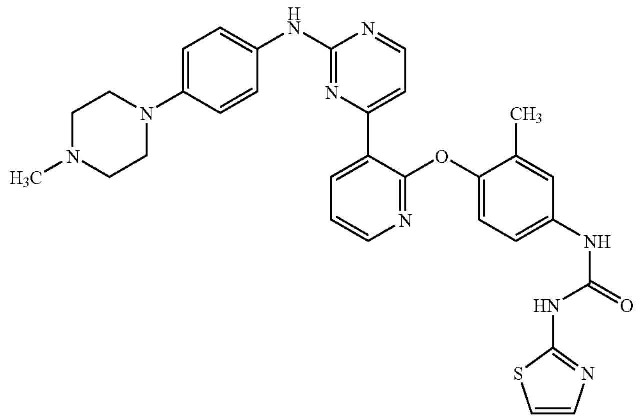 | 593.71 | 594 |
| 1134 | 1-ethyl-3-(3-methyl-4-(3-(2-(4-(4-methylpiperazin-1-yl)phenylamino)pyrimidin-4-yl)pyridin-2-yloxy)phenyl)urea | 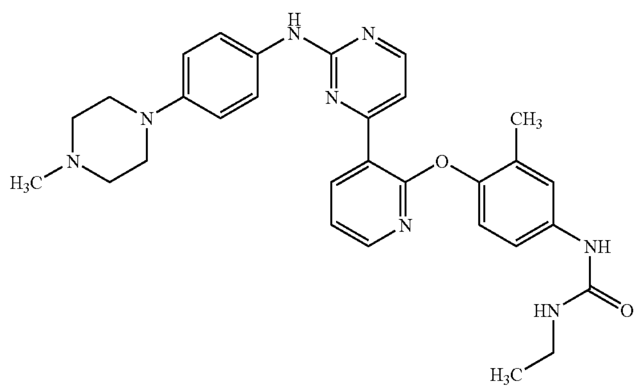 | 538.65 | 539 |
| 1135 | 1-(8-(3-(4-(methylamino)-1,3,5-triazin-2-yl)pyridin-2-yloxy)quinolin-5-yl)-3-(3-(trifluoromethyl)phenyl)urea | 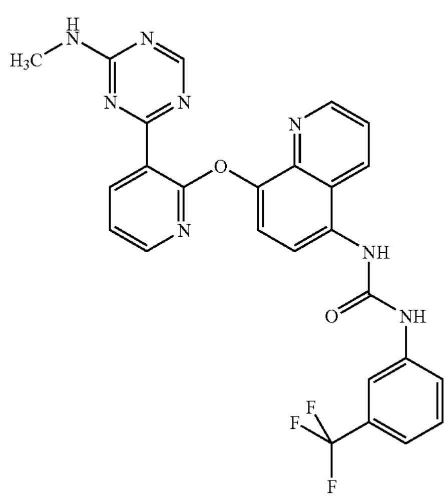 | 532.48 | 533 |

-continued
| Ex. No. | Structure Name | Structure | MW | MS Data |
|---|---|---|---|---|
| 1136 | 1-(5-chloro-2-methoxyphenyl)-3-(8-(3-(4-(methylamino)-1,3,5-triazin-2-yl)pyridin-2-yloxy)quinolin-5-yl)urea | 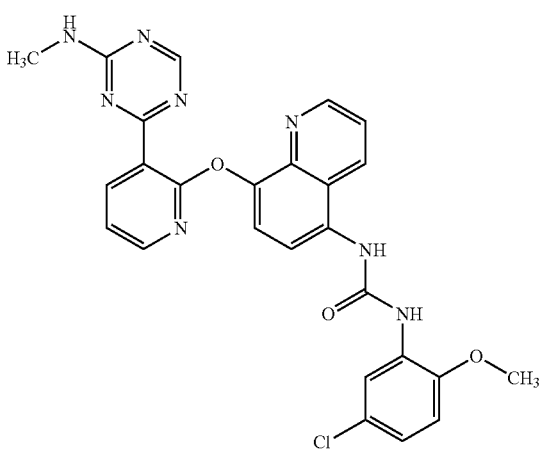 | 528.96 | 529 |
| 1137 | ethyl 4-(3-(2-(methylamino)pyrimidin-4-yl)pyridin-2-yloxy)phenylcarbamoyl-carbamate | 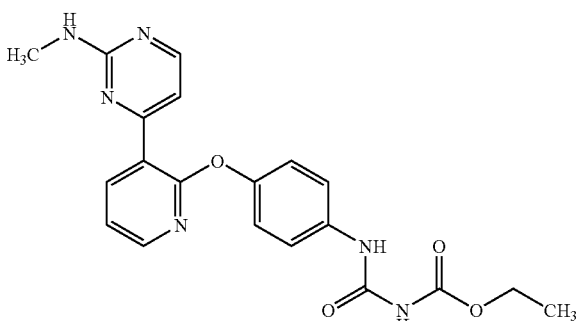 | 408.42 | 409 |
| 1138 | 1-(4-chlorophenyl)-3-(4-(3-(2-(4-(4-methylpiperazin-1-yl)benzamido)pyrimidin-4-yl)pyridin-2-yloxy)phenyl)urea | 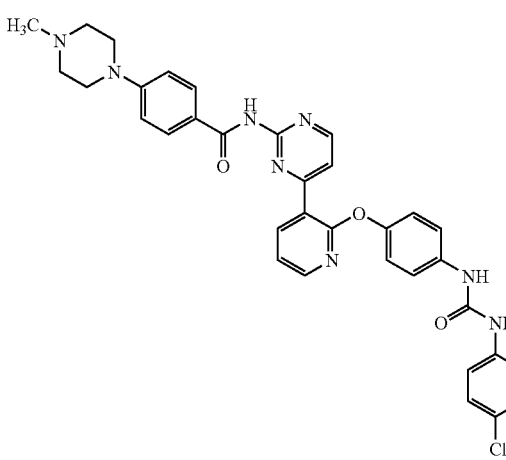 | 635.13 | 635 |

-continued

| Ex. No. | Structure Name | Structure | MW | MS Data |
|---|---|---|---|---|
| 1139 | 1-(4-methoxyphenyl)-N-(4-(3-(2-(methylamino)pyrimidin-4-yl)pyridin-2-yloxy)phenyl)-2-oxopyrrolidine-3-carboxamide | 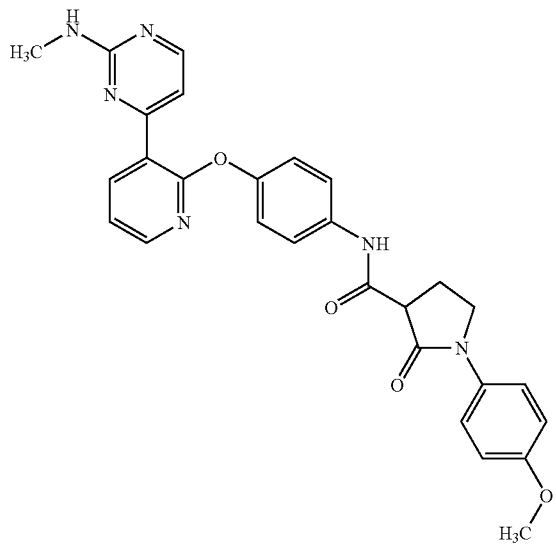 | 510.55 | 511 |
| 1140 | 1-(2-fluorophenyl)-N-(4-(3-(2-(methylamino)pyrimidin-4-yl)pyridin-2-yloxy)phenyl)-2-oxopyrrolidine-3-carboxamide | 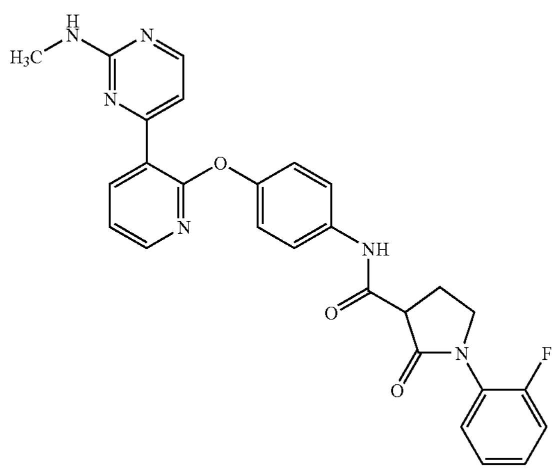 | 498.52 | 499 |
| 1141 | N-(4-(3-(2-(methylamino)pyrimidin-4-yl)pyridin-2-yloxy)phenyl)-2-(phenylamino)benzamide | 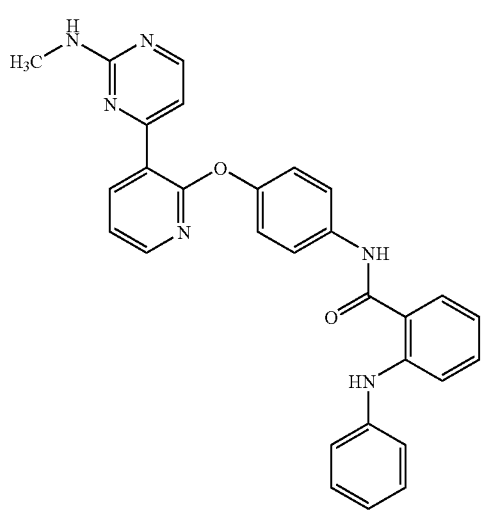 | 488.55 | 489 |

| Ex. No. | Structure Name | Structure | MW | MS Data |
|---|---|---|---|---|
| 1142 | 1-(4-chlorophenyl)-3-(3-fluoro-4-(3-(2-(methylamino)pyrimidin-4-yl)pyridin-2-yloxy)phenyl)urea | 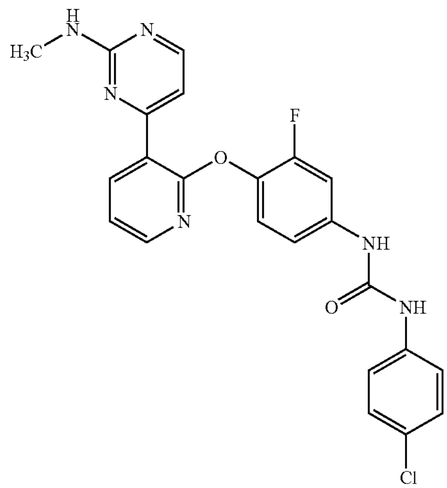 | 464.89 | 465 |
| 1143 | 1-(3-fluoro-4-(3-(2-(methylamino)pyrimidin-4-yl)pyridin-2-yloxy)phenyl)-phenylurea | 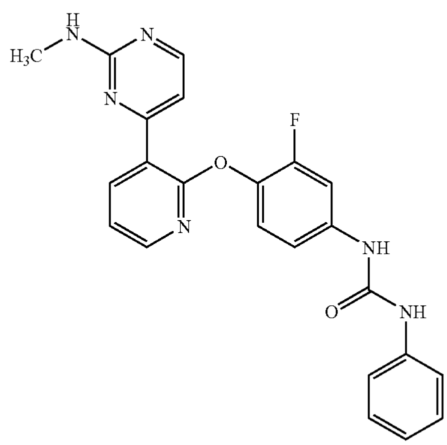 | 430.44 | 431 |
| 1144 | N-(3-fluoro-4-(3-(2-(methylamino)pyrimidin-4-yl)pyridin-2-yloxy)phenyl)-3-(trifluoromethyl)benzamide | 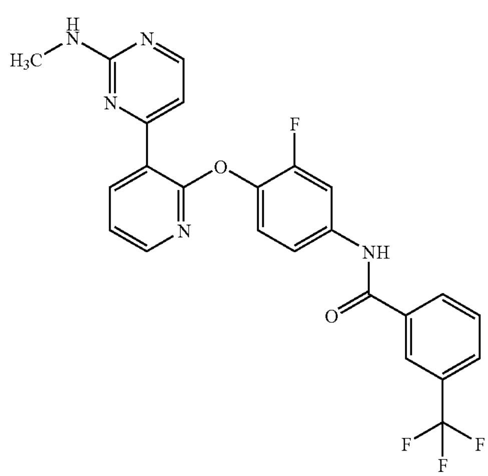 | 483.42 | 484 |

| Ex. No. | Structure Name | Structure | MW | MS Data |
|---|---|---|---|---|
| 1145 | 1-(3-methoxy-4-(3-(2-(methylamino)pyrimidin-4-yl)pyridin-2-yloxy)phenyl)-3-phenylurea | 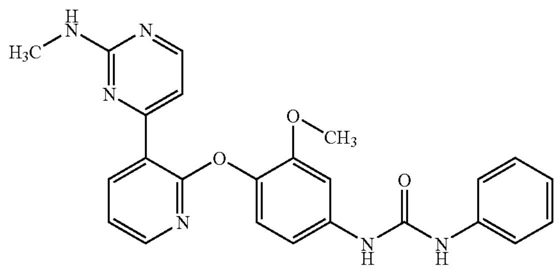 | 442.48 | 443 |
| 1146 | 1-(4-chlorophenyl)-3-(3-methoxy-4-(3-(2-(methylamino)pyrimidin-4-yl)pyridin-2-yloxy)phenyl)urea | 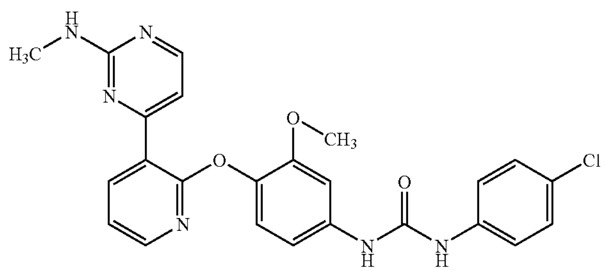 | 476.92 | 477 |
| 1147 | N-(4-(3-(2-(methylamino)pyrimidin-4-yl)pyridin-2-yloxy)phenyl)-5-phenylisoxazole-4-carboxamide | 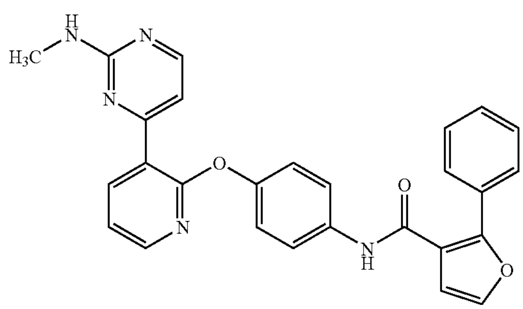 | 464.48 | 465 |
| 1148 | N-(3-methoxy-4-(3-(2-(methylamino)pyrimidin-4-yl)pyridin-2-yloxy)phenyl)-3-(trifluoromethyl)benzamide | 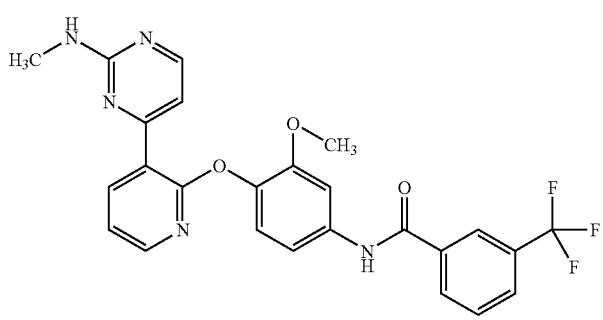 | 495.46 | 496 |
| 1149 | N-(4-(3-(2-(methylamino)pyrimidin-4-yl)pyridin-2-yloxy)phenyl)-2-(5-oxo-1-phenyl-2-thioxoimidazolidin-4-yl)acetamide | 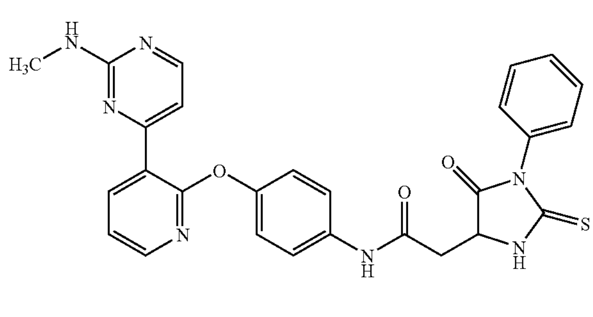 | 525.59 | 526 |

-continued

| Ex. No. | Structure Name | Structure | MW | MS Data |
|---|---|---|---|---|
| 1150 | 1-tert-butyl-3-(3-methoxy-4-(3-(2-(methylamino)pyrimidin-4-yl)pyridin-2-yloxy)phenyl)urea | 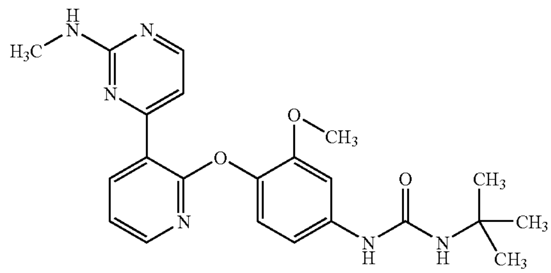 | 422.49 | 423 |
| 1151 | 1-benzoyl-3-(4-(3-(2-(methylamino)pyrimidin-4-yl)pyridin-2-yloxy)phenyl)thiourea | 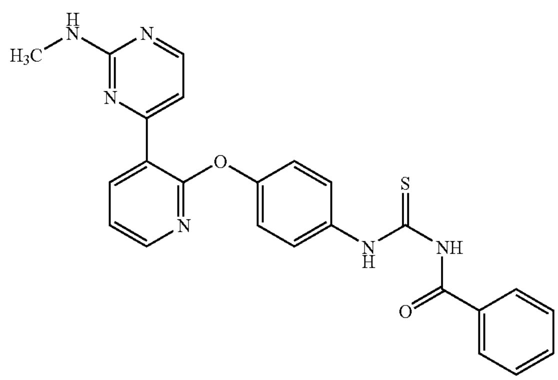 | 456.53 | 457 |

Method K

EXAMPLE 1152

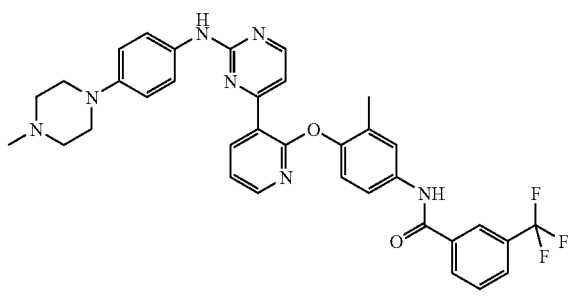

Synthesis of N-(3-methyl-4-((3-(2-((4-(4-methyl-1-piperazinyl)phenyl)amino)-4-pyrimidinyl)-2-pyridinyl)oxy)phenyl)-3-(trifluoromethyl)benzamide To 4-(2-chloropyridin-3-yl)-N-(4-(4-methylpiperazin-1-yl)phenyl)pyrimidin-2-amine (35 mg, 0.092 mmol), N-(4-hydroxy-3-methylphenyl)-3-(trifluoromethyl)benzamide (27 mg, 0.092 mmol) and $Cs_2CO_3$ (60 mg, 0.18 mmol) was added DMSO (0.6 mL). The mixture was heated overnight at 130° C. The crude material was purified by reverse-phase HPLC (Gilson, acidic mobile phase) to yield the title compound as a light yellow solid after aqueous workup. MS m/z=640 [M+1]$^+$Calc'd for $C_{35}H_{32}F_3N_7O_2$: 639.69.

| Ex. No. | Structure Name | Structure | MW | MS Data |
|---|---|---|---|---|
| 1153 | N-(3-methyl-4-((3-(4-pyrimidinyl)-2-pyridinyl)oxy)phenyl)-3-(trifluoromethyl)benzamide | 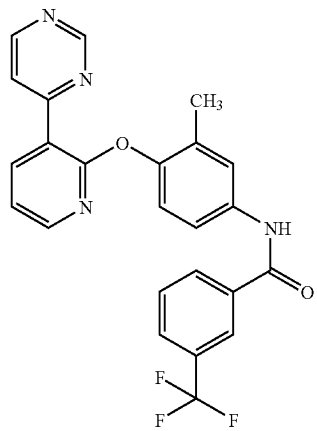 | 450.42 | 451 |
| 1154 | N-(3-methyl-4-((3-(4-pyrimidinyl)-2-pyridinyl)oxy)phenyl) benzamide | 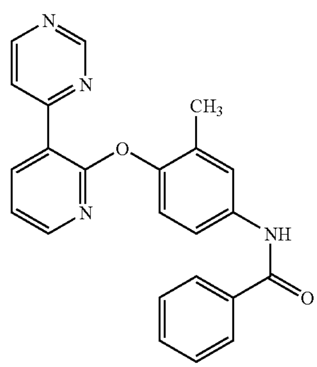 | 382.42 | 383 |
| 1155 | N-(3-methyl-4-((3-(4-pyrimidinyl)-2-pyridinyl)oxy)phenyl)-N'-(3-(trifluoromethyl)phenyl)urea | 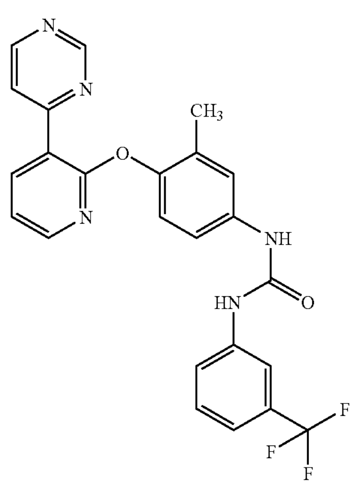 | 465.43 | 466 |

| Ex. No. | Structure Name | Structure | MW | MS Data |
|---|---|---|---|---|
| 1156 | N-(3-methyl-4-((3-(4-pyrimidinyl)-2-pyridinyl)oxy)phenyl)-N'-phenylurea | 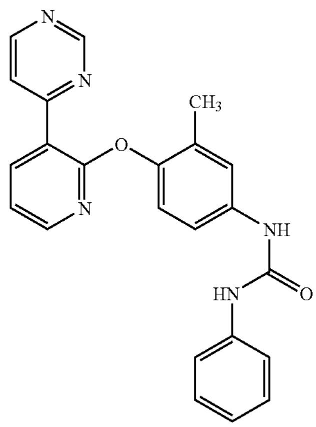 | 397.44 | 398 |
| 1157 | N-(4-((3-(2-((2-(diethylamino)ethyl)amino)-4-pyrimidinyl)-2-pyridinyl)oxy)-3-methylphenyl)-3-(trifluoromethyl)benzamide | 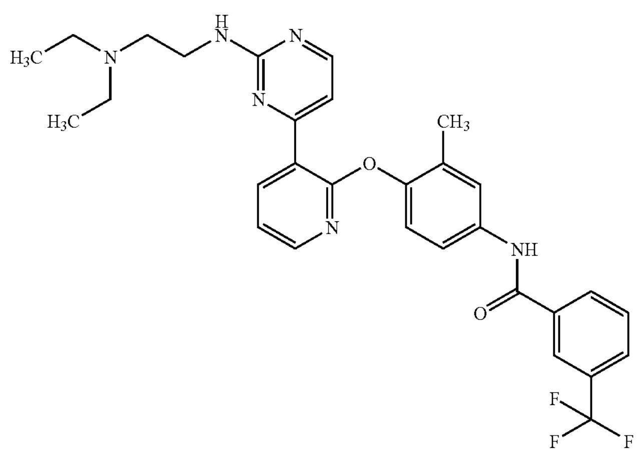 | 564.61 | 565 |
| 1158 | N-(4-((5-chloro-3-(2-(methylamino)-4-pyrimidinyl)-2-pyridinyl)oxy)-3-methylphenyl)-3-(trifluoromethyl)benzamide | 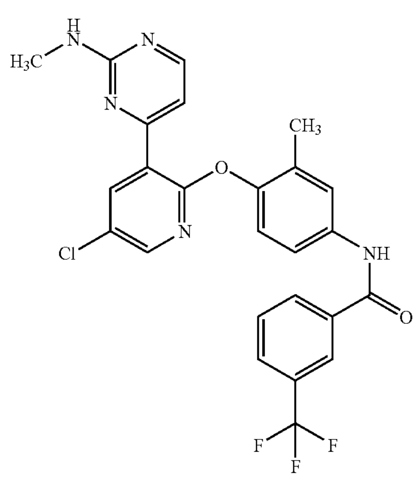 | 513.9 | 514 |

-continued

| Ex. No. | Structure Name | Structure | MW | MS Data |
|---|---|---|---|---|
| 1159 | N-(3-methyl-4-((3-(2-((1-methyl-4-piperidinyl)amino)-4-pyrimidinyl)-2-pyridinyl)oxy)phenyl)-3-(trifluoromethyl)benzamide | 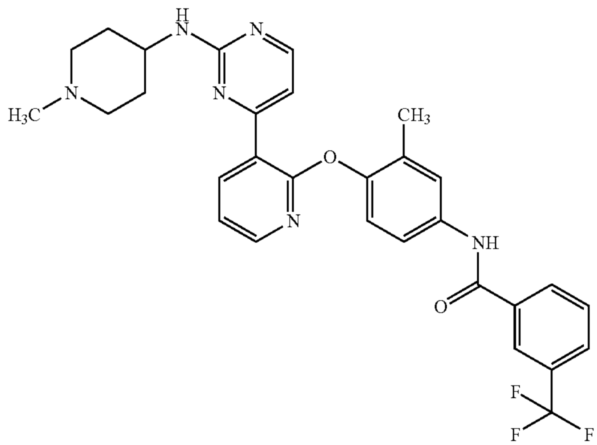 | 562.59 | 563 |
| 1160 | N-(3-methyl-4-((3-(2-(((3-(4-morpholinyl)propyl)amino)-4-pyrimidinyl)-2-pyridinyl)oxy)phenyl)-3-(trifluoromethyl)benzamide | 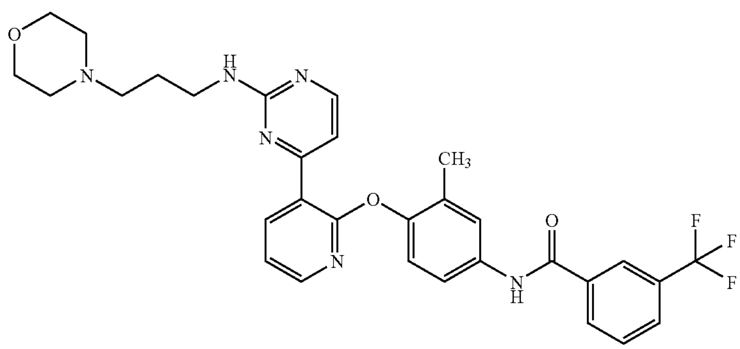 | 592.62 | 593 |
| 1161 | N-(3-methyl-4-((3-(2-(phenylamino)-4-pyrimidinyl)-2-pyridinyl)oxy)phenyl)-3-(trifluoromethyl)benzamide | 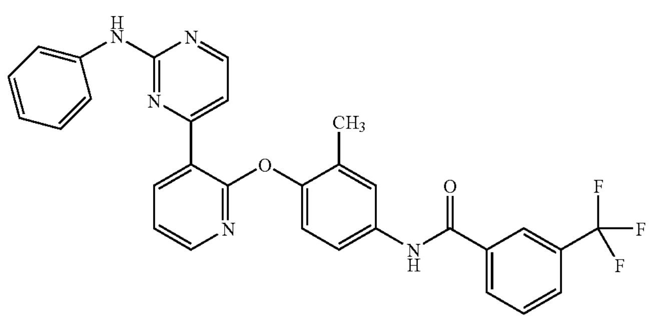 | 541.53 | 542 |
| 1162 | N-(3-methyl-4-((3-(2-((3-(4-methyl-1-piperazinyl)propyl)amino)-4-pyrimidinyl)-2-pyridinyl)oxy)phenyl)-3-(trifluoromethyl)benzamide | 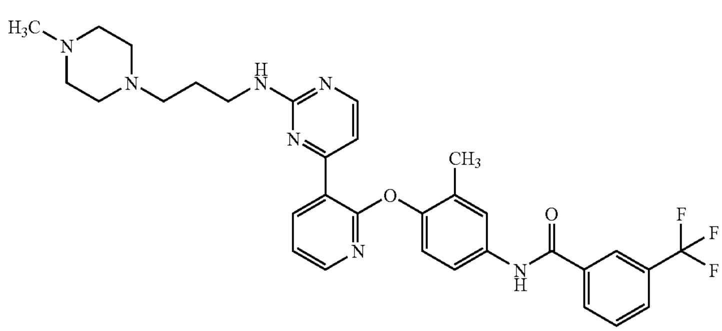 | 605.66 | 606 |

-continued

| Ex. No. | Structure Name | Structure | MW | MS Data |
|---|---|---|---|---|
| 1163 | N-(4-((3-(2-((2-(dimethylamino)ethyl)amino)-4-pyrimidinyl)-2-pyridinyl)oxy)-3-methylphenyl)-3-(trifluoromethyl)benzamide | 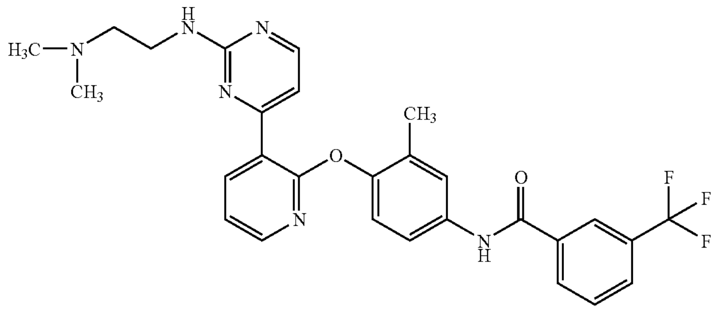 | 536.55 | 537 |
| 1164 | N-(4-((3-(2-((4-(dimethylamino)butyl)amino)-4-pyrimidinyl)-2-pyridinyl)oxy)-3-methylphenyl)-3-(trifluoromethyl)benzamide | 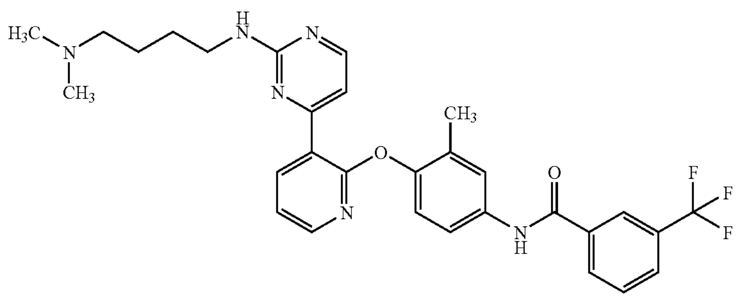 | 564.61 | 565 |
| 1165 | N-(4-((3-(2-((3-(dimethylamino)propyl)amino)-4-pyrimidinyl)-2-pyridinyl)oxy)-3-methylphenyl)-3-(trifluoromethyl)benzamide | 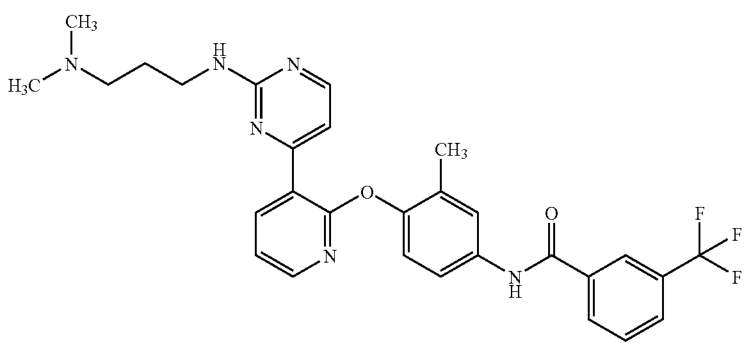 | 550.58 | 551 |
| 1166 | N-(4-(3-(1H-pyrrolo[2,3-b]pyridin-4-yl)pyridin-2-yloxy)-3-methylphenyl)-3-(trifluoromethyl)benzamide | 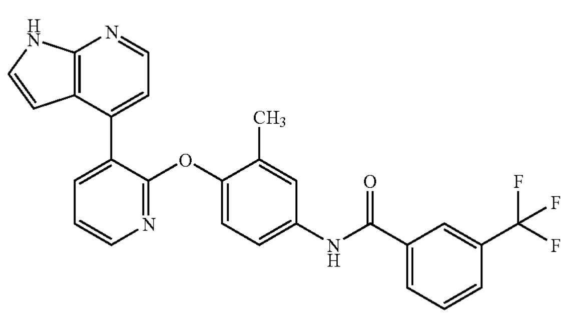 | 488.47 | 489 |

-continued

| Ex. No. | Structure Name | Structure | MW | MS Data |
|---|---|---|---|---|
| 1167 | N-(3-methyl-4-(3-(2-(3-(pyrrolidin-1-yl)propylamino)pyrimidin-4-yl)pyridin-2-yloxy)phenyl)-3-(trifluoromethyl)benzamide | 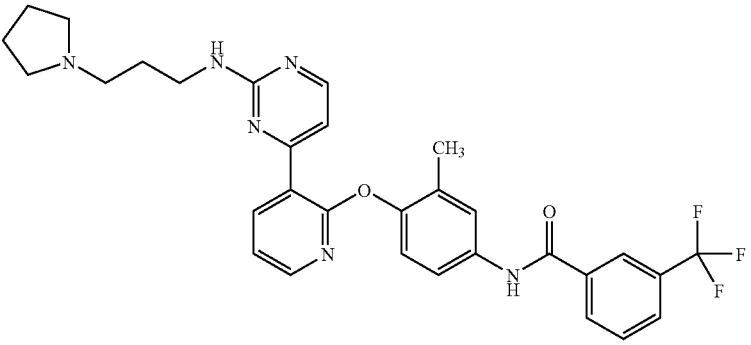 | 576.62 | 577 |
| 1168 | N-(3-methyl-4-(3-(2-(3-(piperidin-1-yl)propylamino)pyrimidin-4-yl)pyridin-2-yloxy)phenyl)-3-(trifluoromethyl)benzamide | 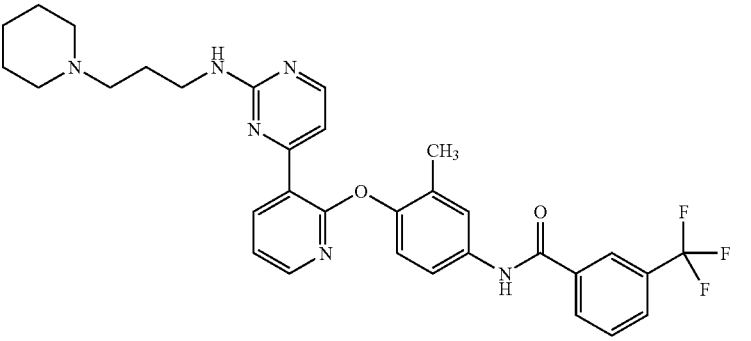 | 590.65 | 591 |
| 1169 | 4-(3-(2-(4-(4-methylpiperazin-1-yl)phenylamino)pyrimidin-4-yl)pyridin-2-yloxy)-N-(3-(trifluoromethyl)phenyl)benzamide | 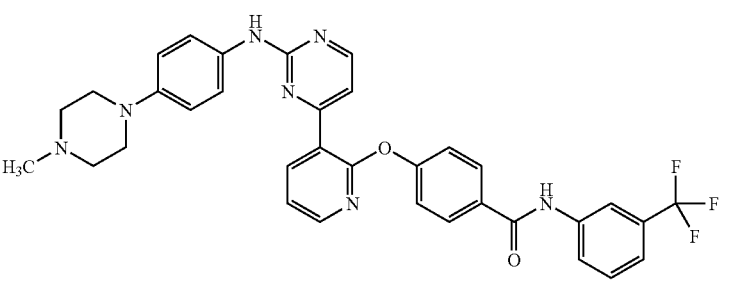 | 625.65 | 626 |
| 1170 | 3-methyl-4-(3-(2-(4-(4-methylpiperazin-1-yl)phenylamino)pyrimidin-4-yl)pyridin-2-yloxy)-N-(3-(trifluoromethyl)phenyl)benzamide | 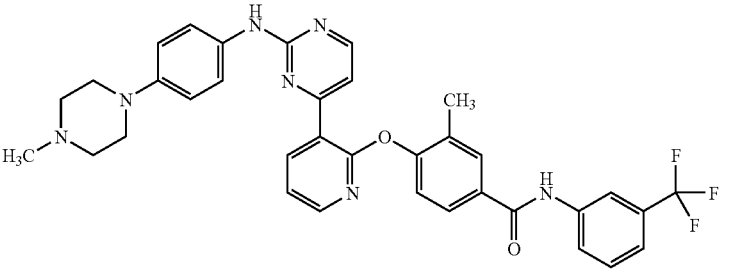 | 639.68 | 640 |

Method L

EXAMPLE 1171

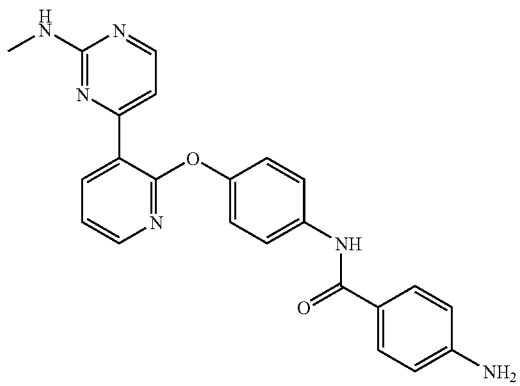

Synthesis of 4-amino-N-(4-((3-(2-(methylamino)-4-pyrimidinyl)-2-pyridinyl)oxy)phenyl)benzamide In a manner analogous to that described in Klappars, A.; Antilla, J. C.; Huang, X.; Buchwald, S. L. *J. Am. Chem. Soc.* 2001, 123, 7727, 4-(2-(4-iodophenoxy)pyridin-3-yl)-N-methylpyrimidin-2-amine (202 mg, 0.500 mmol), 4-aminobenzamide (102 mg, 0.750 mmol), finely ground CuI (4.8 mg, 0.0250 mmol, 5 mol %), and anhydrous potassium phosphate (212 mg, 1 mmol) were added into a screw cap test tube. The tube was purged with argon for 5 minutes. Then trans-1,2-diaminocyclohexane (15.0 mL, 0.100 mmol, 10 mol %) and dioxane were added into the reaction mixture via syringe. The tube was sealed and placed in a preheated oil bath at 110° C. After a day, the reaction was cooled to room temperature. The reaction mixture was passed through a pad of celite with the aid of ethyl acetate. The filtrate was concentrated under reduced pressure. The product was purified by column chromatography using 10:90 Hex:EtOAc. 4-Amino-N-(4-(3-(2-(methylamino)pyrimidin-4-yl)pyridin-2-yloxy)phenyl)benzamide was obtained as an off-white solid.

| Ex. No. | Structure Name | Structure | MW | MS Data |
|---|---|---|---|---|
| 1172 | 3-amino-N-(4-((3-(2-(methylamino)-4-pyrimidinyl)-2-pyridinyl)oxy)phenyl) benzamide | 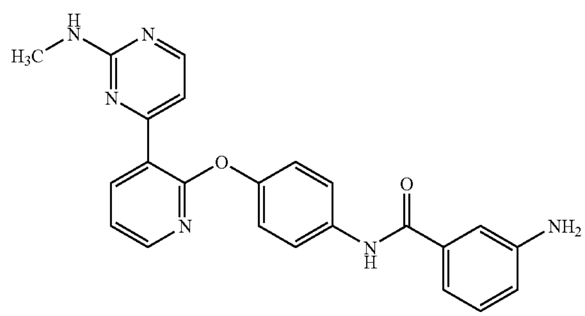 | 412.45 | 413 |
| 1173 | 2-amino-N-(4-((3-(2-(methylamino)-4-pyrimidinyl)-2-pyridinyl)oxy)phenyl) benzamide | 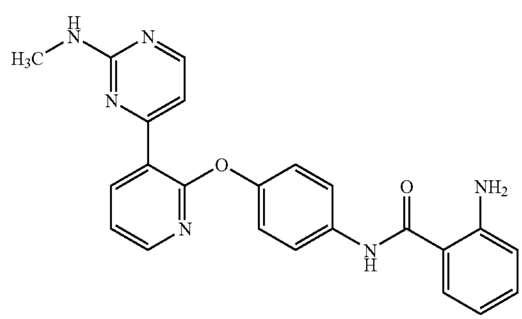 | 412.45 | 413 |
| 1174 | N-(4-(3-(2-(methylamino)pyrimidin-4-yl)pyridin-2-yloxy) phenyl)piperidine-4-carboxamide | 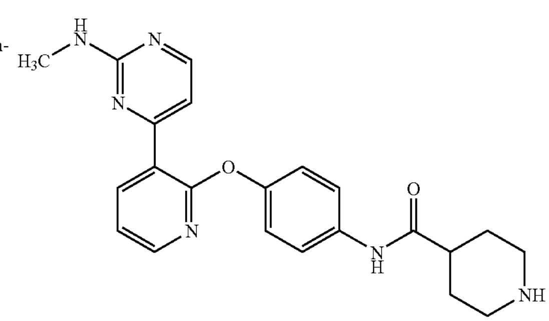 | 404.47 | 405 |

793
Method M

EXAMPLE 1175

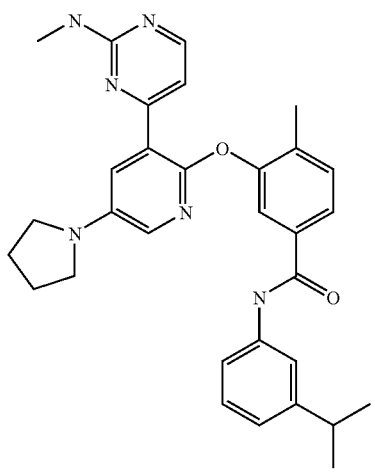

794
Synthesis of N-(3-Isopropyl-phenyl)-4-methyl-3-[3-(2-methylamino-pyrimidin-4-yl)-5-pyrrolidin-1-yl-pyridin-2-yloxy]-benzamide The title compound was prepared using the procedure of Harris et. al. [*Organic Letters* 2002, 4 (17), 2885-2888.]: In a $N_2$-flushed sealing tube, 3-[5-Chloro-3-(2-methylamino-pyrimidin-4-yl)-pyridin-2-yloxy]-N-(3-isopropyl-phenyl)-4-methyl-benzamide (100 mg, 0.21 mmol), pyrrolidine (0.022 mL, 0.26 mmol), $Pd_2(dba)_3$ (5.1 mg, 0.0055 mmol), and 2-dicyclohexylphosphino-2'-(N,N-dimethylamino)biphenyl (5.2 mg, 0.13 mmol) were combined. The tube was flushed with argon, and 1 M $Li(TMS)_2$ in THF (Aldrich, 0.67 ml) was added. The sealed tube was heated at 70° C. for 20 h. 1 N HCl was added, the mixture was stirred 5 minutes, then saturated aqueous $NaHCO_3$ was added. After extraction, the organic layer was dried over $Na_2SO_4$. After concentration, the residue was purifed by HPLC (Gilson, acidic mobile phase), desalted by aqueous $NaHCO_3$/EtOAc extraction, and purified by flash chromatography (2:1 to 1:1 hexanes/EtOAc. The resulting solid was triturated with a small amount of t-BuOMe to provide the product. MS m/z=523 $[M+H]^+$. Calc'd for $C_{31}H_{34}N_6O_2$: 522.65.

| Ex. No. | Structure Name | Structure | MW | MS Data |
|---|---|---|---|---|
| 1176 | 4-methyl-3-((3-(2-(methylamino)-4-pyrimidinyl)-5-(4-morpholinyl)-2-pyridinyl)oxy)-N-(3-(1-methylethyl)phenyl)benzamide | 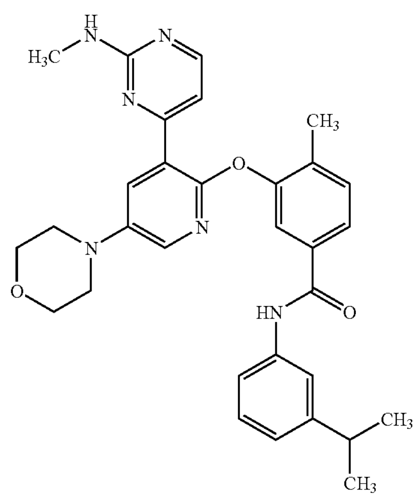 | 538.65 | 539 |

-continued

| Ex. No. | Structure Name | Structure | MW | MS Data |
|---|---|---|---|---|
| 1177 | 4-methyl-3-((3-(2-(methylamino)-4-pyrimidinyl)-5-(4-methyl-1-piperazinyl)-2-pyridinyl)oxy)-N-(3-(1-methylethyl)phenyl)benzamide | 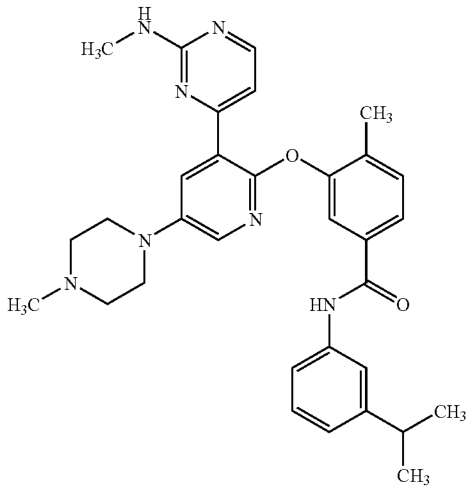 | 551.69 | 552 |
| 1178 | 3-((5-((3-(dimethylamino)propyl)(methyl)amino)-3-(2-(methylamino)-4-pyrimidinyl)-2-pyridinyl)oxy)-4-methyl-N-(3-(1-methylethyl)phenyl)benzamide | 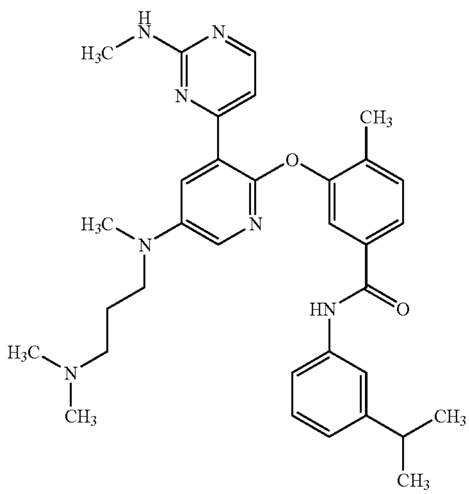 | 567.73 | 568 |
| 1179 | N-(3-methyl-4-((3-(2-(methylamino)-4-pyrimidinyl)-5-(4-methyl-1-piperazinyl)-2-pyridinyl)oxy)phenyl)-3-(trifluoromethyl)benzamide | 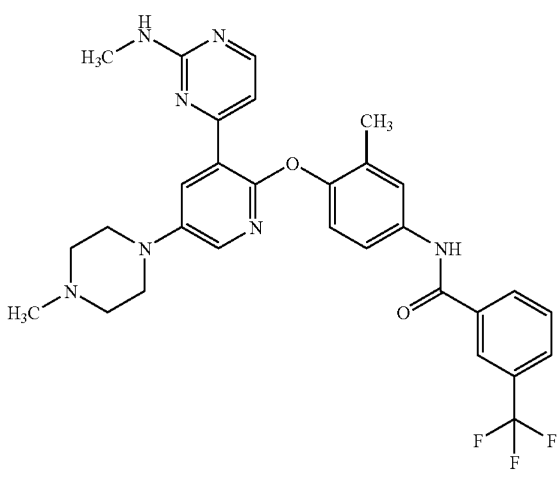 | 577.61 | 578 |

Method N

EXAMPLE 1180

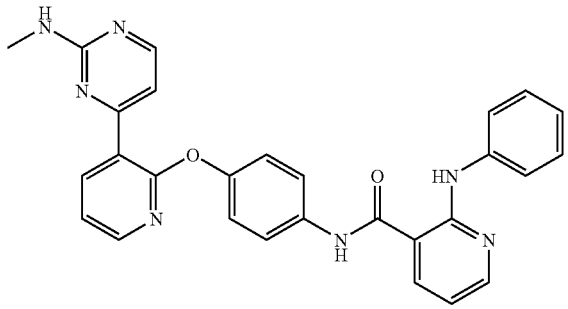

Synthesis of N-(4-(3-(2-(methylamino)pyrimidin-4-yl)pyridin-2-yloxy)phenyl)-2-(phenylamino)nicotinamide Step 1. Preparation of 2-fluoro-N-(4-(3-(2-(methylamino)pyrimidin-4-yl)pyridin-2-yloxy)phenyl)nicotinamide To a mixture of 2-fluoro-3-pyridinecarboxylic acid (1.06 g, 7.50 mmol) and HATU (3.11 g, 8.18 mmol) in CHCl$_3$ at ambient temperature under nitrogen was added n,n-diisopropylethylamine (2.38 ml, 13.6 mmol) via syringe. The mixture was allowed to stir for 5 min. at which point 4-(2-(4-aminophenoxy)pyridin-3-yl)-N-methylpyrimidin-2-amine (2.00 g, 6.82 mmol) was added. The reaction was allowed to stir 16 h, resulting in the formation of a fine precipitate. The reaction was filtered, rinsing with 2×dichloromethane and the solid dried in vacuo to give 2-fluoro-N-(4-(3-(2-(methylamino)pyrimidin-4-yl)pyridin-2-yloxy)phenyl)nicotinamide as a tan solid. MS m/z=417 [M+1]$^+$. Calc'd for C$_{22}$H$_{17}$FN$_6$O$_2$: 416.41.

Step 2. Preparation of N-(4-(3-(2-(methylamino)pyrimidin-4-yl)pyridin-2-yloxy)phenyl)-2-(phenylamino)nicotinamide To a brown solution of aniline (0.18 ml, 1.9 mmol) in lithium bis(trimethylsilyl)amide, 11.0m solution in tetrahydrofuran (1.9 ml, 1.9 mmol) was added 2-fluoro-N-(4-(3-(2-(methylamino)pyrimidin-4-yl)pyridin-2-yloxy)phenyl)nicotinamide (0.200 g, 0.48 mmol). The mixture was sealed and heated to 70° C. After 2 h, the reaction was cooled to ambient temperature. Water was added, and the pH was adjusted with 6N HCl until slightly acidic. Add to EtOAc/water. Wash the mixture 1× with brine. The organic layer was dried over anhyd. sodium sulfate, filtered, and concentrated to give a brown solid. This material was purified by silica gel chromatography using 90/10 dichloromethane/methanol as eluent to give a yellow solid. Further purification was performed by trituration with dichloromethane and methanol to give N-(4-(3-(2-(methylamino)pyrimidin-4-yl)pyridin-2-yloxy)phenyl)-2-(phenylamino)nicotinamide as a yellow solid. MS m/z=490 [M+1]$^+$. Calc'd for C$_{28}$H$_{23}$N$_7$O$_2$: 489.53.

| Ex. No. | Structure Name | Structure | MW | MS Data |
|---|---|---|---|---|
| 1181 | 2-(benzylamino)-N-(4-(3-(2-(methylamino)pyrimidin-4-yl)pyridin-2-yloxy)phenyl)nicotinamide | 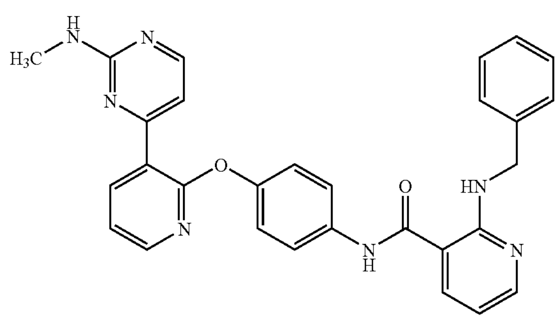 | 503.56 | 504 |
| 1182 | 2-(cyclopropylamino)-N-(4-(3-(2-(methylamino)pyrimidin-4-yl)pyridin-2-yloxy)phenyl)nicotinamide | 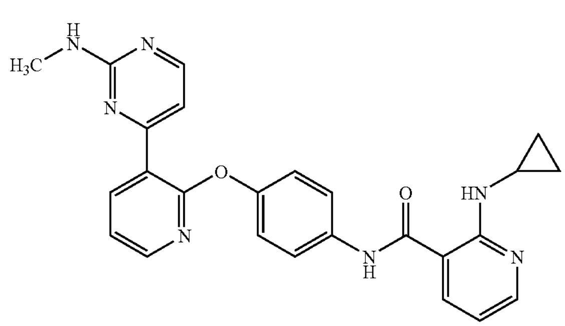 | 453.5 | 454 |

-continued

| Ex. No. | Structure Name | Structure | MW | MS Data |
|---|---|---|---|---|
| 1183 | 2-(cyclopropylmethylamino)-N-(4-(3-(2-(methylamino)pyrimidin-4-yl)pyridin-2-yloxy)phenyl)nicotinamide | 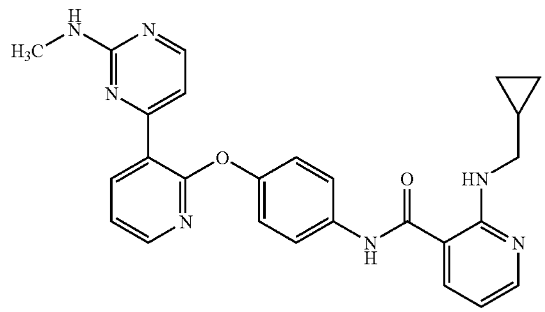 | 467.53 | 468 |
| 1184 | 2-(2-fluorophenylamino)-N-(4-(3-(2-(methylamino)pyrimidin-4-yl)pyridin-2-yloxy)phenyl)nicotinamide | 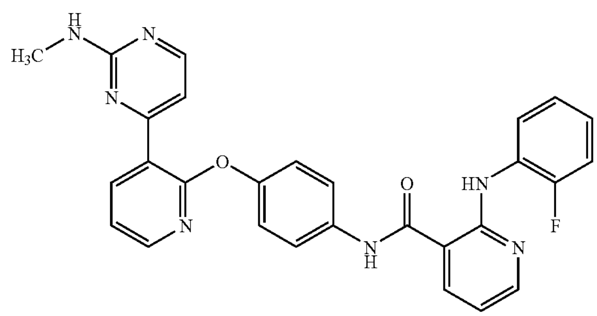 | 507.53 | 508 |
| 1185 | 2-(3-fluorophenylamino)-N-(4-(3-(2-(methylamino)pyrimidin-4-yl)pyridin-2-yloxy)phenyl)nicotinamide | 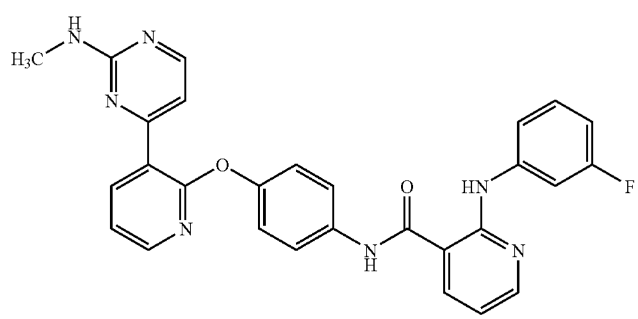 | 507.53 | 508 |
| 1186 | 2-(4-fluorophenylamino)-N-(4-(3-(2-(methylamino)pyrimidin-4-yl)pyridin-2-yloxy)phenyl)nicotinamide | 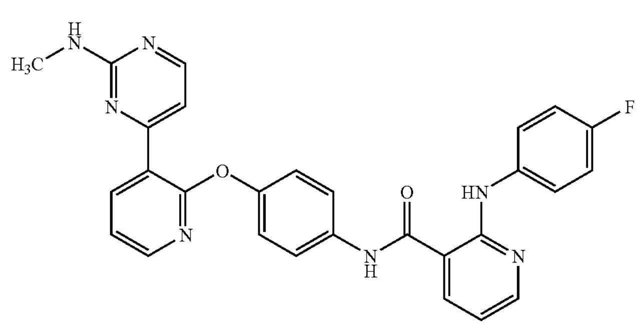 | 507.53 | 508 |

Method O

EXAMPLE 1187

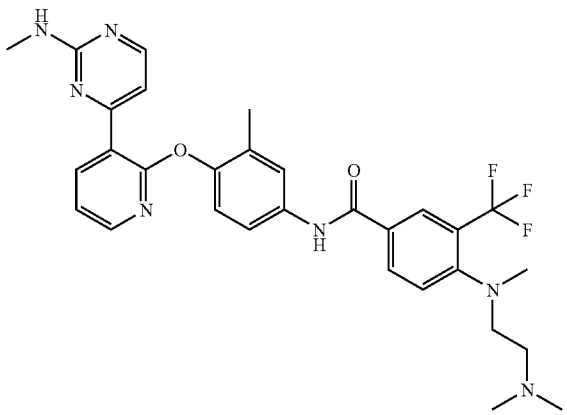

Synthesis of 4-((2-(dimethylamino)ethyl)(methyl)amino)-N-(3-methyl-4-(3-(2-(methylamino)pyrimidin-4-yl)pyridin-2-yloxy)phenyl)-3-(trifluoromethyl)benzamide A solution of 4-fluoro-N-(3-methyl-4-(3-(2-(methylamino)pyrimidin-4-yl)pyridin-2-yloxy)phenyl)-3-(trifluoromethyl)benzamide (0.10 g, 0.22 mmol) and N1,N1,N2-trimethylethane-1,2-diamine (0.045 g, 0.44 mmol) in DMF (2 mL) was heated to 100 deg. C. for 48 h. Additional N1,N1,N2-trimethylethane-1,2-diamine (0.045 g, 0.44 mmol) was added, and the reaction heated for 6 h. Additional N1,N1,N2-trimethylethane-1,2-diamine (0.045 g, 0.44 mmol) was added, and the reaction heated for 48 h. The reaction was cooled to ambient temperature, was diluted with ethyl acetate, and washed with saturated aqueous sodium bicarbonate. The organic layer was dried over anhydrous sodium sulfate, filtered, and concentrated in vacuo to give a solid. Purification by reverse-phase HPLC using acetonitrile/water/TFA as eluent gave 4-((2-(dimethylamino)ethyl)(methyl)amino)-N-(3-methyl-4-(3-(2-(methylamino)pyrimidin-4-yl)pyridin-2-yloxy)phenyl)-3-(trifluoromethyl)benzamide as a white solid. MS m/z=580 [M+1]$^+$. Calc'd for $C_{30}H_{32}F_3N_7O_2$: 579.62.

| Ex. No. | Structure Name | Structure | MW | MS Data |
|---|---|---|---|---|
| 1188 | N-(3-methyl-4-((3-(2-(methylamino)-4-pyrimidinyl)-2-pyridinyl)oxy)phenyl)-4-(4-methyl-1-piperazinyl)-3-(trifluoromethyl)benzamide | 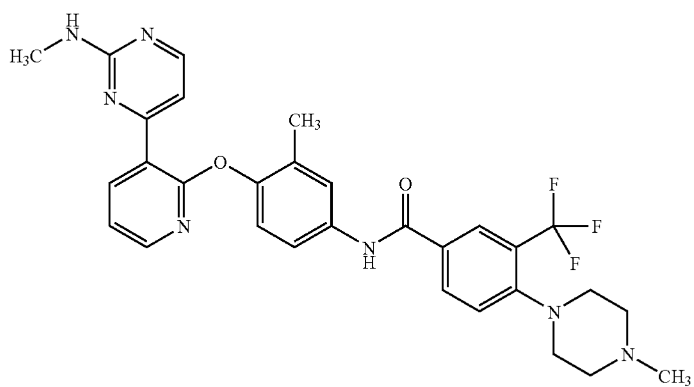 | 577.61 | |
| 1189 | N-(3-methyl-4-((3-(2-(methylamino)-4-pyrimidinyl)-2-pyridinyl)oxy)phenyl)-4-((2-(4-morpholinyl)ethyl)amino)-3-(trifluoromethyl)benzamide | 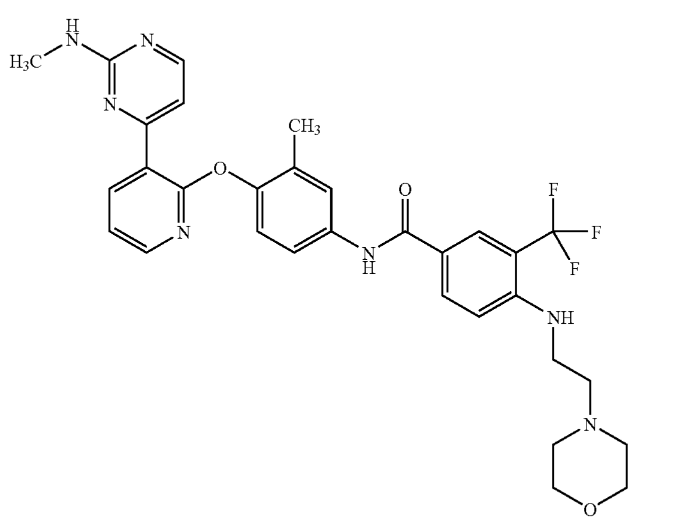 | 607.63 | |

-continued

| Ex. No. | Structure Name | Structure | MW | MS Data |
|---|---|---|---|---|
| 1190 | 4-((3-(dimethylamino)propyl)(methyl)amino)-N-(3-methyl-4-((3-(2-(methylamino)-4-pyrimidinyl)-2-pyridinyl)oxy)phenyl)-3-(trifluoromethyl)benzamide | 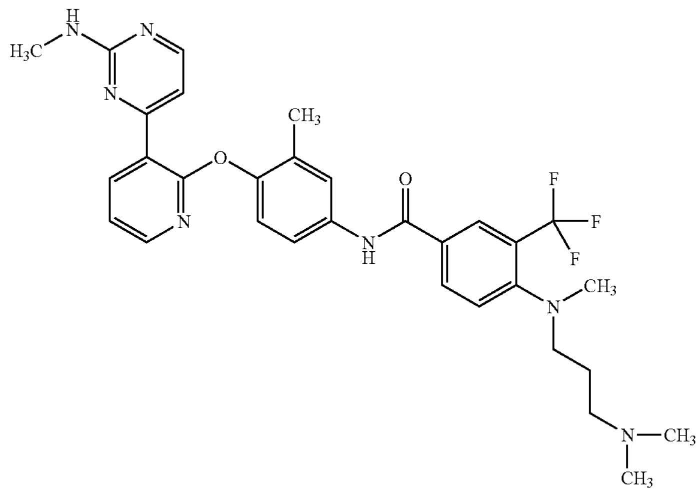 | 593.65 | 594 |
| 1191 | N-(3-methyl-4-((3-(2-(methylamino)-4-pyrimidinyl)-2-pyridinyl)oxy)phenyl)-4-((1-methyl-4-piperidinyl)amino)-3-(trifluoromethyl)benzamide | 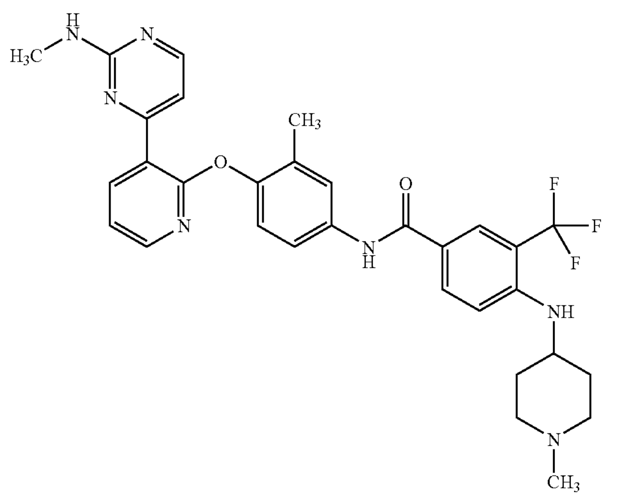 | 591.63 | 592 |
| 1192 | N-(3-methyl-4-((3-(2-(methylamino)-4-pyrimidinyl)-2-pyridinyl)oxy)phenyl)-4-((3-(1-pyrrolidinyl)propyl)amino)-3-(trifluoromethyl)benzamide | 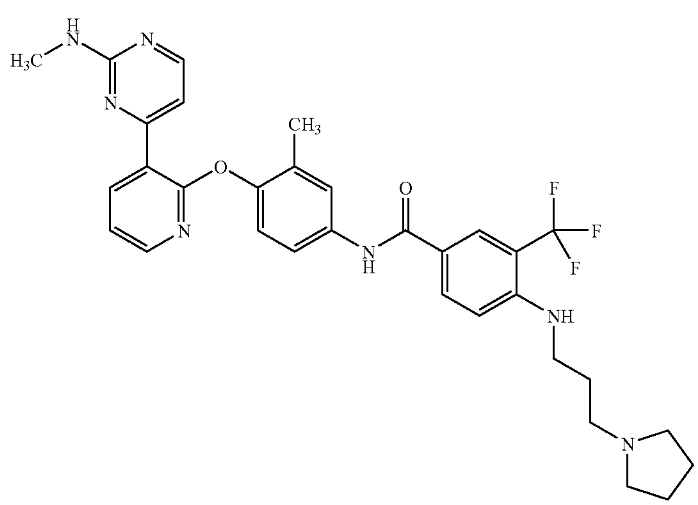 | 605.66 | |

-continued

| Ex. No. | Structure Name | Structure | MW | MS Data |
|---|---|---|---|---|
| 1193 | 4-(dimethylamino)-N-(3-methyl-4-((3-(2-(methylamino)-4-pyrimidinyl)-2-pyridinyl)oxy)phenyl)-3-(trifluoromethyl)benzamide | 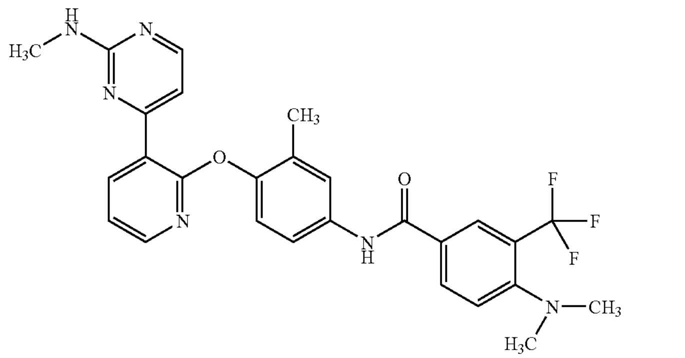 | 522.53 | |
| 1194 | N-(3-methyl-4-((3-(2-(methylamino)-4-pyrimidinyl)-2-pyridinyl)oxy)phenyl)-4-(4-methyl-1-piperazinyl)-3-(trifluoromethyl)benzamide | 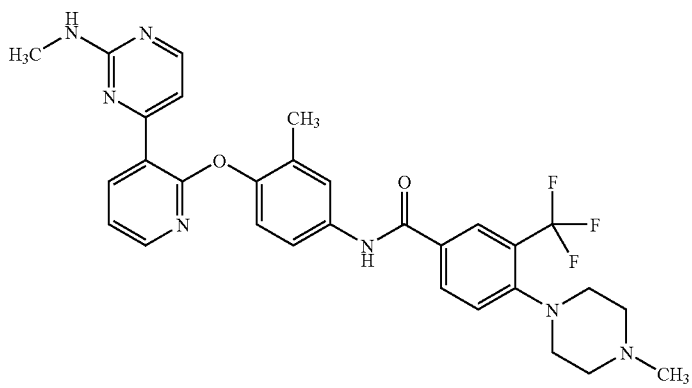 | 577.61 | |

Method P

EXAMPLE 1195

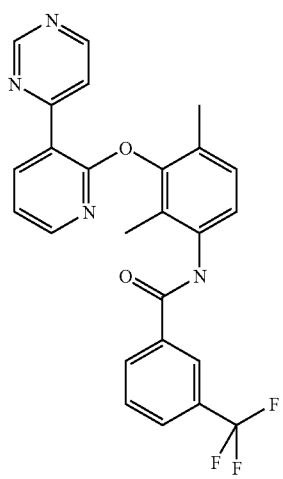

Synthesis of N-(2,4-dimethyl-3-(3-(pyrimidin-4-yl)pyridin-2-yloxy)phenyl)-3-(trifluoromethyl)benzamide Step 1. Preparation of 2,6-dimethyl-3-nitrophenol 2,6-Dimethyl-3-nitrobenzenamine (10.4 g, 62.6 mmol) was dissolved in 75% sulfuric acid (200 ml). Mixture cooled to 0° C. and treated with a solution of sodium nitrite (4.53 g, 65.7 mmol) in concentrated sulfuric acid (25.0 ml). After the mixture had been stirred for 1 hour at this temperature, water (200 ml) was added and the mixture warmed to 60° C. until the evolution of gas ceased. The mixture was allowed to cool to room temperature and then filtered to afford 2,6-dimethyl-3-nitrophenol. MS m/z=168 (M+H)$^+$. Calc'd for $C_8H_9NO_3$: 169.18.

Step 2. Preparation of 4-(2-(2,6-dimethyl-3-nitrophenoxy)pyridin-3-yl)pyrimidine Dissolved 2,6-dimethyl-3-nitrophenol (1.96 g, 11.7 mmol) and 4-(2-chloropyridin-3-yl)pyrimidine (1.50 g, 7.83 mmol) in dimethylsulfoxide (15.0 ml) and added cesium carbonate (5.10 g, 15.7 mmol). Reaction mixture was heated to 1200C in a sealed tube for 8 hours. Reaction mixture was then allowed to cool to room temperature and then poured into 250 mL of rapidly stirring water in an Erlenmeyer flask. After 10 minutes, the opaque brown aqueous solution was cooled to 0° C. and allowed to stand for 10 minutes, then filtered. The precipitate was collected as the title compound. MS m/z=323 (M+H)$^+$. Calc'd for $C_{17}H_{16}N_4O_3$: 324.34.

Step 3. Preparation of 2,4-Dimethyl-3-(3-(pyrimidin-4-yl)pyridin-2-yloxy)benzenamine Added tin(II) chloride dihydrate (6.13 g, 27.1 mmol) to a stirring solution/suspension of 4-(2-(2,6-dimethyl-3-nitrophenoxy)pyridin-3-yl)pyrimidine (1.75 g, 5.43 mmol) in methanol (20.0 ml). Heated reaction mixture to 65° C. for 1.25 hours. Filtered hot suspension through Celite which was washed with 20 mL MeOH and 200 mL EtOAc. The organic solution was then extracted with 3×100 1N HCl. The acidic aqueous phase was then basified with 5N NaOH and allowed to stand for 5 minutes. The aqueous phase was then extracted with 3×150 mL portions of $CHCl_3$ which was collected as a bright red-orange solution, dried over sodium sulfate and concentrated in vacuo to afford a brown solid. This was purified by column chromatography (10-100% (2.0 M $NH_3$ in MeOH) in dichloromethane) and concentrated to afford 2,4-dimethyl-3-(3-(pyrimidin-4-yl)pyridin-2-yloxy)benzenamine as a bright red-orange solid. MS m/z=293 $(M+H)^+$. Calc'd for $C_{17}H_{16}N_4O$: 292.34.

Step 4. Preparation of N-(2,4-dimethyl-3-(3-(pyrimidin-4-yl)pyridin-2-yloxy)phenyl)-3-(trifluoromethyl)benzamide Dissolved 2,4-dimethyl-3-(3-(pyrimidin-4-yl)pyridin-2-yloxy)benzenamine (100 mg, 0.342 mmol) in dichloromethane (1.0 mL), added 3-(trifluoromethyl)benzoyl chloride (107 mg, 0.513 mmol) and triethylamine (0.12 mL). Stirred at ambient temp for 4 hours and then concentrated and purified by reverse-phase HPLC (Gilson, acidic mobile phase) to yield the title compound. MS m/z=465 $(M+H)^+$. Calc'd for $C_{25}H_{19}F_3N_4O_2$: 464.45.

| Ex. No. | Structure Name | Structure | MW | MS Data |
|---|---|---|---|---|
| 1196 | N-(2,4-dimethyl-3-(3-(pyrimidin-4-yl)pyridin-2-yloxy)phenyl)-4-(trifluoromethyl)benzamide | 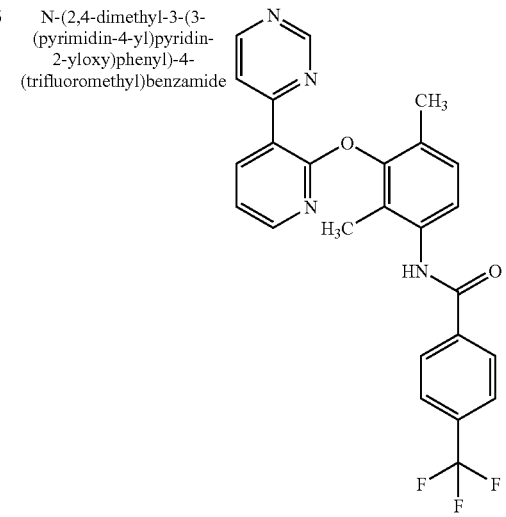 | 464.44 | 465 |
| 1197 | N-(2,4-dimethyl-3-(3-(pyrimidin-4-yl)pyridin-2-yloxy)phenyl)-3-chlorobenzamnide | 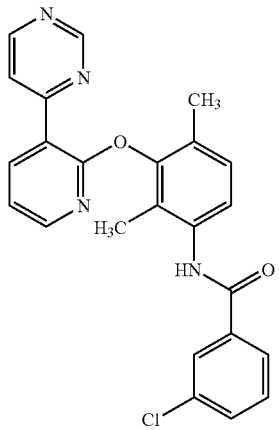 | 430.89 | 431 |

-continued

| Ex. No. | Structure Name | Structure | MW | MS Data |
|---|---|---|---|---|
| 1198 | N-(2,4-dimethyl-3-(3-(pyrimidin-4-yl)pyridin-2-yloxy)phenyl)-4-chlorobenzamide | 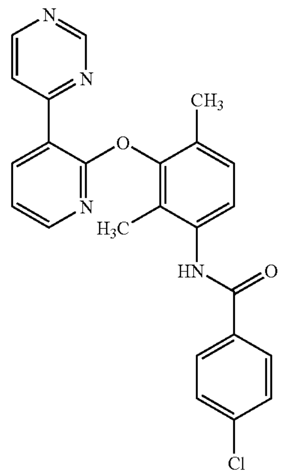 | 430.89 | 431 |
| 1199 | N-(2,4-dimethyl-3-(3-(pyrimidin-4-yl)pyridin-2-yloxy)phenyl)-3-methoxybenzamide | 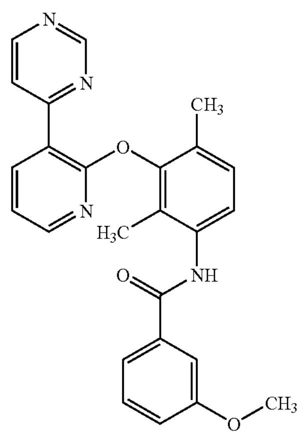 | 426.47 | 427 |
| 1200 | 4-tert-butyl-N-(2,4-dimethyl-3-(3-(pyrimidin-4-yl)pyridin-2-yloxy)phenyl)benzamide | 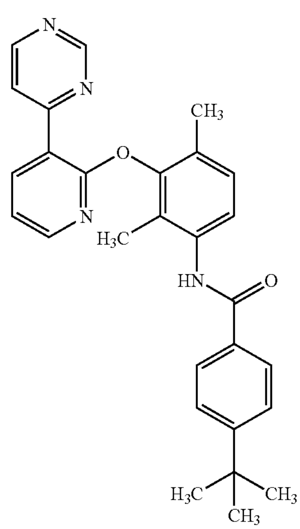 | 452.56 | 453 |

| Ex. No. | Structure Name | Structure | MW | MS Data |
|---|---|---|---|---|
| 1201 | N-(2,4-dimethyl-3-(3-(pyrimidin-4-yl)pyridin-2-yloxy)phenyl)-4-methoxybenzamide | 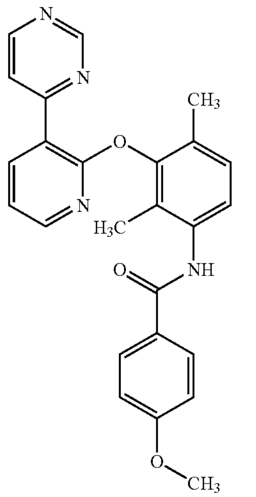 | 426.47 | 427 |
| 1202 | N-(2,4-dimethyl-3-(3-(pyrimidin-4-yl)pyridin-2-yloxy)phenyl)-3-fluorobenzamide | 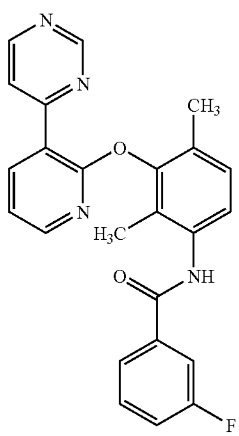 | 414.44 | 415 |
| 1203 | N-(2,4-dimethyl-3-(3-(pyrimidin-4-yl)pyridin-2-yloxy)phenyl)-3-methylbenzamide | 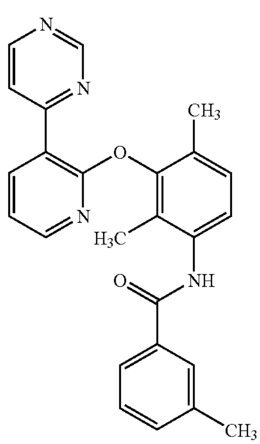 | 410.48 | 411 |

| Ex. No. | Structure Name | Structure | MW | MS Data |
|---|---|---|---|---|
| 1204 | N-(2,4-dimethyl-3-(3-(pyrimidin-4-yl)pyridin-2-yloxy)phenyl)-4-methylbenzamide | 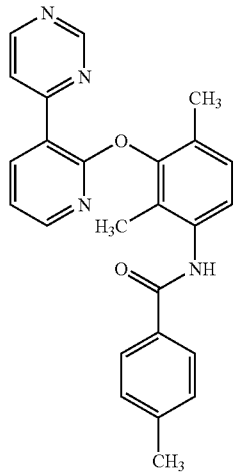 | 410.48 | 411 |

Method Q

EXAMPLE 1205

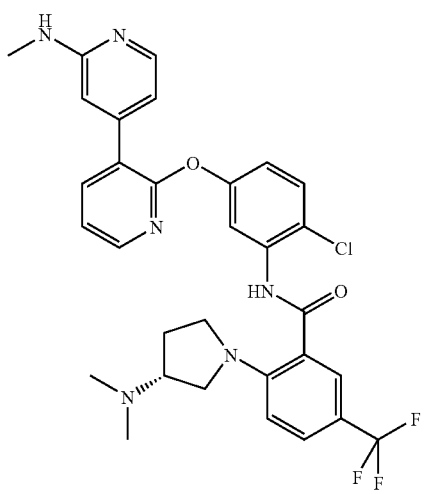

Synthesis of N-[2-Chloro-5-(2'-methylamino-[3,4']bipyridinyl-2-yloxy)-phenyl]-2-(3-dimethylamino-pyrrolidin-1-yl)-5-trifluoromethyl-benzamide Step 1. Preparation of N-[2-Chloro-5-(2'-methylamino-[3,4']bipyridinyl-2-yloxy)-phenyl]-2-fluoro-5-trifluoromethyl-benzamide In a sealed tube, [2-(3-Amino-4-chloro-phenoxy)-[3,4']bipyridinyl-2'-yl]-methyl-amine (300 mg, 0.918 mmol) and 2-Fluoro-5-trifluoromethyl-benzoyl chloride (0.180 mL, 1.19 mmol) were dissolved in 2.0 mL chloroform. The solution was heated to 75° C. and stirred for 48 h. The reaction was then cooled to RT, quenched with triethylamine (0.128 mL, 0.918 mmol), and concentrated in vacuo to yield the title compound as a crude light yellow solid. MS m/z (M+H)$^+$= 517; Calc'd 516.87 for $C_{25}H_{17}ClF_4N_4O_2$.

Step 2. Preparation of N-[2-Chloro-5-(2'-methylamino-[3,4']bipyridinyl-2-yloxy)-phenyl]-2-(3-dimethylamino-pyrrolidin-1-yl)-5-trifluoromethyl-benzamide N-[2-Chloro-5-(2'-methylamino-[3,4']bipyridinyl-2-yloxy)-phenyl]-2-fluoro-5-trifluoromethyl-benzamide (65 mg, 0.13 mmol) and dimethyl-pyrrolidin-3-yl-amine (22 mg, 0.189 mmol) were dissolved in 0.3 mL DMSO. The solution was heated to 80° C. and stirred for 22 h. The reaction was then cooled to RT, quenched with water, extracted into EtOAc, washed twice with water, once with brine, dried over Mg$_2$SO$_4$, filtered, and concentrated in vacuo to yield a crude mixture that was purified by preparative TLC (10% MeOH/CH$_2$Cl$_2$) to give the title compound as an off-white solid. MS m/z (M+H)$^+$=611; Calc'd 611.06 for $C_{31}H_{30}ClF_3N_6O_2$.

| Ex. No. | Structure Name | Structure | MW | MS Data |
|---|---|---|---|---|
| 1206 | N-(2-chloro-5-((3-(2-(methylamino)-4-pyrimidinyl)-2-pyridinyl)oxy)phenyl)-2-((3-(dimethylamino)propyl)(methyl)amino)-5-(trifluoromethyl)benzamide | 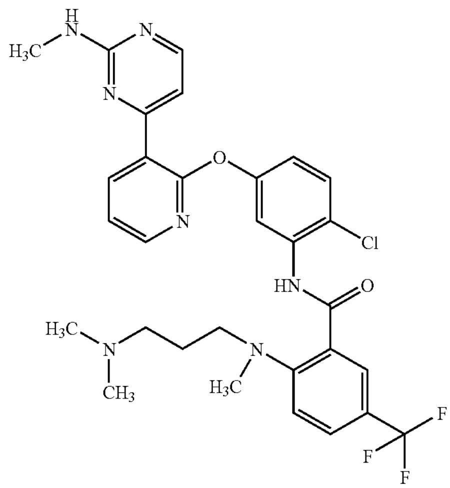 | 614.07 | 614 |
| 1207 | N-(2-chloro-5-((3-(4-(methylamino)-1,3,5-triazin-2-yl)-2-pyridinyl)oxy)phenyl)-2-((3-(dimethylamino)propyl)(methyl)amino)-5-(trifluoromethyl)benzamide | 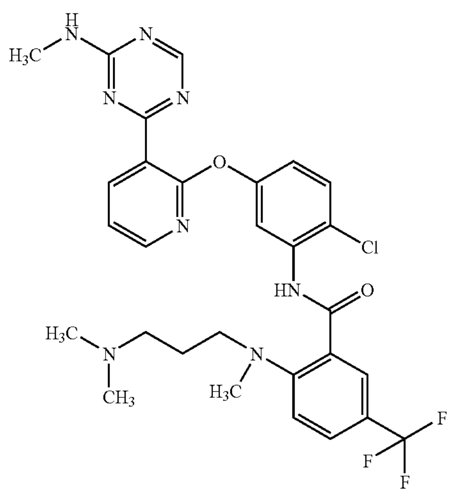 | 615.06 | 615 |
| 1208 | N-(2-chloro-5-((3-(2-(methylamino)-4-pyrimidinyl)-2-pyridinyl)oxy)phenyl)-2-((3R)-3-(dimethylamino)-1-pyrrolidinyl)-5-(trifluoromethyl)benzamide | 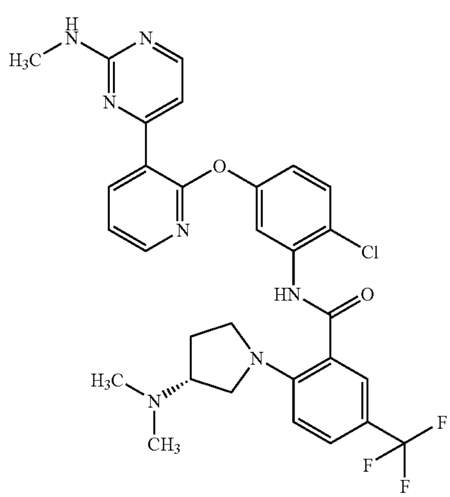 | 612.05 | 612 |

-continued

| Ex. No. | Structure Name | Structure | MW | MS Data |
|---|---|---|---|---|
| 1209 | N-(2-chloro-5-((3-(2-(methylamino)-4-pyrimidinyl)-2-pyridinyl)oxy)phenyl)-2-((3S)-3-(dimethylamino)-1-pyrrolidinyl)-5-(trifluoromethyl)benzamide | 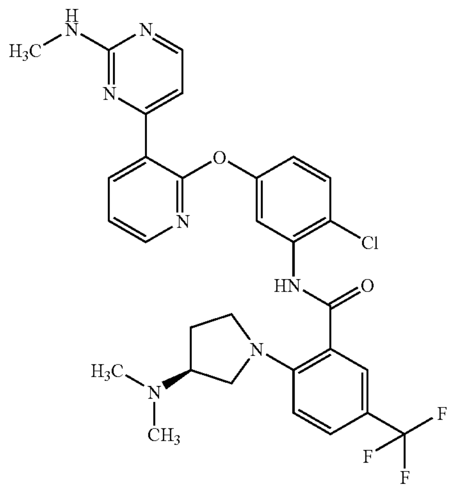 | 612.05 | 612 |
| 1210 | N-(2-chloro-5-((2'-(methylamino)-3,4'-bipyridin-2-yl)oxy)phenyl)-2-((3-(dimethylamino)propyl)(methyl)amino)-5-(trifluoromethyl)benzamide | 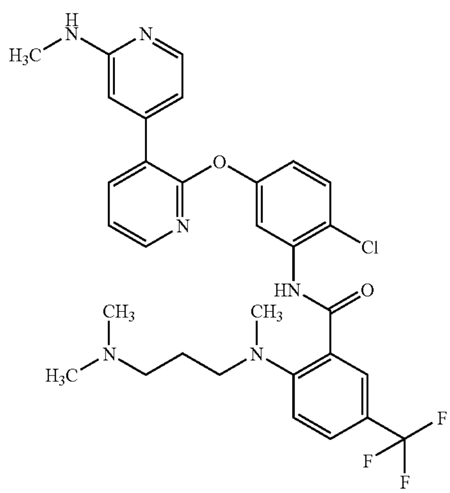 | 613.08 | 613 |
| 1211 | N-(2-chloro-5-((3-(4-(methylamino)-1,3,5-triazin-2-yl)-2-pyridinyl)oxy)phenyl)-2-((2-(dimethylamino)ethyl)(methyl)amino)-5-(trifluoromethyl)benzamide | 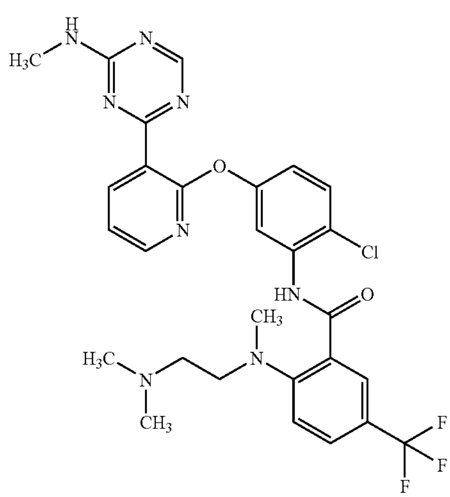 | 601.03 | 601 |

-continued
| Ex. No. | Structure Name | Structure | MW | MS Data |
|---|---|---|---|---|
| 1212 | N-(2-chloro-5-((3-(4-(methylamino)-1,3,5-triazin-2-yl)-2-pyridinyl)oxy)phenyl)-2-(methyl(1-methyl-3-pyrrolidinyl)amino)-5-(trifluoromethyl)benzamide | 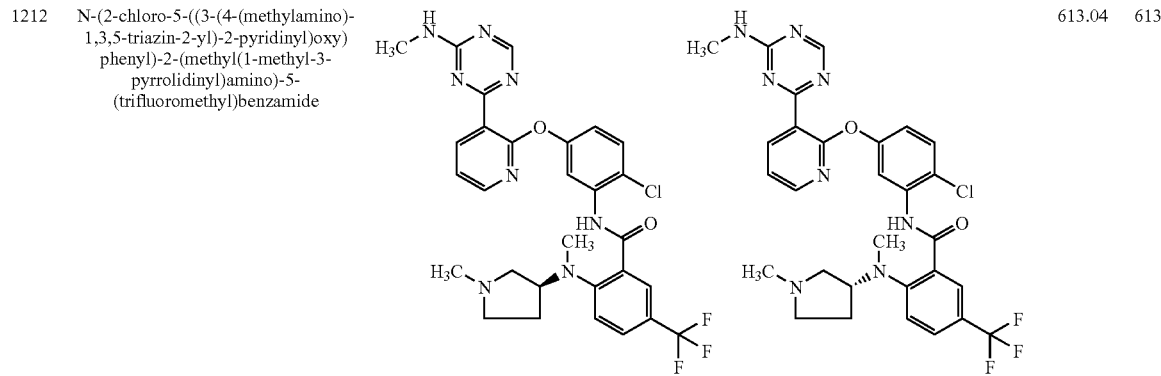 | 613.04 | 613 |
| 1213 | 2-((3-(dimethylamino)propyl)(methyl)amino)-N-(4-fluoro-3-((3-(4-(methylamino)-1,3,5-triazin-2-yl)-2-pyridinyl)oxy)phenyl)-5-(trifluoromethyl)benzamide | 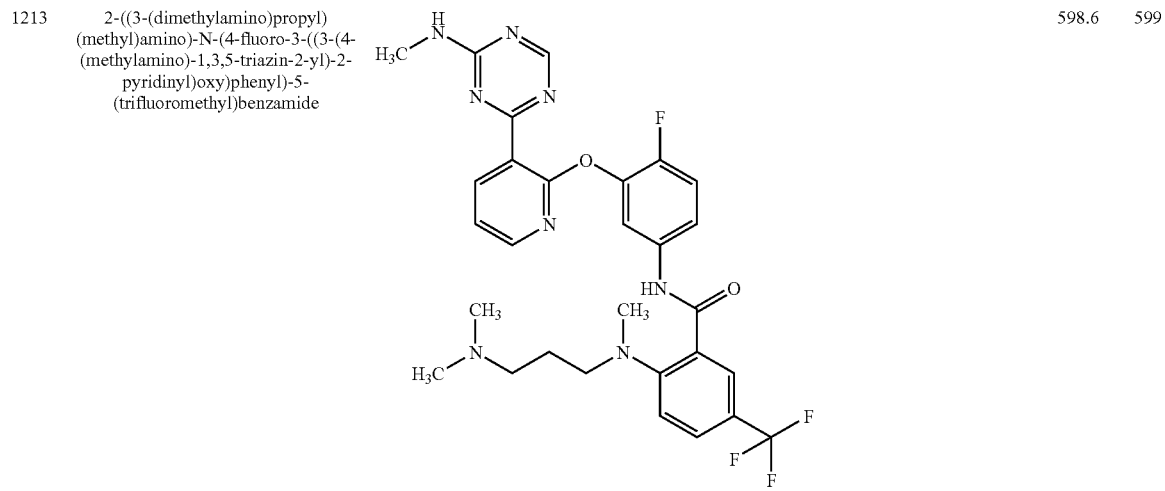 | 598.6 | 599 |

The following additional Examples will further assist in the understanding and appreciation of the scope of the invention.

EXAMPLE 1214

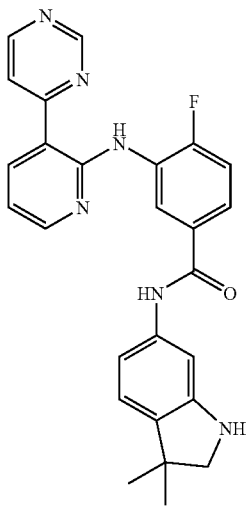

Synthesis of N-(3,3-Dimethyl-2,3-dihydro-1H-indol-6-yl)-4-fluoro-3-(3-pyrimidin-4-yl-pyridin-2-ylamino)-benzamide N-(1-Acetyl-3,3-dimethyl-2,3-dihydro-1H-indol-6-yl)-4-fluoro-3-(3-pyrimidin-4-yl-pyridin-2-ylamino)-benzamide (137 mg, 0.28 mmol, Example Norman) was dissolved in 3:1 ethanol/concentrated HCl and heated under $N_2$ at 47° C. for 20 h. After concentration, the residue was diluted with sat'd aqueous $NaHCO_3$ and extracted with EtOAc. The organic layer was dried with $Na_2SO_4$, concentrated, triturated with methanol, and filtered to provide yellow solid product. MS m/z=455 $[M+H]^+$. Calc'd for $C_{26}H_{23}FN_6O$: 454.51.

EXAMPLE 1215

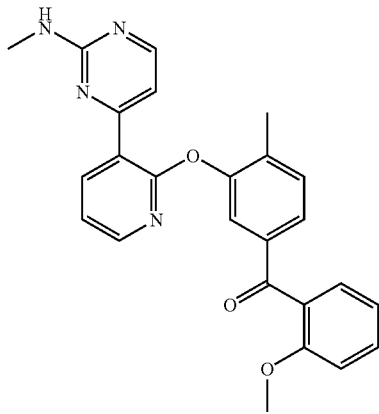

Synthesis of (2-Methoxy-phenyl)-{4-methyl-3-[3-(2-methylamino-pyrimidin-4-yl)-pyridin-2-yloxy]-phenyl}-methanone To 4-methyl-3-[3-(2-methylamino-pyrimidin-4-yl)-pyridin-2-yloxy]-benzoyl chloride (50 mg, 0.14 mmol) in a flame dried, round-bottom flask under nitrogen and cooled to −78° C. was added 4 ml of THF, 2 ml methylene chloride and magnesium-bromide-2-methoxy-benzene in THF (0.3 ml, 0.6 mmol). After addition of the magnesium-bromide, the −78° C. dry ice bath was removed and the reaction allowed to warm to room temperature over 4 h. The reaction was quenched with saturated sodium bicarbonate solution and extracted with methylene chloride and brine. The organic layers were combined, dried with sodium sulfate and filtered. The solvent was removed under vacuum and the product was purified via preparative HPLC (Gilson). MS m/z=427 $[M+H]^+$. Calc'd for $C_{25}H_{22}N_4O_3$: 426.48.

EXAMPLE 1216

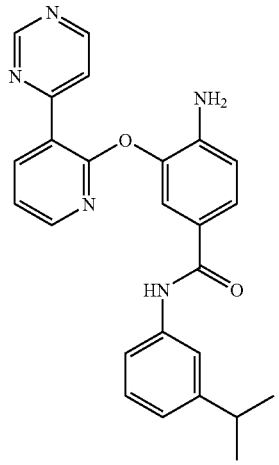

Synthesis of 4-amino-N-(3-isopropylphenyl)-3-(3-(pyrimidin-4-yl)pyridin-2-yloxy)benzamide To a solution of N-(3-isopropylphenyl)-4-nitro-3-(3-(pyrimidin-4-yl)pyridin-2-yloxy)benzamide (0.090 g, 0.20 mmol) in MeOH (3 mL) and EtOAc (3 mL) was added $NH_4OAc$ (0.030 g) and Pd/C (10%) (0.020 g). The reaction was capped with a septum, and positive $H_2$ pressure was applied with a balloon/needle. The reaction was stirred for several hours, at which point LCMS indicated formation of product. The mixture was filtered through sand/celite, concentrated onto silica gel, and chromatographed with 8:8:8:1 t-BuOMe:hexanes:$CH_2Cl_2$:MeOH to afford 4-amino-N-(3-isopropylphenyl)-3-(3-(pyrimidin-4-yl)pyridin-2-yloxy)benzamide as a yellow solid. MS m/z=426 $[M+H]^+$. Calc'd for $C_{25}H_{23}N_5O_2$: 425.49.

EXAMPLE 1217

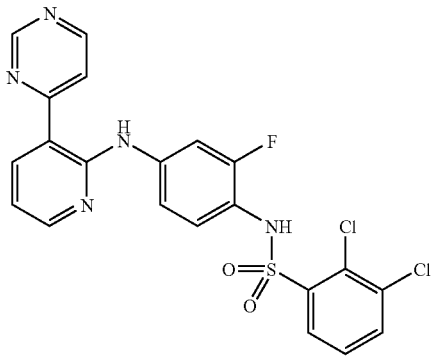

Synthesis of 2,3-dichloro-N-(2-fluoro-4-(3-(pyrimidin-4-yl)pyridin-2-ylamino)phenyl)benzenesulfonamide Step 1. Preparation of 2-fluorobenzene-1,4-diamine 3,4-Difluorobenzenamine (3.0 mL) and NH$_4$OH (15.0 mL) were heated in a sealed tube at 150° C. with vigorous stirring for several hours, forming a solid yellow precipitate. The reaction was filtered, washed with water, and then hexanes to afford 2-fluorobenzene-1,4-diamine as a yellow solid.

Step 2. Preparation of 2,3-dichloro-N-(2-fluoro-4-nitrophenyl)benzenesulfonamide To NaH (60% dispersion in mineral oil) (0.734, 18.3 mmol) in THF (100 mL) at 0° C. was added dropwise a solution of 2-fluoro-4-nitrobenzenamine (2.20 g, 14.1 mmol) in THF (25 mL). The solution turned deep red in color and was stirred at 0° C. for 1 hour. A solution of 2,3-dichlorobenzene-1-sulfonyl chloride (3.80 g, 15.5 mmol) in THF (25 mL) was then added dropwise, at which point the reaction turned orange/yellow in color. The mixture was allowed to warm to room temperature and then was stirred for and additional 30 minutes. The reaction was quenched by addition of NH$_4$Cl (aq., sat.), and then concentrated. The mixture was partitioned between water and ethyl acetate. The organics were dried with MgSO$_4$, filtered, and concentrated to afford 2,3-dichloro-N-(2-fluoro-4-nitrophenyl)benzenesulfonamide.

Step 3. Preparation of N-(4-amino-2-fluorophenyl)-2,3-dichlorobenzenesulfonamide To a solution of 2,3-dichloro-N-(2-fluoro-4-nitrophenyl)benzenesulfonamide (5.0 g, 13.7 mmol) and Raney Nickel (0.600 g) in THF (200 mL) was applied positive H$_2$ pressure through a balloon/needle. The reaction was stirred at room temperature for 4 hours and then filtered. The mixture was concentrated and triturated with CH$_2$Cl$_2$ to afford N-(4-amino-2-fluorophenyl)-2,3-dichlorobenzenesulfonamide as a grey solid.

Step 4. Preparation of 2,3-dichloro-N-(2-fluoro-4-(3-(pyrimidin-4-yl)pyridin-2-ylamino)phenyl)benzenesulfonamide To N-(4-amino-2-fluorophenyl)-2,3-dichlorobenzenesulfonamide (0.150 g, 0.45 mmol) and 4-(2-chloropyridin-3-yl)pyrimidine (0.086 g, 0.45 mmol) was added NEt$_3$.TFA. The mixture was heated at 100° C. CH$_2$Cl$_2$/MeOH was added, producing a yellow precipitate, which was filtered. Trituration with a further portion of CH$_2$Cl$_2$/MeOH, followed by filtration, afforded 2,3-dichloro-N-(2-fluoro-4-(3-(pyrimidin-4-yl)pyridin-2-ylamino)phenyl)benzenesulfonamide as an orange solid. MS m/z=491 [M+H]$^+$. Calc'd for C$_{21}$H$_{14}$Cl$_2$FN$_5$O$_2$S: 490.35.

EXAMPLE 1218

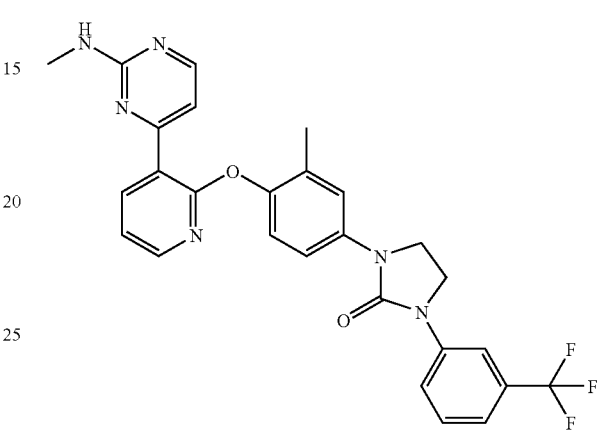

Synthesis of 1-(3-methyl-4-(3-(2-(methylamino)pyrimidin-4-yl)pyridin-2-yloxy)phenyl)-3-(3-(trifluoromethyl)phenyl)imidazolidin-2-one Step 1. Preparation of 1-(2-chloroethyl)-3-(3-methyl-4-(3-(2-(methylamino)pyrimidin-4-yl)pyridin-2-yloxy)phenyl)urea To a slurry of 4-(2-(4-amino-2-methylphenoxy)pyridin-3-yl)-N-methylpyrimidin-2-amine (0.500 g, 1.63 mmol) in THF (3.3 mL) under nitrogen was added 1-chloro-2-isocyanatoethane (0.157 mL, 1.79 mmol). The reaction became clear and brown, and then a precipitate formed. Additional THF (4 mL) was added to promote stirring, and the reaction was allowed to stir for 16 h. The mixture was filtered, the solid was rinsed with diethyl ether, and dried in vacuo to give 1-(2-chloroethyl)-3-(3-methyl-4-(3-(2-(methylamino)pyrimidin-4-yl)pyridin-2-yloxy)phenyl)urea as a tan solid. MS m/z=413 [M+1]$^+$. Calc'd for C$_{20}$H$_{21}$ClN$_6$O$_2$: 412.14.

Step 2. Preparation of 1-(3-methyl-4-(3-(2-(methylamino)pyrimidin-4-yl)pyridin-2-yloxy)phenyl)imidazolidin-2-one To a slurry of NaH (60% in mineral oil, 0.109 g, 2.73 mmol) in THF (13 mL) in a sealable tube under nitrogen was added 1-(2-chloroethyl)-3-(3-methyl-4-(3-(2-(methylamino)pyrimidin-4-yl)pyridin-2-yloxy)phenyl)urea (0.537 g, 1.30 mmol) in portions. The reaction was sealed and heated to 80 deg. C. for 3 h. The reaction was cooled to ambient temperature and was concentrated under a stream of nitrogen. The resulting solid was suspended in 50 mL water, acidified to pH 1 with 6 N HCl, and filtered. The solid was rinsed with water, diethyl ether, and dried in vacuo to give 1-(3-methyl-4-(3-(2-(methylamino)pyrimidin-4-yl)pyridin-2-yloxy)phenyl)imidazolidin-2-one as a tan solid. MS m/z=377 [M+1]$^+$. Calc'd for C$_{20}$H$_{20}$N$_6$O$_2$: 376.16.

Step 3. Preparation of 1-(3-methyl-4-(3-(2-(methylamino)pyrimidin-4-yl)pyridin-2-yloxy)phenyl)-3-(3-(trifluoromethyl)phenyl)imidazolidin-2-one 1-(3-methyl-4-(3-(2-(methylamino)pyrimidin-4-yl)pyridin-2-yloxy)phenyl)imidazolidin-2-one (0.100 g, 0.266 mmol), 1-iodo-3-(trifluoromethyl)benzene (0.050 mL, 0.35 mmol), 9,9-dimethyl-4,5-bis(diphenylphosphino)xanthene (0.012 g, 0.020 mmol), palladium (II) acetate (0.009 g, 0.013 mmol), and cesium carbonate (0.130 g, 0.399 mmol) were combined in dioxane under argon. The reaction vessel was sealed and the mixture was heated to 100 deg. C. for 48 h. The reaction was cooled to ambient temperature and diluted with dichloromethane, filtered, and concentrated in vacuo. The resulting material was adsorbed onto silica gel and purified by silica gel chromatography. The resulting material was further purified by reverse-phase HPLC using acetonitrile/water/TFA eluent to give 1-(3-methyl-4-(3-(2-(methylamino)pyrimidin-4-yl)pyridin-2-yloxy)phenyl)-3-(3-(trifluoromethyl)phenyl)imidazolidin-2-one as a white solid.

MS m/z=521 [M+1]$^+$. Calc'd for $C_{27}H_{23}F_3N_6O_2$: 520.51.

EXAMPLE 1219

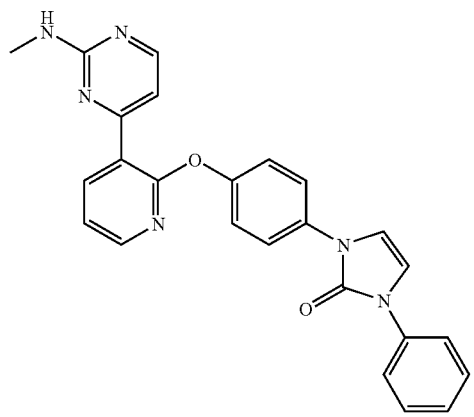

Synthesis of 1-(4-(3-(2-(methylamino)pyrimidin-4-yl)pyridin-2-yloxy)phenyl)-3-phenyl-1H-imidazol-2 (3H)-one To a slurry of 4-(2-(4-amino-phenoxy)pyridin-3-yl)-N-methylpyrimidin-2-amine (0.200 g, 0.682 mmol) in THF (3 mL) under nitrogen was added 4-nitrophenyl chloroformate (0.138 mg, 0.682 mmol). The dark brown mixture was allowed to stir for 1 h, at which point N-(2,2-diethoxyethyl)benzenamine (0.285 mL, 1.36 mmol) was added. The reaction was heated to 80 deg. C. for 30 min. The reaction was cooled to ambient temperature, diluted with ethyl acetate, and washed with 3×saturated aqueous sodium bicarbonate, 2×1N NaOH, 1× water, and 1×brine. The organic layer was dried over anhydrous sodium sulfate, filtered, and concentrated in vacuo. The resulting solid was suspended in dichloromethane and filtered. The filtrate was concentrated to a brown oil, which was treated with 5 mL 1N HCl and was heated to 80 deg. C. in a sealed tube. After 1 h, the reaction was cooled to ambient temperature, filtered, and the solid was rinsed with small amounts of water and ethanol, and was dried in vacuo to give a tan solid. This material was further purified by reverse-phase HPLC using acetonitrile/water/TFA as eluent to give 1-(4-(3-(2-(methylamino)pyrimidin-4-yl)pyridin-2-yloxy)phenyl)-3-phenyl-1H-imidazol-2 (3H)-one as an off-white solid. MS m/z=437 [M+1]$^+$. Calc'd for $C_{25}H_{20}N_6O_2$: 436.47.

EXAMPLE 1220

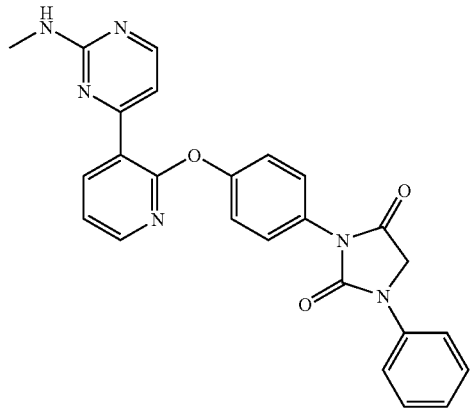

Synthesis of 3-(4-(3-(2-(methylamino)pyrimidin-4-yl)pyridin-2-yloxy)phenyl)-1-phenylimidazolidine-2,4-dione To a slurry of 4-(2-(4-amino-phenoxy)pyridin-3-yl)-N-methylpyrimidin-2-amine (0.200 g, 0.682 mmol) and diisopropylethylamine (0.130 mL, 0.750 mmol) in THF (2 mL) under nitrogen was added phenyl chloroformate (0.100 mL, 0.682 mmol). After 30 min, ethyl 2-(phenylamino)acetate (0.244 g, 1.36 mmol) was added, and the sealed reaction was heated to 80 deg. C. for 16 h and 100 deg. C. for 8 h. The reaction was cooled to ambient temperature, and diluted with ethyl acetate and saturated aqueous sodium bicarbonate. The organic layer was dried over anhydrous sodium sulfate, filtered, and concentrated in vacuo. The resulting solid was purified by silica gel chromatography, 0 to 10% MeOH/dichloromethane, to give a solid which was slurried in methanol and filtered, rinsed with diethyl ether, and dried in vacuo to give 3-(4-(3-(2-(methylamino)pyrimidin-4-yl)pyridin-2-yloxy)phenyl)-1-phenylimidazolidine-2,4-dione as an off-white solid. MS m/z=453 [M+1]$^+$. Calc'd for $C_{25}H_{20}N_6O_2$: 452.47.

EXAMPLE 1221

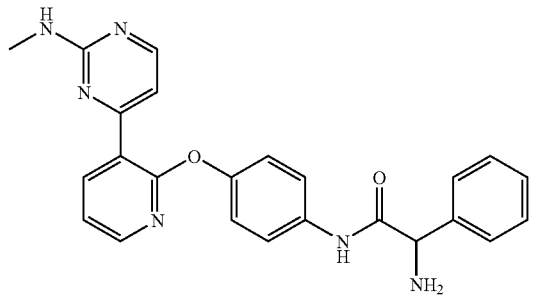

Synthesis of (rac)-2-amino-N-(4-(3-(2-(methylamino)pyrimidin-4-yl)pyridin-2-yloxy)phenyl)-2-phenylacetamide Tert-butyl (rac)-2-(4-(3-(2-(methylamino)pyrimidin-4-yl)pyridin-2-yloxy)phenylamino)-2-oxo-1-phenylethylcarbamate (0.040 g, 0.076 mmol) was treated with 1 mL TFA at ambient temperature. After 16 h, saturated aqueous sodium bicarbonate was added until pH=9, and the aqueous layer extracted once with ethyl acetate. The organic layer was dried over anhydrous sodium sulfate, filtered, and concentrated in vacuo to give (rac)-2-amino-N-(4-(3-(2-(methylamino)pyrimidin-4-yl)pyridin-2-yloxy)phenyl)-2-phenylacetamide. MS m/z=441 [M+1]$^+$. Calc'd for $C_{25}H_{24}N_6O_2$: 440.51.

EXAMPLE 1222

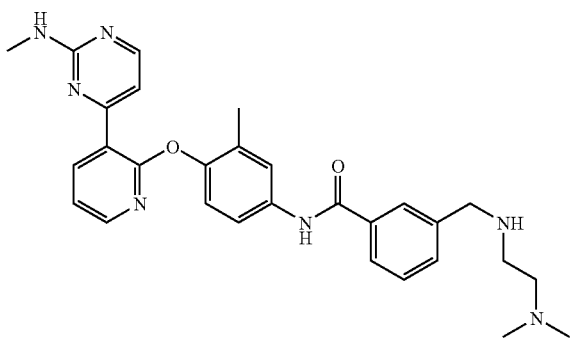

Synthesis of 3-((2-(dimethylamino)ethylamino)methyl)-N-(3-methyl-4-(3-(2-(methylamino)pyrimidin-4-yl)pyridin-2-yloxy)phenyl)benzamide To 3-formyl-N-(3-methyl-4-(3-(2-(methylamino)pyrimidin-4-yl)pyridin-2-yloxy)phenyl)benzamide (0.100 g, 0.23 mmol) in MeOH (6 mL) was added N1,N1-dimethylethane-1,2-diamine (0.13 mL, 1.1 mmol) and AcOH (0.010 mL, 0.23 mmol). The reaction was allowed to stir for 2.5 h, at which point sodium triacetoxyborohydride (0.096 g, 0.46 mmol) was added. After approximately 16 h, the reaction was quenched by the addition of saturated aqueous sodium bicarbonate. The aqueous layer was extracted four times with dichloromethane. The combined organic layers were dried over anhydrous sodium sulfate, filtered, and concentrated in vacuo to give a solid. Purification by reverse-phase HPLC using acetonitrile/water/TFA as eluent gave 3-((2-(dimethylamino)ethylamino)methyl)-N-(3-methyl-4-(3-(2-(methylamino)pyrimidin-4-yl)pyridin-2-yloxy)phenyl)benzamide as a white solid. MS m/z=512 [M+1]$^+$. Calc'd for $C_{29}H_{33}N_7O_2$: 511.63.

The following two Examples were synthesized according to the procedure described in the Example immediately above.

EXAMPLE 1223

3-((dimethylamino)methyl)-N-(4-(3-(2-(methylamino)pyrimidin-4-yl)pyridin-2-yloxy)phenyl)benzamide MS m/z=469 [M+1]$^+$. Calc'd for $C_{27}H_{28}N_6O_2$: 468.56.

EXAMPLE 1224

N-(4-(3-(2-(methylamino)pyrimidin-4-yl)pyridin-2-yloxy)phenyl)-3-((4-methylpiperazin-1-yl)methyl)benzamide MS m/z=524 [M+1]$^+$. Calc'd for $C_{30}H_{33}N_7O_2$: 523.64.

EXAMPLE 1225

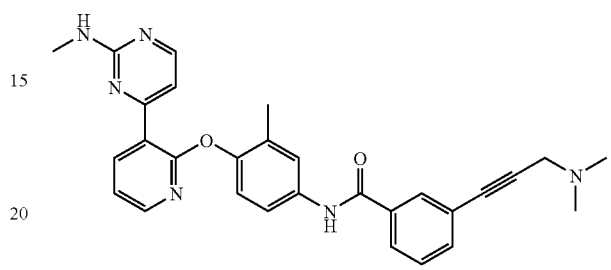

Synthesis of 3-(3-(dimethylamino)prop-1-ynyl)-N-(3-methyl-4-(3-(2-(methylamino)pyrimidin-4-yl)pyridin-2-yloxy)phenyl)benzamide A mixture of 3-iodo-N-(3-methyl-4-(3-(2-(methylamino)pyrimidin-4-yl)pyridin-2-yloxy)phenyl)benzamide (0.20 g, 0.37 mmol), N,N-dimethylprop-2-yn-1-amine (0.080 mL, 0.74 mmol), bis(triphenylphosphine)palladium (II) dichloride (0.013 g, 0.020 mmol), copper (I) iodide (0.0035 g, 0.020 mmol) in triethylamine (1.5 mL) and acetonitrile (5 mL) was heated in a sealed tube to 100 deg. C. for 3.5 h. The reaction was diluted in dichloromethane and filtered. The filtrate was concentrated in vacuo and the resulting material was purified by silica gel chromatography using MeOH/dichloromethane as eluent to give 3-(3-(dimethylamino)prop-1-ynyl)-N-(3-methyl-4-(3-(2-(methylamino)pyrimidin-4-yl)pyridin-2-yloxy)phenyl)benzamide as a brown solid. MS m/z=493 [M+1]$^+$. Calc'd for $C_{29}H_{28}N_6O_2$: 492.58.

EXAMPLE 1226

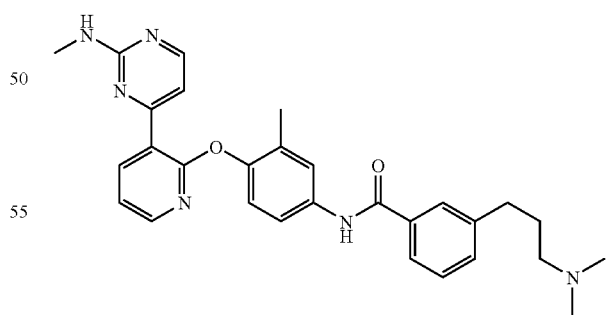

Synthesis of 3-(3-(dimethylamino)propyl)-N-(3-methyl-4-(3-(2-(methylamino)pyrimidin-4-yl)pyridin-2-yloxy)phenyl)benzamide To a mixture of 3-(3-(dimethylamino)prop-1-ynyl)-N-(3-methyl-4-(3-(2-(methylamino)pyrimidin-4-yl)pyridin-2- yloxy)phenyl)benzamide (0.060 g, 0.12 mmol) in EtOH (4 mL) was added a suspension of 10% Pd/C (0.012 g, 0.012 mmol) in ethanol. The reaction was exposed to approximately 30 psi hydrogen and was shaken in a Parr apparatus for 5 h. The reaction was filtered through celite, and the filtrate was concentrated in vacuo. The resulting yellow oil was purified by reverse-phase HPLC using acetonitrile/water/TFA to give 3-(3-(dimethylamino)propyl)-N-(3-methyl-4-(3-(2-(methylamino)pyrimidin-4-yl)pyridin-2-yloxy)phenyl)benzamide as an off-white solid. MS m/z=497 [M+1]$^+$. Calc'd for $C_{29}H_{32}N_6O_2$: 496.61.

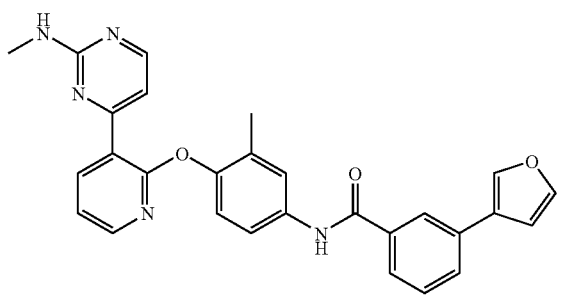

EXAMPLE 1227

Synthesis of 3-(furan-3-yl)-N-(3-methyl-4-(3-(2-(methylamino)pyrimidin-4-yl)pyridin-2-yloxy)phenyl)benzamide A mixture of 3-iodo-N-(3-methyl-4-(3-(2-(methylamino)pyrimidin-4-yl)pyridin-2-yloxy)phenyl)benzamide (0.100 g, 0.186 mmol), furan-3-ylboronic acid (0.025 g, 0.22 mmol), [1,1'bis(diphenylphosphino)ferrocene] palladium(II) methylene chloride complex (0.0073 g, 0.01 mmol), sodium carbonate (2M solution in water, 0.20 mL, 0.41 mmol) and dioxane was heated to 80 deg. C. for 3 h. The reaction was cooled to ambient temperature and was allowed to stand overnight. Additional [1,1'bis(diphenylphosphino)ferrocene] palladium(II) methylene chloride complex (0.0073 g, 0.01 mmol) was added and the reaction was heated to 85 deg. C. for 3 hr. The reaction was cooled to ambient temperature and was diluted with water and ethyl acetate. The organic layer was dried over anhydrous sodium sulfate, filtered, and concentrated in vacuo. The material was further purified by reverse-phase HPLC using acetonitrile/water/TFA as eluent to give 3-(furan-3-yl)-N-(3-methyl-4-(3-(2-(methylamino)pyrimidin-4-yl)pyridin-2-yloxy)phenyl)benzamide. MS m/z=478 [M+1]$^+$. Calc'd for $C_{28}H_{23}N_5O_3$: 477.52.

The following Example was synthesized according to the procedure described in the Example immediately above.

EXAMPLE 1228

3-(3,5-dimethylisoxazol-4-yl)-N-(4-(3-(2-(methylamino)pyrimidin-4-yl)pyridin-2-yloxy)phenyl)benzamide MS m/z=507 [M+1]$^+$. Calc'd for $C_{29}H_{26}N_6O_3$: 506.56.

EXAMPLE 1229

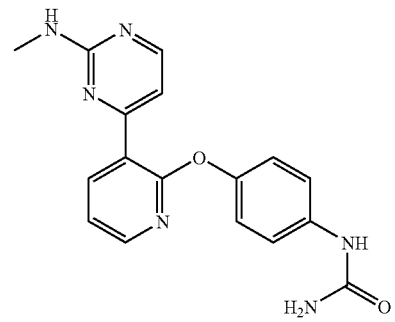

Synthesis of 1-(4-(3-(2-(methylamino)pyrimidin-4-yl)pyridin-2-yloxy)phenyl)urea

Dissolved 4-(2-(4-aminophenoxy)pyridin-3-yl)-N-methylpyrimidin-2-amine (75 mg, 0.26 mmol) in acetic acid (1.0 mL), then added potassium isocyanate (0.01 ml, 0.33 mmol), water (0.1 ml), and stirred at RT for 18 hours. Concentrated and purified by reverse phase HPLC (Gilson, acidic mobile phase), extracted into $CH_2Cl_2$ washed with $NaHCO_3$ and $H_2O$. Product began to crash out of $CH_2Cl_2$ layer, transfered to round bottom flask, concentrated to yield 1-(4-(3-(2-(methylamino)pyrimidin-4-yl)pyridin-2-yloxy)phenyl)urea as off-white solid. MS m/z=337 [M+1]$^+$. Calc'd for $C_{17}H_{16}N_6O_2$: 336.35.

EXAMPLE 1230

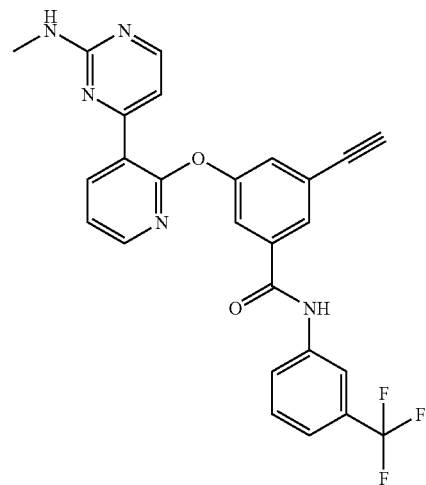

Synthesis of 3-Ethynyl-5-[3-(2-methylamino-pyrimidin-4-yl)-pyridin-2-yloxy]-N-(3-trifluoromethyl-phenyl)-benzamide To a solution of 3-Bromo-5-[3-(2-methylamino-pyrimidin-4-yl)-pyridin-2-yloxy]-N-(3-trifluoromethyl-phenyl)-benzamide (110 mg, 0.20 mmol), acetonitrile (5 mL) and Et$_3$N (1 mL) in a sealed tube was added trimethylsilyl acetylene (0.14 mL, 1.0 mmol) followed by PdCl$_2$(PPh$_3$)$_2$ (14 mg, 0.02 mmol) and CuI (4.0 mg, 0.02 mmol). The tube was sealed and heated at 85° C. for 15 h. The mixture was allowed to cool to room temperature and concentrated under reduced pressure. The resulting crude mixture was reconstituted in methanol (5 mL), saturated with solid K$_2$CO$_3$ (~200 mg) and allowed to stir at room temperature for 1 h. The resulting mixture was concentrated under reduced pressure and reconstituted in EtOAc (20 mL). The organic phase was washed successively with water (2×5 mL) and brine (1×5 mL), dried over anhydrous Na$_2$SO$_4$, filtered and concentrated under reduced pressure. The crude was purified via RP-HPLC to afford the title compound as an off-white solid. MS m/z=490 [M+1]$^+$, Calc'd for C$_{26}$H$_{18}$F$_3$N$_5$O$_2$: 489.45.

EXAMPLE 1231

N-(5-cyclohexyl-2-(methyloxy)phenyl)-2-fluoro-5-((3-(2-(methylamino)-4-pyrimidinyl)-2-pyridinyl)oxy)benzamide

EXAMPLE 1232

2-fluoro-5-((3-(2-(methylamino)-4-pyrimidinyl)-2-pyridinyl)oxy)-N-(3-(((((2S)-1-methyl-2-pyrrolidinyl)methyl)oxy)-5-(trifluoromethyl)phenyl)benzamide

EXAMPLE 1233

2-fluoro-5-((3-(2-(methylamino)-4-pyrimidinyl)-2-pyridinyl)oxy)-N-(2-(methyloxy)phenyl)benzamide

EXAMPLE 1234

2-fluoro-5-((3-(2-(methylamino)-4-pyrimidinyl)-2-pyridinyl)oxy)-N-(4-(1-methylethyl)phenyl)benzamide

EXAMPLE 1235

2-fluoro-5-((3-(2-(methylamino)-4-pyrimidinyl)-2-pyridinyl)oxy)-N-(2-methyl-3-(trifluoromethyl)phenyl)benzamide

EXAMPLE 1236

N-(2-((2-(dimethylamino)ethyl)(methyl)amino)-5-(trifluoromethyl)phenyl)-4-methyl-3-((3-(2-(methylamino)-4-pyrimidinyl)-2-pyridinyl)oxy)benzamide

EXAMPLE 1237

4-methyl-3-((3-(2-(methylamino)-4-pyrimidinyl)-2-pyridinyl)oxy)-N-(2-(4-methyl-1-piperazinyl)-5-(trifluoromethyl)phenyl)benzamide

EXAMPLE 1238

N-(2-((3-(dimethylamino)propyl)(methyl)amino)-5-(trifluoromethyl)phenyl)-4-methyl-3-((3-(2-(methylamino)-4-pyrimidinyl)-2-pyridinyl)oxy)benzamide

EXAMPLE 1239

N-(2-((2-(dimethylamino)ethyl)(methyl)amino)-5-(trifluoromethyl)phenyl)-4-methyl-3-((3-(4-(methylamino)-1,3,5-triazin-2-yl)-2-pyridinyl)oxy)benzamide

EXAMPLE 1240

3-((3-(2-(methylamino)-4-pyrimidinyl)-2-pyridinyl)sulfanyl)-N-(3-(trifluoromethyl)phenyl)benzamide

EXAMPLE 1241

3-((3-(2-(methylamino)-4-pyrimidinyl)-2-pyridinyl)sulfanyl)-N-(2-(1-piperidinyl)-5-(trifluoromethyl)phenyl)benzamide

EXAMPLE 1242

N-(4-(2-hydroxyethyl)phenyl)-4-methyl-3-(3-(pyrimidin-4-yl)pyridin-2-ylamino)benzamide

EXAMPLE 1243

4-chloro-3-(3-(pyrimidin-4-yl)pyridin-2-ylamino)-N-(3-(trifluoromethyl)phenyl)benzamide

EXAMPLE 1244

4-chloro-N-(3-chlorophenyl)-3-(3-(pyrimidin-4-yl)pyridin-2-ylamino)benzamide

EXAMPLE 1245

N-(4-tert-butylphenyl)-4-chloro-3-(3-(pyrimidin-4-yl)pyridin-2-ylamino)benzamide

EXAMPLE 1246

4-chloro-N-(4-(dimethylamino)phenyl)-3-(3-(pyrimidin-4-yl)pyridin-2-ylamino)benzamide

EXAMPLE 1247

4-chloro-3-(3-(pyrimidin-4-yl)pyridin-2-ylamino)-N-(3-((S)-pyrrolidin-2-ylmethoxy)-5-(trifluoromethyl)phenyl)benzamide

EXAMPLE 1248

4-methyl-N-(3-(((((2S)-1-methyl-2-pyrrolidinyl)methyl)oxy)-5-(trifluoromethyl)phenyl)-3-((3-(4-pyrimidinyl)-2-pyridinyl)amino)benzamide

EXAMPLE 1249

N-(3-((2-chloroethyl)oxy)-5-(trifluoromethyl)phenyl)-4-methyl-3-((3-(4-pyrimidinyl)-2-pyridinyl)amino)benzamide While the examples described above provide processes for synthesizing compounds of Formulas I-III, other methods may be utilized to prepare such compounds. In the procedures described herein, the steps may be performed in an alternate order and may be preceded, or followed, by additional protection/deprotection steps as necessary. The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like, many of which were utilized in the Examples above. Reactions conditions such as temperature, duration, pressure, and atmosphere (inert gas, ambient) are known in the art and may be adjusted as appropriate for the reaction.

Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. Those of ordinary skill in the art know, or can easily establish, which protecting groups are suitable with the reactions described herein.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, 4$^{th}$ edition, Volume 15/1, Georg Thieme Verlag, Stuttgart (1974), in H.-D. Jakubke and H. Jescheit, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

Synthetic procedures may also be carried out where functional groups of starting compounds, which are not intended to take part in the reaction, may be present in unprotected form without the added step of protecting that group by, for example, one or more of the protecting groups mentioned above or taught in the references above.

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Suitable acid and base addition salts are further described in the Definition Section herein.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent (s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of the invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

These detailed descriptions fall within the scope, and serve to exemplify, the above-described General Synthetic Procedures which form part of the invention. These detailed descriptions are presented for illustrative purposes only and are not intended as a restriction on the scope of the invention.

Biological Evaluation

Although the pharmacological properties of the compounds of the invention (Formulas I-III) vary with structural change, in general, activity possessed by compounds of Formulas I-III may be demonstrated both in vitro as well as in vivo. Particularly, the pharmacological properties of the compounds of this invention may be confirmed by a number of pharmacological in vitro and/or in vivo assays. The following exemplified pharmacological assays have been carried out with the compounds according to the invention. Briefly, representative compounds of the invention were found to inhibit the activity of the Tie-2 receptor kinase, Aurora kinase, Lck, VEFG-R kinase, and others, selectively or non-selectively, at doses less than 25 µM. This activity demonstrates the utility of the compounds of the invention as protein kinase inhibitors and in the prophylaxis and treatment of immune diseases, proliferative disorders, etc., as described herein.

The following assays can be employed to determine the degree of activity of a compound as a protein kinase inhibitor.

TIE-2-Homogenous Time Resolved Flourescent (HTRF) Kinase Assay $IC_{50}$'s for the inhibition of the Tie-2 kinase enzyme for individual compounds were measured using an HTRF assay, utilizing the following procedure:

In a 96 well plate (available from Costar Co.) was placed 1 uL of each test and standard compound per well in 100% DMSO having a 25 uM final compound concentration (3-fold, 10 point dilution). To each well was added 20 uL of a reaction mix formed from Tie-2 (4.0 uL; of a 10 mM stock solution available from Gibco), 0.05% BSA (0.1 uL; from a 10% stock solution available from Sigma-Aldrich Co.), 0.002 mM of BLC HER-2 KKK (Biotinylated Long chain peptide; 0.04 uL; from a 0.002 mM stock solution), 0.01 mM concentration of ATP (0.02 uL; commercially available from Sigma-Aldrich Co.) and the remaining solution was water (15.84 uL) to make to a total volume of 20 uL/well.

The reaction was initiated in each well by adding 20 uL per well of an enzyme preparation consisting of a 50 mM concentration of Hepes (1.0 uL; from a 1000 mM stock solution commercially available from Gibco Co.), 0.05% concentration of BSA (0.1 uL), 4 mM of DTT (0.08 uL; from a 1000 mM stock solution available from Sigma-Aldrich Co.), a $2.4 \times 10^{-7}$ concentration of Tie-2 (0.02 uL, from a 4 mM concentration stock), with the remaining volume being water (18.8 uL) to dilute the enzyme preparation to a total volume of 20 uL. The plate was incubated for about 90 minutes at RT. After incubation, a 160 uL of a filtered detection mixture, prepared from 0.001 mg/ml of SA-APC (0.0765 uL; available as a 2.09 mg/ml stock solution from Gibco), 0.03125 nM concentration of Eu-Ab (0.1597 uL; available in a 31.3 nM stock solution from Gibco), with the remaining volume being Detection buffer (159.73 uL), was added to each well to stop the reaction therein. The plate was then allowed to equilibrate for about 3 hr and read on a Ruby Star fluorescent reader (available from BMG Technologies, Inc.) using a 4 parameter fit using activity base to calculate the corresponding $IC_{50}$'s for the test and standard compounds in each well. Examples 81a, 83, 84, 87-94, 97-101, 103-107, 109-113, 115-119, 122, 123, 125, 129, 131, 133-137, 139, 142-144, 146, 148-149, 151, 156, 159-164, 166, 168-170, 172-174, 200, 204, 211, 212, 223, 229, 243, 247-259, 261-270, 272-277, 279-282, 285-290, 292-294, 297, 299-302, 305-326, 328, 329, 331, 333-342, 344-347, 350-353, 355-371, 373-378, 381-401, 405-407, 409, 410, 412-418, 420-446, 448-472, 474-513, 515, 518-539, 542, 544, 552, 554, 556, 559, 563, 564, 566, 567, 573, 574, 580, 604, 606, 627, 630-638, 640-649, 651-661, 667, 669-671, 675-678, 680, 681, 684, 686, 687, 688-708, 710-717, 719-742, 744-747, 749-775, 778-782, 784, 785, 790-810, 812-867, 870-899, 901-912, 914, 918, 920, 923, 924, 926, 928, 929, 931-936, 939, 941-949, 951-953, 956-961, 963-975, 977-981, 983, 987, 989-992, 994, 995-998, 1000, 1002-1005, 1008-1020, 1022-1024, 1027-1031, 1033-1035, 1037, 1038, 1040-1058, 1070-1076, 1078-1086, 1090-1092, 1095-1117, 1119, 1120, 1126-1128, 1131-1136, 1138, 1141-1148, 1155, 1158-1165, 1167-1170, 1173, 1176-1179, 1181-1183, 1189-1193, and 1206-1213 were found to have $IC_{50}$'s for the inhibition of Tie-2 as measured by the HTRF assay of less than 5 uM.

TIE-2 Cell-Based Delfia Assay

Day 1-Plate Preparation

Three 175 ml flasks of EAHY926 cells were obtained from the University of N. Carolina. All cells were trypsinized (i.e., washed with 20 mL of PBS followed by 3 mL of trypsin-EDTA obtained from Gibco Co., cat. no. 25300-054, for 5 min at RT), then cultured in a growth medium solution containing DMEM (High glucose, Gibco Co., cat. no. 1965-092), 10% FBS serum (Gibco Co., cat. no. 10099-141) and P/S (Penicillin-Streptomycin-Glutamine; Gibco Co., cat. no. 10378-016) culture media. The cells were counted using a Z2® coulter® counter. The cells were plated in four 24-well tissue culture plates (Costar Co., cat. no. 353047) to initially contain $4 \times 10^5$ cells/ml per well, and then loaded to 500 uL volume having a final cell density of $2 \times 10^5$ cells/well. The cells were incubated for 5 or more hours at 37° C. under 5% $CO_2$. The DMEM+10% serum+P/S culture media was removed and the cells washed twice with 500 uL of PBS (without Ca+ and Mg++; Gibco Co., cat. no. 14190-136) at RT. 500 uL of 0.5% FBS+F12 (F12 nutrient mixture; Gibco Co., cat. no. 11765-054) was added to each well and the cells were incubated at 37° C. overnight (about 15 hr).

100 ug of anti-hTie2 antibody (R & D Systems, Inc., Cat. No. AF313) was diluted with 10 mL of ice-cold PBS to prepare a 10 ug/mL antibody concentration stock. A 96-well microplate (Perkin-Elmer Wallac, cat. no. AAAND-0001) was coated with 100 uL of the anti-Tie2 antibody stock and the coated plate was stored at 4° C. overnight.

Day 2-Compound Plate Preparation

The media in the microplate was replaced with a preparation of 500 uL DMEM+1% BSA (Bovine Serum Albumin; ICN Biomedicals, Inc., cat. no. 160069). 20 uL of a selected Tie2 reference compound was placed in a selected well of the 96-well plate, and diluted 1:4 with 100% DMSO from an initial concentration of about 10 mM to a final concentration of about 2.5 mM, then diluted 1:3 with 100% DMSO for a 10 point dilution to a final concentration of about 0.128 uM.

Test compounds (10 uL of a 10 mM concentration) were similarly diluted 1:4 with 100% DMSO to obtain a sample concentration of about 2.5 mM, then diluted 1:3 for a 10 point dilution to finally obtain a concentration of about 0.128 uM for each test compound. 20 uL of 100% DMSO served as positive controls, while and 10 uL of the 2.5 mM concentration of the reference compound served as the negative control.

A 2 uL aliquot from each well (test compounds, positive and negative controls) in the 96-well plate was added to designated wells in the 24-well cell culture plate (1:250).

The culture plate was incubated for 2.5 at 37° C. in an atmosphere of about 5% $CO_2$.

The Tie-2 ligand was stimulated with the following series of preparations: (1) about 0.5 mL of a protease inhibitor cocktail (Sigma-Aldrich Co., cat. no. P8340) was thawed; (2) to prepare the phosphatase inhibitor, a 300 mM $NaVO_4$ (Sigma-Aldrich Chem. Co., cat. no. S6508-10 g) stock solution in PBS was made and stored at RT. Two 1 mL aliquots of the $NaVO_4$ solution was prepared in separate two vials by adding 100 uL of the $NaVO_4$ stock solution to 900 uL RT PBS and each solution was activated by adding 6 uL of $H_2O_2$ to each vial. Both $NaVO_4$ solutions were mixed, wrapped in aluminum foil and stored at RT for 15 min.

The Delfia plates, containing 200 uL of PBS+0.1% TWEEN20, were washed three times and blocked by adding 200 uL of a diluted solution of 5% BSA (16 mL of stock 7.5% BSA solution, available from Perkin-Elmer Wallac, Cat. No. CR84-100, was diluted with 8 mL of room temperature PBS). The plates were then stored at room temperature for about one hour.

100 uL of 35% BSA solution was diluted with 3.4 mL of ice cold PBS to make a 1% BSA/PBS solution. 100 uL of this 1% BSA/PBS solution was diluted with 900 uL of ice cold PBS. hAng1 was reconstituted with 250 uL of ice cold PBS+0.1% BSA to make a 100 ug/mL concentration in solution. The solution was separated into 70 uL aliquots and stored at −80° C.

1 mL of the 30 mM solution of $NaVO_4$/PBS was diluted with 99 mL of ice cold PBS to form a 300 uM concentration. The solution was kept cold on ice. 210 uL of the activated $NaVO_4$ and 280 uL of the protease inhibitor preparation was added to 21 mL of RIPA buffer and kept cold on ice.

Dilute hAng1 and Stimulate Cells:

70uL 100ug/mL stock↑700uL in 1% BSA/DMEM (1:10) to 10ug/mL. Kept on ice.

5 uL of 10 ug/mL hAng1 was added to each well of the 24-well plate. The plate was shaken at 700 rpm at 37° C. for about 2.5 minutes.

After shaking, the wells were incubated for 7.5 min at 37° C. The media was removed and 400 uL of ice cold PBS+300 uM $NaVO_4$ was added. The wells were kept on ice for at least 5 min and washed 1× with ice cold PBS+300 uM $NaVO_4$. the wells were tapped against a dry paper towel. The cells were lysed with 150 uL of RIPA, 300 uM of $NaVO_4$, and 100 uL/1*$10^7$ cells protease inhibitor cocktail (purchased from Sigma-Aldrich, Cat. No. P8340). The solution was incubated, then shaken on ice for 30 min.

The BSA blocking solution was removed from the 96-well plates, which were then tapped dry. 140 uL of cell lysate was added to the antibody coated plate and the plate was incubated at 4° C. for 2 hours.

Delfia 25×Wash Buffer Concentrate (purchased from Perkin-Elmer Wallac, Cat. No. 1244-114) was diluted with 24 parts DDI water to obtain a washing solution. The lysate was removed and the plate was washed three times each with 400 uL of Delfia washing solution. The plate was tap dried with a paper towel.

The Anti-Phosphotyrosine clone 4G10 (purchased from Upsatebiotech Co., Cat. No. 05-321) was diluted with Delfia Assay Buffer (purchased from Perkin-Elmer Wallac, cat. no. 1244-1111) to make a solution of about 1 ug/mL in concentration. 100 uL of antibody was added to the plate and the plate was incubated at room temperature for one hour. The plate was again washed three times with 400 uL pre-time of the Delfia Washing solution.

The Eu-N1 labeled anti-mouse antibody (purchased from Perkin-Elmer Wallac, cat. no. AD0124) was diluted with Delfia Assay Buffer to make a solution of about 0.1 ug/mL in concentration.

100 uL of antibody was added to the plate and the plate was incubated at room temperature for one hour. The plate was again washed with Delfia Wash Buffer three times as described above. 100 uL of Delfia Enhancement Solution (purchased from Perkin-Elmer Wallac, Cat. No. 1244-105) was added to each well and the plate was incubated at room temperature for 5 min in the dark.

The Europium signal was measured with a Victor multilabel counter (Wallac Model 1420) while shaking (shake fast, linear, 0.10 mm for 1 s) using a Europium protocol.

Raw data was analyzed using a fit equation in XLFit. $IC_{50}$ values were then determined using Grafit software. Each of the examples described herein exhibited activity in the HTRF assay and the delfia cell-based assay with $IC_{50}$ values less than 10.0 μM.

The compounds of the invention also were found to have inhibitory activity with respect to other kinase enzymes as well. For example, the compounds were found to be inhibitors of Lck, Aurora kinase and/or c-Met enzymes. The exemplary assays described as follows were used to make such determination.

LCK-Homogenous Time Resolved Flourescent (HTRF) Kinase Assay

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 1 μL of compound in 100% DMSO, 15 μL of ATP and biotinylated Gastrin, and 15 μL of LCK KD GST (225-509) for a final volume of 40 μL. The final concentration of gastrin is 1.2 μM. The final concentration of ATP is 0.5 μM (Km app=0.6 μM+/−0.1) and the final concentration of LCK is 250 Pm, after a 3-fold, 10 point dilution. Buffer conditions are as follows: 50 mM HEPES pH 7.5, 50 mM NaCl, 20 mM MgCl, 5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween2O. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Assays for other kinases are done in a similar way as described above, varying the concentrations of enzyme, peptide substrate, and ATP added to the reaction, depending on the specific activity of the kinase and measured Km's for the substrates.

The following exemplary compounds exhibited activity of better than 1 μM in the LCK-HTRF Kinase Assay:

3-((3-(4-amino-1,3,5-triazin-2-yl)-2-pyridinyl)amino)-N-(3-(1-methylethyl)phenyl)benzamide;

4-fluoro-3-((3-(4-((3-(1H-imidazol-1-yl)propyl)amino)-1,3,5-triazin-2-yl)-2-pyridinyl)amino)-N-(3-(1-methylethyl)phenyl) benzamide;

4-methyl-3-((3-(4-pyrimidinyl)-2-pyridinyl)amino)-N-(4-(trifluoromethyl)phenyl)benzamide;

4-methyl-3-((3-(4-pyrimidinyl)-2-pyridinyl)amino)-N-(3-(trifluoromethyl)phenyl)benzamide;

N-((1R)-1-cyclohexylethyl)-4-methyl-3-((3-(4-pyrimidinyl)-2-pyridinyl)amino)benzamide;

4-(methyloxy)-3-((3-(4-pyrimidinyl)-2-pyridinyl)amino)—N-(3-(trifluoromethyl)phenyl)benzamide;

4-methyl-3-((3-(4-pyrimidinyl)-2-pyridinyl)oxy)-N-(3-(trifluoromethyl)phenyl)benzamide;

N-(3-chlorophenyl)-4-methyl-3-((3-(4-pyrimidinyl)-2-pyridinyl)amino)benzamide;

N-(3-(ethyloxy)phenyl)-4-methyl-3-((3-(4-pyrimidinyl)-2-pyridinyl)amino)benzamide;
N-(3-(1,1-dimethylethyl)-1-phenyl-1H-pyrazol-5-yl)-4-methyl-3-((3-(4-pyrimidinyl)-2-pyridinyl)oxy)benzamide;
N-(4-((3-(4-pyrimidinyl)-2-pyridinyl)oxy)-1-naphthalenyl)-N'-(3-(trifluoromethyl)phenyl)urea;
N-(5-cyclohexyl-2-(methyloxy)phenyl)-4-methyl-3-((3-(4-pyrimidinyl)-2-pyridinyl)oxy)benzamide;
N-(2-chloro-5-(trifluoromethyl)phenyl)-4-methyl-3-((3-(4-pyrimidinyl)-2-pyridinyl)oxy)benzamide;
4-methyl-3-((3-(2-(methylamino)-4-pyrimidinyl)-2-pyridinyl)oxy)-N-(3-(trifluoromethyl)phenyl)benzamide;
4-methyl-N-(2-(methyloxy)-5-(trifluoromethyl)phenyl)-3-((3-(4-pyrimidinyl)-2-pyridinyl)oxy)benzamide;
N-(5-cyclohexyl-2-(methyloxy)phenyl)-4-methyl-3-((3-(2-(methylamino)-4-pyrimidinyl)-2-pyridinyl)oxy)benzamide;
4-methyl-3-((3-(2-(methylamino)-4-pyrimidinyl)-2-pyridinyl)oxy)-N-(4-(methyloxy)-1,1'-biphenyl-3-yl)benzamide;
4-methyl-3-((3-(2-(methylamino)-4-pyrimidinyl)-2-pyridinyl)oxy)-N-(2-(1-piperidinyl)-5-(trifluoromethyl) 4-methyl-3-((3-(2-(methylamino)-4-pyrimidinyl)-2-pyridinyl)oxy)-N-(3-((((2R)-1-methyl-2-pyrrolidinyl)methyl) oxy)-5-(trifluoromethyl)phenyl)benzamide phenyl)benzamide;
N-(3-(1,1-dimethylethyl)-1-phenyl-1H-pyrazol-5-yl)-4-methyl-3-((3-(2-(methylamino)-4-pyrimidinyl)-2-pyridinyl)oxy)benzamide;
4-chloro-2-((2,6-dimethylphenyl)oxy)-3-pyridinyl)-N-methyl-2-pyrimidinamine;
N-(2-fluoro-5-(trifluoromethyl)phenyl)-N'-(4-((3-(2-(methylamino)-4-pyrimidinyl)-2-pyridinyl)oxy)-1-naphthalenyl)urea;
4-methyl-N-(3-(1-methylethyl)phenyl)-3-((3-(4-((3-(4-morpholinyl)propyl)amino)-1,3,5-triazin-2-yl)-2-pyridinyl) oxy)benzamide;
4-methyl-3-((3-(2-(methylamino)-4-pyrimidinyl)-5-(4-morpholinyl)-2-pyridinyl)oxy)-N-(3-(1-methylethyl)phenyl)benzamide;
4-methyl-3-((3-(2-(methylamino)-4-pyrimidinyl)-2-pyridinyl)oxy)-N-((1R)-1-phenylethyl)benzamide;
4-methyl-3-((3-(2-(methylamino)-4-pyrimidinyl)-5-(4-methyl-1-piperazinyl)-2-pyridinyl)oxy)-N-(3-(1-methylethyl) phenyl)benzamide;
N-(5-cyclohexyl-2-(methyloxy)phenyl)-3-((3-(4-((4-(dimethylamino)butyl)amino)-1,3,5-triazin-2-yl)-2-pyridinyl) oxy)-4-methylbenzamide;
3-((5-((3-(dimethylamino)propyl)(methyl)amino)-3-(2-(methylamino)-4-pyrimidinyl)-2-pyridinyl)oxy)-4-methyl-N-(3-(1-methylethyl)phenyl)benzamide;
4-methyl-3-((3-(2-(methylamino)-4-pyrimidinyl)-2-pyridinyl)oxy)-N-(4-(1-methylethyl)phenyl)benzamide;
4-methyl-3-((3-(2-(methylamino)-4-pyrimidinyl)-2-pyridinyl)oxy)-N-(3-((phenylmethyl)oxy)phenyl)benzamide;
4-methyl-3-((3-(2-(methylamino)-4-pyrimidinyl)-2-pyridinyl)oxy)-N-(3-(phenylmethyl)phenyl)benzamide;
4-methyl-3-((3-(2-(methylamino)-4-pyrimidinyl)-2-pyridinyl)oxy)-N-((3-(trifluoromethyl)phenyl)methyl) benzamide;
4-methyl-3-((3-(4-(methylamino)-1,3,5-triazin-2-yl)-2-pyridinyl)oxy)-N-(3-(1-methylethyl)phenyl)benzamide;
N-(5-cyclohexyl-2-(methyloxy)phenyl)-4-methyl-3-((3-(4-(methylamino)-1,3,5-triazin-2-yl)-2-pyridinyl)oxy) benzamide;
3-((3-(4-(ethylamino)-1,3,5-triazin-2-yl)-2-pyridinyl) oxy)-4-methyl-N-(3-(1-methylethyl)phenyl)benzamide;
N-(5-cyclohexyl-2-(methyloxy)phenyl)-3-((3-(4-(ethylamino)-1,3,5-triazin-2-yl)-2-pyridinyl)oxy)-4-methylbenzamide;
N-(5-(1,1-dimethylethyl)-2-(methyloxy)phenyl)-4-methyl-3-((3-(2-(methylamino)-4-pyrimidinyl)-2-pyridinyl) oxy) benzamide;
3-((3-(2-((2-(diethylamino)ethyl)amino)-4-pyrimidinyl) -2-pyridinyl)oxy)-4-methyl-N-(2-(4-morpholinyl)-5-(trifluoromethyl)phenyl)benzamide;
N-(5-cyclohexyl-2-(methyloxy)phenyl)-3-((3-(4-((2-hydroxyethyl)amino)-1,3,5-triazin-2-yl)-2-pyridinyl)oxy)-4-methylbenzamide;
5-(1,1-dimethylethyl)-N-(4-methyl-3-((3-(2-(methylamino)-4-pyrimidinyl)-2-pyridinyl)oxy)phenyl)-2-(methyloxy)benzamide;
N-(5-cyclohexyl-2-(methyloxy)phenyl)-4-methyl-3-((2'-(methylamino)-3,4'-bipyridin-2-yl)oxy)benzamide;
4-chloro-3-((3-(2-(methylamino)-4-pyrimidinyl)-2-pyridinyl)oxy)-N-(2-(1-piperidinyl)-5-(trifluoromethyl) phenyl) benzamide;
4-fluoro-3-((3-(2-(methylamino)-4-pyrimidinyl)-2-pyridinyl)oxy)-N-(2-(1-piperidinyl)-5-(trifluoromethyl) phenyl) benzamide;
N-(4-methyl-3-((3-(4-(methylamino)-1,3,5-triazin-2-yl)-2-pyridinyl)oxy)phenyl)-3-((trifluoromethyl)oxy) benzamide;
N-(2-((3-(dimethylamino)propyl)(methyl)amino)-5-(trifluoromethyl)phenyl)-4-methyl-3-((3-(2-(methylamino)-4-pyrimidinyl)-2-pyridinyl)oxy)benzamide;
N-(2-((3-(dimethylamino)propyl)(methyl)amino)-5-(trifluoromethyl)phenyl)-4-methyl-3-((3-(4-(methylamino)-1,3, 5-triazin-2-yl)-2-pyridinyl)oxy)benzamide;
N-(2-((3-(dimethylamino)propyl)(methyl)amino)-5-(trifluoromethyl)phenyl)-4-methyl-3-((2'-(methylamino)-3,4'-bipyridin-2-yl)oxy)benzamide;
4-methyl-3-((3-(4-(methylamino)-1,3,5-triazin-2-yl)-2-pyridinyl)oxy)-N-(2-(1-piperidinyl)-5-(trifluoromethyl) phenyl)benzamide;
N-(2-((3-(dimethylamino)propyl)(methyl)amino)-5-(trifluoromethyl)phenyl)-2-fluoro-5-((3-(4-(methylamino)-1,3, 5-triazin-2-yl)-2-pyridinyl)oxy)benzamide;
4-methyl-3-((3-(4-(methylamino)-1,3,5-triazin-2-yl)-2-pyridinyl)oxy)-N-(2-methyl-3-(trifluoromethyl)phenyl) benzamide;
4-methyl-3-((3-(4-(methylamino)-1,3,5-triazin-2-yl)-2-pyridinyl)oxy)-N-(3-((phenylmethyl)oxy)phenyl)benzamide;
4-methyl-3-((3-(4-(methylamino)-1,3,5-triazin-2-yl)-2-pyridinyl)oxy)-N-(3-(trifluoromethyl)phenyl)benzamide;
N-(5-(1,1-dimethylethyl)-3-isoxazolyl)-4-methyl-3-((3-(4-(methylamino)-1,3,5-triazin-2-yl)-2-pyridinyl)oxy) benzamide;
N-(2-chloro-5-(trifluoromethyl)phenyl)-4-methyl-3-((3-(4-(methylamino)-1,3,5-triazin-2-yl)-2-pyridinyl)oxy) benzamide;
N-(2-((3S)-3-(dimethylamino)-1-pyrrolidinyl)-5-(trifluoromethyl)phenyl)-4-methyl-3-((3-(2-(methylamino)-4-pyrimidinyl)-2-pyridinyl)oxy)benzamide;
4-methyl-3-((2'-(methyloxy)-3,4'-bipyridin-2-yl)oxy)-N-(3-(trifluoromethyl)phenyl)benzamide;
4-methyl-3-((3-(6-(methylamino)-4-pyrimidinyl)-2-pyridinyl)oxy)-N-(3-(trifluoromethyl)phenyl)benzamide;
3-(1-methylethyl)-N-(4-methyl-3-((2'-(methylamino)-3,4'-bipyridin-2-yl)oxy)phenyl)benzamide;
2-fluoro-5-((3-(2-(methylamino)-4-pyrimidinyl)-2-pyridinyl)oxy)-N-(2-(methyl(1-methyl-3-pyrrolidinyl)amino)-5-(trifluoromethyl)phenyl)benzamide;

N-(3-((3-(4-(methylamino)-1,3,5-triazin-2-yl)-2-pyridinyl)oxy)phenyl)-3-(1-methylethyl)benzamide;

5-(1,1-dimethylethyl)-N-(3-((3-(2-(methylamino)-4-pyrimidinyl)-2-pyridinyl)oxy)phenyl)-2-(methyloxy)benzamide;

3,5-dichloro-N-(3-((3-(2-(methylamino)-4-pyrimidinyl)-2-pyridinyl)oxy)phenyl)benzamide;

3-bromo-5-((3-(2-(methylamino)-4-pyrimidinyl)-2-pyridinyl)oxy)-N-(3-(1-methylethyl)phenyl)benzamide;

2-fluoro-4-methyl-5-((3-(2-(methylamino)-4-pyrimidinyl)-2-pyridinyl)oxy)-N-(2-(methyl(1-methyl-4-piperidinyl)amino)-5-(trifluoromethyl)phenyl)benzamide;

3-bromo-5-((3-(2-(methylamino)-4-pyrimidinyl)-2-pyridinyl)oxy)-N-(2-(methyl((3S)-1-methyl-3-pyrrolidinyl)amino)-5-(trifluoromethyl)phenyl)benzamide;

3-((3-(2-(methylamino)-4-pyrimidinyl)-2-pyridinyl)oxy)-N-(3-(1-methylethyl)phenyl)benzamide;

N-(3-((2'-(methylamino)-3,4'-bipyridin-2-yl)oxy)-5-(trifluoromethyl)phenyl)-3-(1-methylethyl)benzamide;

3-fluoro-5-((3-(4-(methylamino)-1,3,5-triazin-2-yl)-2-pyridinyl)oxy)-N-(3-(1-methylethyl)phenyl)benzamide;

3-(dimethylamino)-N-(3-((3-(2-(methylamino)-4-pyrimidinyl)-2-pyridinyl)oxy)-5-(trifluoromethyl)phenyl) benzamide;

N-(2-chloro-5-((2'-(methylamino)-3,4'-bipyridin-2-yl)oxy)phenyl)-3-(1-methylethyl)benzamide;

N-(2-((3-(dimethylamino)propyl)(methyl)amino)-5-(1-methylethyl)phenyl)-2-fluoro-5-((3-(4-(methylamino)-1,3,5-triazin-2-yl)-2-pyridinyl)oxy)benzamide;

2-fluoro-5-((3-(2-(methylamino)-4-pyrimidinyl)-2-pyridinyl)oxy)-N-(3-(1-methylethyl)phenyl)benzamide;

2-fluoro-5-((3-(2-(methylamino)-4-pyrimidinyl)-2-pyridinyl)oxy)-N-(2-(methyl(1-methyl-3-pyrrolidinyl)amino)-5-(trifluoromethyl)phenyl)benzamide;

N-(3-(1,1-dimethylethyl)phenyl)-2-fluoro-5-((3-(4-(methylamino)-1,3,5-triazin-2-yl)-2-pyridinyl)oxy)benzamide;

3-ethynyl-5-((3-(2-(methylamino)-4-pyrimidinyl)-2-pyridinyl)oxy)-N-(3-(trifluoromethyl)phenyl)benzamide;

N-(2-((3-(dimethylamino)propyl)(methyl)amino)-5-ethynylphenyl)-2-fluoro-5-((3-(2-(methylamino)-4-pyrimidinyl)-2-pyridinyl)oxy)benzamide;

N-(2-((3-(dimethylamino)propyl)(methyl)amino)-5-(pentafluoroethyl)phenyl)-2-fluoro-5-((3-(4-(methylamino)-1,3,5-triazin-2-yl)-2-pyridinyl)oxy)benzamide;

N-(3-chlorophenyl)-N'-(3-methyl-4-((3-(2-(methylamino)-4-pyrimidinyl)-2-pyridinyl)oxy)phenyl)urea;

N-(2-((3-(dimethylamino)propyl)(methyl)amino)-5-(1,1-dimethylethyl)phenyl)-2-fluoro-5-((2'-(methylamino)-3,4'-bipyridin-2-yl)oxy)benzamide;

N-(3-fluorophenyl)-N'-(3-methyl-4-((3-(2-(methylamino)-4-pyrimidinyl)-2-pyridinyl)oxy)phenyl)urea;

N-(2-chloro-5-(trifluoromethyl)phenyl)-N'-(3-methyl-4-((3-(2-(methylamino)-4-pyrimidinyl)-2-pyridinyl)oxy)phenyl) urea;

N-(3-fluoro-5-(trifluoromethyl)phenyl)-N'-(3-methyl-4-((3-(2-(methylamino)-4-pyrimidinyl)-2-pyridinyl)oxy)phenyl) urea;

N-(2-((3S)-3-(dimethylamino)-1-pyrrolidinyl)-5-(trifluoromethyl)phenyl)-N'-(4-((3-(4-(methylamino)-1,3,5-triazin-2-yl)-2-pyridinyl)oxy)-1-naphthalenyl)urea;

N-(2-((3-(dimethylamino)propyl)(methyl)amino)-5-(trifluoromethyl)phenyl)-N'-(4-((3-(4-(methylamino)-1,3,5-triazin-2-yl)-2-pyridinyl)oxy)-1-naphthalenyl)urea;

N-(2-(((3R)-3-(dimethylamino)-1-pyrrolidinyl)methyl)-5-(trifluoromethyl)phenyl)-N'-(4-((3-(4-(methylamino)-1,3,5-triazin-2-yl)-2-pyridinyl)oxy)-1-naphthalenyl)urea;

N-(3-chloro-2-((3-(dimethylamino)propyl)(methyl)amino)-5-(trifluoromethyl) phenyl)-2-fluoro-5-((3-(2-(methylamino)-4-pyrimidinyl)-2-pyridinyl)oxy)benzamide;

N-(3-bromophenyl)-N'-(3-methyl-4-((3-(2-(methylamino)-4-pyrimidinyl)-2-pyridinyl)oxy)phenyl)urea;

N-(2,5-dichlorophenyl)-N'-(3-methyl-4-((3-(2-(methylamino)-4-pyrimidinyl)-2-pyridinyl)oxy)phenyl)urea;

N-(5-chloro-2-methylphenyl)-N'-(3-methyl-4-((3-(2-(methylamino)-4-pyrimidinyl)-2-pyridinyl)oxy)phenyl)urea;

N-(3-methyl-4-((3-(2-(methylamino)-4-pyrimidinyl)-2-pyridinyl)oxy)phenyl)-3-(trifluoromethyl)benzamide;

N-(3-methyl-4-((3-(2-(methylamino)-4-pyrimidinyl)-2-pyridinyl)oxy)phenyl)-N'-(2-((2-(1-pyrrolidinyl)ethyl)oxy)-5-(trifluoromethyl)phenyl)urea;

N-(3-methyl-4-((3-(2-(methylamino)-4-pyrimidinyl)-2-pyridinyl)oxy)phenyl)-N'-(2-((4-methyl-1-piperazinyl)methyl)-5-(trifluoromethyl)phenyl)urea;

N-(5-(1,1-dimethylethyl)-2-(methyloxy)phenyl)-N'-(3-methyl-4-((3-(2-(methylamino)-4-pyrimidinyl)-2-pyridinyl)oxy)phenyl)urea;

N-(5-chloro-2-((3-(dimethylamino)propyl)(methyl)amino)phenyl)-N'-(3-methyl-4-((3-(2-(methylamino)-4-pyrimidinyl)-2-pyridinyl)oxy)phenyl)urea;

N-(5-cyclopropyl-2-((3-(dimethylamino)propyl)(methyl)amino)phenyl)-2-fluoro-5-((3-(2-(methylamino)-4-pyrimidinyl)-2-pyridinyl)oxy)benzamide;

N-(3-methyl-4-((3-(2-(methylamino)-4-pyrimidinyl)-2-pyridinyl)oxy)phenyl)-N'-(3-(1-methyl-4-piperidinyl)-5-(trifluoromethyl)phenyl)urea;

N-(5-chloro-2-(methyl((3R)-1-methyl-3-pyrrolidinyl)amino)phenyl)-N'-(3-methyl-4-((3-(2-(methylamino)-4-pyrimidinyl)-2-pyridinyl)oxy)phenyl)urea; and N-(2,5-dimethylphenyl)-N'-(3-methyl-4-((3-(2-(methylamino)-4-pyrimidinyl)-2-pyridinyl)oxy)phenyl)urea.

Aurora Kinase HTRF Assays

AuroraA-TPX2-Homogeneous Time Resolved Fluorescent (HTRF) Kinase Assay:

The AuroraA HTRF assay begins with AuroraA in the presence of ATP phosphorylating the biotinylated peptide PLK. The reaction incubates for about 120 min. Detection reagents are added to quench the reaction. These agents stop the reaction by diluting out the enzyme and chelating the metals due to the presence of EDTA. After addition, the assay is incubated overnight to allow the detection reagents to equilibrate.

The AuroraA HTRF assay comprises 1 µL of compound in 100% DMSO, 20 µL of ATP and biotinylated PLK, and 20 µL of AuroraA-TPX2 KD GST for a final volume of 41 µL. The final concentration of PLK is about 1 µM. The final concentration of ATP is about 1 µM (Km(app)=1 µM+/−0.1) and the final concentration of AuroraA is about 5 nM. Buffer conditions are as follows: 60 mM HEPES pH 7.5, 25 mM NaCl, 10 mM MgCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0005 mg/mL, and europilated anti-phosphoPLK Ab (Eu-anti-PLK) at a final conc of 0.02 nM.

The assay plate is read in either a Discovery or a RubyStar. The eu-anti-PLK is excited at 320 nm and emits at 615 nm to excite the SA-APC which in turn emits at 655 nm. The ratio of SA-APC at 655 nm (excited due to close proximity to the Eu-anti-PLK because of phosphorylation of the peptide) to free Eu-anti-PLK at 615 nm will give substrate phosphorylation.

The following exemplary compounds 211, 223, 243, 271, 282, 299, 302, 339, 493, 529, 539, 542-554, 556-559, 563, 564, 566-568, 570, 573-574, 577, 606, 627, 659, 667-673, 675-679, 681, 682, 684-686, 688-689, 698-702, 703-708, 776-785, 787-790, 792-794, 799, 800, 802-811, 815-818, 820, 823, 825-827, 834, 836-839, 841, 843, 844, 846, 851, 852, 859, 860, 862-864, 867, 869, 873-875, 878, 880-921, 923-1058, 1070-1112, 1114-1117, 1119, 1120-1136, 1153-1165, 1166-1168, 1172-1173, 1179, 1181-1183, and 1188-1193, exhibited activity of better than 10 µM in the Aurora kinase A HTRF assay.

AuroraB-Homogeneous Time Resolved Fluorescent (HTRF) Kinase Assay:

The AuroraB HTRF assay begins with AuroraB in the presence of ATP phosphorylating the biotinylated peptide Histone H3. The reaction incubates for about 90 min. the reaction is quenched by addition of detection reagents, which stop the reaction by diluting out the enzyme and chelating the metals due to the presence of EDTA. After addition, the assay is incubated for about 60 min to allow detection reagents to equilibrate.

The AuroraB HTRF assay comprises 1 µL of compound in 100% DMSO, 20 µL of ATP and biotinylated Histone H3, and 20 µL of AuroraB FL His for a final volume of 41 µL. The final concentration of Histone H3 is 0.1 µM. The final concentration of ATP is 23 µM (Km(app)=23 µM+/−2.6) and the final concentration of AuroraB is 400 pM. Buffer conditions are as follows: 50 mM HEPES pH 7.5, 5 mM NaCl, 0.5 mM MgCl, 0.5 mM MnCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.001 mg/mL, and europilated anti-phosphoHistoneH3 Ab (Eu-anti-H is H3) at a final conc of 0.064 nM.

The assay plate is read in either a Discovery or a RubyStar. The eu-anti-H isH3 is excited at 320 nm and emits at 615 nm to excite the SA-APC which in turn emits at 655 nm. The ratio of SA-APC at 655 nm (excited due to close proximity to the Eu-anti-H is H3 because of phosphorylation of the peptide) to free Eu-anti-H isH3 at 615 nm will give substrate phosphorylation.

The following exemplary compounds 100, 107, 111, 116, 117, 139, 169, 172-174, 223, 229, 243, 282, 299, 302, 339 370, 493, 552, 556-559, 563, 564, 566-568, 570, 572-574, 577, 580, 581, 604, 606, 628, 659, 670, 678, 702, 706, 776, 778, 780-783, 789-793, 796, 798, 799, 802, 806, 810, 818, 837, 841, 888-890, 897, 898, 899, 903, 905, 907, 914, 917, 928, 930, 939, 943, 945, 948, 952, 953, 956, 961, 966-968, 970, 971, 973-975, 978, 979, 990-991, 994, 995, 997-1020, 1022-1058, 1070-1117, 1119-1151, 1159-1170, 1172-1173, 1179, 1181-1183, and 1188-1193, exhibited activity of better than 10 µM in the Aurora kinase B HTRF assay.

Aurora Kinase Cell-based Assays

HeLa Cell 1-hour Phospho-Histone Assay

The purpose of this assay is to test the inhibitory effect of Aurora compounds with respect to phosphorylation of Histone H3 in the cellular context. HeLa cells ($9 \times 10^4$/well) are plated in black 96-well flat-bottom tissue culture plates and incubated for 40 hours prior to compound addition. Compounds are serially diluted in DMSO, followed by dilution into MEM containing 10 mM HEPES; 10ul/well of diluted compounds are added to cells (0.5% DMSO final). Cells are incubated for 1 hour at 37° C. in 5% $CO_2$. Cells are then fixed with 3.7% formaldehyde for 10 minutes, washed with wash buffer (1% goat serum and 0.1% Tween 20 in PBS), then permeabilized with 0.5% Triton X in PBS for 15 minutes. After washing with wash buffer, cells are incubated with primary antibody (Upstate #06-507 anti-phospho-histone (Ser 10) antibody (pHH3) for 1 hour at 10 ug/ml. After 2 washes with wash buffer, cells are incubated with secondary antibody (Molecular Probes #A11034 goat anti-rabbit Alexa-488 for 1 hour at 1ug/ml+Hoechst 33342 nuclear dye at 1ug/ml (Molecular Probes). Cells are washed 2 times with wash buffer, and buffer replaced with PBS. Plates are scanned on the Cellomics Array Scan (6 fields, ~2000 cells/well) and % of cells that are pHH3 positive were calculated using the Cellomics algorithm.

Flow Cytometry-Based Mitotic Synchronized HeLa Cell 1-Hour Autophospho-Aurora A (thr-288) Assay The purpose of this assay is to measure Aurora A threonine-288 autophosphorylation flux after 1 hour of treatment with aurora inhibitor compounds in the cellular context. HeLa cells are blocked with 0.1ug/ml nocodazole (Sigma-Aldrich) for 12 hours in p100 round tissue culture plates ($5 \times 10^6$/plate) and removed the semi-adherent mitotic cells by pipetting. The cells are then added onto 96-well, 0.2 ml PCR tube strips ($3 \times 10^5$/well). Compounds are serially diluted in DMSO, followed by dilution into complete media. Cells are incubated for 1 hour at 37° C. in 5% $CO_2$, pelleted and fixed in 1% formaldehyde for 15 minutes at room temperature followed by fixed in 90% MEOH. The cells are washed with 200ul wash/stain buffer (1×PBS supplemented with 1% BSA) and 0.2% Triton X-100. The cells are stained in 30 ul wash/stain buffer using antibody cocktail containing 2.5 ug/ml anti-total Aurora A (BD Bioscience) and 1:150 dilution anti-phospho-Aurora A threonine-288 (Cell Signaling Technologies). Cells are then incubated for 2 hours at room temperature. The cells are washed twice with 200 ul wash/stain buffer. 1ug/ml goat anti-rabbit alexa-647 (Molecular Probes) and 1ug/ml goat anti-mouse alexa-488 (Molecular Probes) are used to detect unconjugated primary antibodies by incubating for 30 minutes at room temperature in the dark. The cells are washed and resuspended in 200 ul DNA counterstain containing 20 mg/ml of propidium iodide (PI) (BD Bioscience) and 2 ul/ml RNase (Roche) in PBS. The data acquisition is obtained on a LSR II flow cytometer (BD Bioscience) supported by a 96-well plate sipper (Cytek). Double discrimination gating (FL-2 area vs. width) determines single events. The G2M (+) and Aurora A-alexa-488 (+) cells are gated, this population of double positive gated cells are then plotted on a histogram measuring phospho-Aurora A threonine-288-alexa647 signal intensity flux (linear). The Aurora A inhibitors shift the histogram from a phospho (+) gate to a phospho (−) gate in a dose dependent manner. EC50s are determined using batching exporting % phospho-Aurora A (+) values (11-point dose curve) for each compound. DMSO controls are used for each row on the 96-well plate. The EC50s are determined using GraFit (Erithacus Software Limited).

HeLa Cell 24-hour DNA Ploidy Phenotype Assay

The purpose of this assay is to test the effect of Aurora compounds with respect to causing an increase in polyploidy status in the cellular context. HeLa cells ($1.2 \times 10^4$/well) are plated in black 96-well flat-bottom tissue culture plates and incubated for 24 hours prior to compound addition. Compounds are serially diluted in DMSO, followed by dilution into MEM containing 10% FBS; 10 ul/well of diluted compounds are added to cells (0.5% DMSO final). Cells are incubated for 24 hrs at 37° C. in 5% $CO_2$. Cells are then fixed with 3.7% formaldehyde for 10 minutes, washed with 1×PBS, then permeabilized with 0.5% Triton X in PBS for 15 minutes. After washing cells with 1×PBS, cells are incubated with Hoechst 33342 nuclear dye at 0.5 ug/ml (Molecular Probes) in 1×PBS. Cells are washed 1 time with PBS, and then left in PBS. Plates are scanned on an Cellomics ArrayScan (6 fields, ~2000 cells/well) and % of cells that have a 4N and above 4N DNA content are calculated using the a Cellomic algorithm.

c-MET Cell-Based Autophosphorylation Assay

Human PC3 and mouse CT26 cells are available obtained from ATCC. The cells were cultured in a growth medium containing RPMI 1640, penicillin/streptomycin/glutamine (1×) and 5% FBS. $2 \times 10^4$ cells in medium were plated per well in a 96 well plate and incubated at 37° C. overnight. The cells were serum-starved by replacing the growth media with basic medium (DMEM low glucose+0.1 BSA, 120 μL per well) at 37° C. for 16 h. Compounds (either 1 mM and 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 μL per well) were diluted with basic medium (240 μL) in a 96 well plate. The cells were washed once with basic medium (GIBCO, DMEM 11885-076) then compound solution was added (100 μL). The cells were incubated at 37° C. for 1 h. A (2 mg/mL) solution of CHO-HGF (7.5 μL) was diluted with 30 mL basic medium to provide a final concentration of 500 ng/mL. This HGF-containing media (120 μL) was transferred to a 96 well plate. Compounds (1.2 μL) was added to the HGF-containing media and mixed well. The mixture of media/HGF/compound (100 μL) was added to the cells (final HGF concentration–250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 μL, Roche Protease inhibitor (Complete, #1-697-498) 2 tablets, Phosphatase Inhibitor II (Sigma, #P-5726) 200 μL, and a sodium vanadate solution (containing 900 μL PBS, 100 μL 300 mM $NaVO_3$, 6 μl $H_2O_2$ (30% stock) and stirred at RT for 15 min) (90 μL). The cells were washed once with ice cold 1×PBS (GIBCO, #14190-136), then lysis buffer (60 μL) was added and the cells were incubated on ice for 20 min.

The IGEN assay was performed as follows: Dynabeads M-280 streptavidin beads were pre-incubated with biotinylated anti-human HGFR (240 μL anti-human-HGFR (R&D system, BAF527 or BAF328) @ 100 μg/mL+360 μL Beads (IGEN #10029+5.4 μL buffer–PBS/1% BSA/0.1% Tween20) by rotating for 30 min at RT. Antibody beads (25 μL) were transferred to a 96 well plate. Cell lysate solution (25 μL) was transferred added and the plate was shaken at RT for 1 h. Anti-phosphotyrosine 4G10 (Upstate 05-321) (19.7 μL antibody+6 mL 1×PBS) (12.5 μL) was added to each well, then incubated for 1 h at RT. Anti-mouse IgG ORI-Tag (ORIGEN #110087) (24 μL Antibody+6 mL buffer) (12.5 μL) was added to each well, then incubated at RT for 30 min. 1×PBS (175 μL) was added to each well and the electrochemiluminescence was read by an IGEN M8. Raw data was analyzed using a 4-parameter fit equation in XLFit. $IC_{50}$ values are then determined using Grafit software.

The following exemplary compounds exhibited activity of better than 25 μM in the c-Met cell-based autophosphorylation assay:

N-(3-chlorophenyl)-4-methyl-3-((3-(4-pyrimidinyl)-2-pyridinyl)amino)benzamide;
N-(1H-indazol-5-yl)-4-methyl-3-((3-(4-pyrimidinyl)-2-pyridinyl)amino)benzamide N-(1H-indazol-6-yl)-4-methyl-3-((3-(4-pyrimidinyl)-2-pyridinyl)amino)benzamide;
N-(3-(ethyloxy)phenyl)-4-methyl-3-((3-(4-pyrimidinyl)-2-pyridinyl)amino)benzamide;
N-(3-methyl-4-((3-(4-pyrimidinyl)-2-pyridinyl)oxy) phenyl)-3-(trifluoromethyl)benzamide;
N-(3-methyl-4-((3-(4-pyrimidinyl)-2-pyridinyl)oxy) phenyl)-N'-(3-(trifluoromethyl)phenyl)urea;
N-(3-methyl-4-((3-(4-pyrimidinyl)-2-pyridinyl)oxy) phenyl)benzenesulfonamide;
N-(2-fluoro-4-((3-(4-pyrimidinyl)-2-pyridinyl)oxy) phenyl)-N'-(3-(trifluoromethyl)phenyl)urea;
N-(4-((3-(4-pyrimidinyl)-2-pyridinyl)oxy)phenyl)-N'-(3-(trifluoromethyl)phenyl)urea;
N-(3,5-dichloro-4-((3-(4-pyrimidinyl)-2-pyridinyl)oxy) phenyl)-N'-(3-(trifluoromethyl)phenyl)urea;
N-(8-((3-(4-pyrimidinyl)-2-pyridinyl)oxy)-5-quinolinyl)-N'-(3-(trifluoromethyl)phenyl)urea;
N-(3-methyl-4-((3-(2-(methylamino)-4-pyrimidinyl)-2-pyridinyl)oxy)phenyl)-N'-phenylurea;
phenyl 3-methyl-4-((3-(2-(methylamino)-4-pyrimidinyl)-2-pyridinyl)oxy)phenylcarbamate;
N-(3-methyl-4-((3-(2-(methylamino)-4-pyrimidinyl)-2-pyridinyl)oxy)phenyl)benzamide;
N-cyclohexyl-N'-(3-methyl-4-((3-(2-(methylamino)-4-pyrimidinyl)-2-pyridinyl)oxy)phenyl)urea; and
N-cyclopentyl-N'-(3-methyl-4-((3-(2-(methylamino)-4-pyrimidinyl)-2-pyridinyl)oxy)phenyl)urea.

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 μL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 μL of each compound dilution are diluted further in a total of 1 mL DMEM+10% FBS+antibiotics (400× dilution). Medium containing 0.25% DMSO is also prepared for the 0 μM compound sample. At the 22 h timepoint, the medium is removed from the cells, and 100 μL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 μL of each will be added to the cells (110 μL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data is collected and analyzed using a 4-parameter fit equation in XLFit. $IC_{50}$ values are then determined.

Indications

Accordingly, compounds of the invention are useful for, but not limited to, the prevention or treatment of angiogenesis related diseases. The compounds of the invention have kinase modulatory activity in general, and kinase inhibitory activity in particular. In one embodiment of the invention, there is provided a method of modulating a protein kinase enzyme in a subject, the method comprising administering to the subject an effective dosage amount of a compound of a compound of Formulas I-III. In another embodiment, the kinase enzyme is c-Met, b-Raf, Aurora kinase, KDR, Lck or tie2.

Various of the compounds of the invention have selective inhibitory activity for specific kinase receptor enzymes, including Tie-2, Lck, VEGFR/KDR and Aurora kinase. Accordingly, the compounds of the invention would be useful in therapy as antineoplasia agents or to minimize deleterious effects of Tie-2, Lck, VEGF and/or Aurora kinase.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). The compounds are useful for the treatment of neoplasia selected from lung cancer, colon cancer and breast cancer.

The compounds would also be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

Based on the ability to modulate kinases impacting angiogenesis, the compounds of the invention are also useful in treatment and therapy of proliferative diseases. Particularly, these compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further applicable to the treatment of inflammation, e.g. inflammatory disease or condition, of connective tissues including dermatomyositis and myositis.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention can also be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the invention are also useful in the treatment of ulcers including bacterial, fungal, Mooren ulcers and ulcerative colitis.

The compounds of the invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity. The compounds of the invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration. The compounds of the invention are also useful in the treatment of cardiovascular conditions such as atherosclerosis, restenosis, arteriosclerosis, vascular occlusion and carotid obstructive disease.

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the invention are also useful in the treatment of diabetic conditions such as diabetic retinopathy and microangiopathy.

The compounds of the invention may also act as inhibitors of other protein kinases, e.g. src, fgf, c-Met, ron, ckit and ret, and thus be effective in the treatment of diseases associated with other protein kinases.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations

Also embraced within this invention is a class of pharmaceutical compositions comprising the active compounds of Formulas I-III in association with one or more non-toxic, pharmaceutically-acceptable carriers and/or diluents and/or adjuvants (collectively referred to herein as "carrier" materials) and, if desired, other active ingredients. The pharmaceutically active compounds of this invention can be processed in accordance with conventional methods of pharmacy to produce medicinal agents for administration to patients, including humans and other mammals.

The compounds of the present invention may be administered to a subject by any suitable route, preferably in the form of a pharmaceutical composition, adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formulae I and II may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the invention consists of alkylating-type antineoplastic agents. Suitable alkylating-type antineoplastic agents may be selected from but not limited to the group consisting of Shionogi 254-S, aldophosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the compounds of the invention may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the compounds of the invention may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing is merely illustrative of the invention and is not intended to limit the invention to the disclosed compounds. Variations and changes, which are obvious to one skilled in the art, are intended to be within the scope and nature of the invention, which are defined in the appended claims.

All mentioned references, patents, applications and publications, are hereby incorporated by reference in their entirety, as if here written.

What is claimed is:

1. A compound of Formula I:

$$\text{(structure I with substituents } R^1, R^2, R^3, R^4 \text{ on rings A, B, D, E and G linker to ring with } H^1\text{-}H^5\text{)}$$

or a pharmaceutically acceptable salt thereof, wherein

A is N or $CR^{10}$;
B is N or $CR^{11}$, provided that one of and not both of A and B is N;
D is $CR^{12}$;
E is N;
G is $NR^{13}$, O, S, $CR^{13}R^{13}$ or $CR^{13}R^{14}$;
$H^1$ is N or $CR^5$;
$H^2$ is N or $CR^6$;
$H^3$ is $CR^7$;
$H^4$ is $CR^8$;
$H^5$ is N or $CR^9$;
$R^1$ is H, halo, haloalkyl, $NO_2$, CN, $NR^{13}R^{13}$, $OR^{13}$, $SR^{13}$, $(CHR^{13})_n R^{13}$, or $R^{15}$; alternatively $R^1$ taken together with $R^{10}$ forms a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}$, $NR^{13}R^{14}$ or $NR^{14}R^{14}$;
$R^2$ is H, halo, haloalkyl, oxo, $NO_2$, CN, $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C(O)R^{13}$, $NR^{13}C(O)R^{14}$, $NR^{13}C(O)NR^{13}R^{13}$, $NR^{13}C(O)$ $C(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C$ $(O)NR^{13}R^{14}$ or $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted with 1-3 substituents of $R^{13}$;
each of $R^3$ and $R^4$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $C(O)NR^{13}R^{13}$, $C(O)NR^{13}R^{14}$, $NR^{13}C(O)$ $R^{13}$, $NR^{13}C(O)R^{14}$, $S(O)_2R^{13}$, $S(O)_2NR^{13}R^{13}$, $NR^{13}S$ $(O)_2NR^{13}R^{13}$, $NR^{13}S(O)_2R^{13}$, $NR^{13}S(O)_2R^{14}$, $C_{1-10}$alkyl, $C_{1-10}$alkenyl, $C_{1-10}$alkynyl, $C_{3-8}$cycloalkyl or $C_{4-8}$cycloalkenyl, wherein the $C_{1-10}$alkyl, $C_{1-10}$alkenyl, $C_{1-10}$alkynyl, $C_{3-8}$cycloalkyl and $C_{4-8}$cycloalkenyl is optionally substituted independently with 1-3 substituents of $R^{13}$;
each of $R^5$ and $R^6$, independently, is H, halo, haloalkyl, $NO_2$, CN, $SR^{13}$, $OR^{13}$, $NR^{13}R^{13}$, $NR^{13}R^{14}$, $C(O)R^{13}$, $COOR^{13}$, $C(O)NR^{13}R^{13}$, $C(O)NR^{13}R^{14}$, $NR^{13}C(O)$ $R^{13}$, $NR^{13}C(O)R^{14}$, $NR^{13}C(O)NR^{13}R^{13}$, $NR^{13}C(O)$ $(O)R^{13}$, $NR^{13}(COOR^{13})$, $OC(O)NR^{13}R^{13}$, $S(O)_2R^{13}$, $S(O)_2NR^{13}R^{13}$, $NR^{13}S(O)_2NR^{13}R^{13}$, $NR^{13}S(O)_2R^{13}$, $NR^{13}S(O)_2R^{14}$, $NR^{13}C(O)C(O)NR^{13}R^{13}$, $NR^{13}C(O)C$ $(O)NR^{13}R^{14}$, $C_{1-10}$alkyl, $C_{1-10}$alkenyl, $C_{1-10}$alkynyl, or $C_{3-8}$cycloalkyl, wherein the $C_{1-10}$alkyl, $C_{1-10}$alkenyl, $C_{1-10}$alkynyl, and $C_{3-8}$cycloalkyl is optionally substituted independently with 1-3 substituents of $R^{13}$; alternatively $R^5$ taken together with $R^6$ forms a phenyl or pyridyl ring, each of which is optionally substituted independently with 1-3 substituents of $C_{1-10}$alkyl, halo, haloalkyl, $NO_2$, CN or OCF3;
one of $R^7$ and $R^8$, independently, is H, halo, haloalkyl, haloalkoxyl, CN, OH, $NO_2$, $NH_2$, SH, acetyl, $C_{1-10}$-alkyl, $C_{2-10}$-alkenyl, $C_{2-10}$-alkynyl, $C_{1-10}$-alkylamino-, $C_{1-10}$-dialkylamino-, $C_{1-10}$-alkoxyl or $C_{1-10}$-thioalkoxyl;
the other of $R^7$ and $R^8$, independently, is $SR^{13}$, $OR^{13}$, $NR^{13}R^{13}$, $NR^{13}R^{14}$, $C(O)R^{13}$, $COOR^{13}$, $OC(O)R^{13}$, $C(O)C(O)R^{13}$, $C(O)NR^{13}R^{13}$, $C(O)NR^{13}R^{14}$, $NR^{13}C$ $(O)R^{13}$, $NR^{13}(COOR^{13})$, $OC(O)NR^{13}R^{13}$, $NR^{13}C(O)C$ $(O)R^{13}$, $NR^{13}C(O)NR^{13}R^{13}$, $NR^{13}C(O)NR^{13}R^{14}$, $NR^{13}C(O)C(O)NR^{13}R^{13}$, $NR^{13}C(O)C(O)NR^{13}R^{14}$, $C(S)R^{13}$, $C(S)NR^{13}R^{13}$, $C(S)NR^{13}R^{14}$, $NR^{13}C(S)R^{13}$, $NR^{13}C(S)R^{14}$, $NR^{13}C(S)NR^{13}R^{13}$, $NR^{13}C(S)NR^{13}R^{14}$, $S(O)_2R^{13}$, $S(O)_2NR^{13}R^{13}$, $S(O)_2NR^{13}R^{14}$, $NR^{13}S(O)_2$ $NR^{13}R^{13}$ $NR^{13}S(O)_2R^{13}$, $NR^{13}S(O)_2R^{14}$ or $C_{1-10}$alkyl optionally substituted with 1-3 substituents of $R^{15}$ or $R^{16}$;
each of $R^9$, $R^{10}$, $R^{11}$ and $R^{12}$, independently, is H, $R^{13}$, halo, haloalkyl, $NO_2$, CN, $SR^{13}$, $OR^{13}$, $NR^{13}R^{13}$, $NR^{13}R^{14}$, $C(O)R^{13}$, $C(O)NR^{13}R^{13}$, $C(O)NR^{13}R^{14}$, $NR^{13}C(O)R^{13}$, $NR^{13}C(O)R^{16}$, $S(O)_2R^{13}$, $S(O)_2$ $NR^{13}R^{13}$, $S(O)_2NR^{13}R^{14}$, $NR^{13}S(O)_2NR^{13}R^{13}$, $NR^{13}S$ $(O)_2R^{13}$ or $NR^{13}S(O)_2R^{14}$;
each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with 1-3 substituents of $R^{15}$, $R^{16}$ or $R^{18}$;
$R^{14}$ is $C(O)R^{18}$, $COOR^{18}$, $S(O)_2 R^{18}$ or $R^{16}$; alternatively $R^{14}$ taken together with $R^{13}$ forms a partially or fully unsaturated 5- or 6-membered ring of carbon atoms optionally including 1-3 heteroatoms selected from O, N and S, and the ring optionally substituted independently with 1-3 substituents of oxo, halo, haloalkyl, $NO_2$, CN, $R^{17}$ or $R^{18}$;
$R^{15}$ is halo, haloalkyl, oxo, $NO_2$, CN, $SR^{18}$, $OR^{18}$, $OC(O)$ $R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2$ $NR^{16}R^{18}$, $S(O)_2NR^{18}R^{18}$, $S(O)_2R^{16}$, $S(O)_2R^{18}$, $C(O)C$ $(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;
$R^{16}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with 1-3 substituents of $R^{17}$, $R^{18}$ or $R^{20}$;
$R^{17}$ is halo, haloalkyl, oxo, $NO_2$, CN, $SR^{18}$, $OR^{18}$, $OC(O)$ $R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2$ $NR^{18}R^{18}$, $S(O)_2NR^{18}R^{20}$, $S(O)_2R^{18}$, $S(O)_2R^{20}$, $C(O)C$ $(O)R^{18}$, $NR^{18}C(O)NR^{18}R^{18}$, $NR^{18}C(O)NR^{18}R^{20}$, NR$^{18}$C(O)C(O)R$^{18}$, NR$^{18}$C(O)R$^{18}$, NR$^{18}$C(O)R$^{20}$, NR$^{18}$(COOR$^{18}$), NR$^{18}$(COOR$^{20}$), NR$^{18}$S(O)$_2$NR$^{18}$R$^{18}$, NR$^{18}$S(O)$_2$NR$^{18}$R$^{20}$, NR$^{18}$S(O)$_2$R$^{18}$, NR$^{18}$S(O)$_2$R$^{20}$, NR$^{18}$C(O)C(O)NR$^{18}$R$^{18}$ or NR$^{18}$C(O)C(O)NR$^{18}$R$^{20}$;

each R$^{18}$, independently, is H, C$_{1-10}$alkyl, C$_{1-10}$alkenyl, C$_{1-10}$alkynyl, C$_{3-8}$cycloalkyl, C$_{4-8}$cycloalkenyl, R$^{19}$ or R$^{20}$, each of which is optionally substituted with 1-3 substituents of R$^{21}$;

R$^{19}$, independently, is C(O)R$^{20}$, C(O)R$^{21}$, COOR$^{20}$, COOR$^{21}$, S(O)$_2$R$^{20}$or S(O)$_2$R$^{21}$;

R$^{20}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of R$^{21}$;

each R$^{21}$, independently, is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynl, C$_{3-10}$-cycloalkyl, C$_{4-10}$-cycloalkenyl, C$_{1-10}$alkylamino-, C$_{1-10}$-dialkylamino-, C$_{1-10}$-alkoxyl, C$_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl; and n is 0, 1, 2, 3, 4 or 5, provided that (1) no more than one of H$^1$, H$^2$, H$^3$, H$^4$ and H$^5$ is N; (2) when either of R$^1$ or R$^2$ is substituted or unsubstituted NH-phenyl, then no more than four of R$^5$, R$^6$, R$^7$, R$^8$ and R$^9$ is H; and (3) when R$^1$ is phenyl, then neither of R$^6$ and R$^8$ is, independently, NO$_2$.

2. The compound of claim 1, wherein A is N, B is CR$^{11}$.

3. The compound of claim 1, wherein B is N and A is CR$^{10}$.

4. The compound of claim 2, wherein

R$^2$ is H, halo, NO$_2$, CN, C$_{1-10}$alkyl or C$_{1-10}$alkoxyl.

5. The compound of claim 2, wherein

R$^1$ is H, halo, haloalkyl, NO$_2$, NR$^{13}$R$^{13}$ or —(CHR$^{13}$)$_n$NR$^{18}$R$^{18}$;

G is NR$^{13}$, O or S; and

R$^2$ is H, halo, NO$_2$, CN, C$_{1-10}$alkyl or C$_{1-10}$alkoxyl.

6. The compound of claim 2, wherein

R$^1$ is H, halo, haloalkyl, NO$_2$, NR$^{13}$R$^{13}$ or —(CHR$^{13}$)$_n$NR$^{18}$R$^{18}$;

R$^2$ is H, halo, NO$_2$, CN, C$_{1-10}$alkyl or C$_{1-10}$alkoxyl;

G is O or S;

each of R$^3$, R$^4$ and R$^9$, independently, is H; and

D is CH.

7. The compound of claim 1 wherein

R$^7$ is SR$^{13}$, OR$^{13}$, NR$^{13}$R$^{13}$, NR$^{13}$R$^{14}$, C(O)R$^{13}$, COOR$^{13}$, OC(O)R$^{13}$, C(O)C(O)R$^{13}$, C(O)NR$^{13}$R$^{13}$, C(O)NR$^{13}$R$^{14}$, NR$^{13}$C(O)R$^{13}$, NR$^{13}$(COOR$^{13}$), OC(O)NR$^{13}$R$^{13}$, NR$^{13}$C(O)C(O)R$^{13}$, NR$^{13}$C(O)NR$^{13}$R$^{13}$, NR$^{13}$C(O)NR$^{13}$R$^{14}$, NR$^{13}$C(O)C(O)NR$^{13}$R$^{13}$, NR$^{13}$C(O)C(O)NR$^{13}$R$^{14}$, C(S)R$^{13}$, C(S)NR$^{13}$R$^{13}$, C(S)NR$^{13}$R$^{14}$, NR$^{13}$C(S)R$^{13}$, NR$^{13}$C(S)R$^{14}$, NR$^{13}$C(S)NR$^{13}$R$^{13}$, NR$^{13}$C(S)NR$^{13}$R$^{14}$, S(O)$_2$R$^{13}$, S(O)$_2$NR$^{13}$R$^{13}$, S(O)$_2$NR$^{13}$R$^{14}$, NR$^{13}$S(O)$_2$NR$^{13}$R$^{13}$, NR$^{13}$S(O)$_2$R$^{13}$, NR$^{13}$S(O)$_2$R$^{14}$ or C$_{1-10}$alkyl optionally substituted with 1-3 substituents of R$^{15}$ or R$^{16}$; and R$^8$ is H, halo, haloalkyl, haloalkoxyl, CN, OH, NO$_2$, NH$_2$, SH, acetyl, C$_{1-10}$-alkyl, C$_{2-10}$-alkenyl, C$_{2-10}$-alkynyl, C$_{1-10}$-alkylamino-, C$_{1-10}$-dialkylamino-, C$_{1-10}$-alkoxyl or C$_{1-10}$-thioalkoxyl.

8. The compound of claim 1, wherein

R$^7$ is H, halo, haloalkyl, haloalkoxyl, CN, OH, NO$_2$, NH$_2$, SH, acetyl, C$_{1-10}$-alkyl, C$_{2-10}$-alkenyl, C$_{2-10}$-alkynyl, C$_{1-10}$-alkylamino-, C$_{1-10}$-dialkylamino-, C$_{1-10}$-alkoxyl or C$_{1-10}$-thioalkoxyl; and R$^8$ is SR$^{13}$, OR$^{13}$, NR$^{13}$R$^{13}$, NR$^{13}$R$^{14}$, C(O)R$^{13}$, COOR$^{13}$, OC(O)R$^{13}$, C(O)C(O)R$^{13}$, C(O)NR$^{13}$R$^{13}$, C(O)NR$^{13}$R$^{14}$, NR$^{13}$C(O)R$^{13}$, NR$^{13}$C(O)R$^{16}$, NR$^{13}$(COOR$^{13}$), OC(O)NR$^{13}$R$^{13}$, NR$^{13}$C(O)C(O)R$^{13}$, NR$^{13}$C(O)NR$^{13}$R$^{13}$, NR$^{13}$C(O)NR$^{13}$R$^{14}$, NR$^{13}$C(O)C(O)NR$^{13}$R$^{13}$, NR$^{13}$C(O)C(O)NR$^{13}$R$^{14}$, C(S)R$^{13}$, C(S)NR$^{13}$R$^{13}$, C(S)NR$^{13}$R$^{14}$, NR$^{13}$C(S)R$^{13}$, NR$^{13}$C(S)R$^{14}$, NR$^{13}$C(S)NR$^{13}$R$^{13}$, NR$^{13}$C(S)NR$^{13}$R$^{14}$, S(O)$_2$R$^{13}$, S(O)$_2$NR$^{13}$R$^{13}$, S(O)$_2$NR$^{13}$R$^{14}$, NR$^{13}$S(O)$_2$NR$^{13}$R$^{13}$, NR$^{13}$S(O)$_2$R$^{13}$, NR$^{13}$S(O)$_2$R$^{14}$ or C$_{1-10}$alkyl optionally substituted with 1-3.

9. A compound of Formula II:

II or a pharmaceutically acceptable salt thereof, wherein

D is N or CH;

G is NR$^{13}$, O or S,

R$^1$ is H, halo, haloalkyl, NO$_2$, CN, NR$^{13}$R$^{13}$ or (CHR$^{13}$)$_n$R$^{13}$; alternatively R$^1$ taken together with R$^{10}$ forms a partially or fully unsaturated 5- or 6-membered ring of carbon atoms optionally including 1-3 heteroatoms selected from O, N and S, and the ring optionally substituted independently with 1-3 substituents of R$^{13}$, halo, haloalkyl, oxo, NO$_2$, CN, SR$^{13}$, OR$^{13}$, OC(O)R$^{13}$, COOR$^{13}$, C(O)R$^{13}$, C(O)NR$^{13}$R$^{13}$, NR$^{13}$R$^{13}$ or NR$^{13}$R$^{14}$;

R$^2$ is H, halo, haloalkyl, CN, SR$^{13}$, OR$^{13}$, C(O)R$^{13}$, C$_{1-10}$alkyl, C$_{1-10}$alkynyl or C$_{3-8}$cycloalkyl wherein the C$_{1-10}$alkyl, C$_{1-10}$alkynyl, and C$_{3-8}$cycloalkyl is optionally substituted with 1-3 substituents of R$^{13}$;

each of R$^3$ and R$^4$, independently, is H, halo, haloalkyl, CN, SR$^{13}$, OR$^{13}$, NR$^{13}$R$^{13}$, NR$^{13}$C(O)R$^{13}$ or C$_{1-10}$alkyl;

each of R$^5$ and R$^6$, independently, is H, halo, haloalkyl, CN, SR$^{13}$, OR$^{13}$, NR$^{13}$R$^{13}$, NR$^{13}$R$^{14}$, C(O)R$^{13}$, COOR$^{13}$, C$_{1-10}$alkyl, C$_{1-10}$alkynyl, or C$_{3-8}$cycloalkyl, wherein the C$_{1-10}$alkyl, C$_{1-10}$alkenyl, C$_{1-10}$alkynyl and C$_{3-8}$cycloalkyl is optionally substituted independently with 1-3 substituents of R$^{13}$; alternatively R$^5$ taken together with $R^6$ forms a phenyl or pyridyl ring, each ring of which is optionally substituted independently with 1-3 substituents of F, Cl, Br, $CH_3$, —$CH_2CH_3$, $OCF_3$, $CF_3$ or CN;

one of $R^7$ and $R^8$ is $SR^{13}$, $OR^{13}$, $NR^{13}R^{13}$, $NR^{13}R^{14}$, $C(O)R^{13}$, $C(O)NR^{13}R^{13}$, $C(O)NR^{13}R^{14}$, $NR^{13}C(O)R^{13}$, $NR^{13}(COOR^{13})$, $NR^{13}C(O)NR^{13}R^{13}$, $NR^{13}C(O)NR^{13}R^{14}$, $S(O)_2R^{13}$, $S(O)_2NR^{13}R^{13}$, $S(O)_2NR^{13}R^{14}$, $NR^{13}S(O)_2NR^{13}R^{13}$, $NR^{13}S(O)_2R^{13}$, $NR^{13}S(O)_2R^{14}$, or $C_{1-3}$alkyl optionally substituted with 1-3 substituents of $R^{15}$ or $R^{16}$; and the other of $R^7$ and $R^8$ is H, halo, haloalkyl, haloalkoxyl, CN, OH, $NO_2$, $NH^2$, SH, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl;

each of $R^9$, $R^{10}$, and $R^{11}$, independently, is H, halo, haloalkyl, $NO_2$, CN, $C_{1-4}$alkyl, $C_{1-4}$alkoxyl, $C_{1-10}$alkenyl, $C_{1-4}$alkynyl or $C_{3-6}$cycloalkyl;

each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with 1-3 substituents of $R^{15}$, $R^{16}$ or $R^{18}$;

$R_{14}$ is $C(O)R^{18}$, $COOR^{18}$, $S(O)_2R^{18}$ or $R^{16}$;

$R^{15}$ is halo, haloalkyl, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with 1-3 substituents of $R^{17}$, $R^{18}$ or $R^{20}$;

$R^{17}$ is halo, haloalkyl, oxo, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}NR^{18}$, $S(O)_2NR^{18}NR^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{19}$ or $R^{20}$, each of which is optionally substituted with 1-3 substituents of $R^{21}$;

$R^{19}$, independently, is $C(O)R^{20}$, $C(O)R^{21}$, $COOR^{20}$, $COOR^{21}$, $S(O)_2R^{20}$ or $S(O)_2R^{21}$;

$R^{20}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with 1-3 substituents of $R^{21}$;

each $R^{21}$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkenyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl; and n is 1, 2, 3, 4 or 5, provided that when either of $R^1$ or $R^2$ is substituted or unsubstituted NH-phenyl, then no more than four of $R^5$, $R^6$, $R^7$, $R^8$ and $R^9$ is H.

10. The compound of claim 9, wherein

D is CH;

G is NH, O or S;

$R^1$ is H, $NR^{13}R^{13}$ or $CH_2R^{13}$;

$R^2$ is H, halo, $NO_2$, CN, $C_{1-10}$alkyl or $C_{1-10}$alkoxyl;

each of $R^3$ and $R^4$, independently, is H, halo, haloalkyl, CN, methyl, ethyl, propyl, methoxyl, ethoxyl, thiomethyl, thioethyl, OH, $NH_2$, —$NCH_3$ or acetyl;

each of $R^5$ and $R^6$, independently, is H, halo, haloalkyl, CN, methyl, ethyl, propyl, methoxyl, ethoxyl, thiomethyl, thioethyl, OH, $NH_2$, —$NCH_3$ or acetyl;

one of $R^7$ and $R^8$ is $SR^{13}$, $OR^{13}$, $NR^{13}R^{13}$, $NR^{13}R^{14}$, $C(O)R^{13}$, $C(O)NR^{13}R^{13}$, $C(O)NR^{13}R^{14}$, $NR^{13}C(O)R^{13}$ or $C_{1-3}$alkyl optionally substituted with 1-3 substituents of $R^{15}$ or $R^{16}$;

the other of $R^7$ and $R^8$ is H, halo, haloalkyl, haloalkoxyl, CN, OH, $NH_2$, acetyl, methyl, ethyl, propyl, methoxyl, ethoxyl, thiomethyl, thioethyl, —N—$CH_3$ or acetyl;

$R^9$ is H;

each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with 1-3 substituents of $R^{15}$, $R^{16}$ or $R^{18}$;

$R^{14}$ is $C(O)R^{18}$, $COOR^{18}$, $S(O)_2R^{18}$ or $R^{16}$;

$R^{15}$ is halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with 1-3 substituents of $R^{17}$, $R^{18}$ or $R^{20}$;

$R^{17}$ is halo, haloalkyl, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{19}$ or $R^{20}$, each of which is optionally substituted with 1-3 substituents of $R^{21}$;

$R^{19}$, independently, is $C(O)R^{20}$, $C(O)R^{21}$, $COOR^{20}$, $COOR^{21}$, $S(O)_2R^{20}$ or $S(O)_2R^{21}$;

$R^{20}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with 1-3 substituents of $R^{21}$; and each $R^{21}$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl.

11. The compound of claim 9 wherein,

D is CH;

G is O or S;

$R^1$ is H, $NR^{13}R^{13}$ or $CH_2R^{13}$; alternatively $R^1$ taken together with $R^{10}$ forms a partially or fully unsaturated 5- or 6-membered ring of carbon atoms optionally including 1-3 heteroatoms selected from O, N and S, and the ring optionally substituted independently with 1-3 substituents of $R^{13}$, halo, haloalkyl, oxo, $NO_2$, CN, $SR^{13}$, $OR^{13}$, $OC(O)R^{13}$, $COOR^{13}$, $C(O)R^{13}$, $C(O)NR^{13}R^{13}$, $NR^{13}R^{13}$ or $NR^{13}R^{14}$;

$R^2$ is H, halo, $NO_2$, CN, $C_{1-10}$alkyl or $C_{1-10}$alkoxyl;

each of $R^3$ and $R^4$, independently, is H, halo, haloalkyl, CN, methyl, ethyl, propyl, methoxyl, ethoxyl, thiomethyl, thioethyl, OH, $NH_2$, —N—$CH_3$ or acetyl;

each of $R^5$ and $R^6$, independently, is H, halo, haloalkyl, CN, methyl, ethyl, propyl, methoxyl, ethoxyl, thiomethyl, thioethyl, OH, $NH_2$, —N—$CH_3$ or acetyl;

one of $R^7$ and $R^8$ is $SR^{13}$, $OR^{13}$, $NR^{13}R^{13}$, $NR^{13}R^{14}$, $C(O)R^{13}$, $C(O)NR^{13}R^{13}$, $C(O)NR^{13}R^{14}$, $NR^{13}C(O)R^{13}$ or $C_{1-3}$alkyl optionally substituted with 1-3 substituents of $R^{15}$ or $R^{16}$;

the other of $R^7$ and $R^8$ is H, halo, haloalkyl, haloalkoxyl, CN, OH, $NH_2$, acetyl, methyl, ethyl, propyl, methoxyl, ethoxyl, thiomethyl, thioethyl, —N—$CH_3$ or acetyl;

$R^9$ is H;

each $R^{13}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{15}$ or $R^{16}$, each of which is optionally substituted with one or more substituents of $R^{15}$, $R^{16}$ or $R^{18}$;

$R^{14}$ is $C(O)R^{18}$, $COOR^{18}$, $S(O)_2 R^{18}$ or $R^{16}$;

$R^{15}$ is halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $R^{17}$, $R^{20}$, $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with 1-3 substituents of $R^{17}$, $R^{18}$ or $R^{20}$;

$R^{17}$ is halo, haloalkyl, oxo, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, $C_{1-10}$alkyl, $C_{1-10}$alkenyl, $C_{1-10}$alkynyl, $C_{3-8}$cycloalkyl, $C_{4-8}$cycloalkenyl, $R^{19}$ or $R^{20}$, each of which is optionally substituted with 1-3 substituents of $R^{21}$;

$R^{19}$, independently, is $C(O)R^{20}$, $C(O)R^{21}$, $COOR^{20}$, $COOR^{21}$, $S(O)_2R^{20}$ or $S(O)_2R^{21}$;

$R^{20}$ is a saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, the heteroatoms selected from O, N, or S, wherein 0, 1, 2 or 3 atoms of each ring is optionally substituted independently with 1-3 substituents of $C_{1-10}$alkyl, $C_{1-10}$alkenyl, $C_{1-10}$alkynyl, $C_{3-8}$cycloalkyl or $C_{4-8}$cycloalkenyl, each of which is optionally substituted with 1-3 substituents of $R^{21}$; and each $R^{21}$, independently, is H, halo, haloalkyl, haloalkoxyl, oxo, CN, OH, SH, $NO_2$, $NH_2$, acetyl, $C_{1-10}$-alkyl, $C_{2-10}$- alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl.

12. The compound of claim 11, wherein, $R^7$ is $SR^{13}$, $OR^{13}$, $NR^{13}R^{13}$, $NR^{13}R^{14}$, $C(O)R^{13}$, $C(O)NR^{13}R^{13}$, $C(O)NR^{13}R^{14}$, $NR^{13}C(O)R^{13}$ or $C_{1-3}$alkyl optionally substituted with 1-3 substituents of $R^{15}$ or $R^{16}$; and $R^8$ is H, halo, haloalkyl, haloalkoxyl, CN, OH, $NH_2$, SH, acetyl, methyl, ethyl, propyl, methoxyl, ethoxyl, thiomethyl, thioethyl or —$NCH_3$.

13. The compound of claim 11, wherein $R^7$ is H, halo, haloalkyl, haloalkoxyl, CN, OH, $NH_2$, SH, acetyl, methyl, ethyl, propyl, methoxyl, ethoxyl, thiomethyl, thioethyl, or —N—$CH_3$; and $R^8$ is $SR^{13}$, $OR^{13}$, $NR^{13}R^{13}$, $NR^{13}R^{14}$, $C(O)R^{13}$, $C(O)NR^{13}R^{13}$, $C(O)NR^{13}R^{14}$, $NR^{13}C(O)R^{13}$ or $C_{1-3}$alkyl optionally substituted with 1-3 substituents of $R^{15}$ or $R^{16}$.

14. The compound of claim 9 wherein,

D is N or CH;

G is O or S;

$R^1$ is H, $NR^{13}R^{13}$ or $CH_2R^{13}$;

$R^2$ is H;

each of $R^3$ and $R^4$, independently, is H, halo, haloalkyl, CN, methyl, ethyl, propyl, methoxyl, ethoxyl, thiomethyl, thioethyl, OH, $NH_2$, —N—$CH_3$ or acetyl;

each of $R^5$ and $R^6$, independently, is H, halo, haloalkyl, CN, methyl, ethyl, propyl, methoxyl, ethoxyl, thiomethyl, thioethyl, OH, $NH_2$, —N—$CH_3$ or acetyl;

one of $R^7$ and $R^8$ is $NR^{13}R^{13}$, $C(O)R^{13}$, $C(O)NR^{13}R^{13}$, $NR^{13}C(O)R^{13}$, $S(O)_2R^{13}$, $S(O)_2NR^{13}R^{13}$, $NR^{13}S(O)_2R^{13}$ or $C_{1-3}$alkyl optionally substituted with 1-3 substituents of $NR^{18}R^{18}$, $C(O)R^{18}$, $C(O)NR^{18}R^{18}$, $NR^{18}C(O)R^{18}$, $S(O)_2R^{18}$, $S(O)_2NR^{18}R^{18}$, $NR^{18}S(O)_2NR^{18}R^{18}$ or $NR^{18}S(O)_2R^{18}$;

the other of $R^7$ and $R^8$ is H, halo, haloalkyl, haloalkoxyl, CN, OH, $NH_2$, acetyl, methyl, ethyl, propyl, methoxyl, ethoxyl, thiomethyl, thioethyl, —N—$CH_3$ or acetyl;

$R^9$ is H;

each $R^{13}$, independently, is H, $C_{1-10}$alkyl, $C_{1-10}$alkenyl, $C_{1-10}$alkynyl, phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl, naphthyl or benzyl, each of which is optionally independently substituted with 1-3 substituents of $R^{15}$, $R^{16}$ or $R^{18}$;

$R^{15}$ is halo, haloalkyl, oxo, $NO_2$, CN, $SR^{18}$, $OR^{18}$, $OC(O)R^{18}$, $NR^{16}R^{18}$, $NR^{18}R^{18}$, $COOR^{16}$, $C(O)R^{16}$, $COOR^{18}$, $C(O)R^{18}$, $C(O)NR^{16}R^{18}$, $C(O)NR^{18}R^{18}$, $S(O)_2NR^{16}R^{18}$, $S(O)_2NR^{18}R^{18}$, $S(O)_2R^{16}$, $S(O)_2R^{18}$, $C(O)C(O)R^{18}$, $NR^{18}C(O)NR^{16}R^{18}$, $NR^{18}C(O)NR^{18}R^{18}$, $NR^{18}C(O)C(O)R^{18}$, $NR^{18}C(O)R^{16}$, $NR^{18}C(O)R^{18}$, $NR^{18}(COOR^{16})$, $NR^{18}(COOR^{18})$, $NR^{18}S(O)_2NR^{16}R^{18}$, $NR^{18}S(O)_2NR^{18}R^{18}$, $NR^{18}S(O)_2R^{18}$, $NR^{18}S(O)_2R^{16}$, $NR^{18}C(O)C(O)NR^{16}R^{18}$ or $NR^{18}C(O)C(O)NR^{18}R^{18}$;

$R^{16}$ is phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally substituted independently with 1-3 substituents of $R^{17}$, $R^{18}$ or $R^{20}$;

$R^{17}$ is halo, haloalkyl, oxo, $NO_2$, CN, $SR^{18}$, $OR^{18}$, $OC(O)R^{18}$, $NR^{18}R^{18}$, $NR^{18}R^{20}$, $COOR^{18}$, $C(O)R^{18}$, $COOR^{20}$, $C(O)R^{20}$, $C(O)NR^{18}R^{18}$, $C(O)NR^{18}R^{20}$, $S(O)_2NR^{18}R^{18}$, $S(O)_2NR^{18}R^{20}$, $S(O)_2R^{18}$, $S(O)_2R^{20}$, $C(O)C(O)R^{18}$, $NR^{18}C(O)NR^{18}R^{18}$, $NR^{18}C(O)NR^{18}R^{20}$, $NR^{18}C(O)C(O)R^{18}$, $NR^{18}C(O)R^{18}$, $NR^{18}C(O)R^{20}$, $NR^{18}(COOR^{18})$, $NR^{18}(COOR^{20})$, $NR^{18}S(O)_2NR^{18}R^{18}$, $NR^{18}S(O)_2NR^{18}R^{20}$, $NR^{18}S(O)_2R^{18}$, $NR^{18}S(O)_2R^{20}$, $NR^{18}C(O)C(O)NR^{18}R^{18}$ or $NR^{18}C(O)C(O)NR^{18}R^{20}$;

each $R^{18}$, independently, is H, methyl, ethyl, propyl, isopropyl, n-butyl, sec-butyl, t-butyl, pentyl, hexyl, acetyl or $C_{1-10}$-alkoxyl, each of which is optionally independently substituted with 1-3 substituents of $R^{21}$;

$R^{20}$ is phenyl, pyridyl, pyrimidinyl, triazinyl, quinolinyl, dihydroquinolinyl, tetrahydroquinolinyl, isoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl, cycloheptyl, pyranyl or naphthyl, each of which is optionally substituted independently with 1-3 substituents of $R^{21}$;

each $R^{21}$, independently, is H, Cl, Br, F, I, $CF_3$, $CF_2CF_3$, $NO_2$, CN; acetyl, oxo, haloalkyl, haloalkoxyl, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino, benzyl or phenyl; and n is 1, 2 or 3.

15. A pharmaceutical composition comprising a pharmaceutically acceptable carrier and an effective dosage amount of a compound of claim 1.

16. A pharmaceutical composition comprising a pharmaceutically acceptable carrier and an effective dosage amount of a compound of claim 11.

17. A method of treating breast cancer or rheumatoid arthritis in a subject, the method comprising administering to the subject an effective dosage amount of a compound of any of claim 1, 2, 7 or 8.

18. A method of treating breast cancer or rheumatoid arthritis in a subject, the method comprising administering to the subject an effective dosage amount of a compound of any of claims 9, 12, 13 and 14.

19. A method of treating breast cancer or rheumatoid arthritis in a subject, the method comprising administering to the subject an effective dosage amount of a pharmaceutical composition of claim 16.

* * * * *